(12) United States Patent
Shimizu et al.

(10) Patent No.: US 11,760,934 B2
(45) Date of Patent: *Sep. 19, 2023

(54) POLYMERIZABLE COMPOUND, AND LIQUID CRYSTAL COMPOSITION AND LIQUID CRYSTAL DISPLAY ELEMENT IN WHICH THE COMPOUND IS USED

(71) Applicant: DIC Corporation, Tokyo (JP)

(72) Inventors: Kenta Shimizu, Kitaadachi-gun (JP); Masanao Hayashi, Kitaadachi-gun (JP); Yutaka Kadomoto, Kitaadachi-gun (JP); Tetsuo Kusumoto, Kitaadachi-gun (JP); Ayaki Hosono, Kitaadachi-gun (JP); Shinya Yamamoto, Sakura (JP); Masanori Miyamoto, Sakura (JP); Hidetomo Kai, Sakura (JP)

(73) Assignee: DIC CORPORATION, Tokyo (JP)

( * ) Notice: Subject to any disclaimer, the term of this patent is extended or adjusted under 35 U.S.C. 154(b) by 525 days.

This patent is subject to a terminal disclaimer.

(21) Appl. No.: 16/754,409

(22) PCT Filed: Nov. 1, 2018

(86) PCT No.: PCT/JP2018/040671
§ 371 (c)(1),
(2) Date: Apr. 8, 2020

(87) PCT Pub. No.: WO2019/098040
PCT Pub. Date: May 23, 2019

(65) Prior Publication Data
US 2020/0308488 A1 Oct. 1, 2020

(30) Foreign Application Priority Data

Nov. 17, 2017 (JP) ................................. 2017-221803
Apr. 26, 2018 (JP) ................................. 2018-085174

(51) Int. Cl.
C09K 19/46 (2006.01)
C07C 69/604 (2006.01)
C07D 319/06 (2006.01)
C09K 19/38 (2006.01)
C09K 19/56 (2006.01)

(52) U.S. Cl.
CPC ............ *C09K 19/46* (2013.01); *C07C 69/604* (2013.01); *C07D 319/06* (2013.01); *C09K 19/38* (2013.01); *C09K 19/56* (2013.01)

(58) Field of Classification Search
CPC .... C09K 19/38; C09K 19/3833; C09K 19/54; C09K 19/542; C09K 19/56
See application file for complete search history.

(56) References Cited

U.S. PATENT DOCUMENTS

| 3,210,327 A | 10/1965 | Graliano et al. |
| 3,280,078 A | 10/1966 | Hostettler et al. |
| 3,532,715 A | 10/1970 | Hostettler et al. |
| 3,755,420 A | 8/1973 | Stoffey et al. |
| 3,774,305 A | 11/1973 | Stoffey et al. |

(Continued)

FOREIGN PATENT DOCUMENTS

| CN | 1236115 A | 11/1999 |
| CN | 100341852 C | 10/2007 |

(Continued)

OTHER PUBLICATIONS

International Search Report dated Jan. 8, 2019, issued in counterpart application No. PCT/JP2018/040671 (2 pages).
International Search Report dated Apr. 23, 2019, issued in International Application No. PCT/JP2019/005257 counterpart to U.S. Appl. No. 16/968,961. (3 pages).
International Search Report dated Aug. 28, 2018, issued in International Application No. PCT/JP2018/020478 counterpart to U.S. Appl. No. 16/615,503. (5 pages).
Nishikubo et al., "Synthesis of Photocrosslinkable Hyperbranched Polyesters with Terminal Methacryloyl Groups by the One-pot Polyaddition of Bis(oxetane)s with 1,3,5-Benzenetricarboxylic Acid and Methacrylic Acid", Polymer Journal (Tokyo, Japan), 2006, vol. 38, No. 5, p. 447-456, ISSN:0032-3896, cited in ISR (10 pages).

(Continued)

*Primary Examiner* — Cynthia H Kelly
*Assistant Examiner* — Anna Malloy
(74) *Attorney, Agent, or Firm* — WHDA, LLP

(57) ABSTRACT

The compound is represented by general formula (i). In the compound, in a group $K^{i1}$, at least two secondary carbon atoms in an alkyl group (a linear alkyl, halogenated alkyl, or cyanogenated alkyl group having 3 to 40 carbon atoms) are replaced with —C(=$X^{i1}$)— and/or —CH(—CN)—, where $X^{i1}$ is an oxygen atom, a sulfur atom, NH, or $NR^{13}$; in addition, a group $A^{i2}$, a group $A^{i3}$, or the group $K^{i1}$ includes, as a substituent, at least one $P^{i1}$-$Sp^{i1}$- group, where $P^{i1}$ is a polymerizable group, and $SP^{i1}$ is a spacer group or a single bond. The liquid crystal composition including the compound represented by general formula (i) can be adsorbed onto substrates between which a liquid crystal layer is held, and, consequently, without the use of an alignment film, liquid crystal molecules can be maintained in a state in which the liquid crystal molecules are aligned in a vertical direction.

$$R^{i1}-A^{i1}-Z^{i1}+A^{i2}-Z^{i2}\rightarrow_{mi1}A^{i3}-K^{i1} \quad (i)$$

8 Claims, No Drawings

(56) References Cited

U.S. PATENT DOCUMENTS

| | | | |
|---|---|---|---|
| 4,962,163 A | 10/1990 | Hefner, Jr. et al. | |
| 5,395,736 A * | 3/1995 | Grasshoff | C07C 49/593 430/269 |
| 5,919,599 A | 7/1999 | Meador et al. | |
| 5,998,499 A | 12/1999 | Klee et al. | |
| 6,458,908 B1 | 10/2002 | Imai et al. | |
| 6,906,116 B2 | 6/2005 | Nishikubo et al. | |
| 7,541,071 B2 | 6/2009 | Shundo et al. | |
| 9,458,264 B2 | 10/2016 | Aoshima et al. | |
| 9,725,590 B2 | 8/2017 | Chun et al. | |
| 10,190,050 B2 | 1/2019 | Lim et al. | |
| 10,927,300 B2 | 2/2021 | Kimura et al. | |
| 11,174,217 B2 | 11/2021 | Hosono et al. | |
| 2006/0054859 A1 | 3/2006 | Shundo et al. | |
| 2009/0326186 A1* | 12/2009 | He | C07D 309/12 560/81 |
| 2010/0296032 A1 | 11/2010 | Shin et al. | |
| 2014/0018517 A1 | 1/2014 | Busygin et al. | |
| 2014/0138581 A1 | 5/2014 | Archetti et al. | |
| 2014/0175342 A1 | 6/2014 | Uchikawa | |
| 2015/0252265 A1 | 9/2015 | Archetti et al. | |
| 2016/0137921 A1 | 5/2016 | Hayashi et al. | |
| 2016/0362606 A1 | 12/2016 | Tong et al. | |
| 2017/0158793 A1 | 6/2017 | Endo et al. | |
| 2017/0210994 A1 | 7/2017 | Lim et al. | |
| 2018/0002604 A1 | 1/2018 | Yoon et al. | |
| 2018/0045991 A1 | 2/2018 | Lan et al. | |
| 2018/0057743 A1 | 3/2018 | Archetti et al. | |
| 2018/0142152 A1 | 5/2018 | Archetti et al. | |
| 2019/0127376 A1 | 5/2019 | Wu et al. | |
| 2019/0264108 A1 | 8/2019 | Kimura et al. | |
| 2019/0292463 A1 | 9/2019 | Yano et al. | |
| 2019/0308926 A1 | 10/2019 | Lan | |
| 2019/0390076 A1 | 12/2019 | Isonaka et al. | |
| 2019/0391418 A1 | 12/2019 | Yamaguchi et al. | |
| 2020/0087240 A1 | 3/2020 | Hosono et al. | |
| 2020/0208054 A1* | 7/2020 | Yamamoto | C09K 19/3066 |
| 2020/0224098 A1* | 7/2020 | Mamiya | C09K 19/3402 |
| 2020/0308488 A1 | 10/2020 | Shimizu et al. | |
| 2020/0399539 A1* | 12/2020 | Hayashi | C09K 19/56 |
| 2021/0026206 A1 | 1/2021 | Kurisawa et al. | |
| 2021/0214299 A1* | 7/2021 | Hosono | C09K 19/3066 |

FOREIGN PATENT DOCUMENTS

| | | |
|---|---|---|
| CN | 105001879 A | 10/2015 |
| CN | 105061213 A | 11/2015 |
| CN | 105647547 A | 6/2016 |
| CN | 106397752 A | 2/2017 |
| CN | 107557024 A | 1/2018 |
| CN | 109195943 A | 1/2019 |
| CN | 110546176 A | 12/2019 |
| FR | 1434145 A | 4/1966 |
| JP | H02-173031 A | 7/1990 |
| JP | H02-232602 A | 9/1990 |
| JP | H02-240128 A | 9/1990 |
| JP | H03-244615 A | 10/1991 |
| JP | H04-4215 A | 1/1992 |
| JP | H04-316890 A | 11/1992 |
| JP | H07-92674 A | 4/1995 |
| JP | H07-206974 A | 8/1995 |
| JP | H09-157340 A | 6/1997 |
| JP | 2001-509128 A | 7/2001 |
| JP | 2002-502982 A | 1/2002 |
| JP | 2002-123921 A | 4/2002 |
| JP | 2002-145935 A | 5/2002 |
| JP | 2003-138223 A | 5/2003 |
| JP | 2005-206579 A | 8/2005 |
| JP | 2009-215189 A | 9/2009 |
| JP | 2011-514542 A | 5/2011 |
| JP | 2011-213790 A | 10/2011 |
| JP | 2012-008223 A | 1/2012 |
| JP | 2012-242701 A | 12/2012 |
| JP | 2013-542297 A | 11/2013 |
| JP | 2014-524951 A | 9/2014 |
| JP | 2015-155532 A | 8/2015 |
| JP | 2015-168826 A | 9/2015 |
| JP | 2015-535814 A | 12/2015 |
| JP | 2017-222709 A | 12/2017 |
| JP | 2018-16791 A | 2/2018 |
| JP | 2018-25752 A | 2/2018 |
| JP | 2018-90569 A | 6/2018 |
| KR | 10-2016-0115000 A | 10/2016 |
| NO | 2017/209161 A1 | 12/2017 |
| NO | 2018/159637 A1 | 9/2018 |
| WO | 2002/018313 A1 | 3/2002 |
| WO | 2002/064662 A1 | 8/2002 |
| WO | 2009/091225 A2 | 7/2009 |
| WO | 2013/047523 A1 | 4/2013 |
| WO | 2014/007361 A1 | 1/2014 |
| WO | 2014/106799 A2 | 7/2014 |
| WO | 2015/198915 A1 | 12/2015 |
| WO | 2017/041893 A1 | 3/2017 |
| WO | 2018/079333 A1 | 5/2018 |
| WO | 2018/079528 A1 | 5/2018 |
| WO | 2018/105545 A1 | 6/2018 |
| WO | 2018/123821 A1 | 7/2018 |
| WO | 2018/221236 A1 | 12/2018 |
| WO | 2018/230322 A1 | 12/2018 |
| WO | 2019/003935 A1 | 1/2019 |
| WO | 2019/049673 A1 | 3/2019 |

OTHER PUBLICATIONS

Registry [online], U.S.: American Chemical Society [retrieved on Jul. 9, 2018], Retrieved from: STN, CAS RN 2089601-61-4;2089601-60-3; 2089601-57-8; 2089601-55-6; 2089601-53-4; 2089601-51-2; 2089601-49-8 2089601-47-6; 2089601-46-5;2089601-37-4, cited in ISR.

Fujisawa et al., "Mechanisms of Action of (Meth)acrylates in Hemolytic Activity, in Vivo Toxicity and Dipalmitoylphosphatidylcholinc (DPPC) Liposomes Determined Using NMR Spectroscopy", Int. J. Mol. Sci. 2012, v. 13, pp. 758-773 (16 pages).

Non-Final Office Action dated Dec. 9, 2020, issued in U.S. Appl. No. 16/615,503. (20 pages).

Final Office Action dated May 17, 2021, issued in U.S. Appl. No. 16/615,503. (11 pages).

Sun, Xiao-Hong et al., "Diffraction measurement and analysis of slanted holographic polymer dispersed liquid crystal", American Institute pf physics, 2005, vol. 98, pp. 043510-1 to 5; cited in JP Office Action dated Jan. 14, 2020. (6 pages).

Notice of Allowance dated Sep. 14, 2021, issued in U.S. Appl. No. 16/615,503. (15 pages).

International Search Report dated Jan. 16, 2018, issued in International Application No. PCT/JP2017/037481 counterpart to U.S. Appl. No. 16/340,798. (3 pages).

"International Search Report (Form PCT/ISA/210) of PCT/JP2018/044883," dated Mar. 12, 2019, with English translation thereof, pp. 1-5.

Non-Final Office Action dated Jun. 16, 2022, issued in U.S. Appl. No. 16/770,067. (13 pages).

Non-Final Office Action dated Feb. 14, 2022, issued in U.S. Appl. No. 16/968,961. (15 pages).

Non-Final Office Action dated Jun. 30, 2022, issued in U.S. Appl. No. 16/968,961. (18 pages).

* cited by examiner

POLYMERIZABLE COMPOUND, AND LIQUID CRYSTAL COMPOSITION AND LIQUID CRYSTAL DISPLAY ELEMENT IN WHICH THE COMPOUND IS USED

TECHNICAL FIELD

The present invention relates to a polymerizable compound and to a liquid crystal composition and a liquid crystal display element in each of which the compound is used.

BACKGROUND ART

In existing VA mode liquid crystal displays, polyimide alignment film (PI) layers are provided on electrodes to induce a vertical alignment of liquid crystal molecules when no voltage is applied and realize a horizontal alignment of liquid crystal molecules when a voltage is applied. Unfortunately, the production of PI layers is very expensive, and, therefore, in recent years, studies have been conducted to develop a method that realizes alignment of liquid crystal molecules while eliminating the use of PI layers.

For example, PTL 1 discloses a liquid-crystalline medium based on a mixture of polar compounds having a negative dielectric anisotropy which contains at least one self-aligning additive. PTL 1 states that the liquid-crystalline medium is highly suitable for the use in displays which do not contain any orientation layer. According to PTL 1, a specific hydroxy-group-containing compound is used as a self-aligning additive.

CITATION LIST

Patent Literature

PTL 1: Japanese Unexamined Patent Application Publication (Translation of PCT Application) No. 2014-524951

SUMMARY OF INVENTION

Technical Problem

However, studies conducted by the present inventors revealed the following. In a case where the self-aligning additive disclosed in PTL 1 is used, electro-optical characteristics, for example, regarding an alignment-regulating force for vertically aligning liquid crystal molecules and alignment non-uniformity, are still insufficient; in addition, there is room for improvement in the storage characteristics of the liquid crystal composition containing the self-aligning additive.

Accordingly, an object of the present invention is to provide a polar-group-containing polymerizable compound that, when added to a liquid crystal composition, ensures storage characteristics and enables liquid crystal molecules to be aligned even when no PI layers are provided. Furthermore, other objects of the present invention are to provide a liquid crystal composition that has excellent storage characteristics and enables liquid crystal molecules to be vertically aligned even when no PI layers are provided and to provide a liquid crystal display element in which the liquid crystal composition is used.

Solution to Problem

The present invention provides compounds represented by general formula (i)

[Chem. 1]

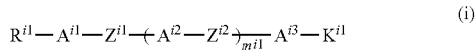

$$R^{i1}-A^{i1}-Z^{i1}-(A^{i2}-Z^{i2})_{mi1}-A^{i3}-K^{i1} \quad (i)$$

For the formula, the following is noted.

$R^{i1}$ independently represents a linear or branched alkyl or halogenated alkyl group having 1 to 40 carbon atoms, and a secondary carbon atom in the group is optionally replaced with —O—, —CH=CH—, or —C≡C— provided that oxygen atoms are not directly adjacent to each other.

$A^{i1}$, $A^{i2}$, and $A^{i3}$ each independently represent a divalent aromatic group, a divalent cycloaliphatic group, or a divalent heterocyclic compound group. A hydrogen atom in $A^{i1}$ is optionally replaced with $L^{i1}$, and hydrogen atoms in $A^{i2}$ and $A^{i3}$ are optionally replaced with $L^{i1}$, $P^{i1}$-$Sp^{i1}$-, or $K^{i1}$. $L^{i1}$ represents a halogen atom, a cyano group, a nitro group, or a linear or branched alkyl or halogenated alkyl group having 1 to 40 carbon atoms, and a secondary carbon atom in the alkyl group is optionally replaced with —CH=CH—, —C≡C—, —O—, —NH—, —COO—, or —OCO— provided that oxygen atoms are not directly adjacent to each other.

$Z^{i1}$ and $Z^{i2}$ each independently represent a single bond, —CH=CH—, —CF=CF—, —C≡C—, —COO—, —OCO—, —OCOO—, —CF$_2$O—, —OCF$_2$—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, —OCH$_2$CH$_2$O—, or an alkylene group having 2 to 20 carbon atoms, and one —CH$_2$— group or two or more non-adjacent —CH$_2$— groups in the alkylene group are optionally replaced with —O—, —COO—, or —OCO—.

$K^{i1}$ represents a linear or branched alkyl, halogenated alkyl, or cyanogenated alkyl group having 3 to 40 carbon atoms. At least two secondary carbon atoms in the alkyl group are replaced with —C(=$X^{i1}$)— and/or —CH(—CN)—. A secondary carbon atom in the alkyl group is optionally replaced with —C(=CH$_2$)—, —C(=CHR$^{i3}$)—, —C(=CR$^{i3}$$_2$)—, —CH=CH—, —C≡C—, —O—, —NH—, —COO—, or —OCO— provided that oxygen atoms are not directly adjacent to each other. A hydrogen atom in the alkyl group is optionally replaced with $P^{i1}$-$Sp^{i1}$-. $X^{i1}$ represents an oxygen atom, a sulfur atom, NH, or NR$^{i3}$. $R^{i3}$ represents a linear or branched alkyl group having 1 to 20 carbon atoms, and a secondary carbon atom in the alkyl group is optionally replaced with —O—, —CH=CH—, or —C≡C— provided that oxygen atoms are not directly adjacent to each other.

$P^{i1}$ represents a polymerizable group.

$SP^{i1}$ represents a spacer group or a single bond.

In general formula (i), at least one $P^{i1}$-$Sp^{i1}$- group is included as a substituent in $A^{i2}$ or $A^{i3}$ or as a substituent in $K^{i1}$.

$m^{i1}$ represents an integer of 0 to 3.

In general formula (i), when any of $R^{i1}$, $A^{i2}$, $Z^{i2}$, $L^{i1}$, $K^{i1}$, $X^{i1}$, $P^{i1}$, and $SP^{i1}$ is a plurality of units, the units are identical to or different from one another.

Furthermore, the present invention provides a liquid crystal composition that includes one or more compounds represented by general formula (i) and provides a liquid crystal display element that includes the liquid crystal composition.

Advantageous Effects of Invention

The present invention provides a polymerizable compound and a liquid crystal composition that have excellent storage characteristics and enable uniform vertical alignment of liquid crystal molecules even when no PI layers are provided and also provides a liquid crystal display element in which the liquid crystal composition is used.

DESCRIPTION OF EMBODIMENTS

A polymerizable compound according to an embodiment is a compound represented by general formula (i).

[Chem. 2]

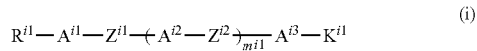
(i)

The compound represented by general formula (i) has, in particular, a structural portion represented by $K^{i1}$. Accordingly, in a case where the compound is used in a liquid crystal composition, the compound can be aligned with respect to substrates between which the liquid crystal composition (liquid crystal layer) is held and can be maintained in a state in which the liquid crystal molecules are aligned in a vertical direction. With regard to the compound represented by general formula (i), it is believed that since the structural portion represented by $K^{i1}$ in general formula (K-1) has a polarity, the compound is adsorbed onto substrates between which the liquid crystal composition (liquid crystal layer) is held; furthermore, since the compound has the structural portion represented by $K^{i1}$ at an end of the compound, liquid crystal molecules are maintained in a state in which the liquid crystal molecules are aligned in a vertical direction. Accordingly, with a liquid crystal composition in which the polymerizable compound of the embodiment is used, liquid crystal molecules can be aligned even when no PI layers are provided (a vertical alignment of liquid crystal molecules can be induced when no voltage is applied, and a horizontal alignment of liquid crystal molecules can be realized when a voltage is applied). Thus, compounds represented by general formula (i) are suitable for use in assisting vertical alignment of liquid crystal molecules in a liquid crystal composition.

In addition, the present inventors found that because of the structural portion represented by $K^{i1}$ included in the polymerizable compound represented by general formula (i) of the embodiment, not only alignment of liquid crystal molecules but also a storage stability of a liquid crystal composition can be ensured.

Furthermore, the compound represented by general formula (i) includes a polymerizable group in a specific position; that is, a polymerizable group is included as a substituent in $A^{i2}$ or $A^{i3}$ or as a substituent in $K^{i1}$. As a result, more favorable alignment characteristics can be maintained.

From the above standpoints, it is sufficient that the polymerizable compound of the embodiment have the structural portion represented by $K^{i1}$ at an end of the molecule, preferably at an end of the backbone of the molecule. That is, the chemical structure of the unit to which the structural portion represented by $K^{i1}$ is to be attached is not particularly limited provided that the functions of the liquid crystal composition are not impaired.

Specific examples of compounds represented by general formula (i) will now be described.

$K^{i1}$ in general formula (i) is preferably a linear or branched alkyl group having 3 to 40 carbon atoms, a linear or branched halogenated alkyl group having 3 to 40 carbon atoms, or a linear or branched cyanogenated alkyl group having 3 to 40 carbon atoms. At least two secondary carbon atoms in $K^{i1}$ are replaced with —C(=$X^{i1}$)— and/or —CH(—CN)—; preferably, at least two secondary carbon atoms in $K^{i1}$ are replaced with —C(=$X^{i1}$)—; preferably, at least three secondary carbon atoms are replaced with —C(=$X^{i1}$)—; or preferably, at least four secondary carbon atoms are replaced with —C(=$X^{i1}$)—. It is preferable that $X^{i1}$ be an oxygen atom, from the standpoint of improving a voltage holding ratio (VHR). Preferably, $K^{i1}$ represents a linear or branched alkyl group, a linear or branched halogenated alkyl group, or a linear or branched cyanogenated alkyl group, having 3 to 30 carbon atoms, and one or more secondary carbon atoms in any of the alkyl groups are optionally replaced with —C(=$CH_2$)—, —C(=$CHR^{i3}$)—, —C(=$CR^{i3}_2$)—, —CH=CH—, —C≡C—, or —O— provided that oxygen atoms are not directly adjacent to each other. More preferably, $K^{i1}$ represents a linear or branched alkyl group or a linear or branched cyanogenated alkyl group, having 3 to 20 carbon atoms, and one or more secondary carbon atoms in any of the alkyl groups are optionally replaced with —C(=$CH_2$)—, —C(=$CHR^{i3}$)—, —C(=$CR^{i3}_2$)—, or —O— provided that oxygen atoms are not directly adjacent to each other. More preferably, $K^{i1}$ represents a branched alkyl group or a branched cyanogenated alkyl group, having 3 to 20 carbon atoms, and one or more secondary carbon atoms in any of the alkyl groups are optionally replaced with —C(=$CH_2$)— or —O— provided that oxygen atoms are not directly adjacent to each other. $R^{i3}$ is preferably a linear or branched alkyl group having 1 to 10 carbon atoms, preferably an alkyl group having 1 to 7 carbon atoms, or preferably an alkyl group having 1 to 3 carbon atoms, and one or more secondary carbon atoms in any of the alkyl groups are optionally replaced with —O—, —CH=CH—, or —C≡C— provided that oxygen atoms are not directly adjacent to each other.

Furthermore, it is preferable that a hydrogen atom in $K^{i1}$ be replaced with a polymerizable group, that is, $P^{i1}$-$Sp^{i1}$-. With the presence of a polar group and a polymerizable group in $K^{i1}$, more favorable alignment characteristics are achieved.

It is preferable that $K^{i1}$ represent general formula (K-1).

[Chem. 3]

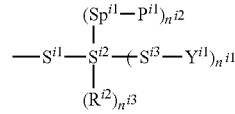
(K-1)

For the formula, the following is noted. $Y^{i1}$ represents a linear or branched alkyl, halogenated alkyl, or cyanogenated alkyl group having 3 to 20 carbon atoms. At least two secondary carbon atoms in the alkyl group are replaced with —C(=$X^{i1}$)— and/or —CH(—CN)—. One or more secondary carbon atoms in the alkyl group are optionally replaced with —CH=CH—, —C≡C—, —O—, —NH—, —COO—, or —OCO— provided that oxygen atoms are not directly adjacent to each other. One or more hydrogen atoms in the alkyl group are optionally replaced with $P^{i1}$-$Sp^{i1}$-. $X^{i1}$ represents an oxygen atom, a sulfur atom, NH, or $NR^{i3}$.

$S^{i1}$ and $S^{i3}$ each independently represent an alkylene group having 1 to 6 carbon atoms or a single bond, and —$CH_2$— in the alkylene group is optionally replaced with —CH=CH—, —C≡C—, —C(=CH$_2$)—, —C(=CHR$^{i3}$)—, —C(=CR$^{i3}{}_2$)—, —O—, —NH—, —C(=O)—, —COO—, or —OCO— provided that oxygen atoms are not directly adjacent to each other.

S$^{i2}$ represents a carbon atom, a nitrogen atom, or a silicon atom.

R$^{i2}$ represents a hydrogen atom or a linear or branched alkyl, halogenated alkyl, or cyanogenated alkyl group having 1 to 20 carbon atoms, and one or more secondary carbon atoms in the group are optionally replaced with —O—, —CH=CH—, —C≡C—, —C(=X$^{i1}$)—, or —CH(—CN)— provided that oxygen atoms are not directly adjacent to each other.

P$^{i1}$ represents a polymerizable group.

SP$^{i1}$ represents a spacer group or a single bond.

n$^{i1}$ represents an integer of 1 to 3, and n$^{i2}$ and n$^{i3}$ each independently represent an integer of 0 to 2 provided that when S$^{i2}$ represents a carbon atom or a silicon atom, n$^{i1}$+n$^{i2}$+n$^{i3}$ is 3, and when S$^{i2}$ represents a nitrogen atom, n$^{i1}$+n$^{i2}$+n$^{i3}$ is 2. R$^{i3}$ has the same meaning as R$^{i3}$ in general formula (i). In general formula (K-1), when any of R$^{i2}$, X$^{i1}$, Y$^{i1}$, S$^{i1}$, S$^{i3}$, p$^{i1}$, and SP$^{i1}$ is a plurality of units, the units may be identical to or different from one another.

Preferably, S$^{i1}$ and S$^{i3}$ in general formula (K-1) are a linear or branched alkylene group having 1 to 6 carbon atoms or a single bond, and —CH$_2$— in the alkylene group is optionally replaced with —CH=CH—, —(C=CH$_2$)—, —O—, —(C=O)—, —COO—, or —OCO— provided that oxygen atoms are not directly adjacent to each other. More preferably, S$^{i1}$ and S$^{i3}$ in general formula (K-1) are a single bond or a linear alkylene group having 1 to 6 carbon atoms, or —CH$_2$— in the alkylene group is a group replaced with —O— provided that oxygen atoms are not directly adjacent to each other. Specifically, it is preferable that S$^{i1}$ and S$^{i3}$ represent —(CH$_2$)n-, —O—(CH$_2$)n-, —(CH$_2$)n-O—, —(CH$_2$)n-O—(CH$_2$)m-, —COO—(CH$_2$)n-, or —OCO—(CH$_2$)n- (n and m represent an integer of 1 to 6).

Preferably, S$^{i2}$ is a carbon atom. Preferably, R$^{i2}$ represents a hydrogen atom or linear or branched alkyl group having 1 to 10 carbon atoms, and —CH$_2$— in the alkyl group is optionally replaced with —O—, —C(=X$^{i1}$)—, or —CH(—CN)— (provided that —O—'s are not next to each other). Preferably, R$^{i2}$ represents a hydrogen atom or a linear or branched alkyl group having 1 to 7 carbon atoms, and —CH$_2$— in the alkyl group is optionally replaced with —O—, —C(=X$^{i1}$)—, or —CH(—CN)— (provided that —O—'s are not next to each other). More preferably, R$^{i2}$ is a hydrogen atom or a linear alkyl group having 1 to 3 carbon atoms.

Y$^{i1}$ is an alkyl group having 3 to 20 carbon atoms, a linear or branched halogenated alkyl group having 3 to 20 carbon atoms, or a linear or branched cyanogenated alkyl group having 3 to 20 carbon atoms. At least two secondary carbon atoms in Y$^{i1}$ are replaced with —C(=X$^{i1}$)— and/or —CH(—CN)—. It is preferable that at least two secondary carbon atoms in Y$^{i1}$ be replaced with —C(=X$^{i1}$)—. It is preferable that X$^{i1}$ be an oxygen atom, from the standpoint of improving a voltage holding ratio (VHR). Preferably, Y$^{i1}$ represents a linear or branched alkyl, halogenated alkyl, or cyanogenated alkyl group having 3 to 10 carbon atoms, and one or more secondary carbon atoms in the alkyl group are optionally replaced with —C(=CH$_2$)—, —C(=CHR$^{i3}$)—, —C(=CR$^{i3}{}_2$)—, —CH=CH—, —C≡C—, or —O— provided that oxygen atoms are not directly adjacent to each other. More preferably, Y$^{i1}$ represents a linear or branched alkyl or cyanogenated alkyl group having 3 to 7 carbon atoms, and one or more secondary carbon atoms in the alkyl group are optionally replaced with —C(=CH$_2$)—, —C(=CHR$^{i3}$)—, —C(=CR$^{i3}{}_2$)—, or —O— provided that oxygen atoms are not directly adjacent to each other. More preferably, Y$^{i1}$ represents a linear or branched alkyl group having 3 to 7 carbon atoms, and one or more secondary carbon atoms in the alkyl group are optionally replaced with —O— provided that oxygen atoms are not directly adjacent to each other. Furthermore, one or more hydrogen atoms in the alkyl group may be replaced with P$^{i1}$-Sp$^{i1}$-.

From the standpoint of improving the alignment characteristics of liquid crystals, it is preferable that Y$^{i1}$ represent a group selected from general formula (Y-1).

[Chem. 4]

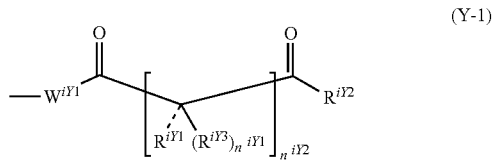

(Y-1)

For the formula, the following is noted. W$^{iY1}$ represents a single bond or an oxygen atom. The dashed line represents a single bond or a double bond. When the dashed line represents a single bond, R$^{iY1}$ represents a hydrogen atom, a linear or branched alkyl group having 1 to 20 carbon atoms, or P$^{i1}$-Sp$^{i1}$-, and one or more secondary carbon atoms in the alkyl group are optionally replaced with —O—, —CH=CH—, —C≡C—, or —CO— provided that oxygen atoms are not directly adjacent to each other. When the dashed line represents a double bond, R$^{iY1}$ represents =CH$_2$, =CHR$^{iY4}$, or =CR$^{iY4}{}_2$, where R$^{iY4}$ represents a hydrogen atom or a linear or branched alkyl group having 1 to 20 carbon atoms, and one or more secondary carbon atoms in the alkyl group are optionally replaced with —O—, —CH=CH—, or —C≡C— provided that oxygen atoms are not directly adjacent to each other. R$^{iY3}$ has the same meaning as R$^{iY1}$ associated with the case where the dashed line represents a single bond. R$^{iY2}$ represents a hydrogen atom or a linear or branched alkyl, halogenated alkyl, or cyanogenated alkyl group having 1 to 20 carbon atoms, and one or more secondary carbon atoms in the alkyl group are optionally replaced with —CH=CH—, —C≡C—, —O—, —NH—, —COO—, —OCO—, —C(=O)—, or —CH$_2$(—CN)— provided that oxygen atoms are not directly adjacent to each other. R$^{iY2}$ represents P$^{i1}$-Sp$^{i1}$-. n$^{iY1}$ is 0 when the dashed line represents a double bond and is 1 when the dashed line represents a single bond. n$^{iY2}$ represents an integer of 0 to 5. P$^{i1}$ represents a polymerizable group. SP$^{i1}$ represents a spacer group or a single bond. When any of R$^{iY1}$, R$^{iY3}$, R$^{iY4}$, p$^{i1}$, and SP$^{i1}$ is a plurality of units, the units may be identical to or different from one another. * is a point of attachment to S$^{i3}$.

When the dashed line represents a single bond, R$^{iY1}$ is preferably a hydrogen atom or a linear or branched alkyl group having 1 to 10 carbon atoms, preferably a hydrogen atom or an alkyl group having 1 to 7 carbon atoms, or preferably a hydrogen atom or an alkyl group having 1 to 3 carbon atoms, and one or more secondary carbon atoms in any of the alkyl groups are optionally replaced with —O—, —CH=CH—, or —C≡C— provided that oxygen atoms are not directly adjacent to each other. Specifically, it is preferable that R$^{iY1}$ represent a hydrogen atom, or, from the standpoint of improving heat resistance, it is preferable that R$^{iY1}$ represent an alkyl group having 1 to 3 carbon atoms, an alkoxy group having 1 to 3 carbon atoms, —CO—CH$_3$, or —CH$_2$—O—CH$_3$. It is also preferable that R$^{iY1}$ represent P$^{i1}$-Sp$^{i1}$-, from the standpoint of improving heat resistance. It is believed that when R$^{iY1}$ represents P$^{i1}$-Sp$^{i1}$-, decomposition products resulting from thermal decomposition of the compound represented by general formula (i) are polymerized, and, accordingly, an increase in impurities is prevented, which consequently reduces adverse effects on a liquid crystal composition. P$^{i1}$ represents a polymerizable group. Preferably, P$^{i1}$ represents an acryloyl group, a methacryloyl group, or a substituent selected from substituents represented by general formulae (P-1) to (P-15), which will be described later. Preferably, SP$^{i1}$ represents a linear alkylene group having 1 to 18 carbon atoms or a single bond. More preferably, SP$^{i1}$ represents a linear alkylene group having 2 to 15 carbon atoms or a single bond. Even more preferably, SP$^{i1}$ represents a linear alkylene group having 2 to 8 carbon atoms or a single bond.

When the dashed line represents a double bond, R$^{iY1}$ represents =CH$_2$, =CHR$^{iY4}$, or =CR$^{iY4}_2$; preferably, R$^{iY1}$ represents =CH$_2$. R$^{iY4}$ is preferably a linear or branched alkyl group having 1 to 10 carbon atoms, preferably an alkyl group having 1 to 7 carbon atoms, or preferably an alkyl group having 1 to 3 carbon atoms. One or more secondary carbon atoms in any of the alkyl groups are optionally replaced with —O—, —CH=CH—, or —C≡C— provided that oxygen atoms are not directly adjacent to each other.

Preferred groups for R$^{iY3}$ are the same as preferred groups for R$^{iY1}$ associated with the case where the dashed line represents a single bond. Preferably, n$^{iY1}$ is 0.

Preferred combinations of R$^{iY1}$ and R$^{iY3}$ are as follows, for example: R$^{iY1}$ and R$^{iY3}$ are both hydrogen atoms, both alkyl groups having 1 to 3 carbon atoms, both alkoxy groups having 1 to 3 carbon atoms, or both —CH$_2$—O—CH$_3$. When one of R$^{iY1}$ and R$^{iY3}$ represents P$^{i1}$-Sp$^{i1}$- or —CO—CH$_3$, it is preferable that the other represent a hydrogen atom.

n$^{iY2}$ is preferably an integer of 0 to 3, preferably 0, 1, or 2, and more preferably 0 or 1.

R$^{iY2}$ is preferably a hydrogen atom or an alkyl, halogenated alkyl, or cyanogenated alkyl group having 1 to 10 carbon atoms, preferably an alkyl, halogenated alkyl, or cyanogenated alkyl group having 1 to 7 carbon atoms, or preferably an alkyl group having 1 to 3 carbon atoms. Furthermore, it is preferable that one or more secondary carbon atoms in any of the alkyl groups be replaced with —O—, —C(=X$^{i2}$)—, or —CH$_2$(—CN)— provided that oxygen atoms are not directly adjacent to each other. It is preferable that X$^{i2}$ be an oxygen atom, from the standpoint of improving a VHR. Furthermore, it is preferable that R$^{iY2}$ represent P$^{i1}$-Sp$^{i1}$-. It is believed that when R$^{iY2}$ represents P$^{i1}$-Sp$^{i1}$-, decomposition products resulting from thermal decomposition of the compound represented by general formula (i) are polymerized, and, accordingly, an increase in impurities is prevented, which consequently reduces adverse effects on a liquid crystal composition.

More specifically, it is preferable that general formula (Y-1) be formula (Y-1-1), (Y-1-2), (Y-1-3a), (Y-1-3b), or (Y-1-4).

[Chem. 5]

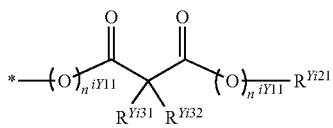

(Y-1-1)

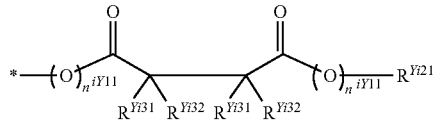

(Y-1-2)

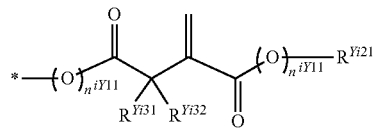

(Y-1-3a)

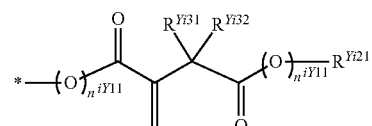

(Y-1-3b)

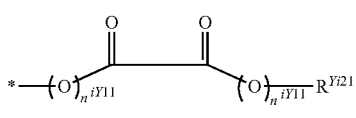

(Y-1-4)

For the formula, the following is noted. n$^{iY11}$ represents 0 or 1. R$^{iY21}$ represents an alkyl, halogenated alkyl, or cyanogenated alkyl group having 1 to 10 carbon atoms, and one or more secondary carbon atoms in the alkyl group are optionally replaced with —CH=CH—, —C≡C—, —O—, —NH—, —COO—, —OCO—, —C(=O)—, or —CH$_2$(—CN)— provided that oxygen atoms are not directly adjacent to each other. R$^{iY21}$ represents P$^{i1}$-Sp$^{i1}$-. R$^{iY31}$ and R$^{iY32}$ each independently represent a hydrogen atom or a linear or branched alkyl group having 1 to 10 carbon atoms, and one or more secondary carbon atoms in the alkyl group are optionally replaced with —O—, —CH=CH—, —C≡C—, or —CO— provided that oxygen atoms are not directly adjacent to each other. R$^{iY31}$ and R$^{iY32}$ represent P$^{i1}$-Sp$^{i1}$-.

Preferably, R$^{iY21}$ is an alkyl, halogenated alkyl, or cyanogenated alkyl group having 1 to 7 carbon atoms, or preferably, R$^{iY21}$ is an alkyl group having 1 to 3 carbon atoms. Furthermore, it is preferable that R$^{iY21}$ represent P$^{i1}$-Sp$^{i1}$-. Preferably, R$^{iY31}$ and R$^{iY32}$ are a hydrogen atom, an alkyl group having 1 to 5 carbon atoms, or an alkoxy group having 1 to 5 carbon atoms, or preferably, R$^{iY31}$ and R$^{iY32}$ represent a hydrogen atom, an alkyl group having 1 to 3 carbon atoms, an alkoxy group having 1 to 3 carbon atoms, —CO—CH$_3$, or —CH$_2$—O—CH$_3$. Furthermore, it is preferable that at least one of R$^{iY31}$ and R$^{iY32}$ represent P$^{i1}$-Sp$^{i1}$-.

A structure of formula (Y-1-1) is preferable from the standpoint of improving compatibility with a liquid crystal compound. It is preferable that formula (Y-1-1) be any of formulae (Y-1-1a) to (Y-1-1h).

[Chem. 6]

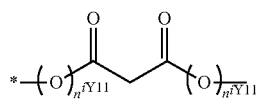

(Y-1-1a)

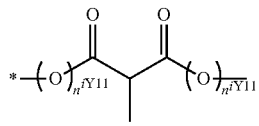

(Y-1-1b)

-continued

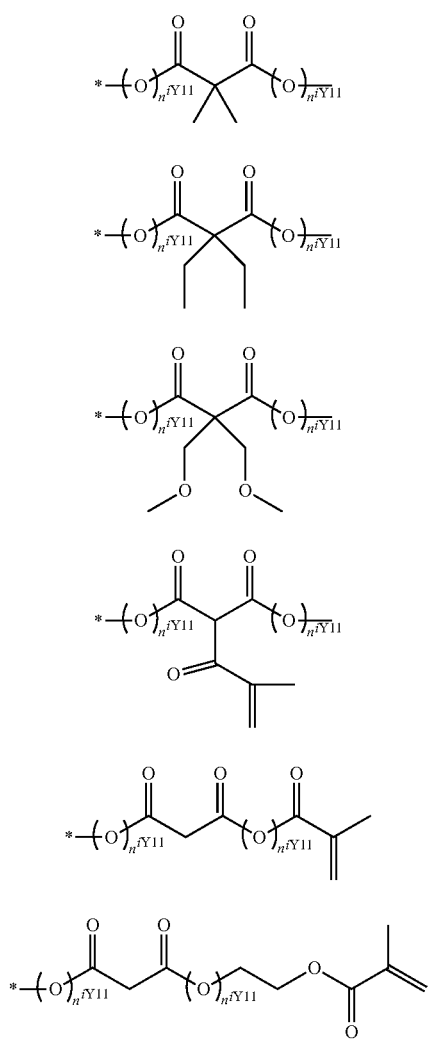

(Y-1-1c)
(Y-1-1d)
(Y-1-1e)
(Y-1-1f)
(Y-1-1g)
(Y-1-1h)

In the formulae, $n^{iY11}$ represents 0 or 1.

A structure of formula (Y-1-2) is preferable from the standpoint of improving compatibility with a liquid crystal compound and heat resistance. It is preferable that formula (Y-1-2) be any of formulae (Y-1-2a) to (Y-1-2f).

[Chem. 7]

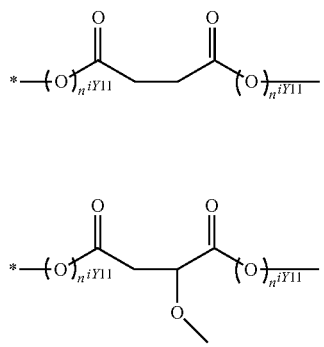

(Y-1-2a)
(Y-1-2b)

-continued

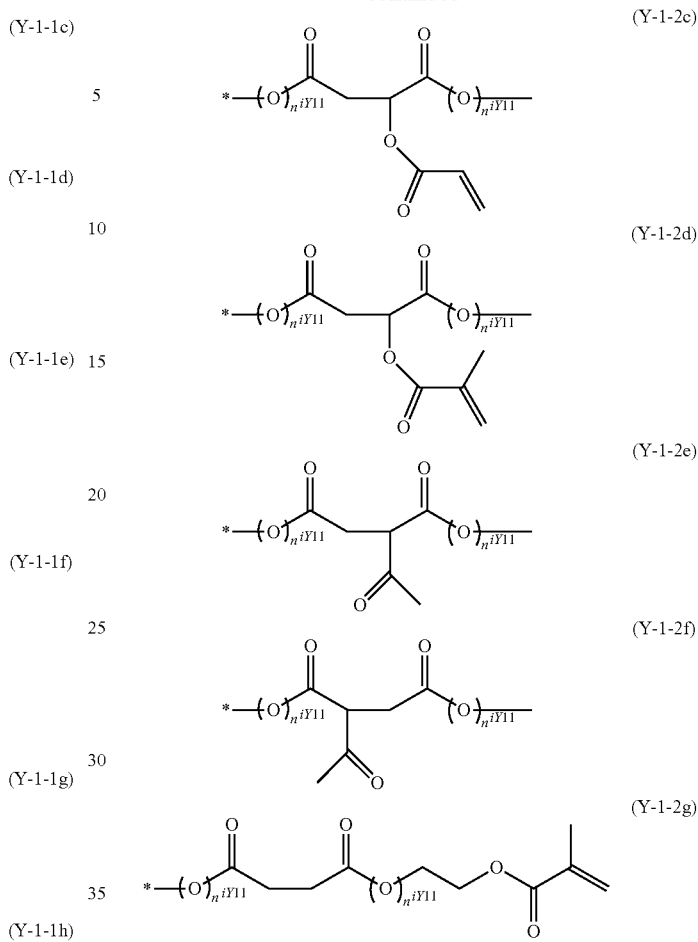

(Y-1-2c)
(Y-1-2d)
(Y-1-2e)
(Y-1-2f)
(Y-1-2g)

In the formulae, $n^{iY11}$ represents 0 or 1. A structure of formula (Y-1-3a) and a structure of formula (Y-1-3b) are preferable from the standpoint of improving heat resistance. It is preferable that formula (Y-1-3a) be formula (Y-1-3aa), and formula (Y-1-3b) be formula (Y-1-3ba).

[Chem. 8]

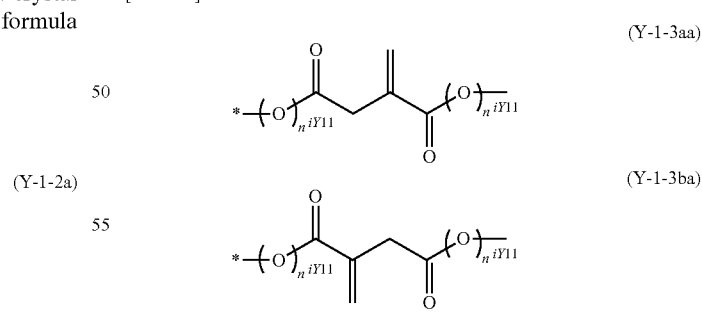

(Y-1-3aa)
(Y-1-3ba)

In the formulae, $n^{iY11}$ represents 0 or 1.

A structure of formula (Y-1-4) is preferable from the standpoint of improving the alignment characteristics and voltage holding ratio of a liquid crystal composition. It is preferable that formula (Y-1-4) be any of formulae (Y-1-4a) to (Y-1-4f). In particular, structures of (Y-1-4a) to (Y-1-4c) are preferable in terms of ensuring a good balance between compatibility with a liquid crystal compound and the alignment characteristics of a liquid crystal composition.

[Chem. 9]

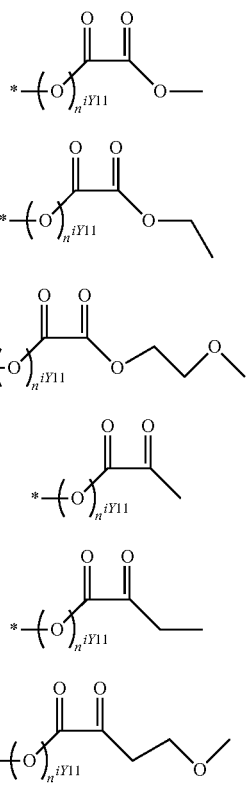

(Y-1-4a)
(Y-1-4b)
(Y-1-4c)
(Y-1-4d)
(Y-1-4e)
(Y-1-4f)

In the formulae, $n^{iY11}$ represents 0 or 1.

Furthermore, it is preferable that $Y^{i1}$ represent a group selected from general formula (Y-2).

[Chem. 10]

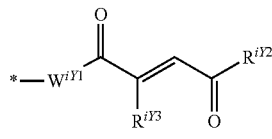

(Y-2)

In the formula, $W^{iY1}$, $R^{iY3}$, and $R^{iY2}$ have the same meaning as, respectively, $W^{iY1}$, $R^{iY3}$, and $R^{iY2}$ in general formula (Y-1).

It is preferable that general formula (Y-2) represent general formula (Y-2-1).

[Chem. 11]

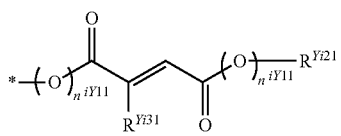

(Y-2-1)

In the formula, $n^{iY11}$, $R^{iY21}$ and $R^{i31}$ have the same meaning as, respectively, $n^{iY11}$, $R^{iY21}$, and $R^{i31}$ in general formula (Y-1-1).

Furthermore, it is preferable that $Y^{i1}$ represent a group selected from general formula (Y-3), from the standpoint of improving heat resistance.

[Chem. 12]

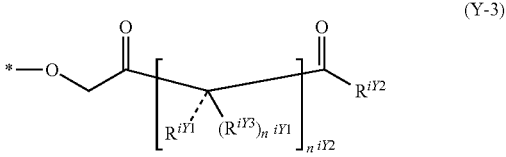

(Y-3)

In the formula, $R^{iY1}$, $R^{iY2}$, $R^{iY3}$, $n^{iY1}$, and $n^{iY1}$ have the same meaning as, respectively, $R^{iY1}$, $R^{iY2}$, $R^{iY3}$, $n^{iY1}$, and $n^{iY1}$ in general formula (Y-1).

It is preferable that general formula (Y-3) represent general formulae (Y-3-1) to (Y-3-4).

[Chem. 13]

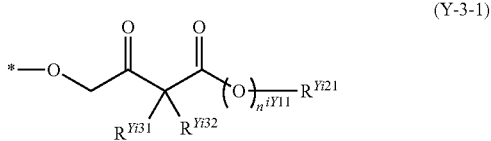

(Y-3-1)
(Y-3-2)
(Y-3-3a)
(Y-3-3b)
(Y-1-4)

In the formulae, $R^{iY21}$, $R^{iY31}$, $R^{iY32}$, and $n^{iY11}$ have the same meaning as, respectively, $R^{iY21}$, $R^{iY31}$, $R^{iY32}$, and $n^{iY11}$ in general formula (Y-1-1).

More specifically, it is preferable that general formula (Y-3-1) be general formula (Y-3-11)

[Chem. 14]

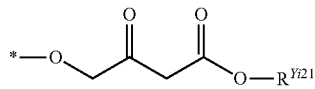

(Y-3-11)

In the formula, $R^{iY21}$ has the same meaning as $R^{iY21}$ in general formula (Y-3-1).

Furthermore, it is preferable that $Y^{i1}$ represent a group selected from general formula (Y-4), from the standpoint of improving heat resistance.

[Chem. 15]

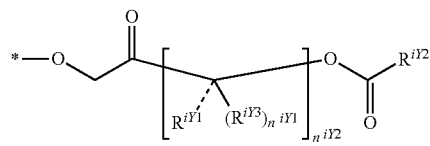

(Y-4)

In the formula, $R^{iY1}$, $R^{iY2}$, $R^{iY3}$, $n^{iY1}$, and $n^{iY1}$ have the same meaning as, respectively, $R^{iY1}$, $R^{iY2}$, $R^{iY3}$, $n^{iY1}$, and $n^{iY1}$ in general formula (Y-1).

It is preferable that general formula (Y-4) represent general formulae (Y-4-1) to (Y-4-3b).

[Chem. 16]

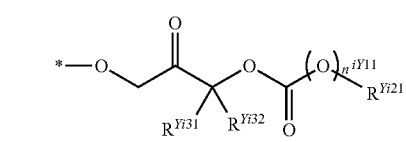

(Y-4-1)

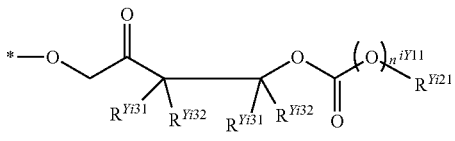

(Y-4-2)

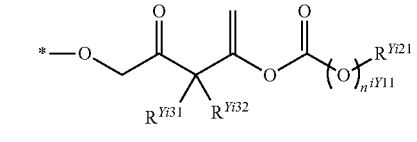

(Y-4-3a)

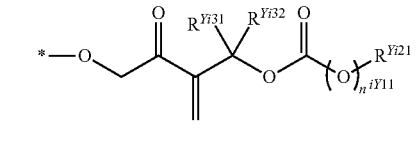

(Y-4-3b)

In the formulae, $R^{iY21}$, $R^{iY31}$, $R^{iY32}$, and $n^{iY11}$ have the same meaning as, respectively, $R^{iY21}$, $R^{iY31}$, $R^{iY32}$, and $n^{iY11}$ in general formula (Y-1-1).

More specifically, it is preferable that general formula (Y-4-1) be general formula (Y-4-11).

[Chem. 17]

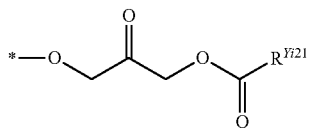

(Y-4-11)

In the formula, $R^{iY21}$ has the same meaning as $R^{iY21}$ in general formula (Y-4-1).

Preferably, $P^{i1}$ represents a substituent selected from substituents represented by formula (P-1) to general formula (P-15), shown below. A substituent of any of formulae (P-1) to (P-3), (P-14), and (P-15) is preferable in terms of ease of handling and reactivity; a substituent of formula (P-1) or (P-2) is more preferable.

[Chem. 18]

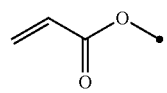

(P-1)

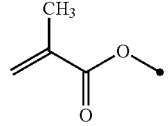

(P-2)

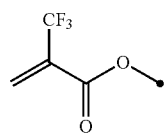

(P-3)

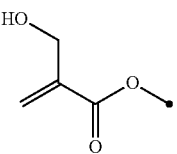

(P-4)

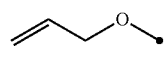

(P-5)

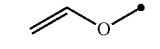

(P-6)

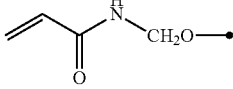

(P-7)

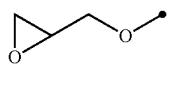

(P-8)

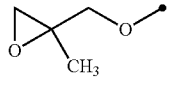

(P-9)

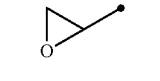

(P-10)

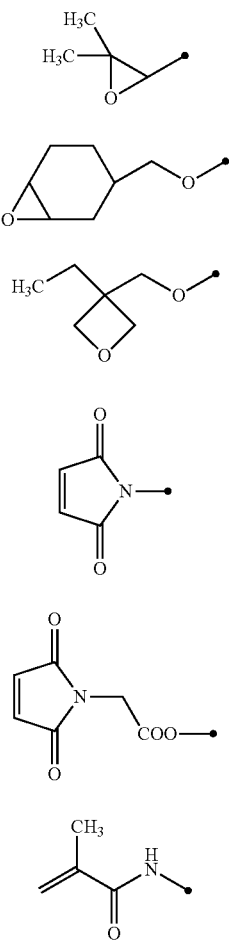

(P-11)
(P-12)
(P-13)
(P-14)
(P-15)
(P-16)

In the formulae, the black dot at the right end represents a bond.

Preferably, $SP^{i1}$ represents a linear alkylene group having 1 to 18 carbon atoms or a single bond. More preferably, $SP^{i1}$ represents a linear alkylene group having 2 to 15 carbon atoms or a single bond. Even more preferably, $SP^{i1}$ represents a linear alkylene group having 2 to 8 carbon atoms or a single bond.

It is preferable that ni1 represent 1 or 2, from the standpoint of improving the alignment characteristics of liquid crystals and solubility in a liquid crystal compound. It is preferable that $n^{i2}$ represent 0 or 1, and it is more preferable that $n^{i2}$ represent 1, from the standpoint of improving alignment characteristics. It is preferable that $n^{i3}$ represent 0 or 1.

It is preferable that general formula (K-1) represent a group selected from general formula (K-1A) or (K-1B).

[Chem. 19]

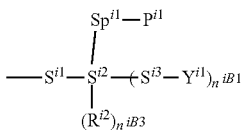

(K-1A)

(K-1B)

For the formula, the following is noted. $S^{i1}$, $S^{i2}$, $S^{i3}$, $Y^{i1}$, $P^{i1}$, and $SP^{i1}$ have the same meaning as, respectively, $S^{i1}$, $S^{i2}$, $S^{i3}$, $Y^{i1}$, $P^{i1}$, and $SP^{i1}$ in general formula (K-1). $n^{iA1}$ represents an integer of 1 to 3, $n^{iA3}$ represents an integer of 0 to 2, $n^{iB1}$ represents an integer of 1 or 2, and $n^{iB3}$ represents 0 or 1 provided that when $S^{i2}$ represents a carbon atom or a silicon atom, $n^{iA1}+n^{iA3}$ is 3, and $n^{i1}+n^{iB3}$ is 2, and when $S^{i2}$ represents a nitrogen atom, $n^{iA1}+n^{iA3}$ is 2, $n^{iB1}$ represents 1, and $n^{iB3}$ represents 0.

$K^{i1}$ in formula (i) is an important structure for achieving vertical alignment in a liquid crystal composition. Because of the configuration in which a polar group and a polymerizable group are adjacent to each other, more favorable alignment characteristics are achieved, and a good solubility in a liquid crystal composition is exhibited. Accordingly, in a case where the alignment characteristics of liquid crystals are regarded as important, general formula (K-1B) is preferable. On the other hand, in a case where solubility in a liquid crystal compound is regarded as important, general formula (K-1A) is preferable.

Preferred examples of general formulae (K-1A) and (K-1B) include formulae (K-1A-1) to (K-1A-4) and formulae (K-1B-1) to (K-1B-6), shown below. From the standpoint of solubility in a liquid crystal composition, formulae (K-1A-1) to (K-1A-3) are preferable, and from the standpoint of alignment characteristics, formulae (K-1B-2) to (K-1B-4) are preferable; formulae (K-1A-1), (K-1B-2), and (K-1B-4) are particularly preferable.

[Chem. 20]

(K-1A-1)

(K-1A-2)

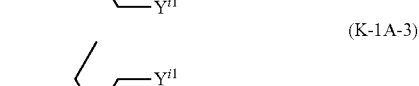

(K-1A-3)

(K-1A-4)

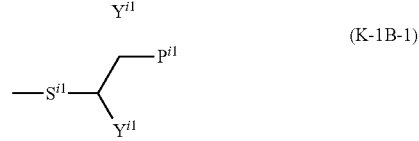

(K-1B-1)

(K-1B-2)
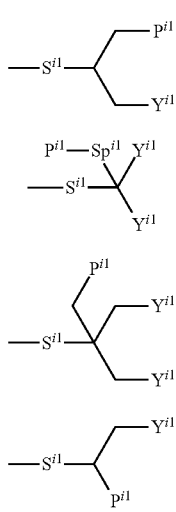
(K-1B-3)
(K-1B-4)
(K-1B-5)
(K-1B-6)
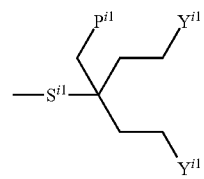
In the formulae, $S^{i1}$, $Y^{i1}$, and $P^{i1}$ have the same meaning as, respectively, $S^{i1}$, $Y^{i1}$, and $P^{i1}$ in general formula (K-1).
Furthermore, it is preferable that general formula (K-1) represent a group selected from general formulae (K-1-1), (K-1-2), (K-1-3a), (K-1-3b), (K-1-4a), (K-1-4b), (K-1-Y2), (K-1-Y3), and (K-1-Y4).
[Chem. 21]
(K-1-1)
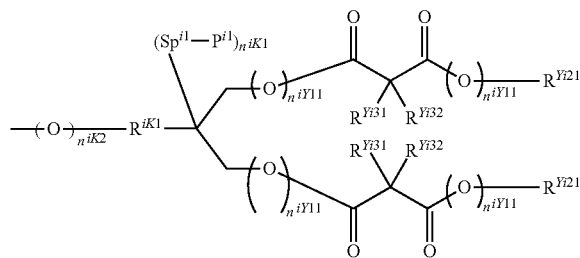
(K-1-2)
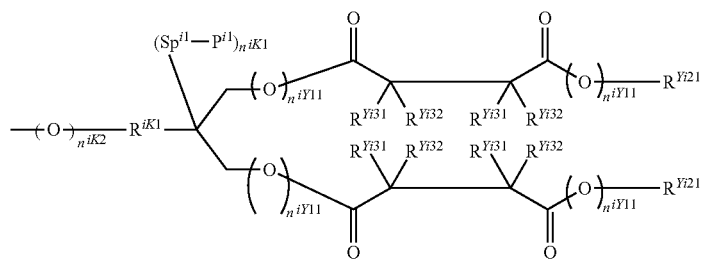
(K-1-3a)
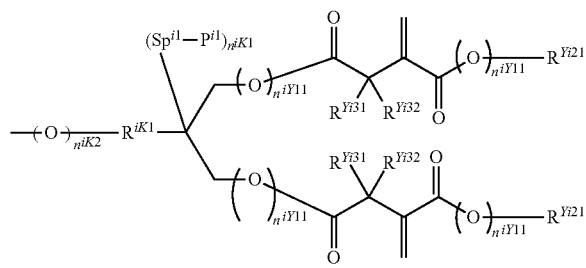
(K-1-3b)
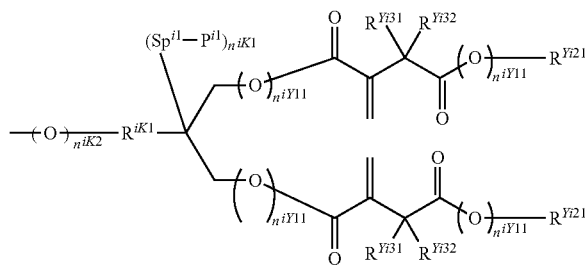

[Chem. 22]

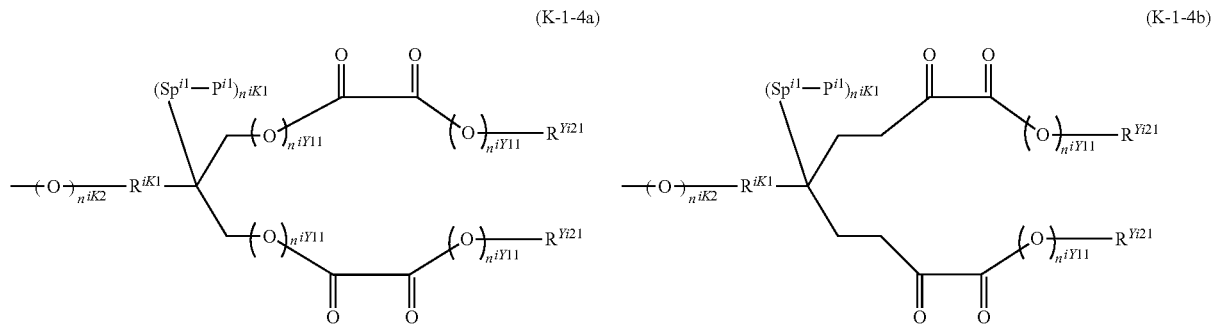

(K-1-4a) (K-1-4b)

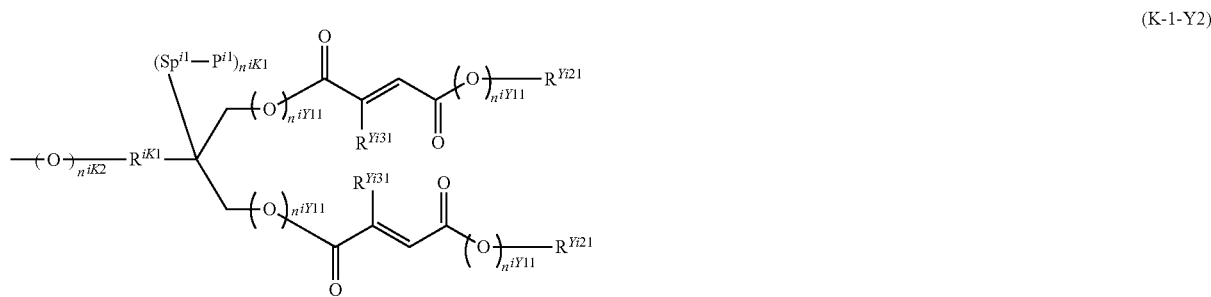

(K-1-Y2)

[Chem. 23]

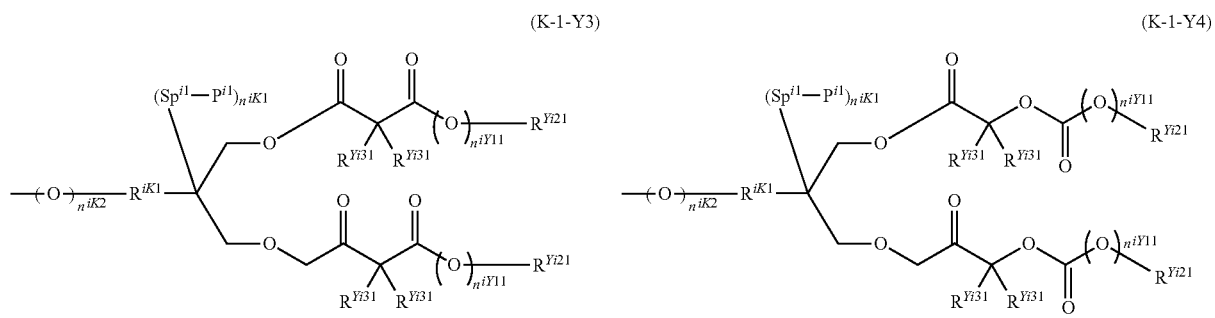

(K-1-Y3) (K-1-Y4)

For the formula, the following is noted. $n^{iY11}$, $R^{iY21}$, $R^{iY31}$, and $R^{iY32}$ have the same meaning as, respectively, $n^{iY11}$, $R^{iY21}$, $R^{iY31}$, and $R^{iY32}$ in general formulae (Y-1-1) to (Y-4). $SP^{i1}$ and $P^{i1}$ have the same meaning as, respectively, $SP^{i1}$ and $P^{i1}$ in general formula (i). $R^{iK1}$ represents an alkylene group having 1 to 6 carbon atoms or a single bond, and —$CH_2$— in the alkylene group is optionally replaced with —CH=CH—, —C≡C—, or —O— provided that oxygen atoms are not directly adjacent to each other. $n^{iK1}$ and $n^{iK2}$ each independently represent 0 or 1.

Preferably, $R^{iK1}$ is a linear alkylene group having 1 to 6 carbon atoms, or preferably, $R^{iK1}$ is a linear alkylene group having 1 to 3 carbon atoms. Note that preferred groups for $R^{iY21}$, $R^{iY31}$, $R^{iY32}$, $SP^{i1}$, and $P^{i1}$ are similar to those for $R^{iY21}$, $R^{iY31}$, $R^{iY32}$, $SP^{i1}$, and $P^{i1}$ in general formulae (Y-1-1) to (Y-1-4) and (Y-2) to (Y-4) and general formula (i).

Furthermore, it is preferable that $K^{i1}$ represent general formulae (K-2) to (K-5).

[Chem. 24]

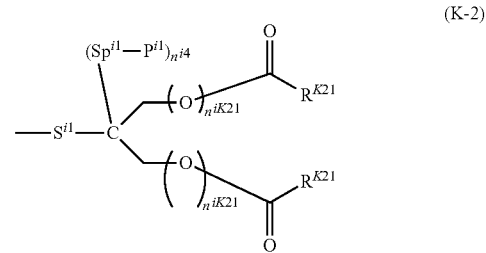

(K-2)

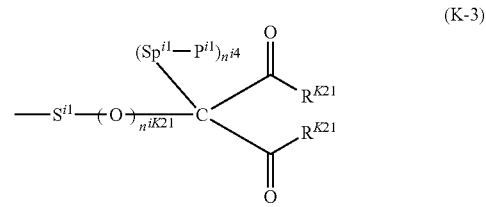

(K-3)

(K-4)

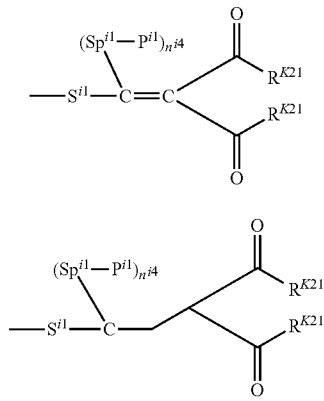

(K-5)

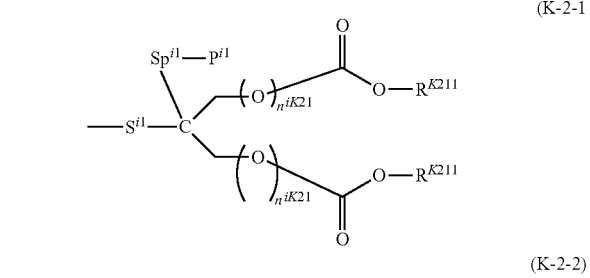

For the formula, the following is noted. $S^{i1}$, $p^{i1}$, and $SP^{i1}$ have the same meaning as, respectively, $S^{i1}$, $p^{i1}$, and $SP^{i1}$ in general formula (K-1). $R^{K21}$ represents a linear or branched alkyl, halogenated alkyl, or cyanogenated alkyl group having 1 to 10 carbon atoms, and at least one secondary carbon atom in the alkyl group is optionally replaced with —CH=CH—, —C≡C—, —O—, or —NH— provided that oxygen atoms are not directly adjacent to each other. $n^{i4}$ and $n^{iK21}$ each independently represent 0 or 1.

Preferably, $R^{K21}$ represents a linear or branched alkyl, halogenated alkyl, or cyanogenated alkyl group having 1 to 5 carbon atoms. More preferably, $R^{K21}$ represents a linear alkyl or cyanogenated alkyl group having 1 to 3 carbon atoms. Furthermore, it is preferable that at least one secondary carbon atom in any of the alkyl groups be replaced with —O— provided that oxygen atoms are not directly adjacent to each other. Specifically, it is preferable that $R^{K21}$ be an alkyl group having 1 to 3 carbon atoms, an alkoxy group having 1 to 3 carbon atoms, or a cyanogenated alkyl group having 1 to 3 carbon atoms.

It is preferable that general formula (K-2) represent general formulae (K-2-1) to (K-2-3), shown below.

[Chem. 25]

(K-2-1)

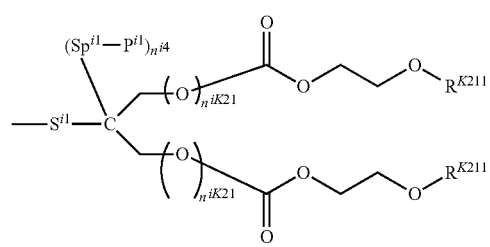

(K-2-2)

(K-2-3)

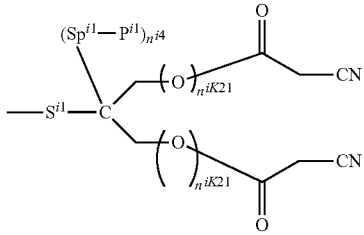

In the formulae, $S^{i1}$, $p^{i1}$, $SP^{i1}$, $n^{i4}$, and $n^{iK21}$ have the same meaning as, respectively, $S^{i1}$, $p^{i1}$, $SP^{i1}$, $n^{i4}$, and $n^{iK21}$ in general formula (K-2), and $R^{K211}$ represents a linear or branched alkyl, halogenated alkyl, or cyanogenated alkyl group having 1 to 3 carbon atoms.

It is preferable that general formula (K-3) represent general formulae (K-3-1) and (K-3-2), shown below.

[Chem. 26]

(K-3-1)

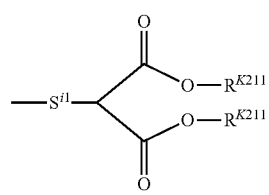

(K-3-2)

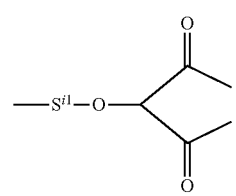

In the formulae, $S^{i1}$ has the same meaning as $S^{i1}$ in general formula (K-3), and $R^{K211}$ represents a linear or branched alkyl, halogenated alkyl, or cyanogenated alkyl group having 1 to 3 carbon atoms.

It is preferable that general formula (K-4) represent general formula (K-4-1), shown below.

[Chem. 27]

(K-4-1)

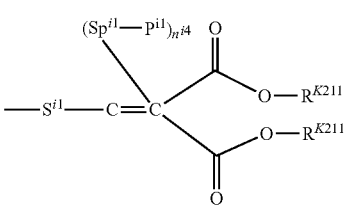

In the formula, $S^{i1}$, $p^{i1}$, $SP^{i1}$, and $n^{i4}$ have the same meaning as, respectively, $S^{i1}$, $p^{i1}$, $SP^{i1}$, and $n^{iK21}$ in general formula (K-4), and $R^{K211}$ represents a linear or branched alkyl, halogenated alkyl, or cyanogenated alkyl group having 1 to 3 carbon atoms.

It is preferable that general formula (K-5) represent general formula (K-5-1), shown below.

[Chem. 28]

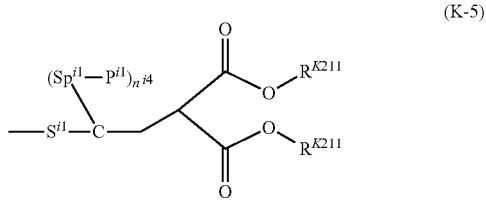

(K-5)

In the formula, $S^{i1}$, $p^{i1}$, $SP^{i1}$, and $n^{i4}$ have the same meaning as, respectively, $S^{i1}$, $p^{i1}$, $SP^{i1}$, and $n^{iK21}$ in general formula (K-4), and $R^{K211}$ represents a linear or branched alkyl, halogenated alkyl, or cyanogenated alkyl group having 1 to 3 carbon atoms.

Note that preferred groups for $S^{i1}$, $p^{i1}$, and $SP^{i1}$ are similar to those for $S^{i1}$, $p^{i1}$, and $SP^{i1}$ in general formula (K-1).

For formula (i), the following is noted. Preferably, $Z^{i1}$ and $Z^{i2}$ represent a single bond, —CH=CH—, —C≡C—, —COO—, —OCO—, —OCOO—, —OOCO—, —CH=CHCOO—, —OCOCH=CH—, —CH=C(CH₃) COO—, —OCOC(CH₃)=CH—, —CH₂—CH(CH₃) COO—, —OCOCH(CH₃)—CH₂—, —OCH₂CH₂O—, a linear or branched alkylene group having 1 to 40 carbon atoms, or a group that is similar to the foregoing alkylene group except that one —CH₂— group or two or more non-adjacent —CH₂— groups are replaced with —O—. More preferably, $Z^{i1}$ and $Z^{i2}$ represent a single bond, —COO—, —OCO—, —CH=CHCOO—, —OCOCH=CH—, —CH=C(CH₃)COO—, —OCOC (CH₃)=CH—, —CH₂—CH(CH₃)COO—, —OCOCH (CH₃)—CH₂—, —OCH₂CH₂O—, a linear or branched alkylene group having 1 to 10 carbon atoms, or a group that is similar to the foregoing alkylene group except that one —CH₂— group or two or more non-adjacent —CH₂— groups are replaced with —O—. More preferably, $Z^{i1}$ and $Z^{i2}$ represent a single bond, a linear alkylene group having 2 to 15 carbon atoms, or a group that is similar to the foregoing alkylene group except that one —CH₂— group or two or more non-adjacent —CH₂— groups are replaced with —O—. Even more preferably, $Z^{i1}$ and $Z^{i2}$ represent a single bond, —COO—, —OCO—, —OCOO—, —OOCO—, —OCH₂CH₂O—, an alkylene group having 2 carbon atoms (an ethylene group (—CH₂CH₂—)), an ethylene group in which one —CH₂— group is replaced with —O— (—CH₂O— or —OCH₂—), or a group corresponding to an ethylene group in which one —CH₂— group is replaced with —COO— or —OCO—(—CH=CHCOO— or —OCOCH=CH—).

Preferably, $R^{i1}$ represents a linear or branched alkyl or halogenated alkyl group having 1 to 20 carbon atoms, and preferably, one or more secondary carbon atoms in the alkyl group are replaced with —O— provided that oxygen atoms are not directly adjacent to each other. More preferably, $R^{i1}$ represents a linear or branched alkyl group having 3 to 18 carbon atoms, and one or more secondary carbon atoms in the alkyl group are optionally replaced with —O— provided that oxygen atoms are not directly adjacent to each other. From the standpoint of improving the alignment characteristics of a liquid crystal compound, it is preferable that the number of carbon atoms of $R^{i1}$ be greater than or equal to 3; the number of carbon atoms is preferably greater than or equal to 4 or preferably greater than or equal to 5.

Preferably, $A^{i1}$ is a divalent 6-membered aromatic group, a divalent 6-membered heteroaromatic group, a divalent 6-membered cycloaliphatic group, a divalent 6-membered heterocycloaliphatic group, a divalent 5-membered aromatic group, a divalent 5-membered heteroaromatic group, a divalent 5-membered cycloaliphatic group, or a divalent 5-membered heterocycloaliphatic group. Specifically, it is preferable that $A^{i1}$ represent a ring system selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, a cyclopentane-1,3-diyl group, an indan-2,5-diyl group, a 1,2,3,4-tetrahydronaphthalene-2,6-diyl group, and a 1,3-dioxane-2,5-diyl group. Preferably, the ring system is unsubstituted or substituted with $L^{i1}$. Preferably, $L^{i1}$ represents an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, or a nitro group. Preferably, $A^{i1}$ represents a divalent 6-membered aromatic group or a divalent 6-membered cycloaliphatic group. Preferably, $A^{i1}$ is a divalent unsubstituted 6-membered aromatic group, a divalent unsubstituted 6-membered cycloaliphatic group, or a group that is similar to any of the foregoing groups except that one or more hydrogen atoms in the ring system are replaced with an alkyl group having 1 to 6 carbon atoms, an alkoxy group having 1 to 6 carbon atoms, or a halogen atom. Preferably, $A^{i1}$ is a divalent unsubstituted 6-membered aromatic group, a group that is similar to the foregoing group except that one or more hydrogen atoms in the ring system are replaced with a fluorine atom, or a divalent unsubstituted 6-membered cycloaliphatic group. More preferably, $A^{i1}$ is a 1,4-phenylene group, 2,6-naphthalene group, or 1,4-cyclohexyl group in which one or more hydrogen atoms on the substituent are optionally replaced with a halogen atom, an alkyl group, or an alkoxy group.

Preferably, $A^{i2}$ and $A^{i3}$ are each independently a divalent 6-membered aromatic group, a divalent 6-membered heteroaromatic group, a divalent 6-membered cycloaliphatic group, a divalent 6-membered heterocycloaliphatic group, a divalent 5-membered aromatic group, a divalent 5-membered heteroaromatic group, a divalent 5-membered cycloaliphatic group, or a divalent 5-membered heterocycloaliphatic group. Specifically, it is preferable that $A^{i2}$ and $A^{i3}$ each independently represent a ring system selected from a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, a cyclopentane-1,3-diyl group, an indan-2,5-diyl group, a 1,2,3,4-tetrahydronaphthalene-2,6-diyl group, and a 1,3-dioxane-2,5-diyl group. Preferably, the ring system is unsubstituted or substituted with $L^{i1}$, $P^{i1}$-$Sp^{i1}$-, or $K^{i1}$. Furthermore, it is also preferable that $A^{i3}$ represent a ring system selected from a 1,3-phenylene group, a 1,3-cyclohexylene group, and a naphthalene 2,5-diyl group.

Preferred groups for $L^{i1}$ are similar to those for $L^{i1}$ in $A^{i1}$. Preferably, $A^{i2}$ and $A^{i3}$ represent a divalent 6-membered aromatic group or a divalent 6-membered cycloaliphatic group. Preferably, $A^{i2}$ and $A^{i3}$ are a divalent unsubstituted 6-membered aromatic group, a divalent unsubstituted 6-membered cycloaliphatic group, or a group that is similar to any of the foregoing groups except that one or more hydrogen atoms in the ring system are replaced with an alkyl group having 1 to 6 carbon atoms, an alkoxy group having 1 to 6 carbon atoms, a halogen atom, or P-Sp-. Preferably, $A^{i2}$ and $A^{i3}$ are a divalent unsubstituted 6-membered aromatic group, a group that is similar to the foregoing group except that one or more hydrogen atoms in the ring system are replaced with a fluorine atom, or a divalent unsubstituted 6-membered cycloaliphatic group. More preferably, $A^{i2}$ and $A^{i3}$ are a 1,4-phenylene group, 2,6-naphthalene group, or 1,4-cyclohexyl group in which one or more hydrogen atoms on the substituent are optionally replaced with a halogen atom, an alkyl group, an alkoxy group or P-Sp-. Furthermore, it is also preferable that $A^{i3}$ be substituted with $K^{i1}$.

In general formula (i), at least one $P^{i1}$-$Sp^{i1}$- group is included as a substituent in $A^{i2}$ or $A^{i3}$ or as a substituent in $K^{i1}$. From the standpoint of further improving reliability, it is preferable that the number of polymerizable groups in general formula (i) be greater than or equal to 2; preferably, the number is greater than or equal to 3. In a case where reliability is regarded as important, by introducing a polymerizable group into the $A^{i2}$ or $A^{i3}$ moiety, multifunctionality can be easily achieved, and, accordingly, a strong polymer can be constructed. It is preferable that, in $A^{i2}$ or $A^{i3}$, the position where $P^{i1}$-$Sp^{i1}$- is substituted be in a vicinity of $K^{i1}$, and it is more preferable that $A^{i3}$ be substituted with $P^{i1}$-$Sp^{i1}$-.

Preferably, $m^{i1}$ represents an integer of 0 to 3. More preferably, $m^{i1}$ represents an integer of 0 or 1.

It is preferable that compounds represented by general formula (i) be compounds represented by general formula (i-1), shown below.

[Chem. 29]

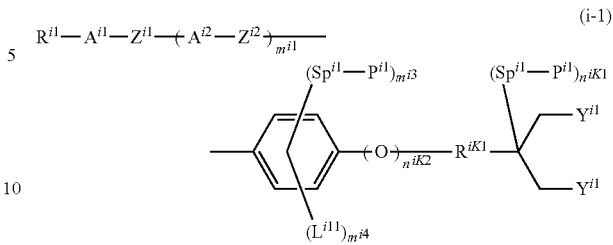

(i-1)

For the formula, the following is noted. $R^{i1}$, $A^{i1}$, $A^{i2}$, $Z^{i1}$, $Z^{i2}$, $m^{i1}$, $p^{i1}$, and $SP^{i1}$ have the same meaning as, respectively, $R^{i1}$, $A^{i1}$, $A^{i2}$, $Z^{i1}$, $Z^{i2}$, $m^{i1}$, $p^{i1}$, and $SP^{i1}$ in general formula (i). $L^{i1}$ represents an alkyl group having 1 to 3 carbon atoms. $Y^{i1}$ independently has the same meaning as $Y^{i1}$ in general formula (K-1). $R^{iK1}$, $n^{iK1}$, and $n^{iK2}$ have the same meaning as, respectively, $R^{iK1}$, $n^{iK1}$, and $n^{iK2}$ in general formula (K-1-1). $m^{i3}$ represents an integer of 0 to 3, and $m^{i4}$ represents an integer of 0 to 3 provided that $m^{i3}+m^{i4}$ is 0 to 4.

It is preferable that compounds represented by general formula (i-1) be compounds of general formulae (i-1-1), (i-1-2), (i-1-3a), (i-1-3b), (i-1-4), (i-1-Y2), (i-1-Y3), and (i-1-Y4), shown below.

[Chem. 30]

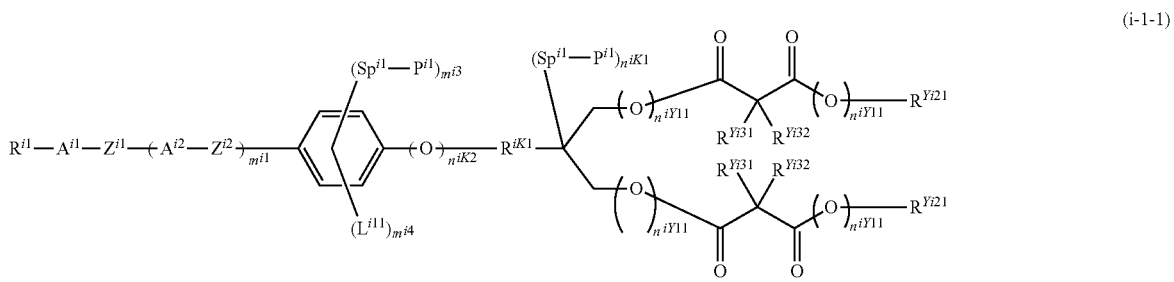

(i-1-1)

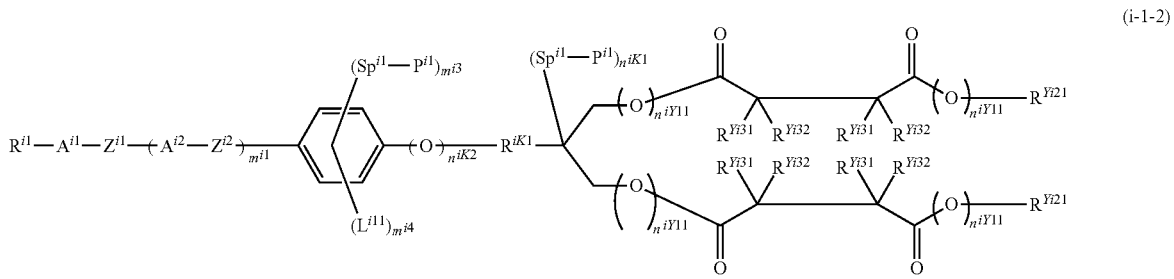

(i-1-2)

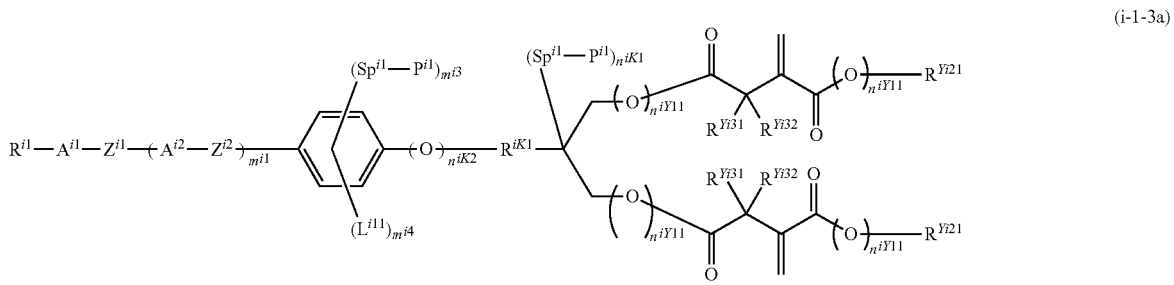

(i-1-3a)

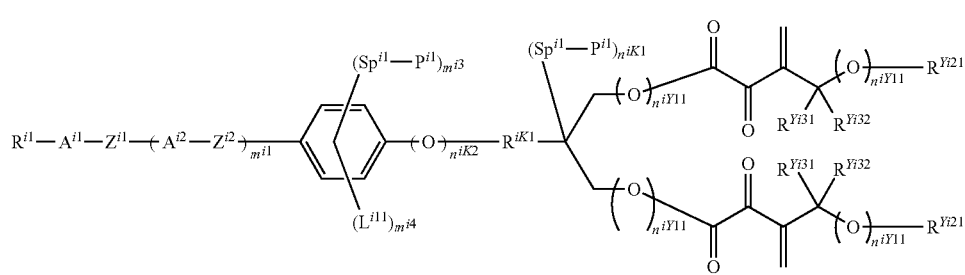
(i-1-3b)
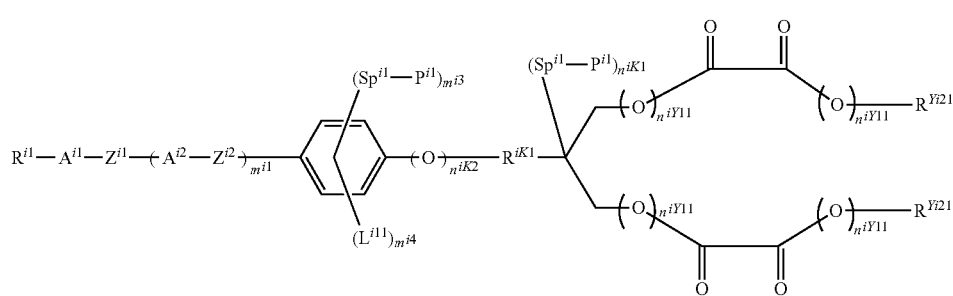
(i-1-4)
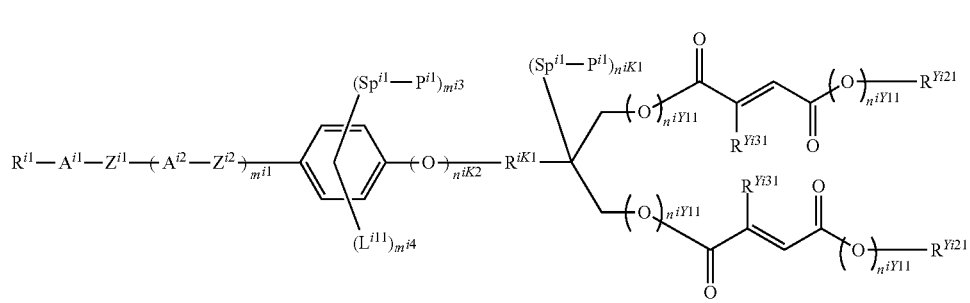
(i-1-Y2)
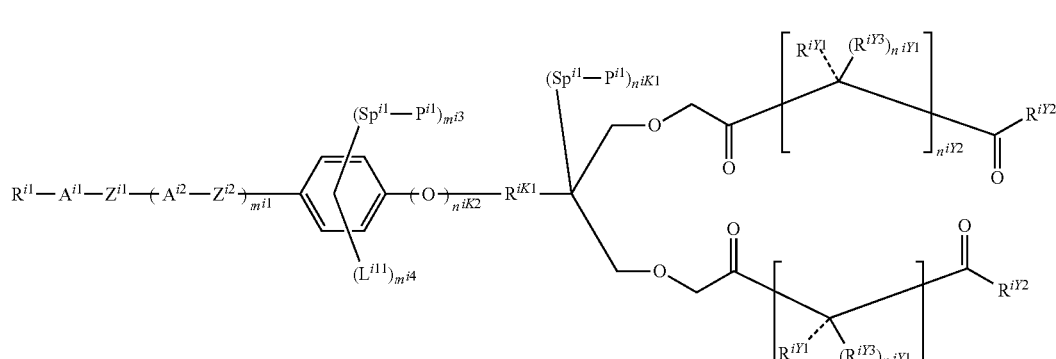
(i-1-Y3)
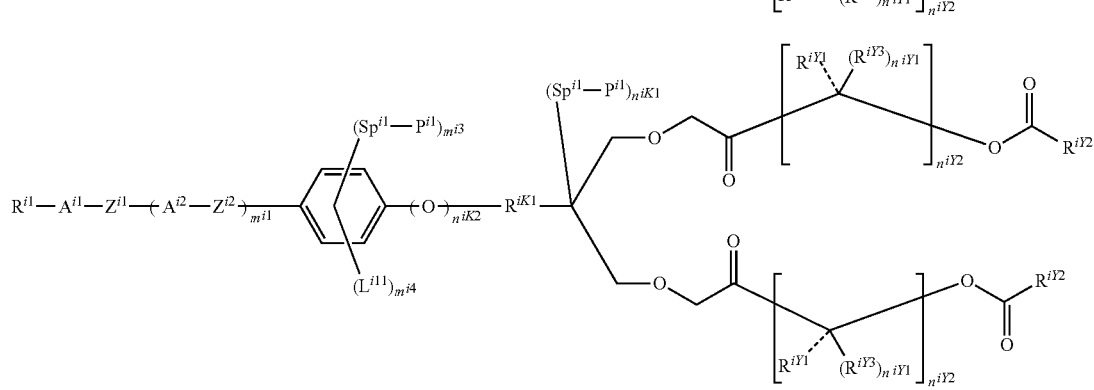
(i-1-Y4)

For the formula, the following is noted. $R^{i1}$, $A^{i1}$, $A^{i2}$, $Z^{i1}$, $Z^{i2}$, $m^{i1}$, $p^{i1}$, and $SP^{i1}$ have the same meaning as, respectively, $R^{i1}$, $A^{i1}$, $A^{i2}$, $Z^{i1}$, $Z^{i2}$, $m^{i1}$, $p^{i1}$, and $SP^{i1}$ in general formula (i). $R^{iK1}$, $R^{iY21}$, $R^{i3Y1}$, $R^{i3Y2}$, $n^{iK1}$, $n^{iK2}$, and $n^{iY11}$ have the same meaning as, respectively, $R^{iK1}$, $R^{iY21}$, $R^{i31}$, $R^{i32}$, $n^{iK1}$, $n^{iK2}$, and $n^{iY11}$ in general formulae (K-1-1) to (K-1-3). $L^{i\prime\prime\prime}$ represents an alkyl group having 1 to 3 carbon atoms. $m^{i3}$ represents an integer of 0 to 3, and $m^{i4}$ represents an integer of 0 to 3 provided that $m^{i3}+m^{i4}$ is 0 to 4.

Note that preferred groups for each of the symbols in general formula (i-1) and general formulae (i-1-1), (i-1-2), and (i-1-3) are similar to preferred groups for general formula (i), which is shown above, general formula (K-1), and general formulae (K-1-1) to (K-1-3).

Furthermore, it is preferable that compounds represented by general formula (i) be compounds represented by general formulae (i-2) to (i-5), shown below.

—O— provided that oxygen atoms are not directly adjacent to each other. $L^{i11}$ represents an alkyl group having 1 to 3 carbon atoms. $n^{i22}$ represents 0 or 1. $m^{i23}$ represents an integer of 0 to 3, and $m^{i24}$ represents an integer of 0 to 3 provided that $m^{i23}+m^{i24}$ is 0 to 4.

Preferably, $R^{i22}$ is a linear alkylene group having 1 to 6 carbon atoms, or preferably, $R^{i22}$ is a linear alkylene group having 1 to 3 carbon atoms. Note that preferred groups for $R^{iY21}$, $R^{iY31}$, $R^{iY32}$, $SP^{i1}$, and $P^{i1}$ are similar to those for $R^{iY21}$, $R^{iY31}$, $R^{iY32}$, $SP^{i1}$, and $P^{i1}$ in general formulae (Y-1-1) to (Y-1-3) and general formula (i). Note that preferred groups for each of the symbols in general formula (i-2) are similar to preferred groups for general formula (i), which is shown above, and general formulae (K-2).

It is preferable that general formula (i) represent general formulae (R-1) to (R-6), shown below.

[Chem. 33]

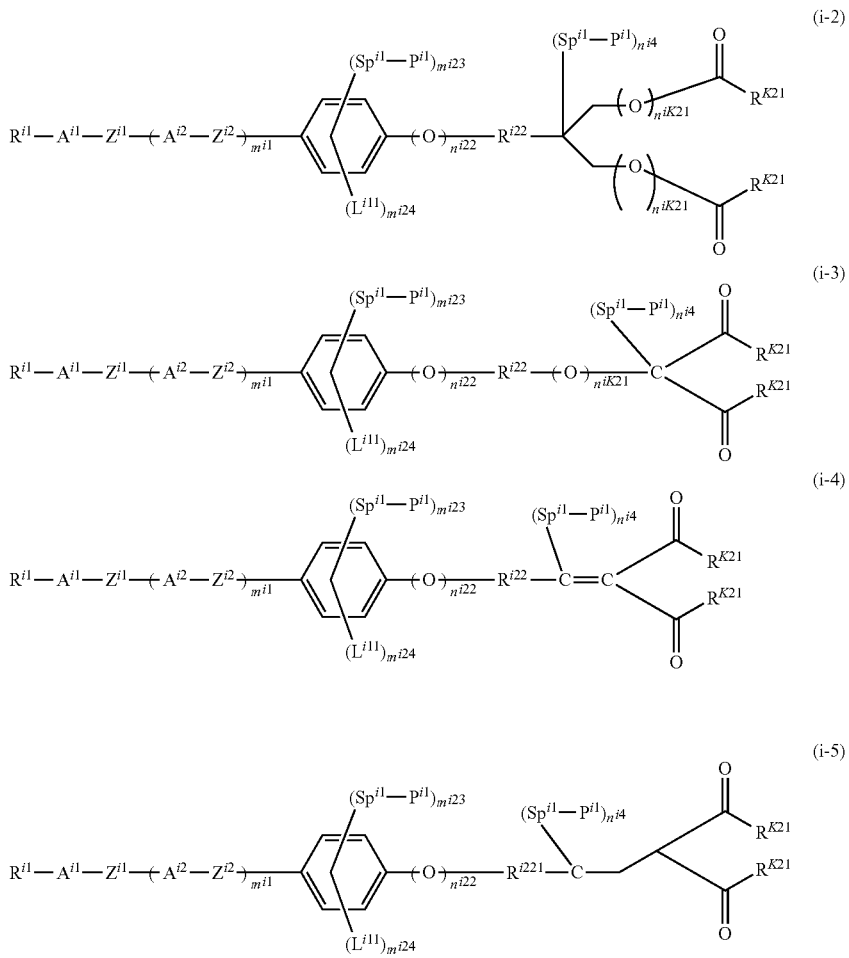

For the formula, the following is noted. $R^{i1}$, $A^{i1}$, $A^{i2}$, $Z^{i1}$, $Z^{i2}$, $m^{i1}$, $P^{i1}$, and $SP^{i1}$ have the same meaning as, respectively, $R^{i1}$, $A^{i1}$, $A^{i2}$, $Z^{i1}$, $Z^{i2}$, $m^{i1}$, $p^{i1}$, and $SP^{i1}$ in general formula (i). $n^{i4}$, $n^{iK21}$, and $R^{K21}$ have the same meaning as, respectively, $n^{i4}$, $n^{iK21}$, and $R^{K21}$ in general formula (K-2). $R^{i22}$ represents an alkylene group having 1 to 6 carbon atoms or a single bond, and —$CH_2$— in the alkylene group is optionally replaced with —CH=CH—, —C≡C—, or

[Chem. 34]

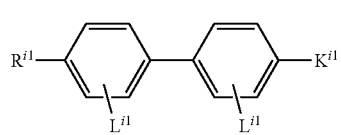

(R-1)

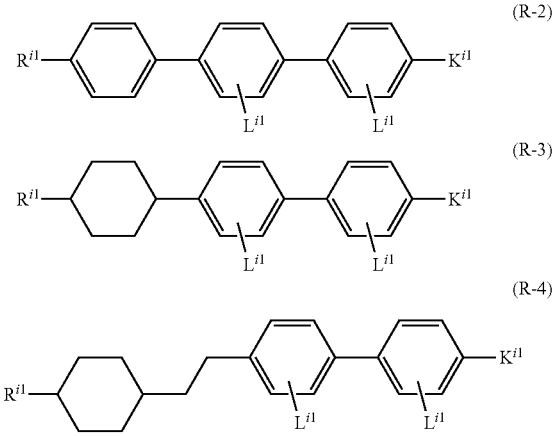
(R-2)
(R-3)
(R-4)
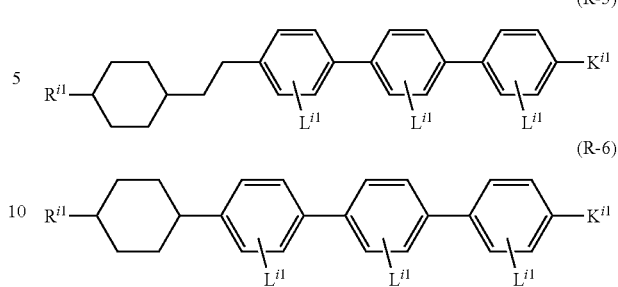
(R-5)
(R-6)
In the formulae, $R^{i1}$, $K^{i1}$, and $L^{i1}$ have the same meaning as, respectively, $R^{i1}$, $K^{i1}$, and $L^{i1}$ in general formula (i). More specific examples of general formula (i) include formulae (R-1-1) to (R-1-370), show below; however, these examples should not be construed as limiting.
[Chem. 35]
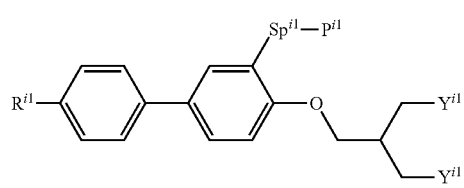
(R-1-1)
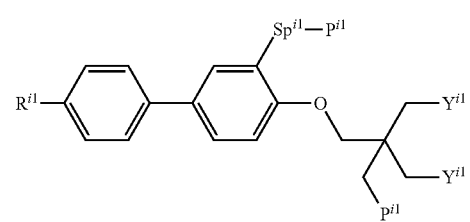
(R-1-2)
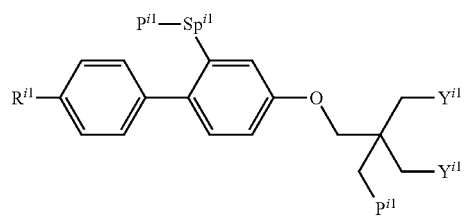
(R-1-3)
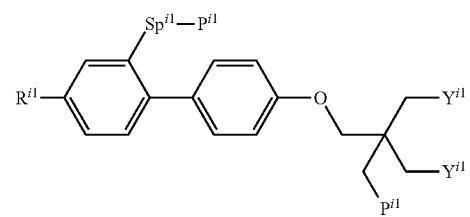
(R-1-4)
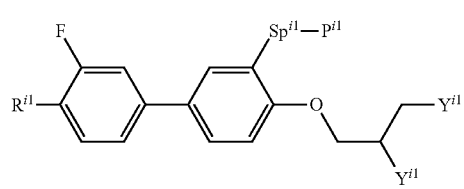
(R-1-5)
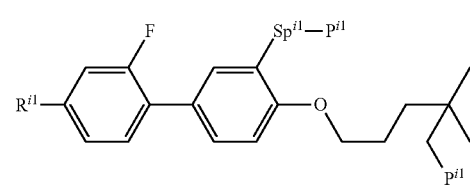
(R-1-6)
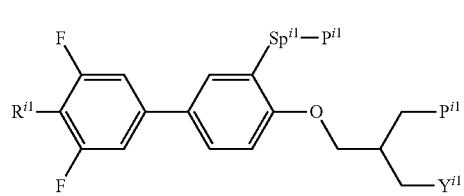
(R-1-7)
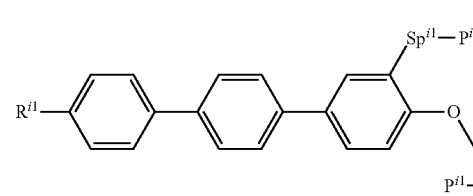
(R-1-8)
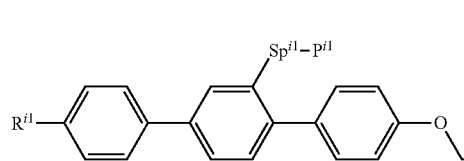
(R-1-9)
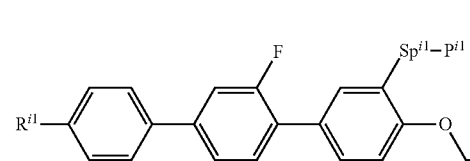
(R-1-10)

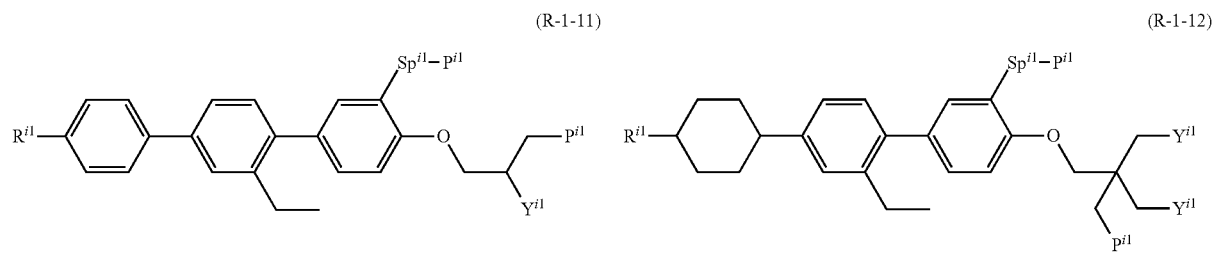
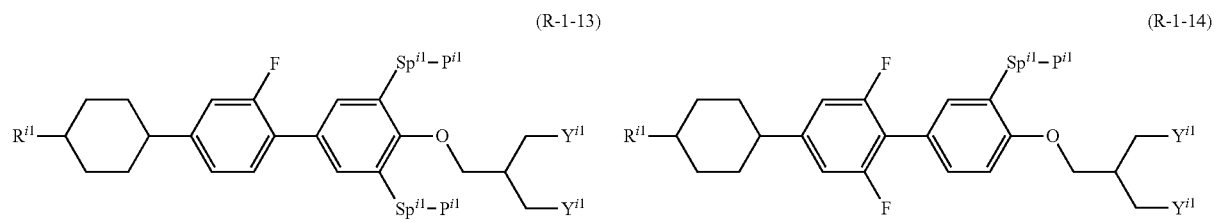
[Chem. 36]
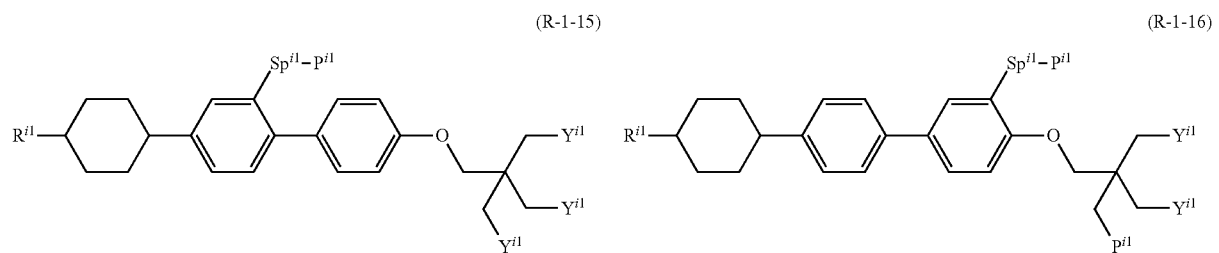
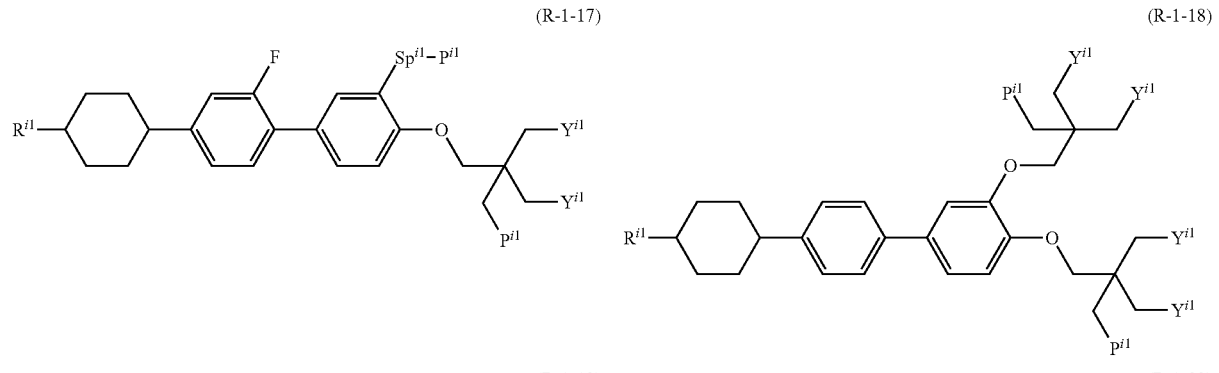
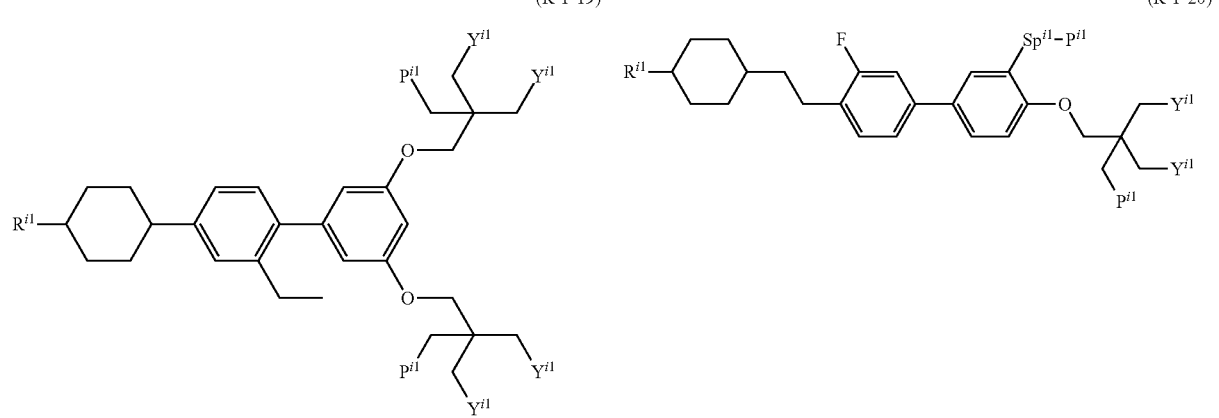

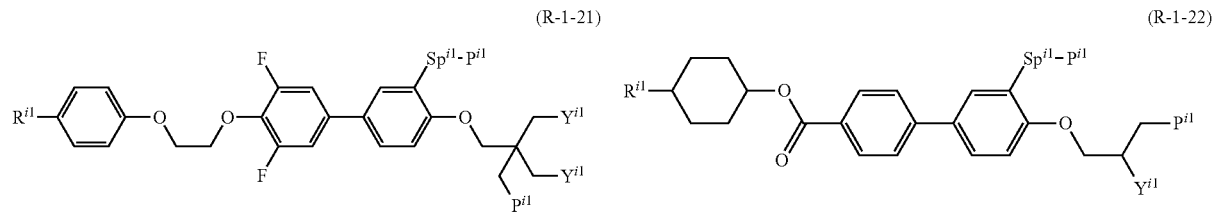
(R-1-21) (R-1-22)
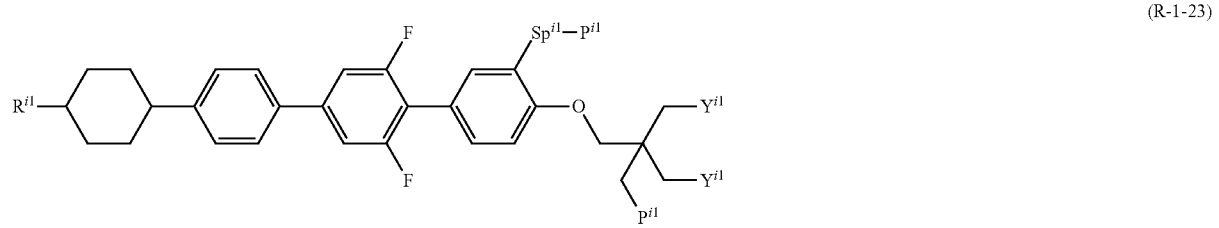
(R-1-23)
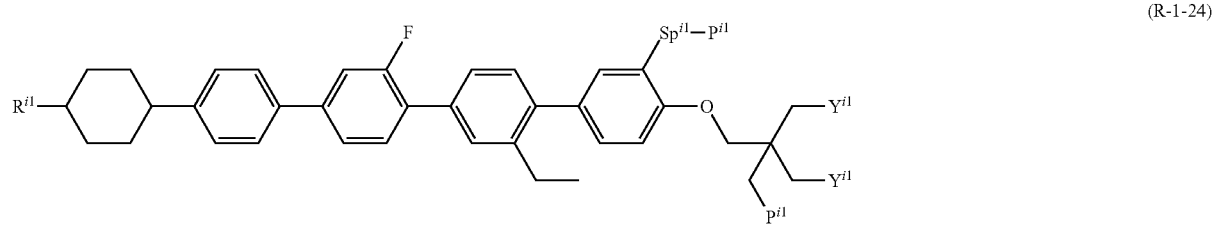
(R-1-24)
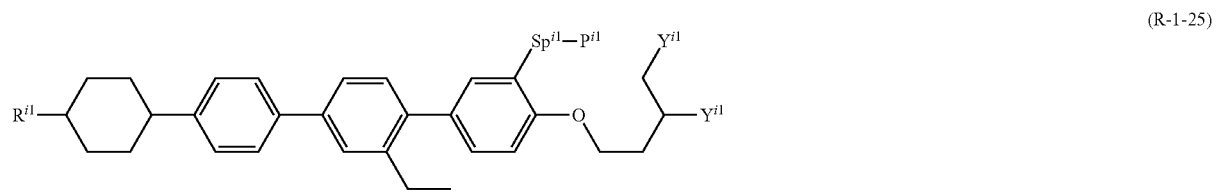
(R-1-25)
[Chem. 37]
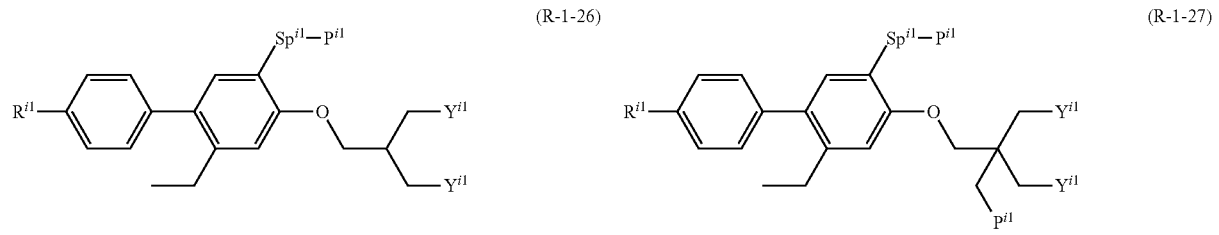
(R-1-26) (R-1-27)
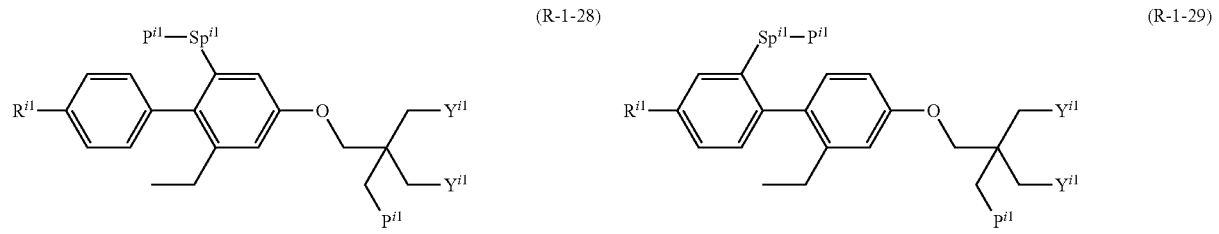
(R-1-28) (R-1-29)
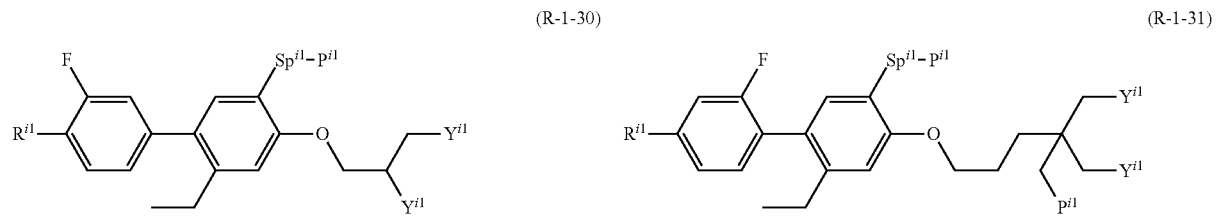
(R-1-30) (R-1-31)

(R-1-32) 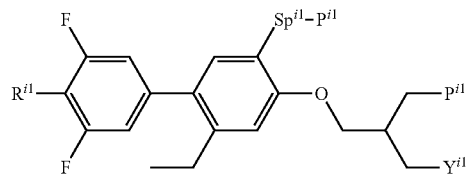
(R-1-33) 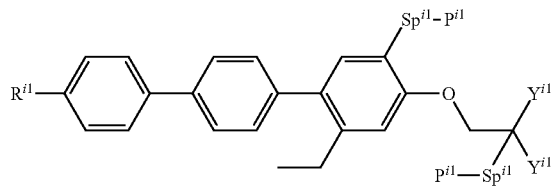
(R-1-34) 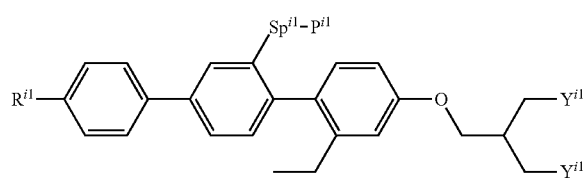
(R-1-35) 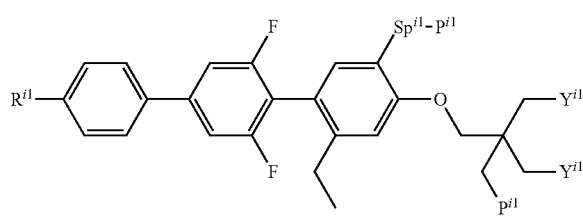
(R-1-36) 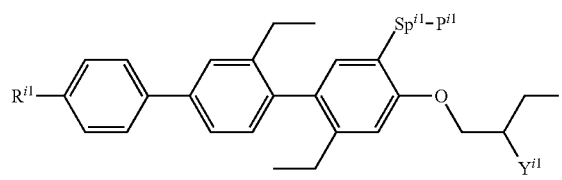
(R-1-37) 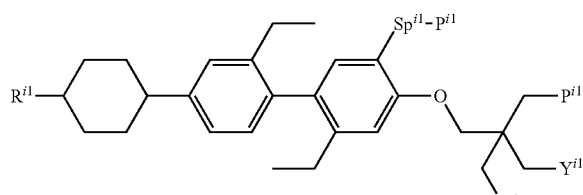
(R-1-38) 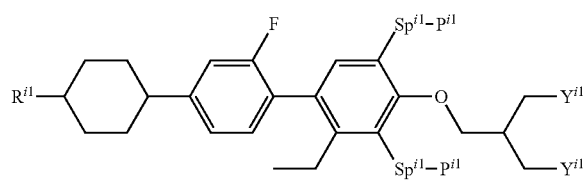
(R-1-39) 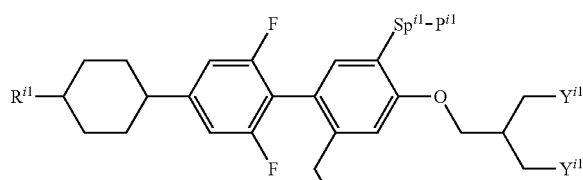
[Chem. 38]
(R-1-40) 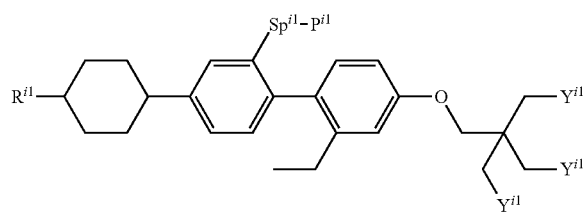
(R-1-41) 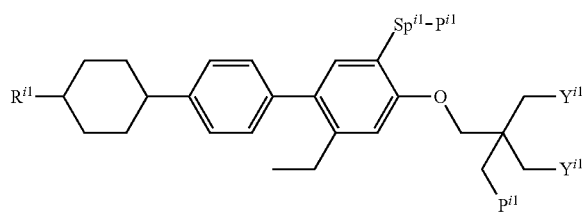
(R-1-42) 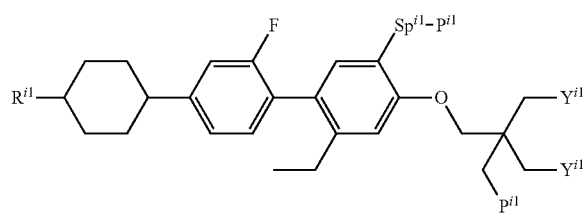
(R-1-43) 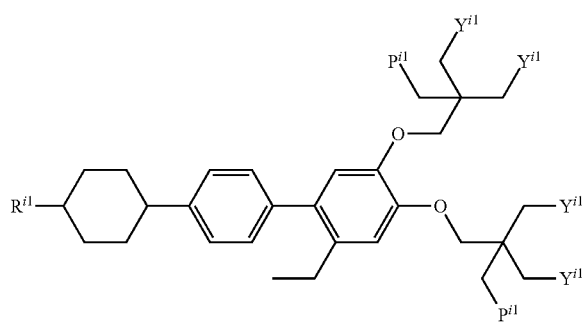

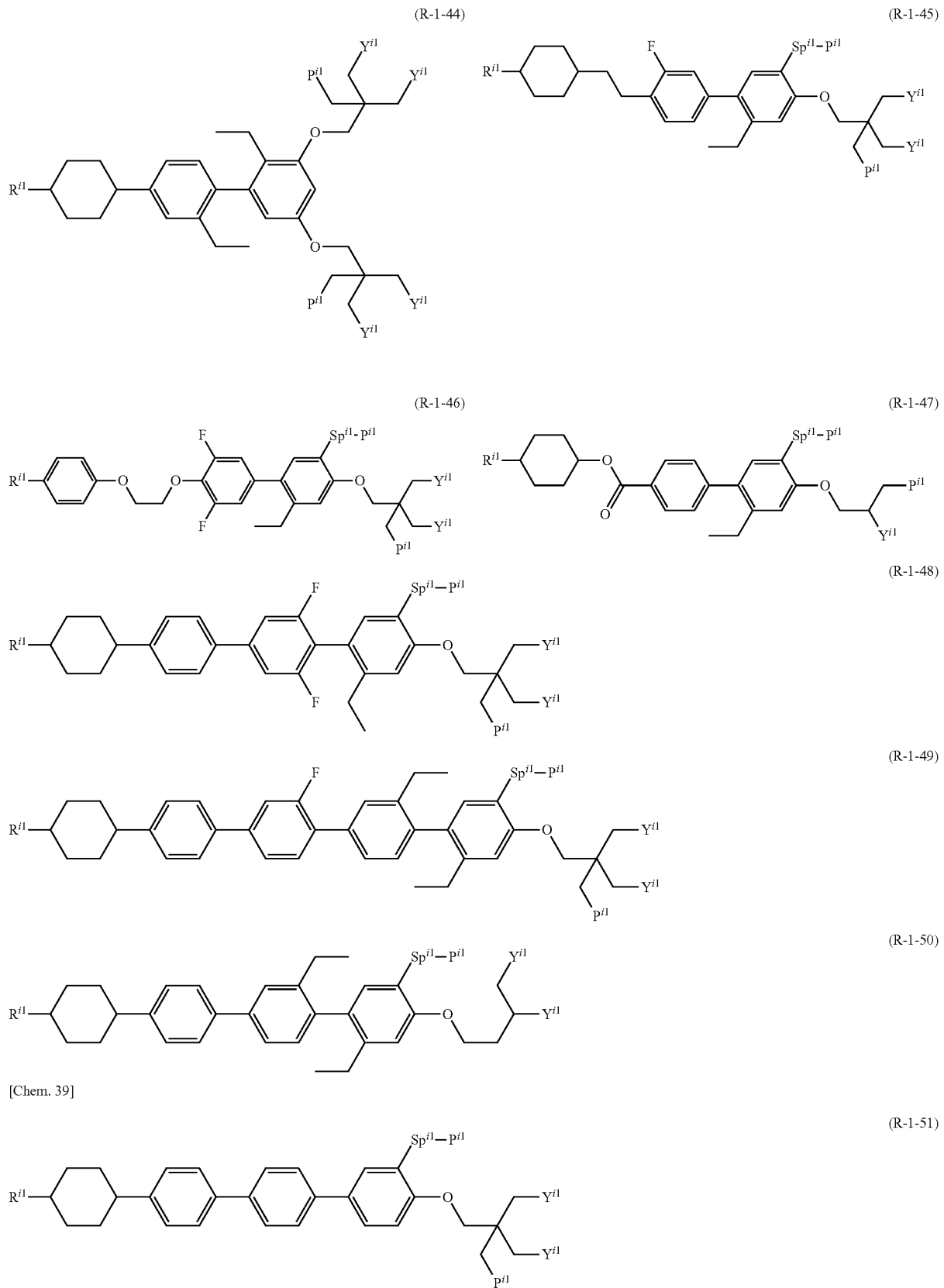

-continued
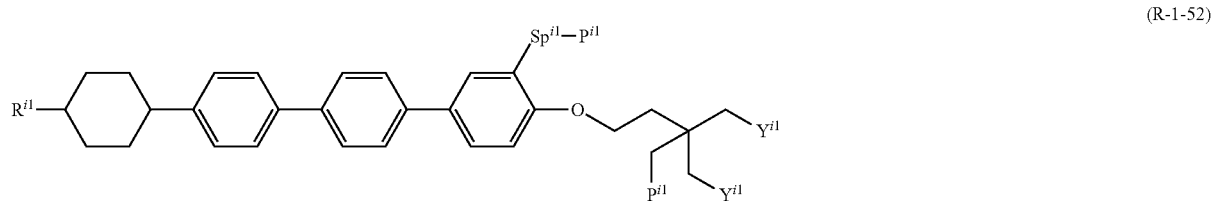
(R-1-52)
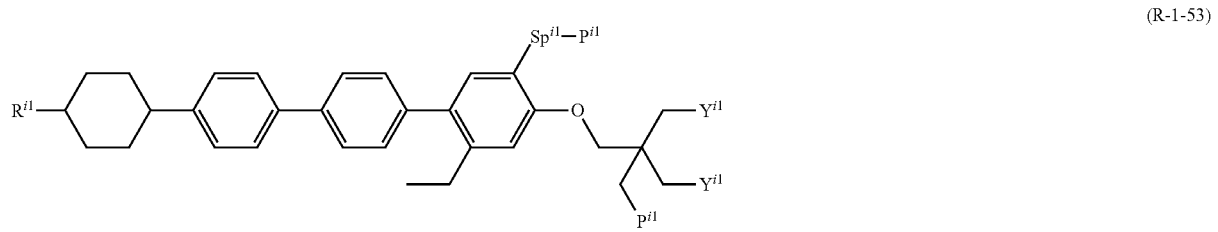
(R-1-53)
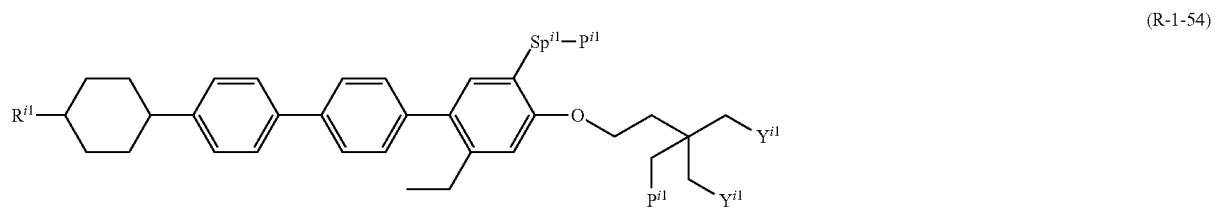
(R-1-54)
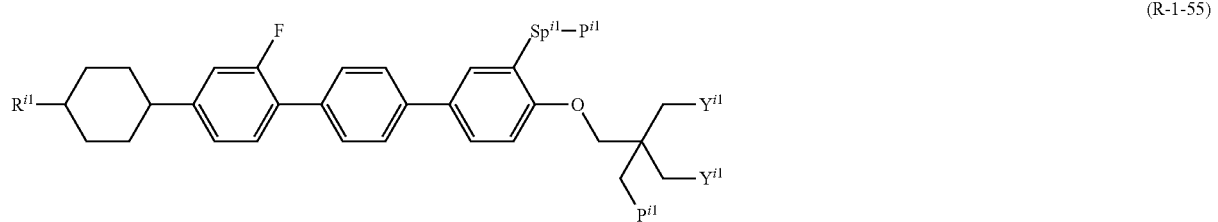
(R-1-55)
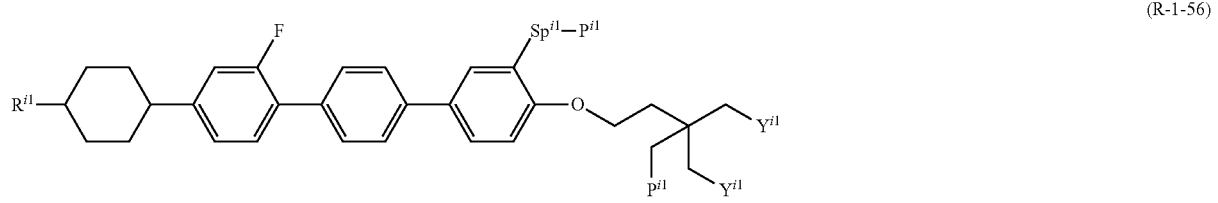
(R-1-56)
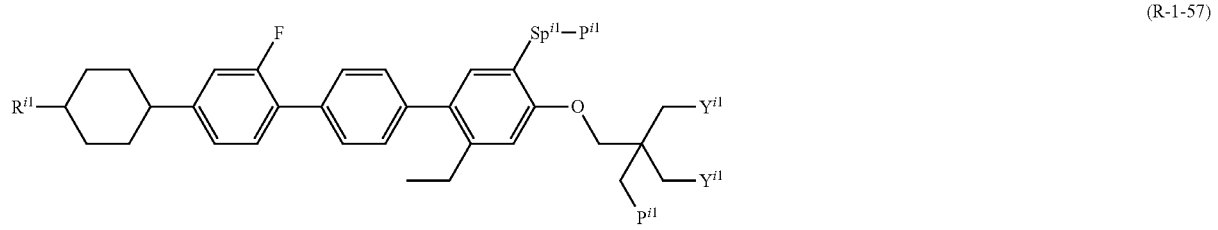
(R-1-57)
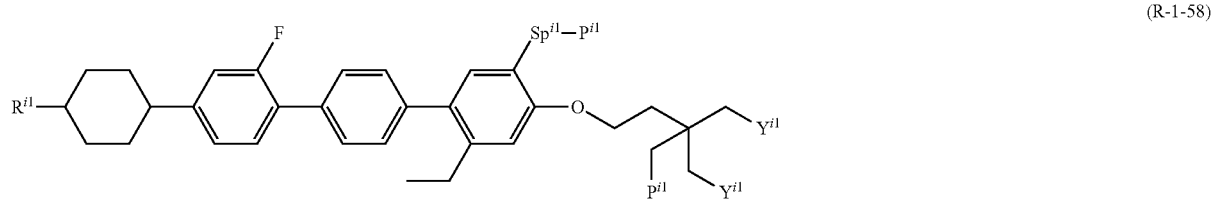
(R-1-58)

-continued
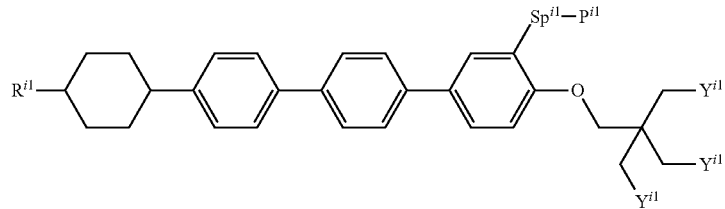
(R-1-59)
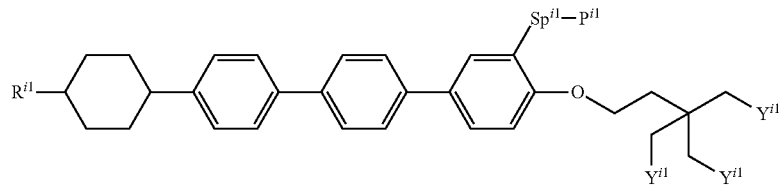
(R-1-60)
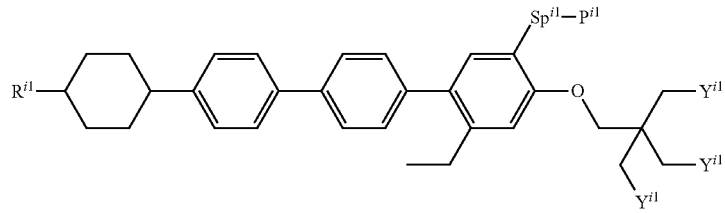
(R-1-61)
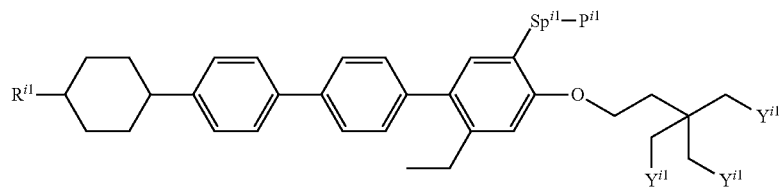
(R-1-62)
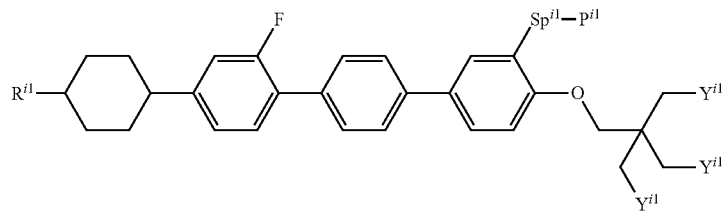
(R-1-63)
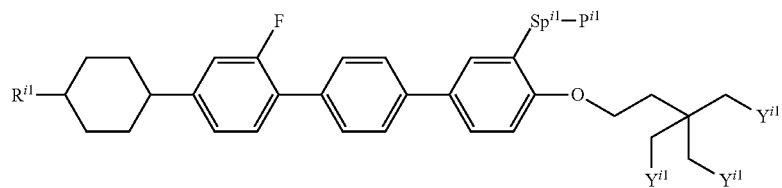
(R-1-64)
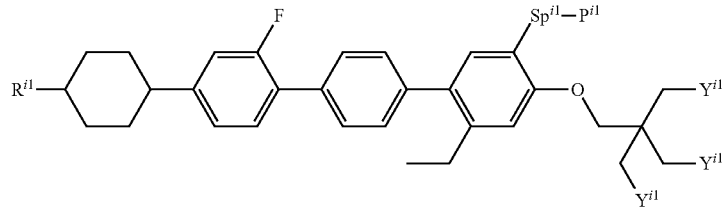
(R-1-65)

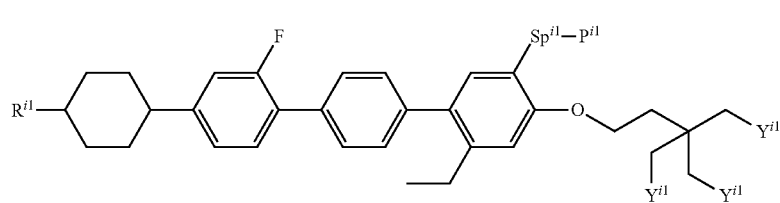
(R-1-66)
[Chem. 40]
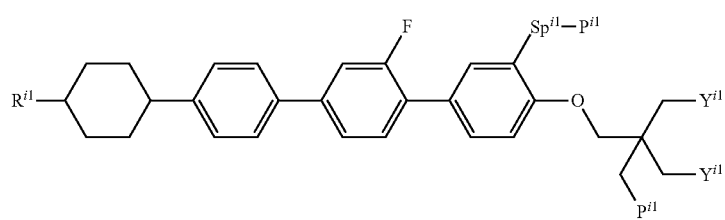
(R-1-67)
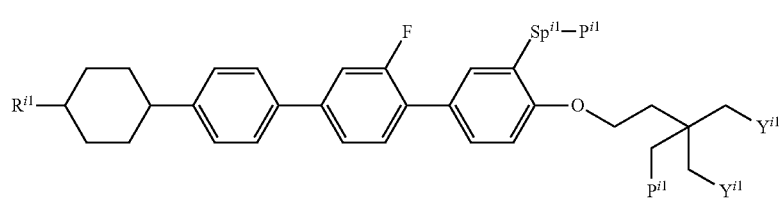
(R-1-68)
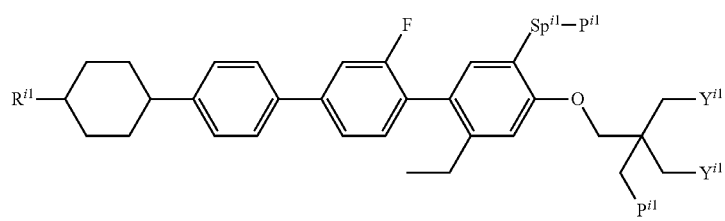
(R-1-69)
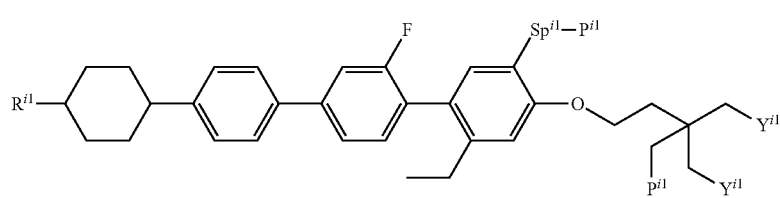
(R-1-70)
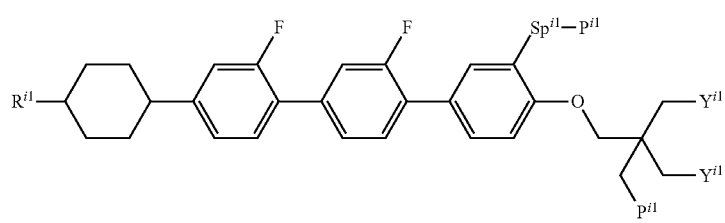
(R-1-71)
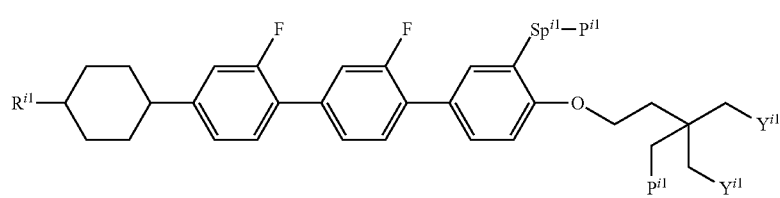
(R-1-72)

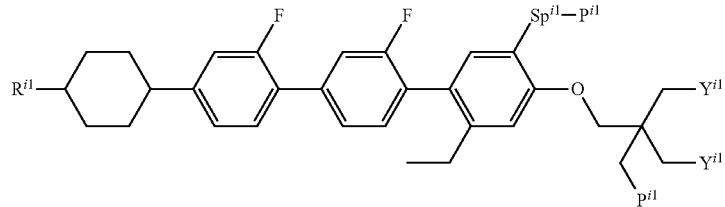
(R-1-73)
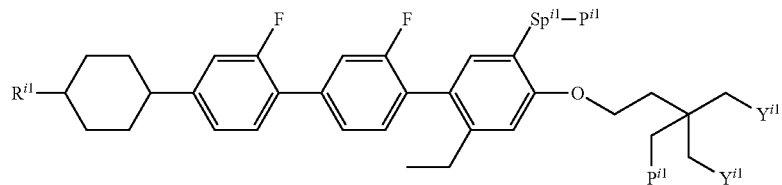
(R-1-74)
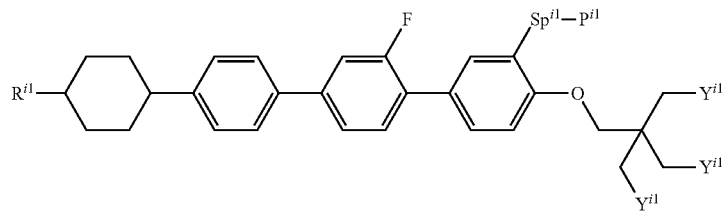
(R-1-75)
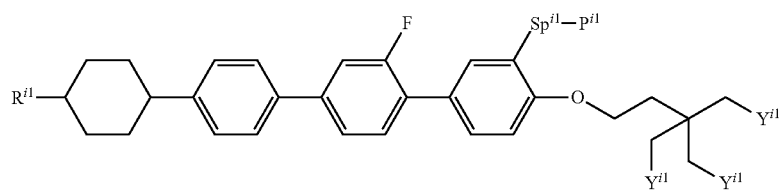
(R-1-76)
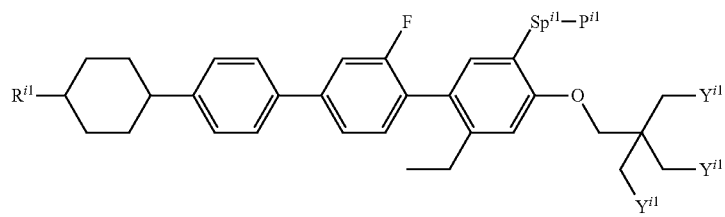
(R-1-77)
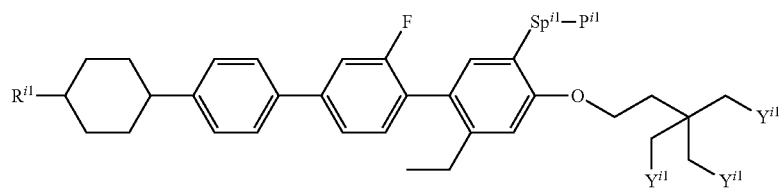
(R-1-78)
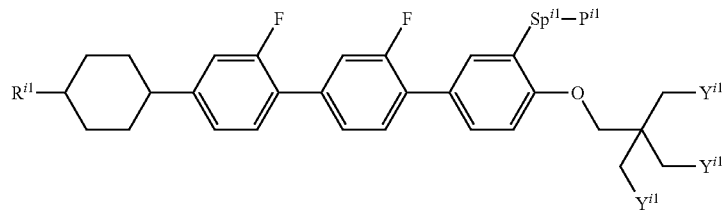
(R-1-79)

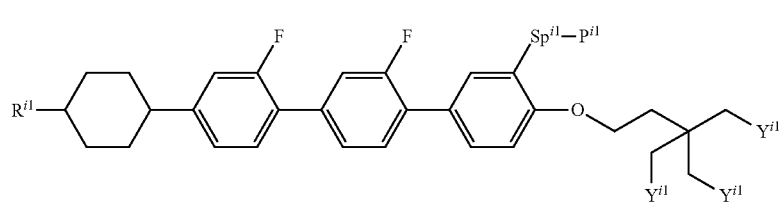
(R-1-80)
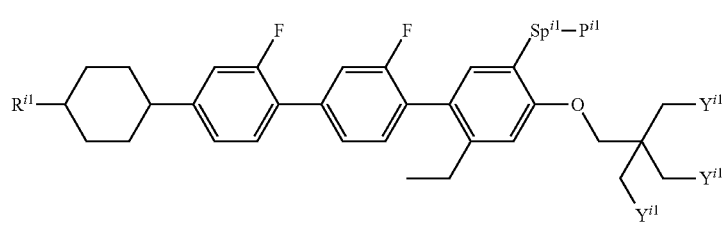
(R-1-81)
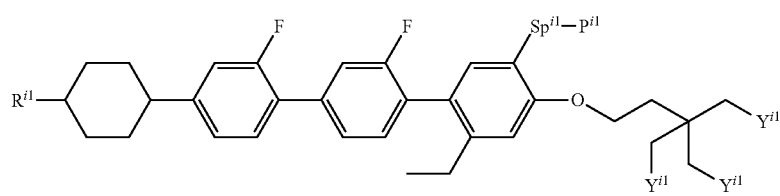
(R-1-82)
[Chem. 41]
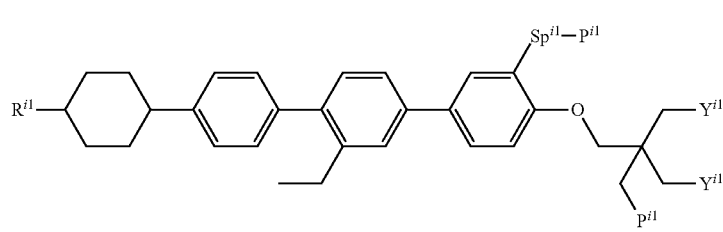
(R-1-83)
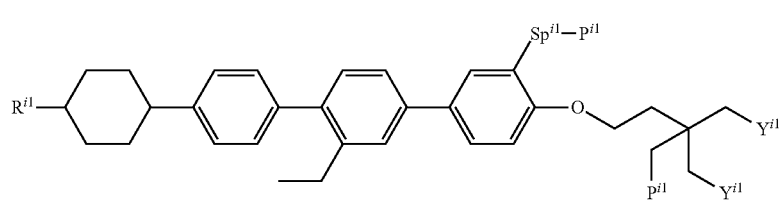
(R-1-84)
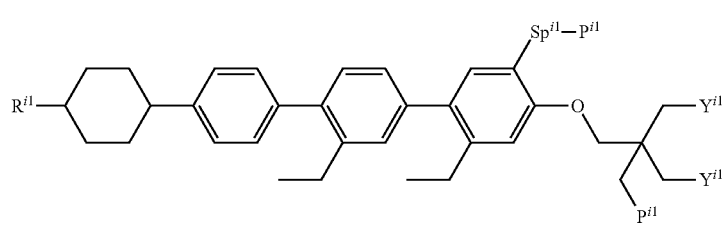
(R-1-85)
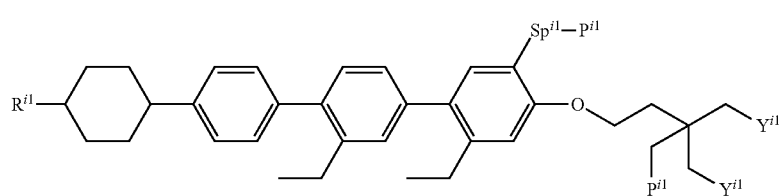
(R-1-86)

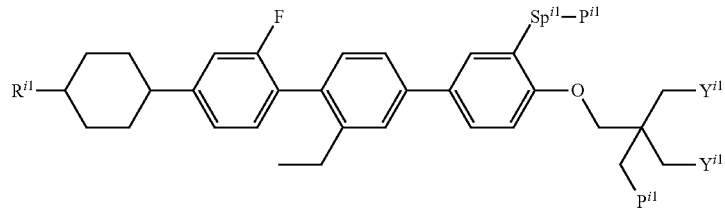
(R-1-87)
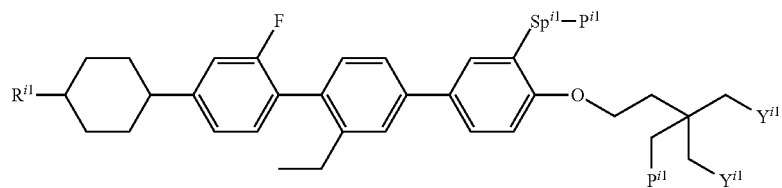
(R-1-88)
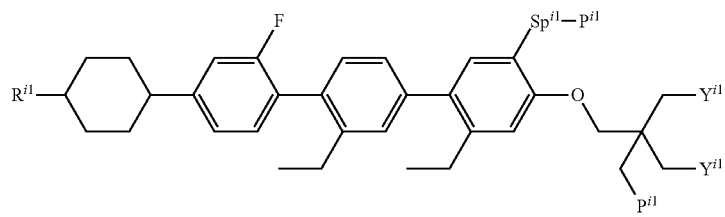
(R-1-89)
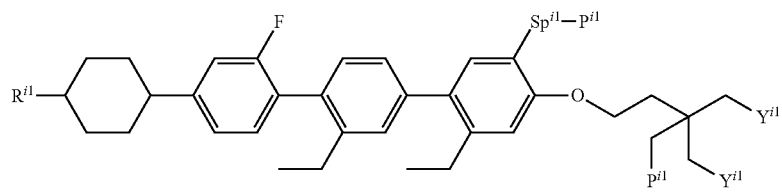
(R-1-90)
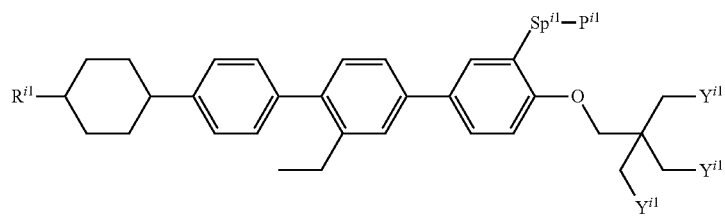
(R-1-91)
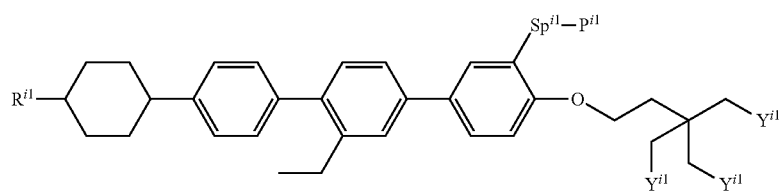
(R-1-92)
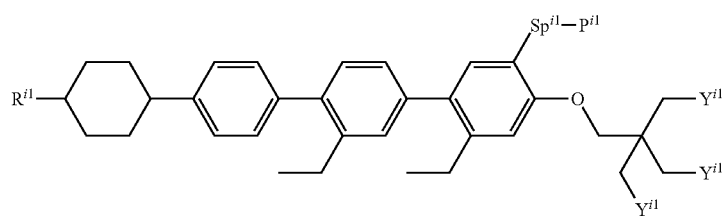
(R-1-93)

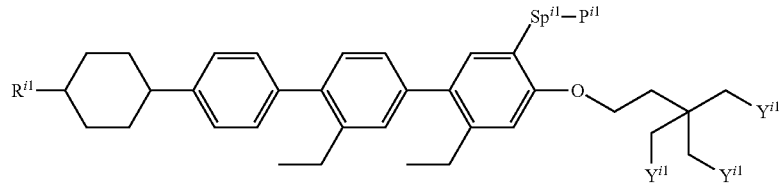
(R-1-94)
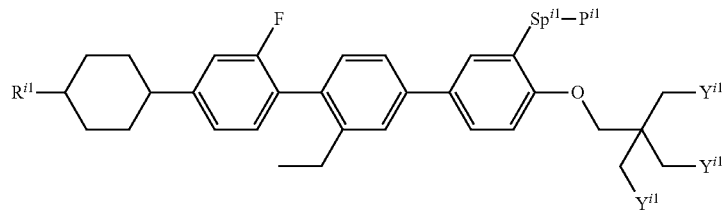
(R-1-95)
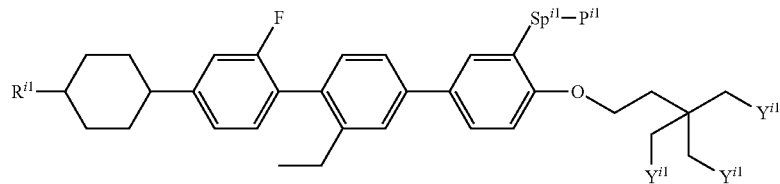
(R-1-96)
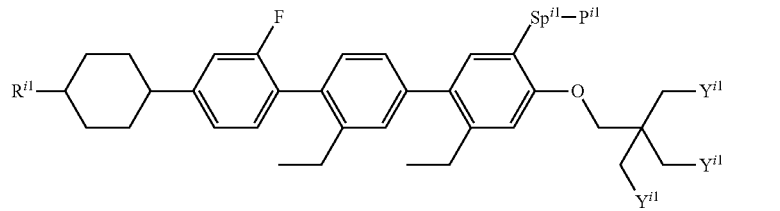
(R-1-97)
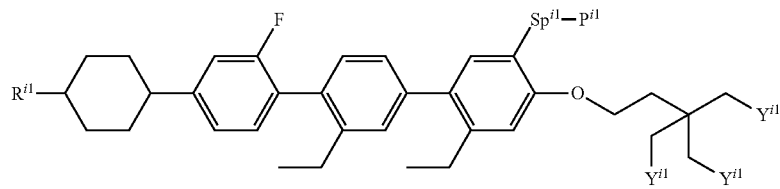
(R-1-98)
[Chem. 42]
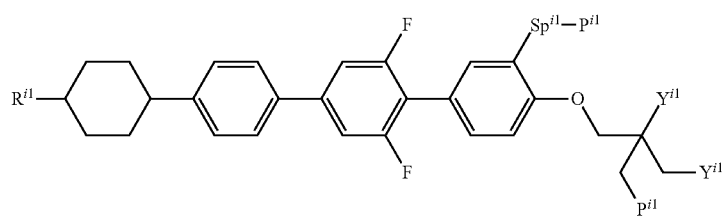
(R-1-99)
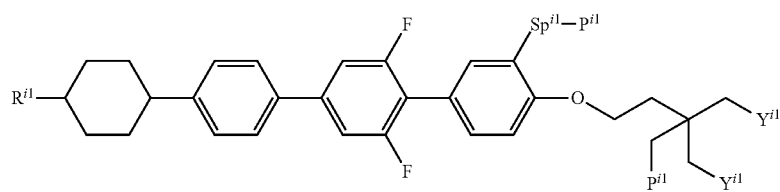
(R-1-100)

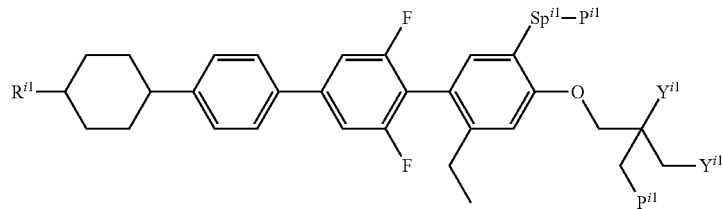
(R-1-101)
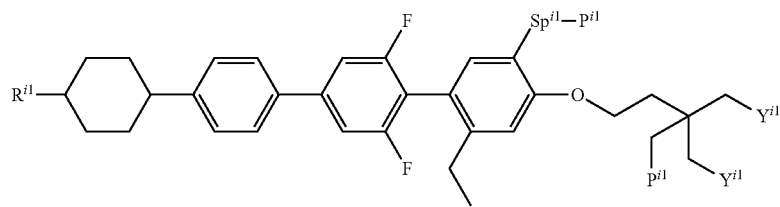
(R-1-102)
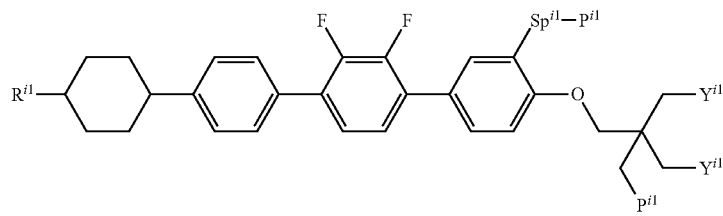
(R-1-103)
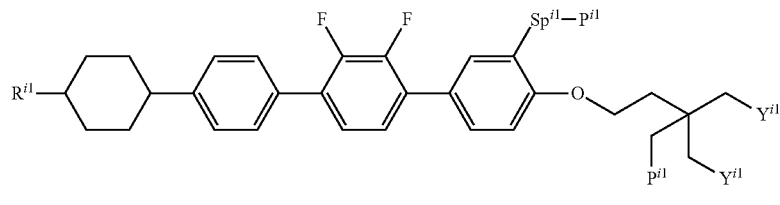
(R-1-104)
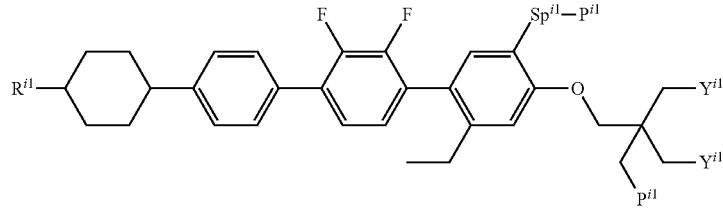
(R-1-105)
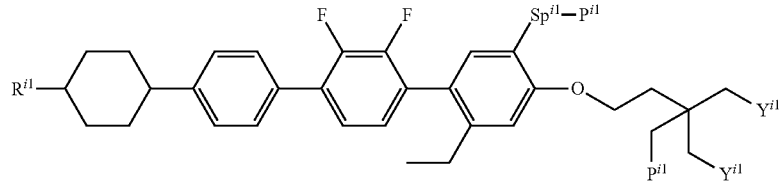
(R-1-106)
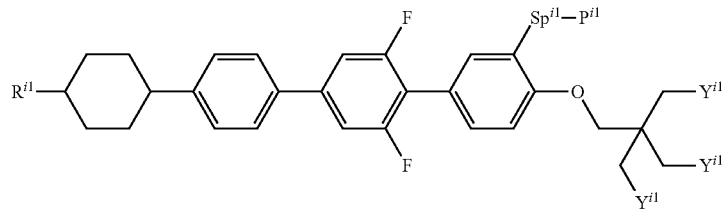
(R-1-107)

-continued
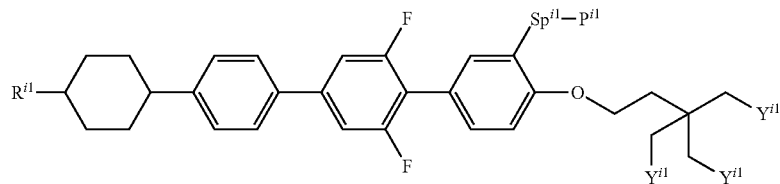
(R-1-108)
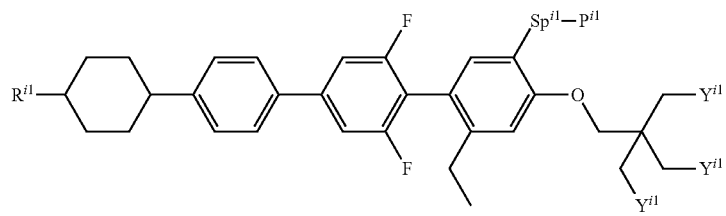
(R-1-109)
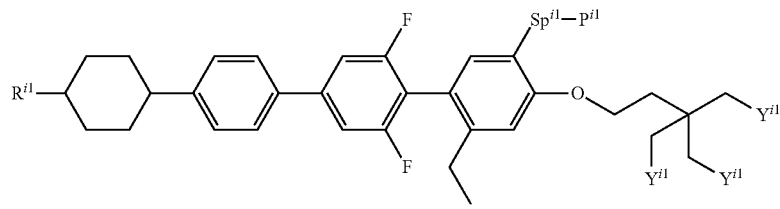
(R-1-110)
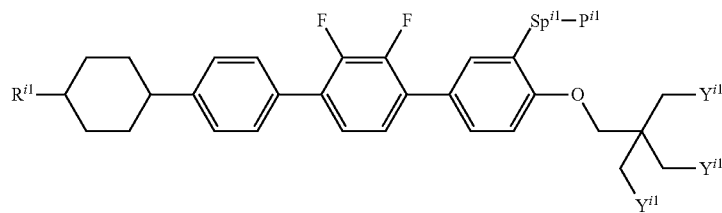
(R-1-111)
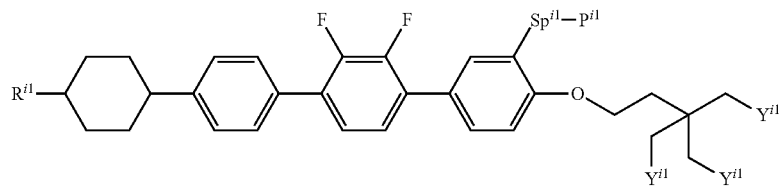
(R-1-112)
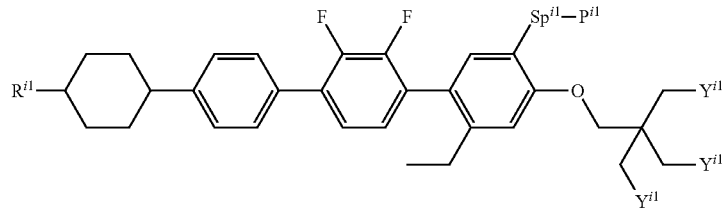
(R-1-113)
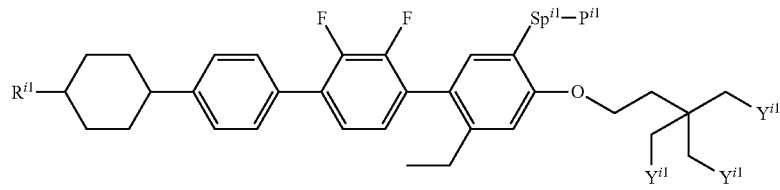
(R-1-114)

-continued
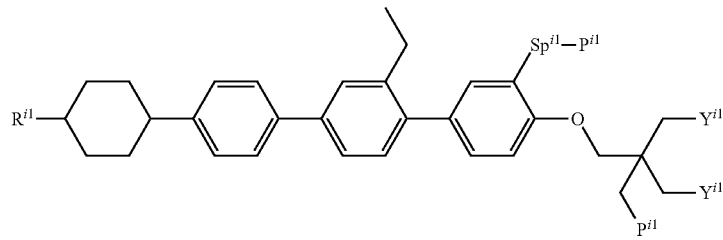 (R-1-115)
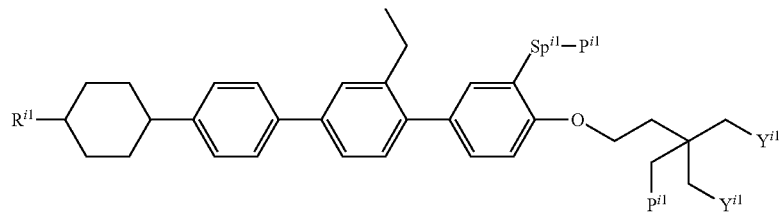 (R-1-116)
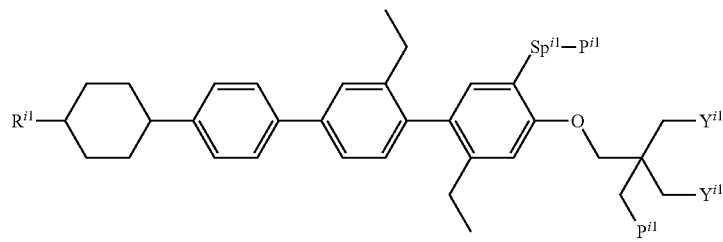 (R-1-117)
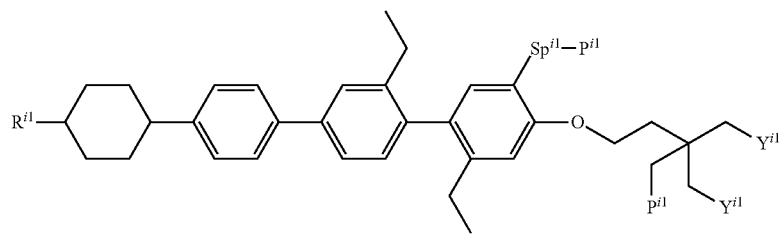 (R-1-118)
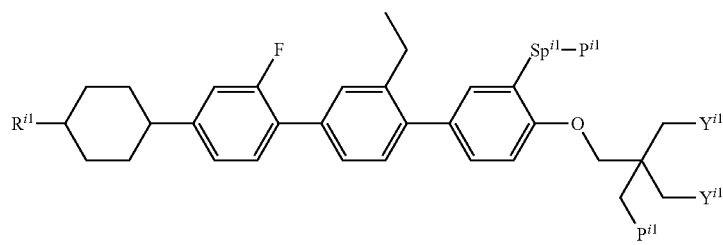 (R-1-119)
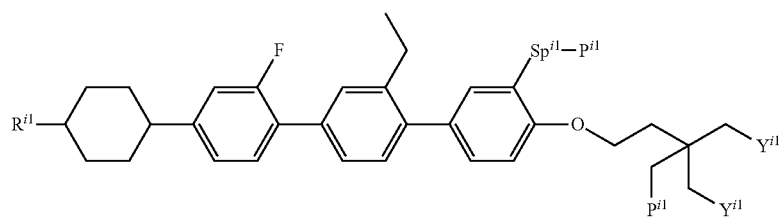 (R-1-120)

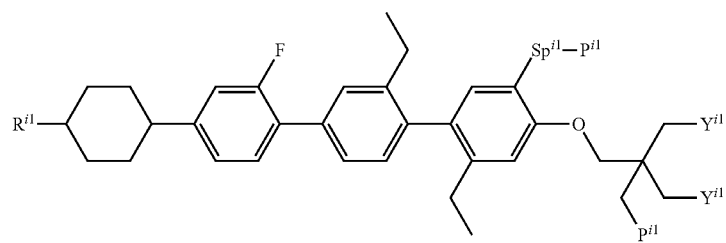
(R-1-121)
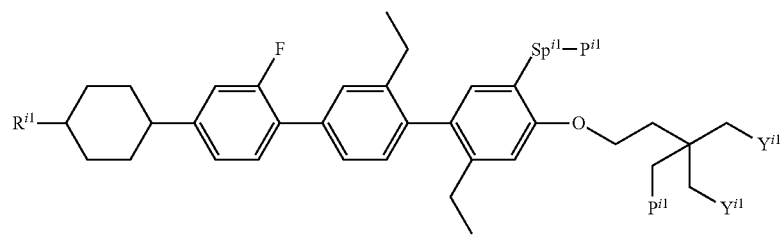
(R-1-122)
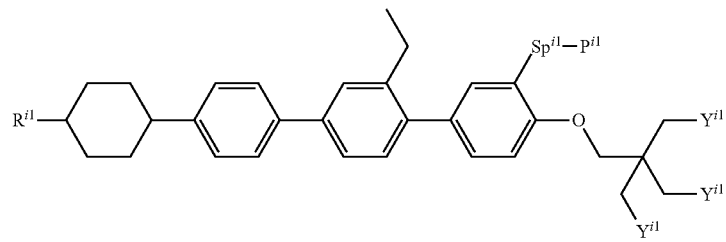
(R-1-123)
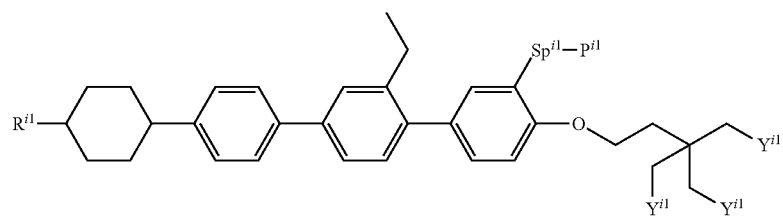
(R-1-124)
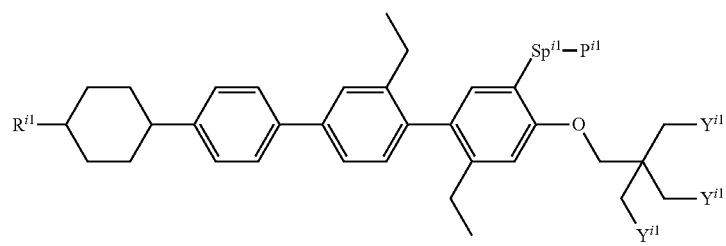
(R-1-125)
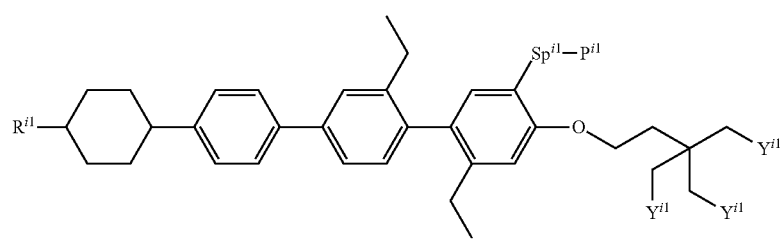
(R-1-126)

-continued
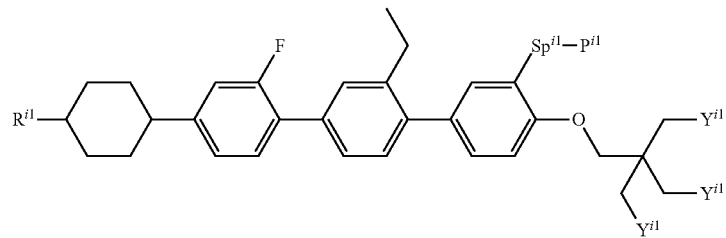
(R-1-127)
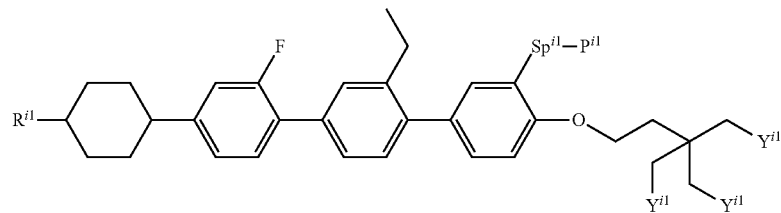
(R-1-128)
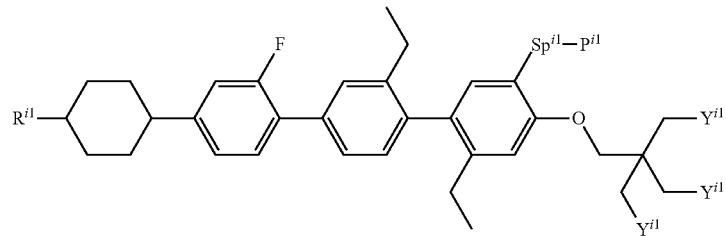
(R-1-129)
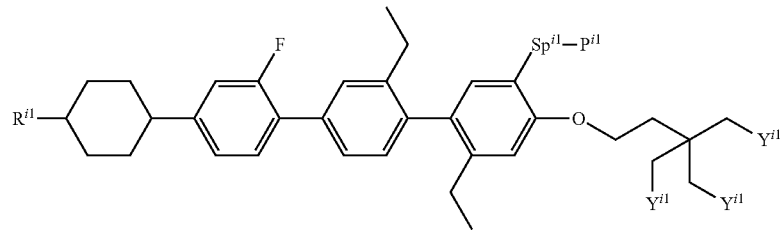
(R-1-130)
[Chem. 44]
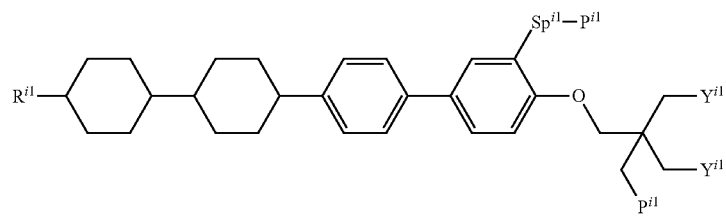
(R-1-131)
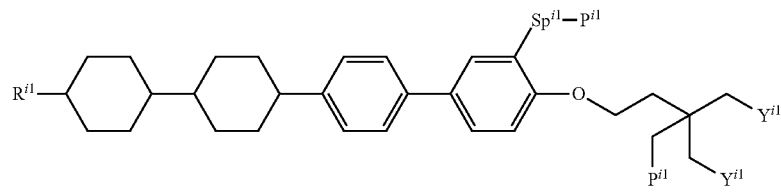
(R-1-132)
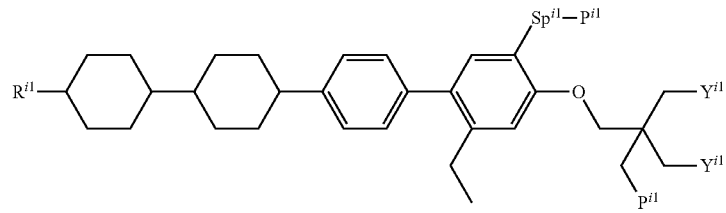
(R-1-133)

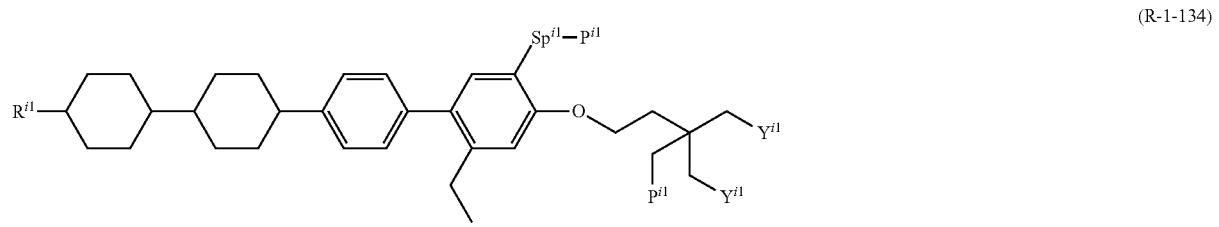
(R-1-134)
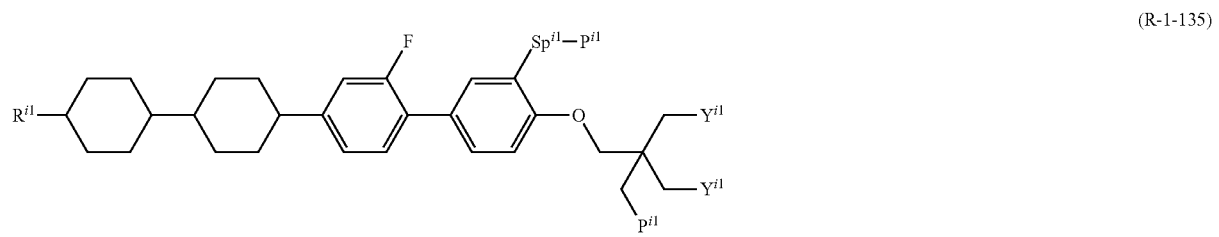
(R-1-135)
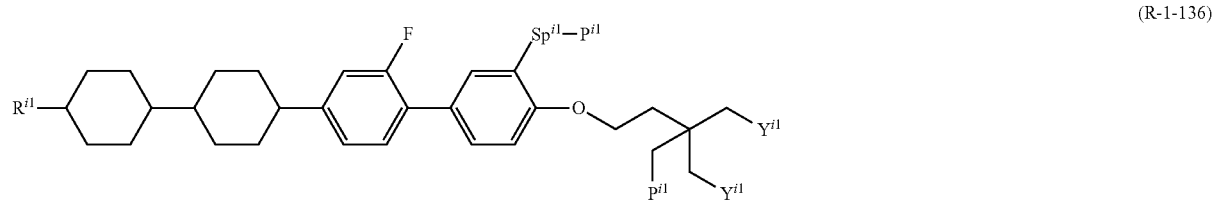
(R-1-136)
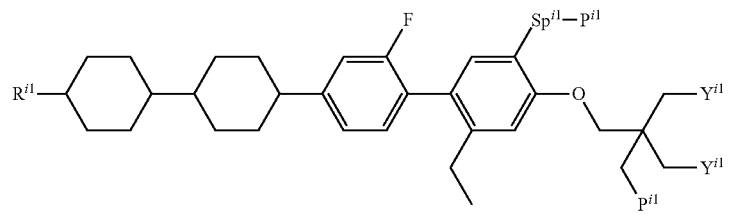
(R-1-137)
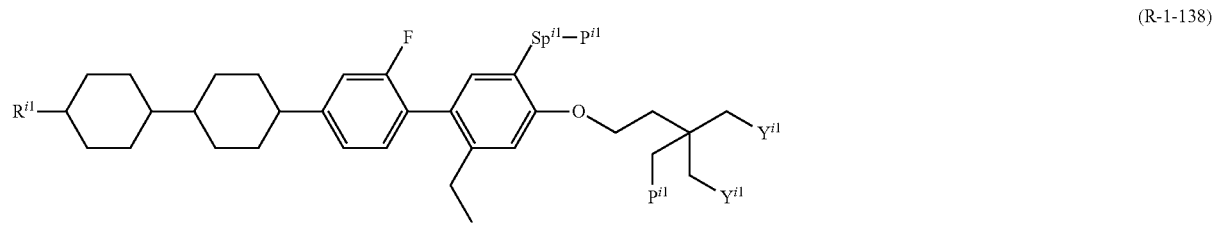
(R-1-138)
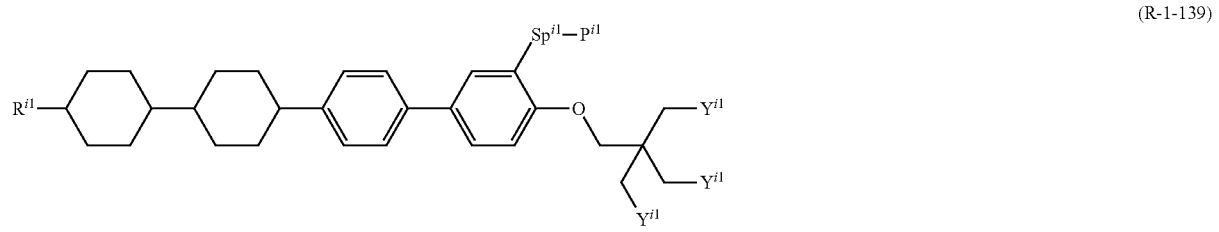
(R-1-139)
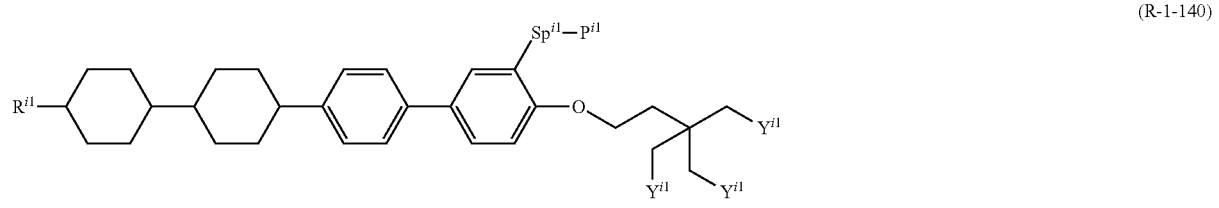
(R-1-140)

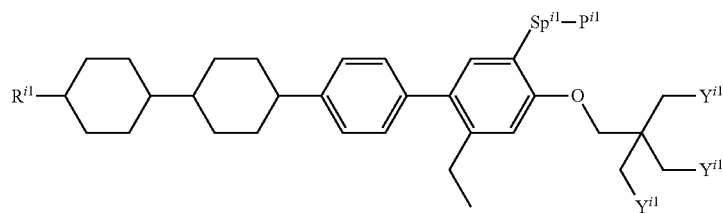
(R-1-141)
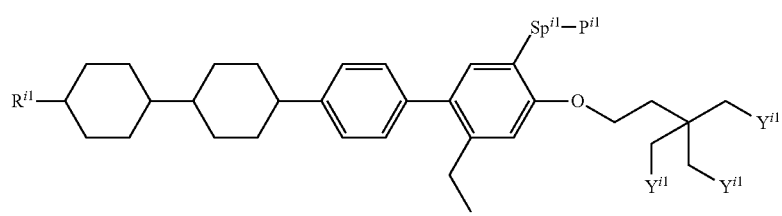
(R-1-142)
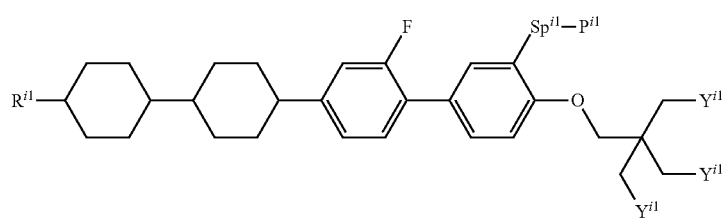
(R-1-143)
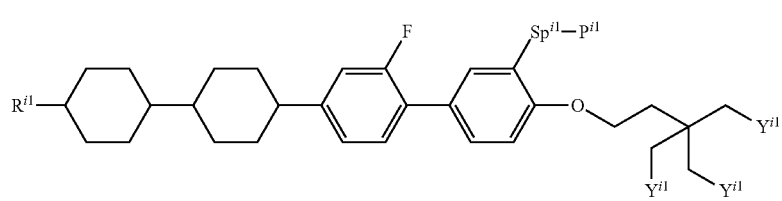
(R-1-144)
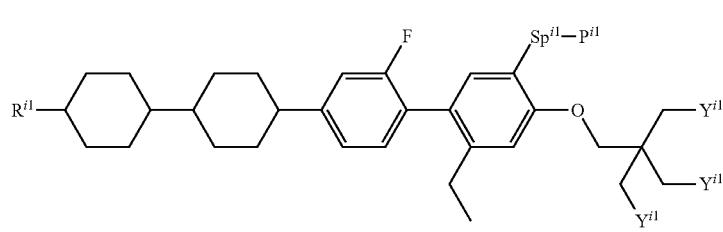
(R-1-145)
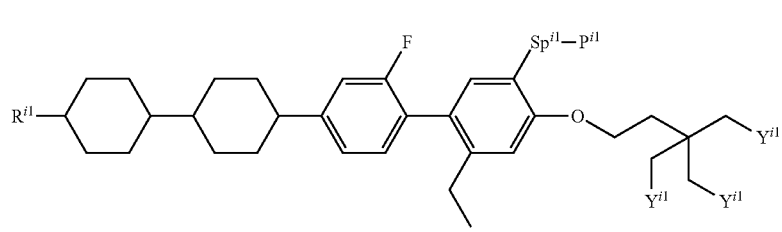
(R-1-146)
[Chem. 45]
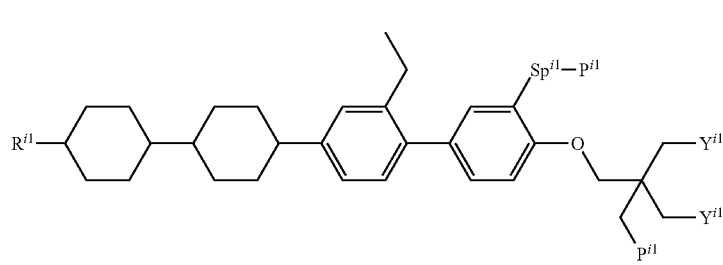
(R-1-147)

-continued
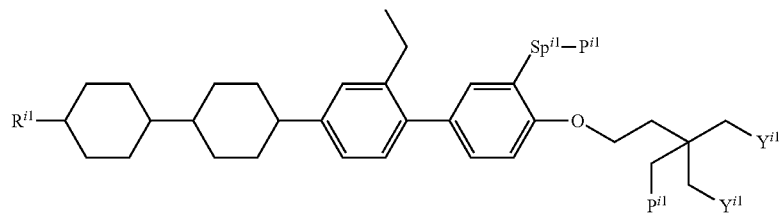
(R-1-148)
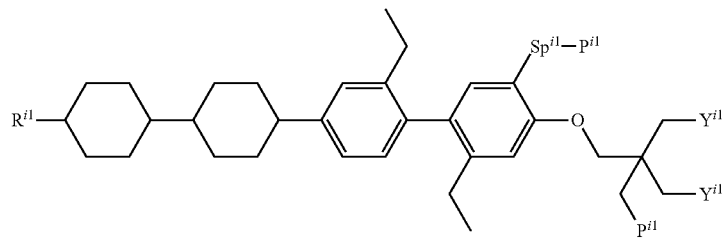
(R-1-149)
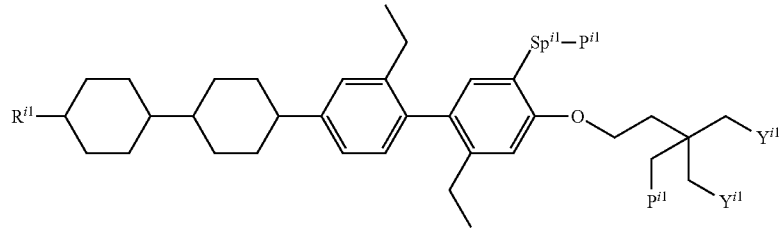
(R-1-150)
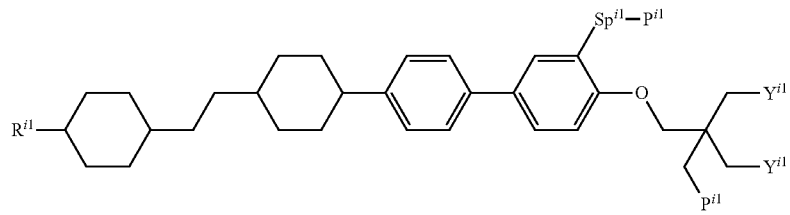
(R-1-151)
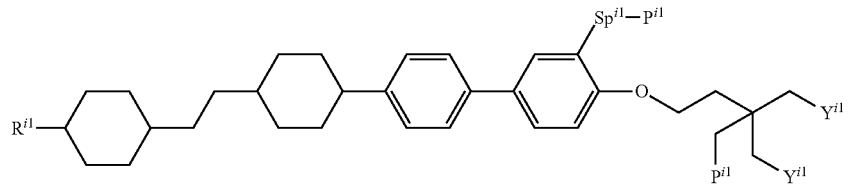
(R-1-152)
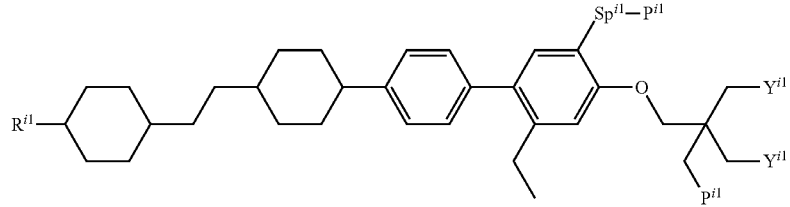
(R-1-153)
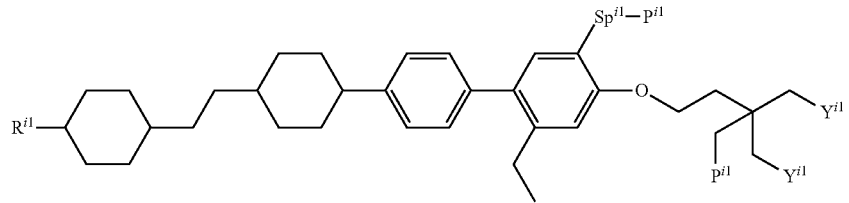
(R-1-154)

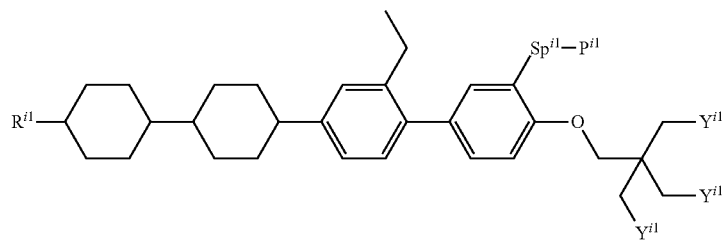
(R-1-155)
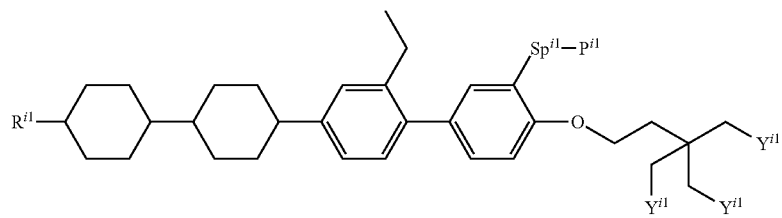
(R-1-156)
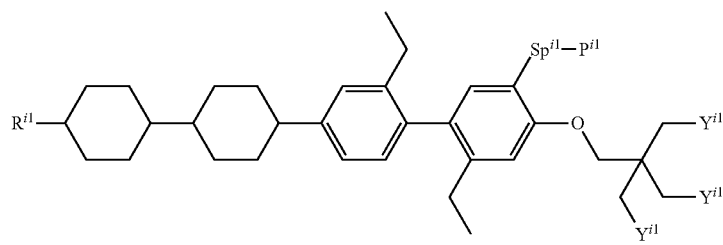
(R-1-157)
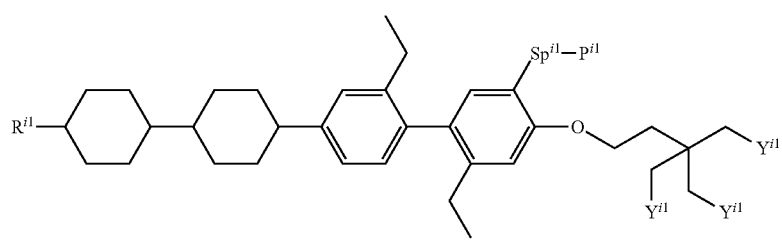
(R-1-158)
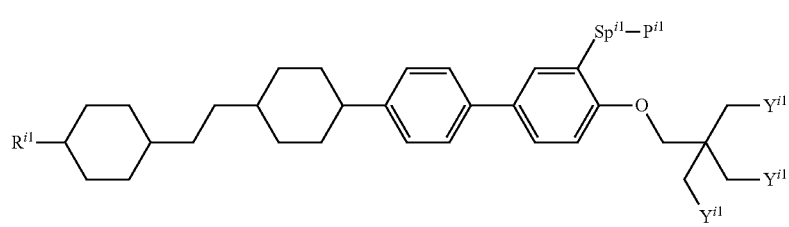
(R-1-159)
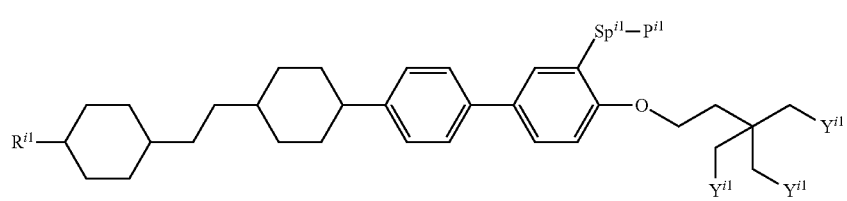
(R-1-160)
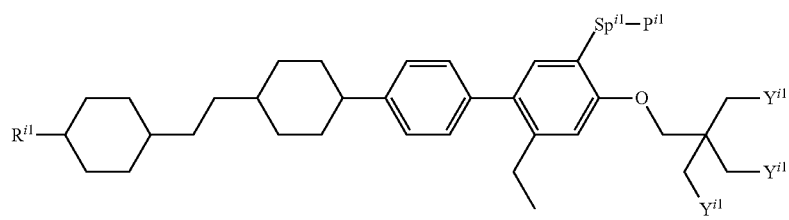
(R-1-161)

-continued
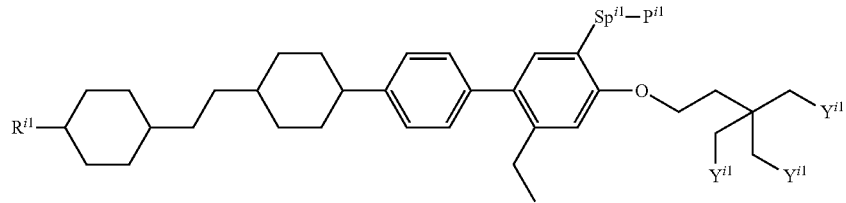
(R-1-162)
[Chem. 46]
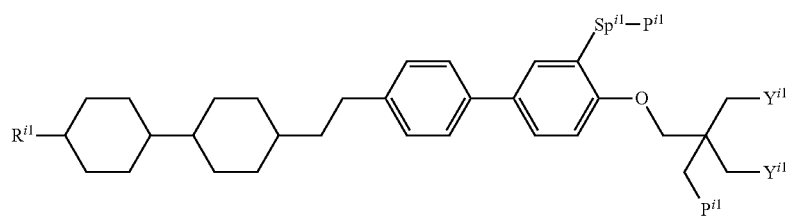
(R-1-163)
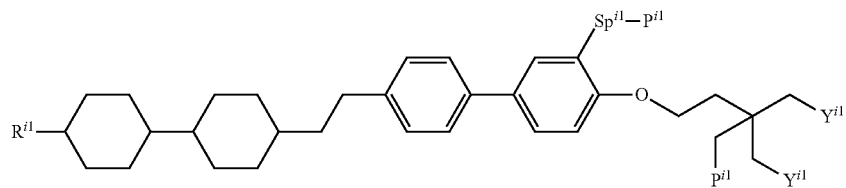
(R-1-164)
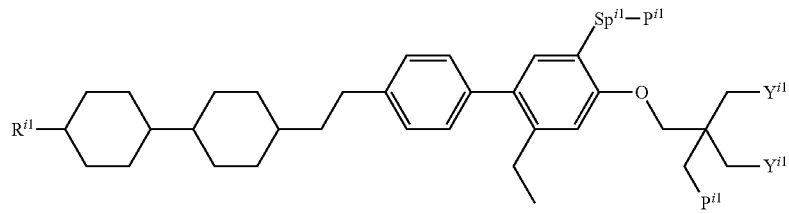
(R-1-165)
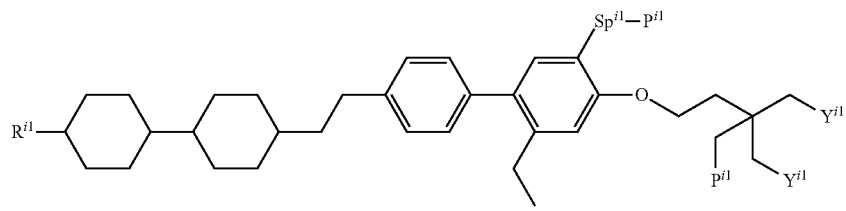
(R-1-166)
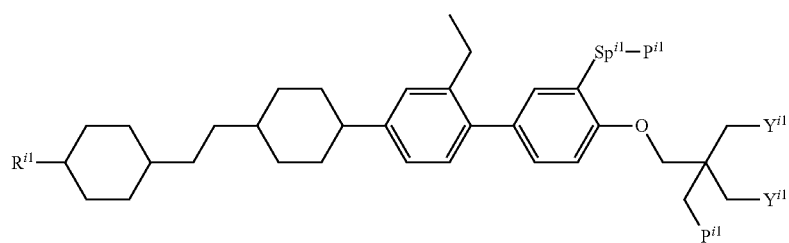
(R-1-167)
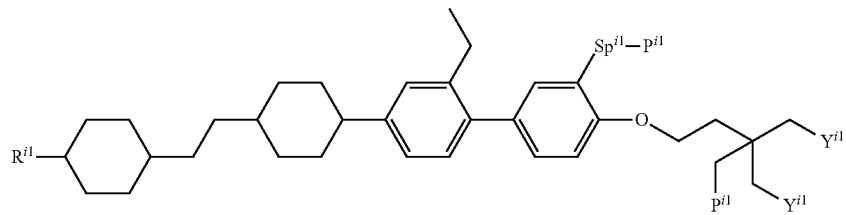
(R-1-168)

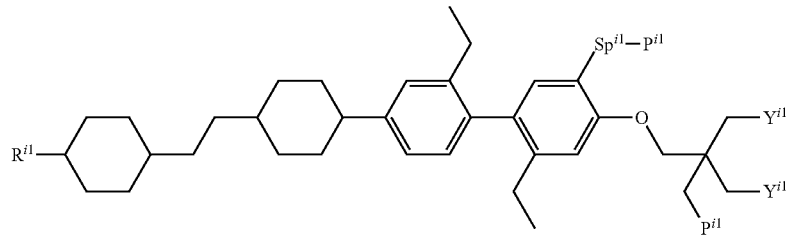
(R-1-169)
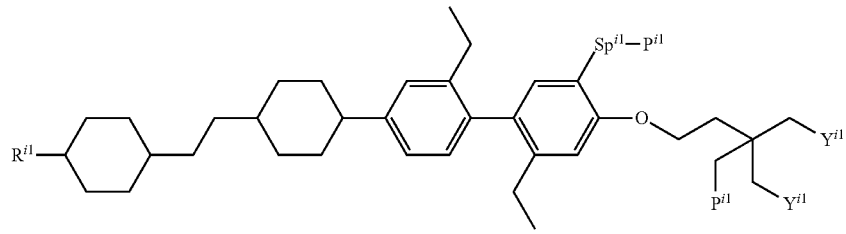
(R-1-170)
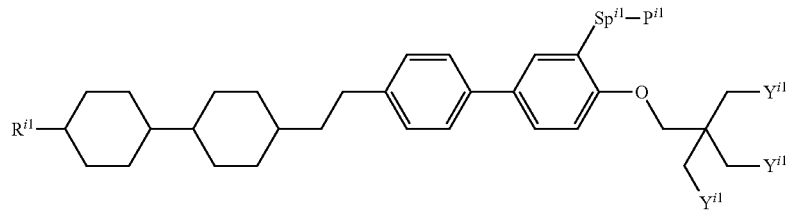
(R-1-171)
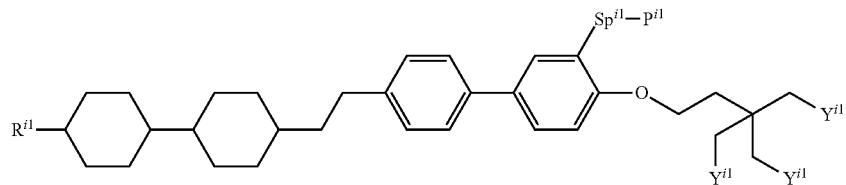
(R-1-172)
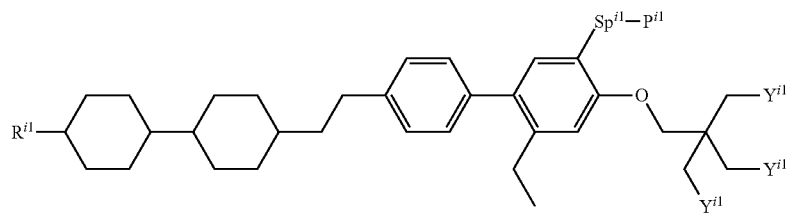
(R-1-173)
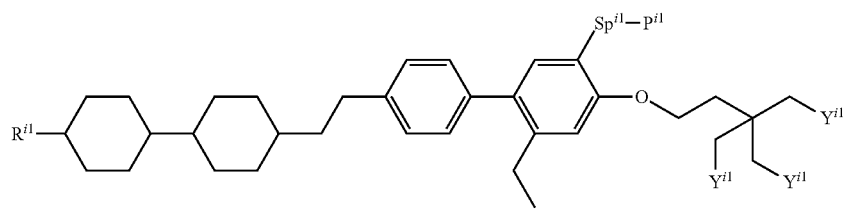
(R-1-174)
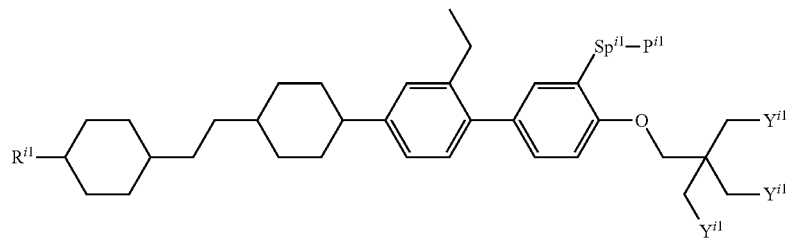
(R-1-175)

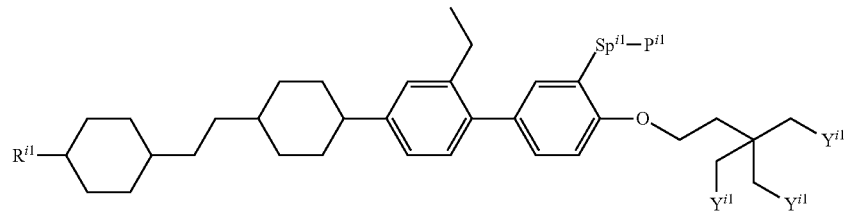 (R-1-176)
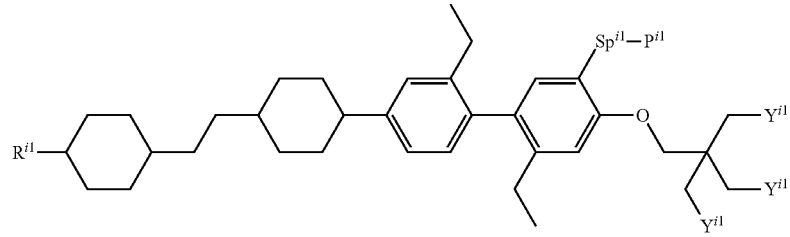 (R-1-177)
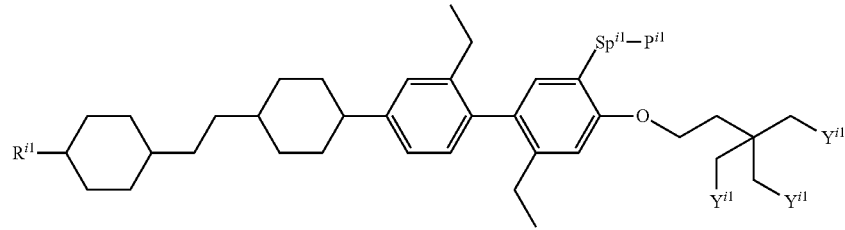 (R-1-178)
[Chem. 47]
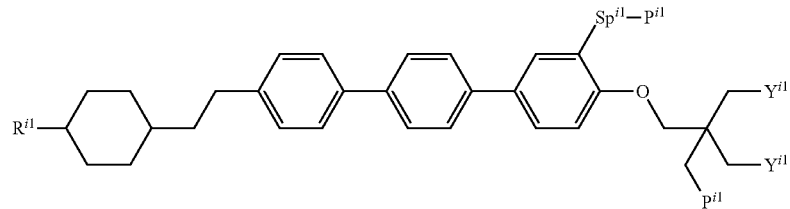 (R-1-179)
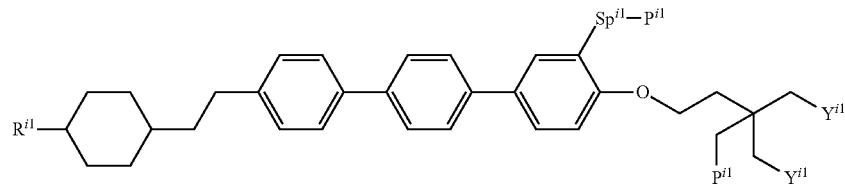 (R-1-180)
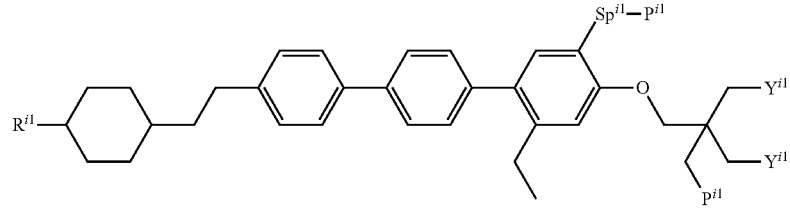 (R-1-181)
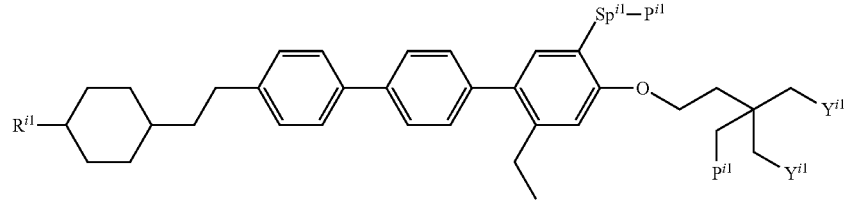 (R-1-182)

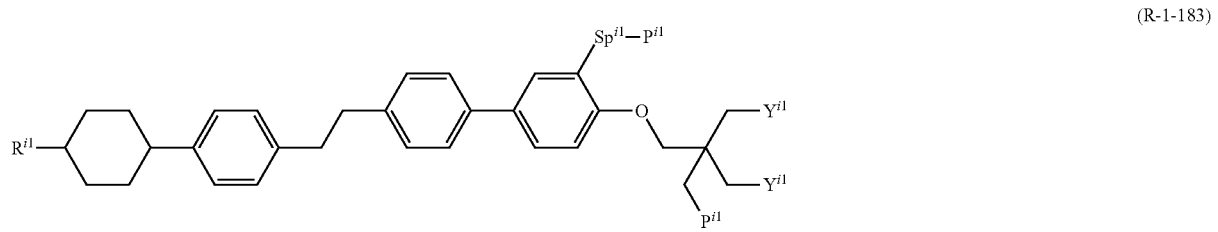
(R-1-183)
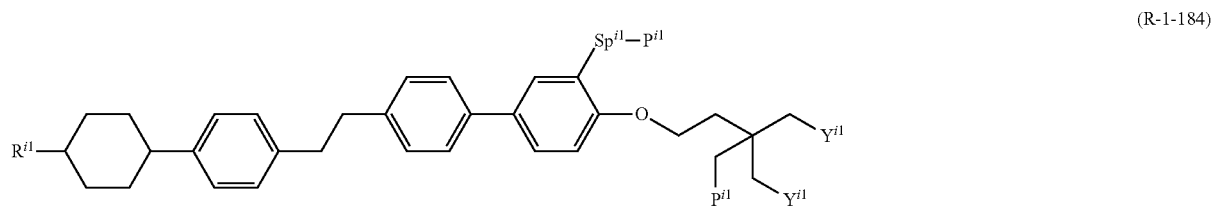
(R-1-184)
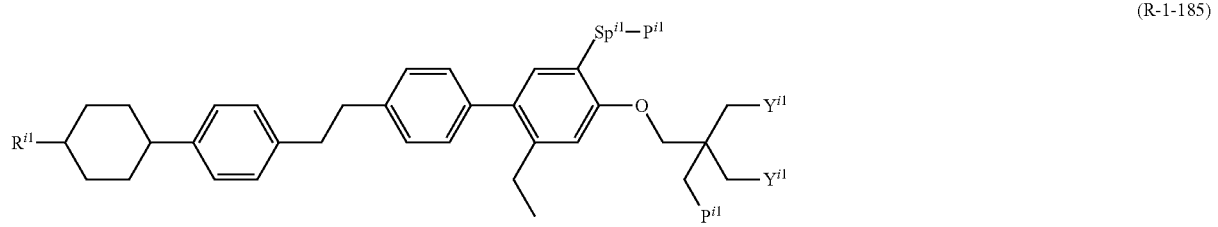
(R-1-185)
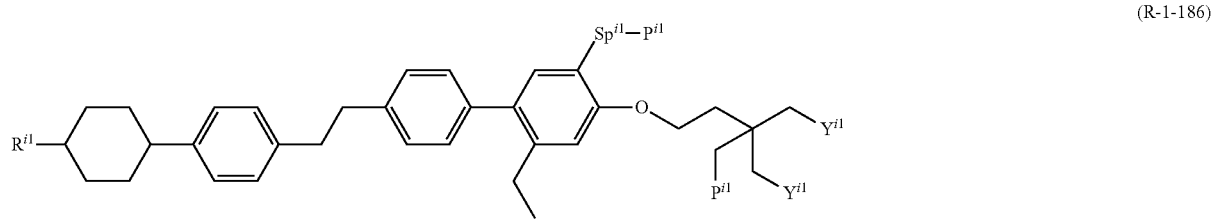
(R-1-186)
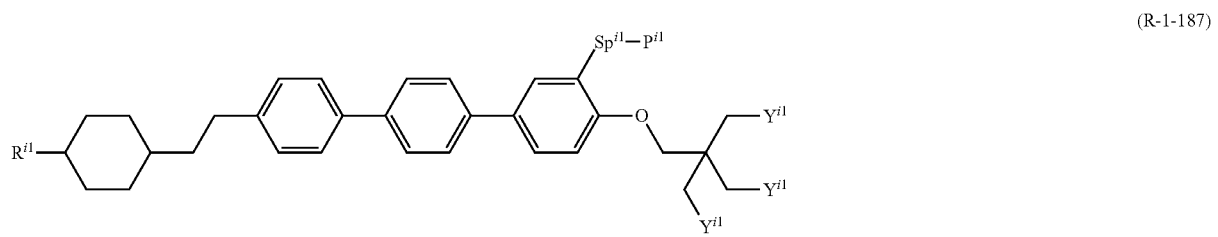
(R-1-187)
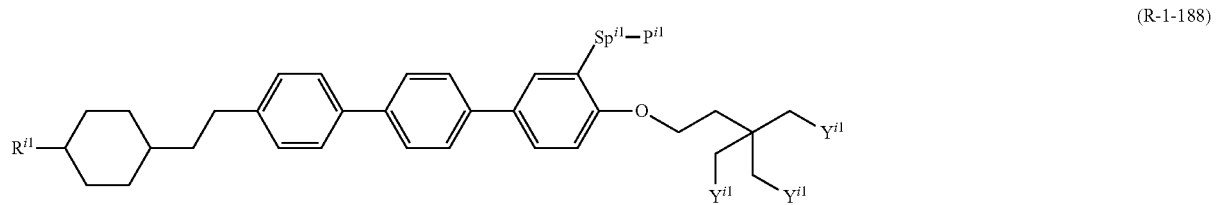
(R-1-188)
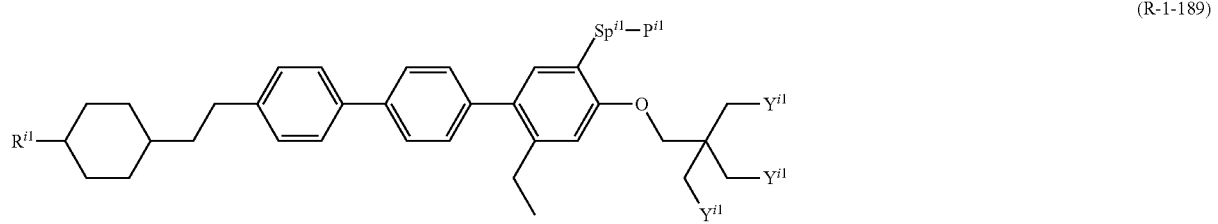
(R-1-189)

-continued
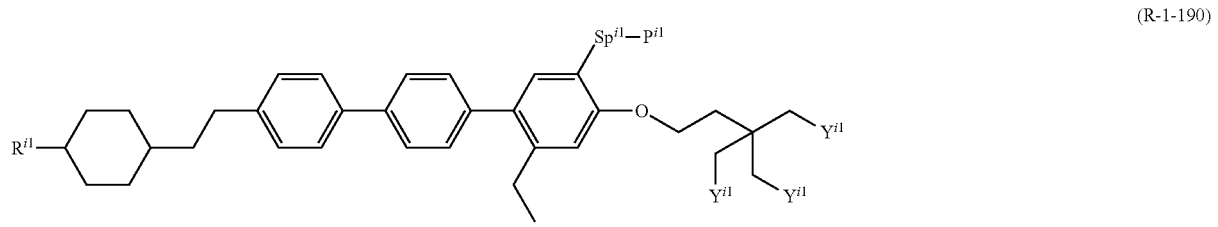
(R-1-190)
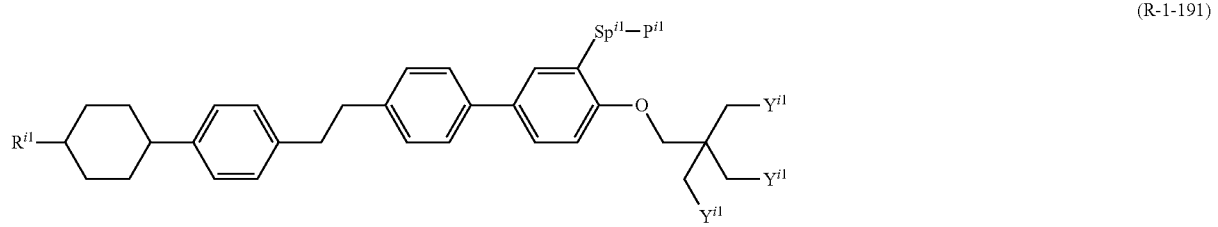
(R-1-191)
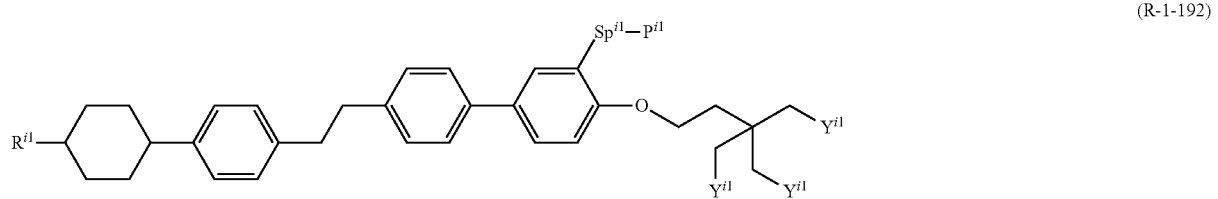
(R-1-192)
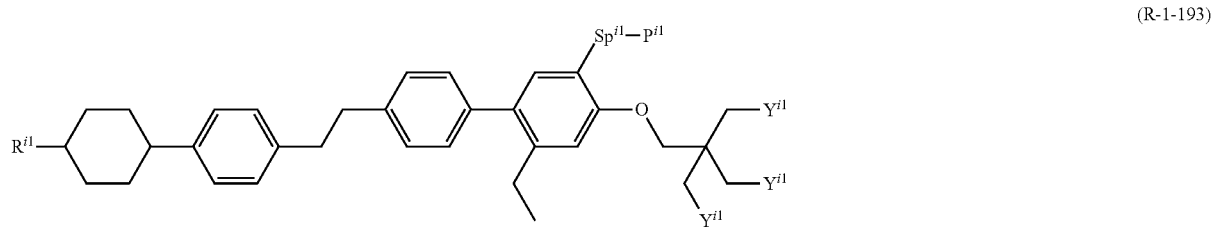
(R-1-193)
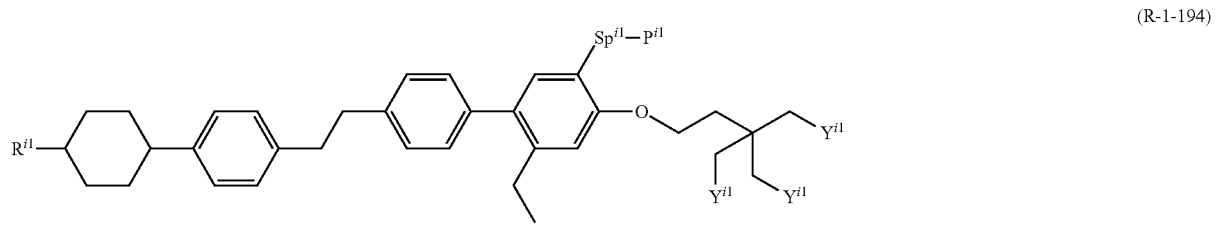
(R-1-194)
[Chem. 48]
(R-1-195) (R-1-196)
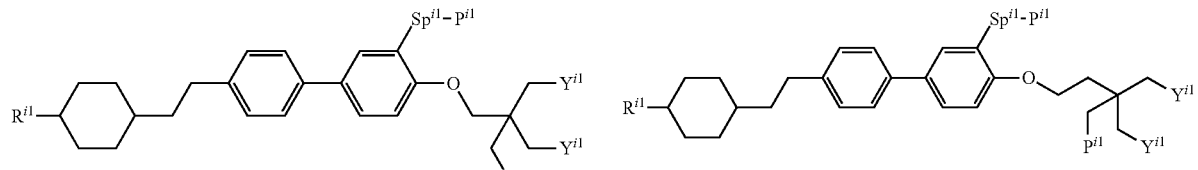
(R-1-197) (R-1-198)
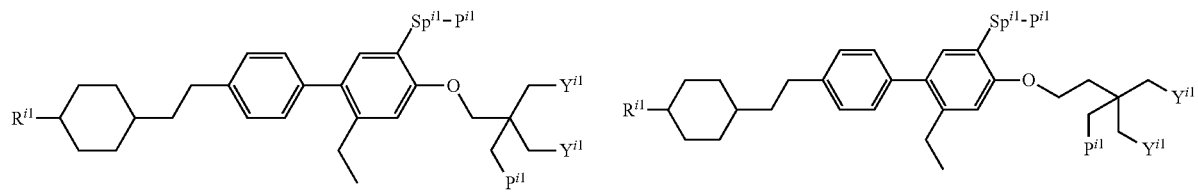

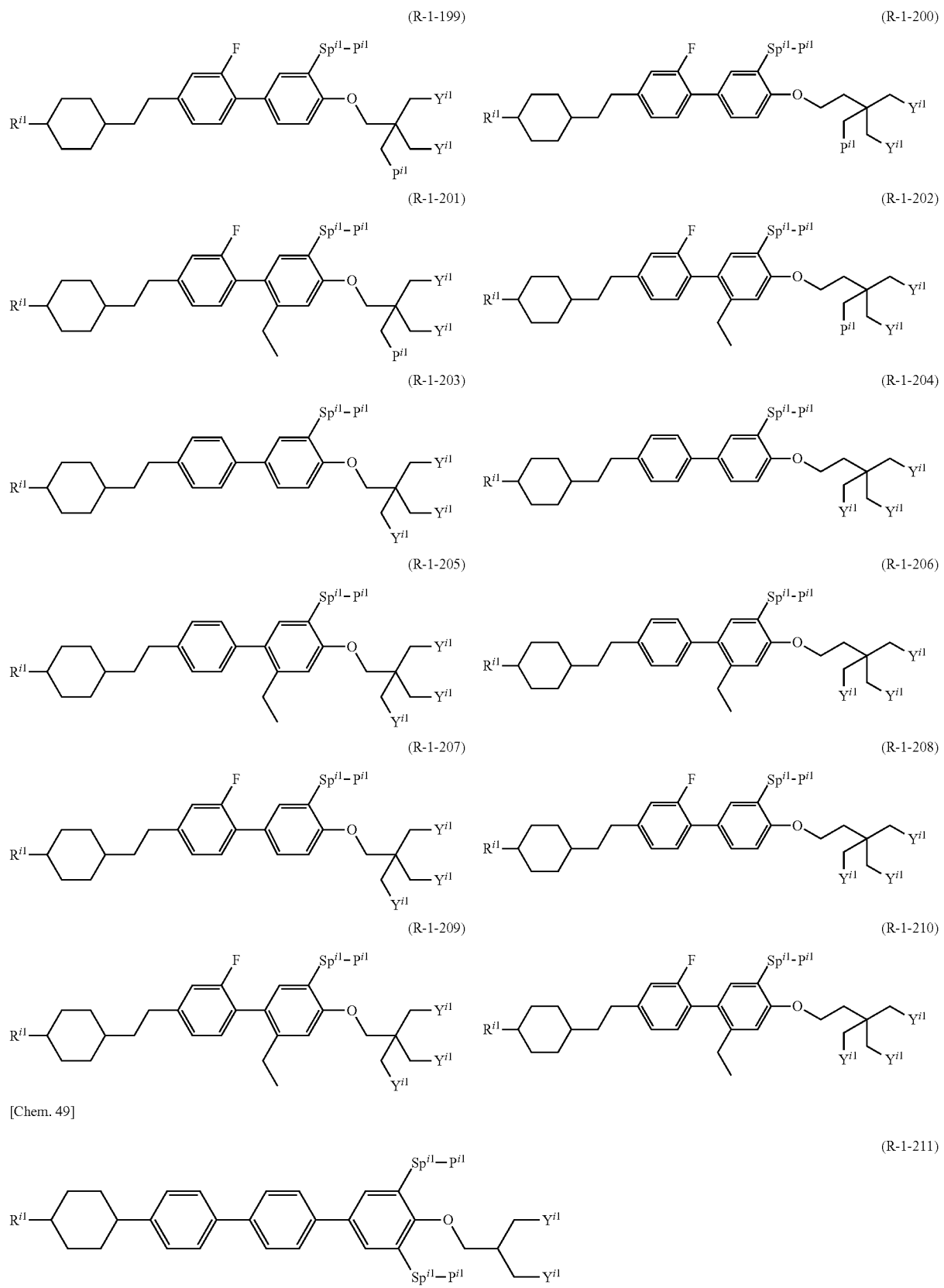

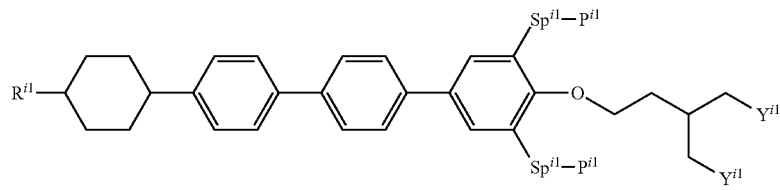
(R-1-212)
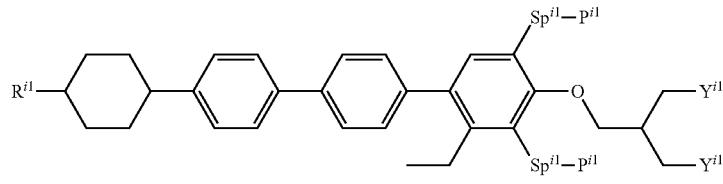
(R-1-213)
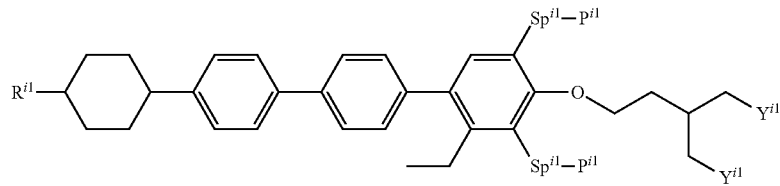
(R-1-214)
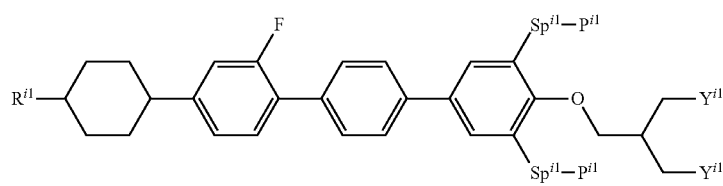
(R-1-215)
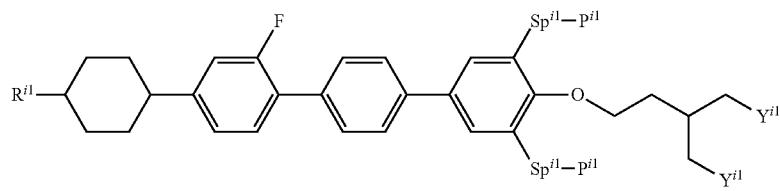
(R-1-216)
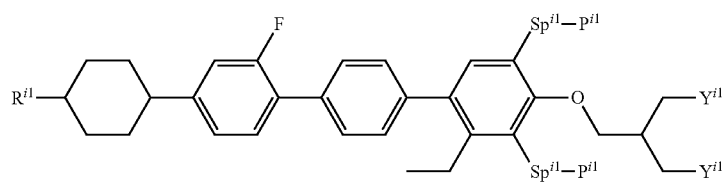
(R-1-217)
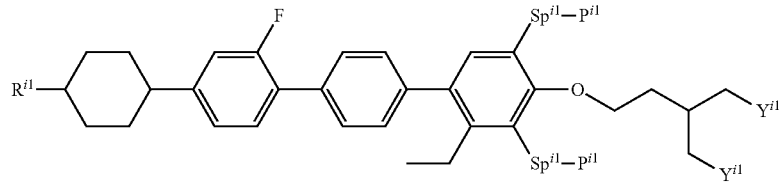
(R-1-218)
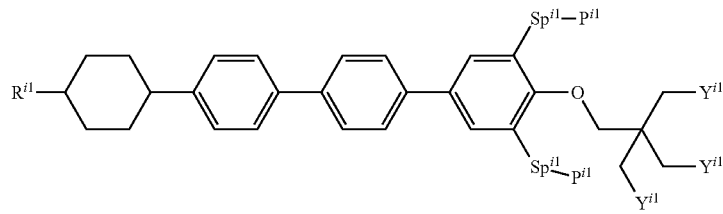
(R-1-219)

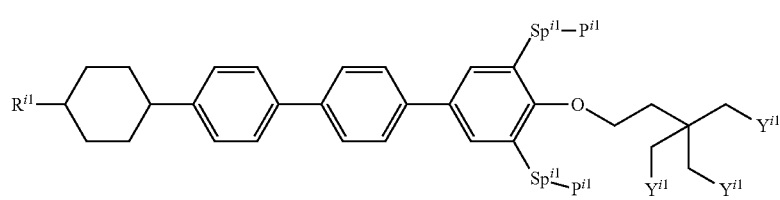
(R-1-220)
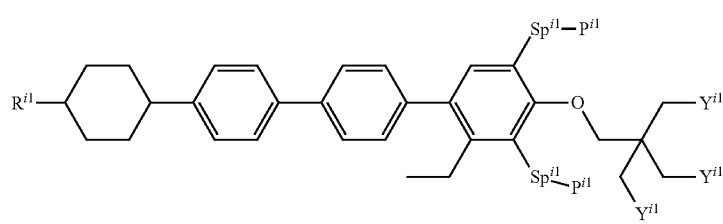
(R-1-221)
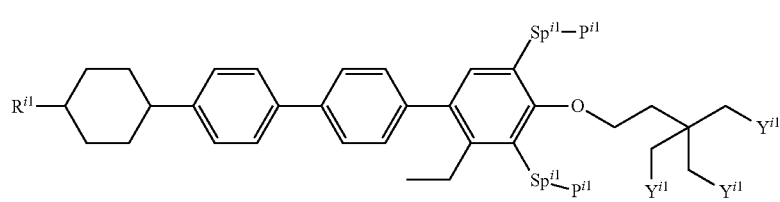
(R-1-222)
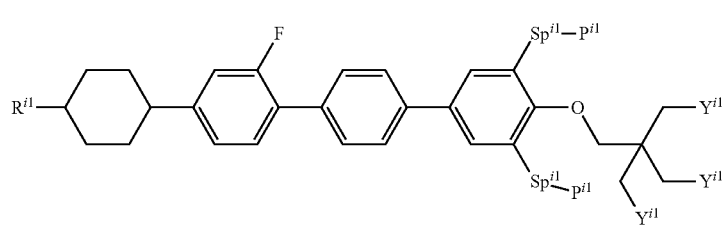
(R-1-223)
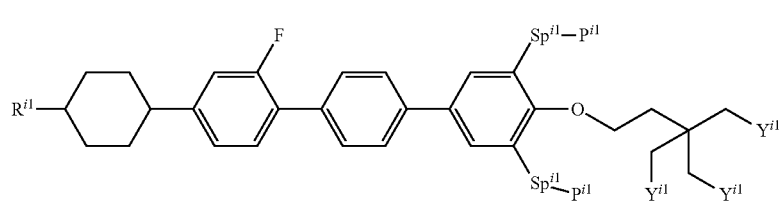
(R-1-224)
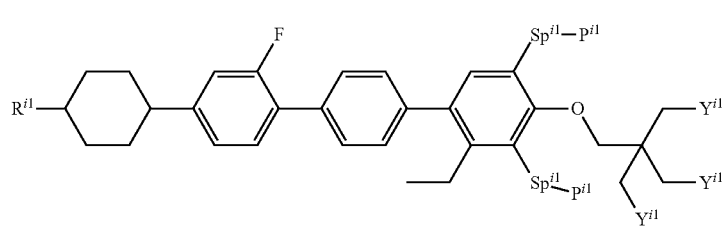
(R-1-225)
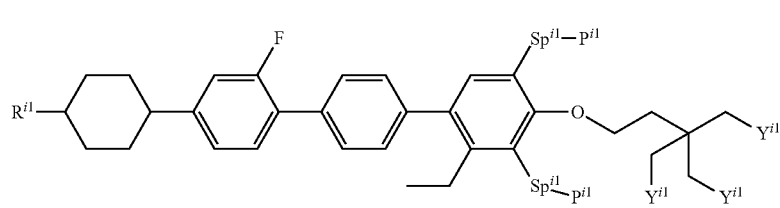
(R-1-226)

-continued
[Chem. 50]
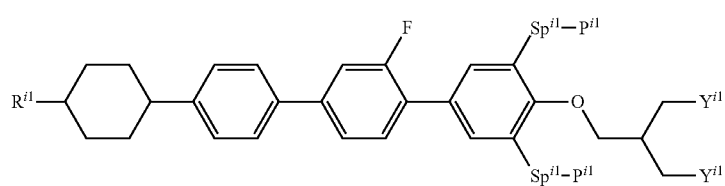
(R-1-227)
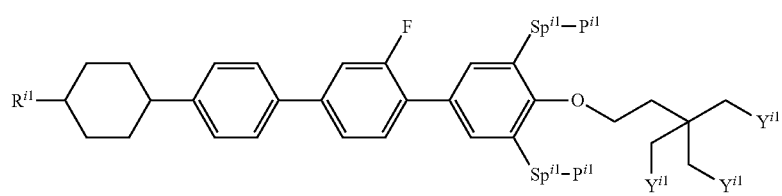
(R-1-228)
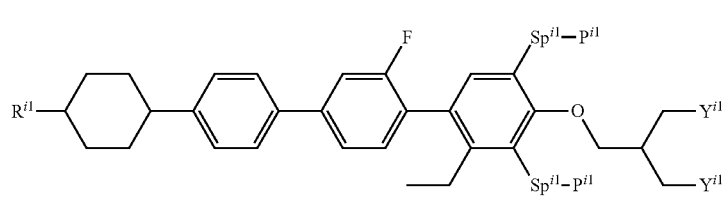
(R-1-229)
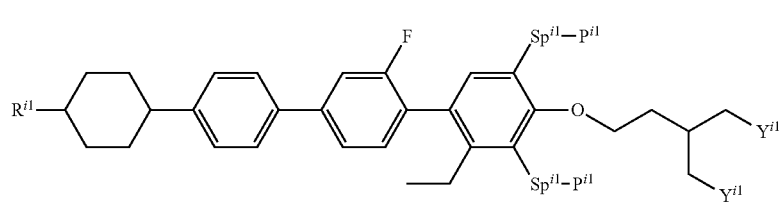
(R-1-230)
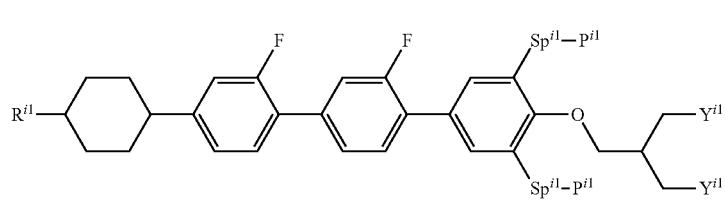
(R-1-231)
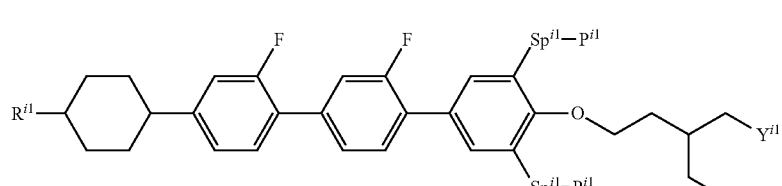
(R-1-232)
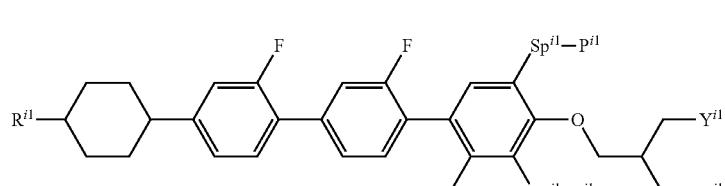
(R-1-233)
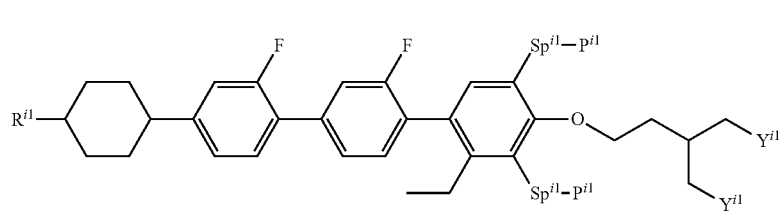
(R-1-234)

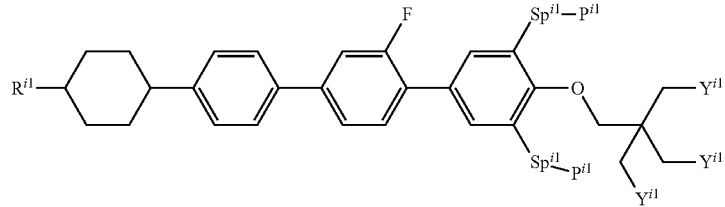
(R-1-235)
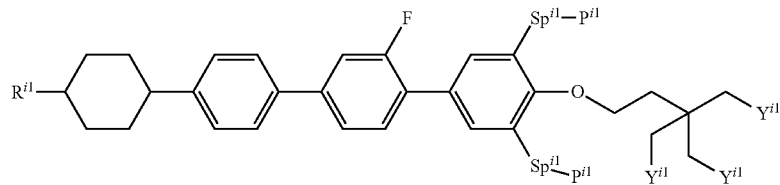
(R-1-236)
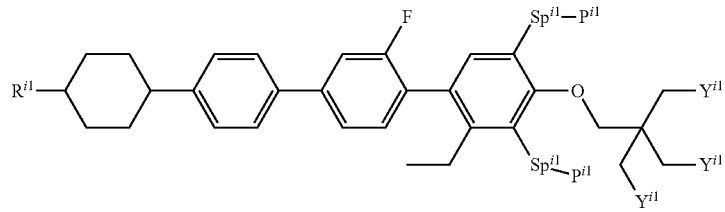
(R-1-237)
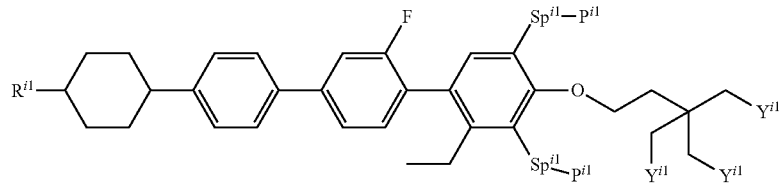
(R-1-238)
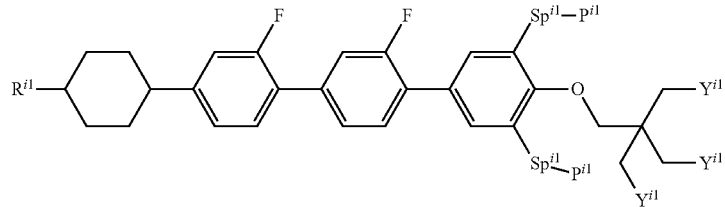
(R-1-239)
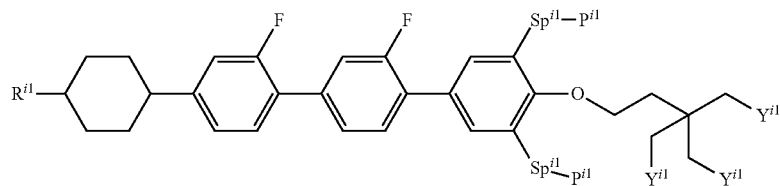
(R-1-240)
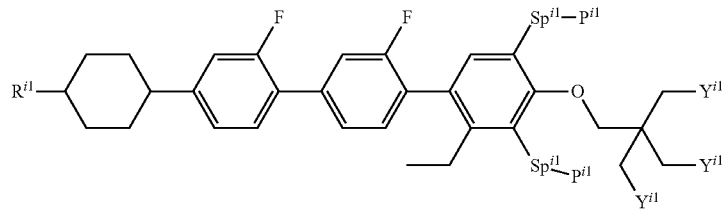
(R-1-241)

(R-1-242)
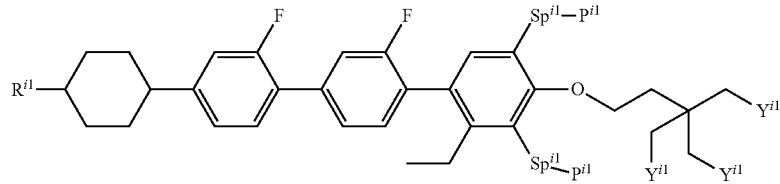
[Chem. 51]
(R-1-243)
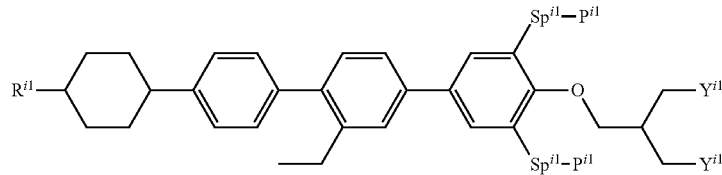
(R-1-244)
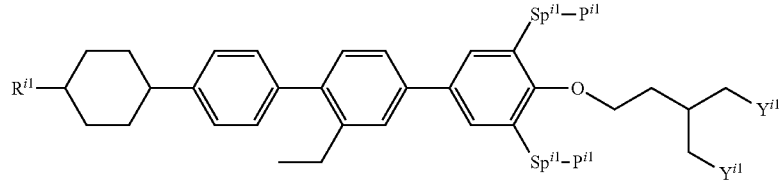
(R-1-245)
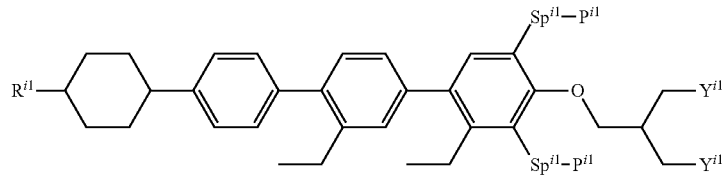
(R-1-246)
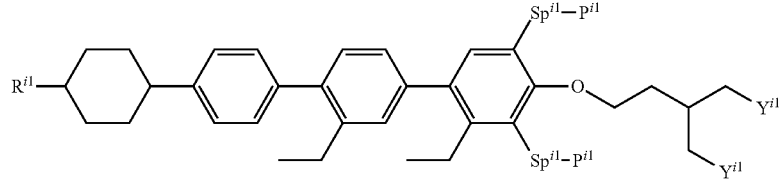
(R-1-247)
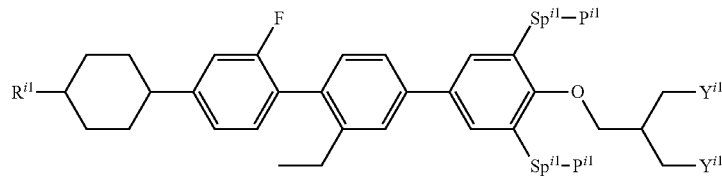
(R-1-248)
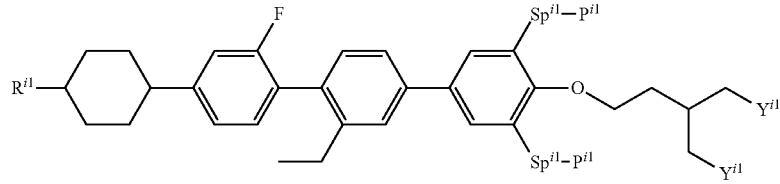
(R-1-249)
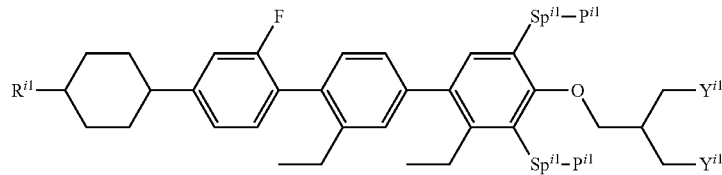

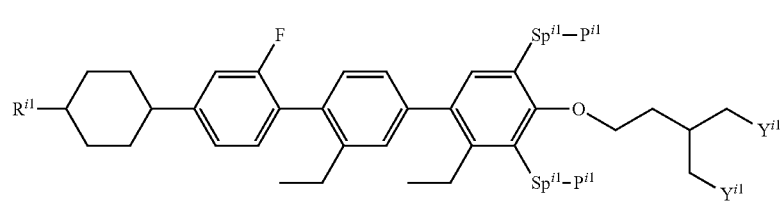
(R-1-250)
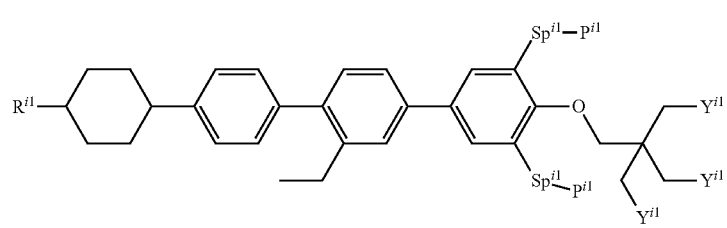
(R-1-251)
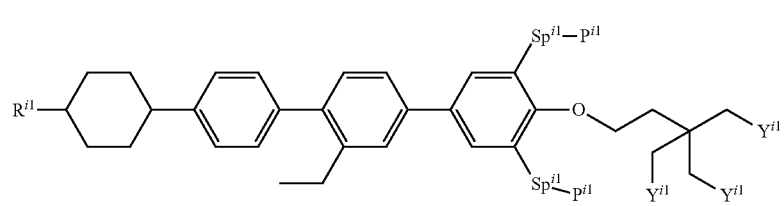
(R-1-252)
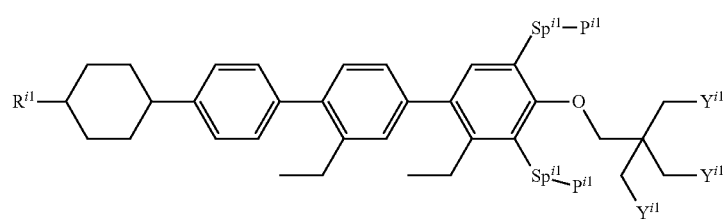
(R-1-253)
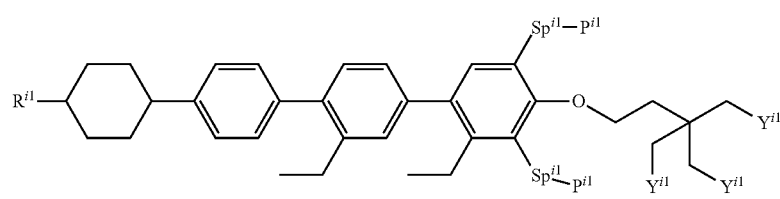
(R-1-254)
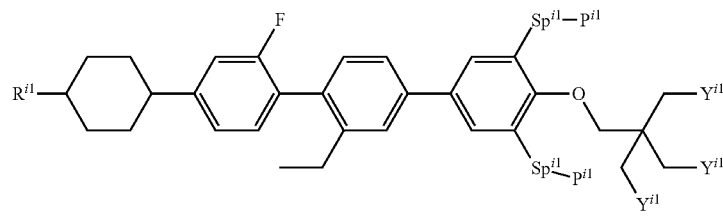
(R-1-255)
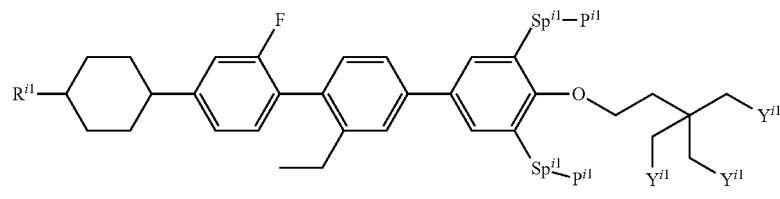
(R-1-256)

-continued
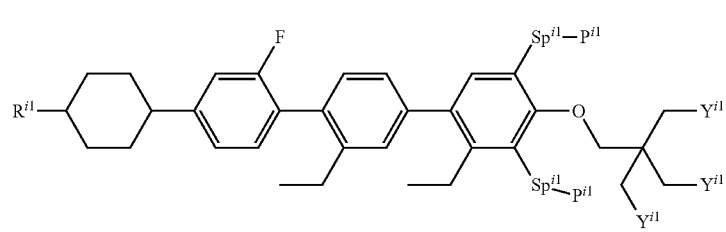
(R-1-257)
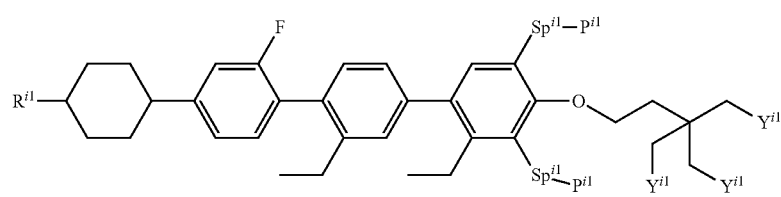
(R-1-258)
[Chem. 52]
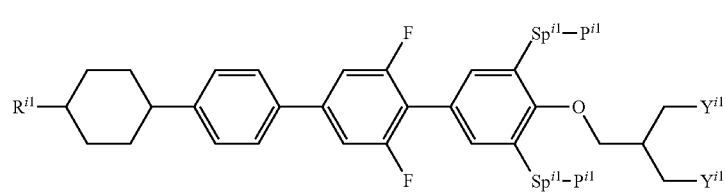
(R-1-259)
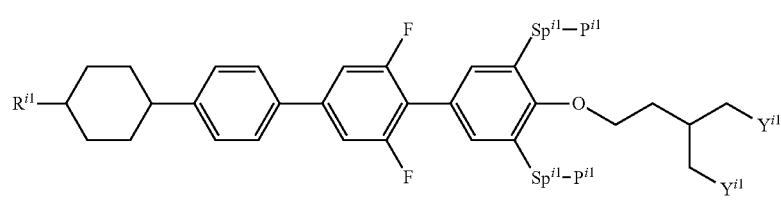
(R-1-260)
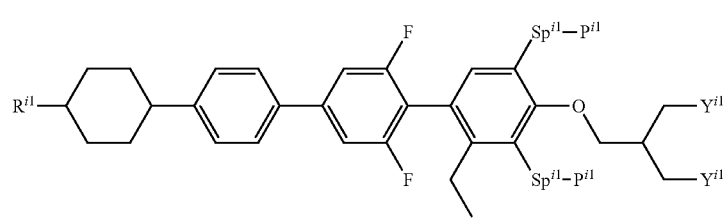
(R-1-261)
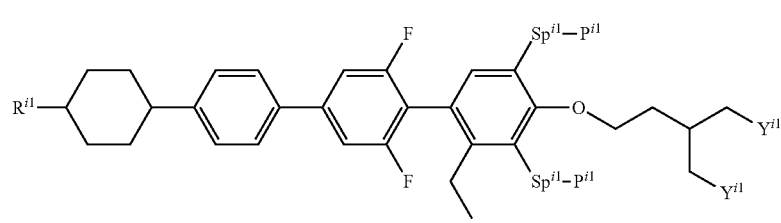
(R-1-262)
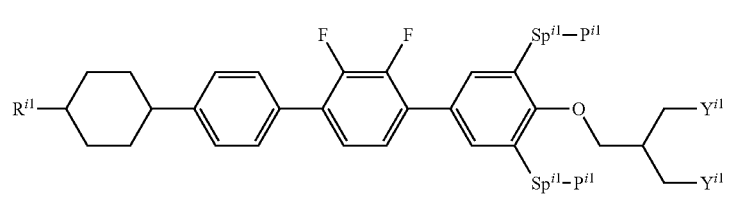
(R-1-263)

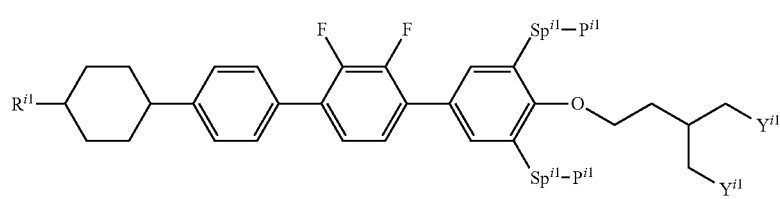
(R-1-264)
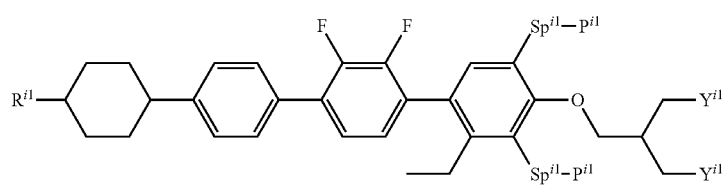
(R-1-265)
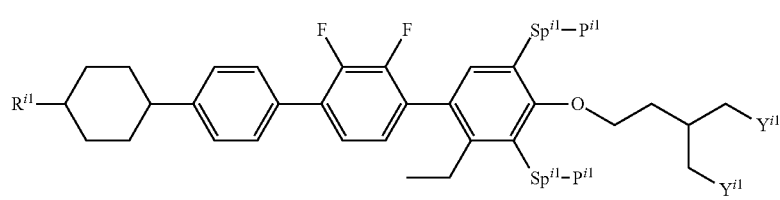
(R-1-266)
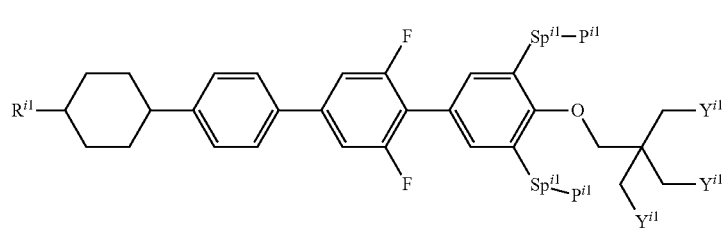
(R-1-267)
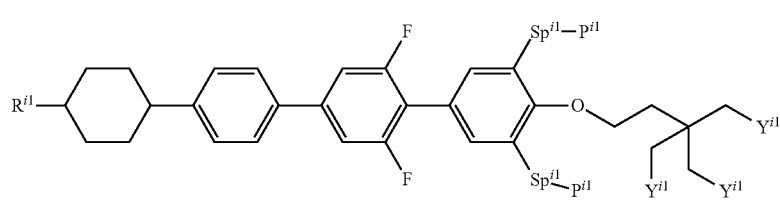
(R-1-268)
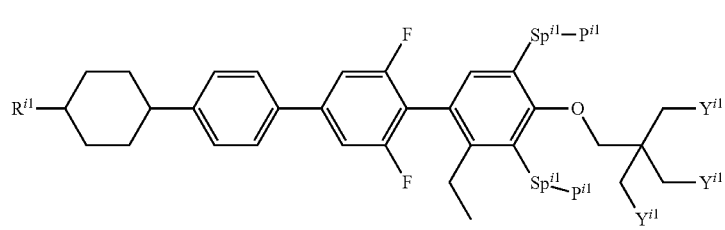
(R-1-269)
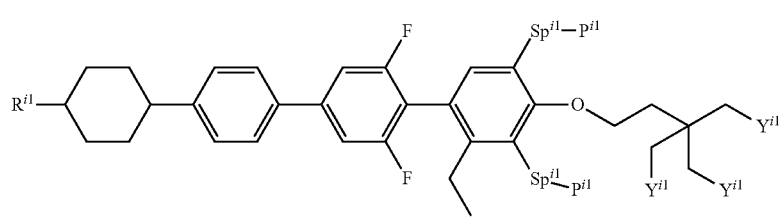
(R-1-270)
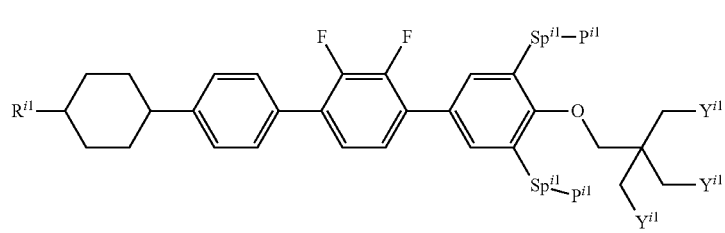
(R-1-271)

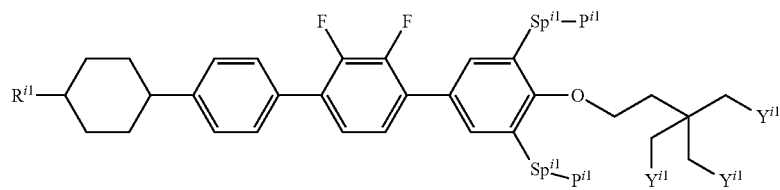
(R-1-272)
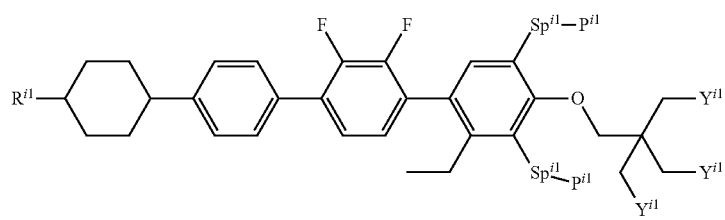
(R-1-273)
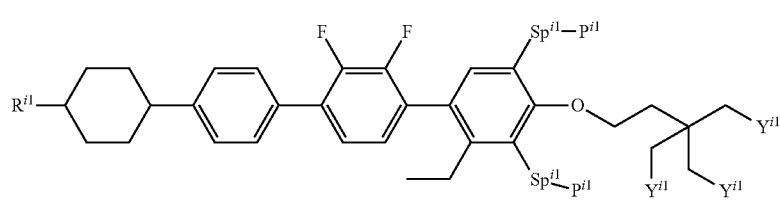
(R-1-274)
[Chem. 53]
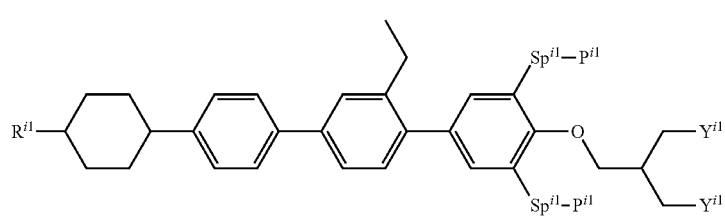
(R-1-275)
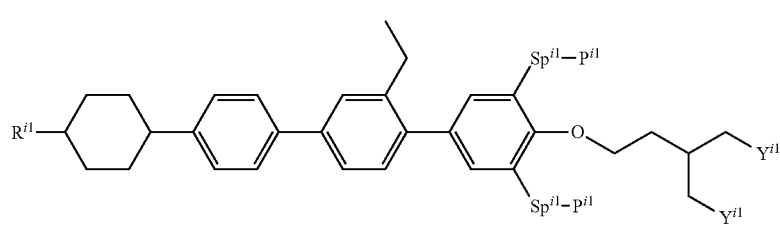
(R-1-276)
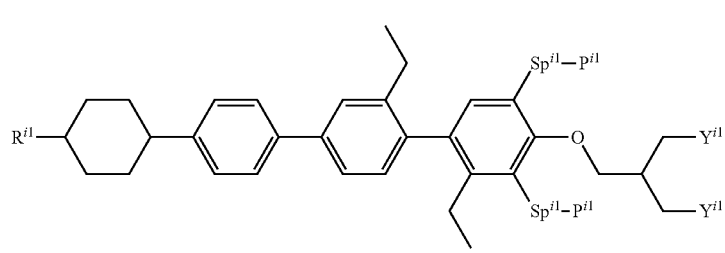
(R-1-277)
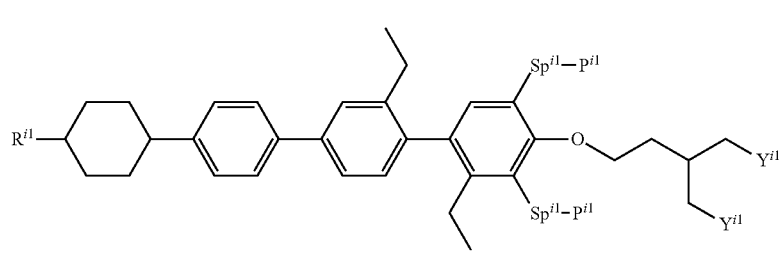
(R-1-278)

-continued
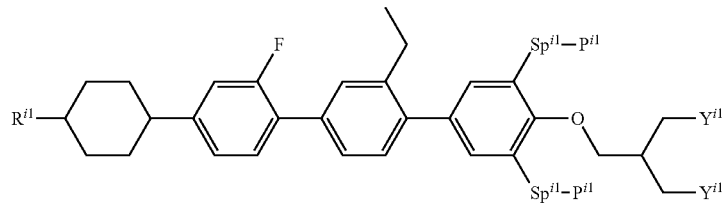
(R-1-279)
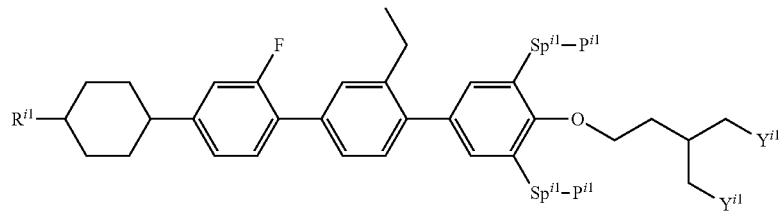
(R-1-280)
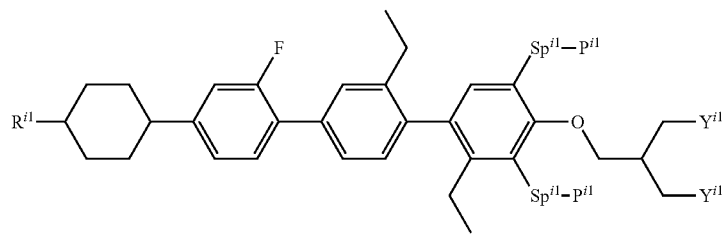
(R-1-281)
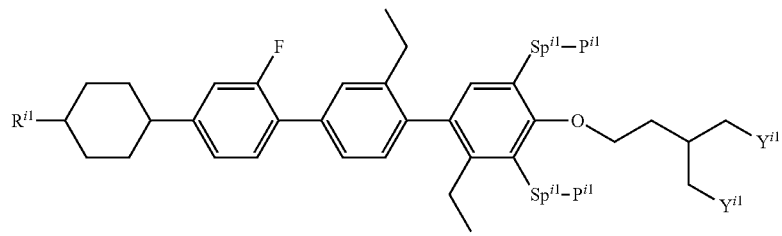
(R-1-282)
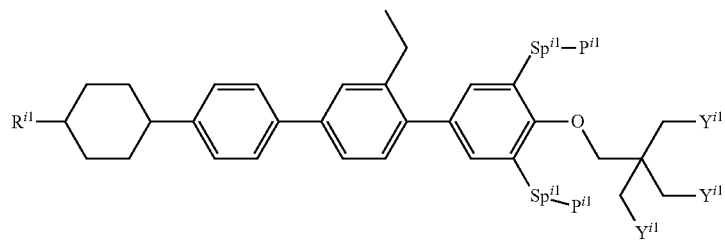
(R-1-283)
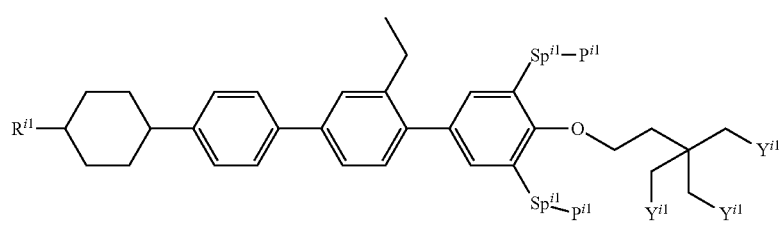
(R-1-284)
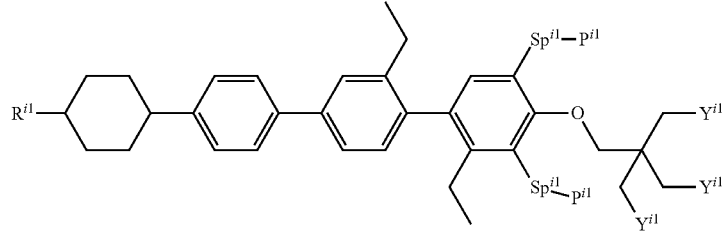
(R-1-285)

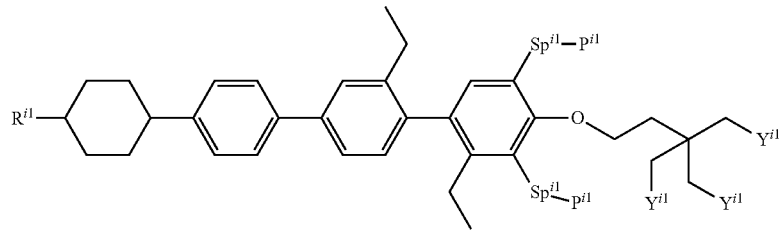
(R-1-286)
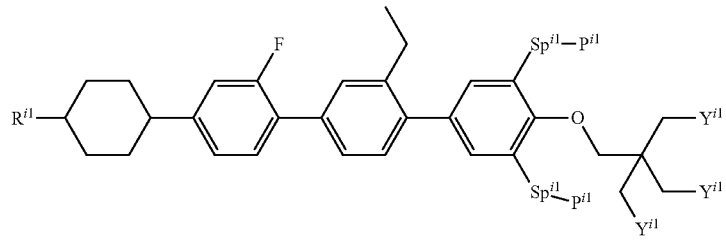
(R-1-287)
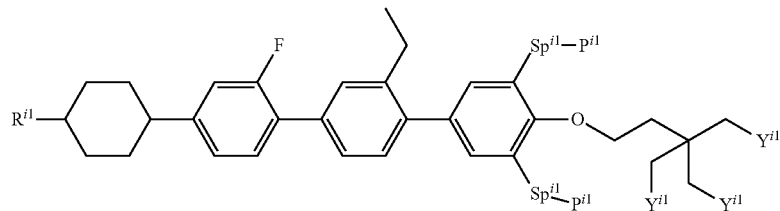
(R-1-288)
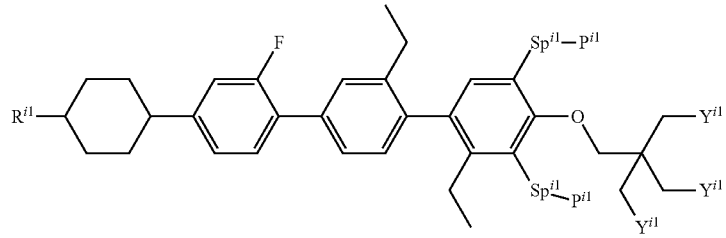
(R-1-289)
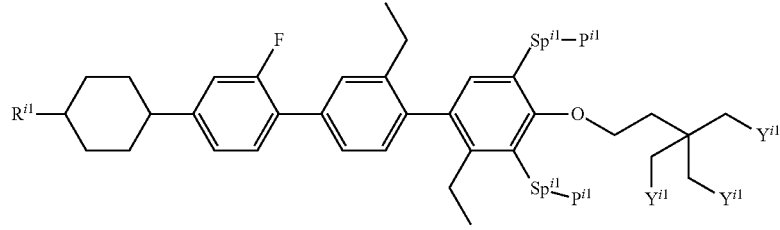
(R-1-290)
[Chem. 54]
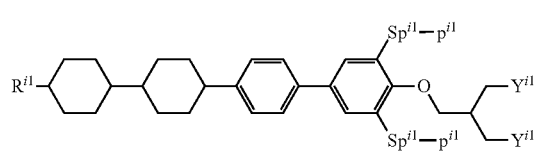
(R-1-291)

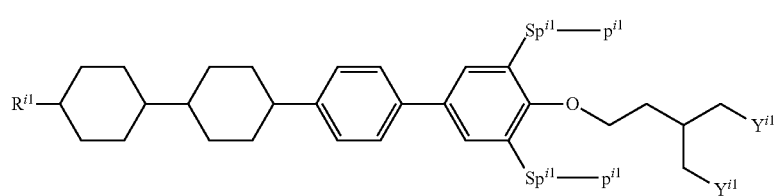
(R-1-292)
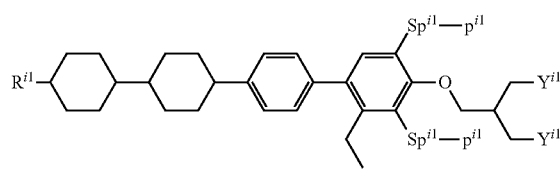
(R-1-293)
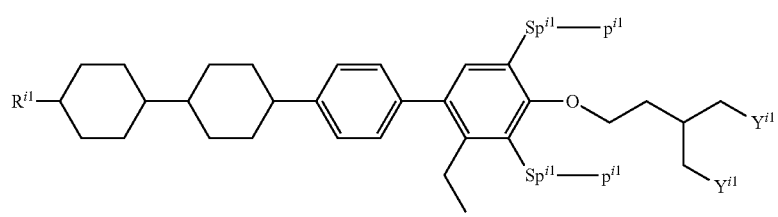
(R-1-294)
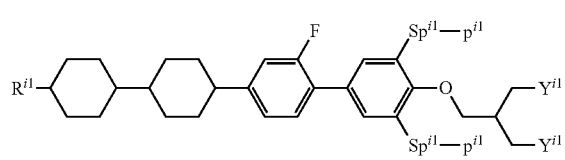
(R-1-295)
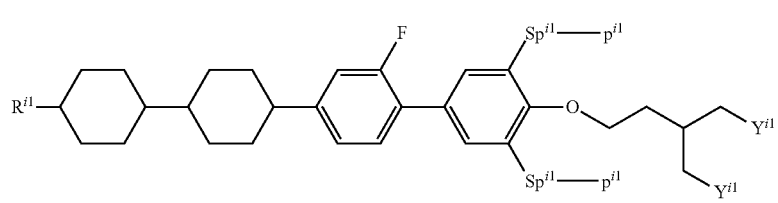
(R-1-296)
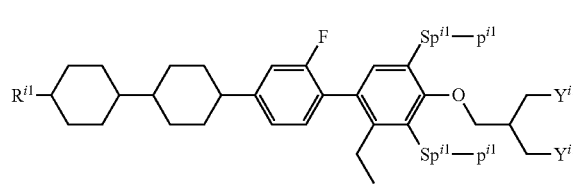
(R-1-297)
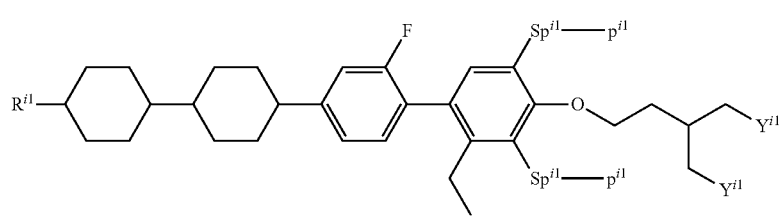
(R-1-298)
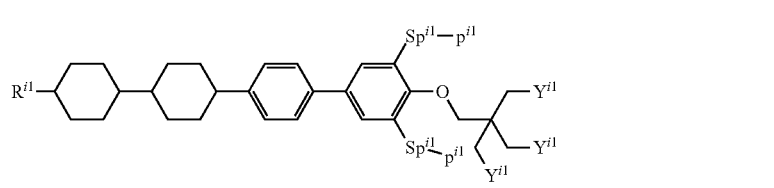
(R-1-299)

-continued
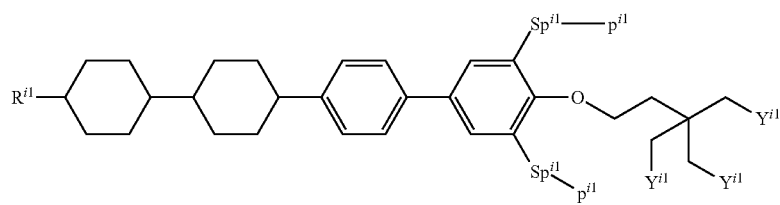
(R-1-300)
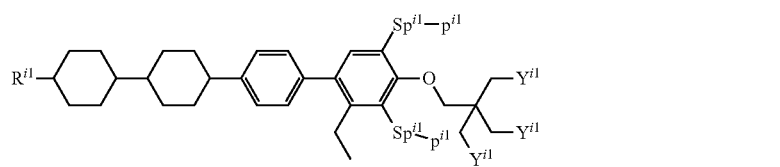
(R-1-301)
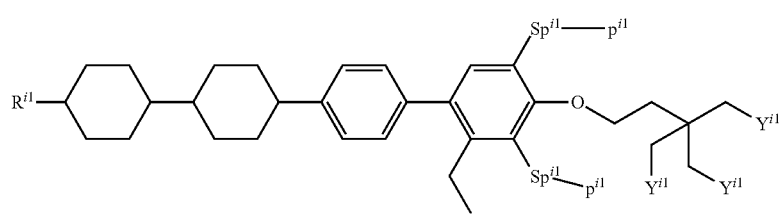
(R-1-302)
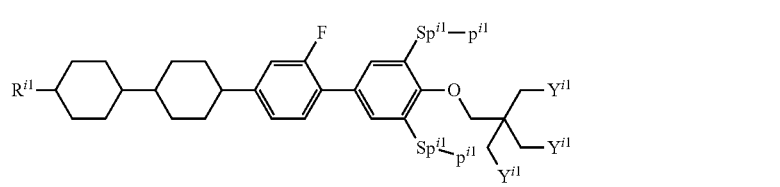
(R-1-303)
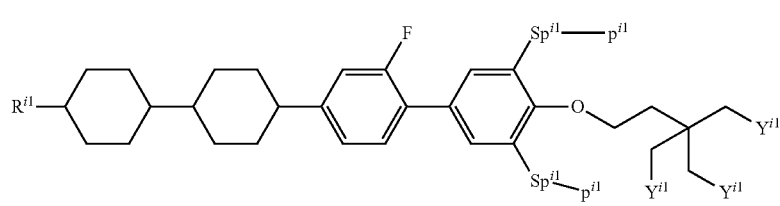
(R-1-304)
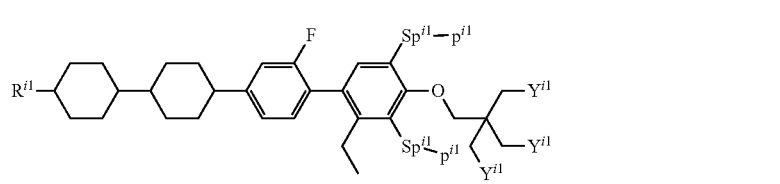
(R-1-305)
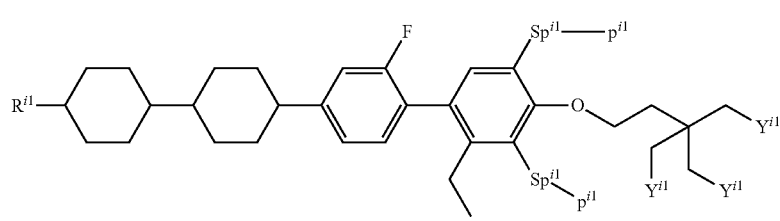
(R-1-306)
[Chem. 55]
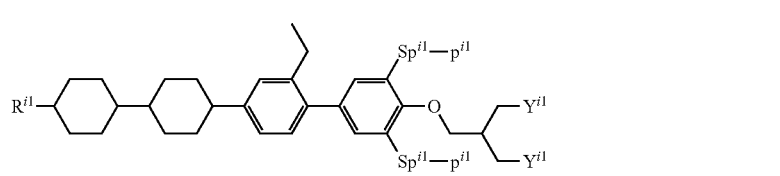
(R-1-307)

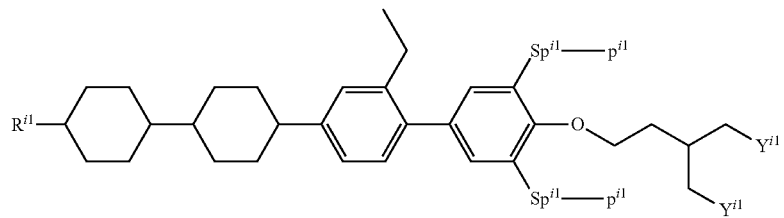
(R-1-308)
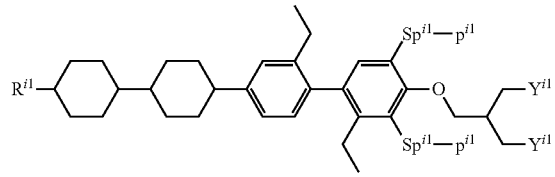
(R-1-309)
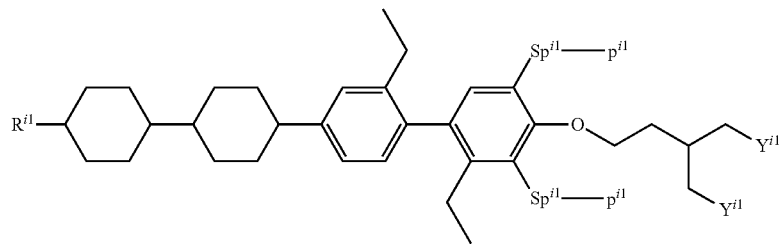
(R-1-310)
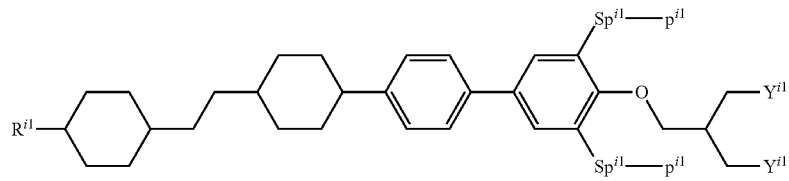
(R-1-311)
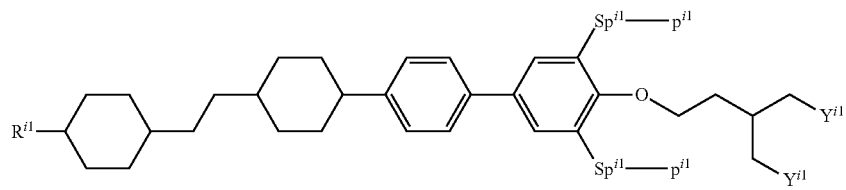
(R-1-312)
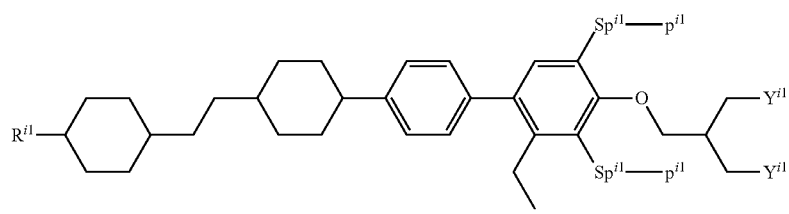
(R-1-313)
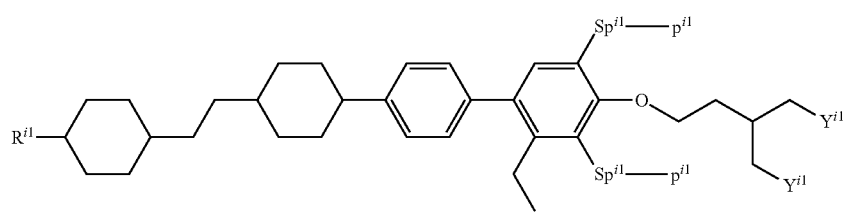
(R-1-314)

-continued
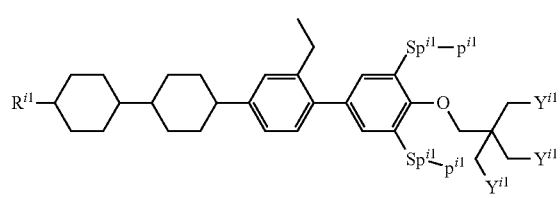
(R-1-315)
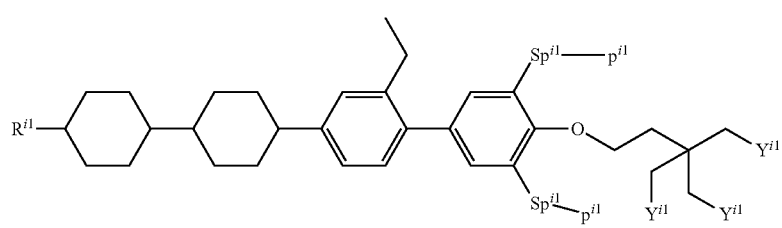
(R-1-316)
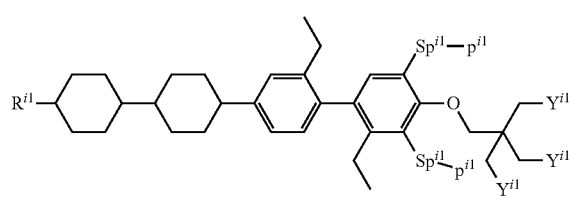
(R-1-317)
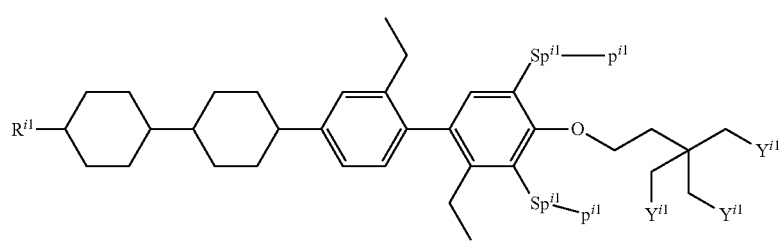
(R-1-318)
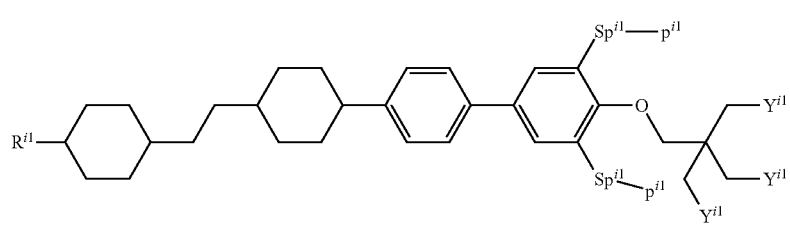
(R-1-319)
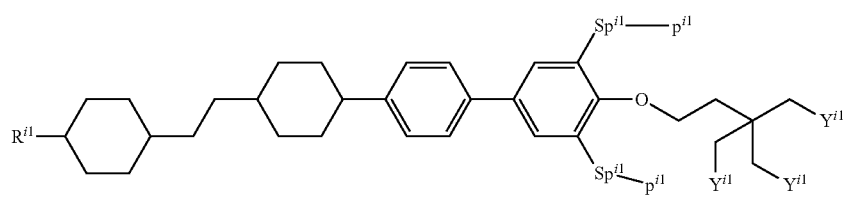
(R-1-320)
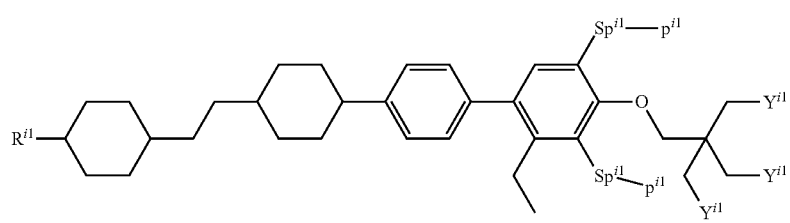
(R-1-321)

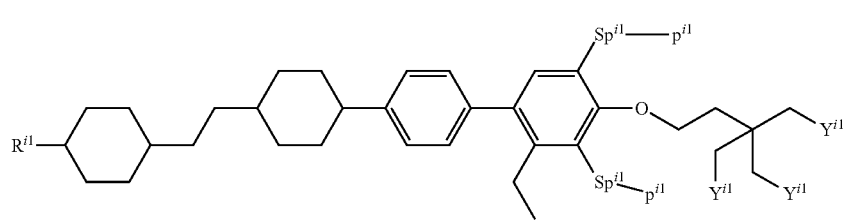
(R-1-322)
[Chem. 56]
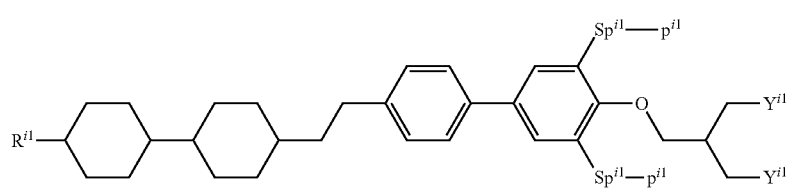
(R-1-323)
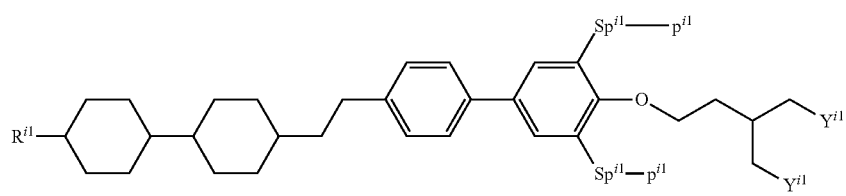
(R-1-324)
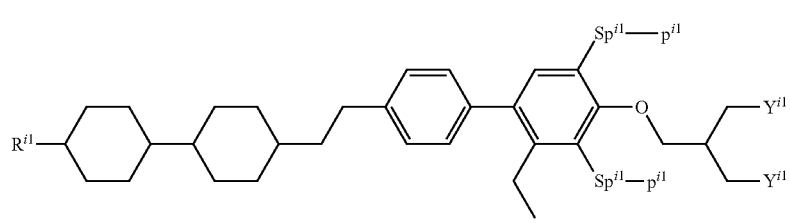
(R-1-325)
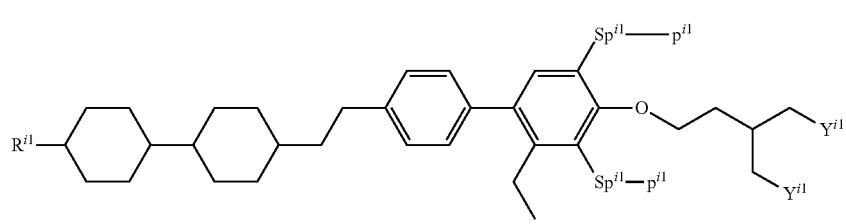
(R-1-326)
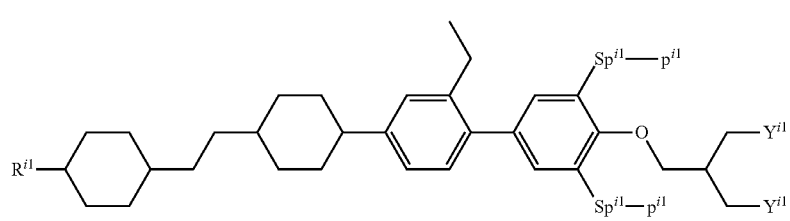
(R-1-327)
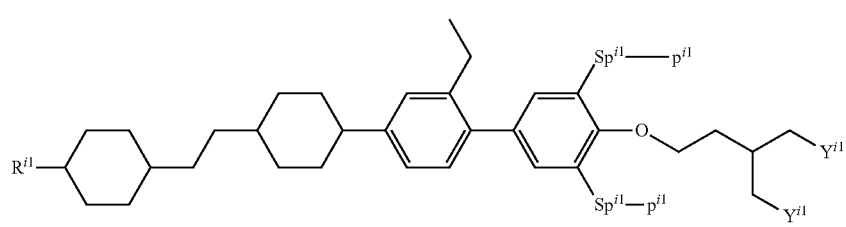
(R-1-328)

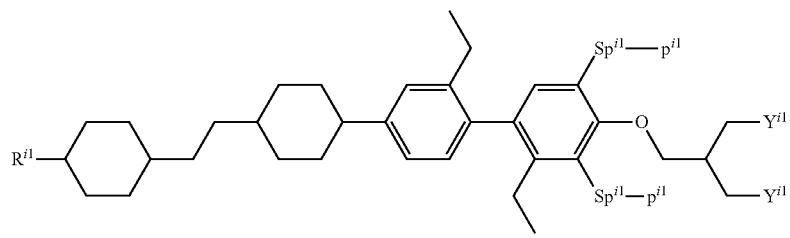
(R-1-329)
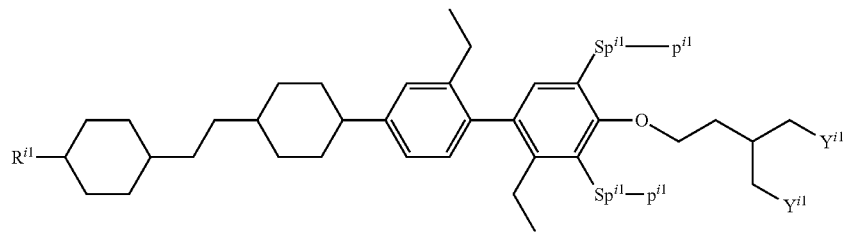
(R-1-330)
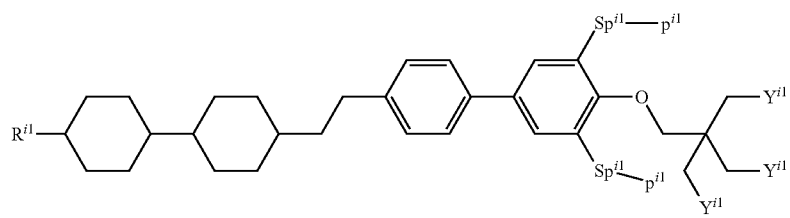
(R-1-331)
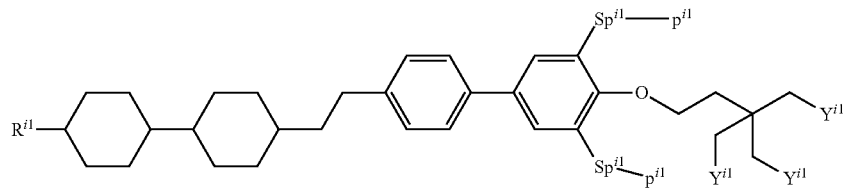
(R-1-332)
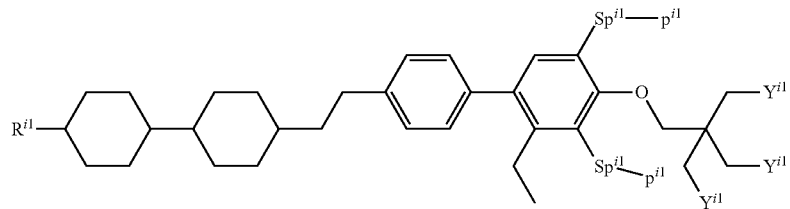
(R-1-333)
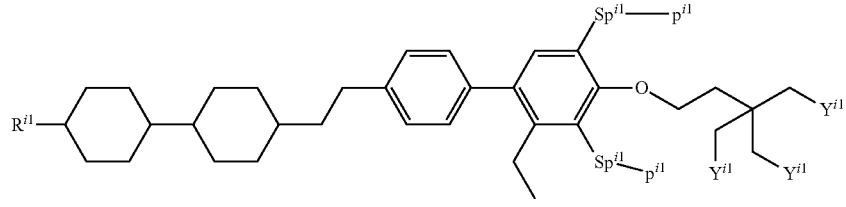
(R-1-334)
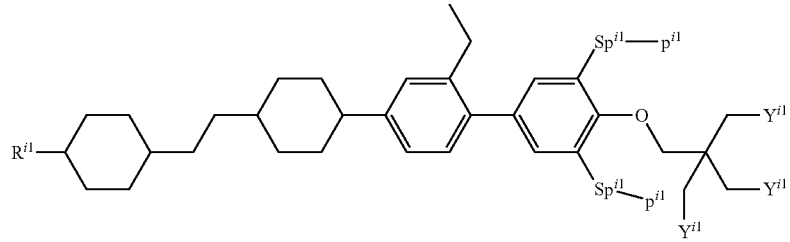
(R-1-335)

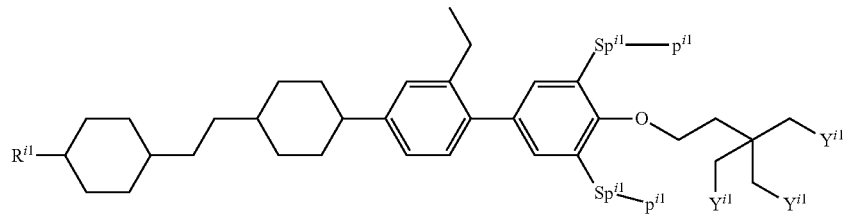
(R-1-336)
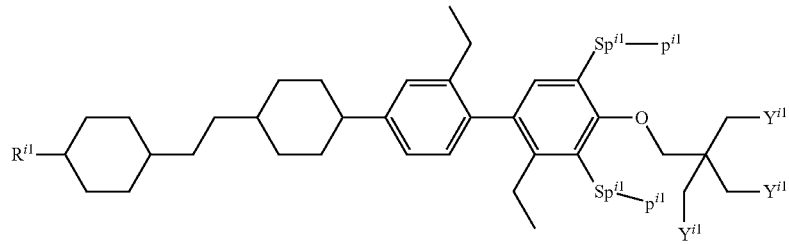
(R-1-337)
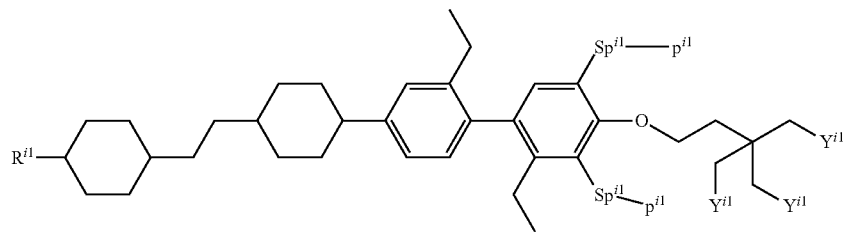
(R-1-338)
[Chem. 57]
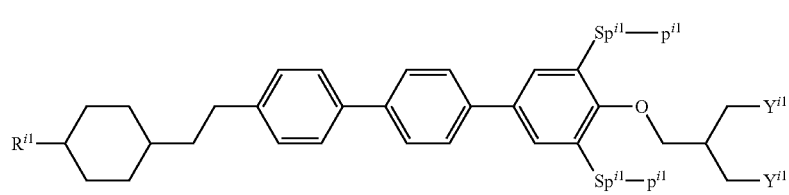
(R-1-339)
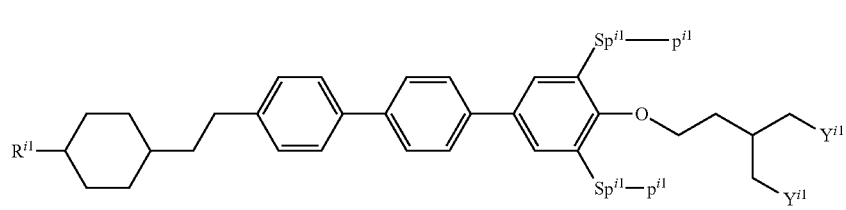
(R-1-340)
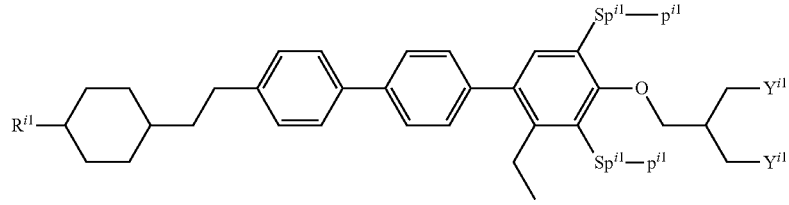
(R-1-341)
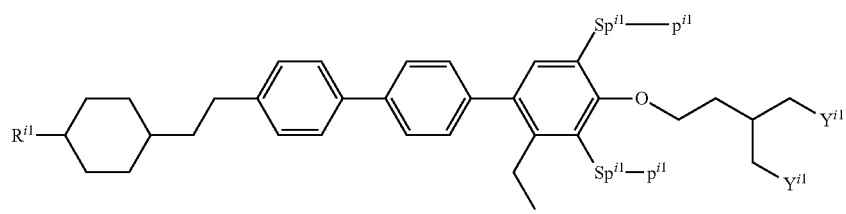
(R-1-342)

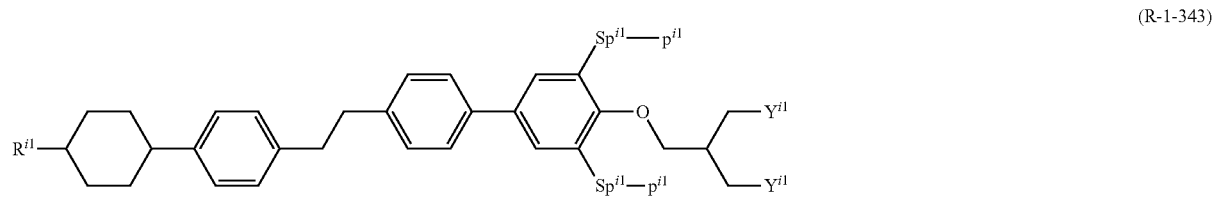
(R-1-343)
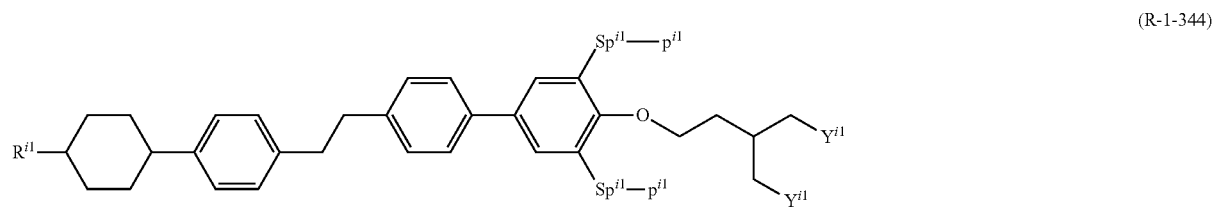
(R-1-344)
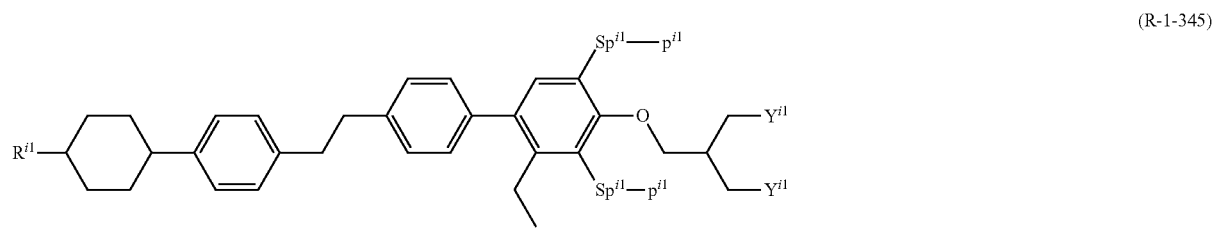
(R-1-345)
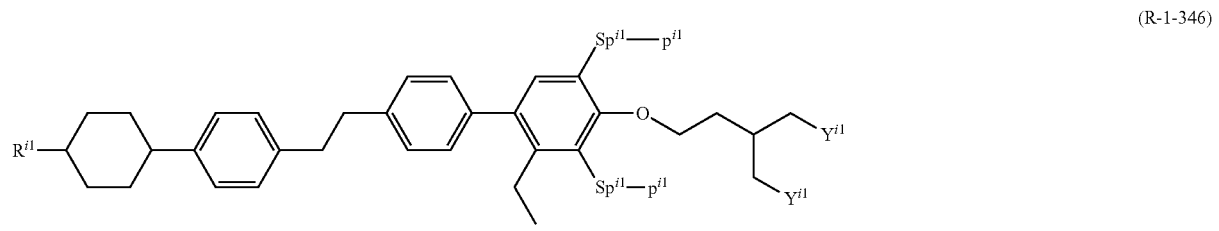
(R-1-346)
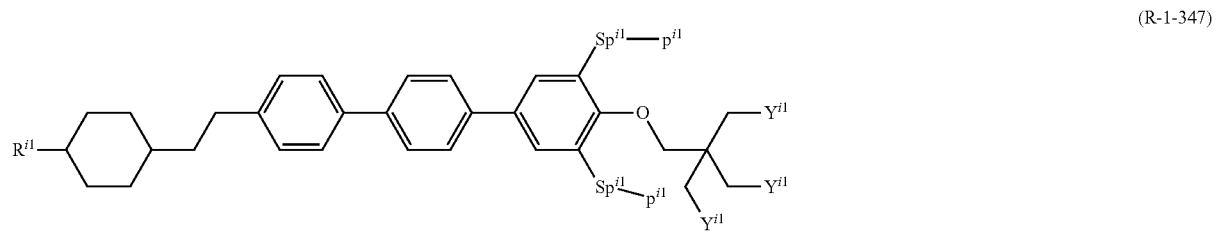
(R-1-347)
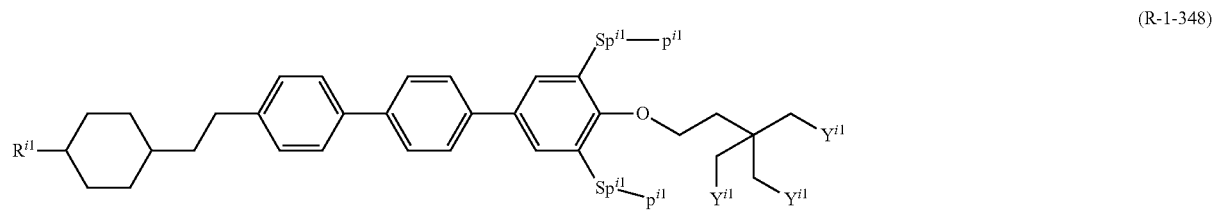
(R-1-348)
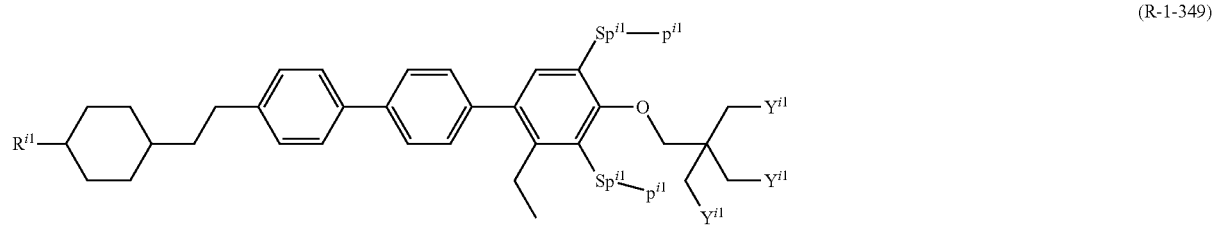
(R-1-349)

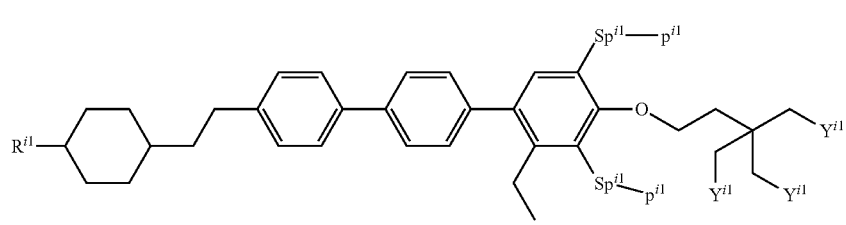
(R-1-350)
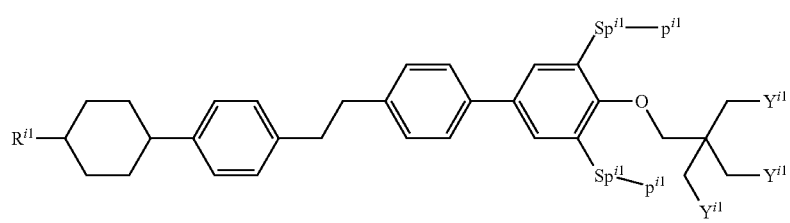
(R-1-351)
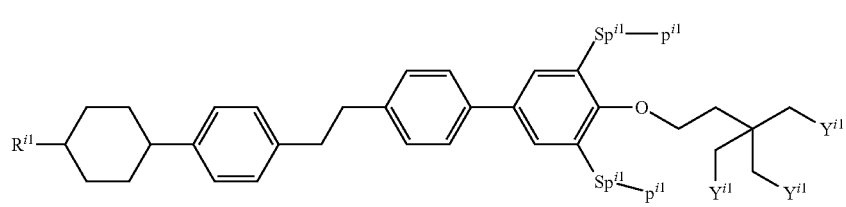
(R-1-352)
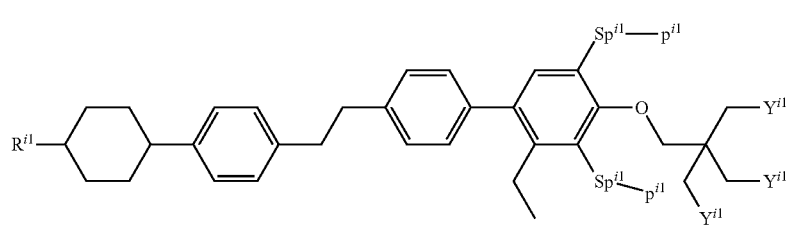
(R-1-353)
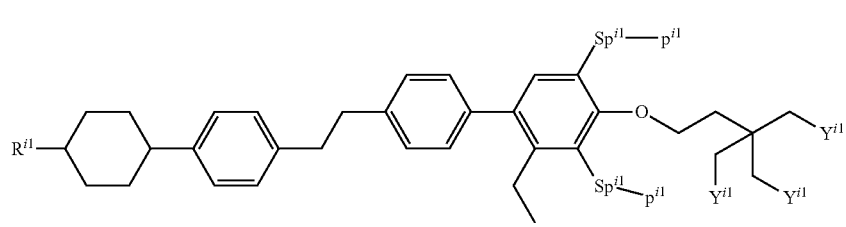
(R-1-354)
[Chem. 58]
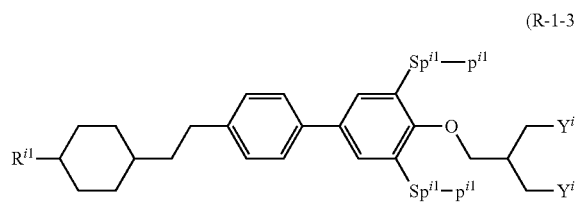
(R-1-355)
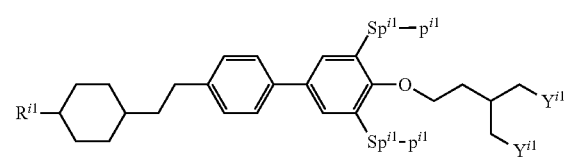
(R-1-356)
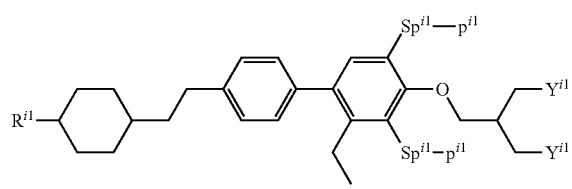
(R-1-357)
(R-1-358)

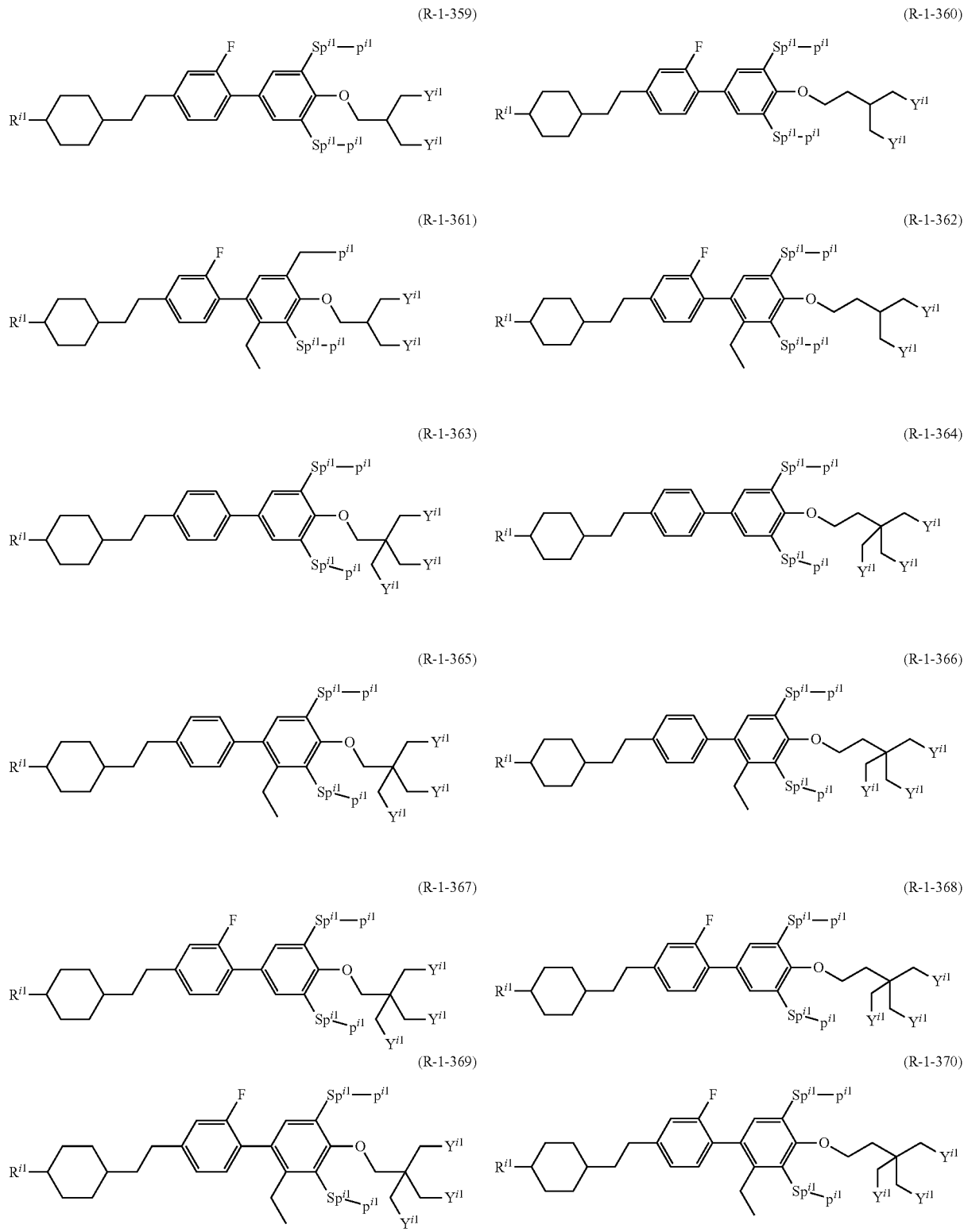
In the formulae, $R^{i1}$, $p^{i1}$, $S^{i1}$, and $Y^{i1}$ have the same meaning as, respectively, $R^{i1}$, $p^{i1}$, $S^{i1}$, and $Y^{i1}$ in general formula (i) and general formula (K-1).
More specific examples of compounds represented by general formula (i) include compounds of (P-1) to (P-695), show below.

[Chem. 59]
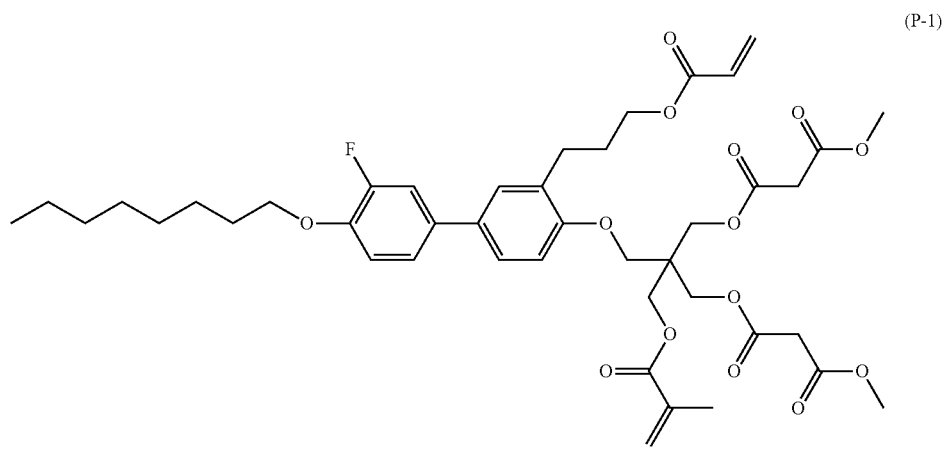
(P-1)
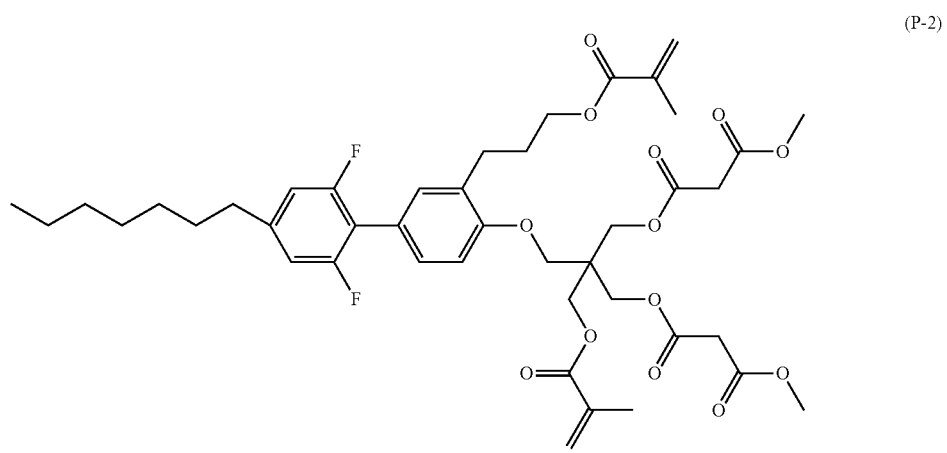
(P-2)
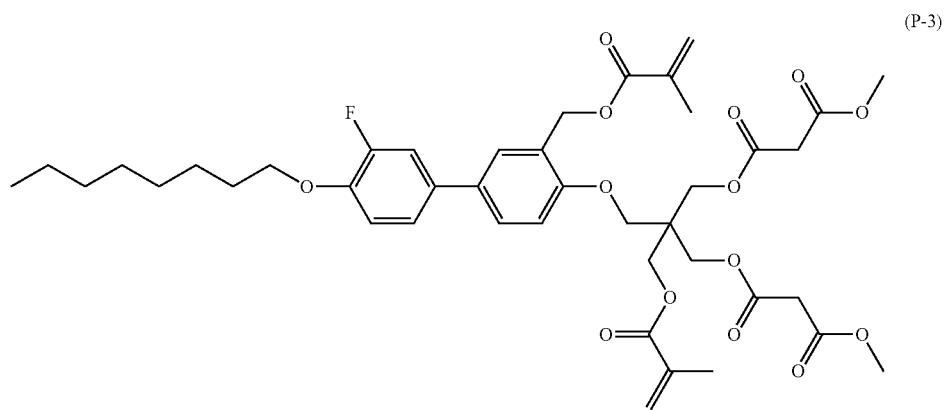
(P-3)

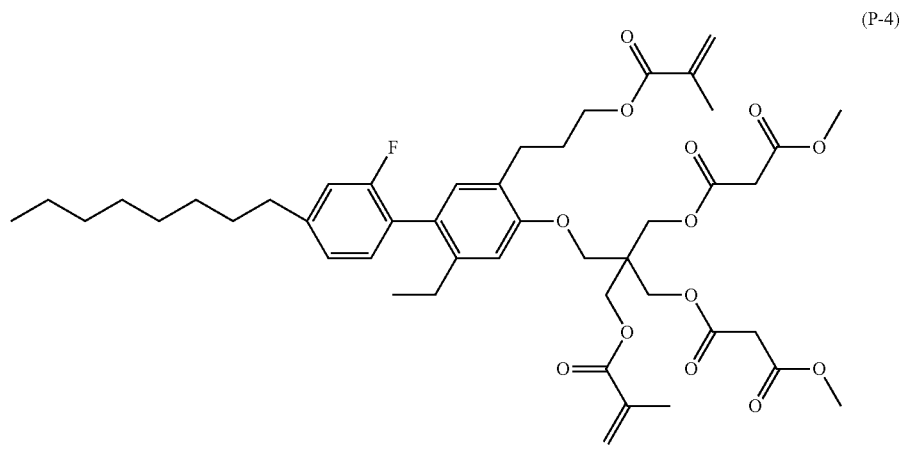
(P-4)
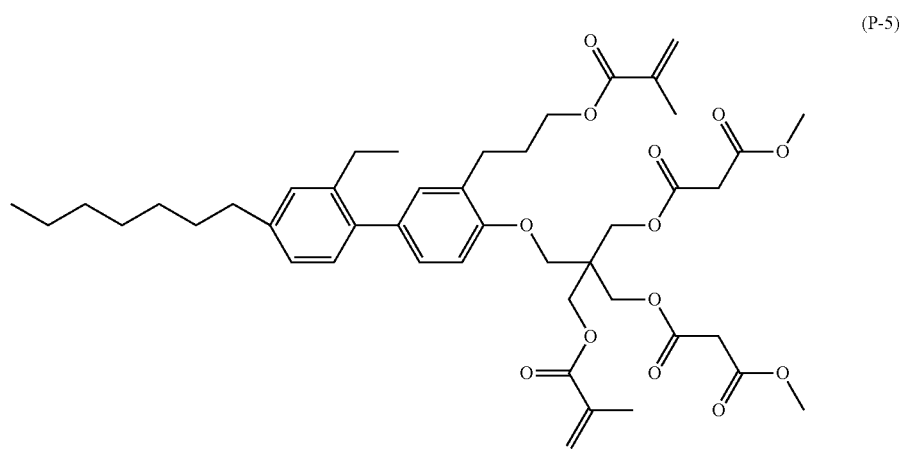
(P-5)
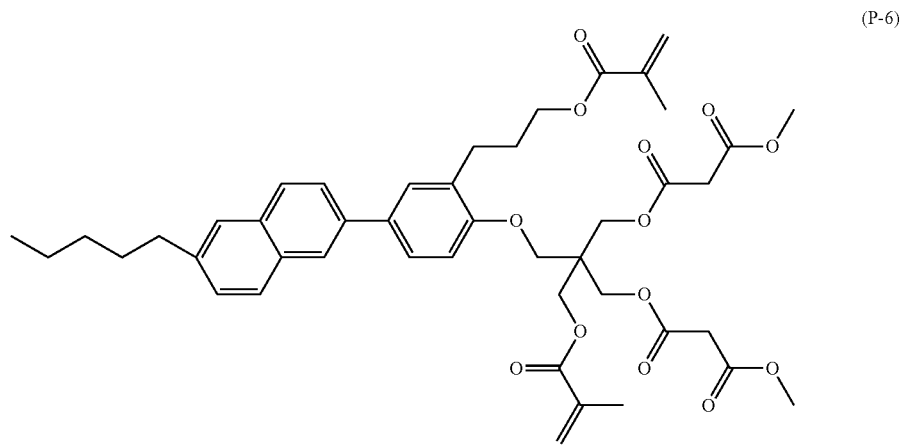
(P-6)

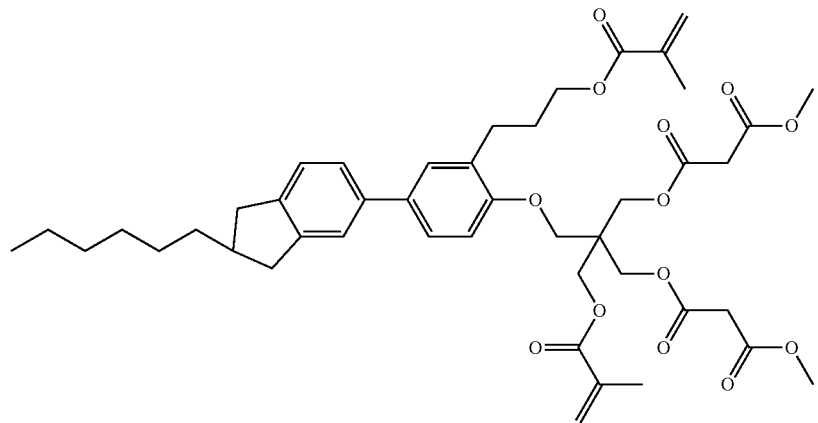
(P-7)
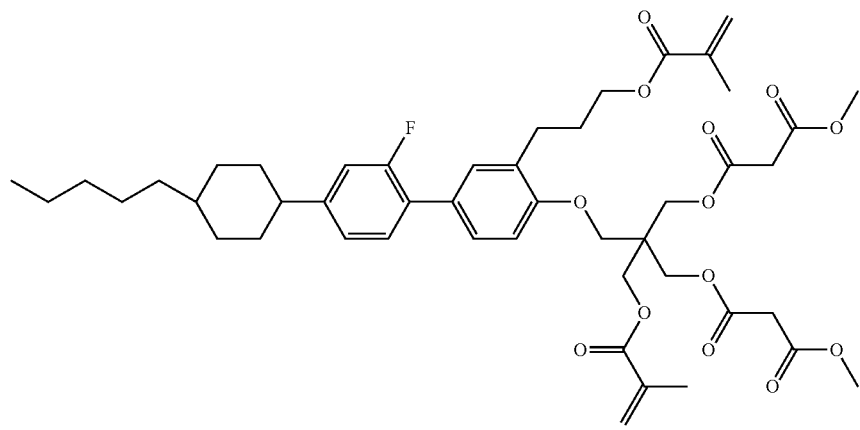
(P-8)
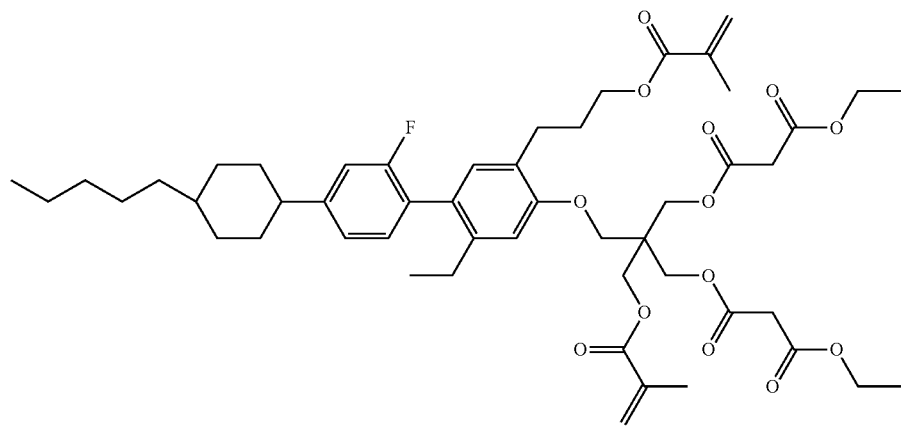
(P-9)

-continued
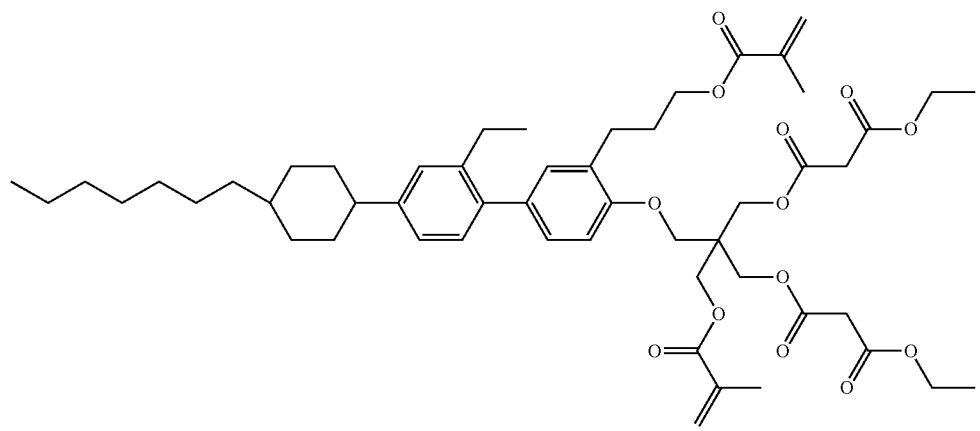
(P-10)
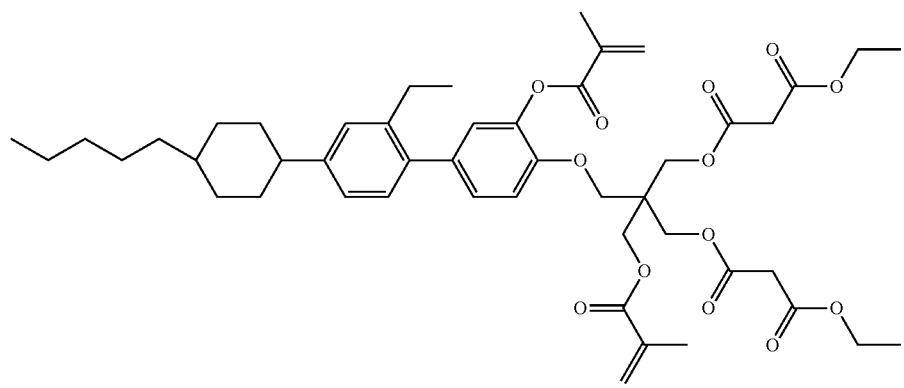
(P-11)
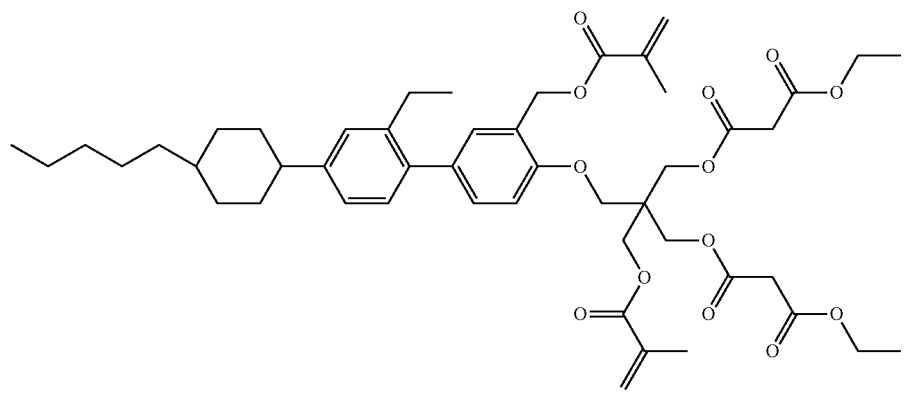
(P-12)
[Chem. 60]
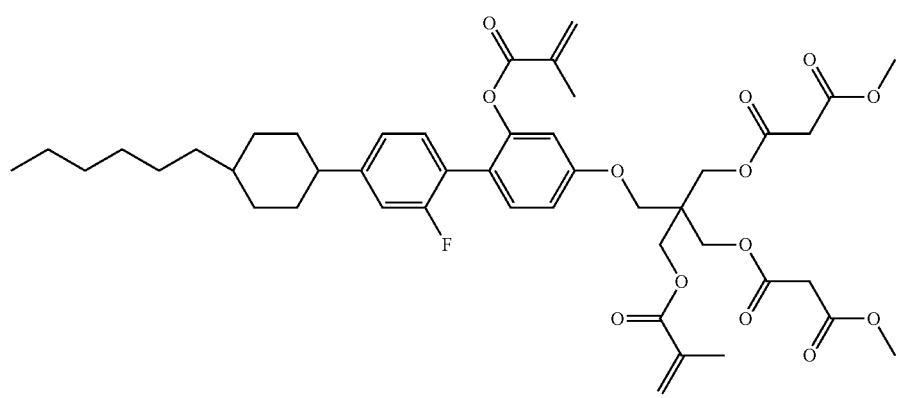
(P-13)

-continued
(P-14)
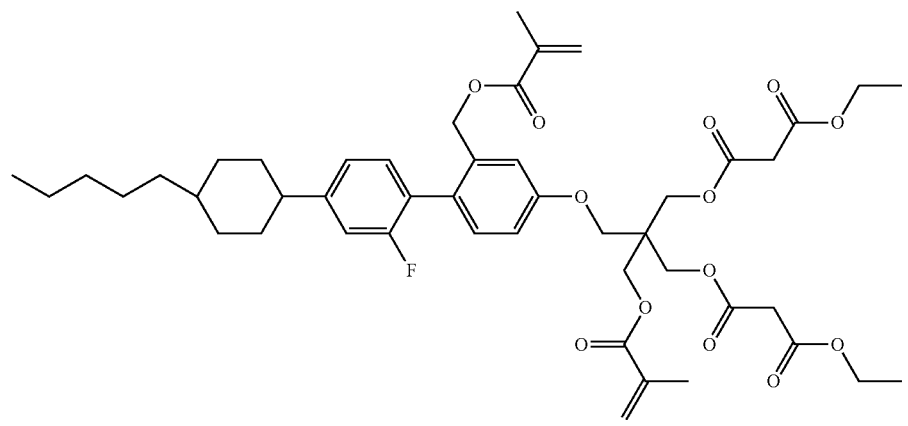
(P-15)
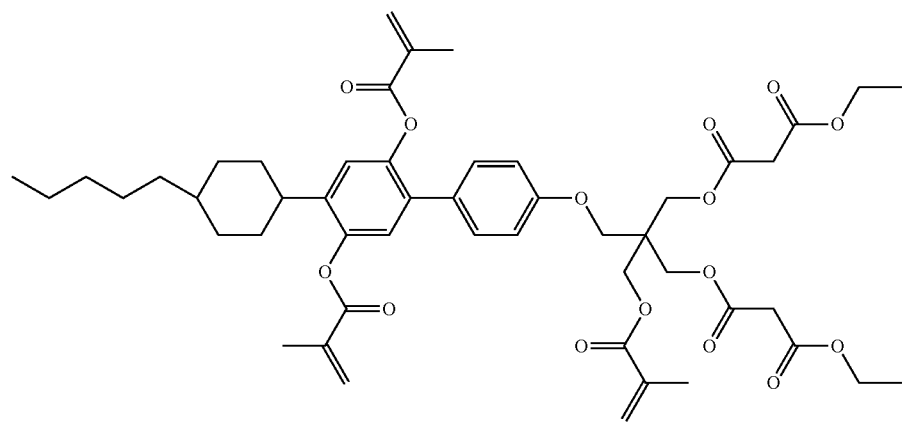
(P-16)
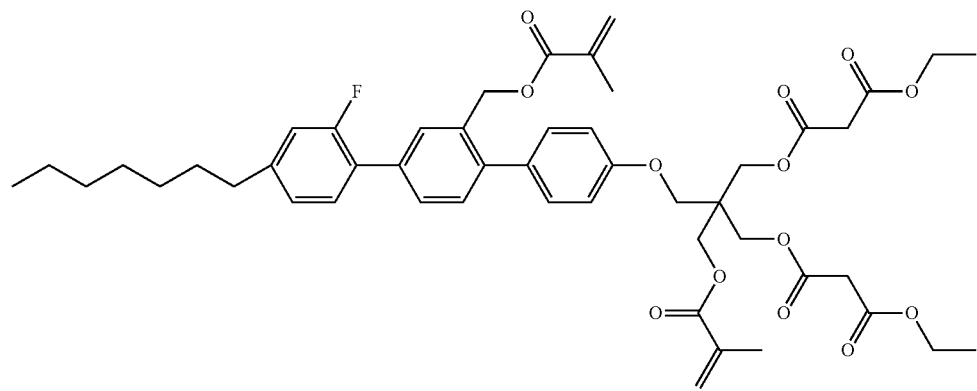
(P-17)
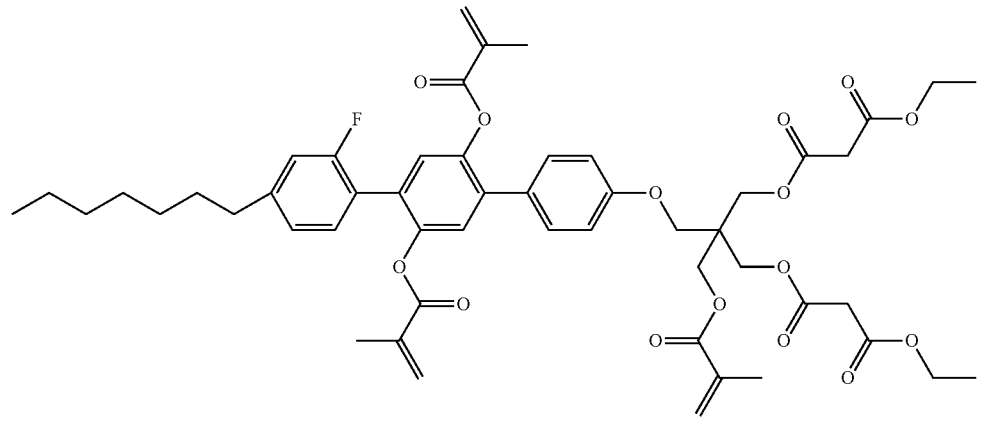

-continued
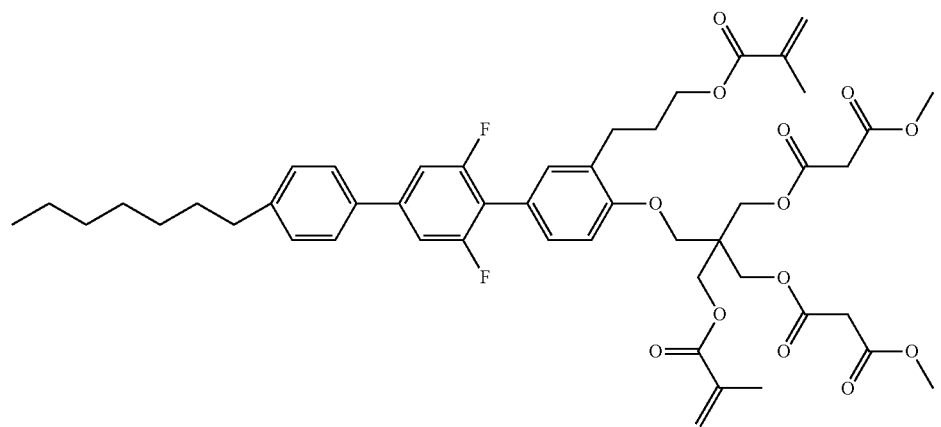
(P-18)
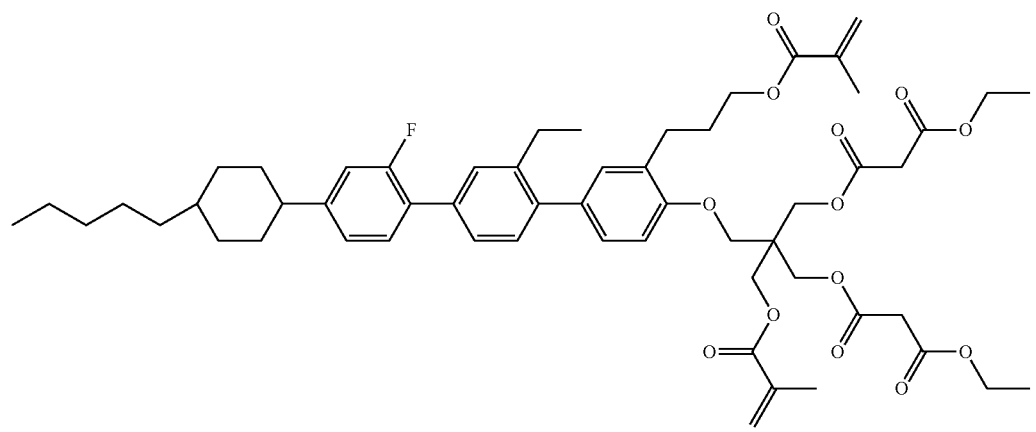
(P-19)
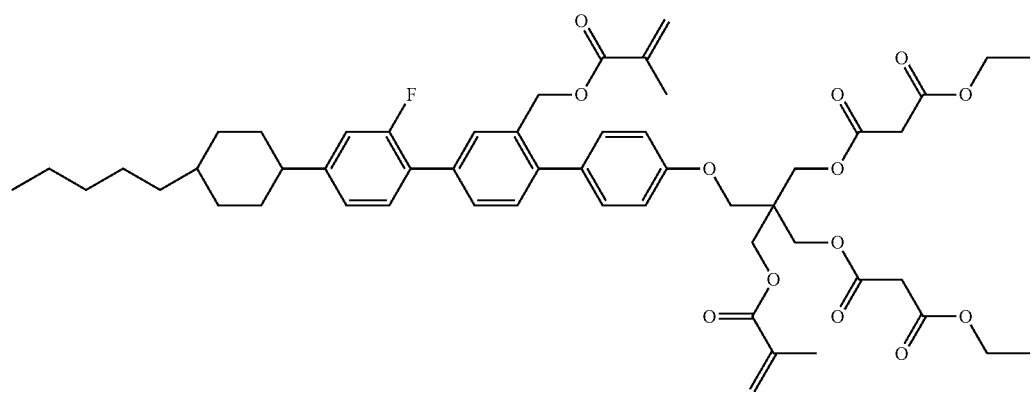
(P-20)

-continued
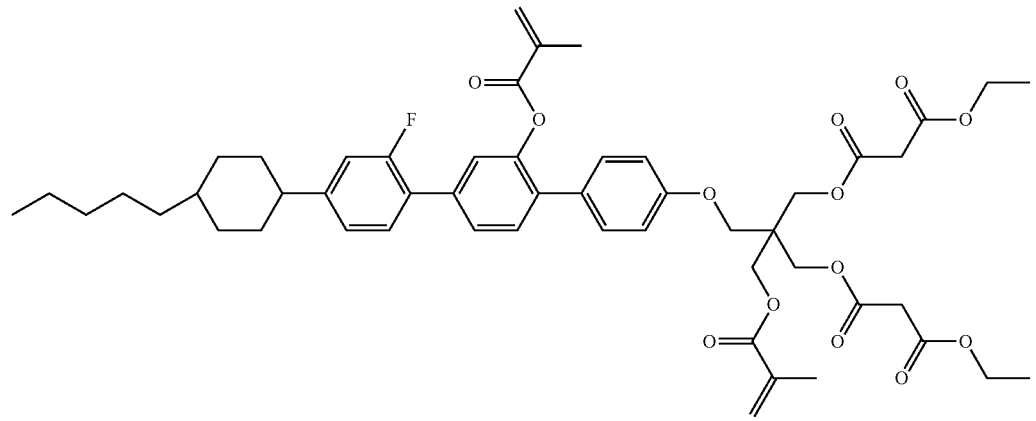
(P-21)
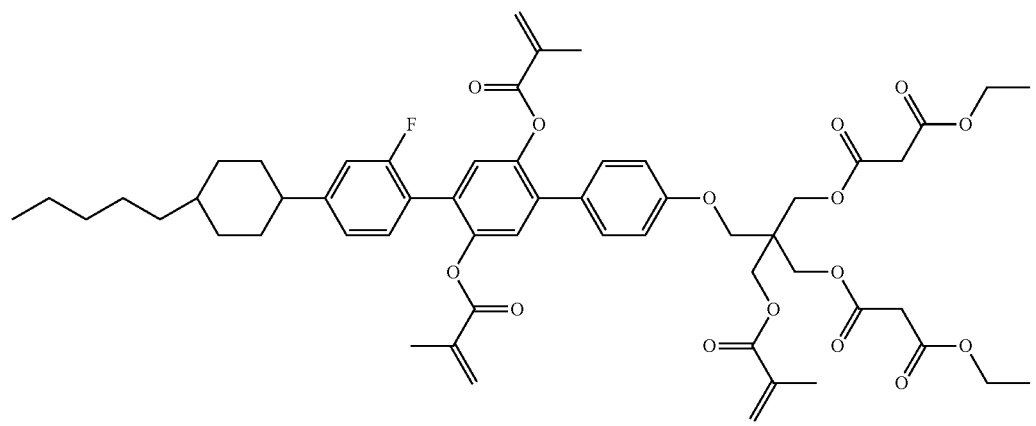
(P-22)
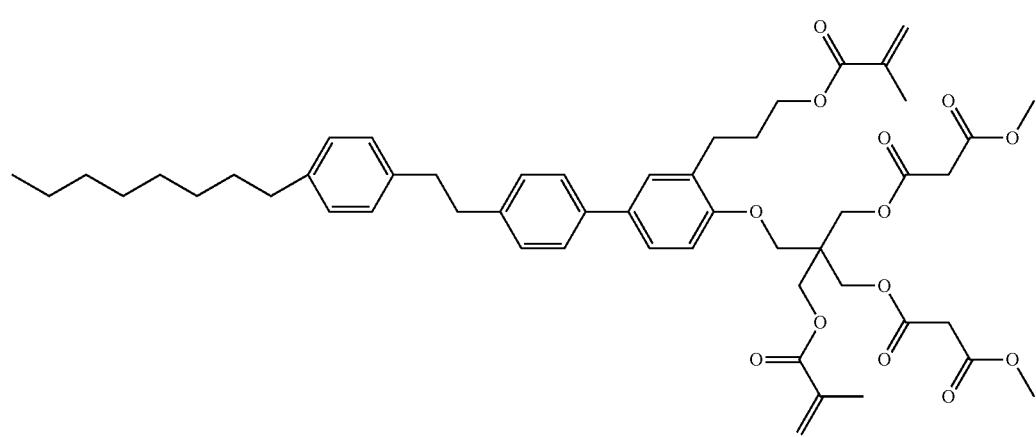
(P-23)

(P-24)
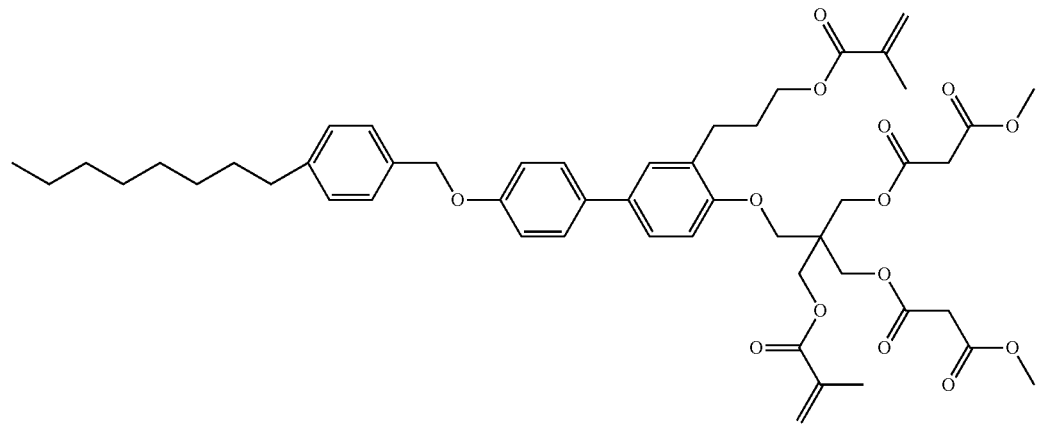
[Chem. 61]
(P-25)
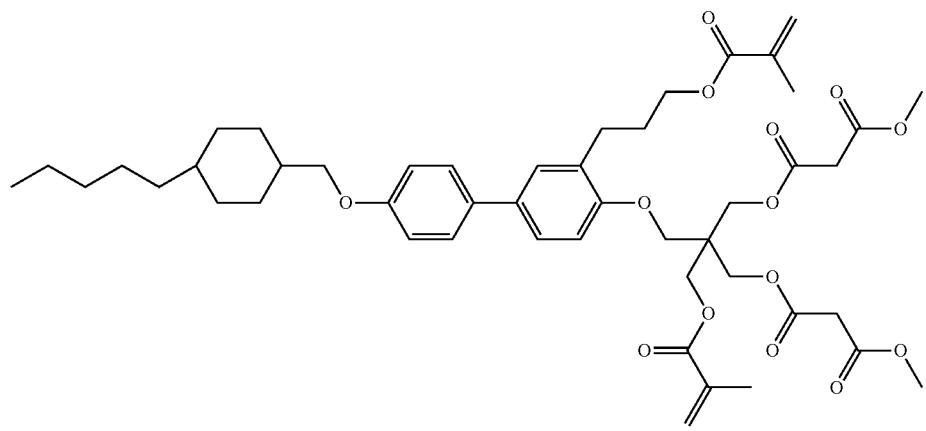
(P-26)
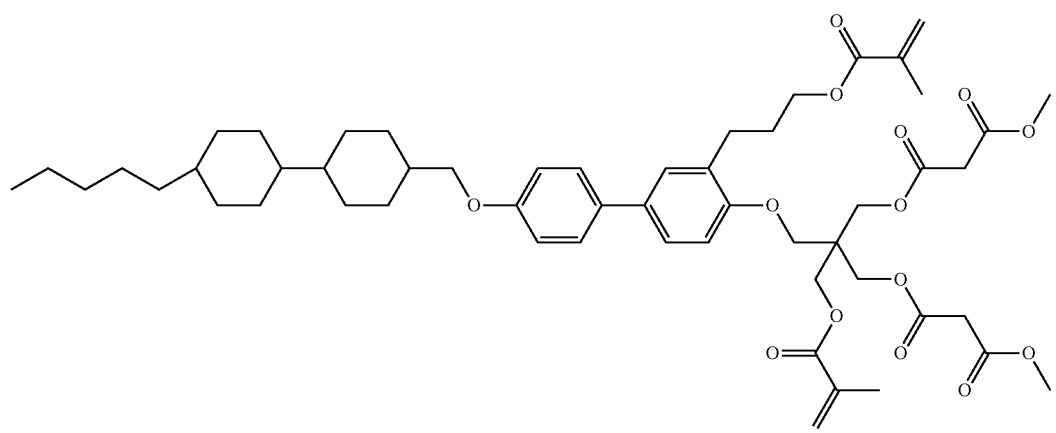

(P-27)
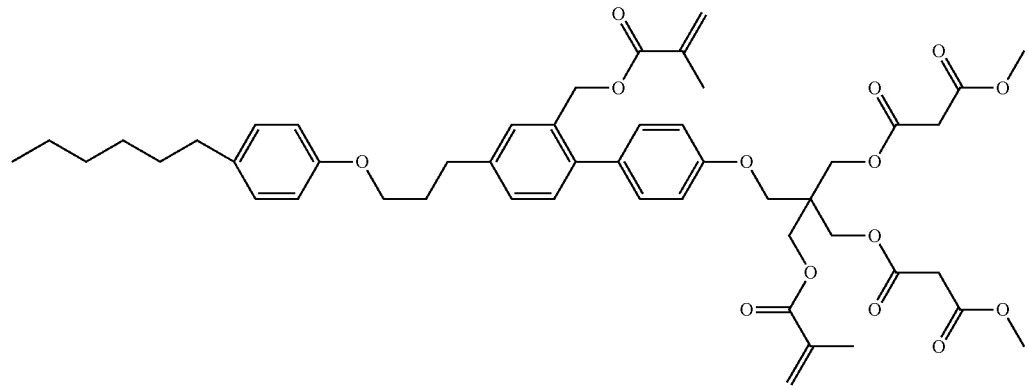
(P-28)
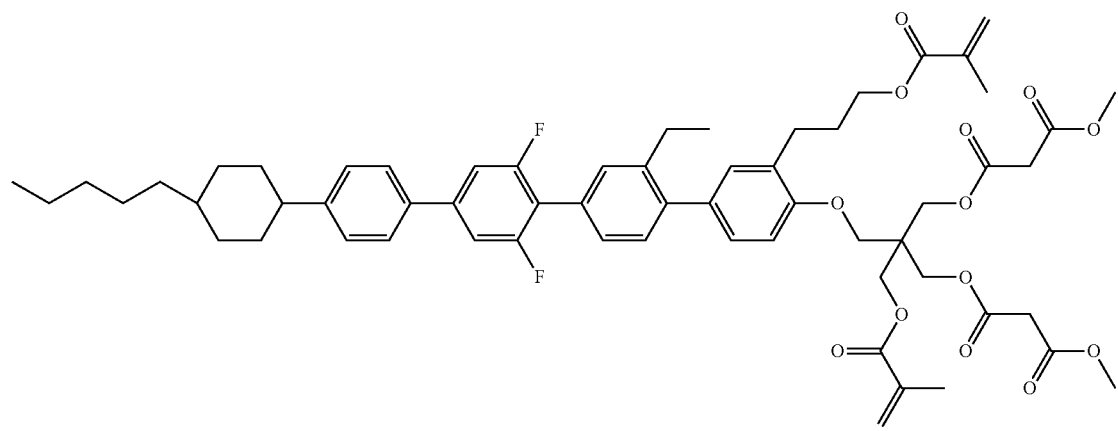
(P-29)
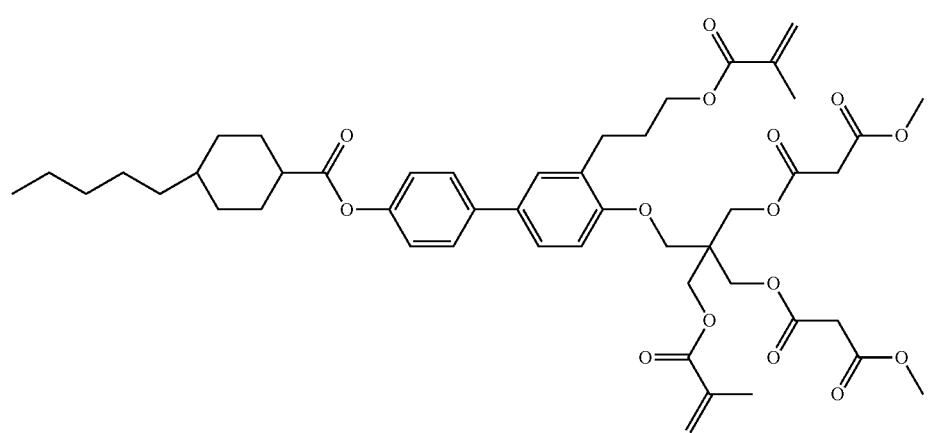

(P-30)
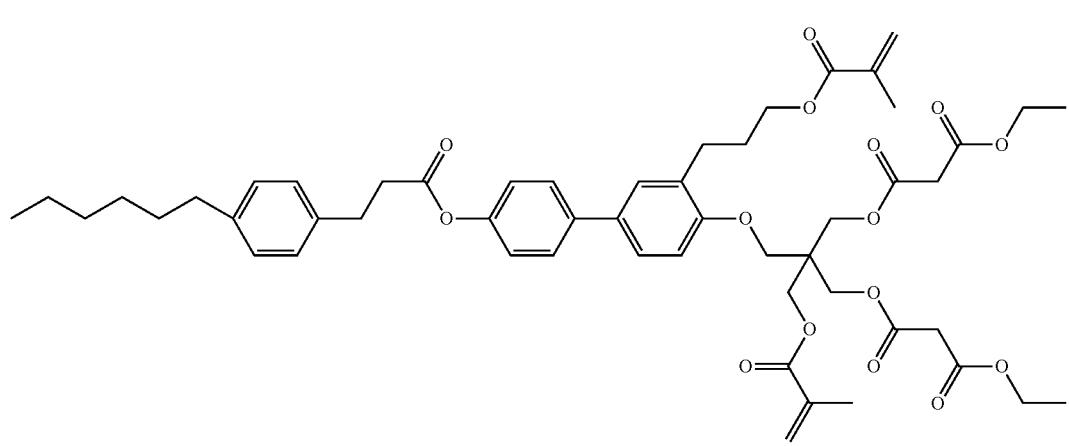
(P-31)
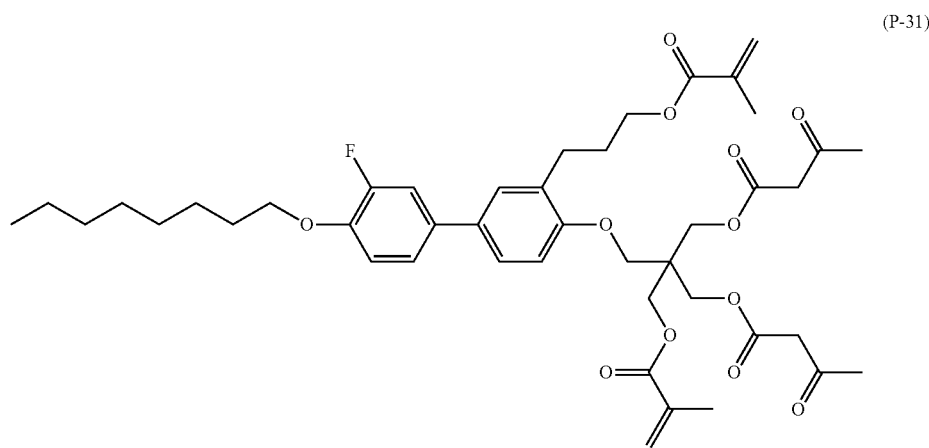
(P-32)
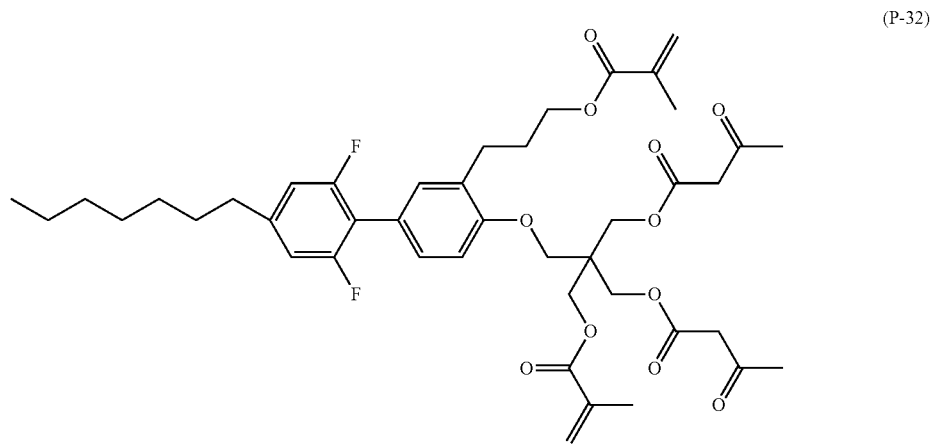

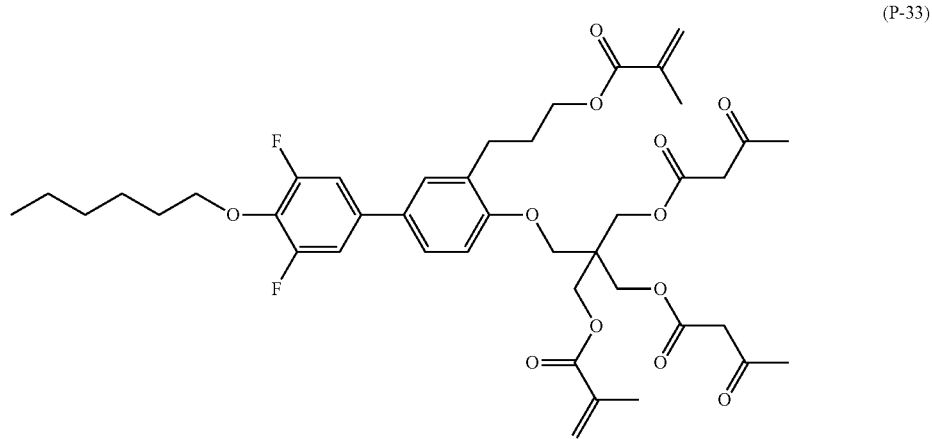
(P-33)
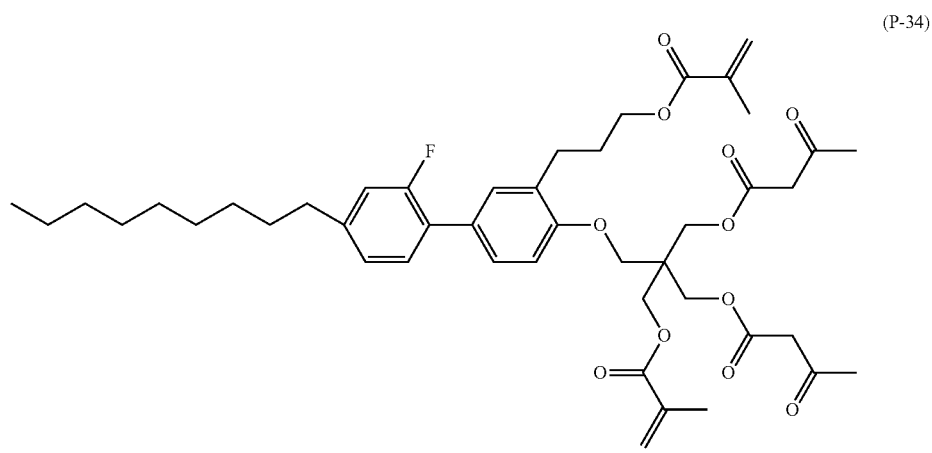
(P-34)
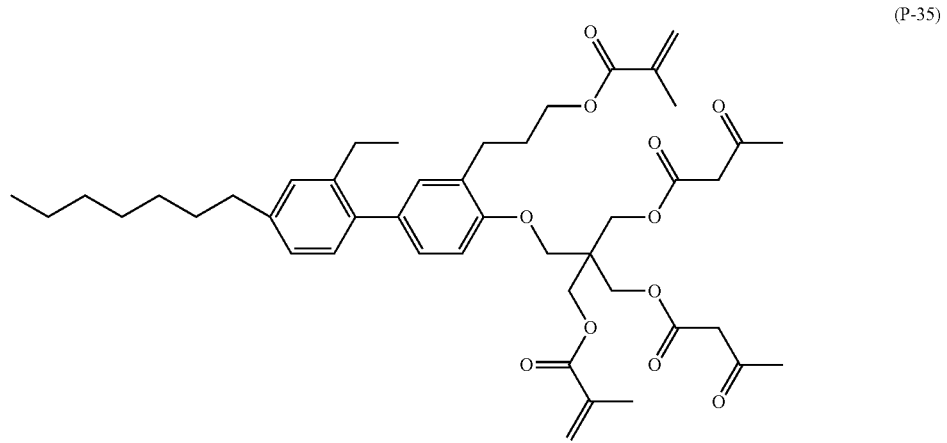
(P-35)

-continued
(P-36)
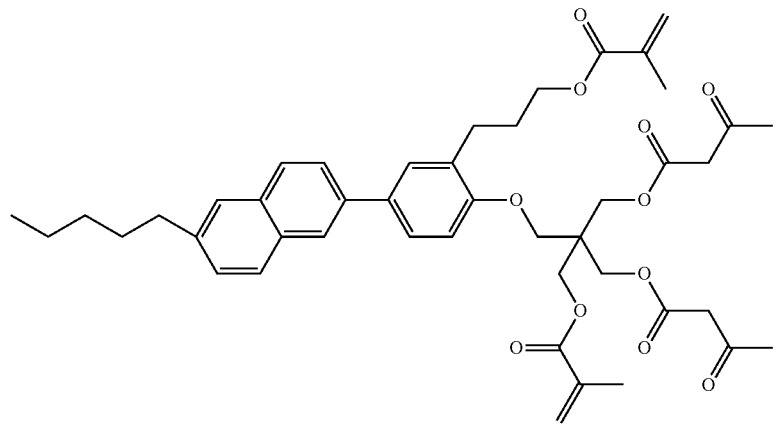
[Chem. 62]
(P-37)
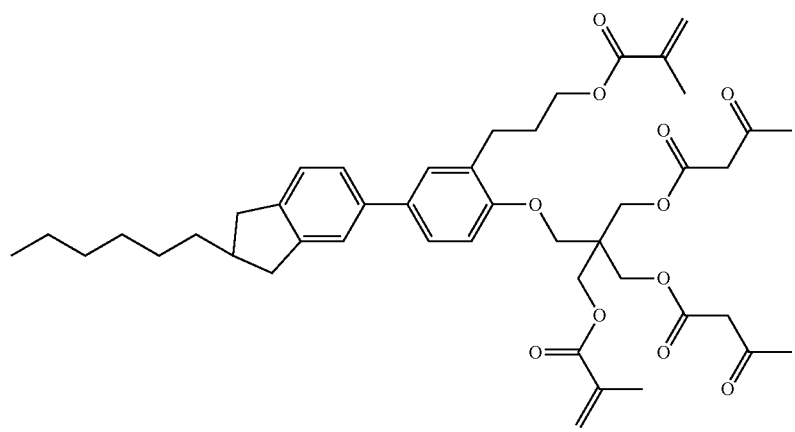
(P-38)
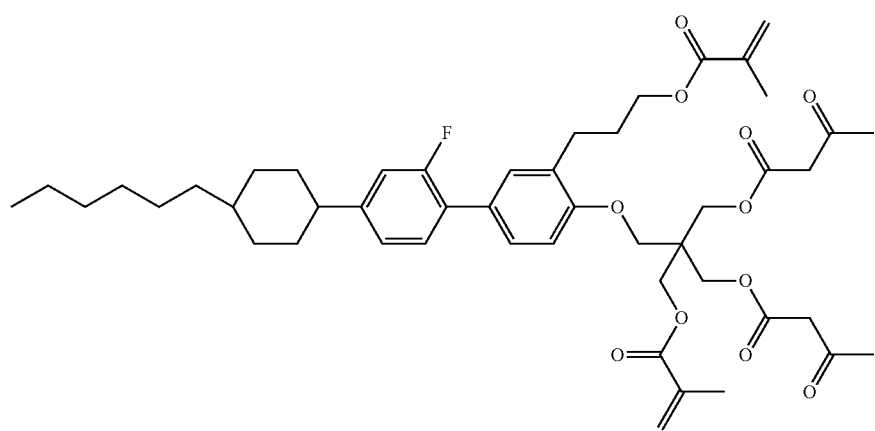

-continued
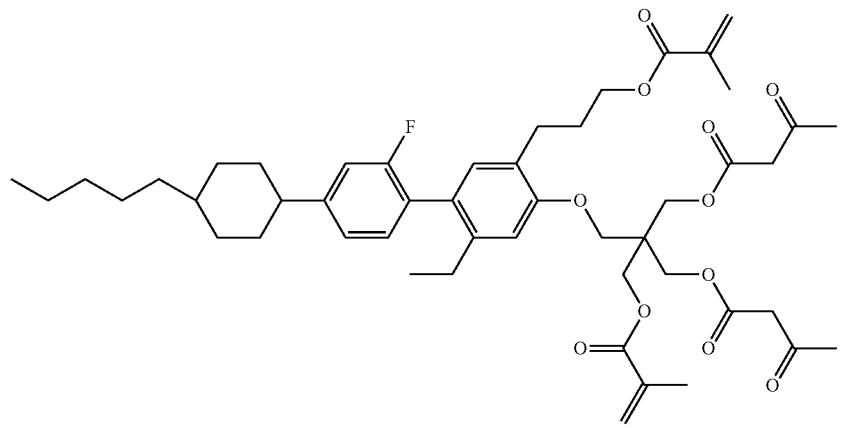
(P-39)
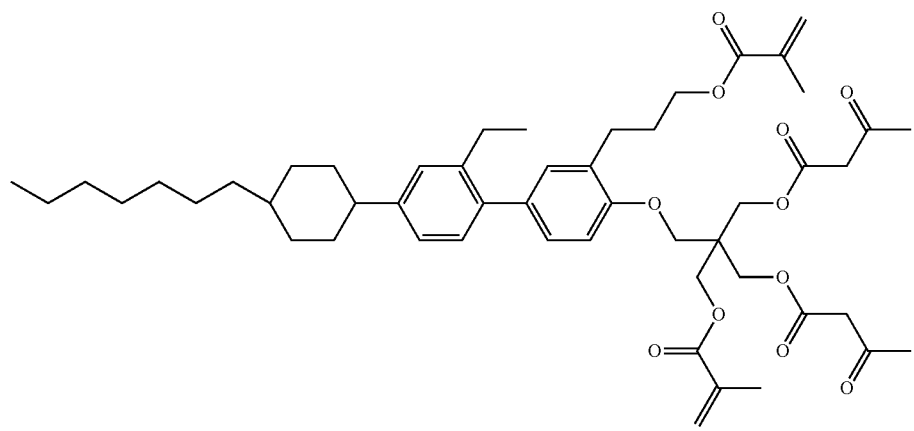
(P-40)
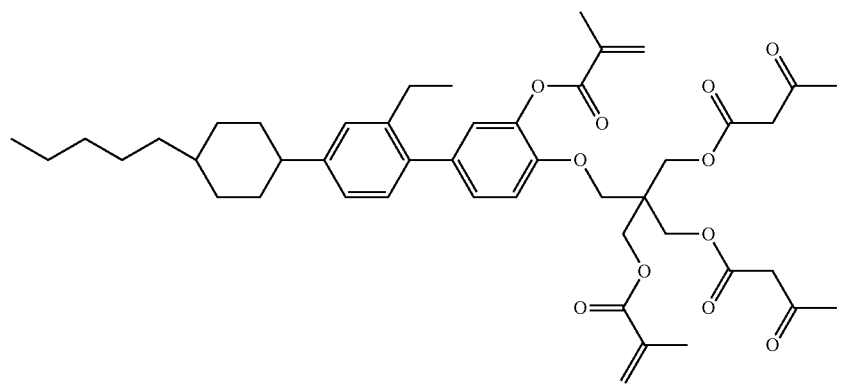
(P-41)
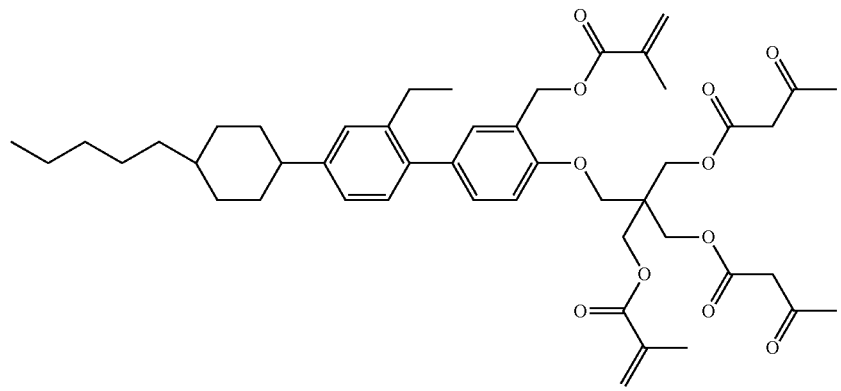
(P-42)

-continued
(P-43)
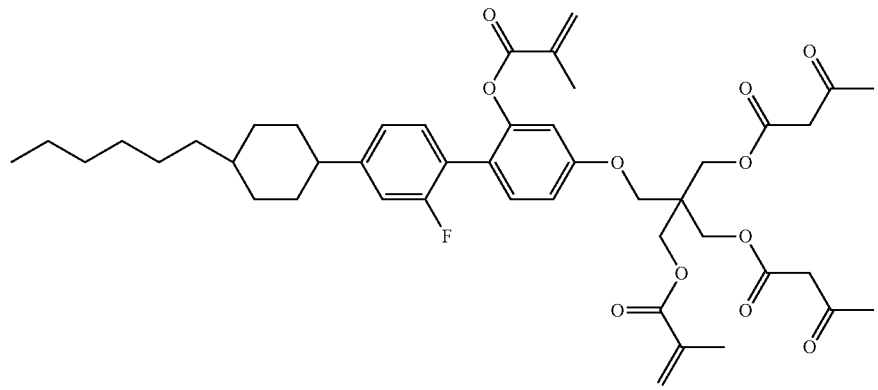
(P-44)
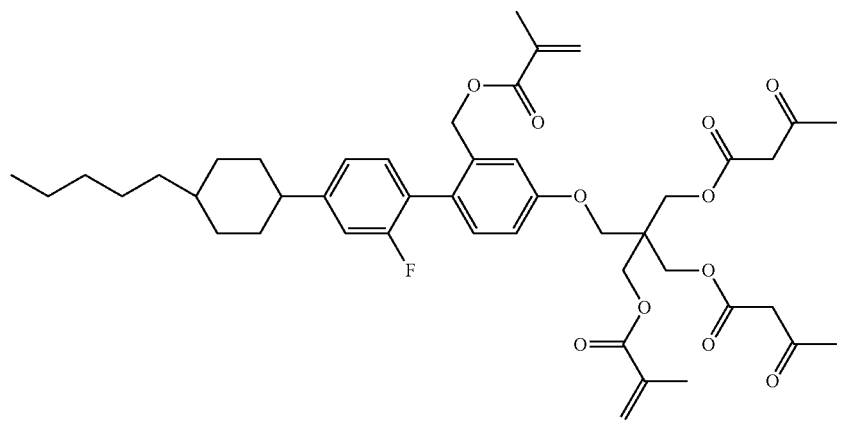
(P-45)
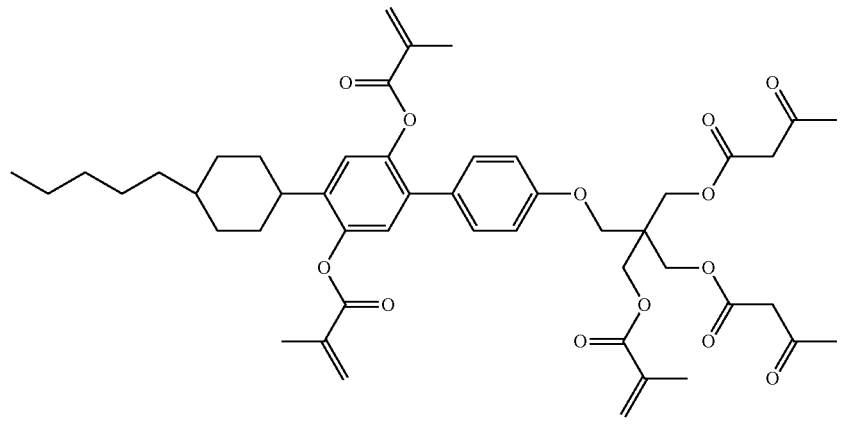
(P-46)
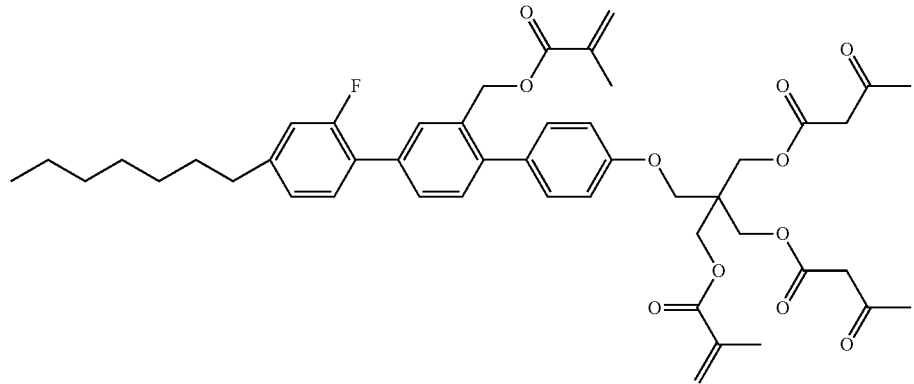

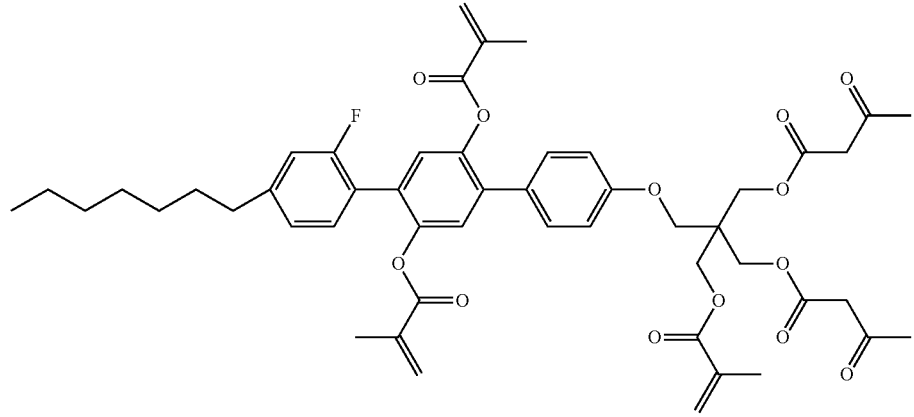
(P-47)
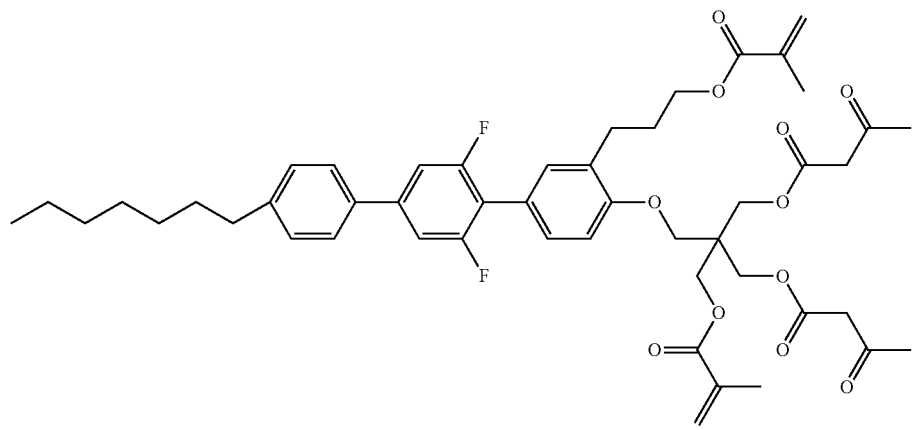
(P-48)
[Chem. 63]
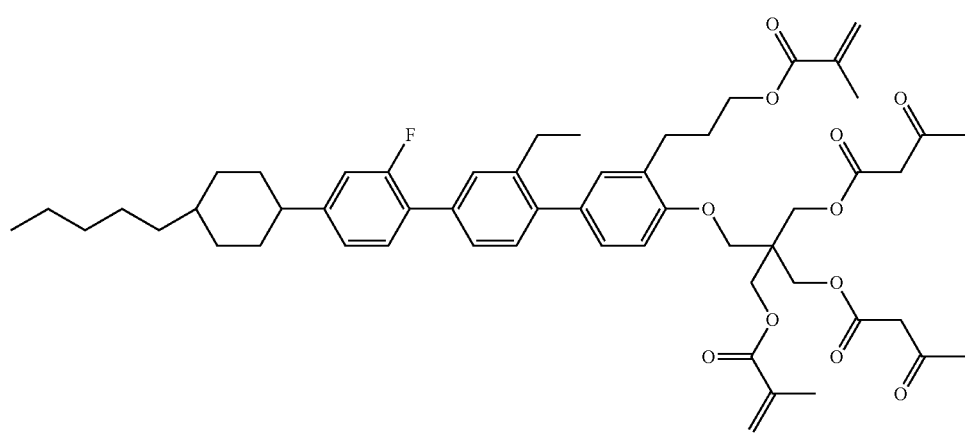
(P-49)

(P-50)
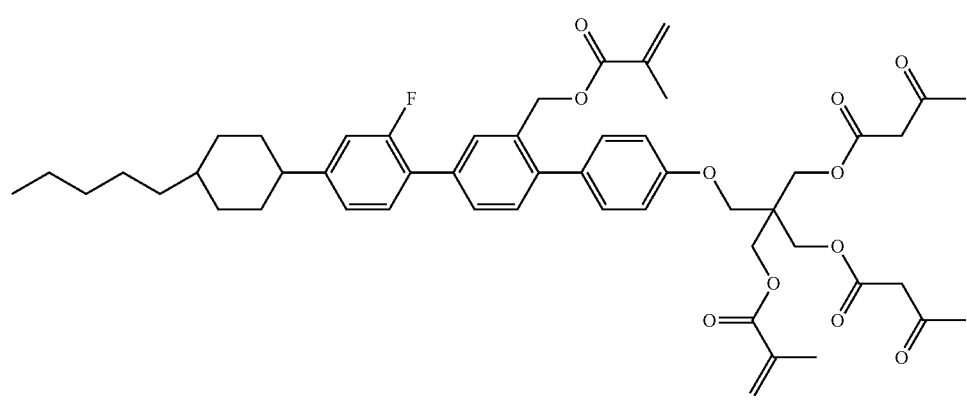
(P-51)
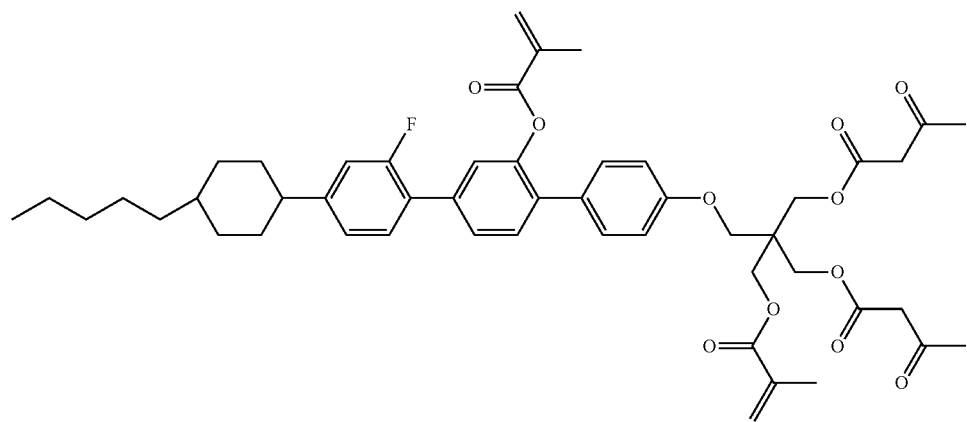
(P-52)
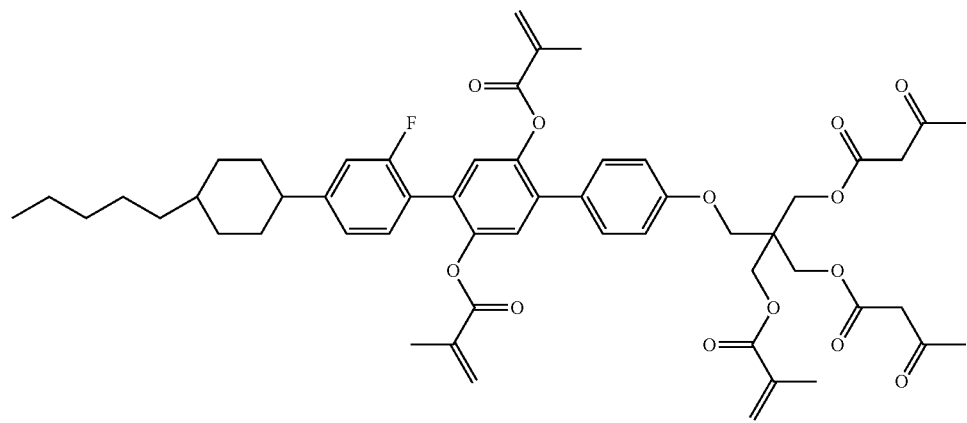
(P-53)
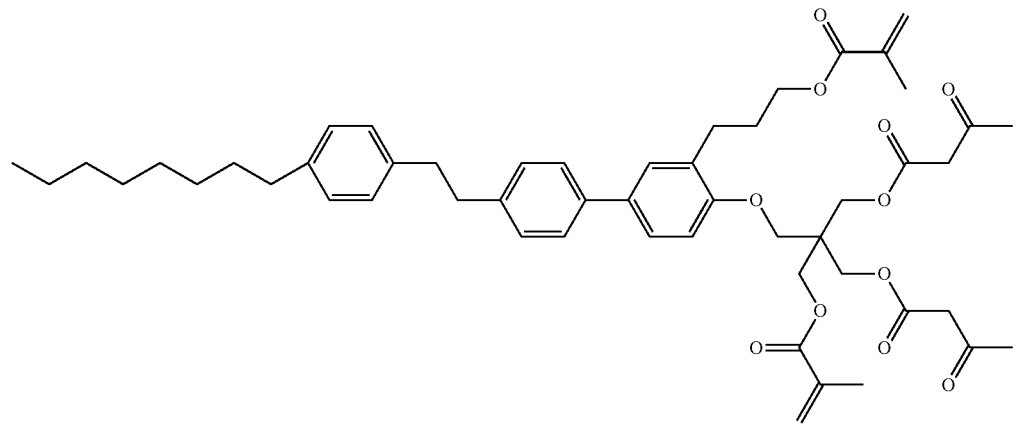

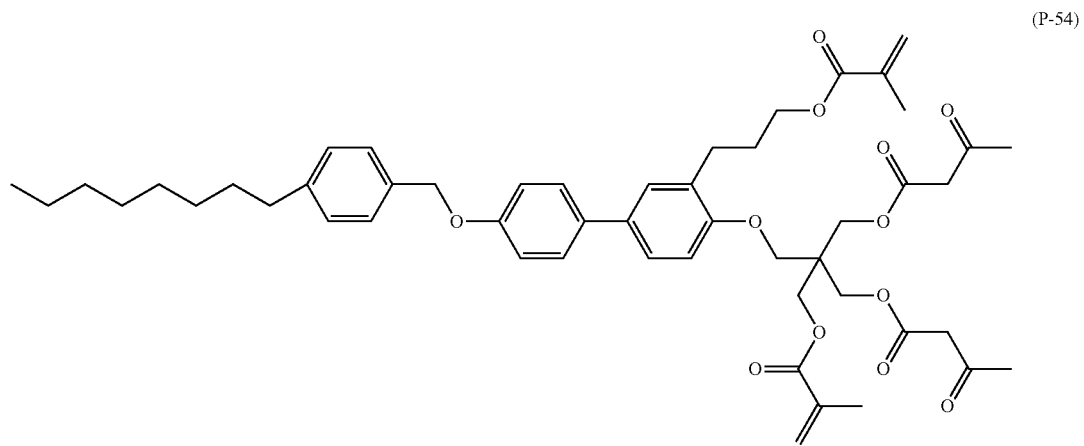
(P-54)
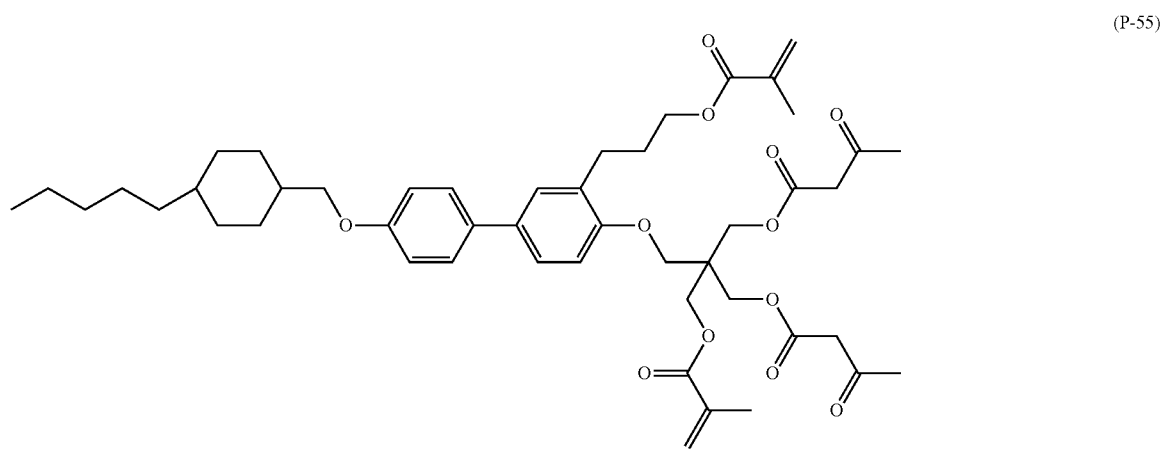
(P-55)
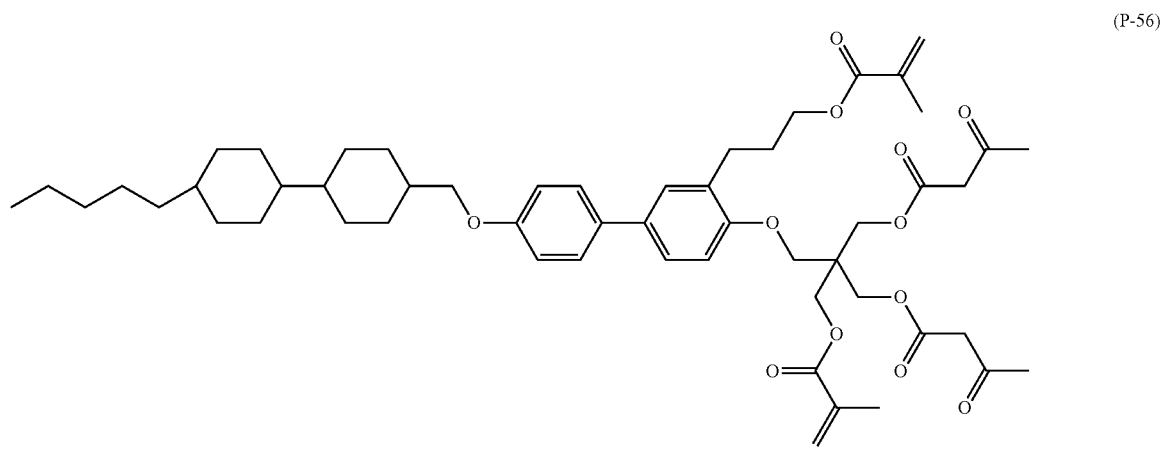
(P-56)

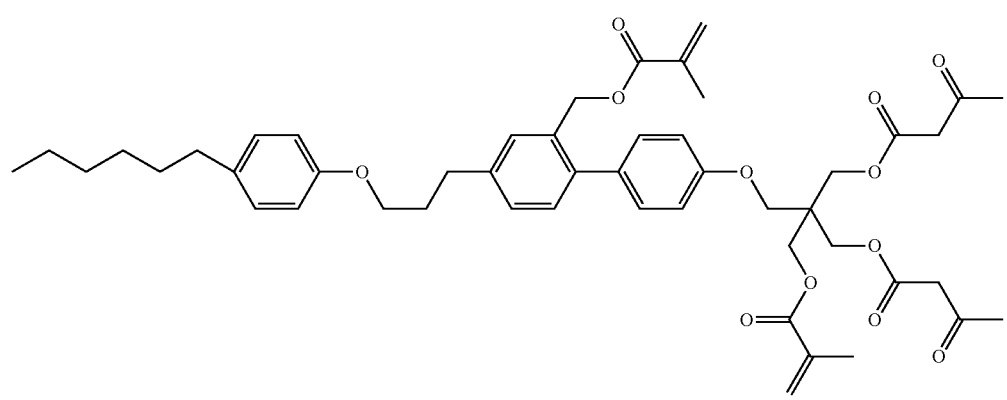
(P-57)
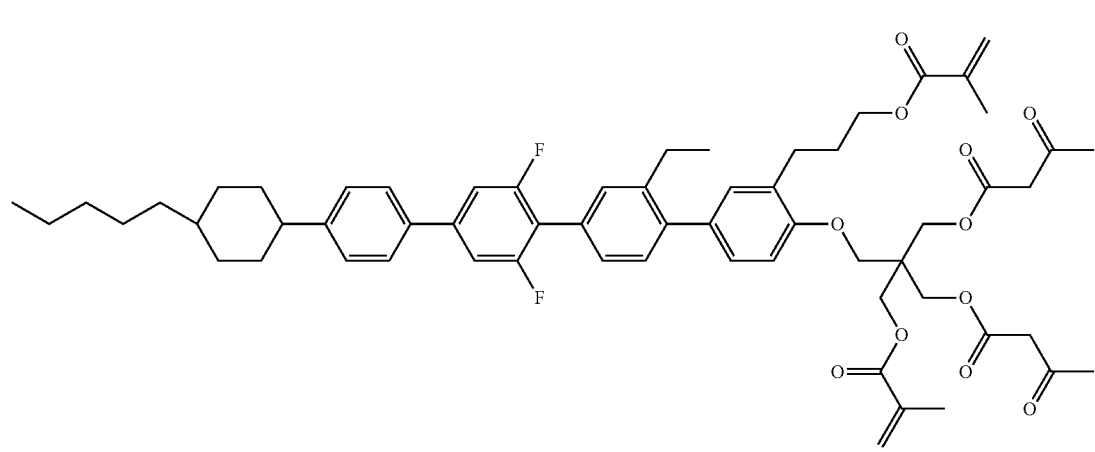
(P-58)
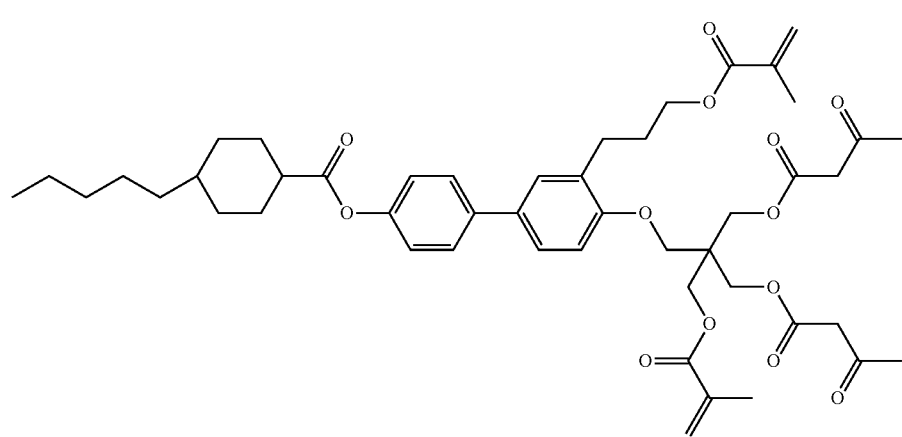
(P-59)

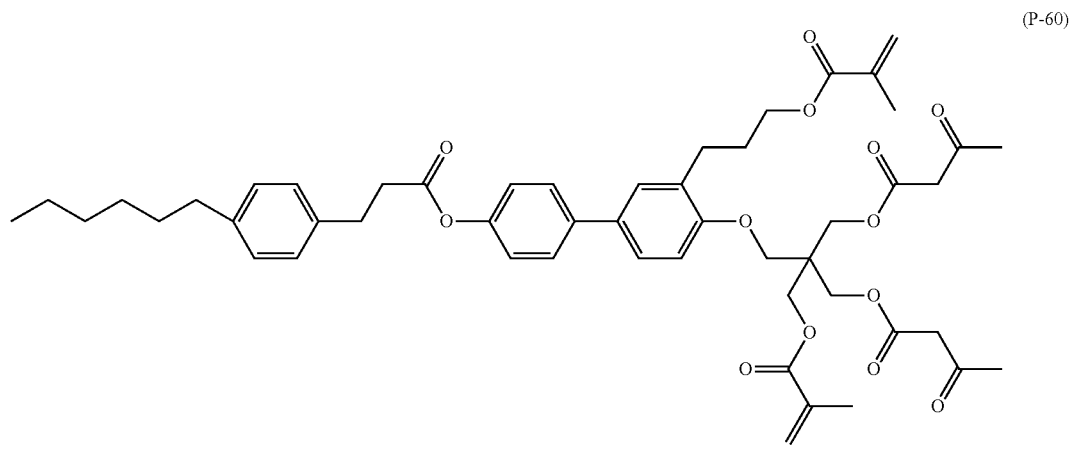
(P-60)
[Chem. 64]
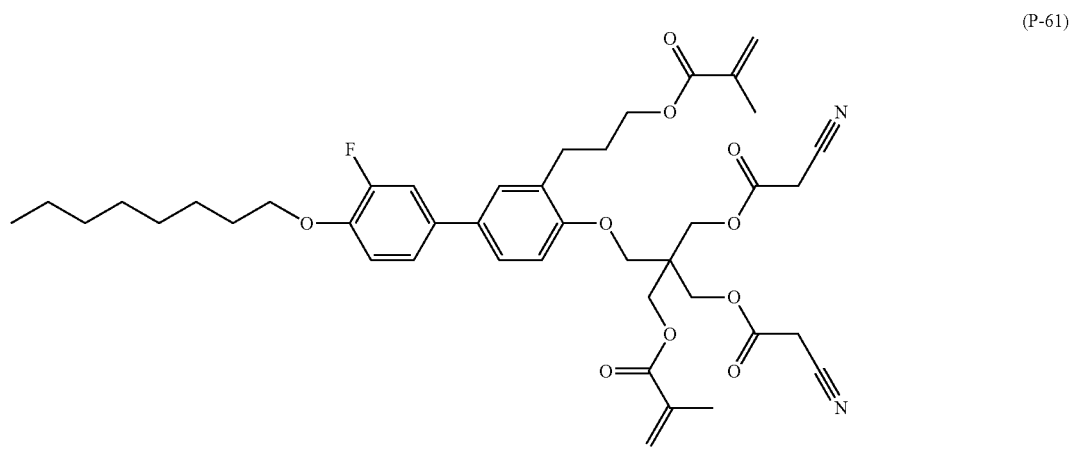
(P-61)
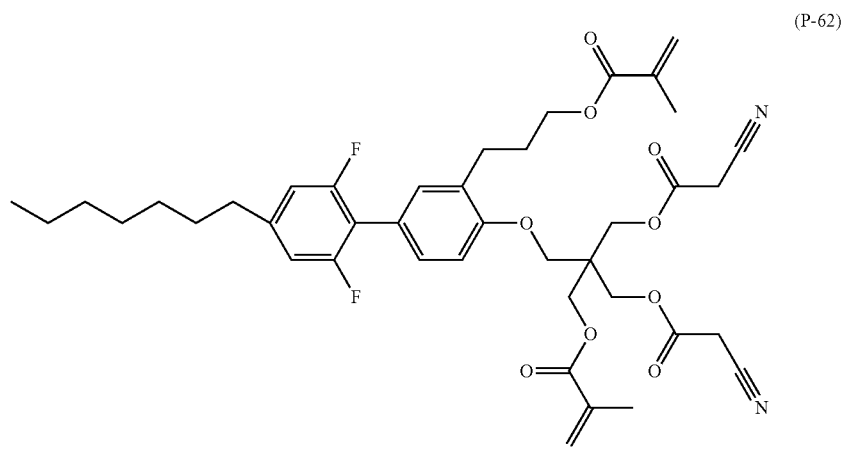
(P-62)

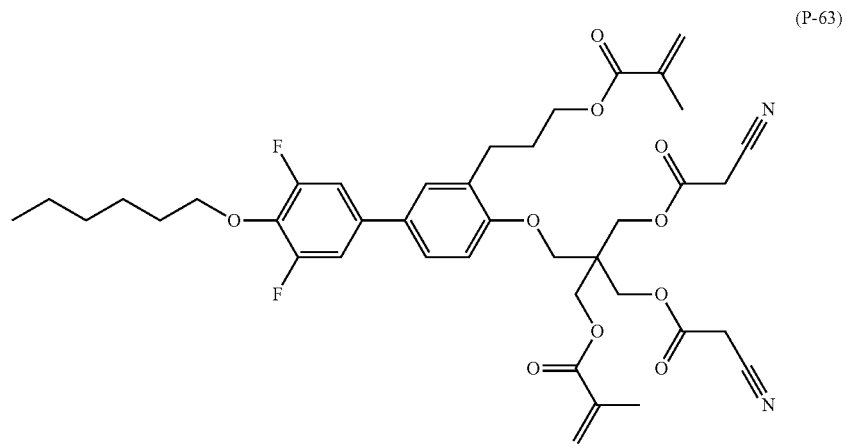
(P-63)
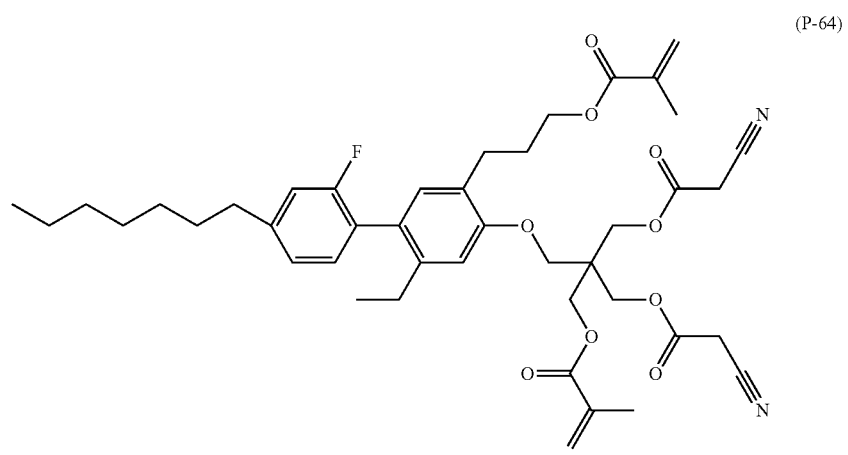
(P-64)
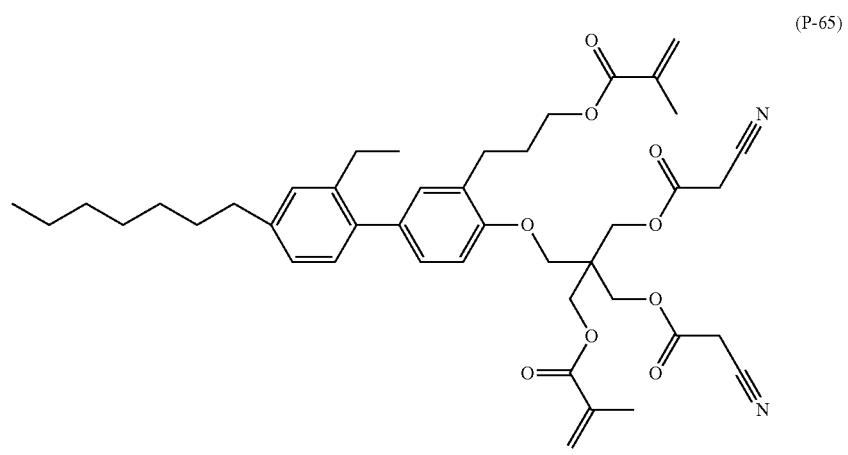
(P-65)

-continued
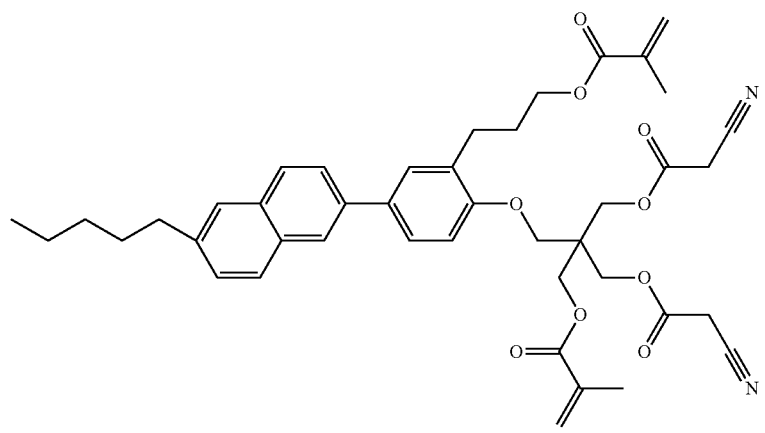
(P-66)
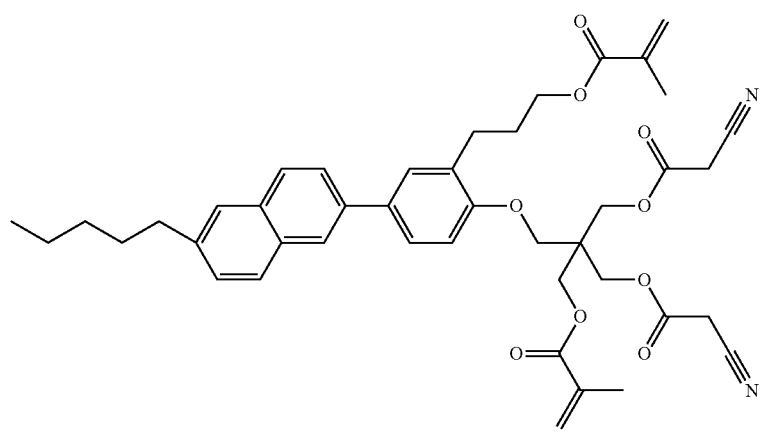
(P-67)
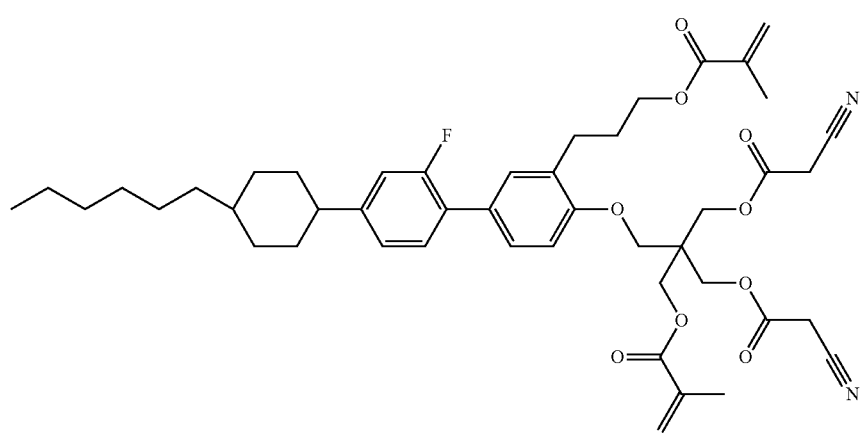
(P-68)

-continued
(P-69)
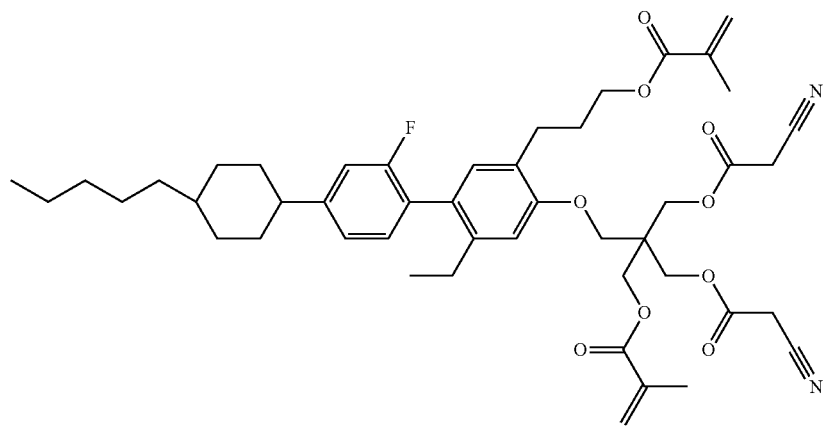
(P-70)
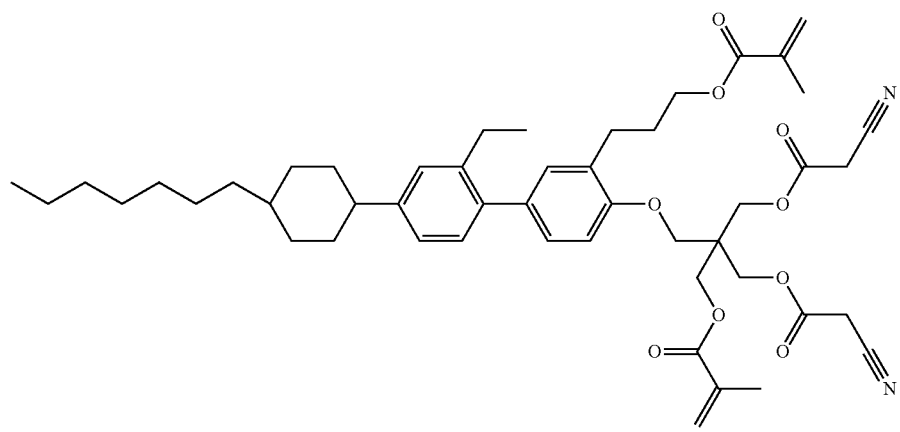
(P-71)
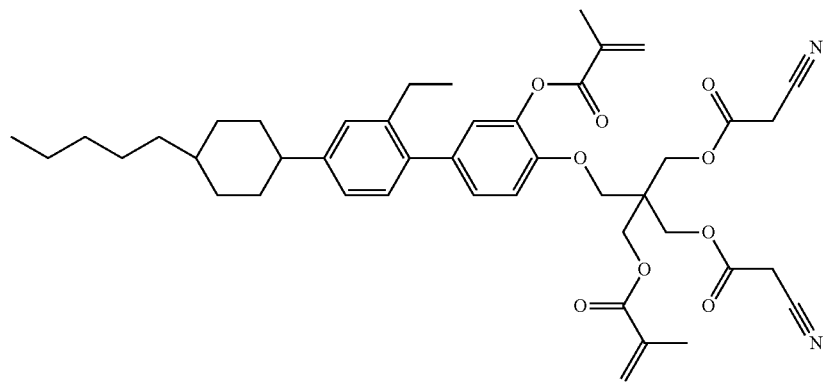
(P-72)
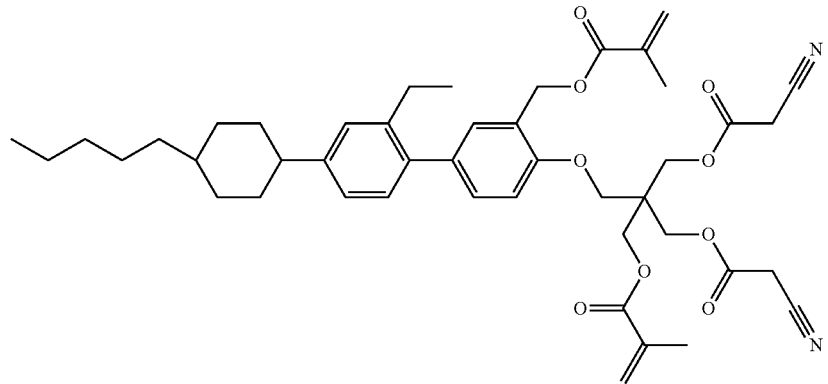

[Chem. 65]
-continued
(P-73)
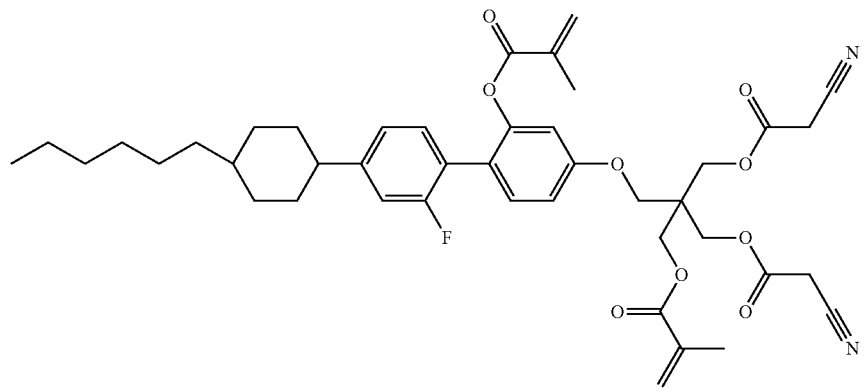
(P-74)
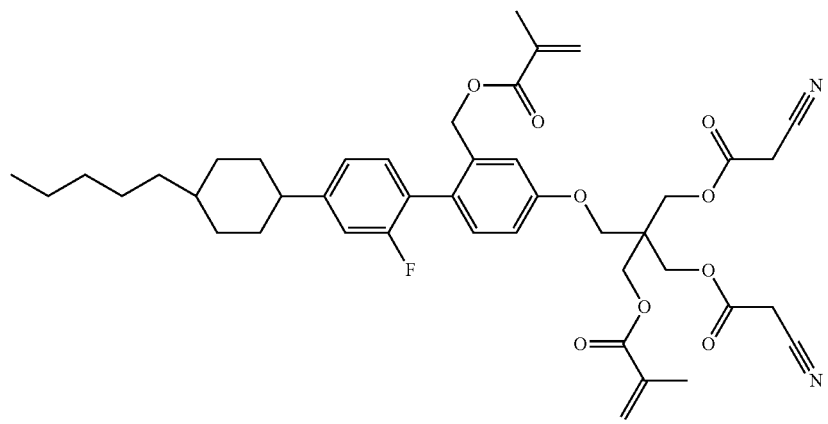
(P-75)
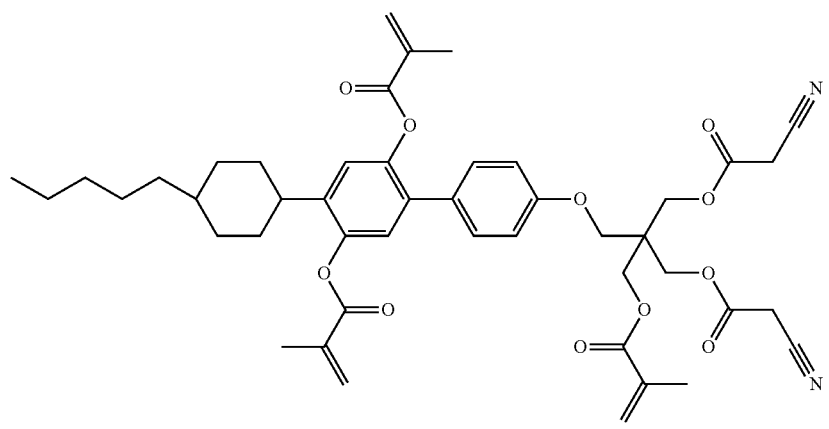
(P-76)
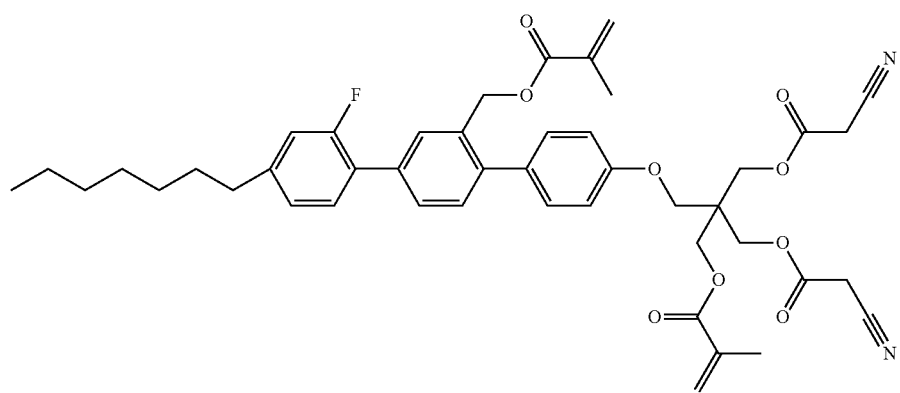

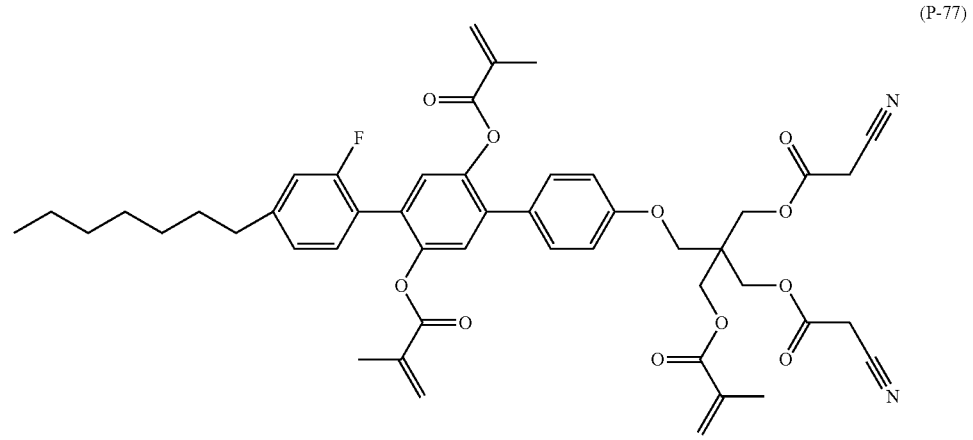
(P-77)
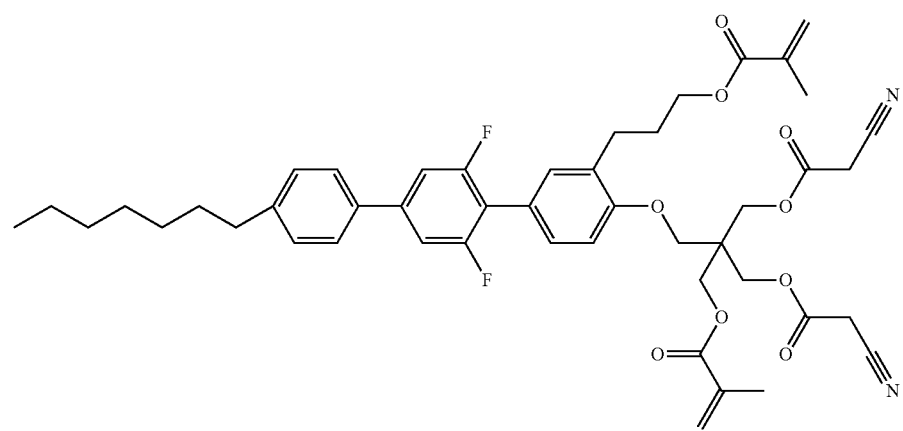
(P-78)
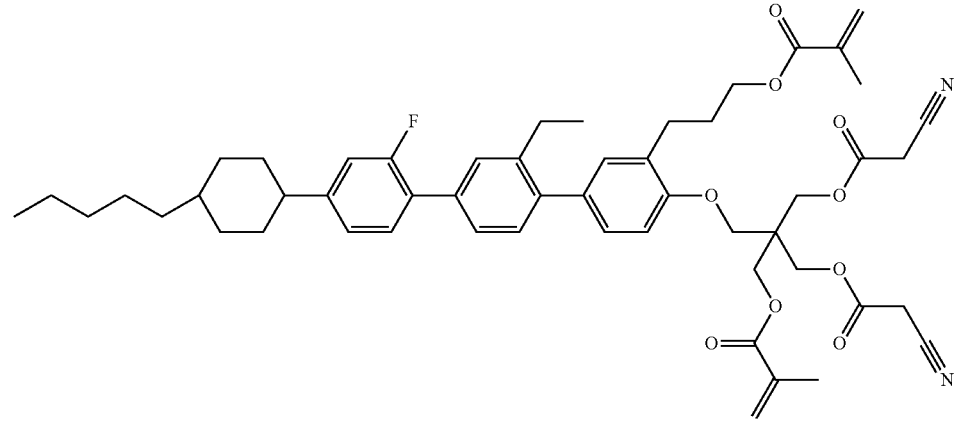
(P-79)

-continued
(P-80)
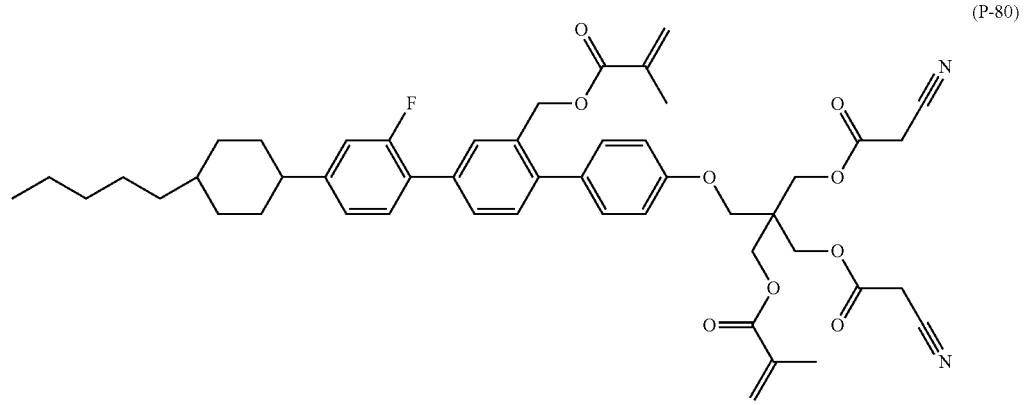
(P-81)
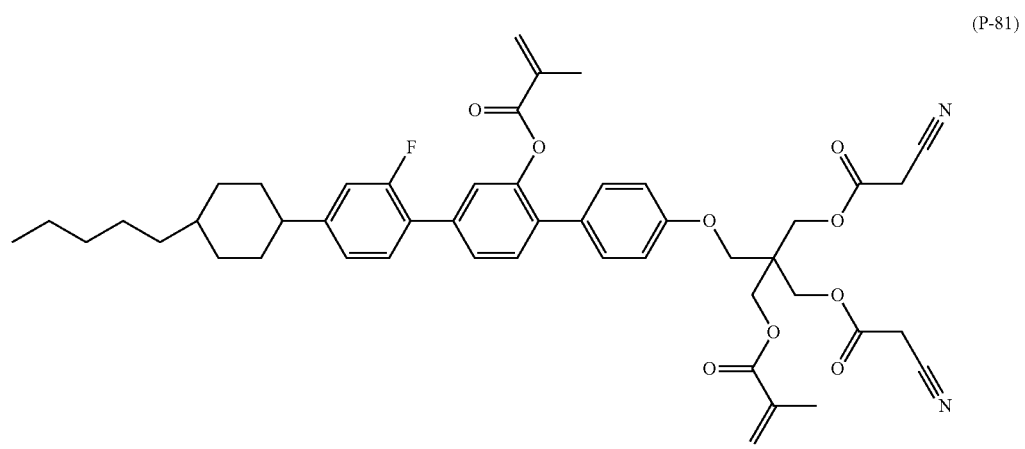
(P-82)
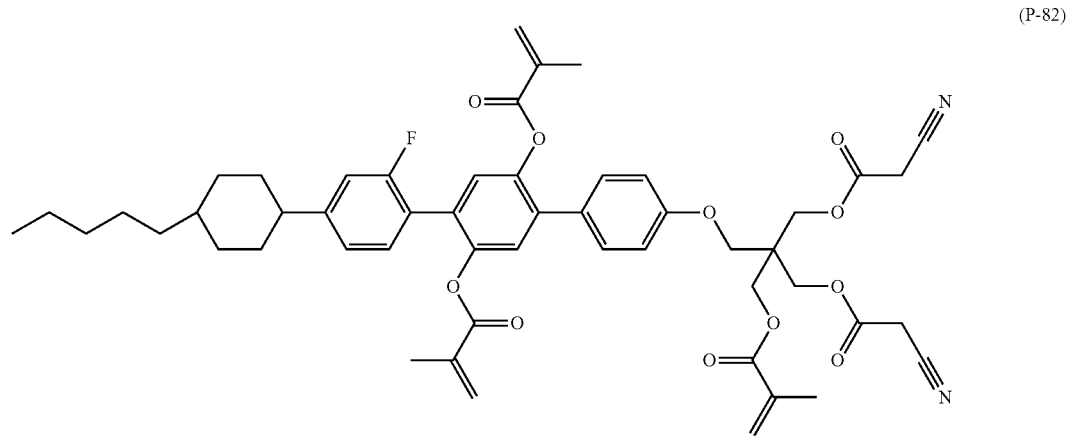

-continued
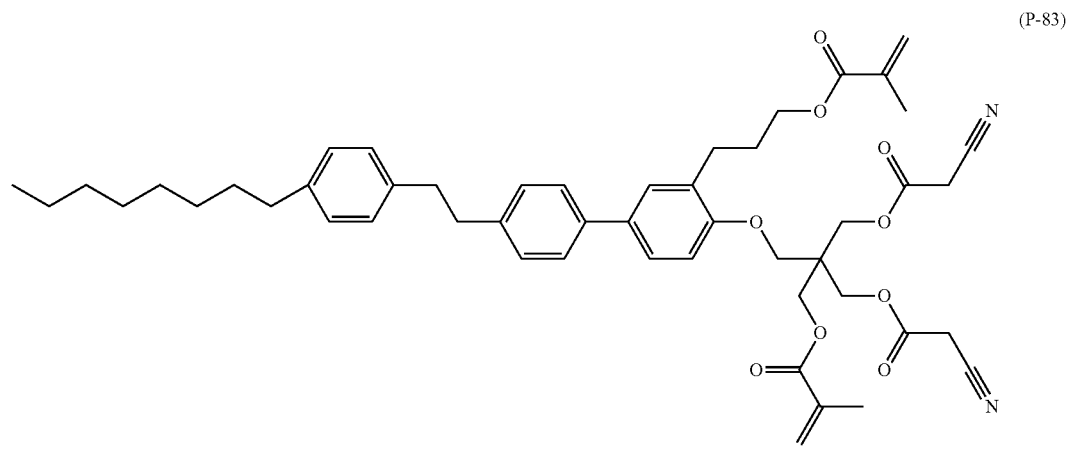
(P-83)
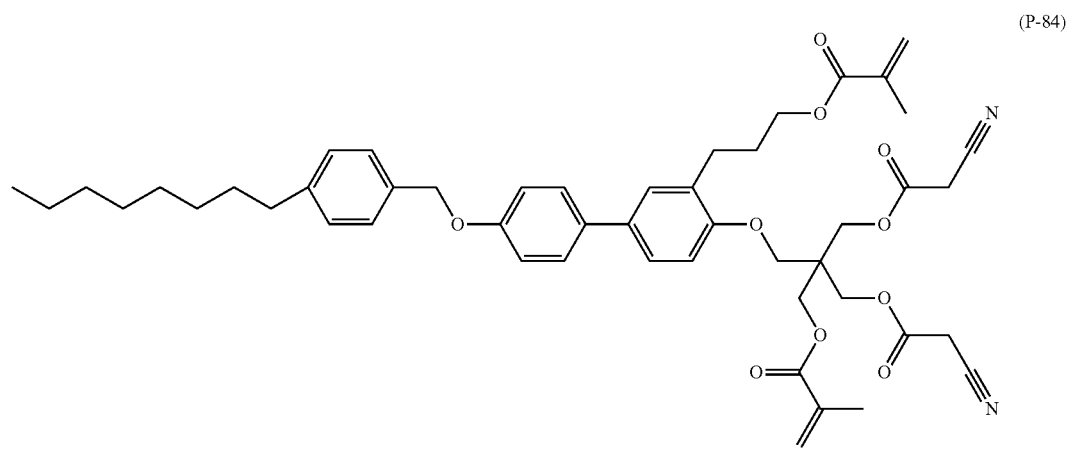
(P-84)
[Chem. 66]
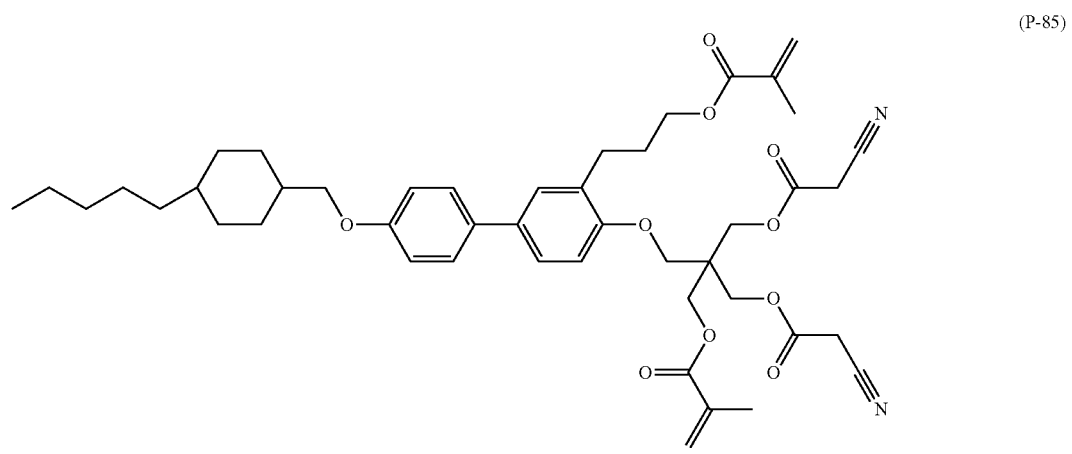
(P-85)

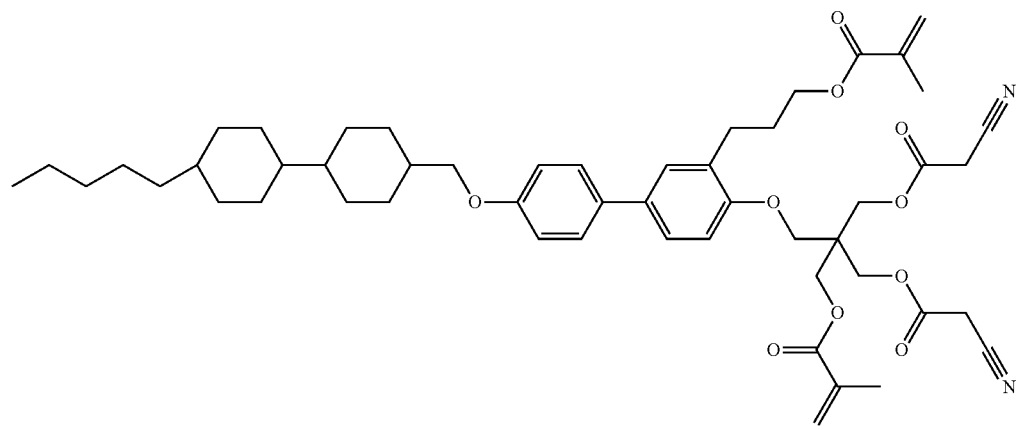
(P-86)
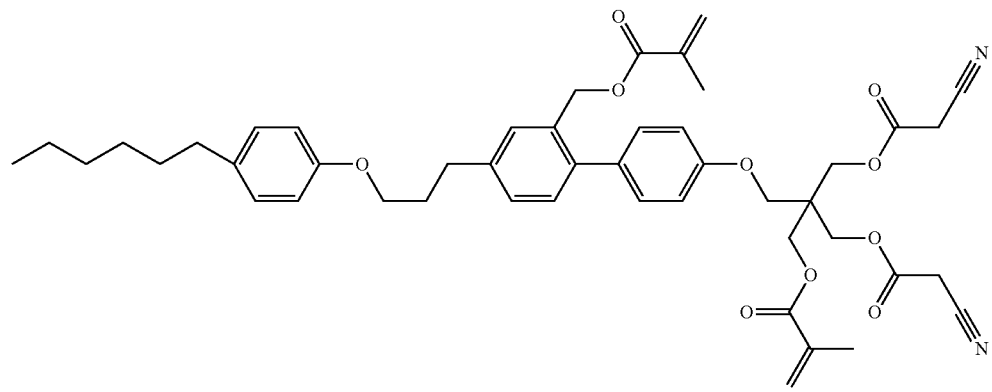
(P-87)
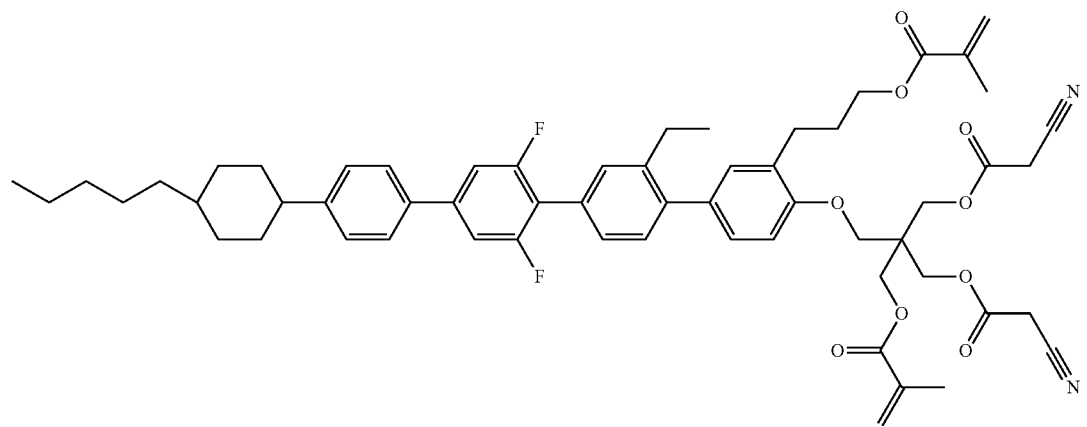
(P-88)

(P-89)
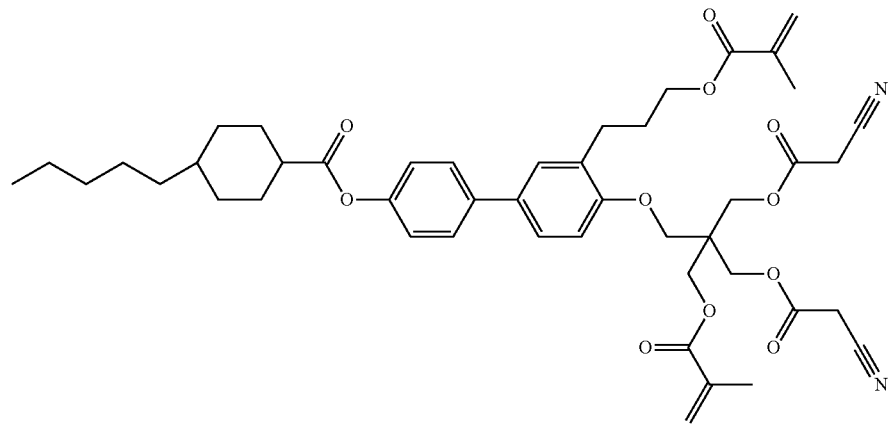
(P-90)
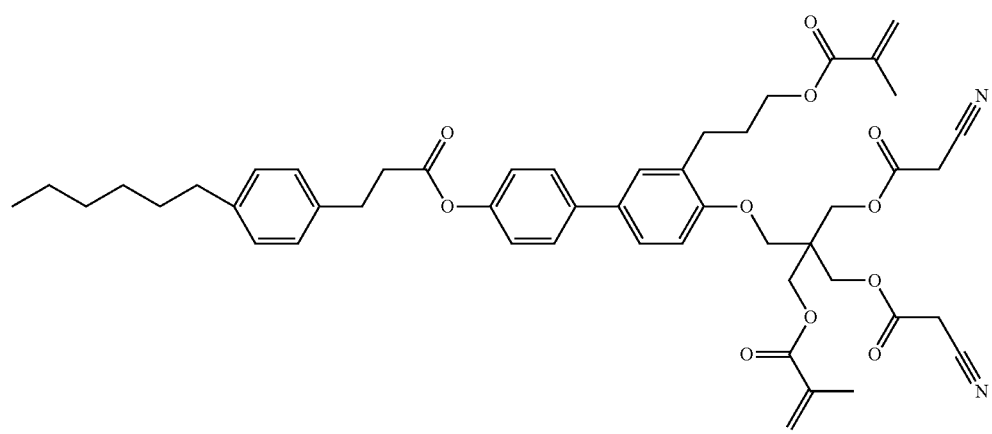
(P-91)
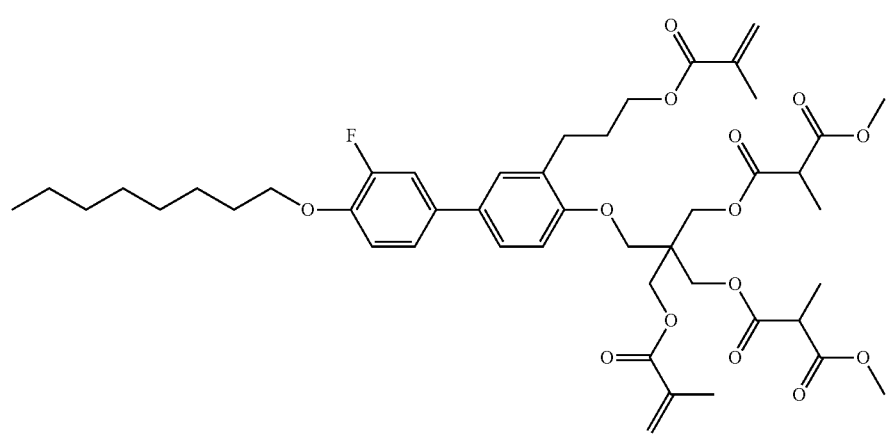

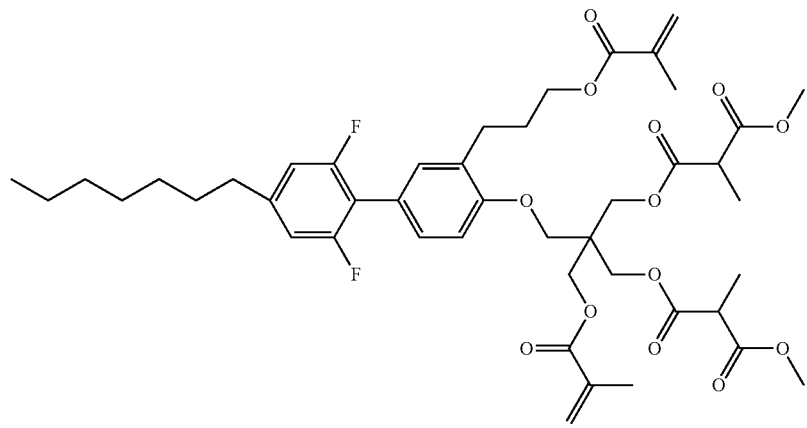
(P-92)
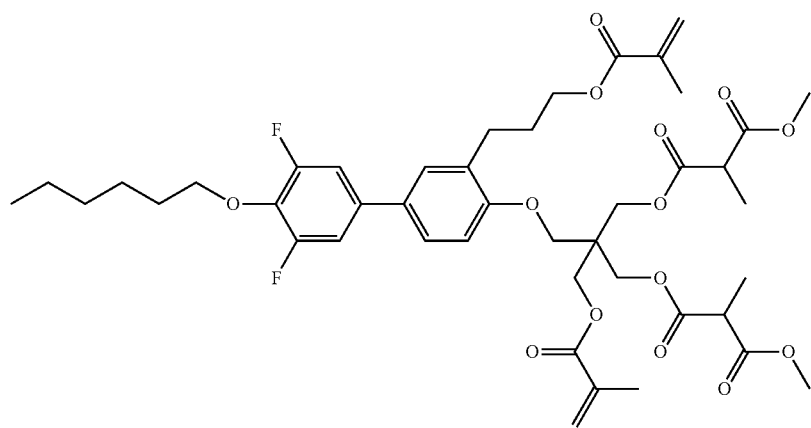
(P-93)
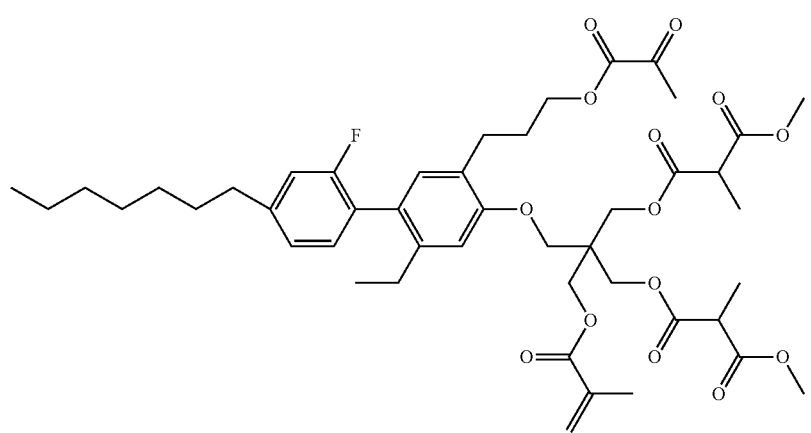
(P-94)

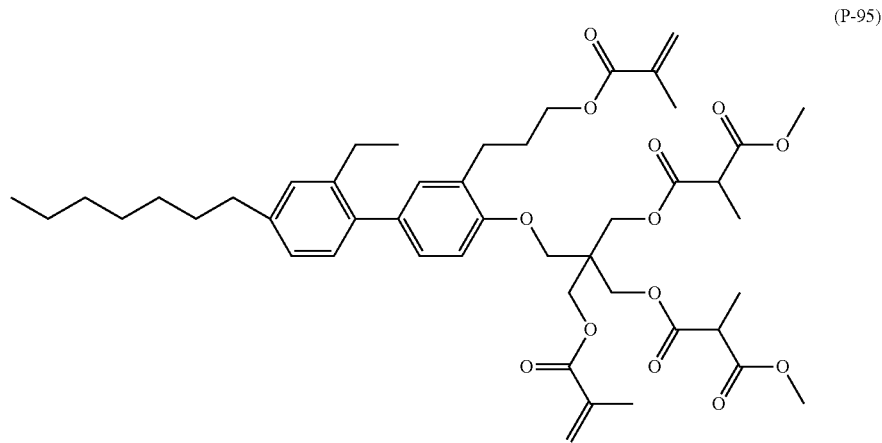
(P-95)
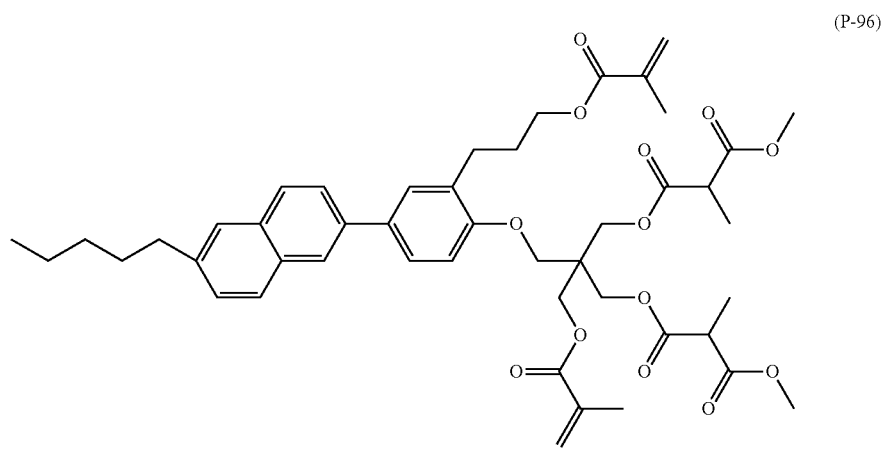
(P-96)
[Chem. 67]
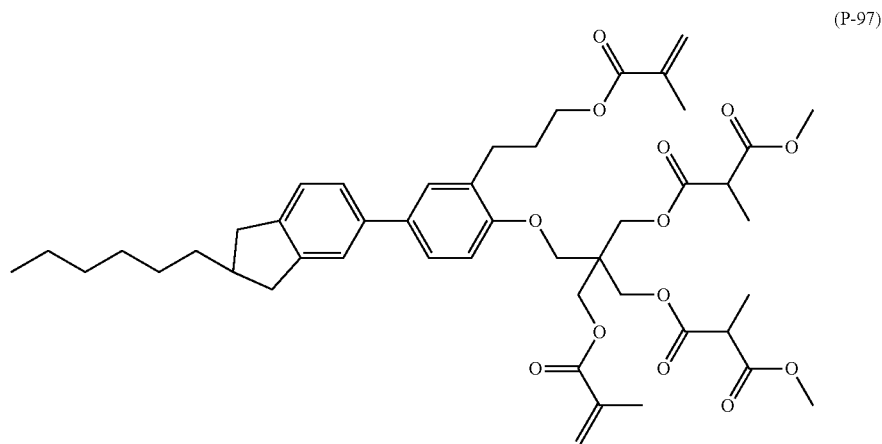
(P-97)

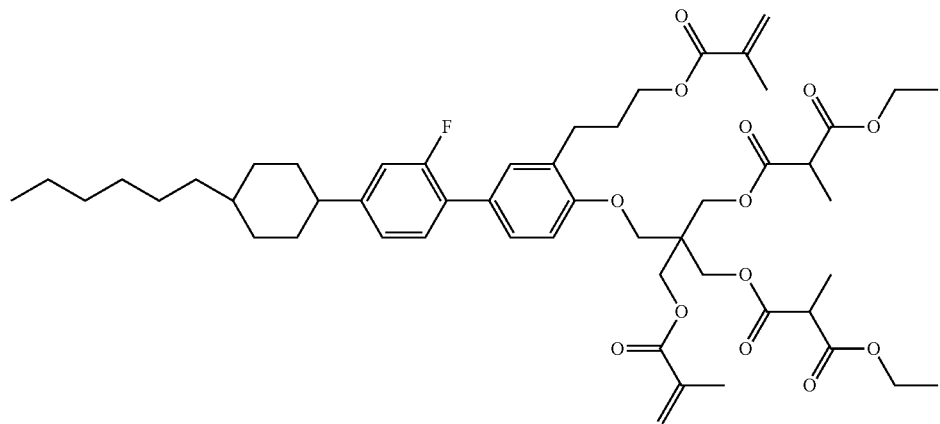
(P-98)
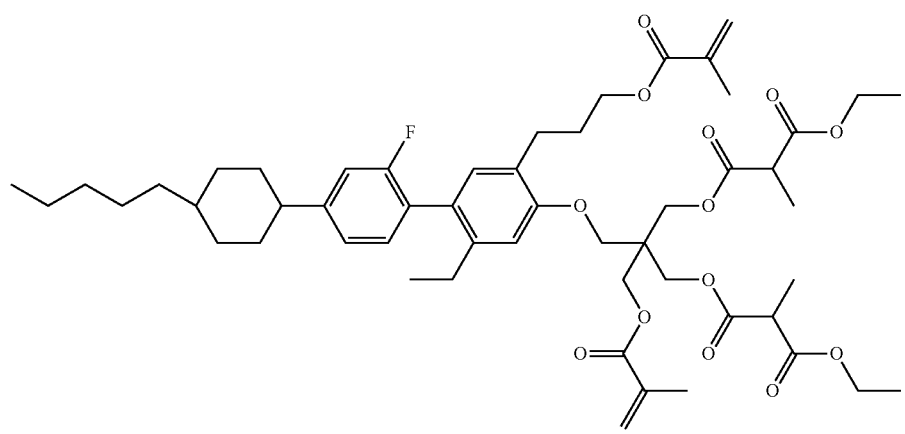
(P-99)
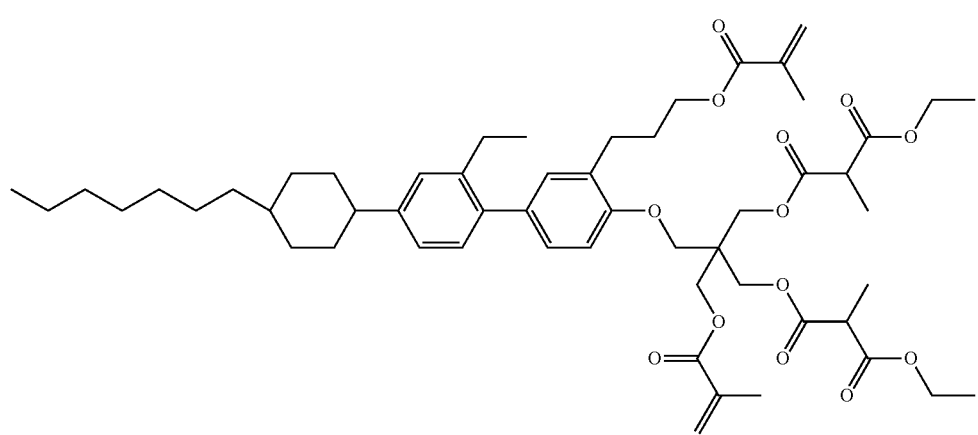
(P-100)

(P-101)
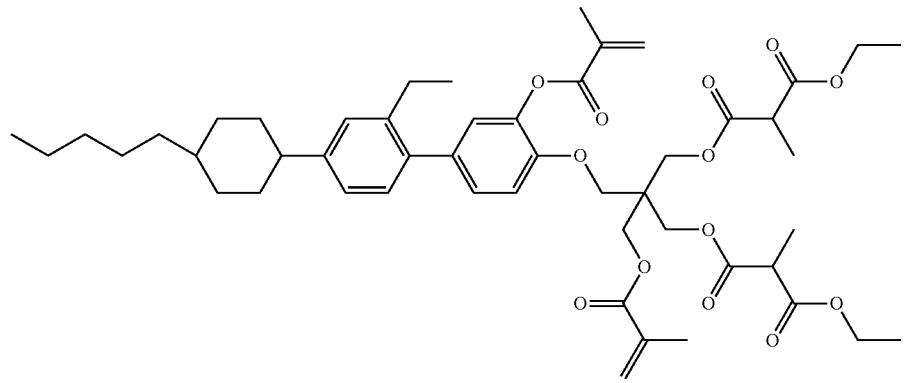
(P-102)
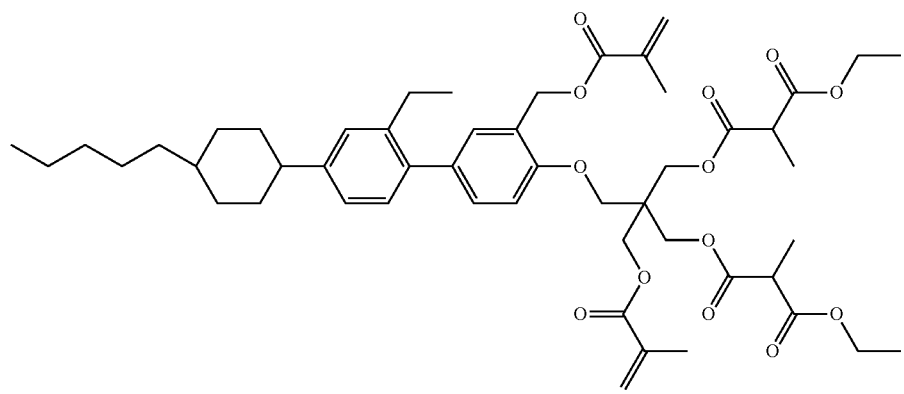
(P-103)
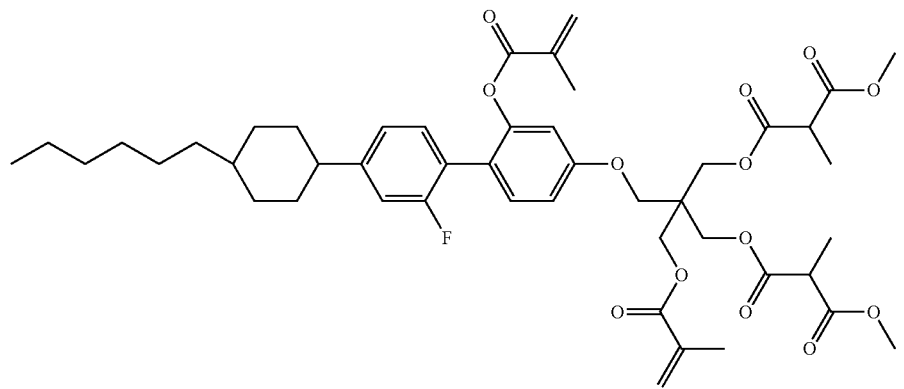
(P-104)
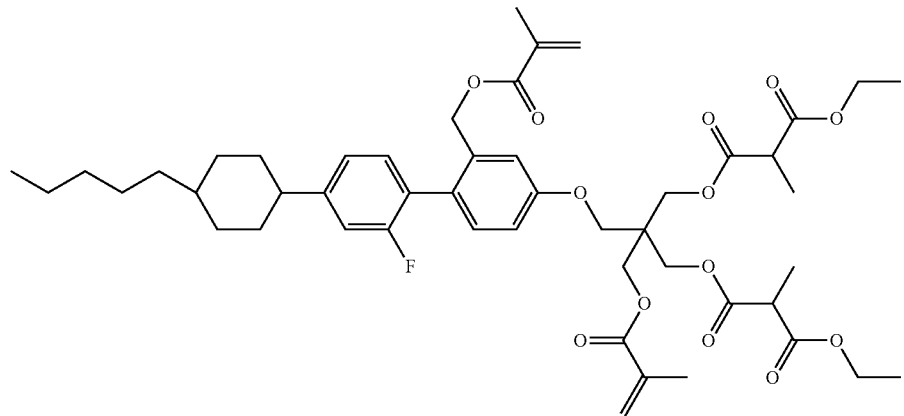

-continued
(P-105)
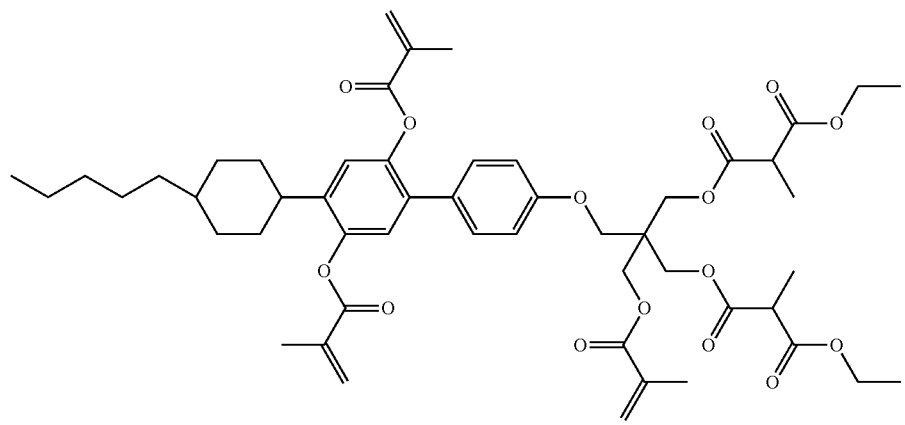
(P-106)
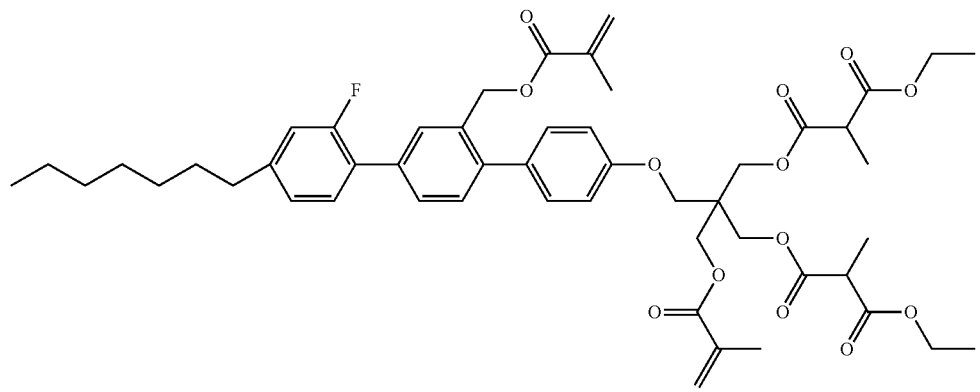
(P-107)
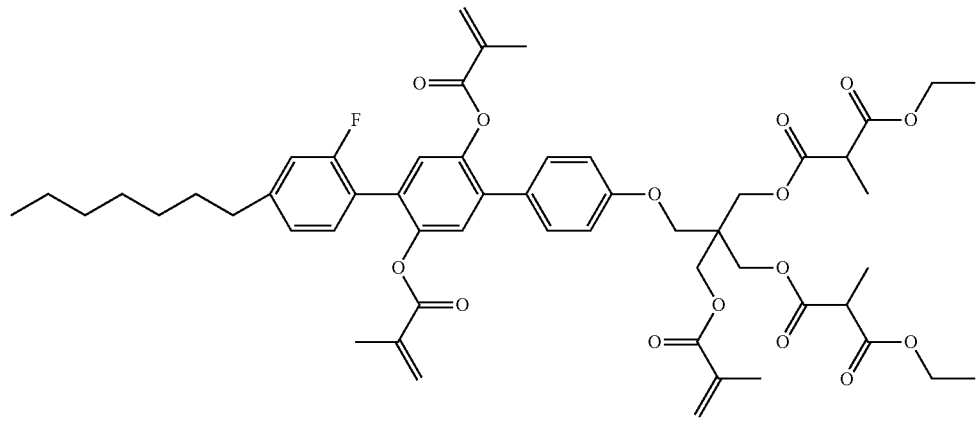
(P-108)
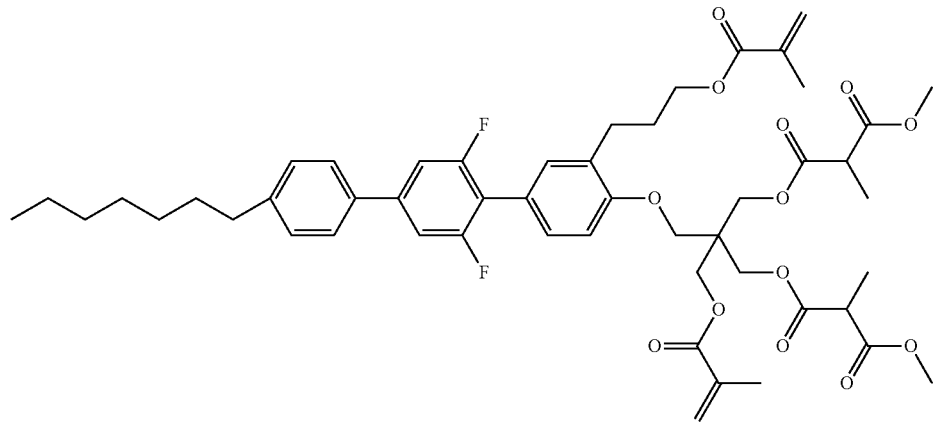

(P-109)
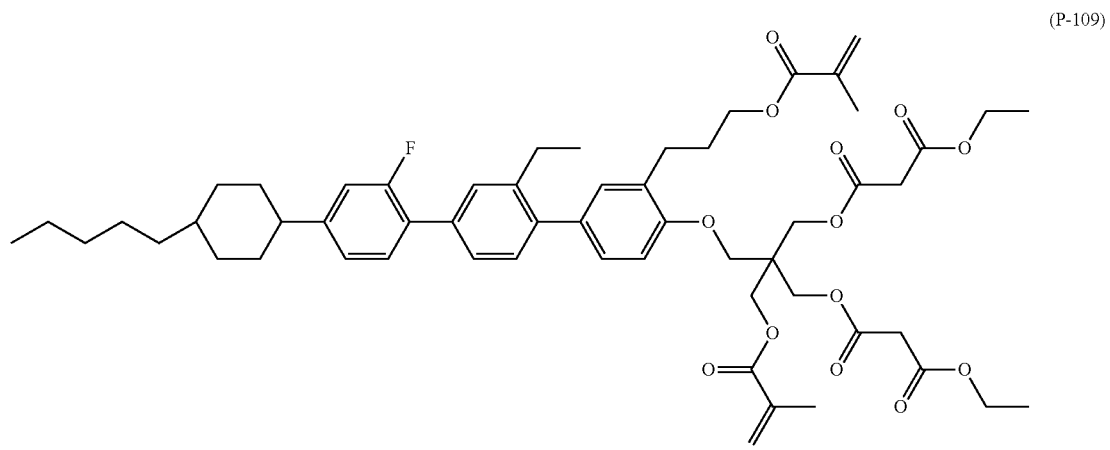
(P-110)
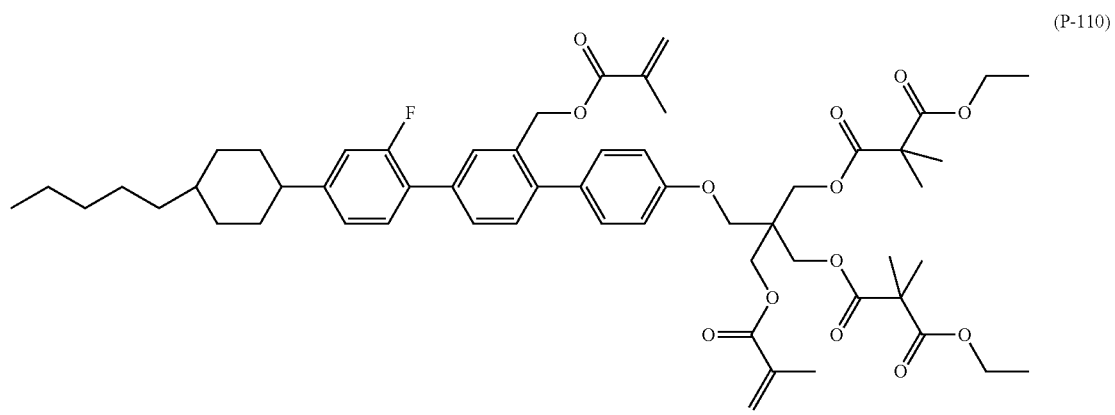
(P-110)
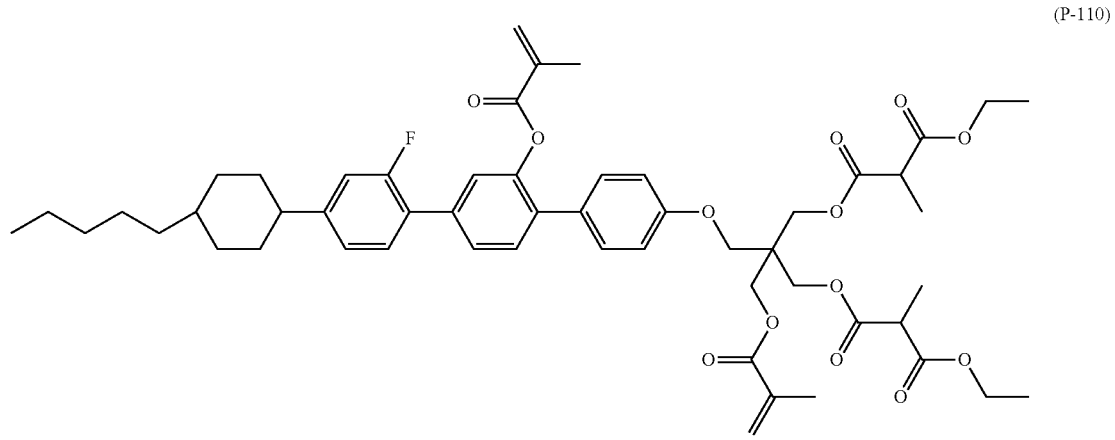

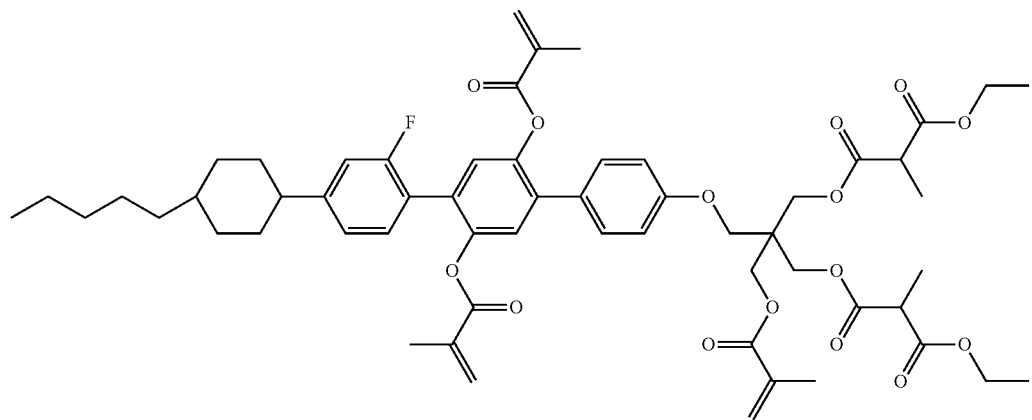
(P-112)
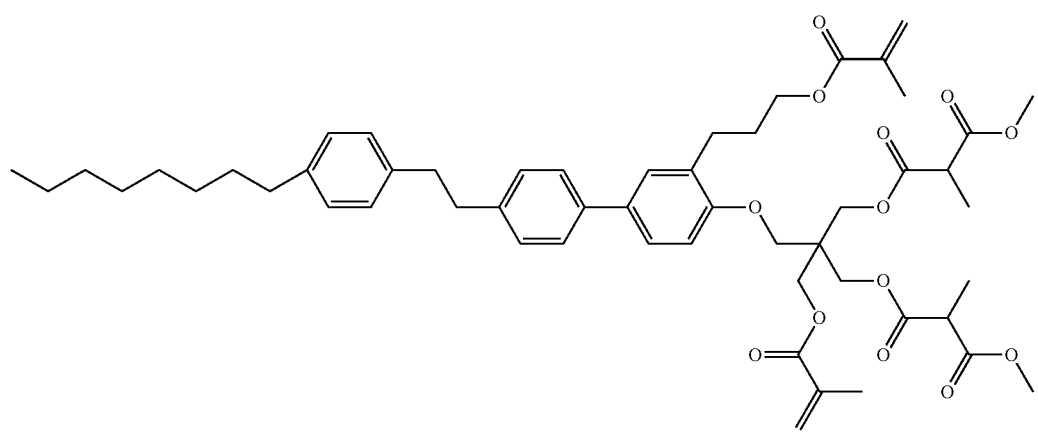
(P-113)
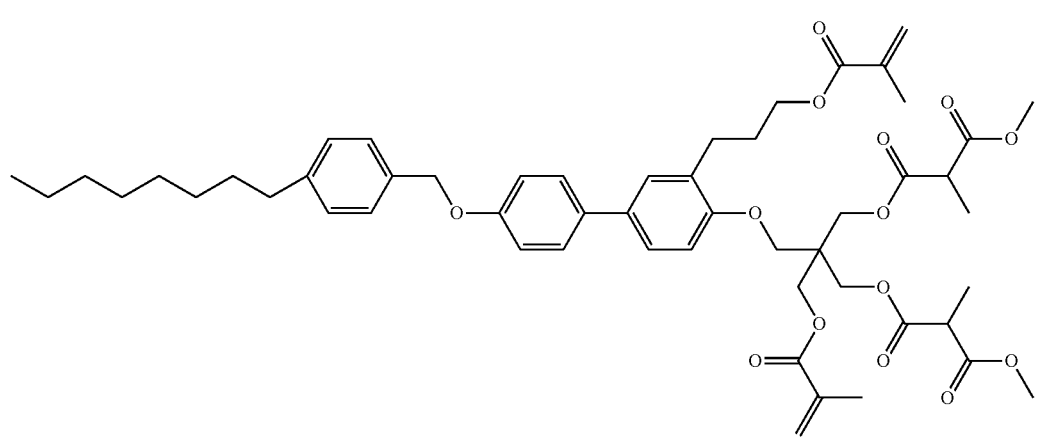
(P-114)

-continued
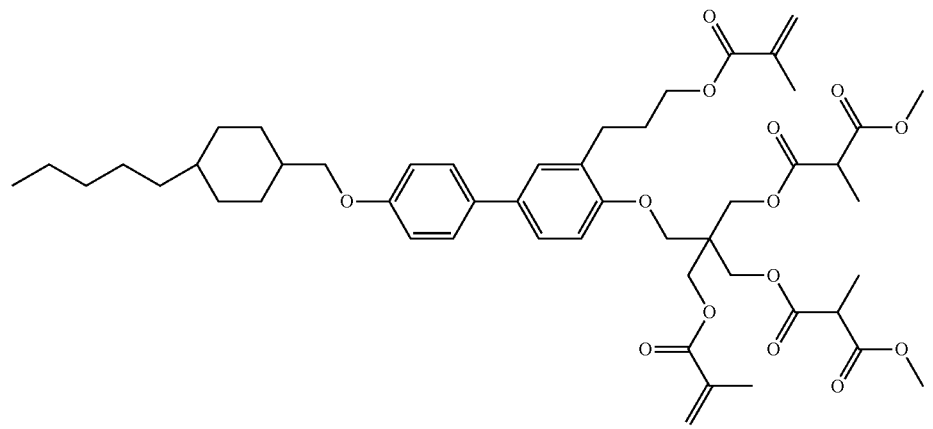
(P-115)
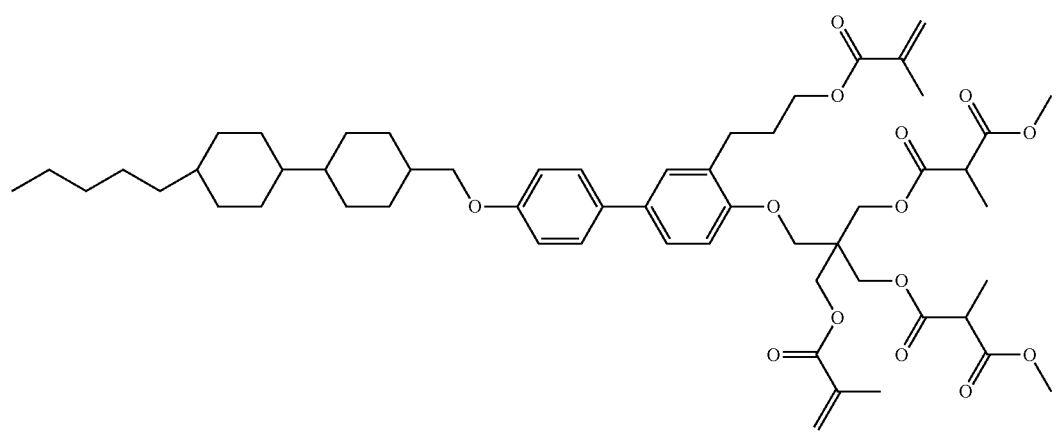
(P-116)
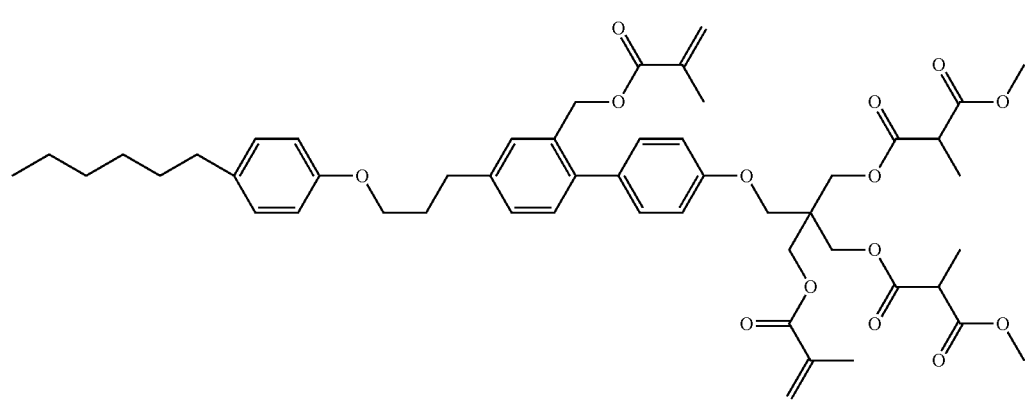
(P-117)

-continued
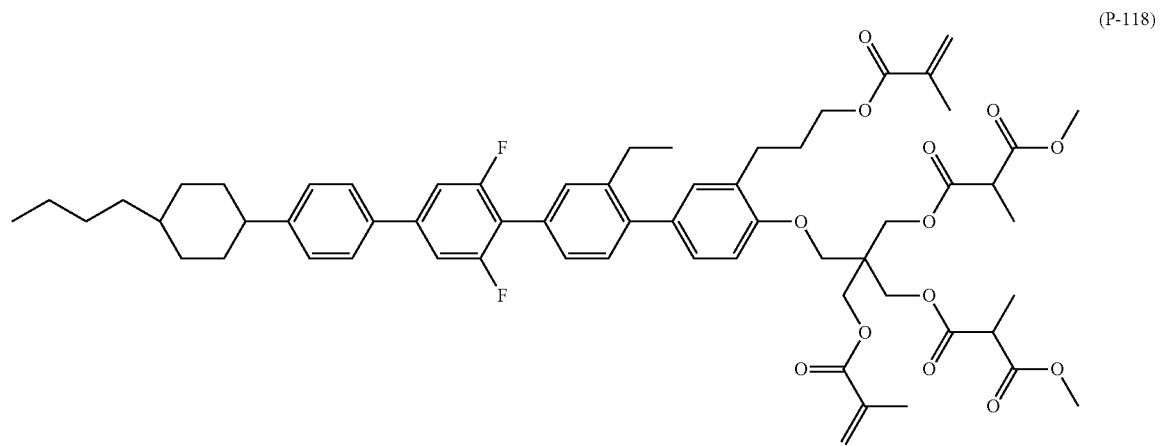
(P-118)
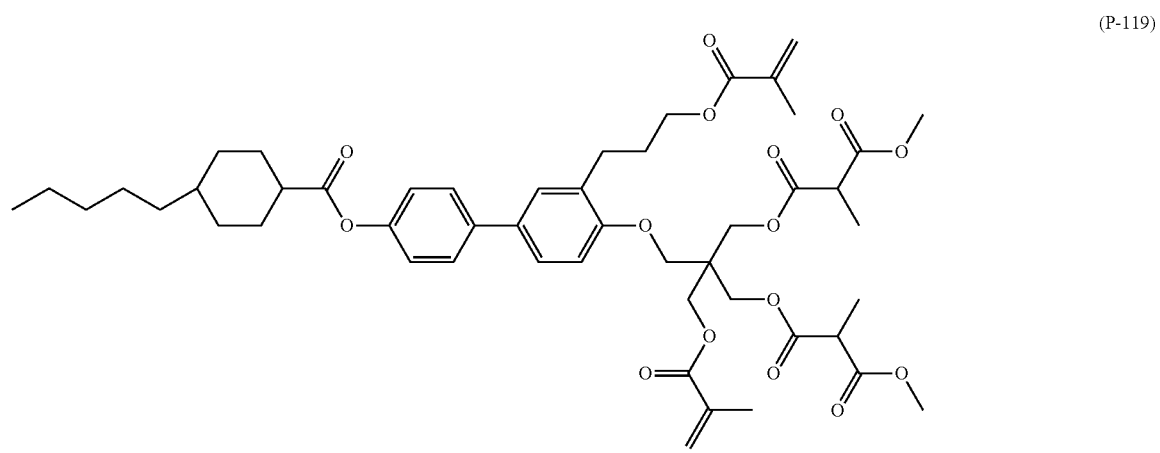
(P-119)
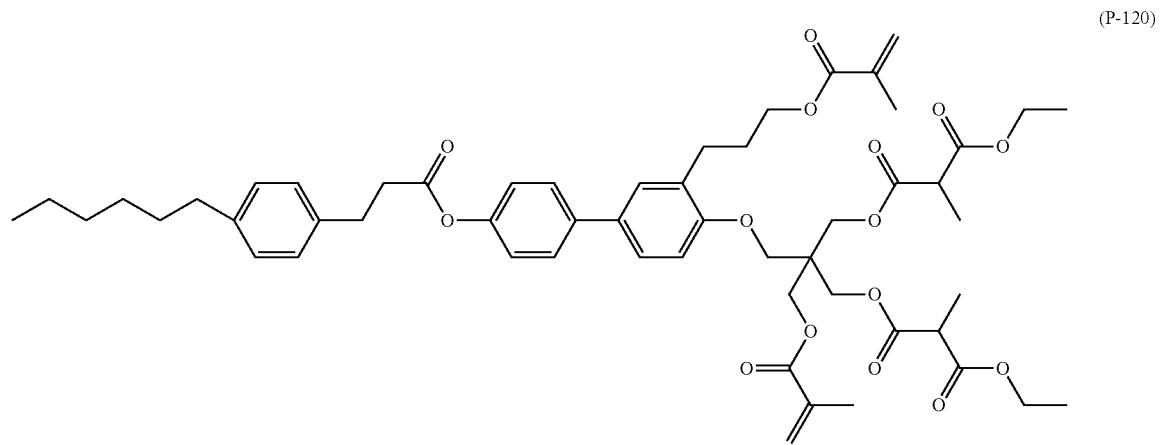
(P-120)

[Chem. 69]
(P-121)
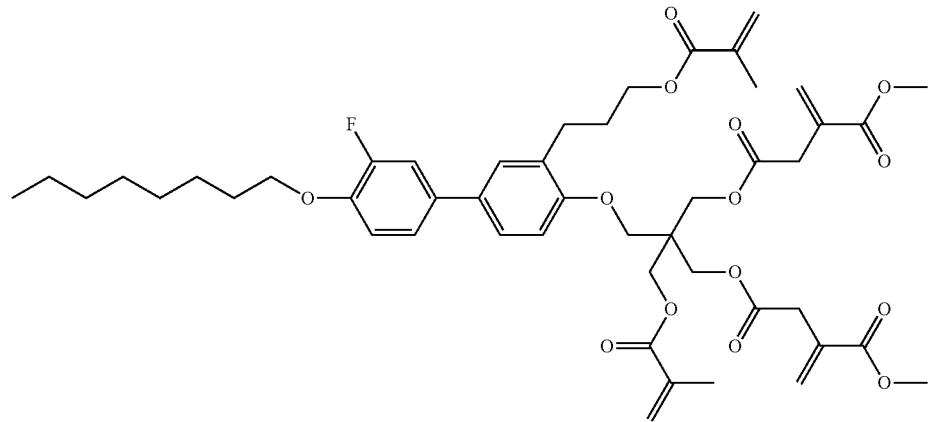
(P-122)
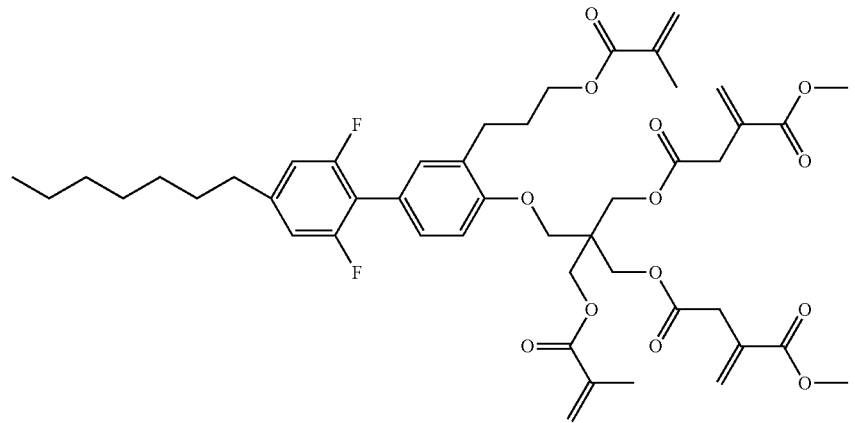
(P-123)
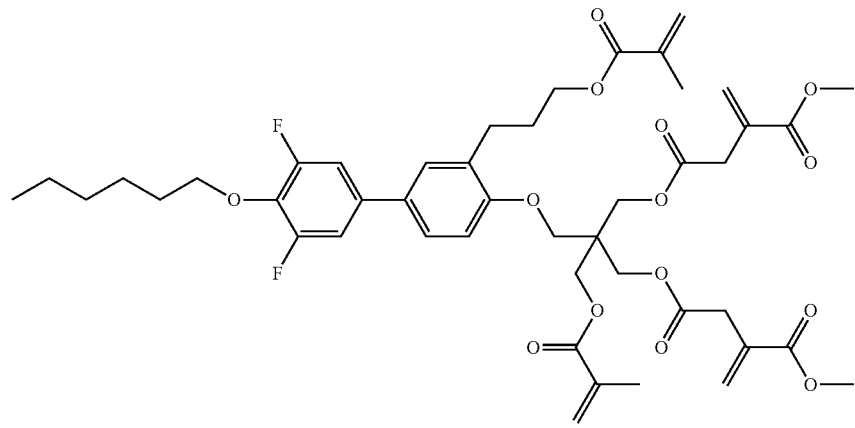

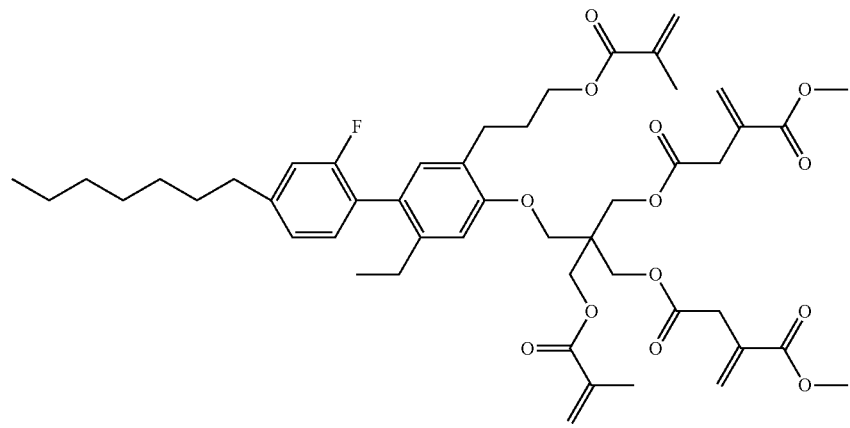
(P-124)
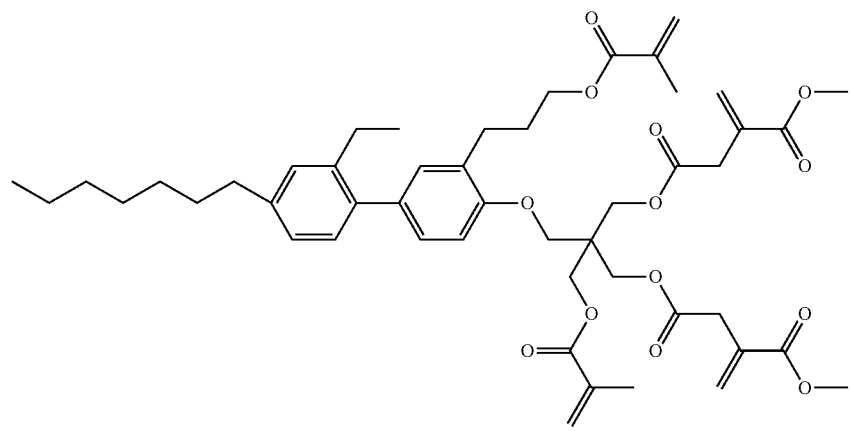
(P-125)
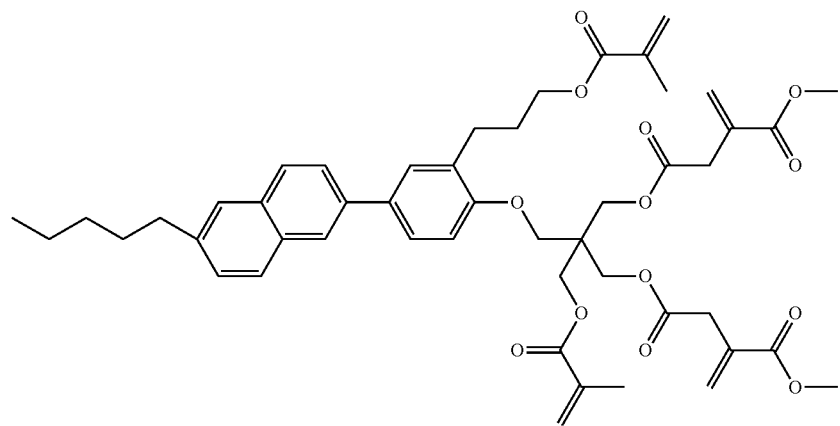
(P-126)

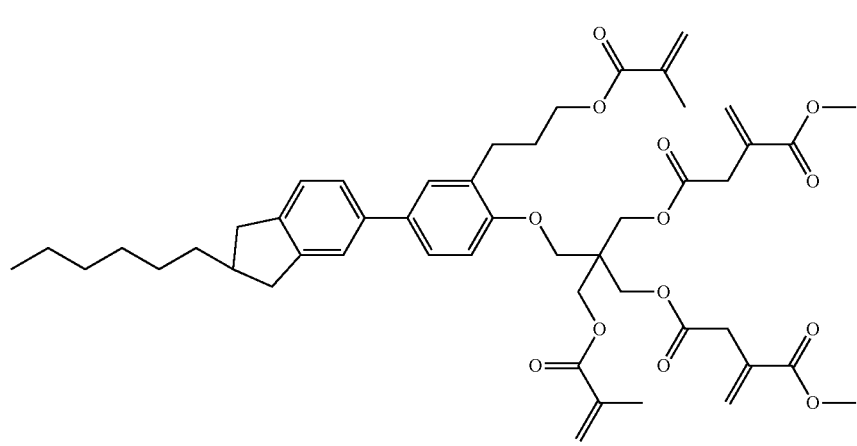
(P-127)
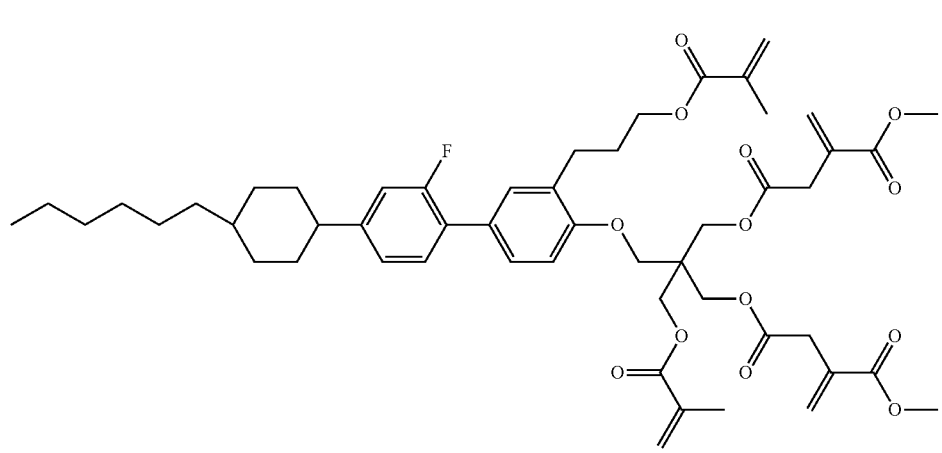
(P-128)
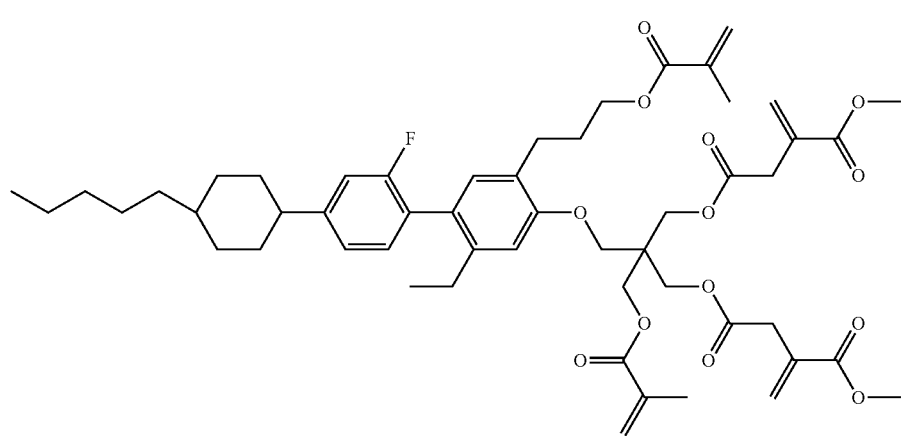
(P-129)

-continued
(P-130)
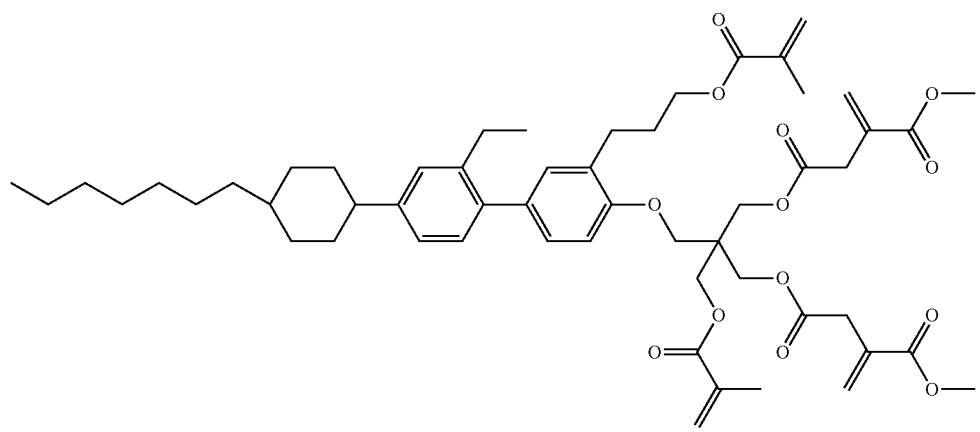
(P-131)
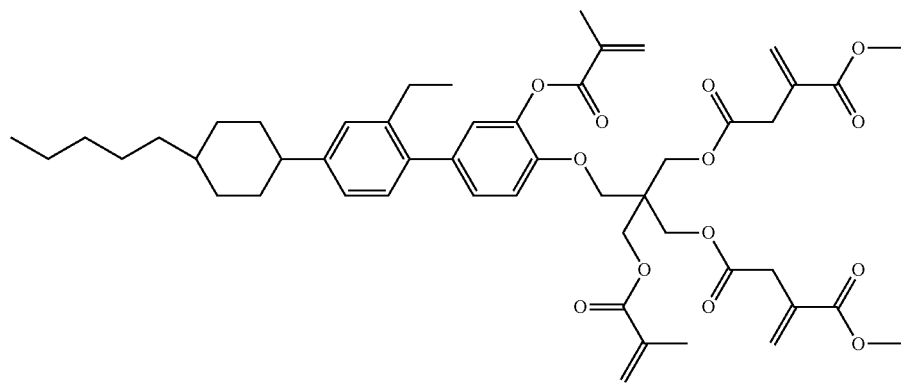
(P-132)
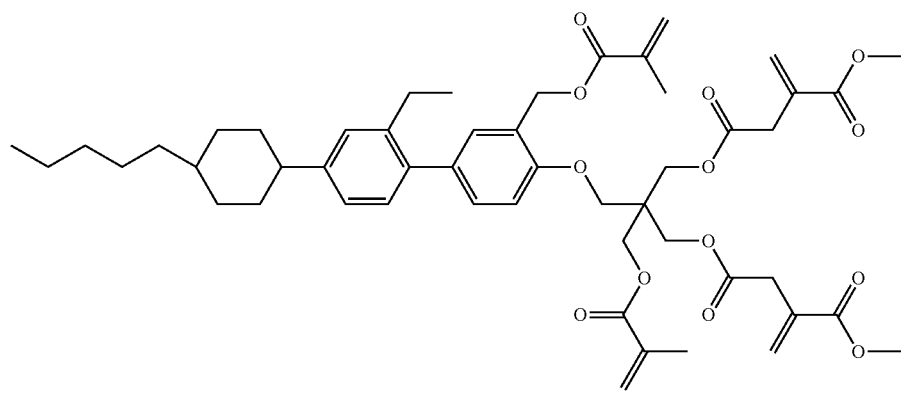
[Chem. 70]
(P-133)
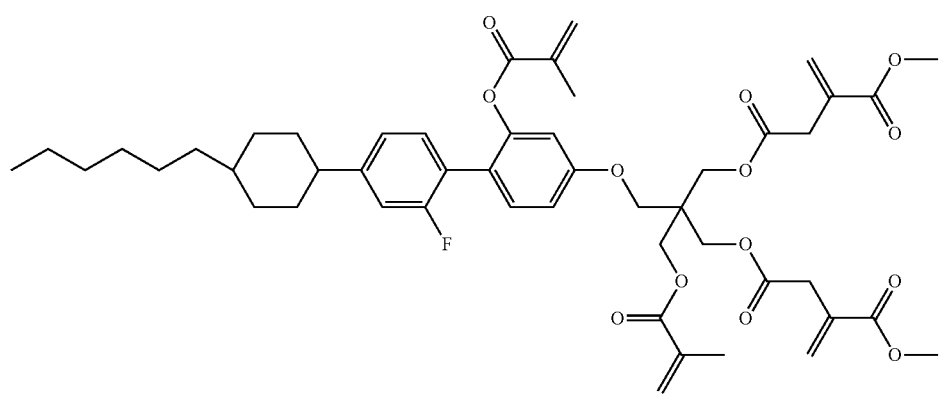

-continued
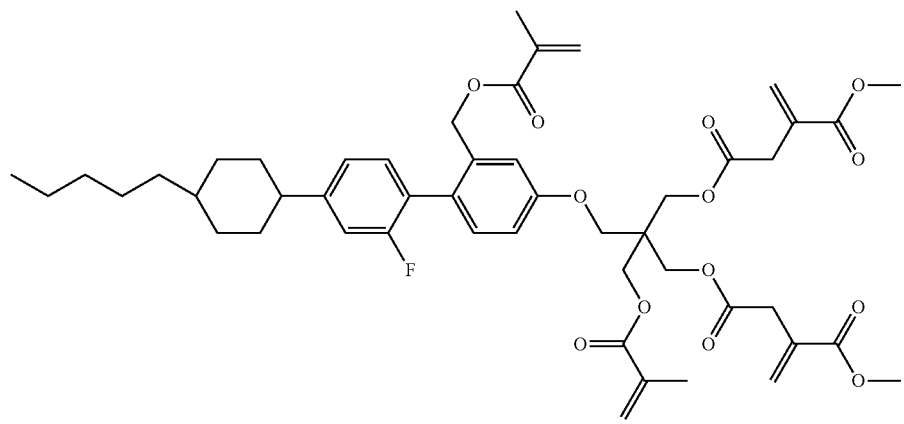
(P-134)
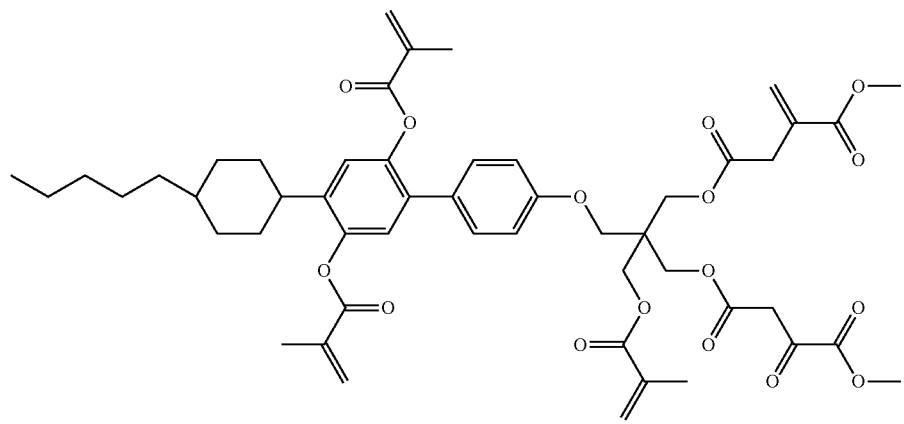
(P-135)
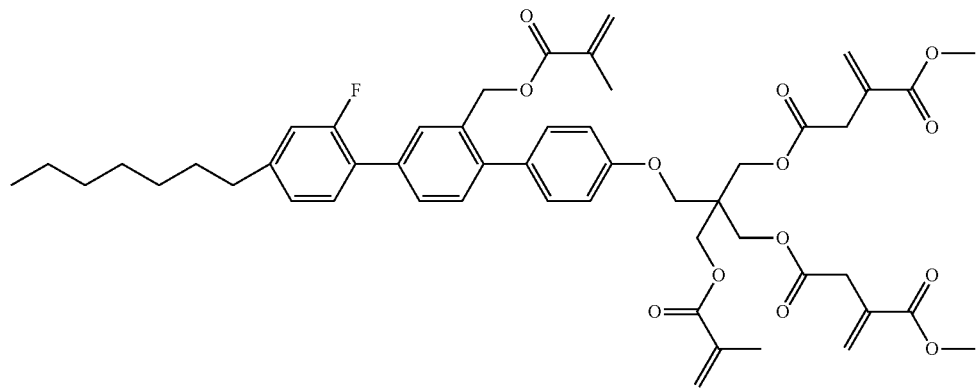
(P-136)
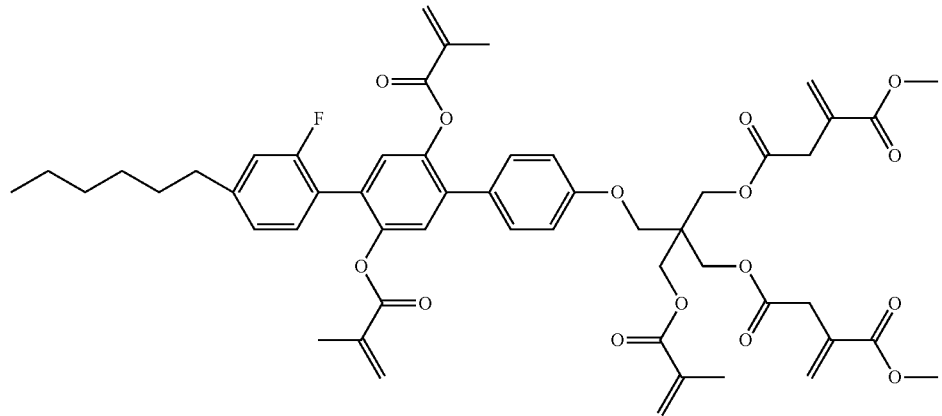
(P-137)

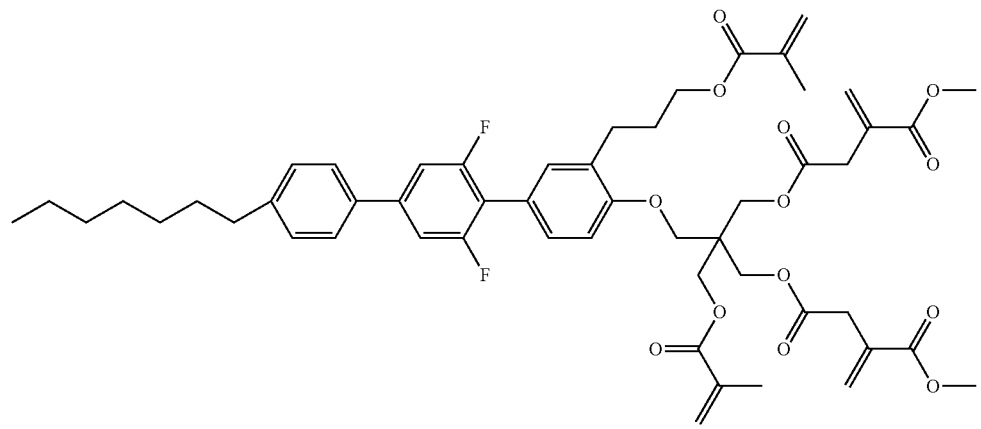
(P-138)
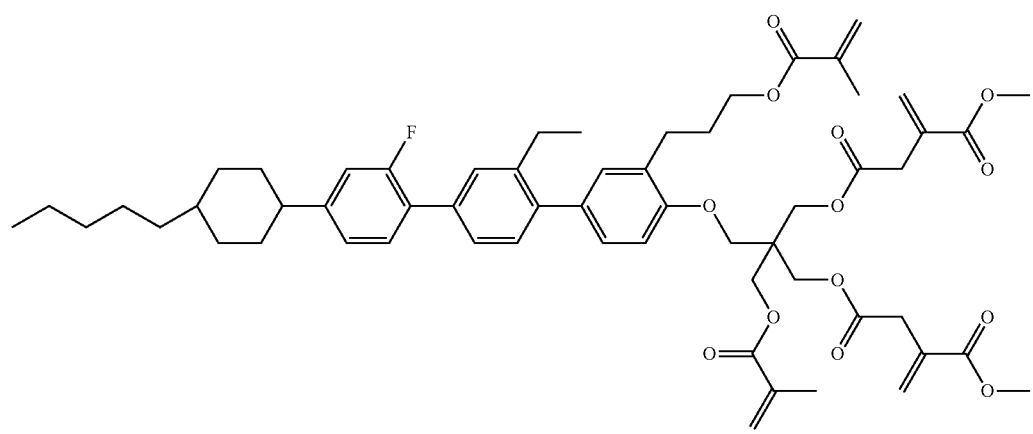
(P-139)
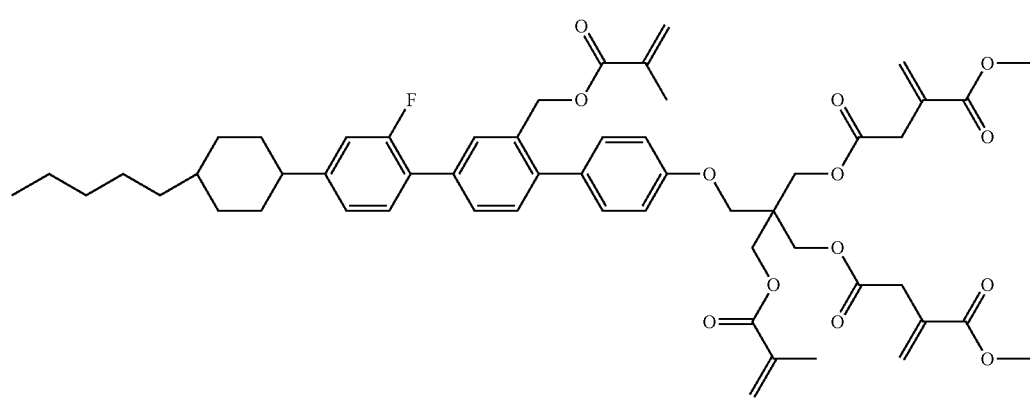
(P-140)

-continued
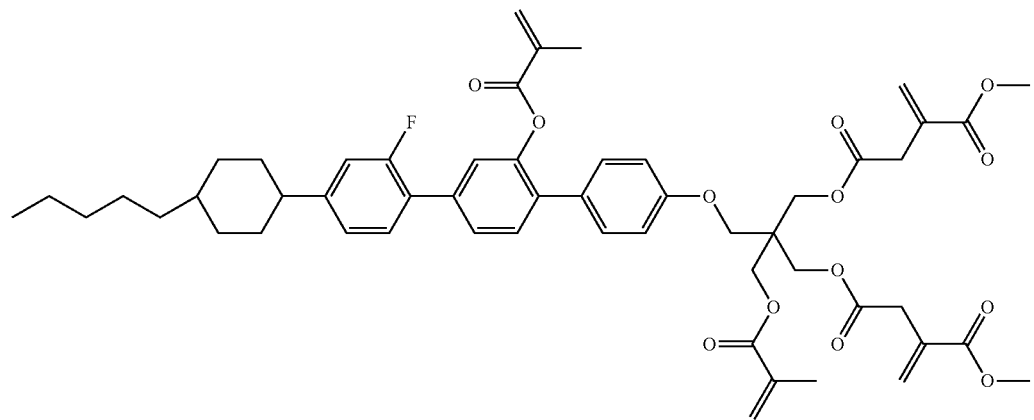
(P-141)
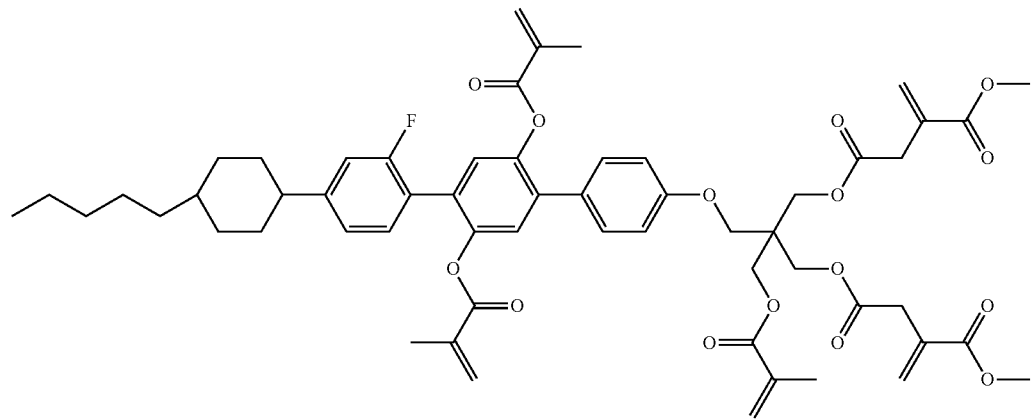
(P-142)
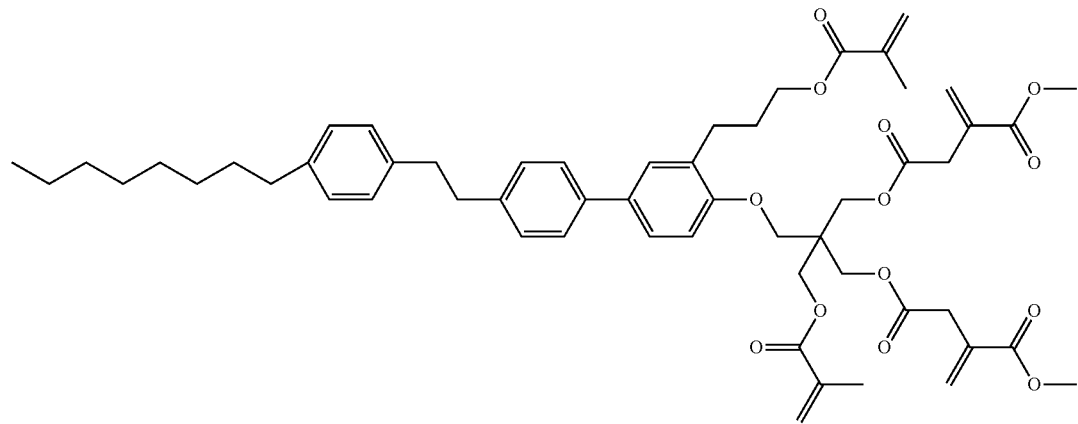
(P-143)

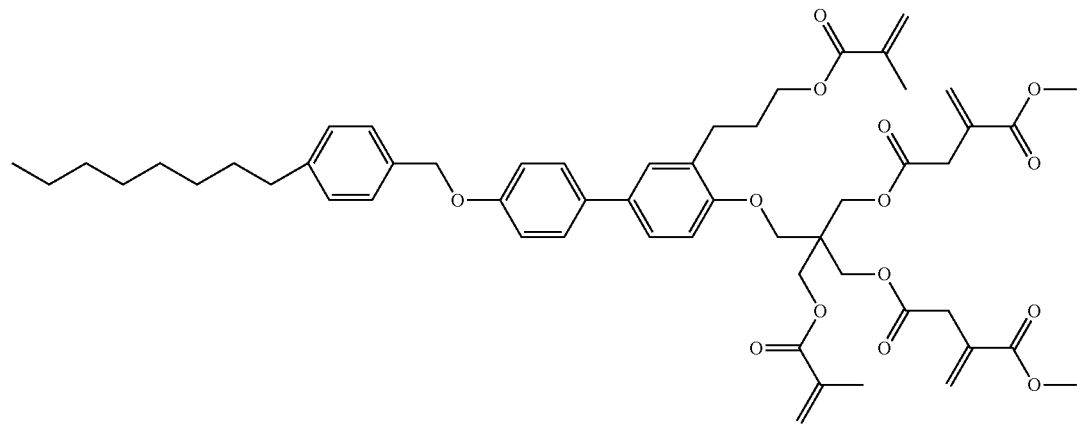
(P-144)
[Chem. 71]
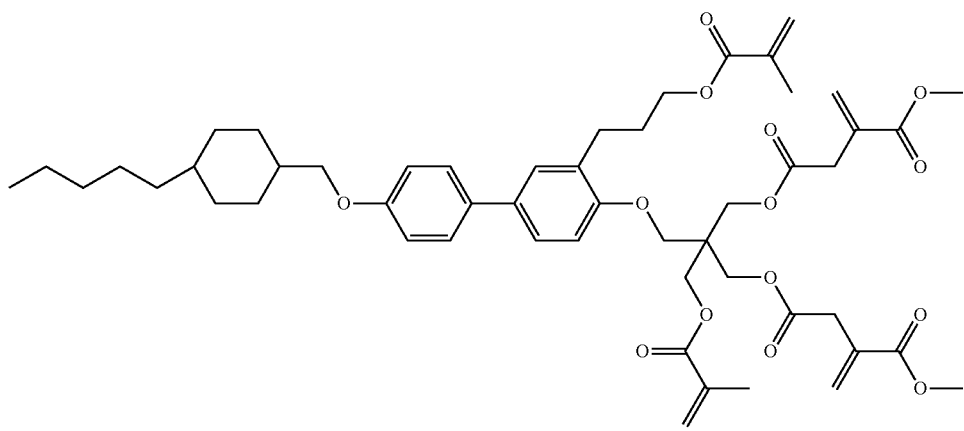
(P-145)
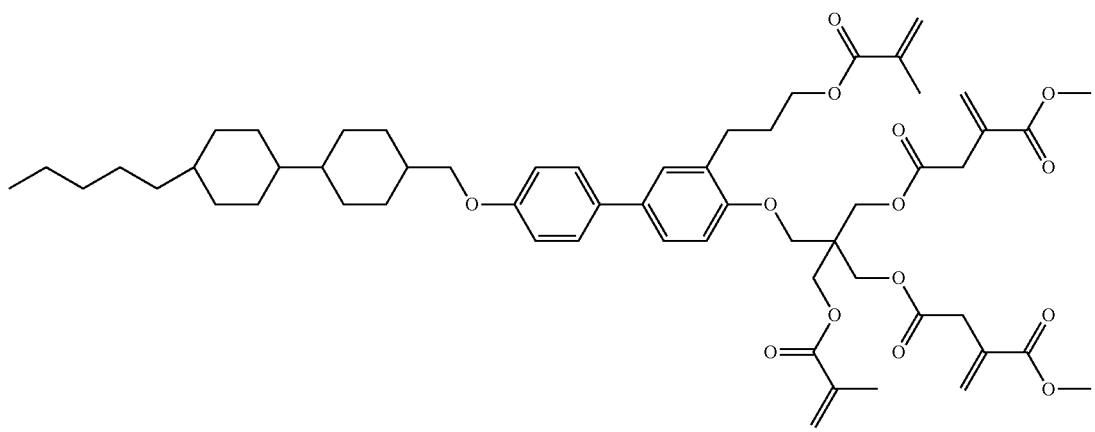
(P-146)

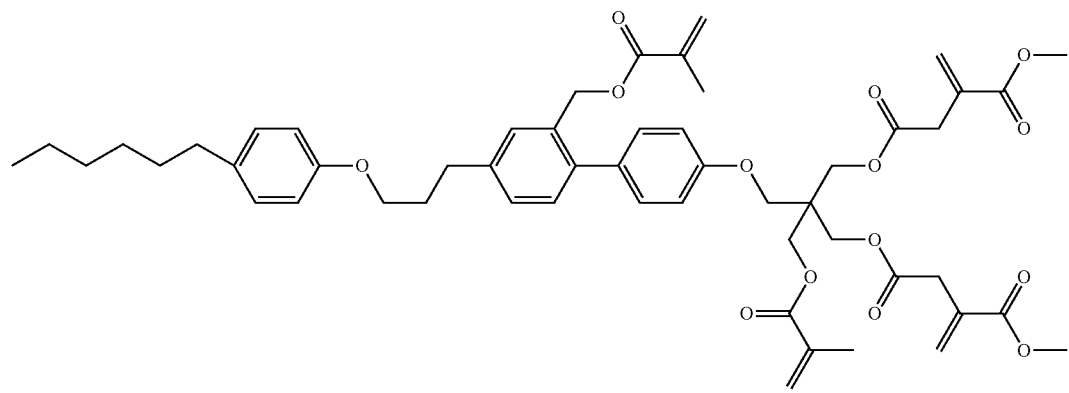
(P-147)
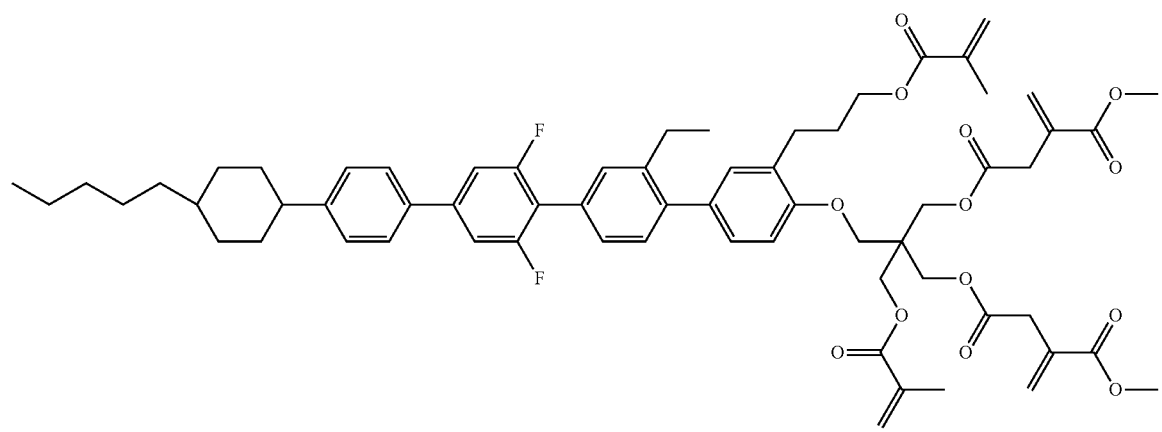
(P-148)
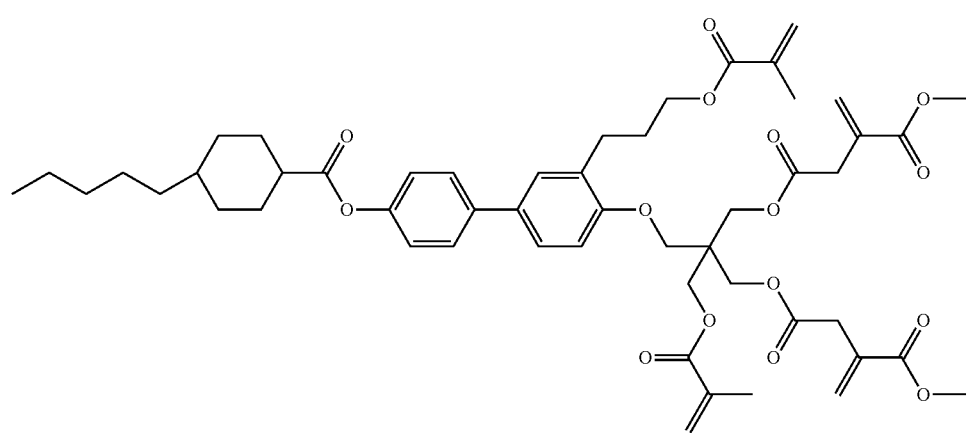
(P-149)

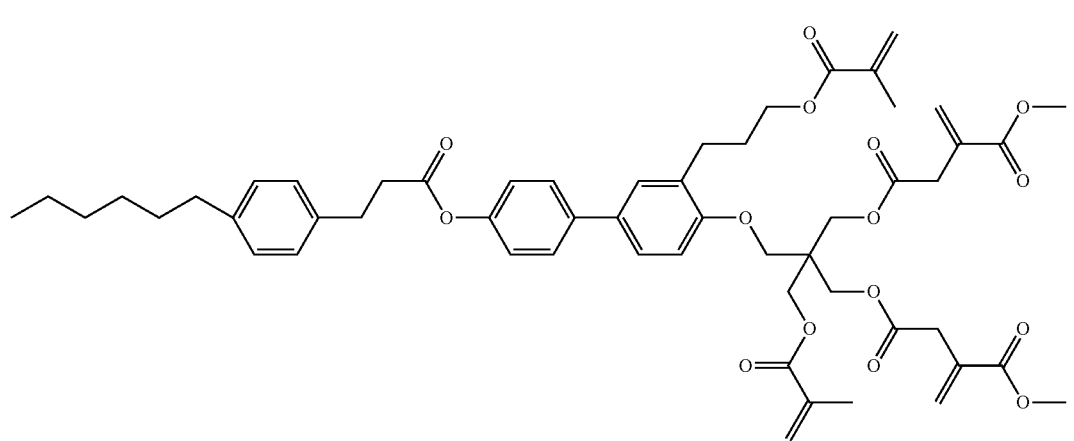
(P-150)
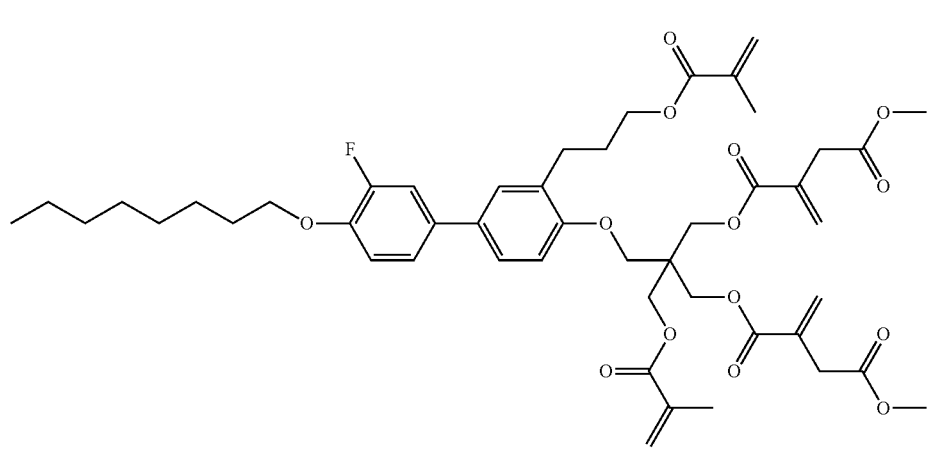
(P-151)
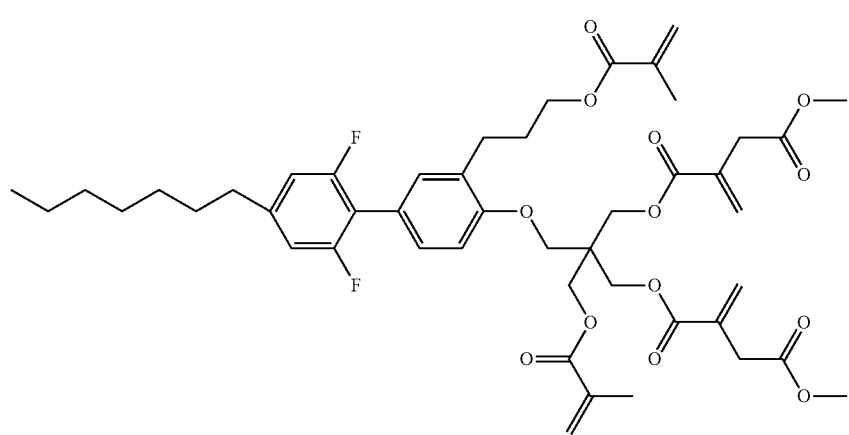
(P-152)

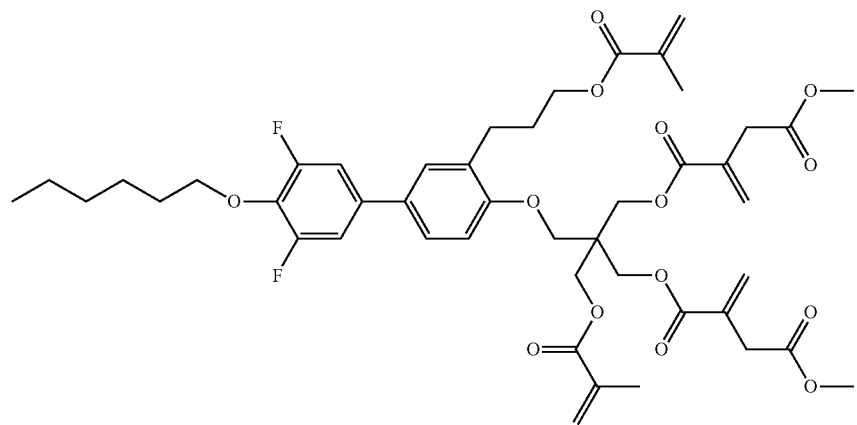
(P-153)
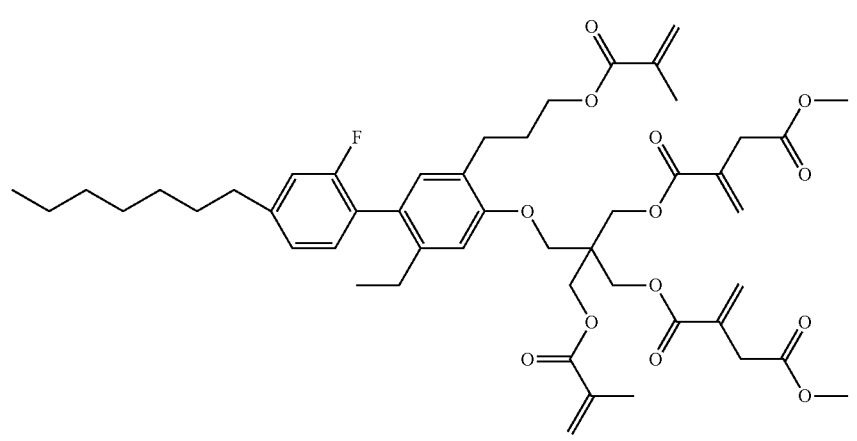
(P-154)
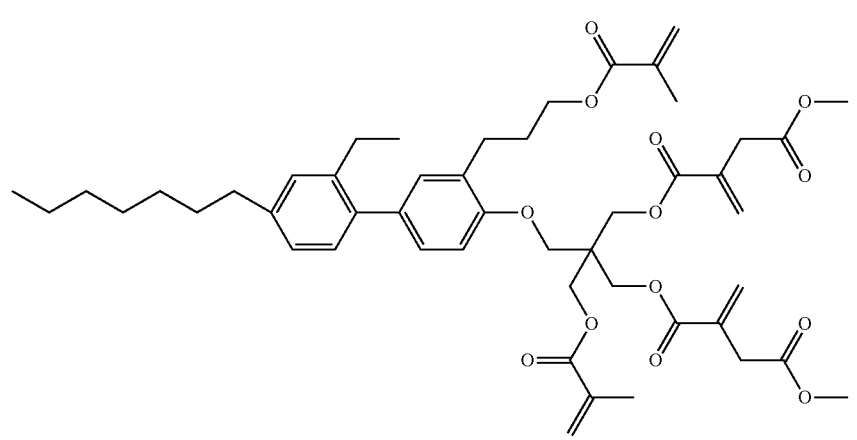
(P-155)

-continued
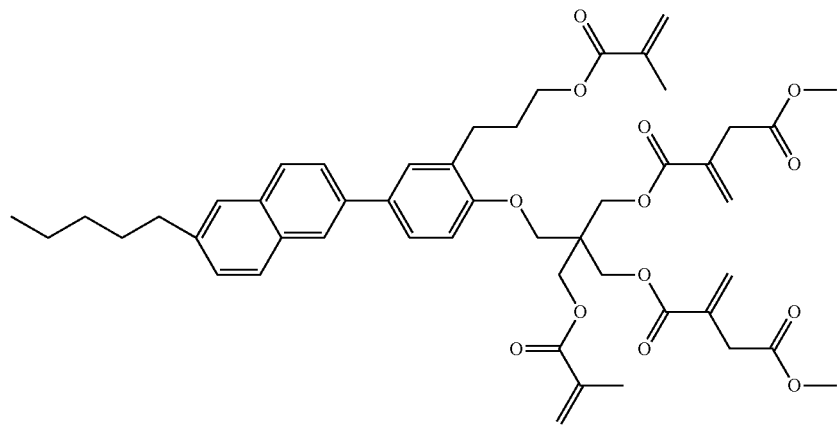
(P-156)
[Chem. 72]
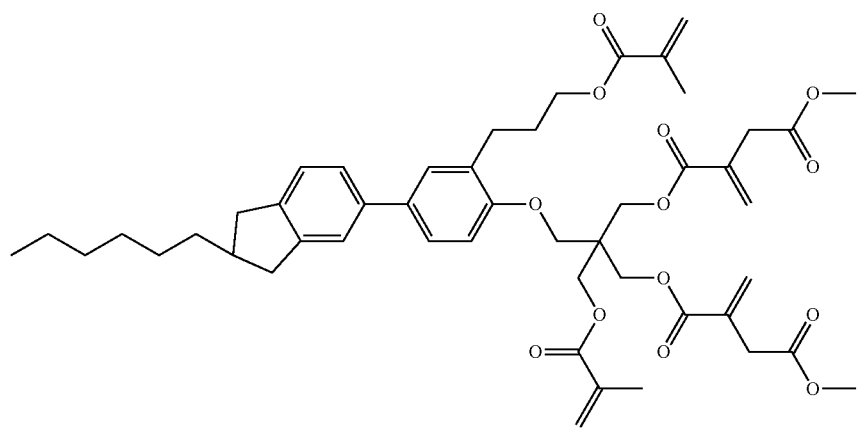
(P-157)
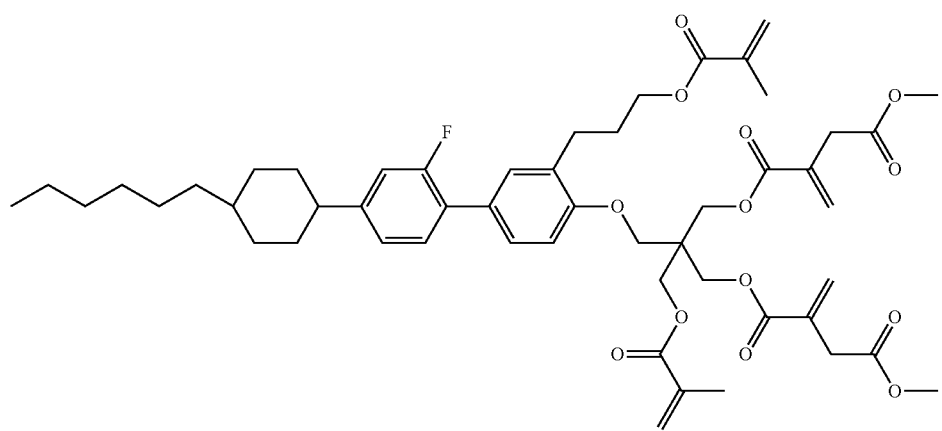
(P-158)

(P-159)
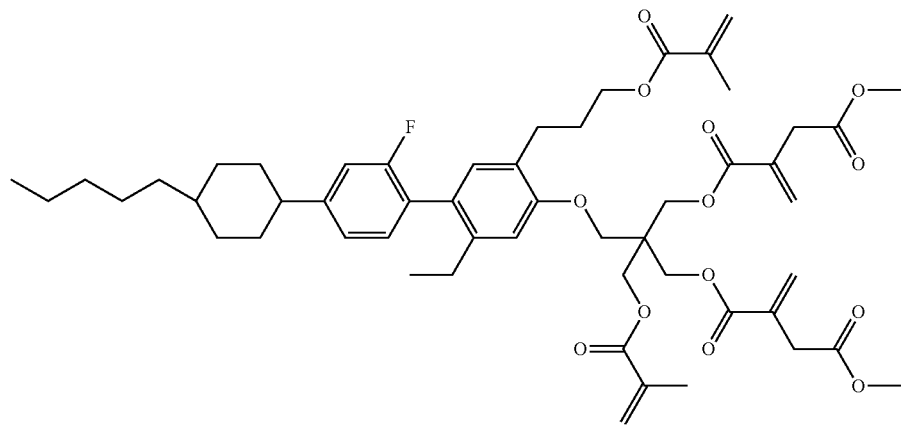
(P-160)
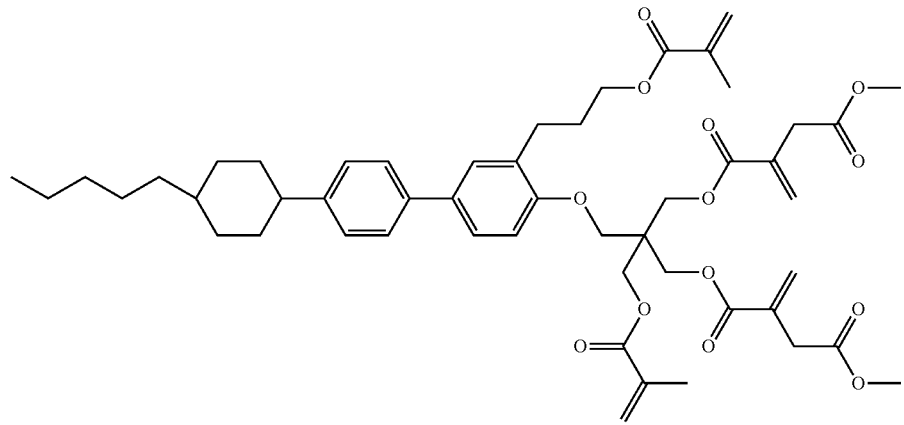
(P-161)
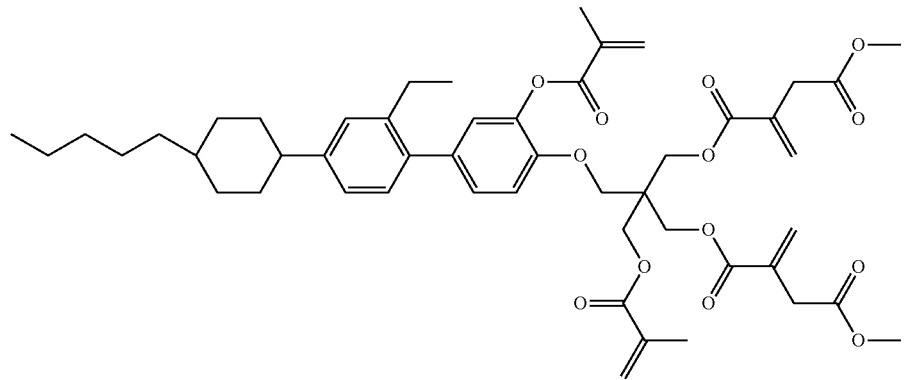
(P-162)
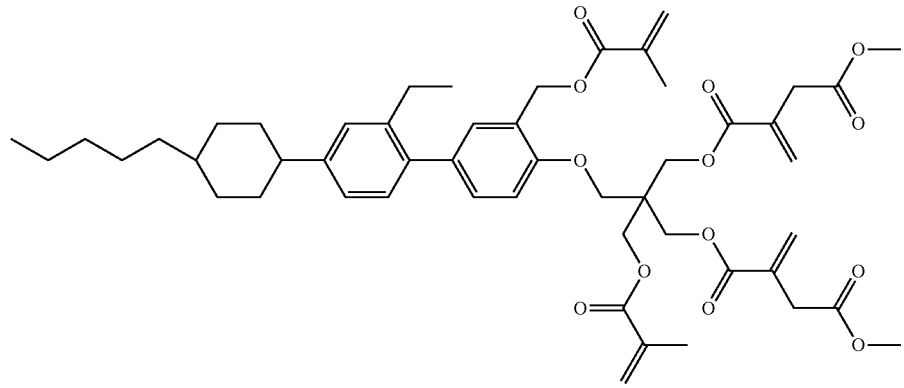

(P-163)
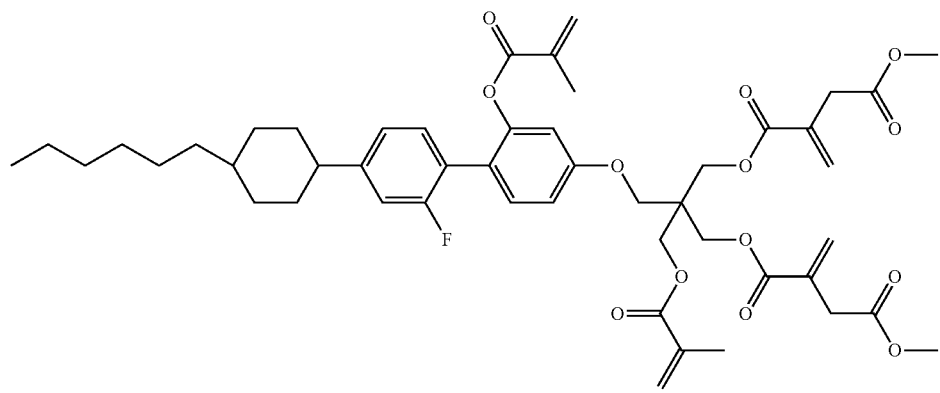
(P-164)
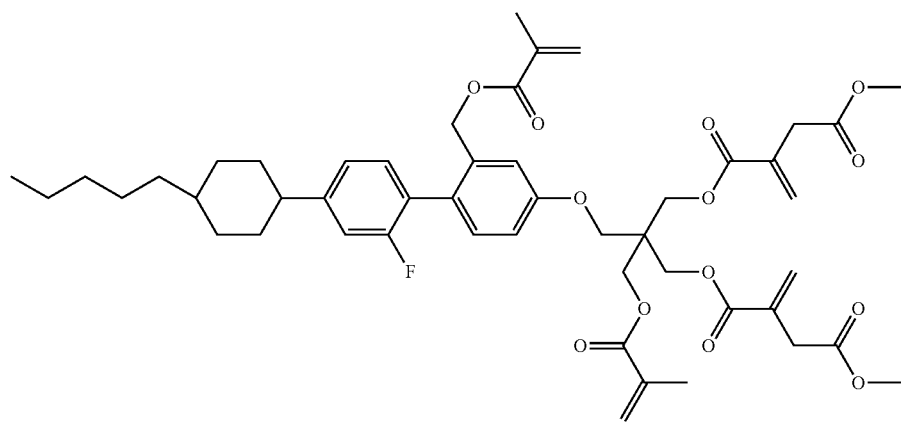
(P-165)
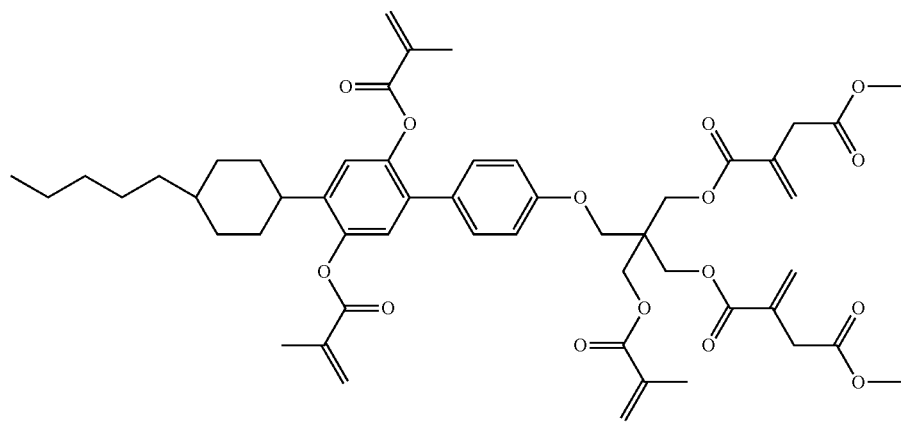
(P-166)
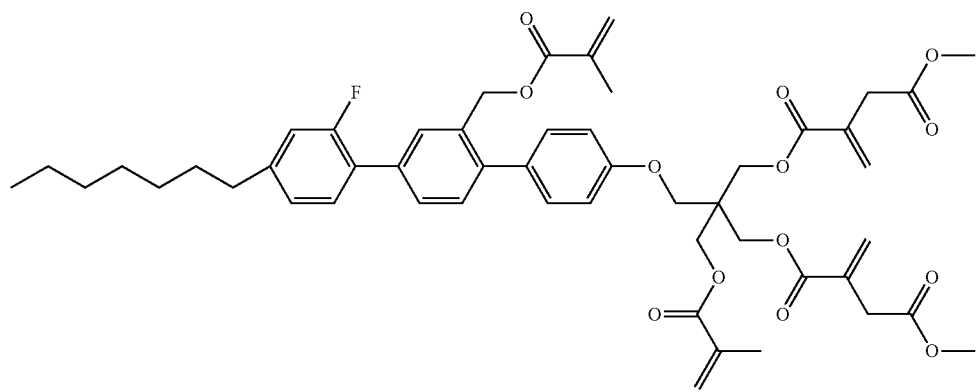

-continued
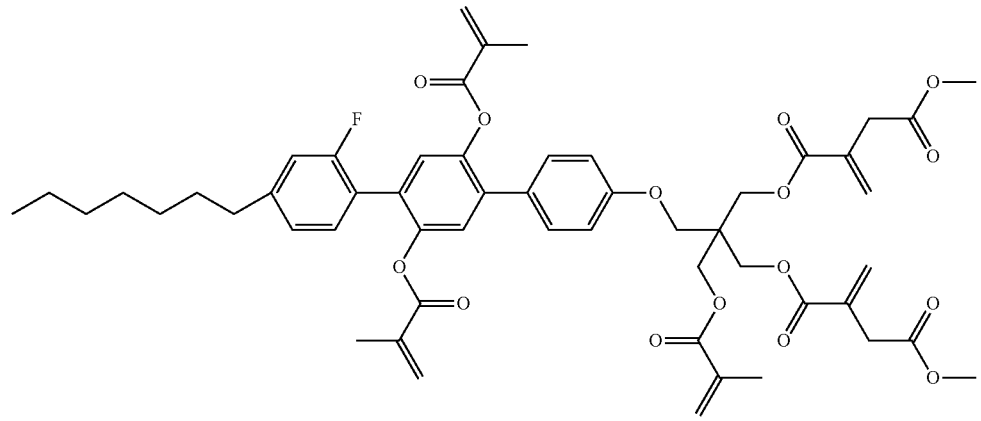
(P-167)
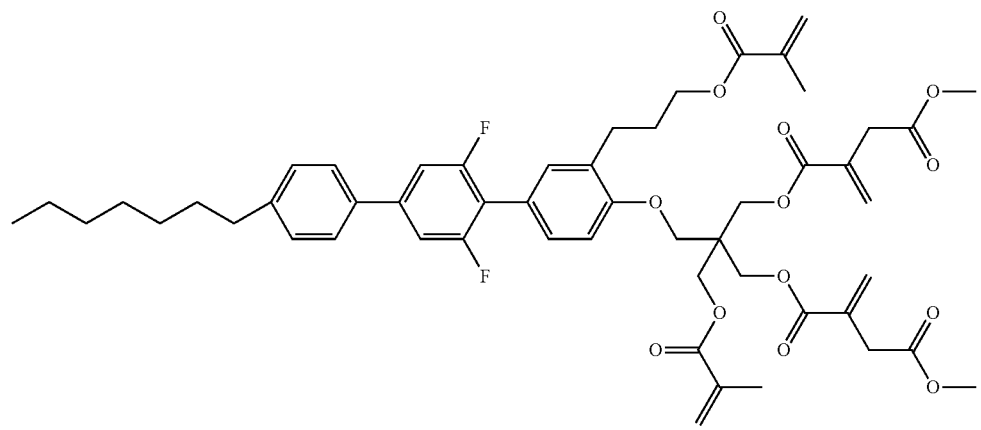
(P-168)
[Chem. 73]
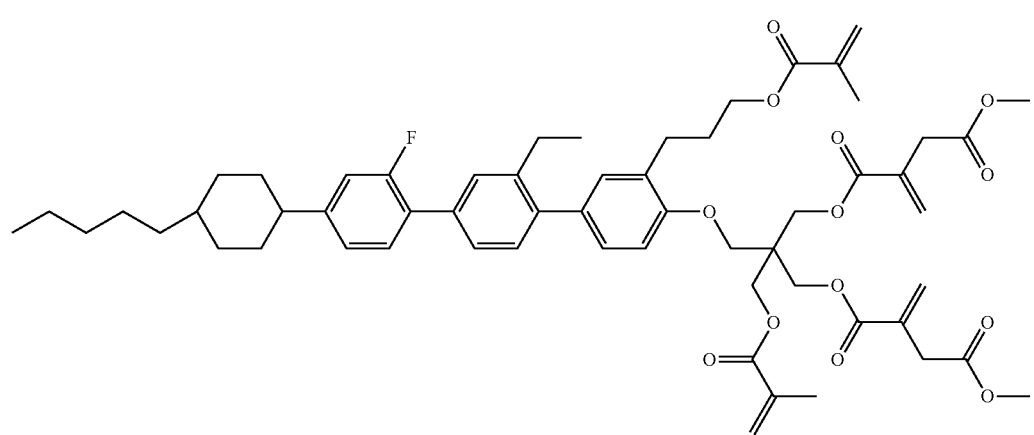
(P-169)

-continued
(P-170)
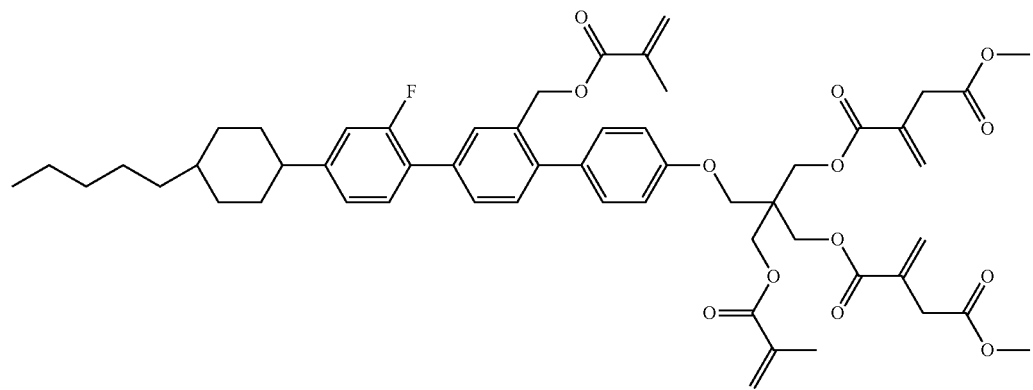
(P-171)
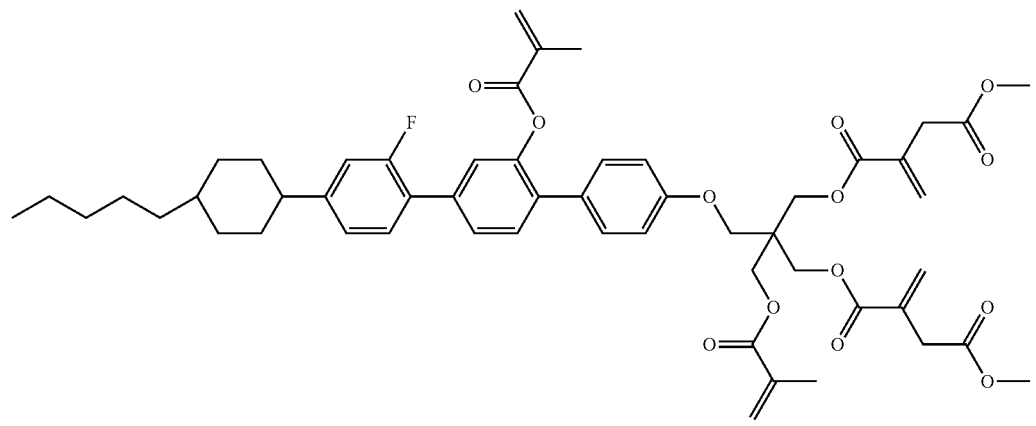
(P-172)
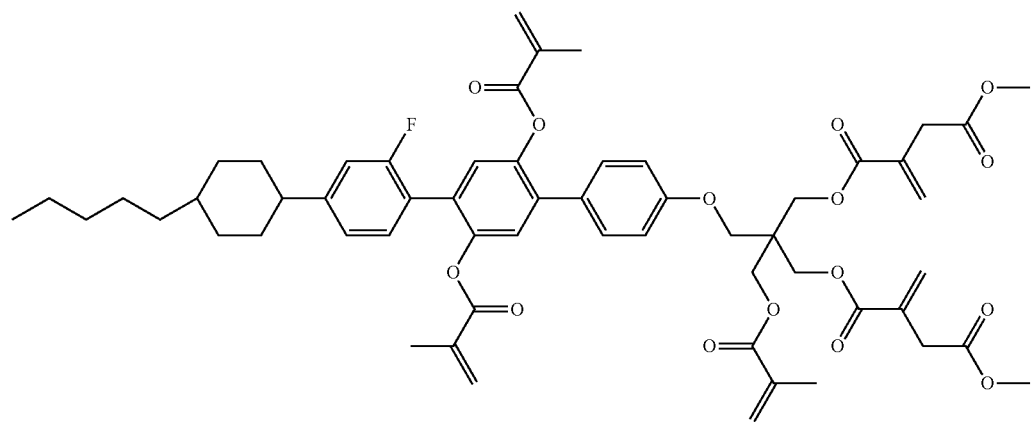

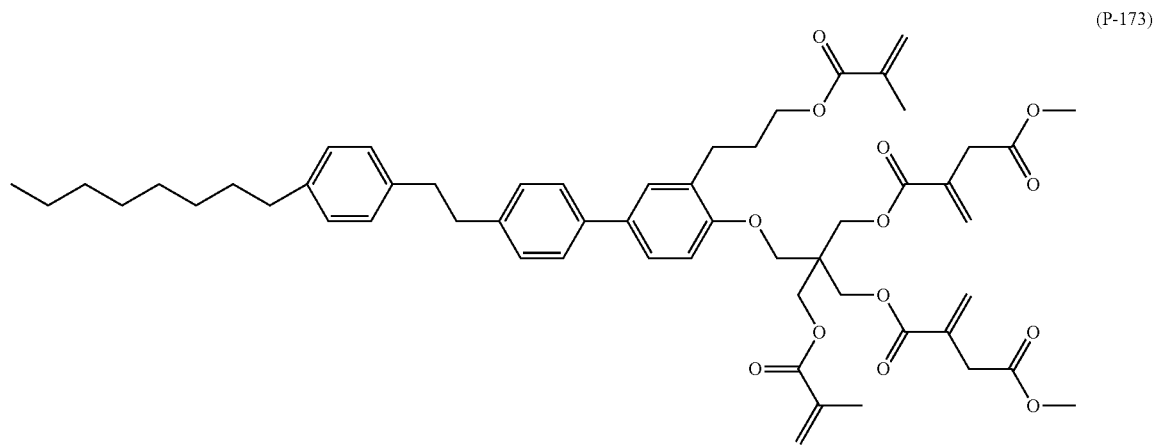
(P-173)
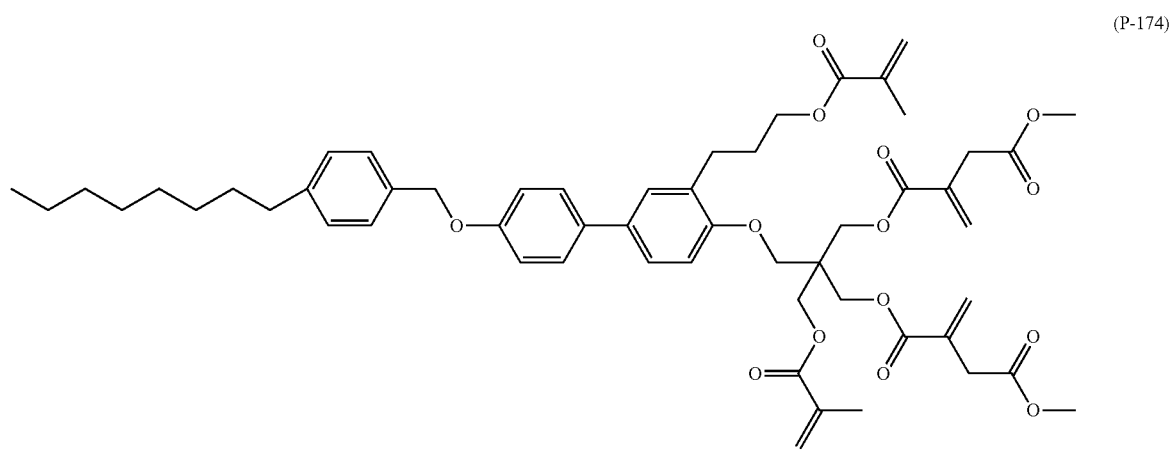
(P-174)
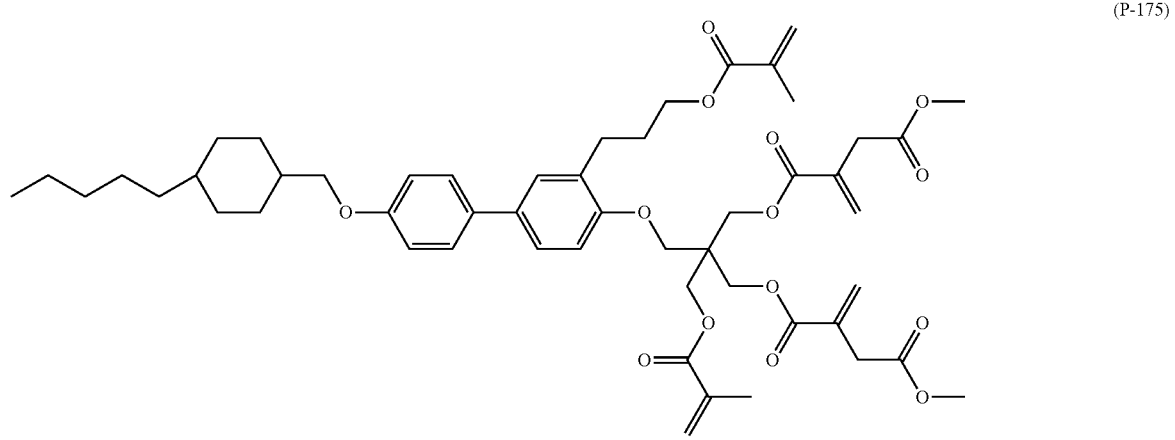
(P-175)

-continued
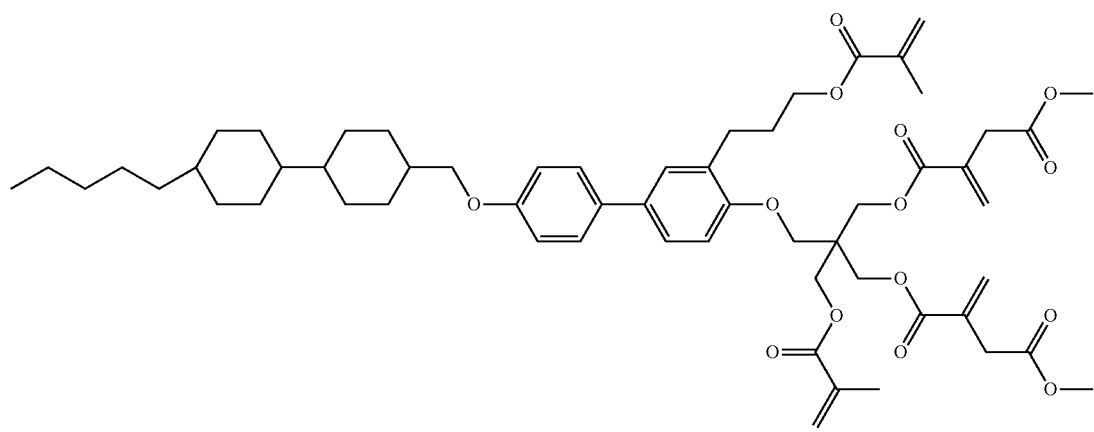
(P-176)
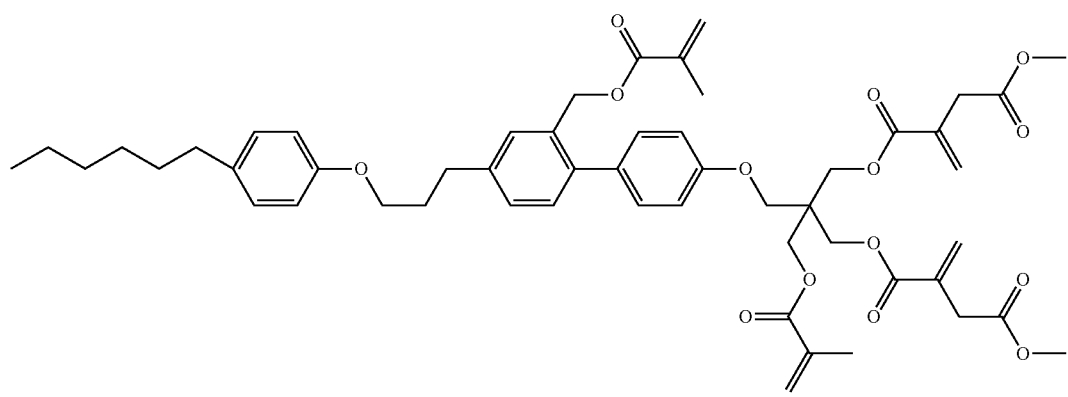
(P-177)
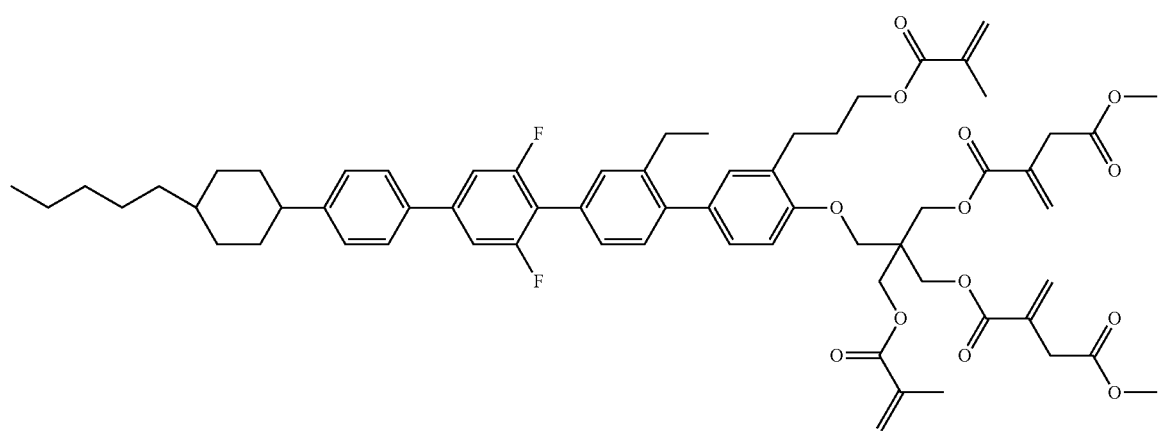
(P-178)

(P-179)
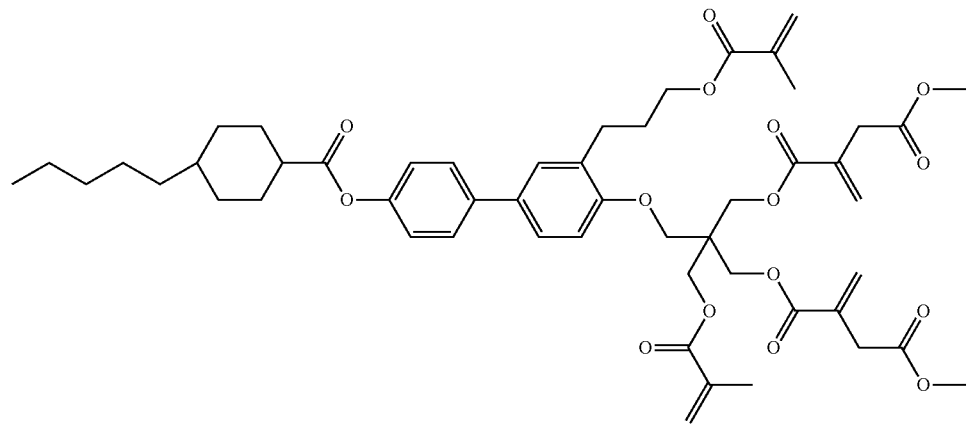
(P-180)
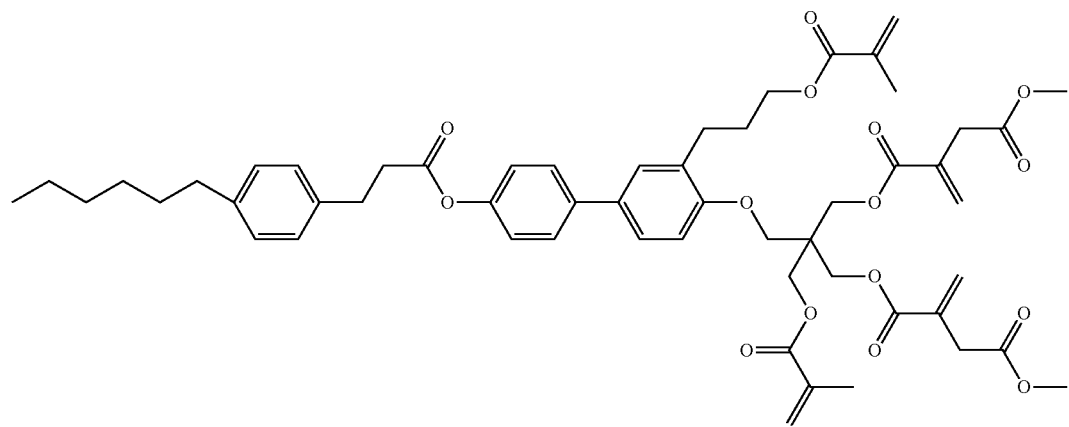
[Chem. 74]
(P-181)
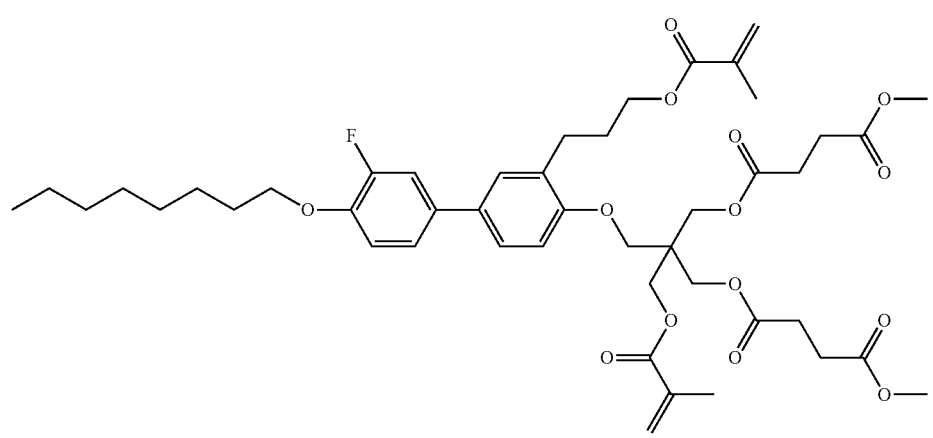

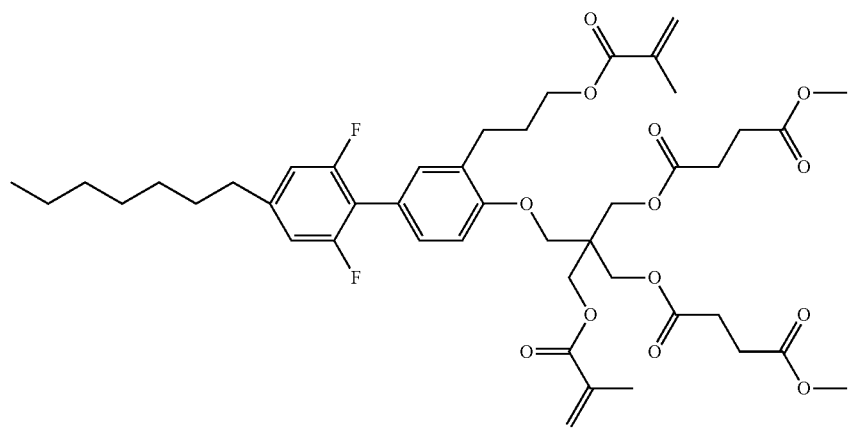
(P-182)

(P-183)
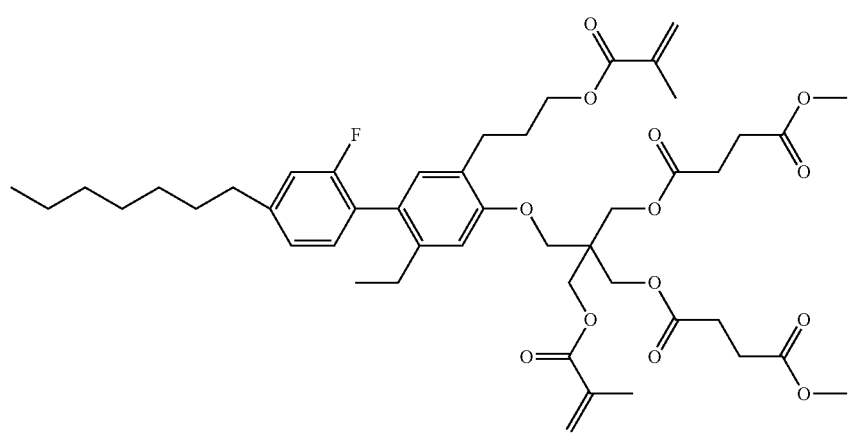
(P-184)

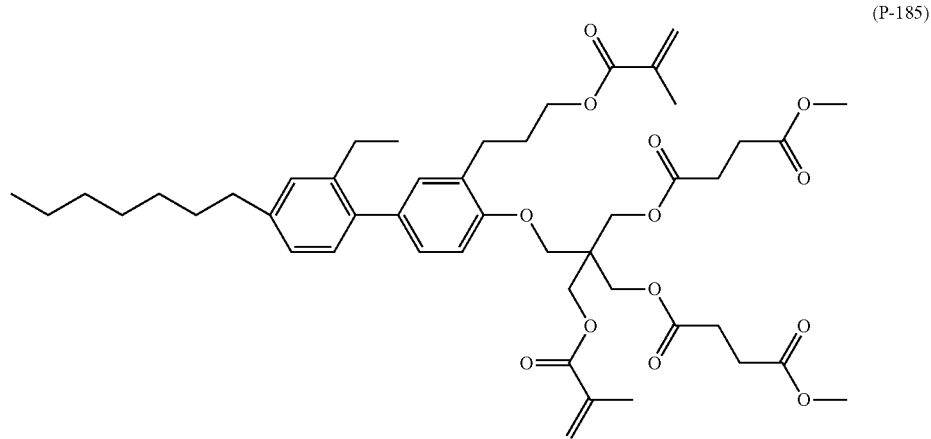
(P-185)
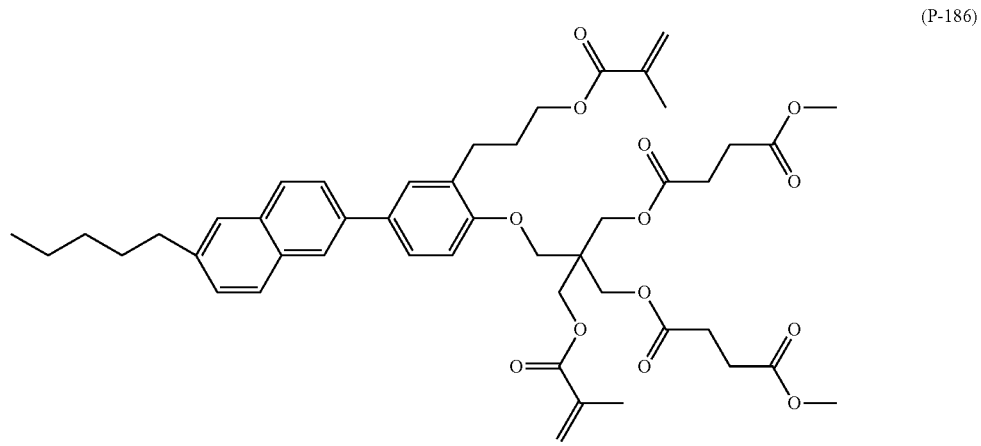
(P-186)
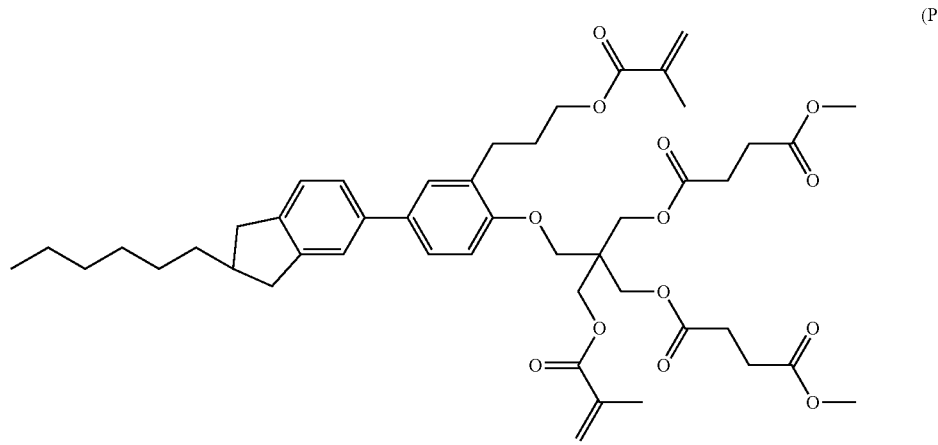
(P-187)

(P-188)
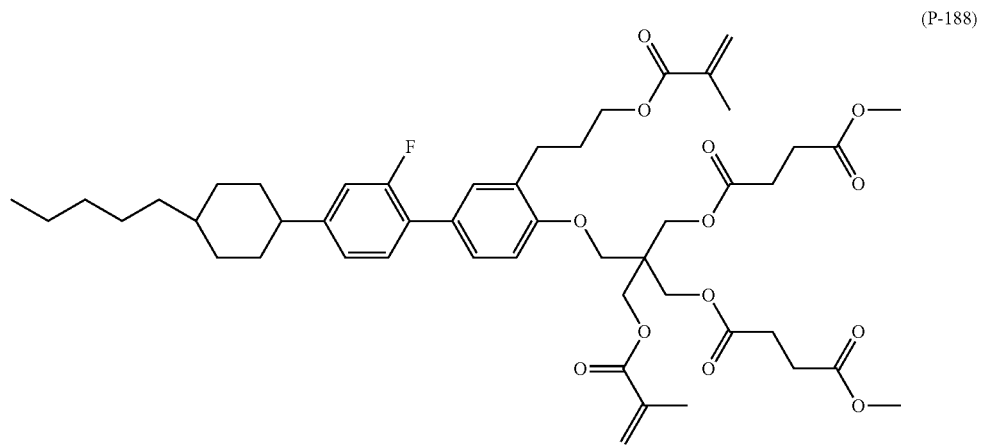
(P-189)
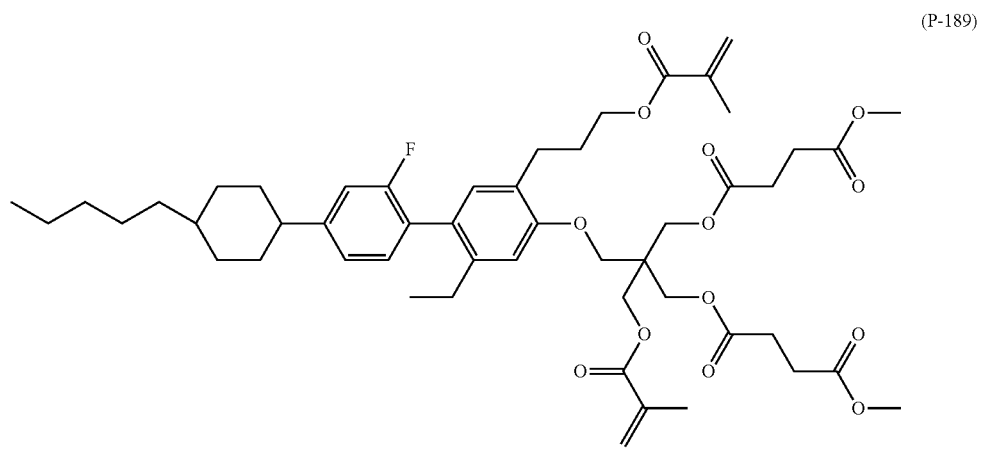
(P-190)
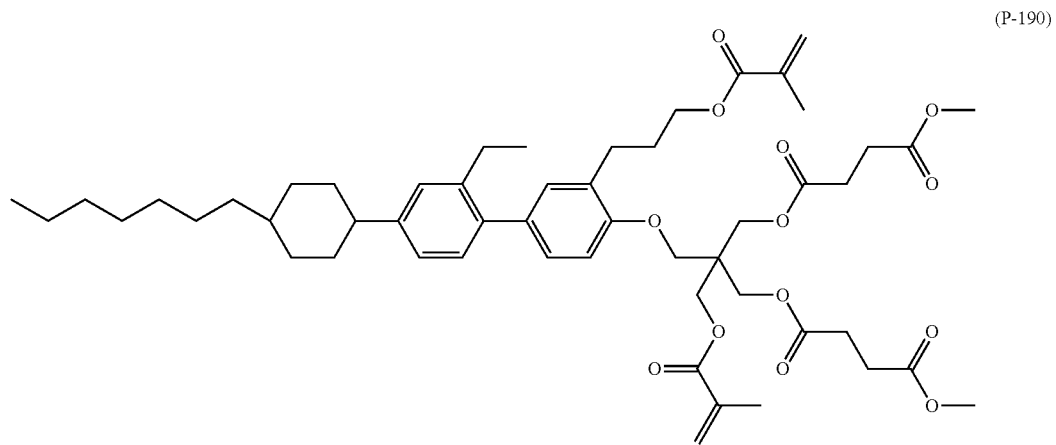

-continued
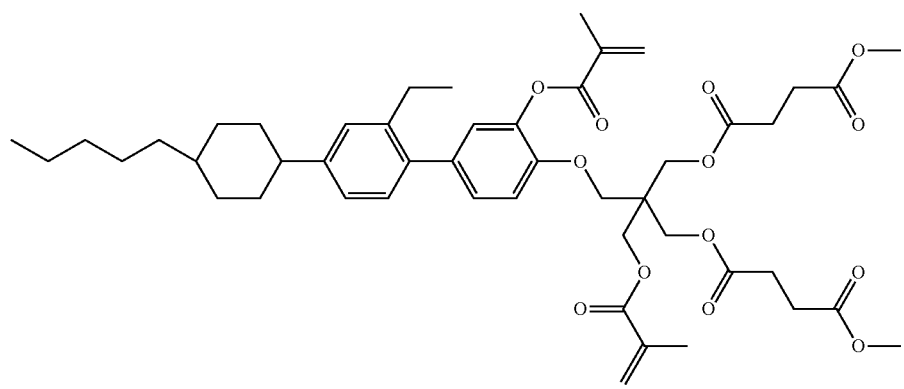
(P-191)
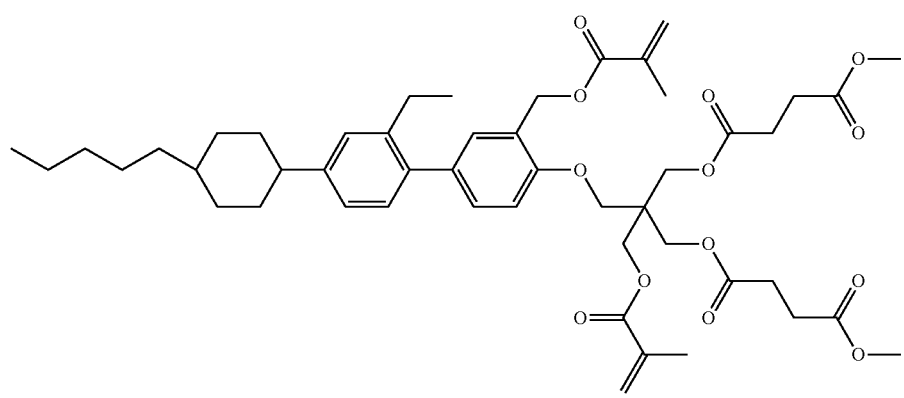
(P-192)
[Chem. 75]
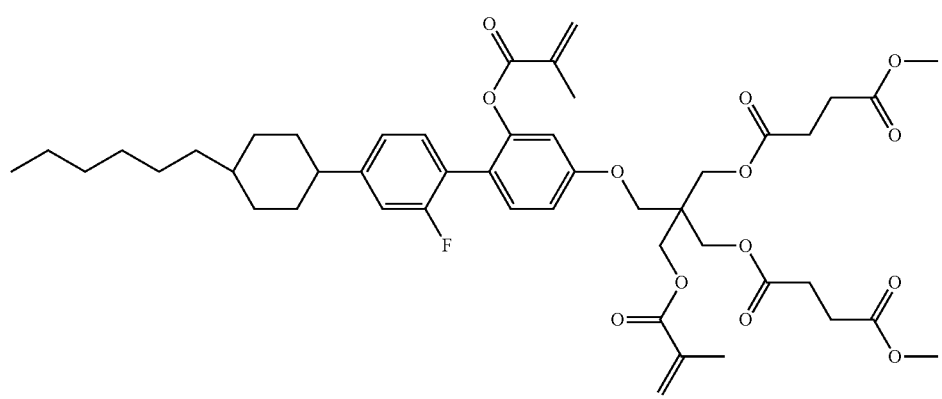
(P-193)
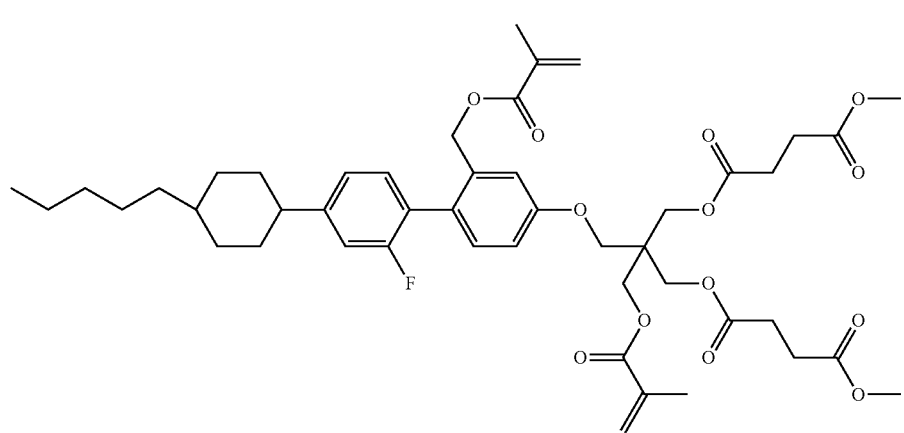
(P-194)

(P-195)
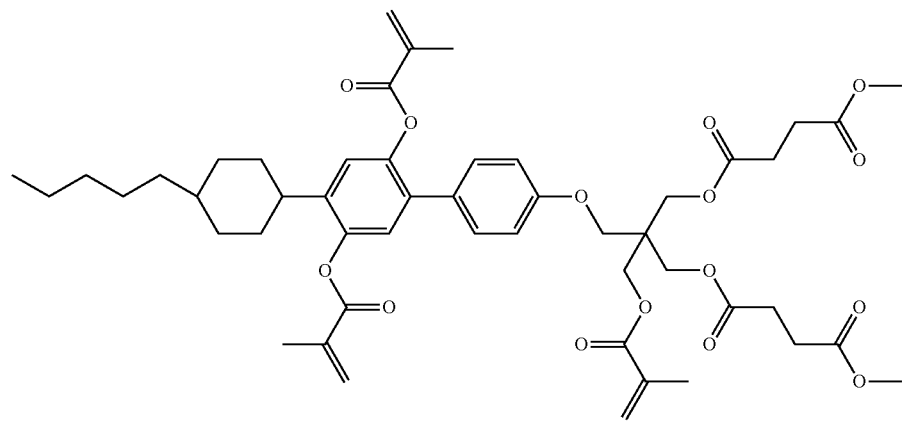
(P-196)
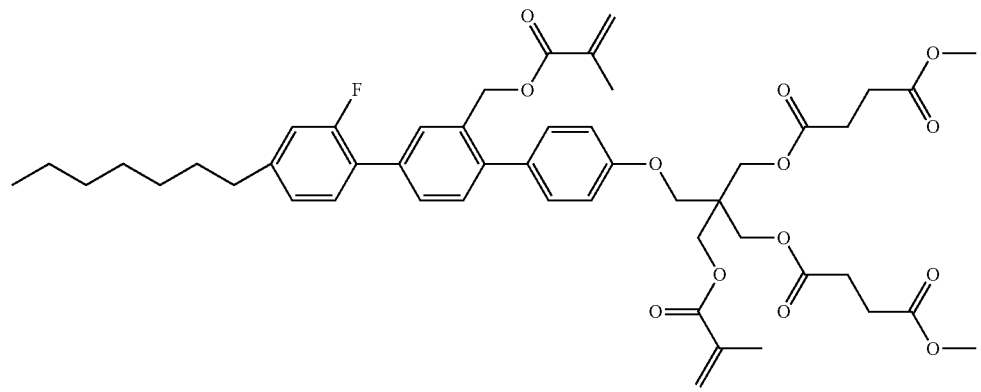
(P-197)
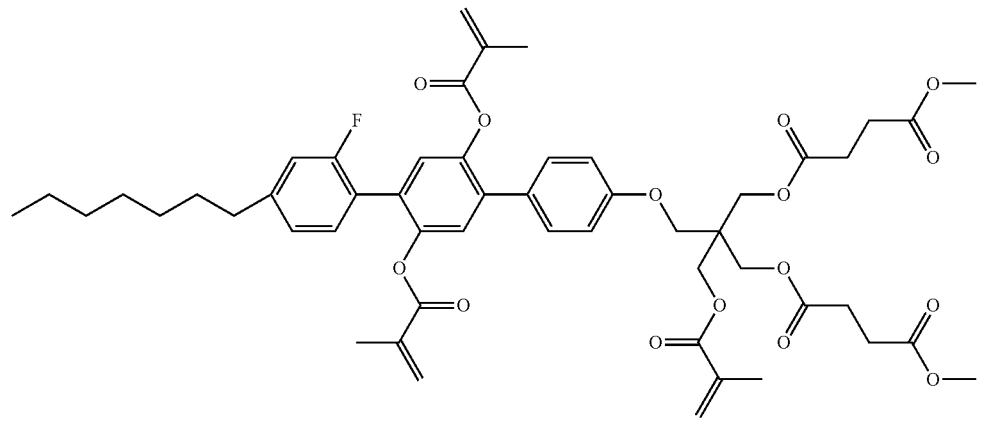
(P-198)
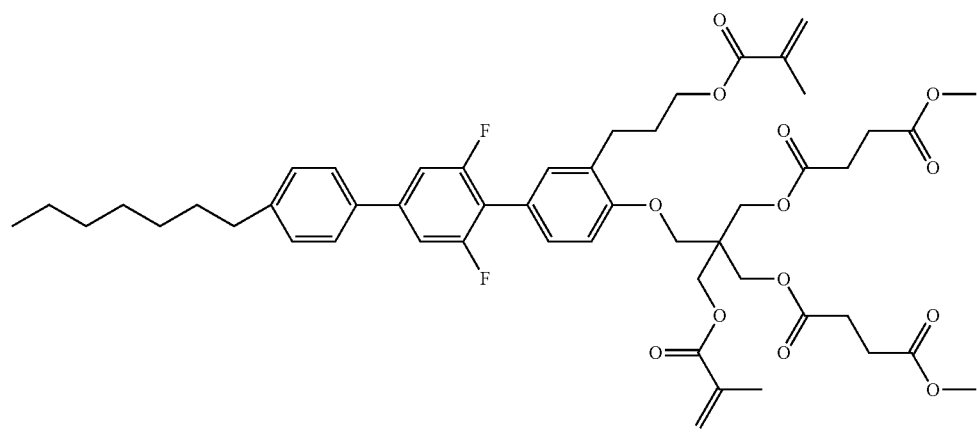

-continued
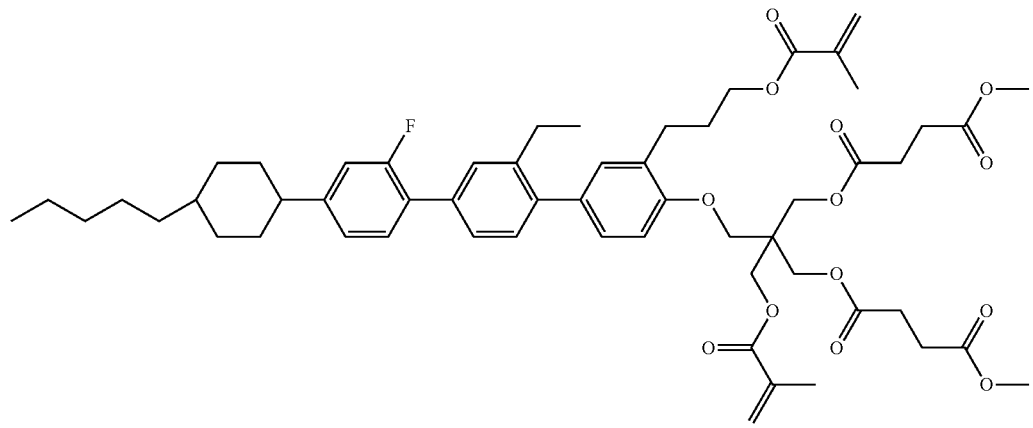
(P-199)
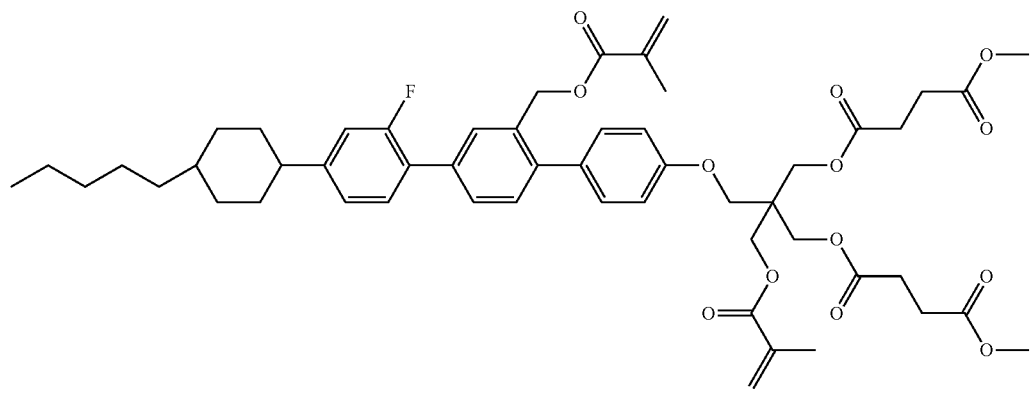
(P-200)
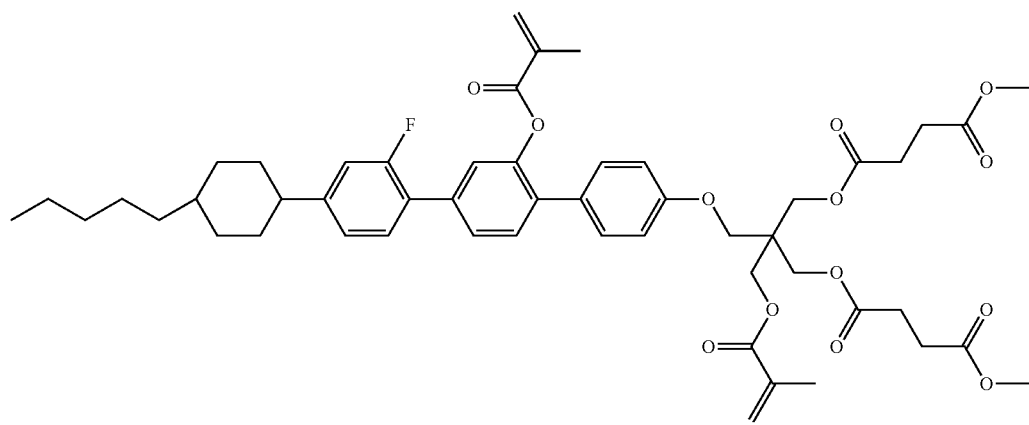
(P-201)
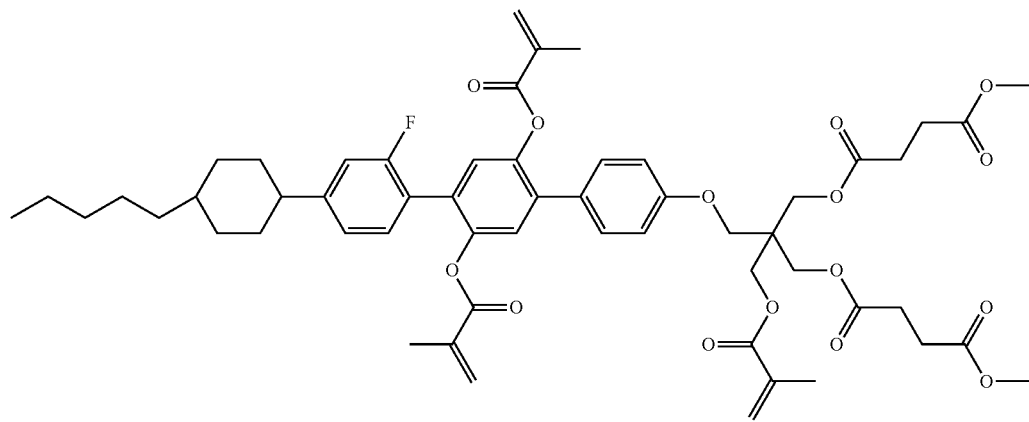
(P-202)

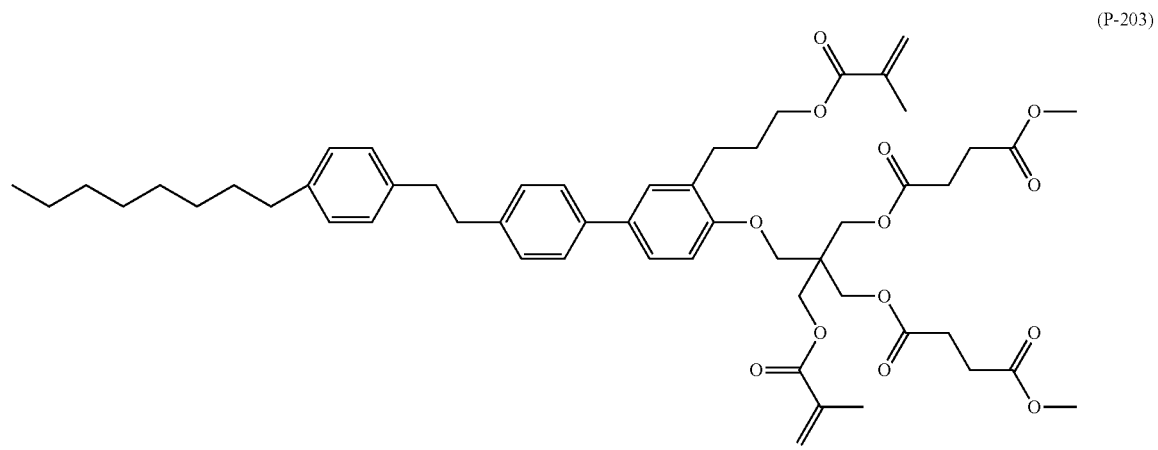
(P-203)
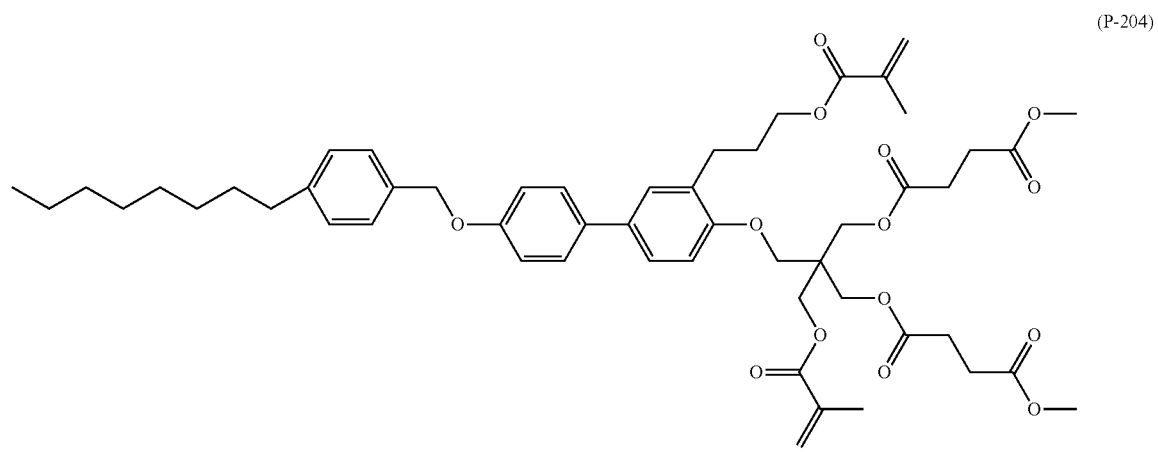
(P-204)
[Chem. 76]
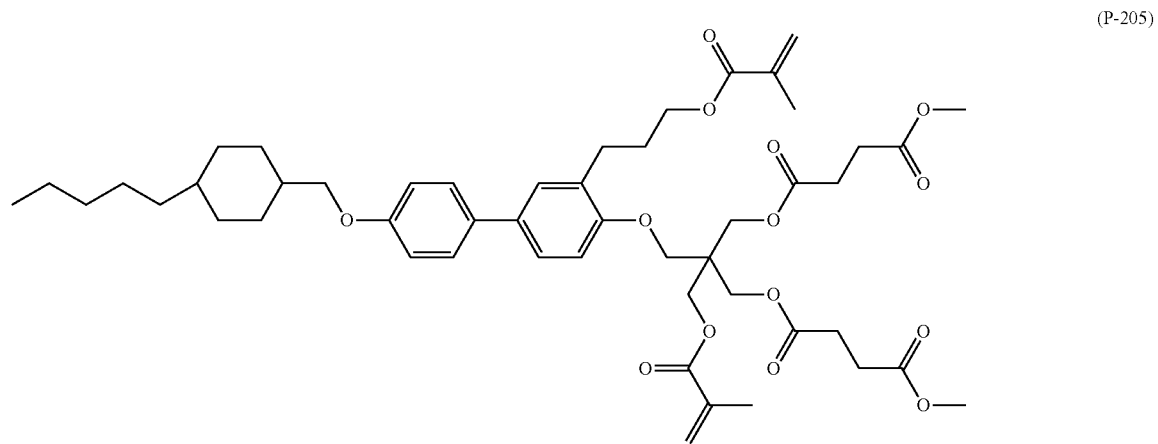
(P-205)

-continued
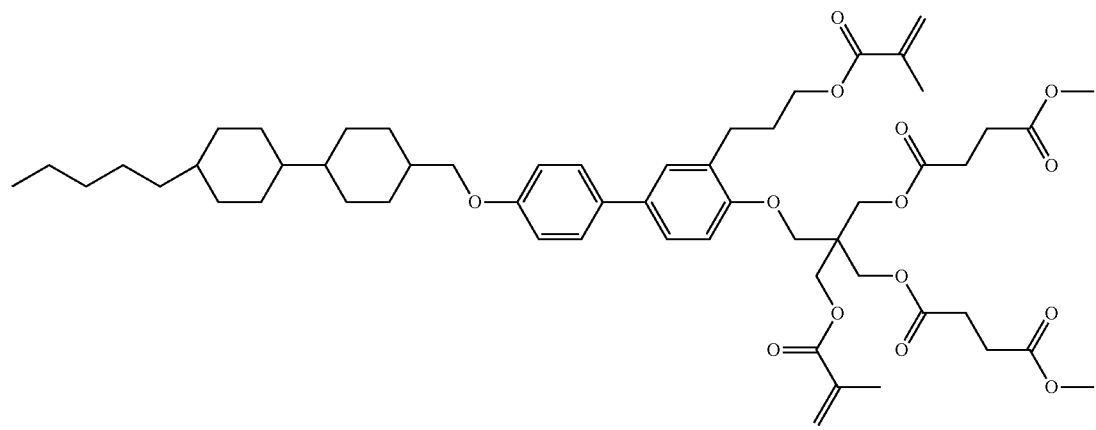
(P-206)
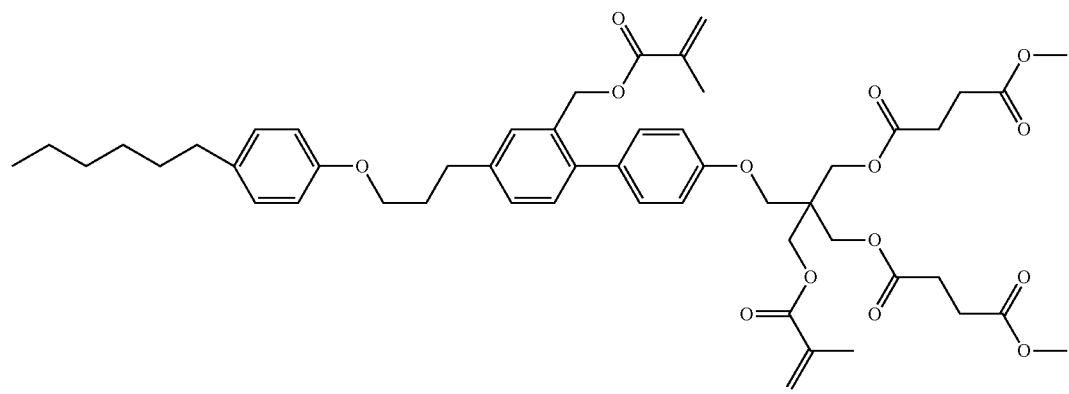
(P-207)
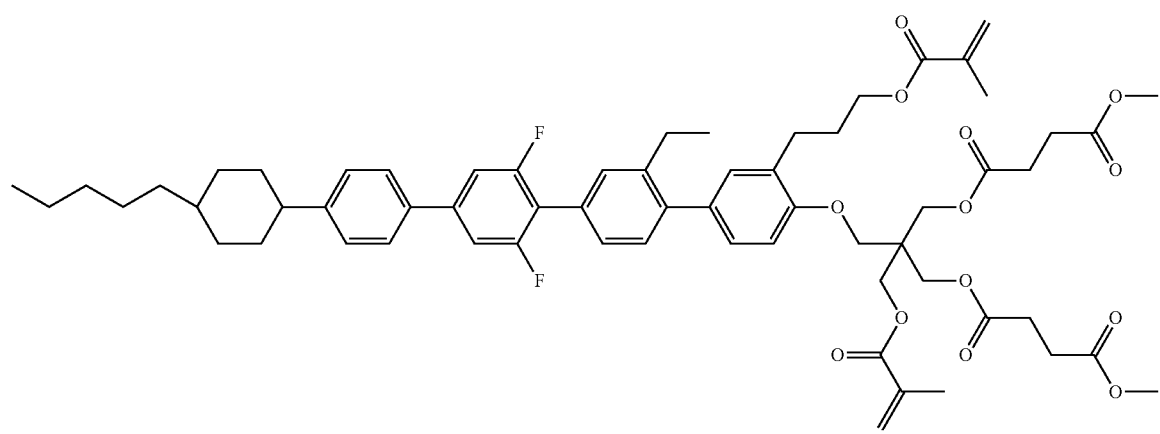
(P-208)

-continued
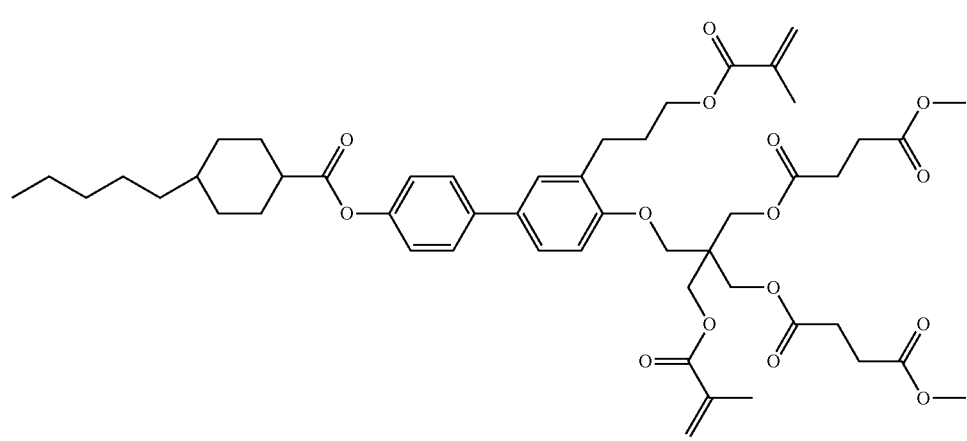
(P-209)
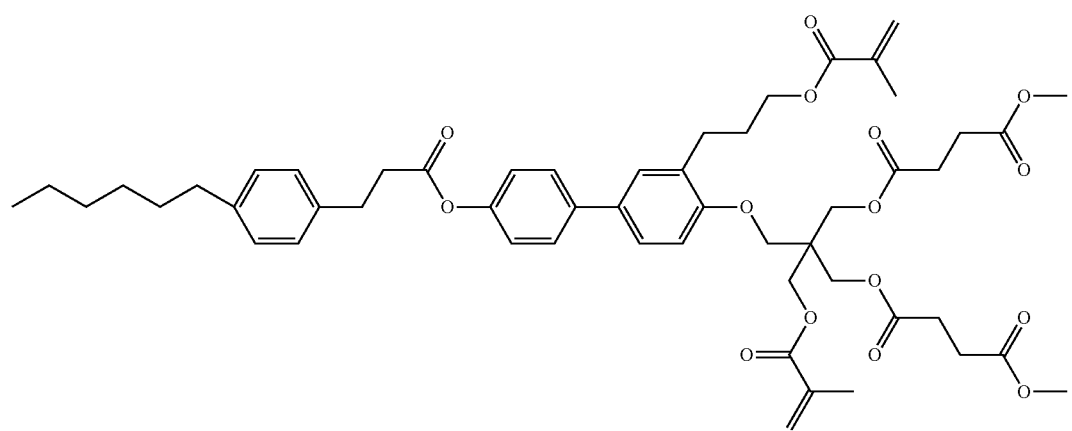
(P-210)
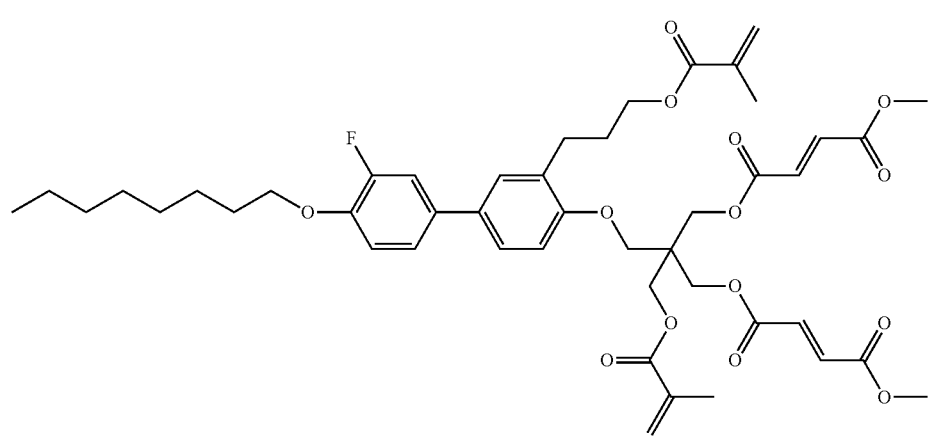
(P-211)

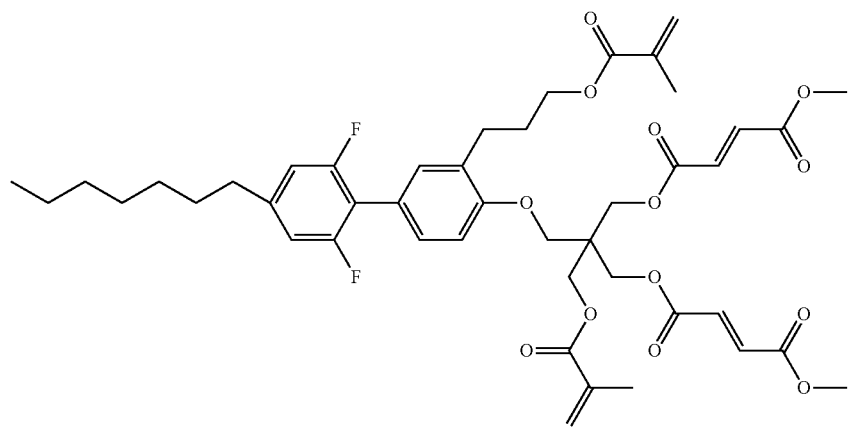
(P-212)
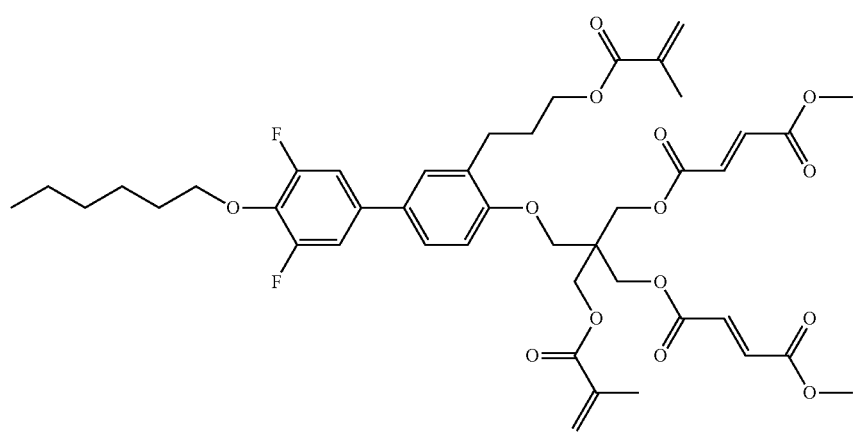
(P-213)
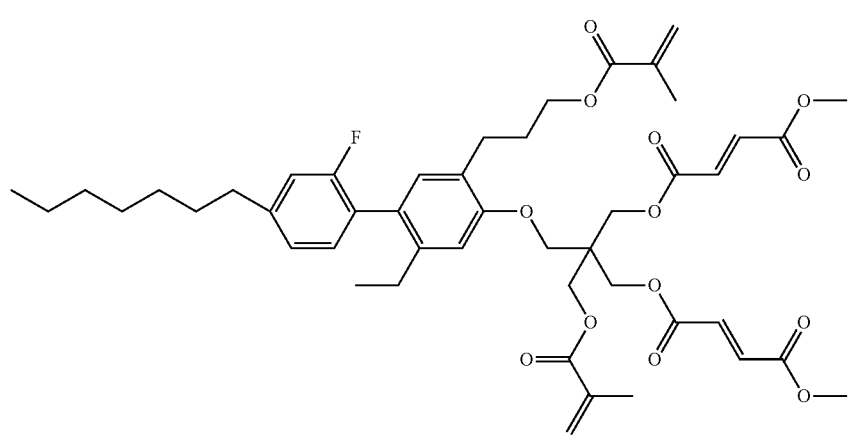
(P-214)

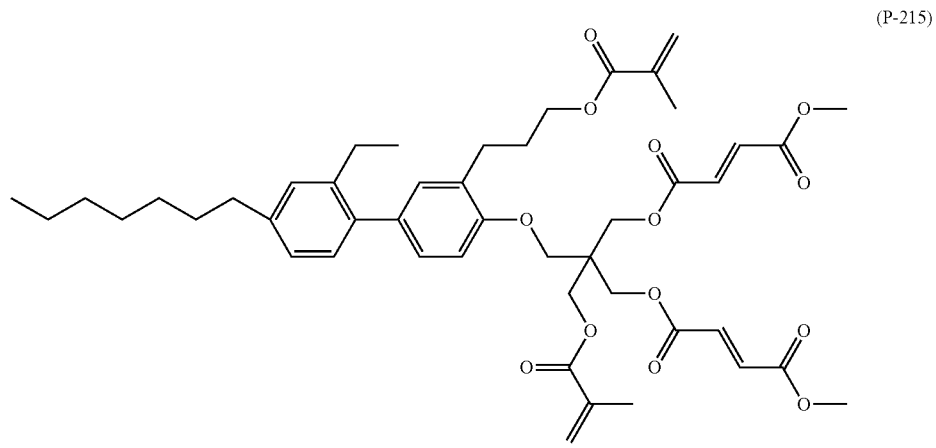
(P-215)
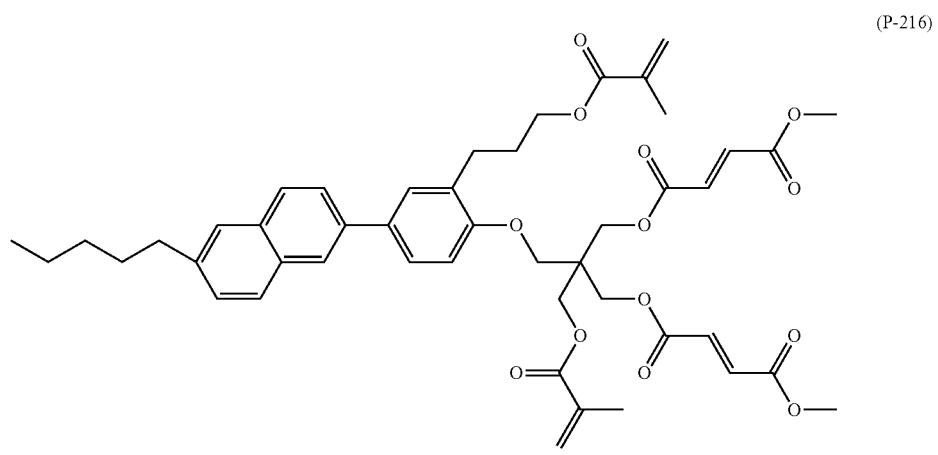
(P-216)
[Chem. 77]
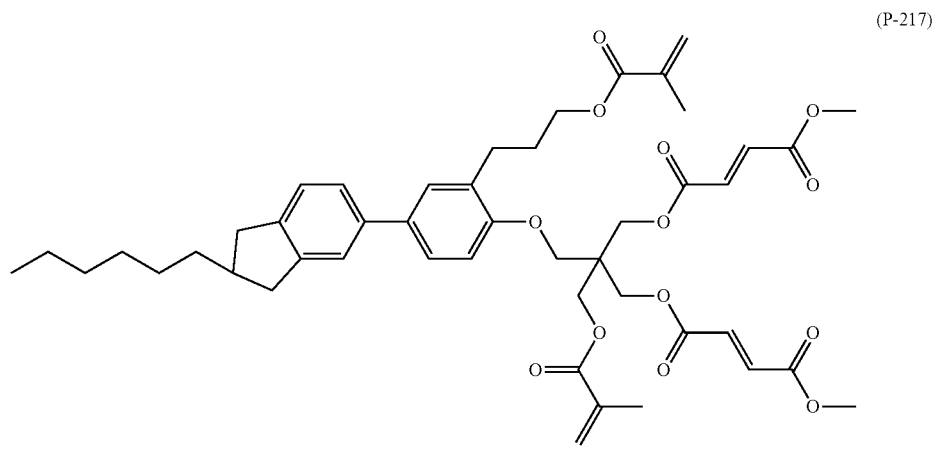
(P-217)

(P-218)
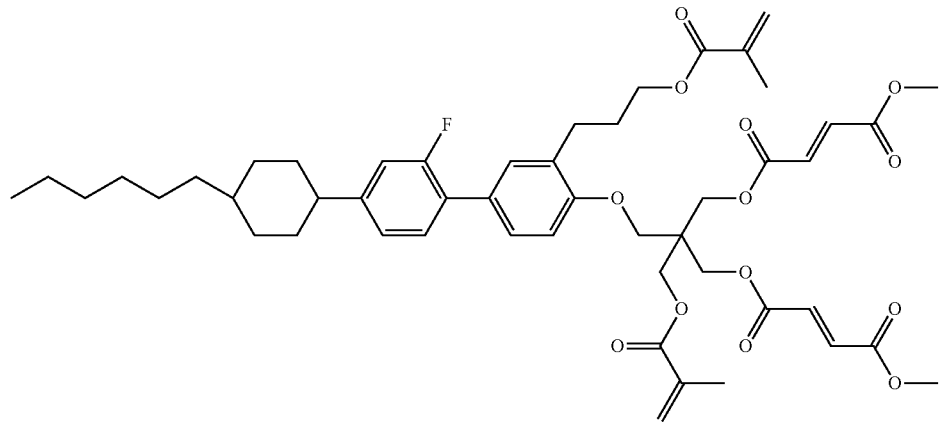
(P-219)
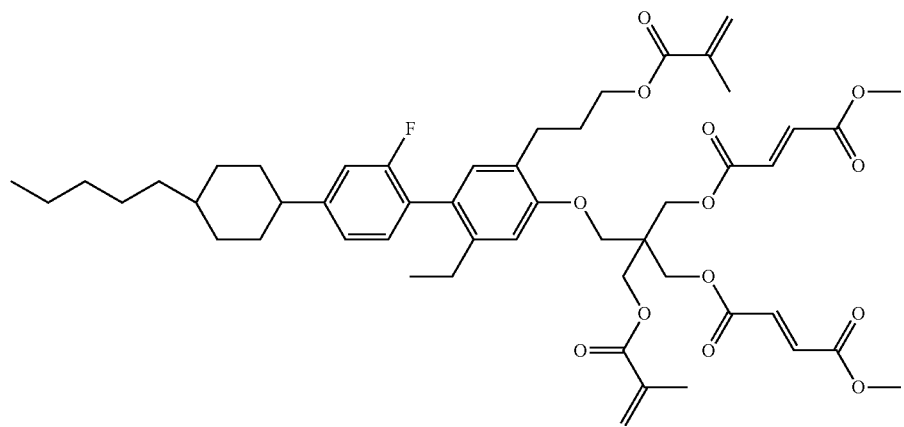
(P-220)
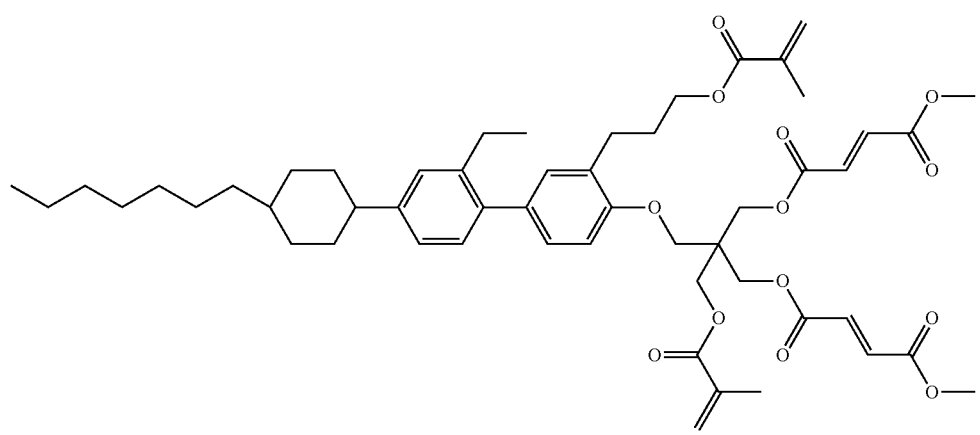

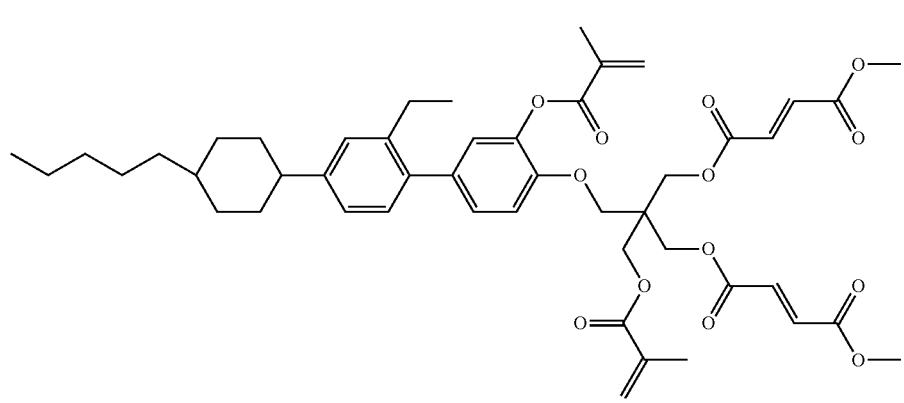
(P-221)
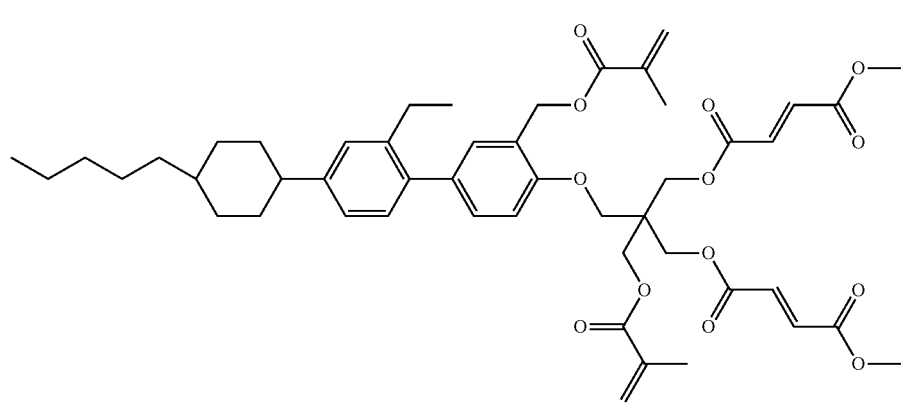
(P-222)
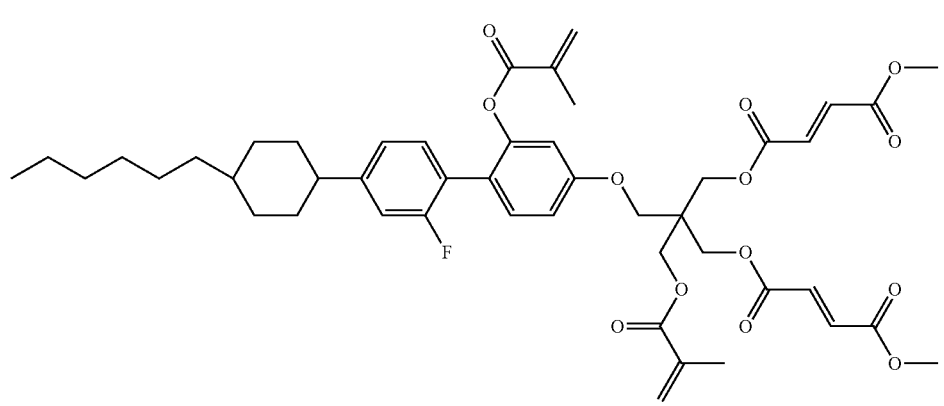
(P-223)
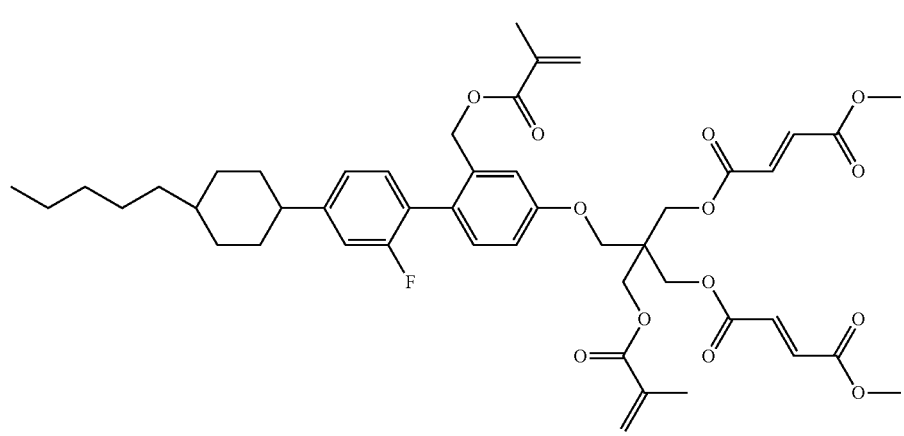
(P-224)

(P-225)
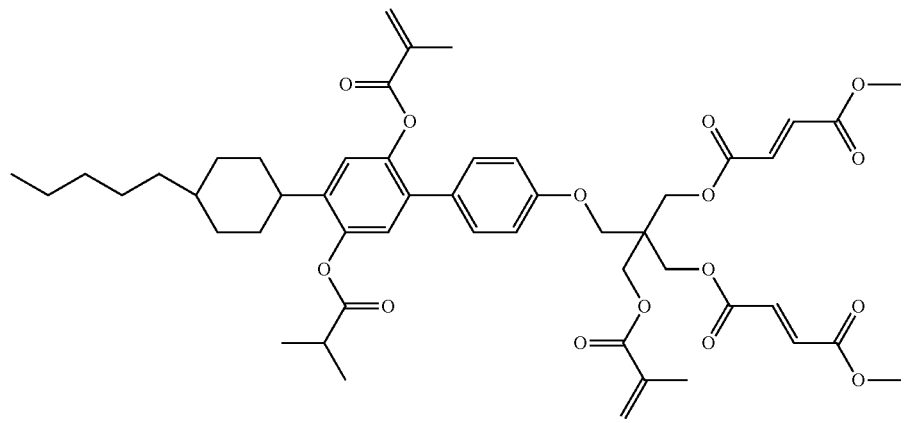
(P-226)
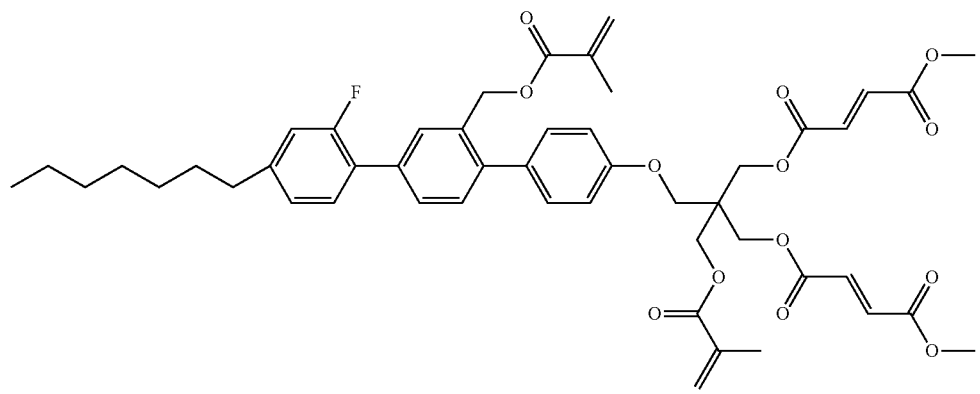
(P-227)
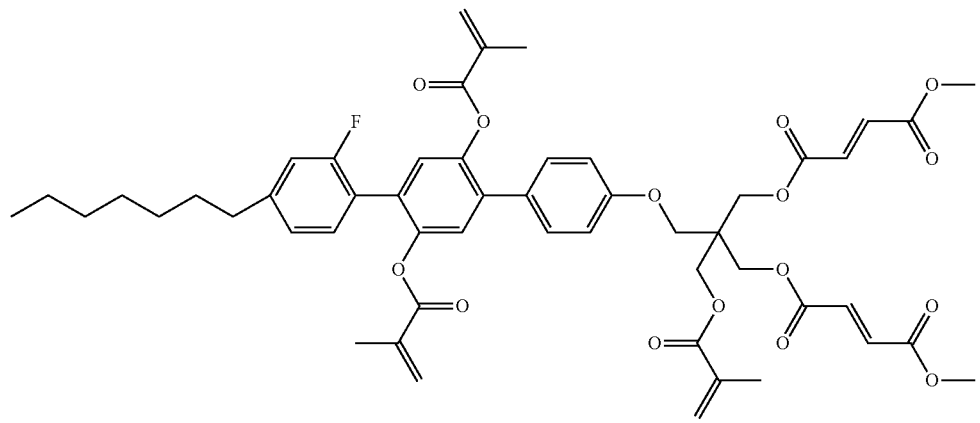
(P-228)
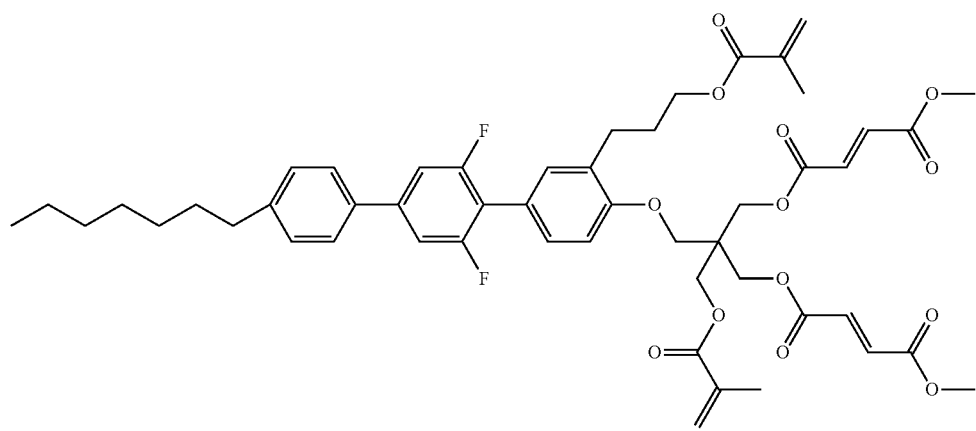

(P-229)
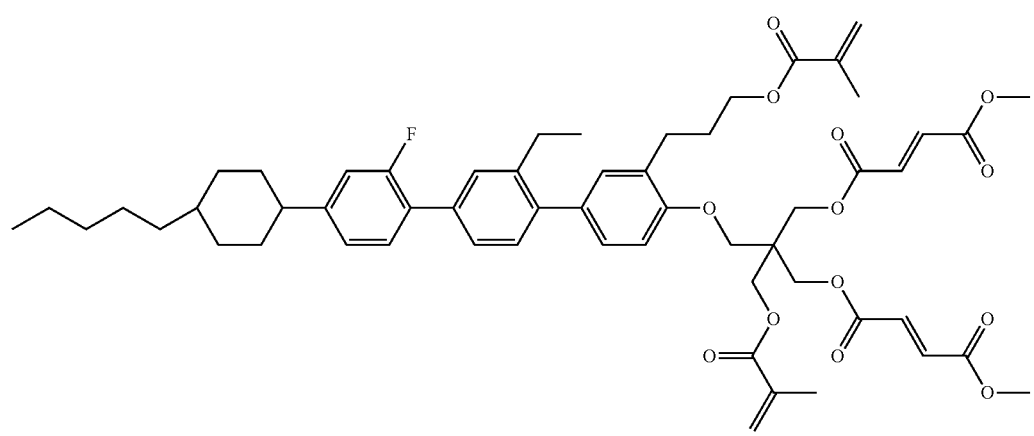
(P-230)
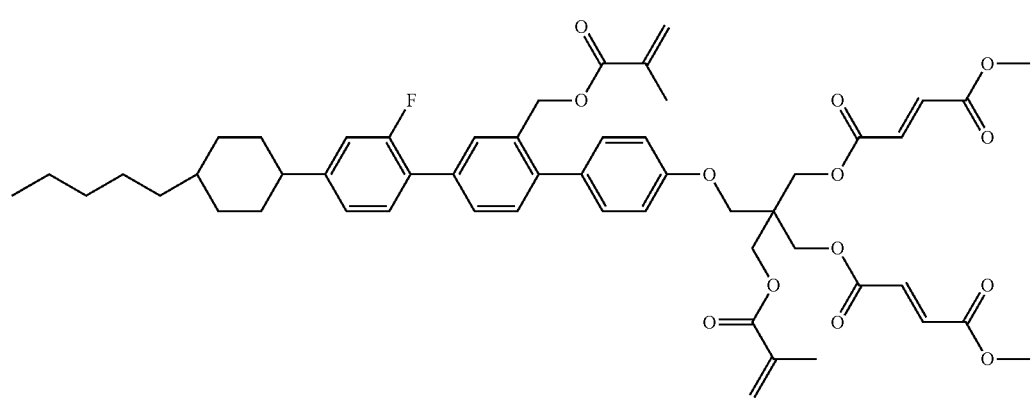
(P-231)
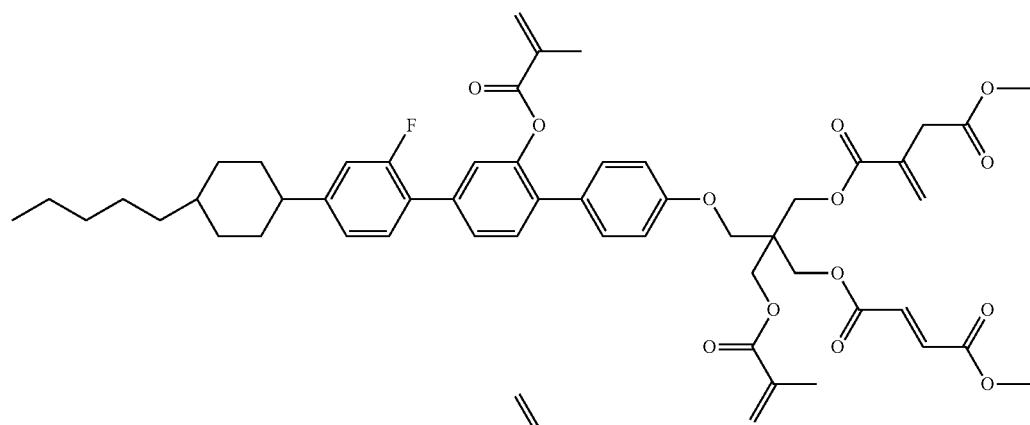
(P-232)
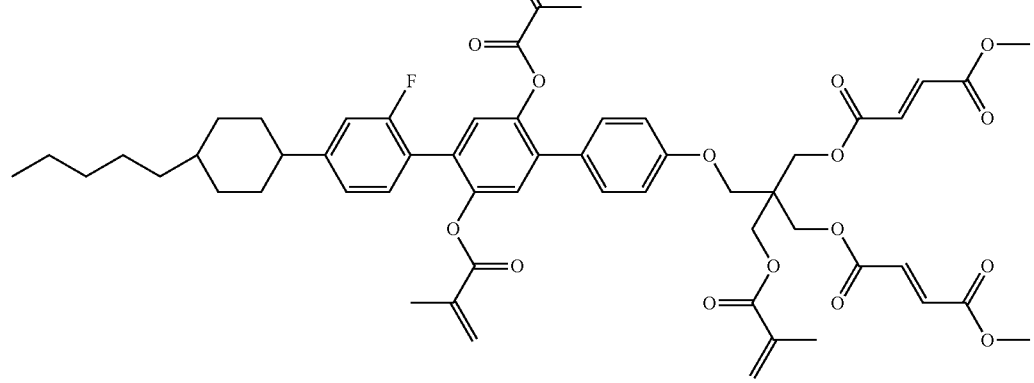

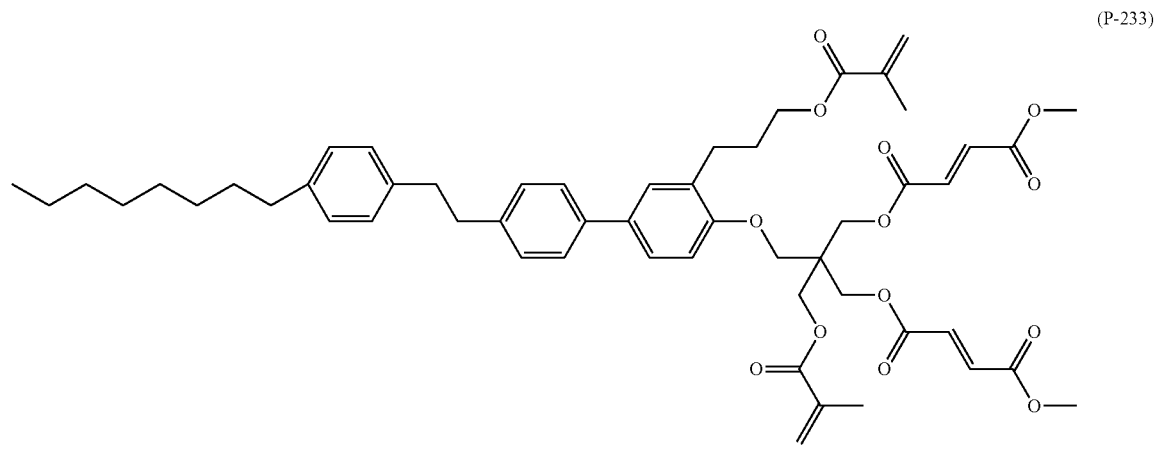
(P-233)
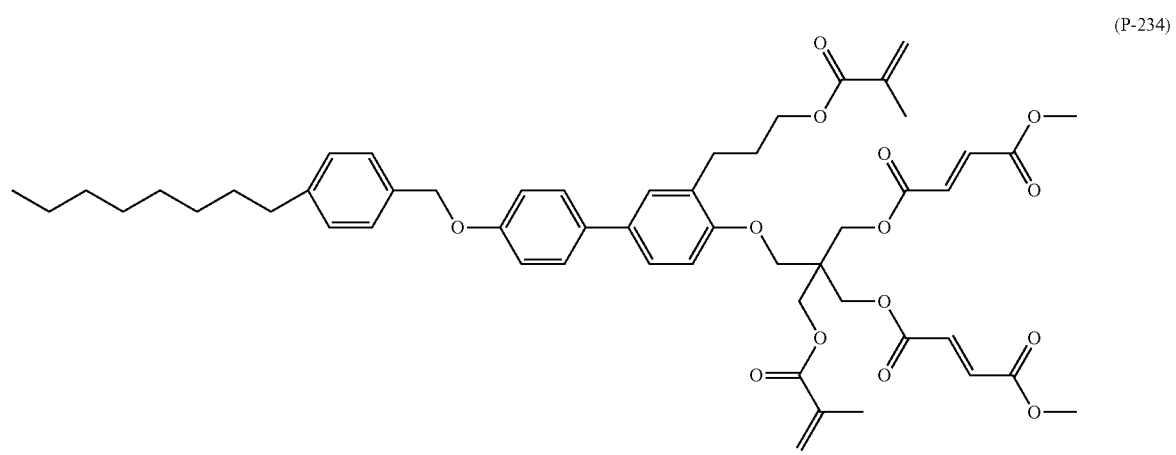
(P-234)
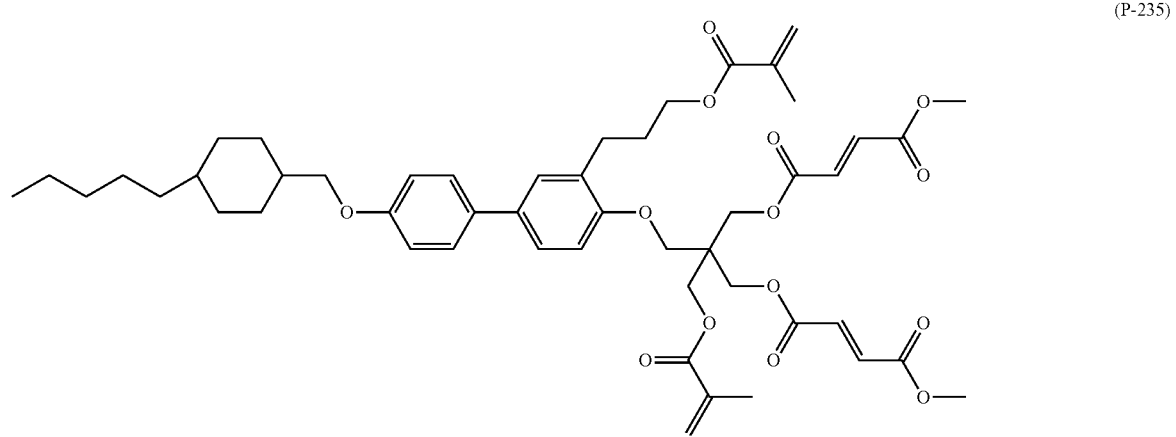
(P-235)

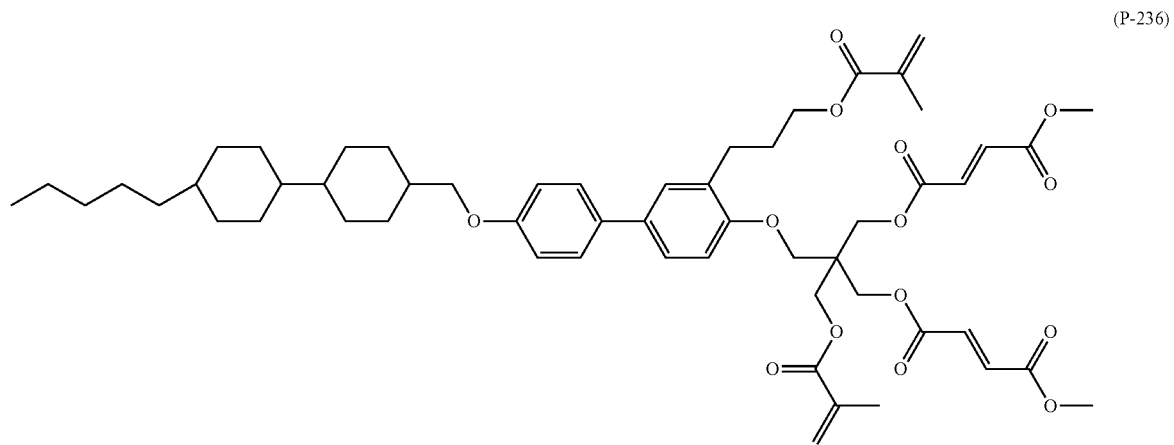
(P-236)
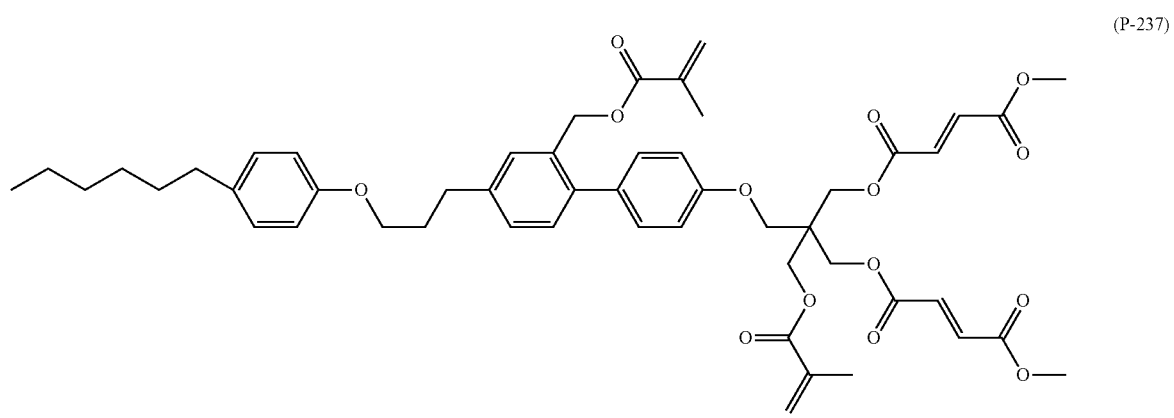
(P-237)
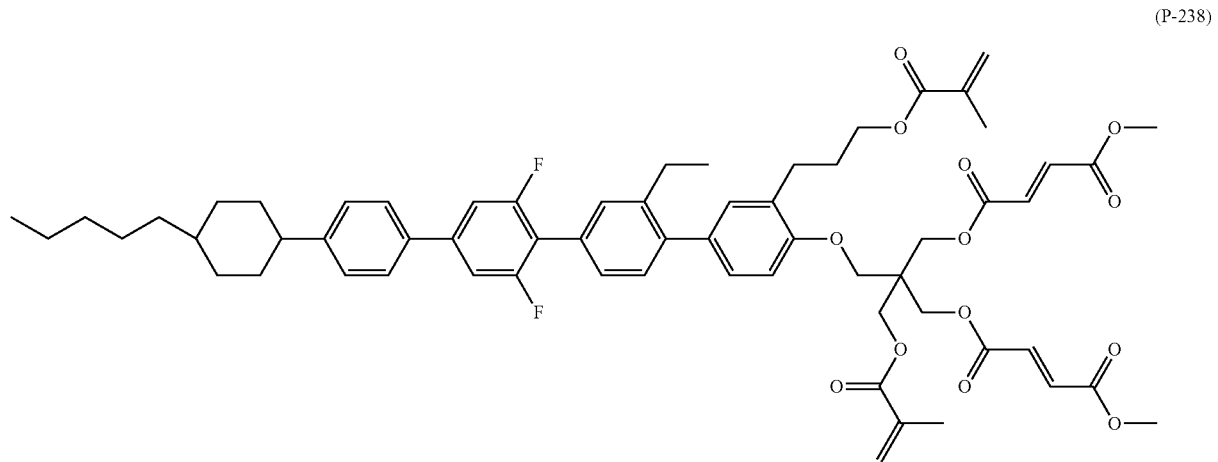
(P-238)

-continued
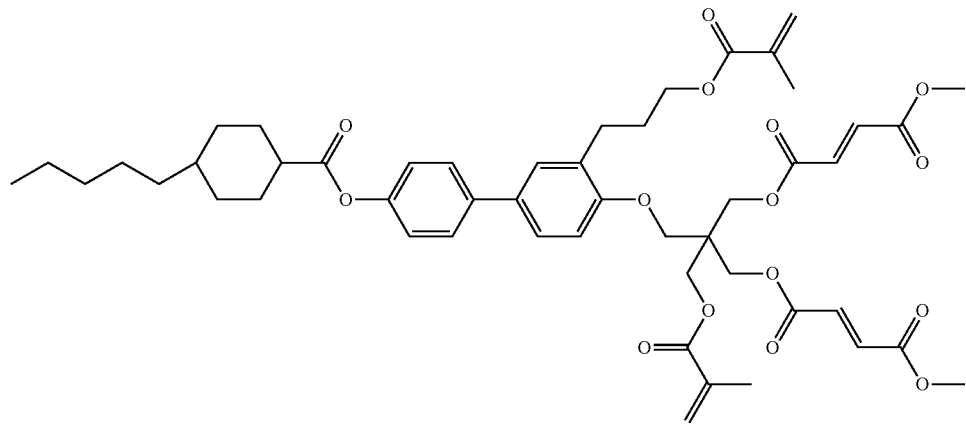
(P-239)
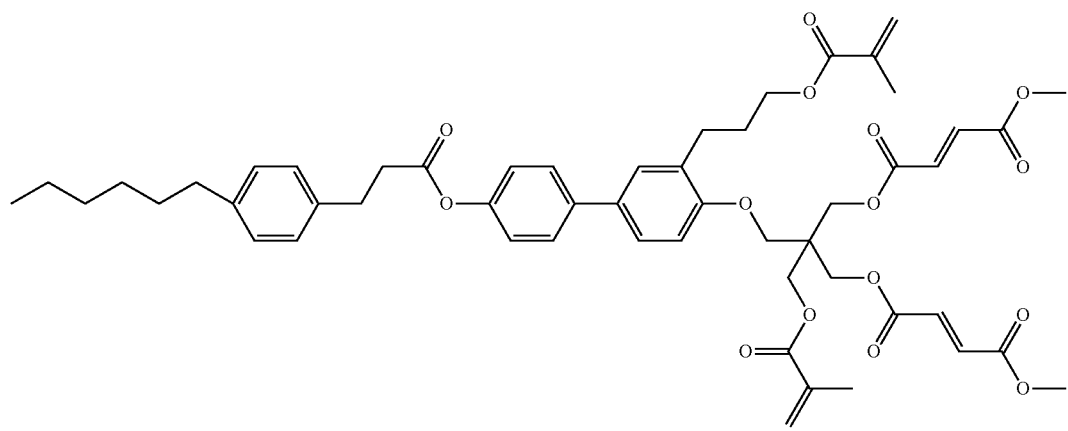
(P-240)
[Chem. 79]
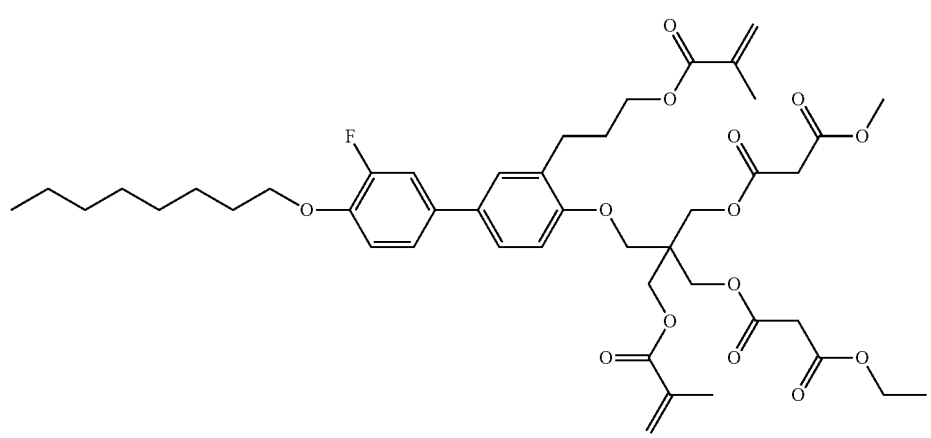
(P-241)

(P-242)
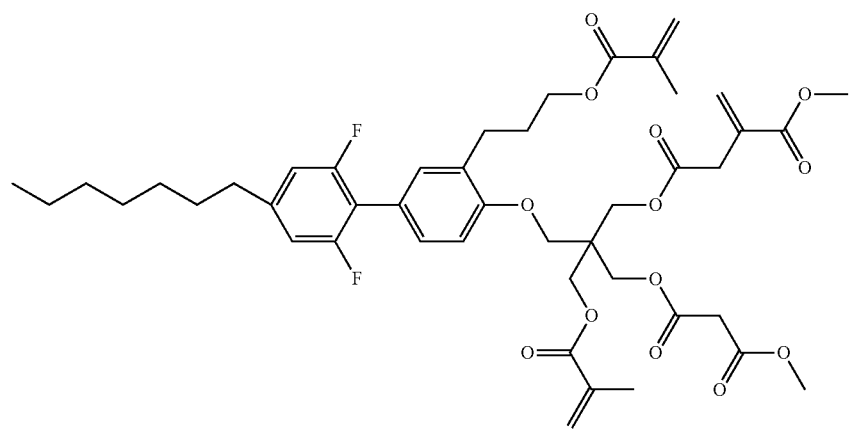
(P-243)
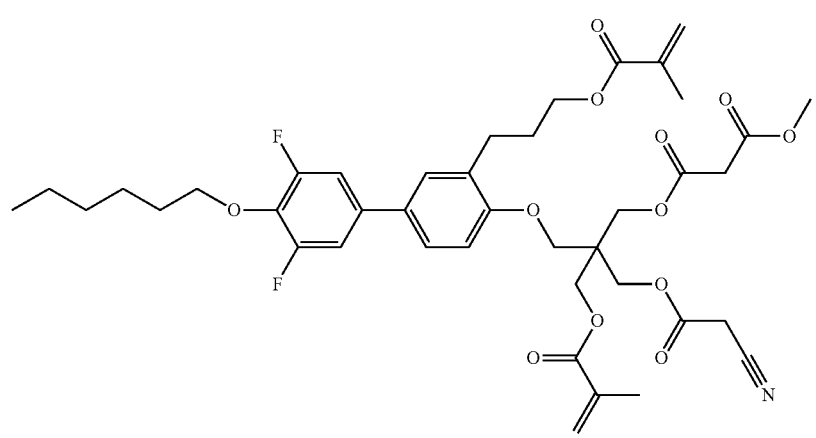
(P-244)
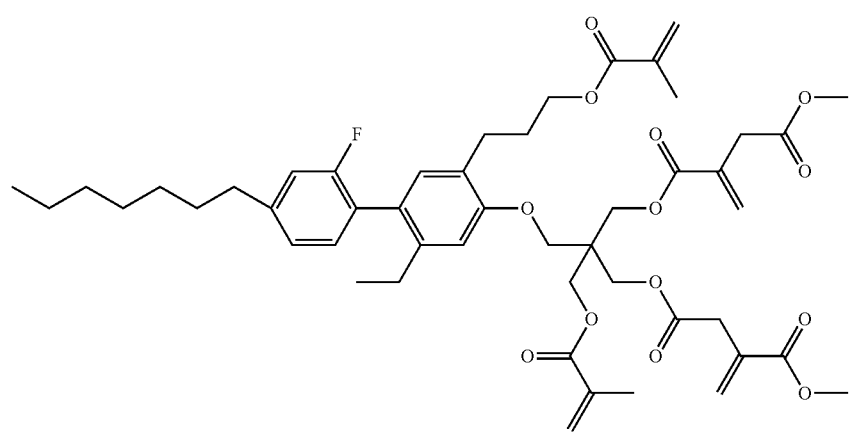

(P-245)
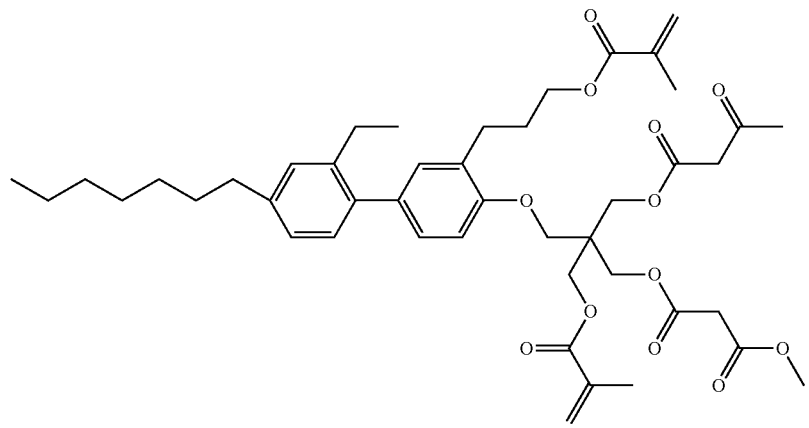
(P-246)
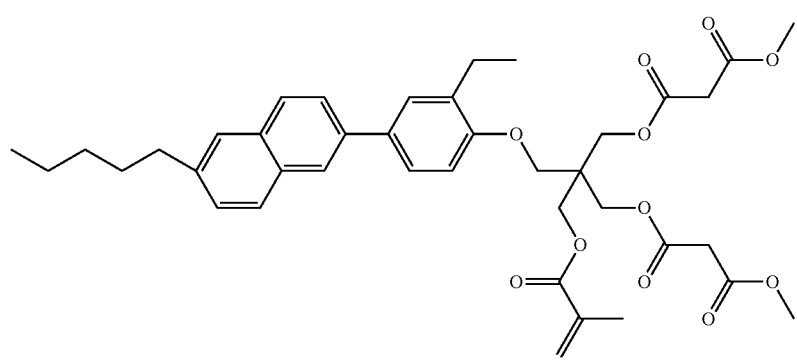
(P-247)
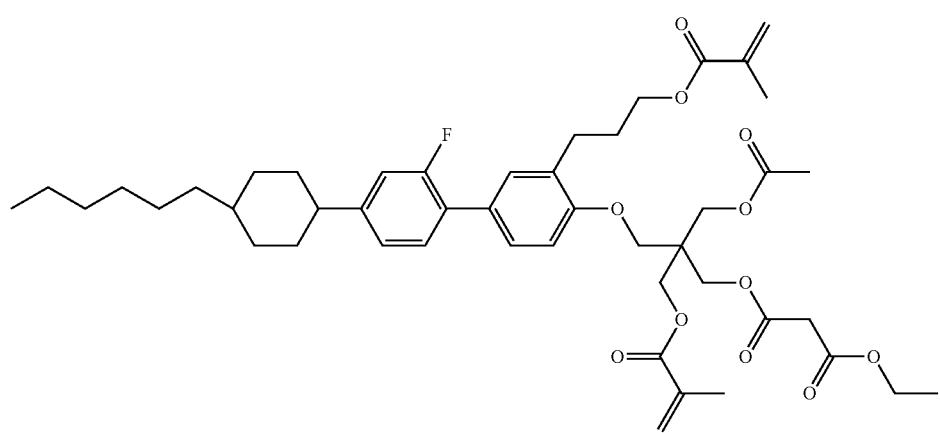

(P-248)
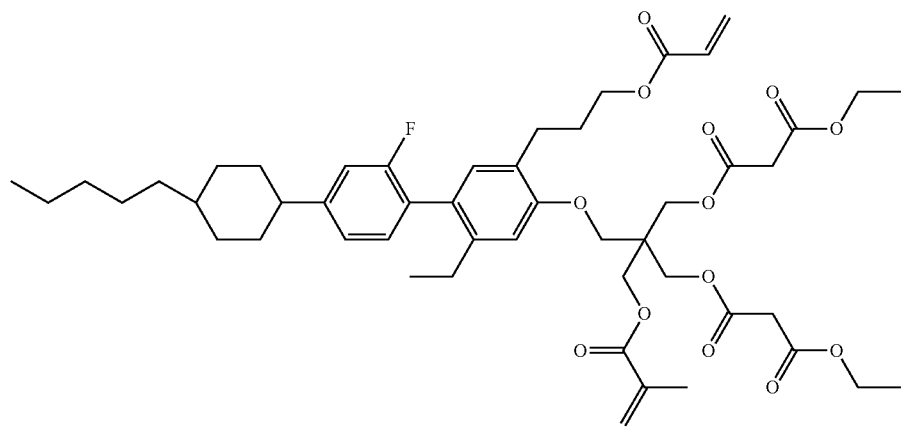
(P-249)
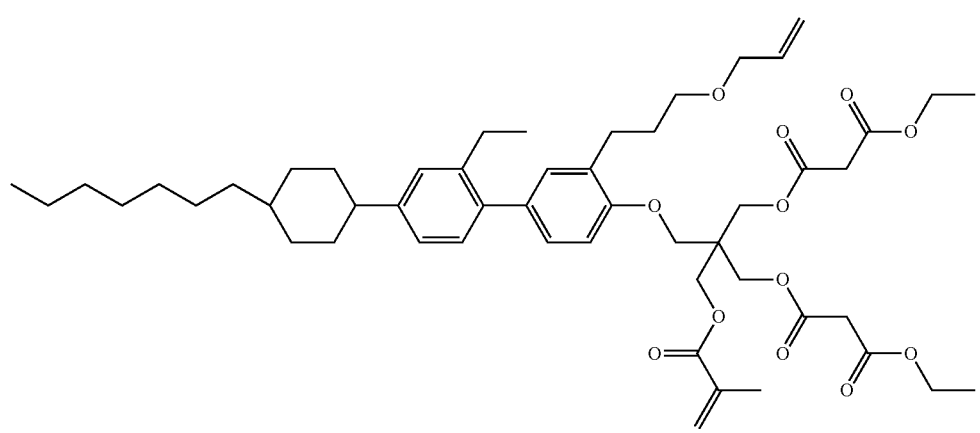
(P-250)
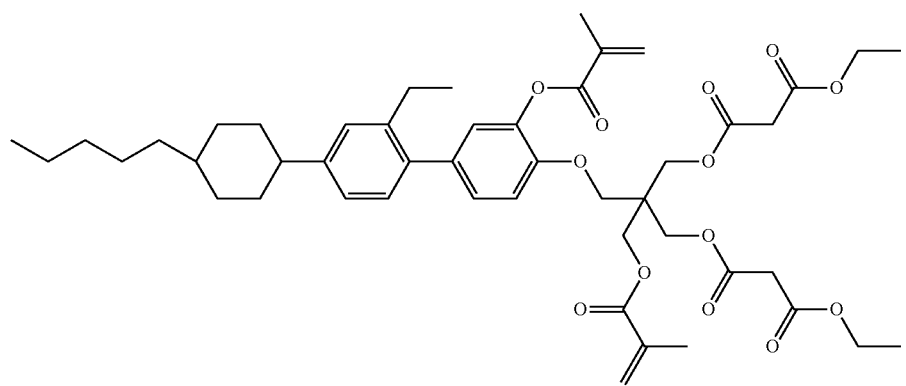

(P-251)
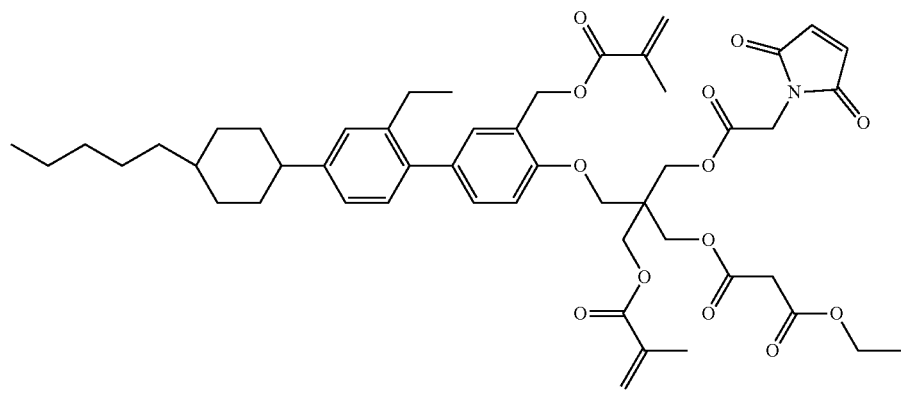
(P-252)
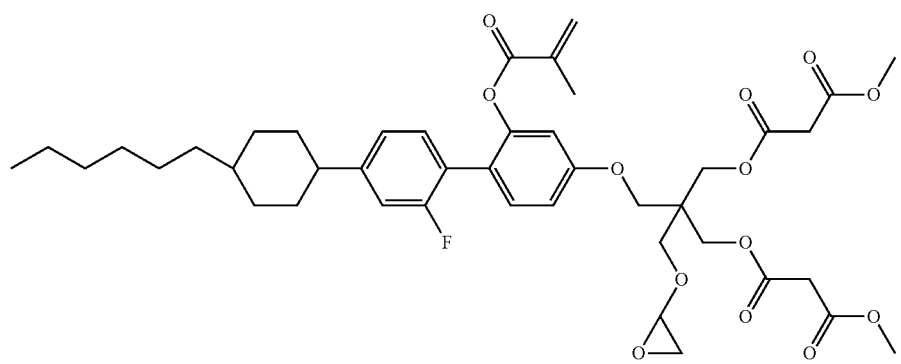
[Chem. 80]
(P-253)
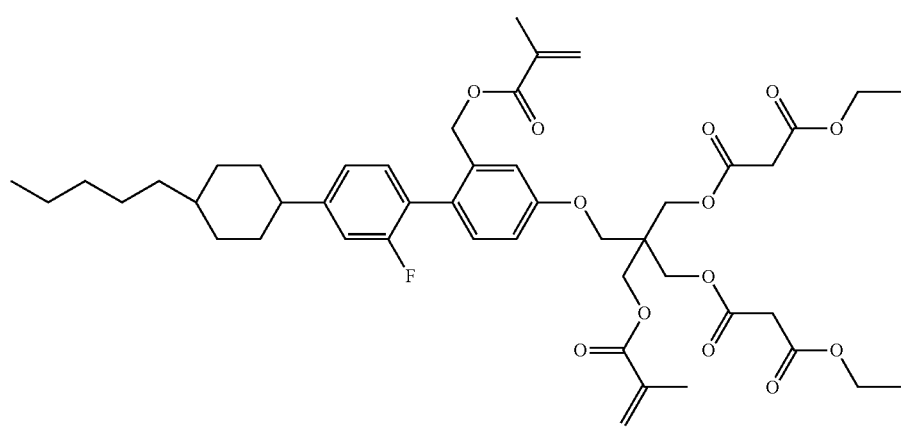

-continued
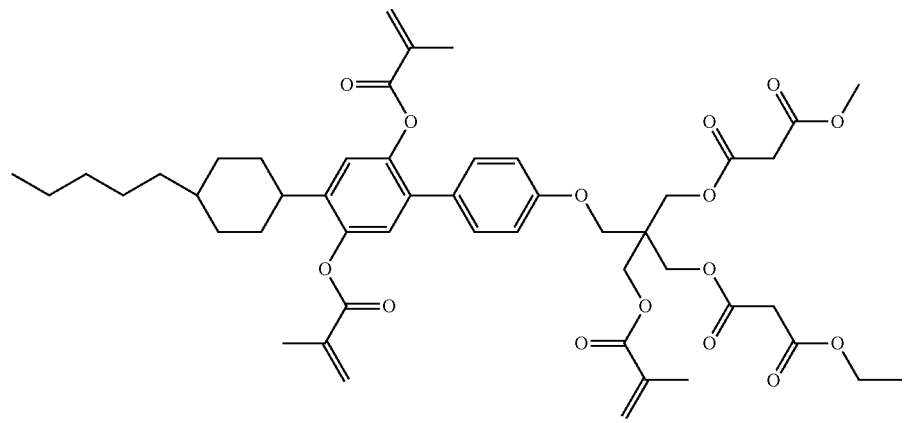
(P-254)
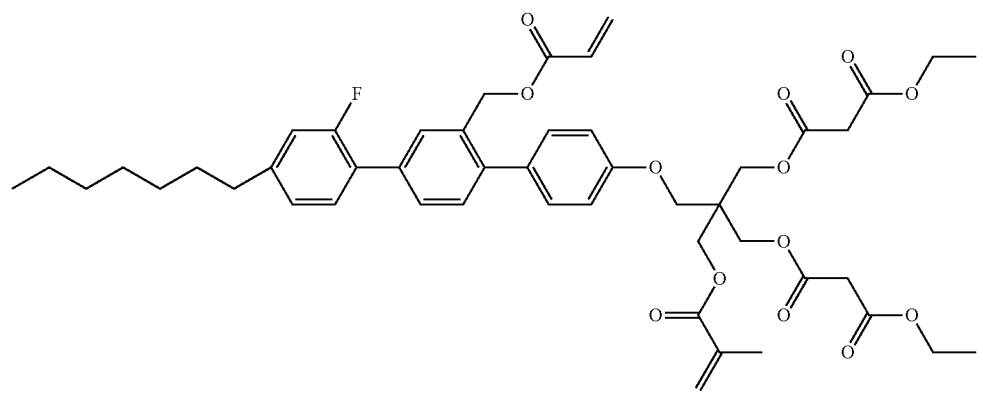
(P-255)
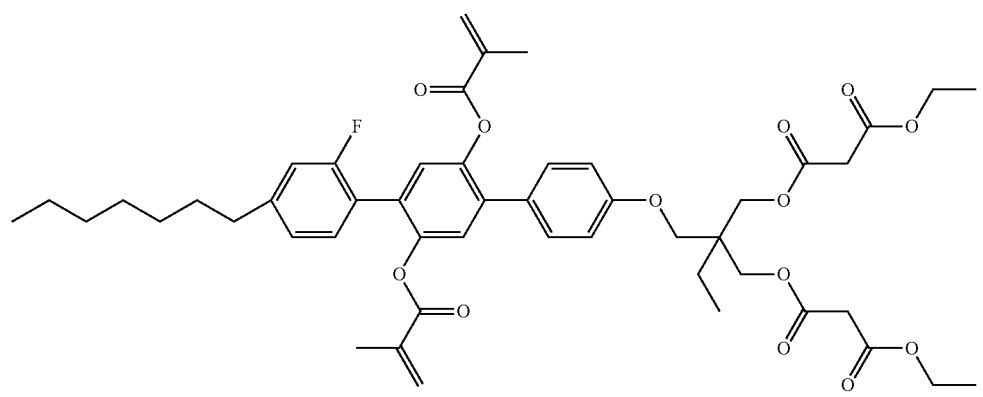
(P-256)
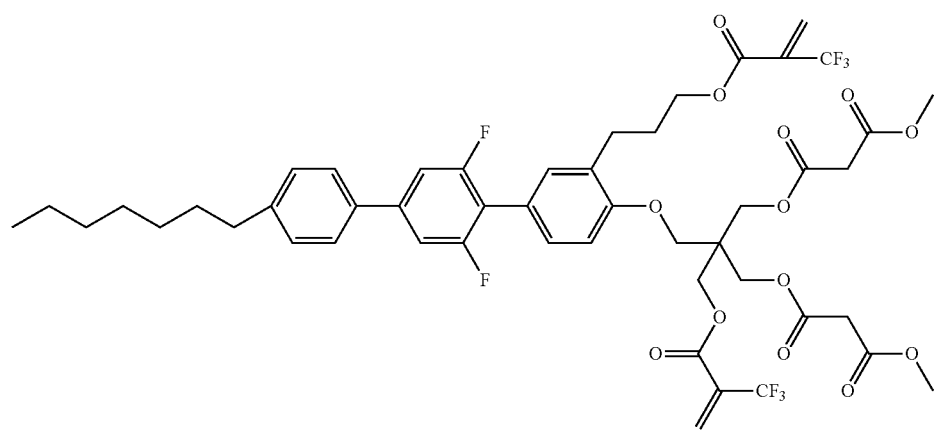
(P-257)

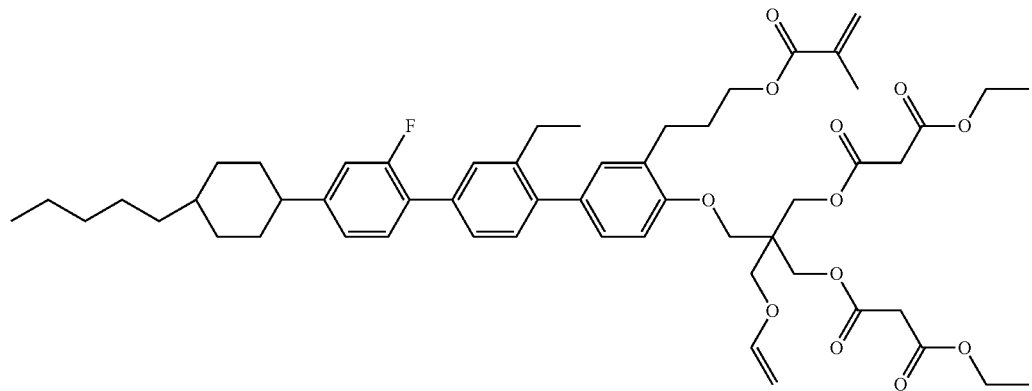
(P-258)
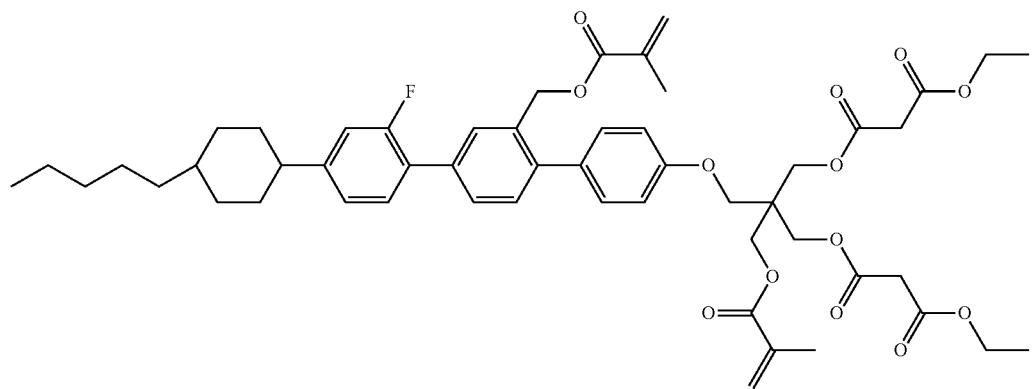
(P-259)
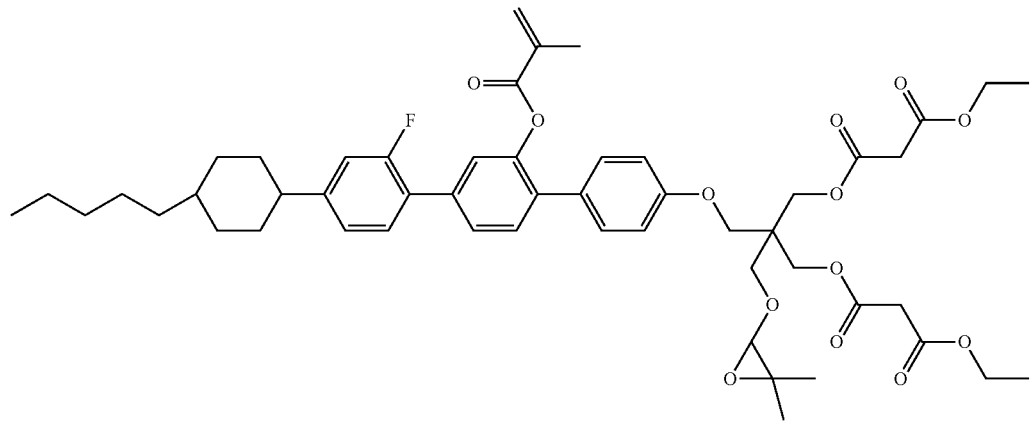
(P-260)

(P-261)
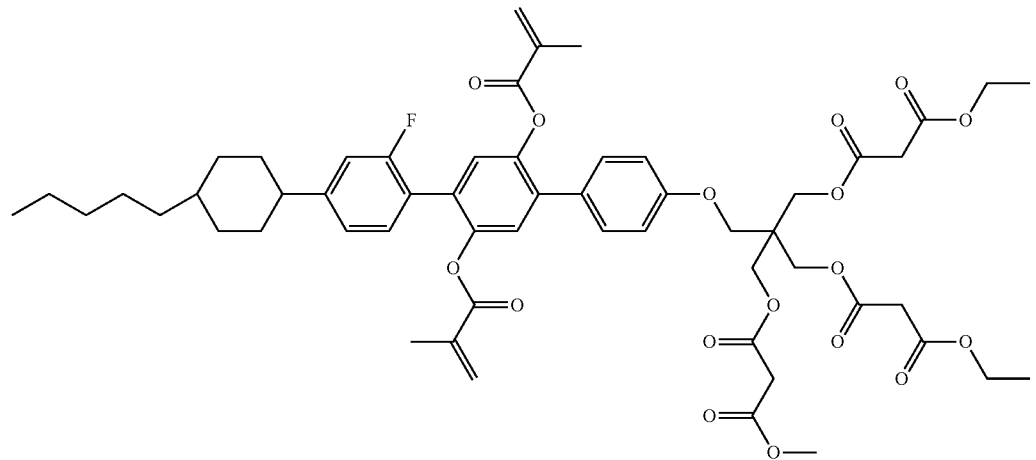
(P-262)
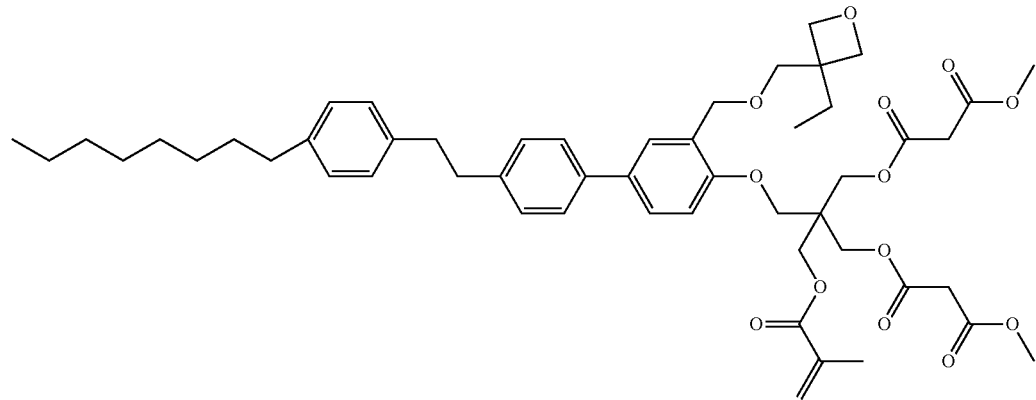
(P-263)
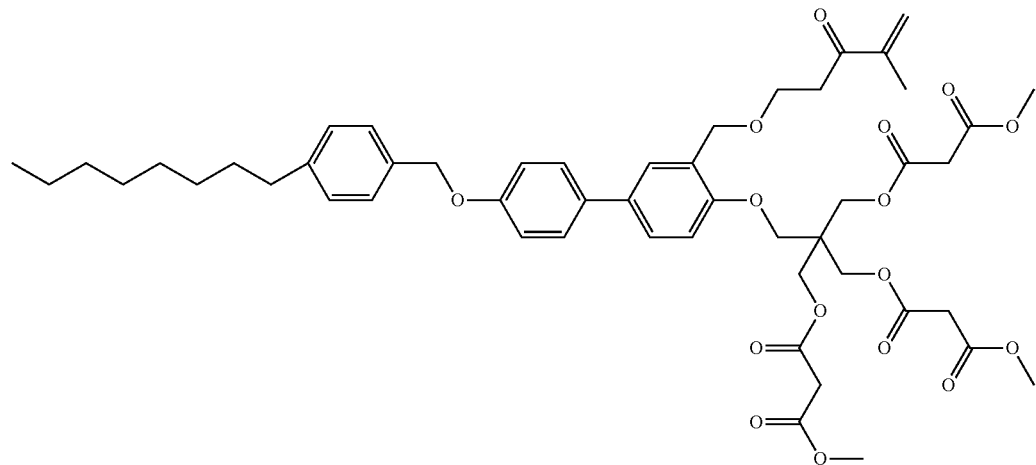

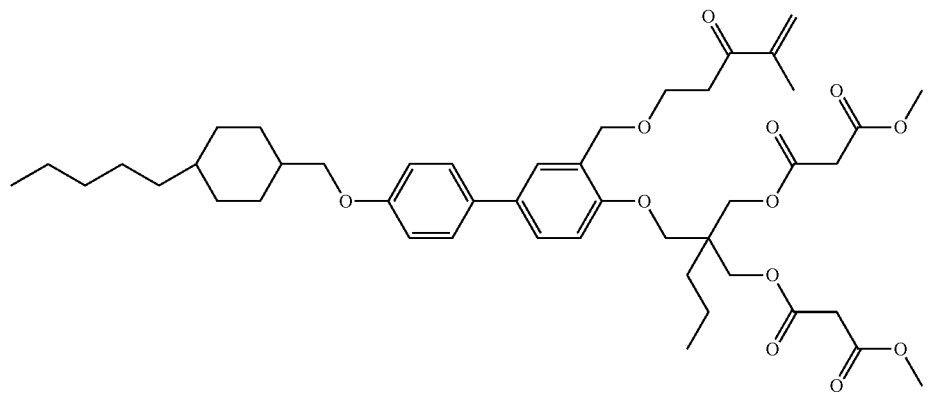
(P-264)
[Chem. 81]
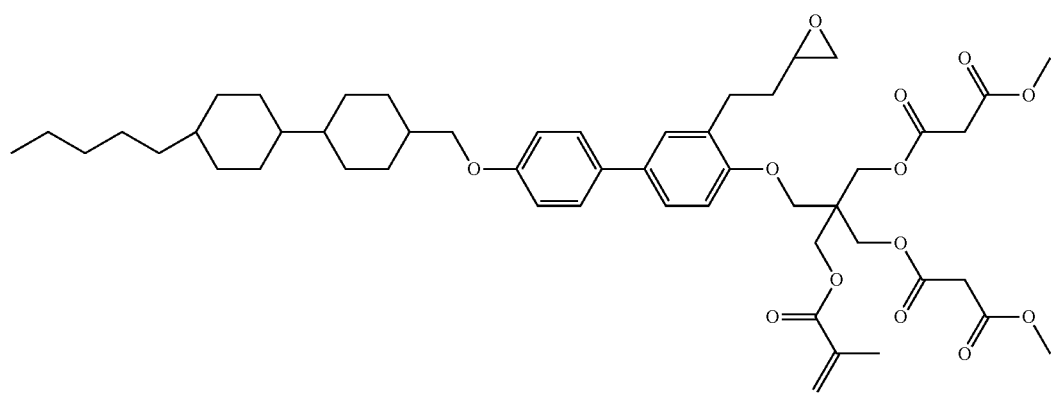
(P-265)
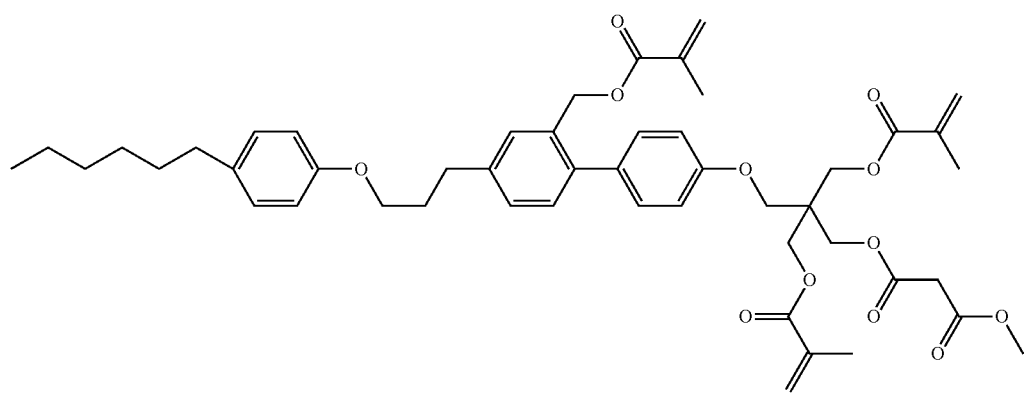
(P-266)

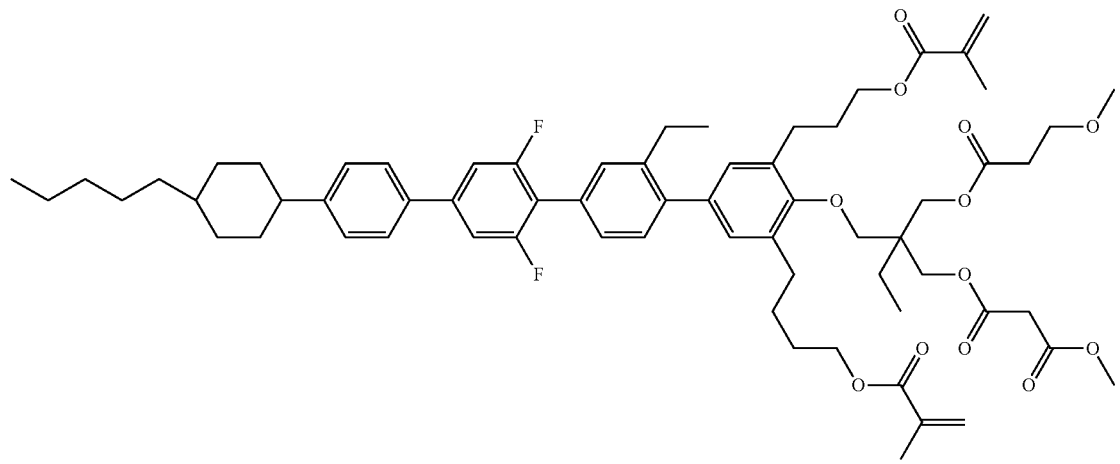
(P-267)
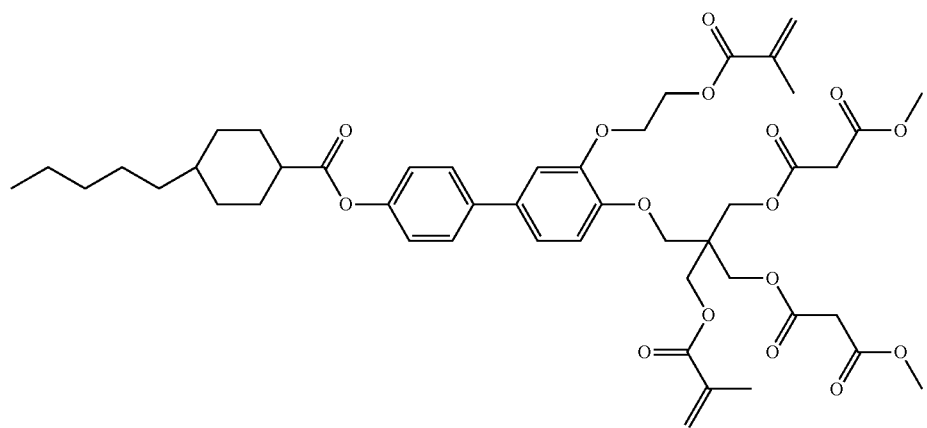
(P-268)
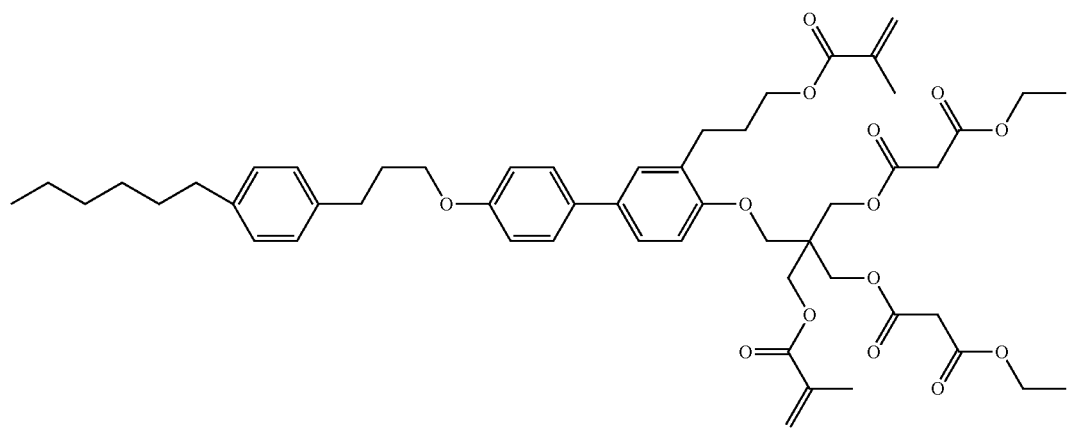
(P-269)

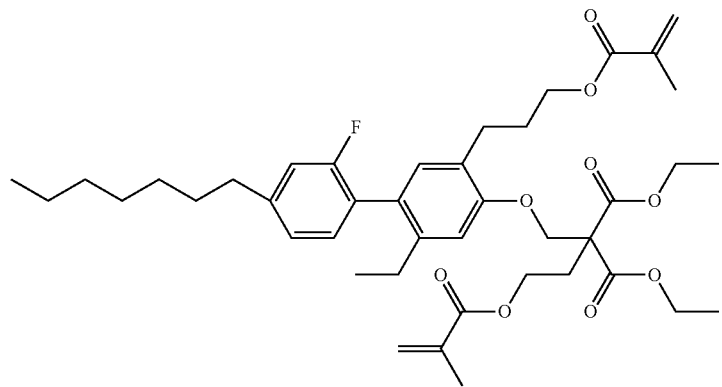
(P-270)
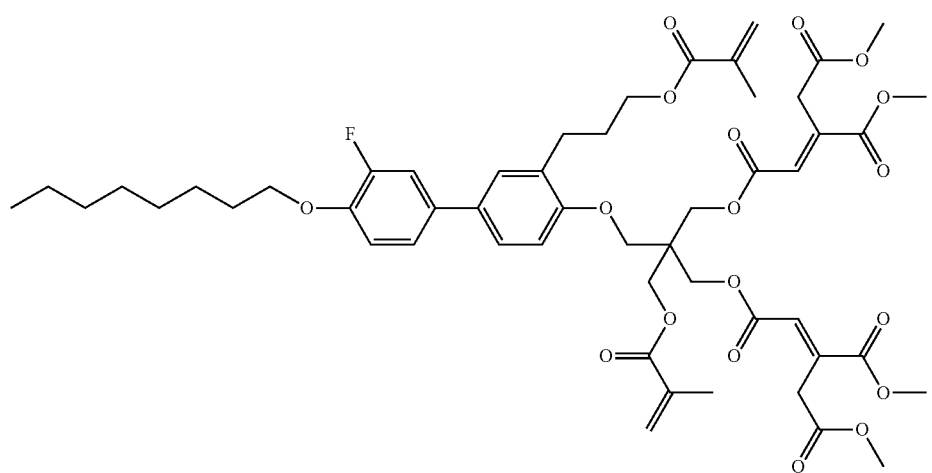
(P-271)
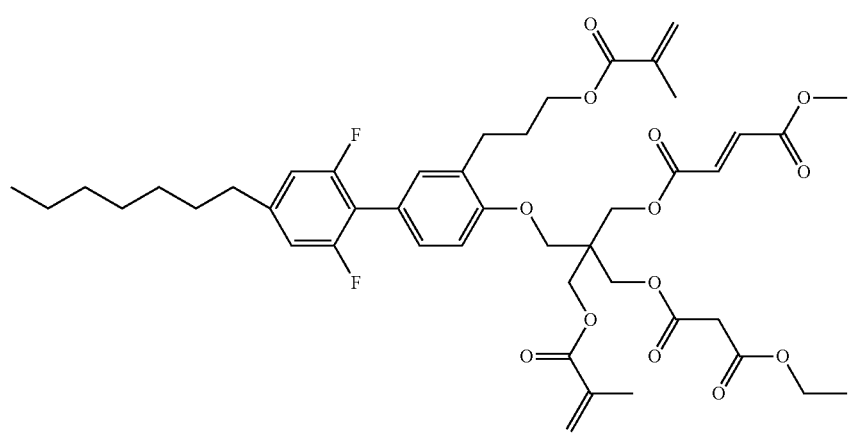
(P-272)

(P-273)
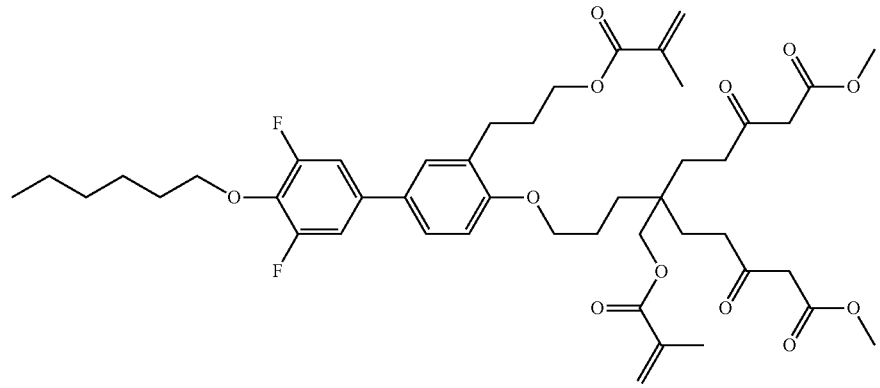
(P-274)
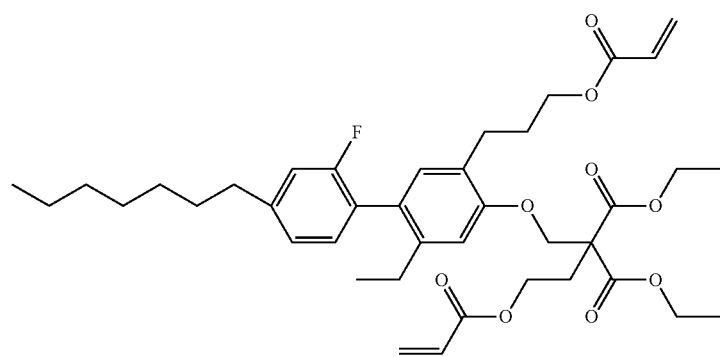
(P-275)
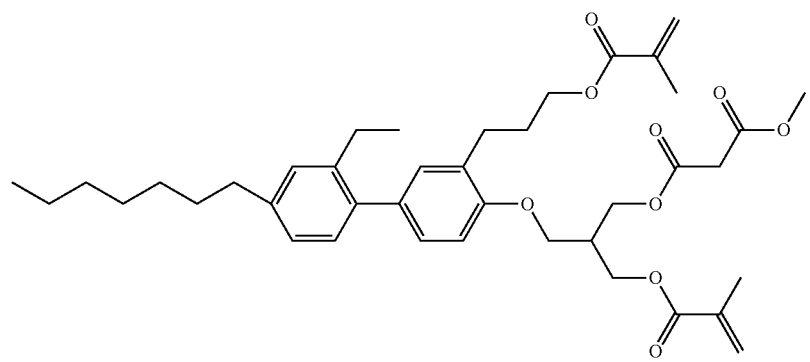
(P-276)
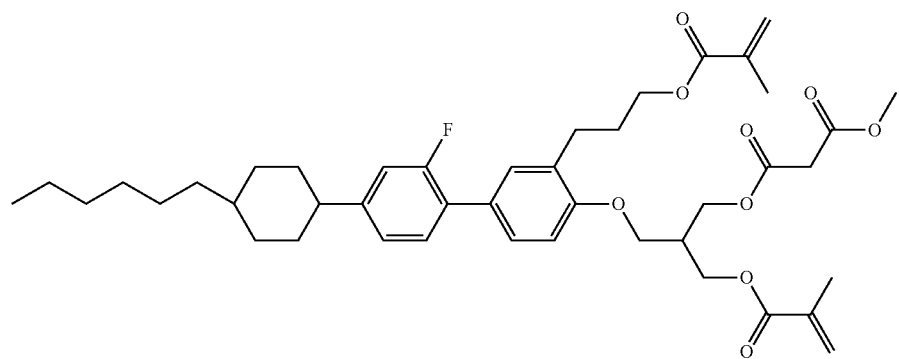

[Chem. 82]
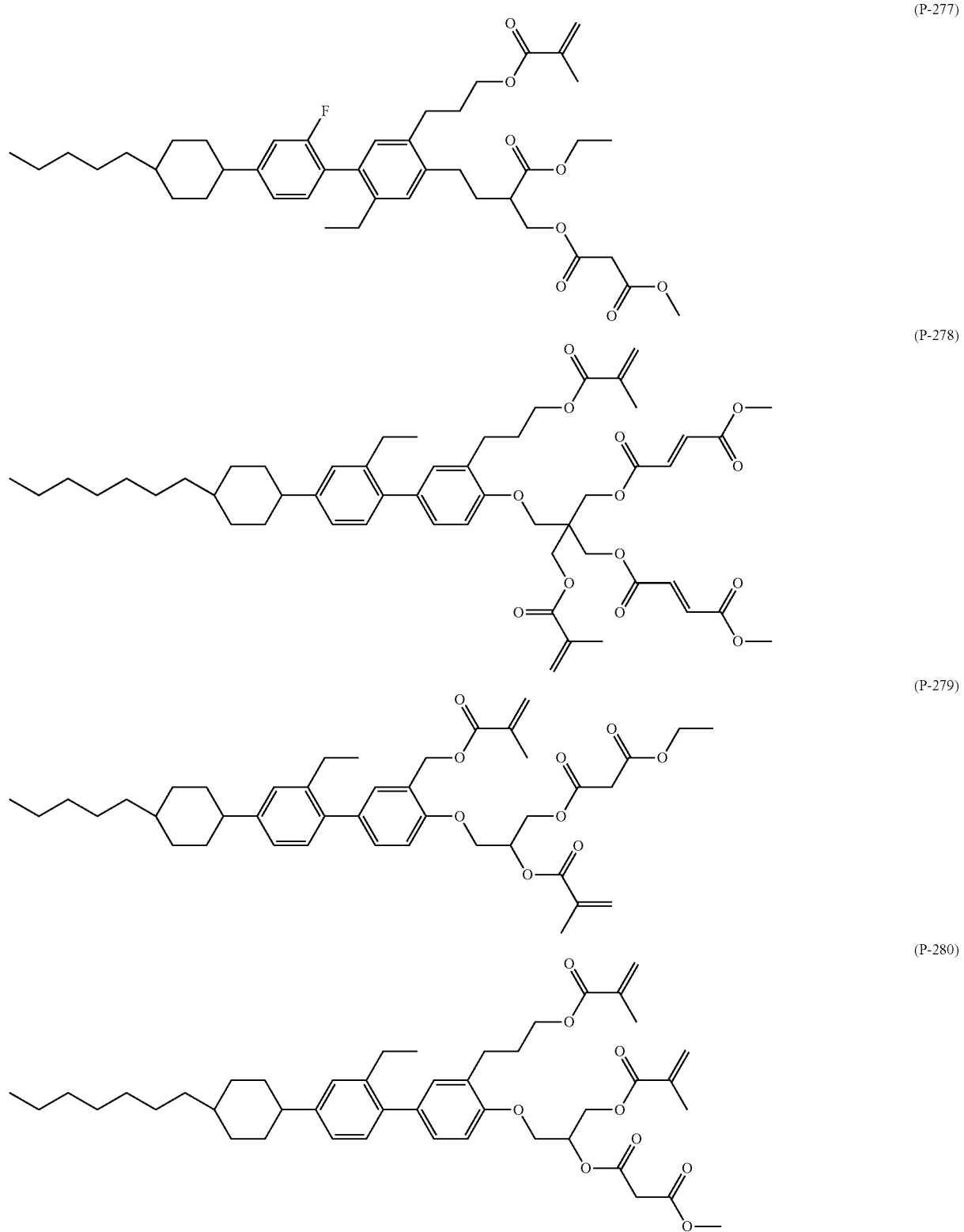
(P-277)
(P-278)
(P-279)
(P-280)

-continued
(P-281)
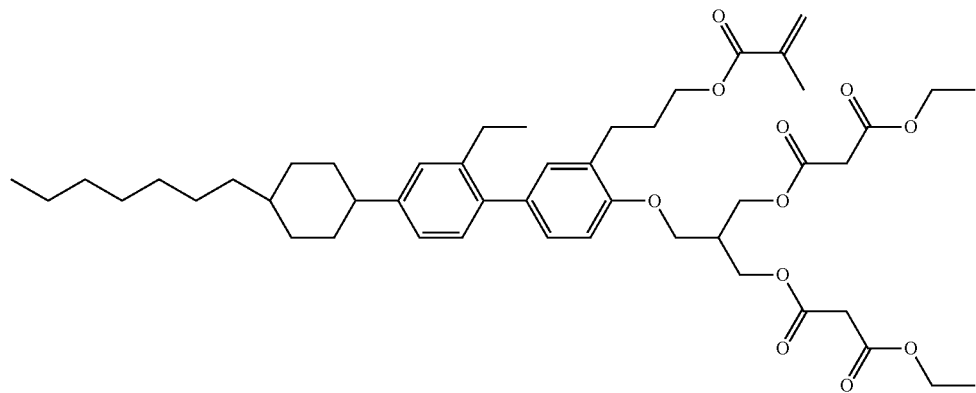
(P-282)
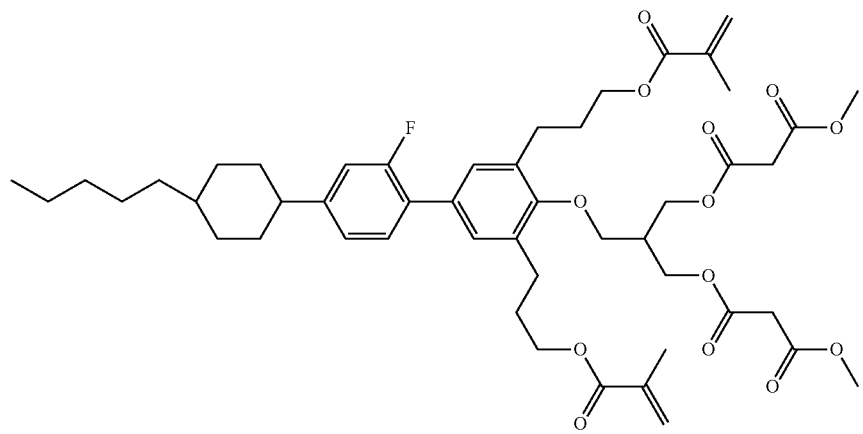
(P-283)
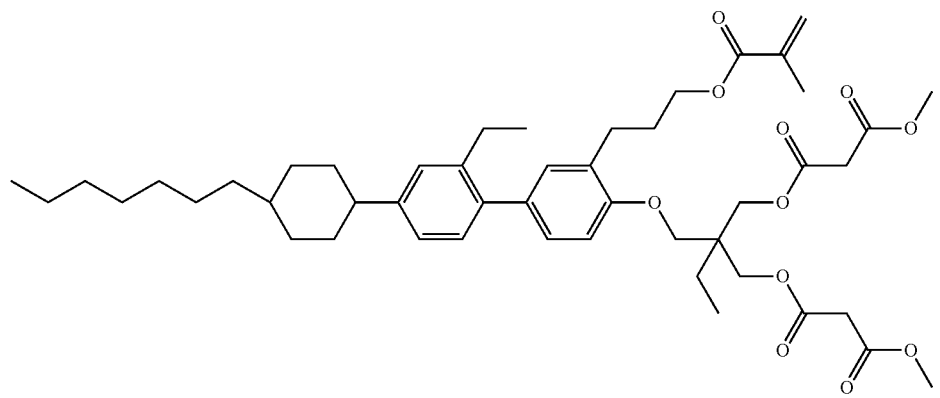
(P-284)
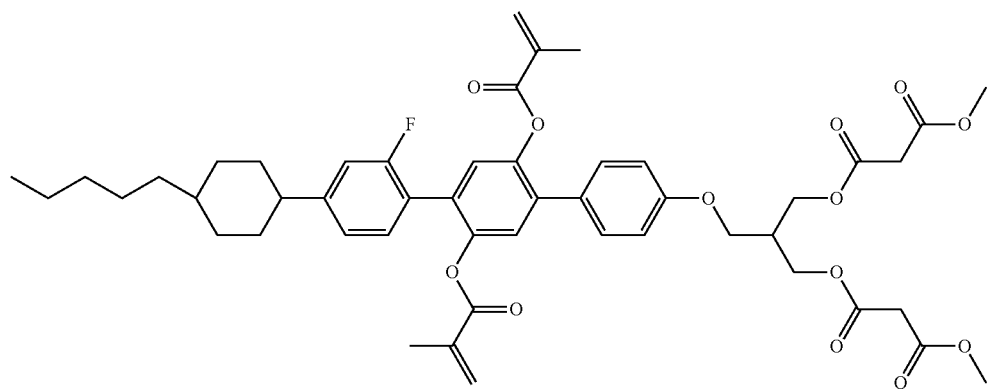

(P-285)
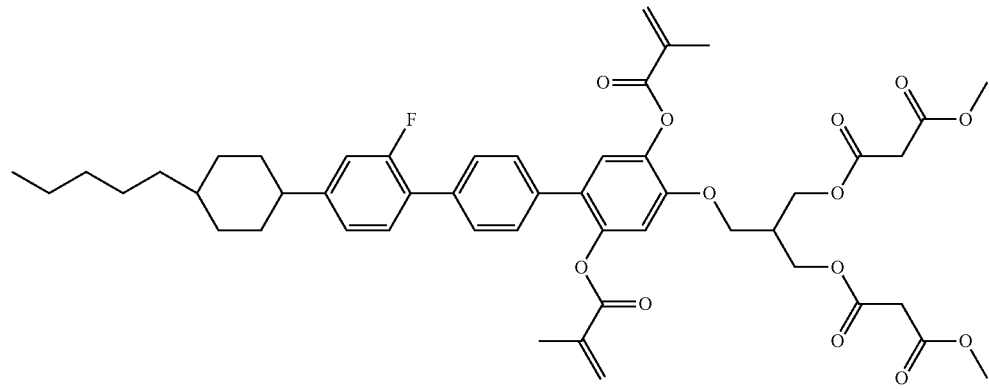
(P-286)
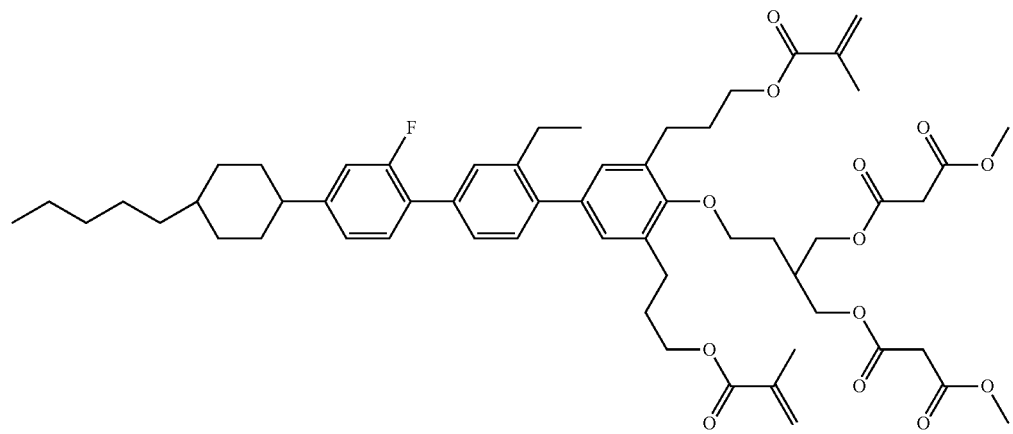
(P-287)
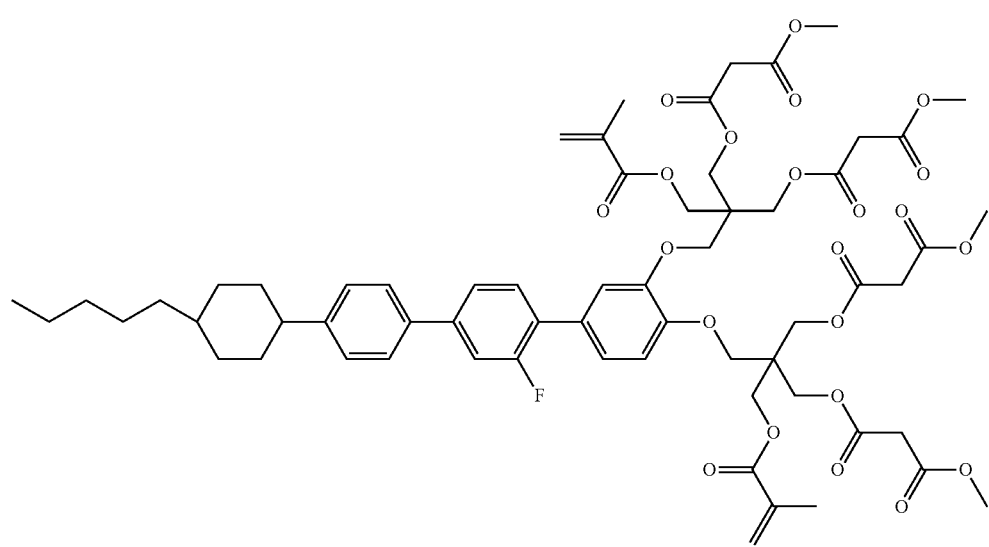

-continued
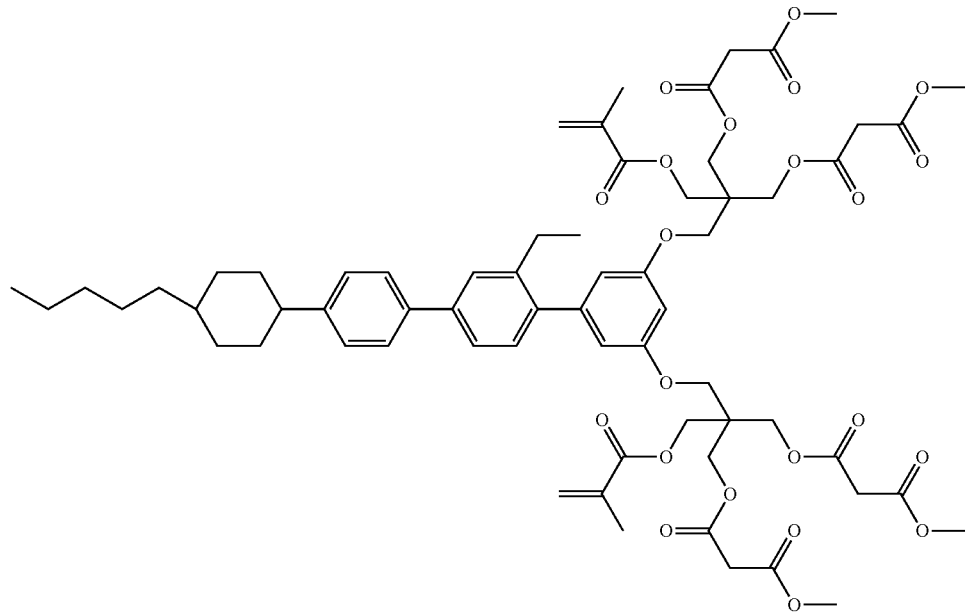
(P-288)
[Chem. 83]
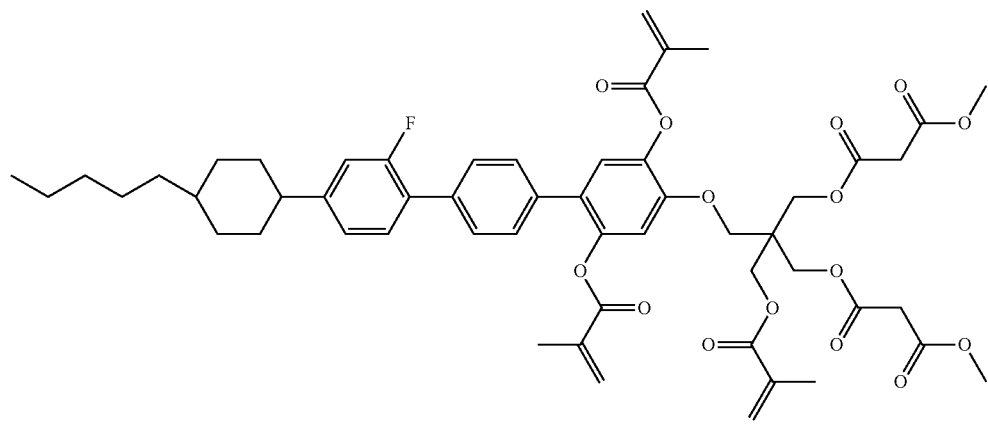
(P-289)
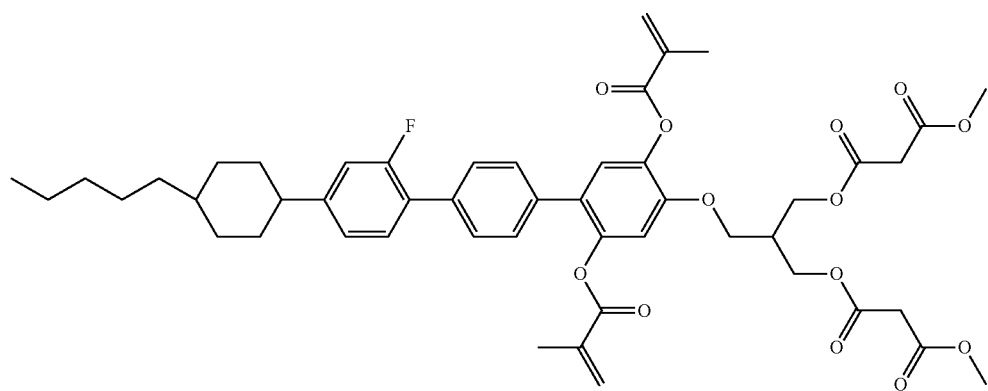
(P-290)

[Chem. 84]
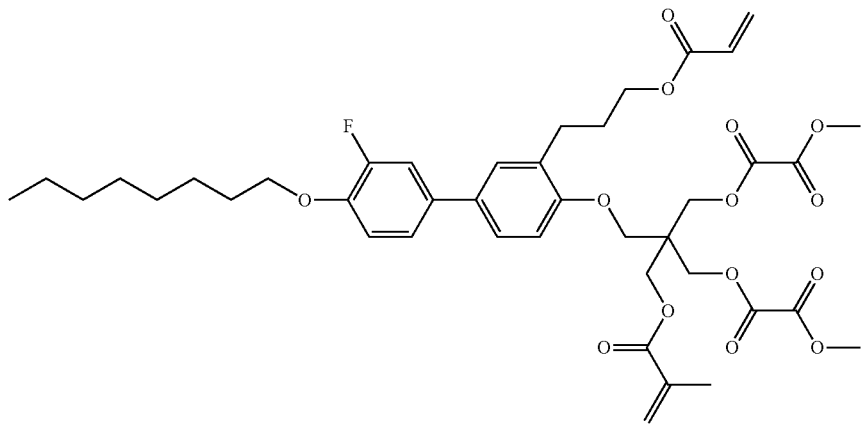
(P-291)
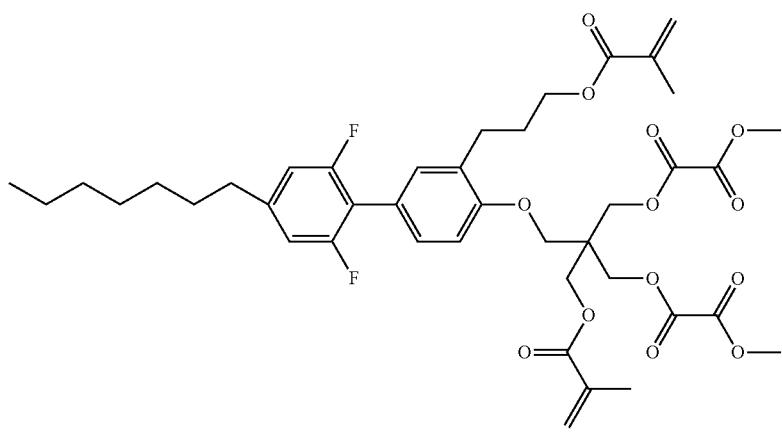
(P-292)
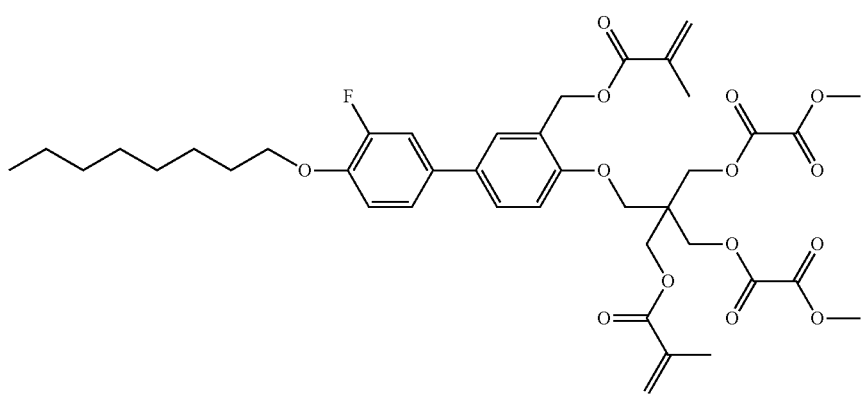
(P-293)

-continued
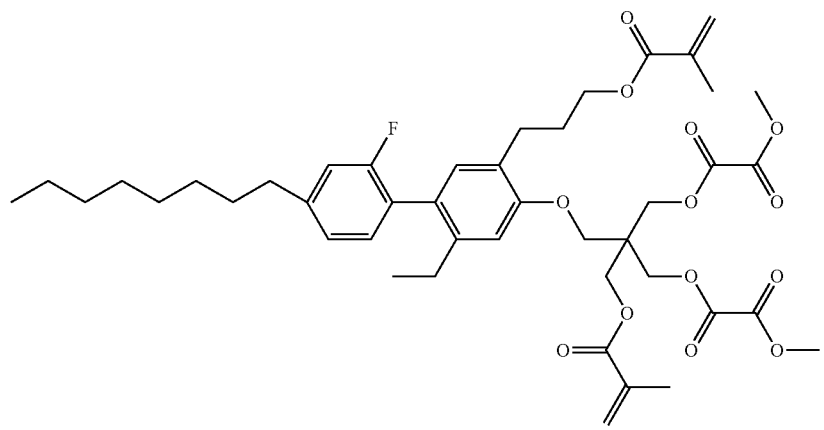
(P-294)
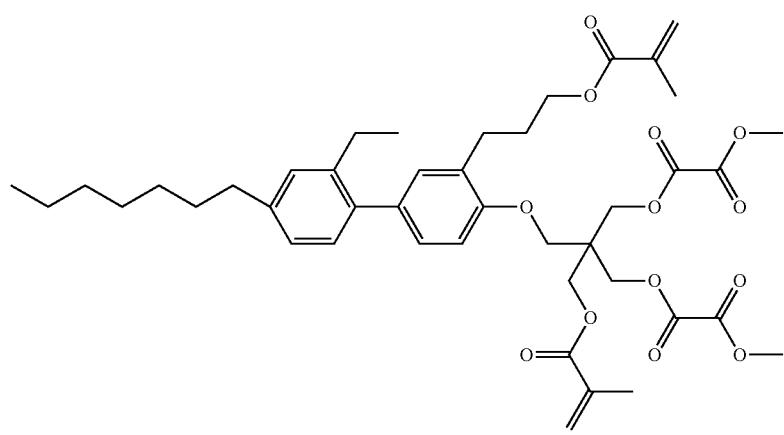
(P-295)
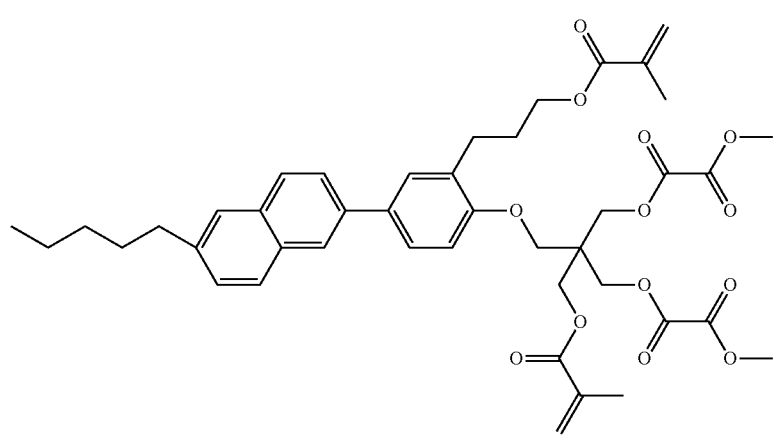
(P-296)

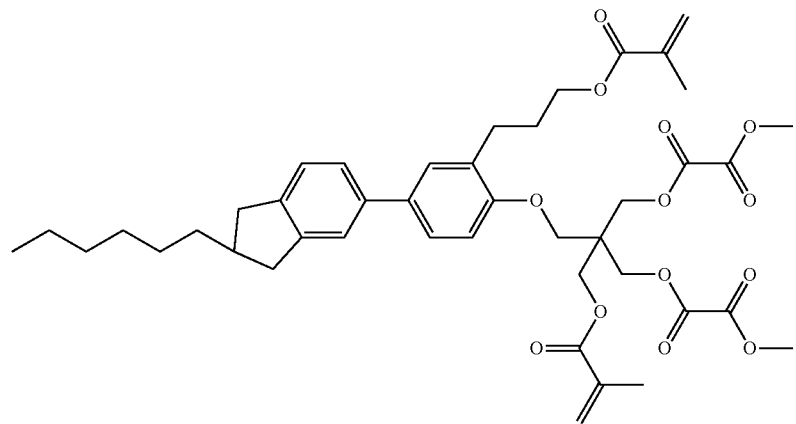
(P-297)
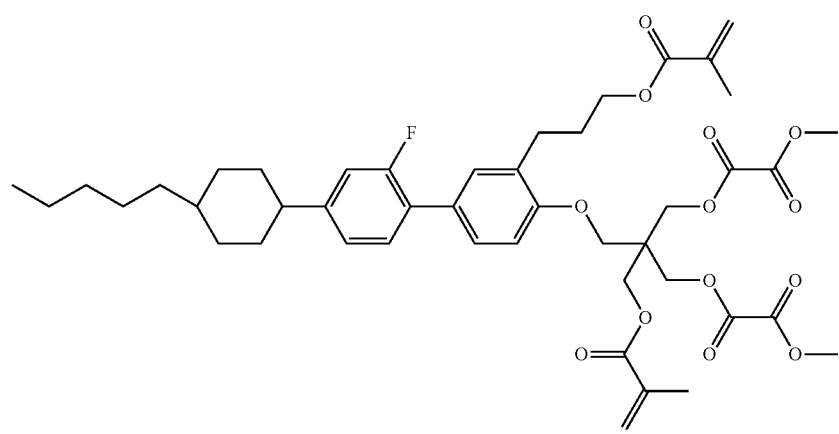
(P-298)
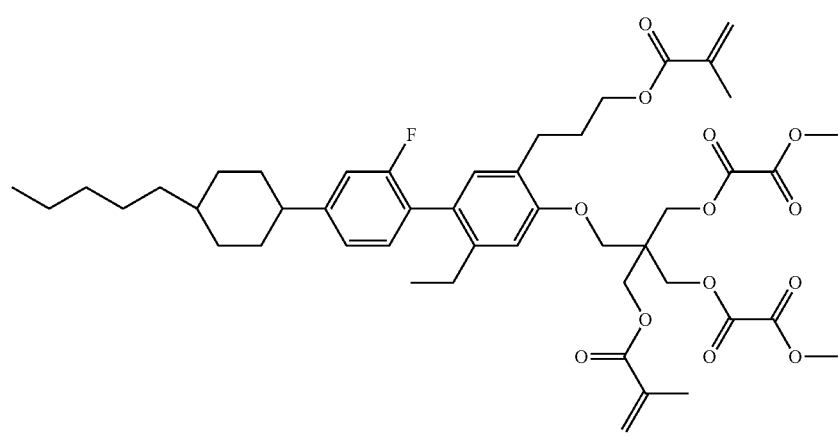
(P-299)

-continued
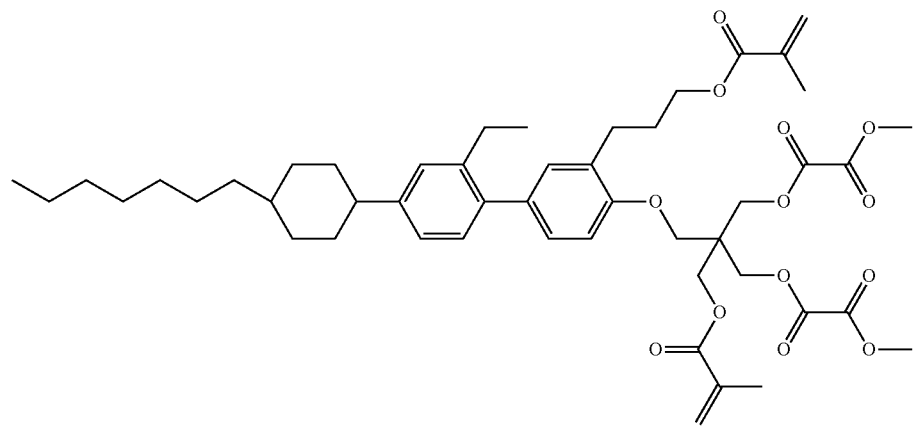
(P-300)
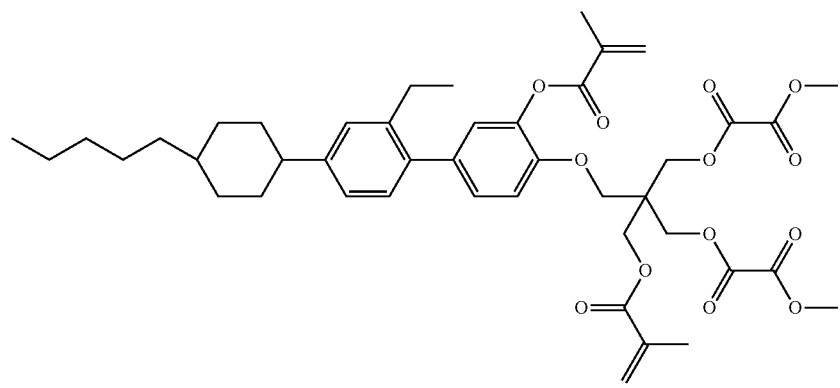
(P-301)
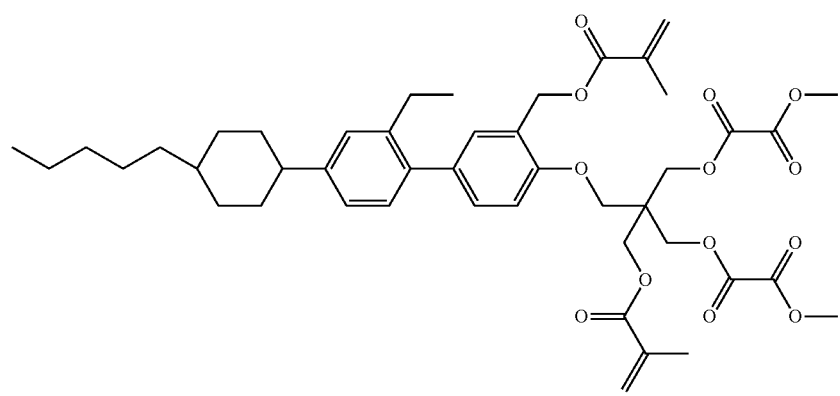
(P-302)

-continued
[Chem. 85]
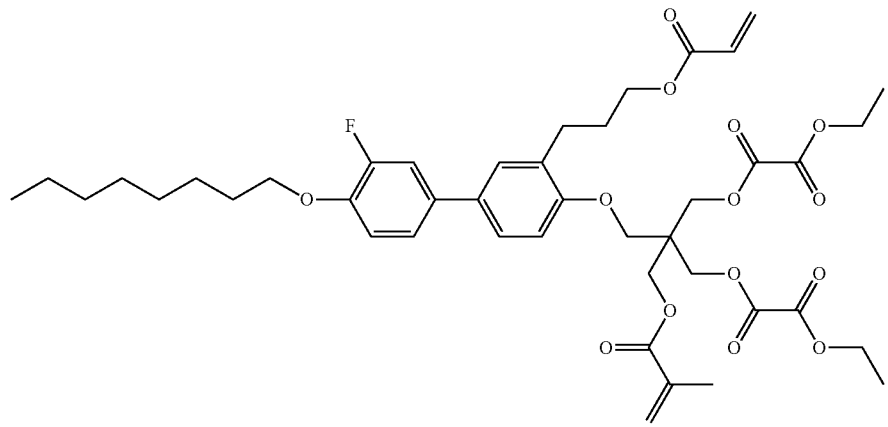
(P-303)
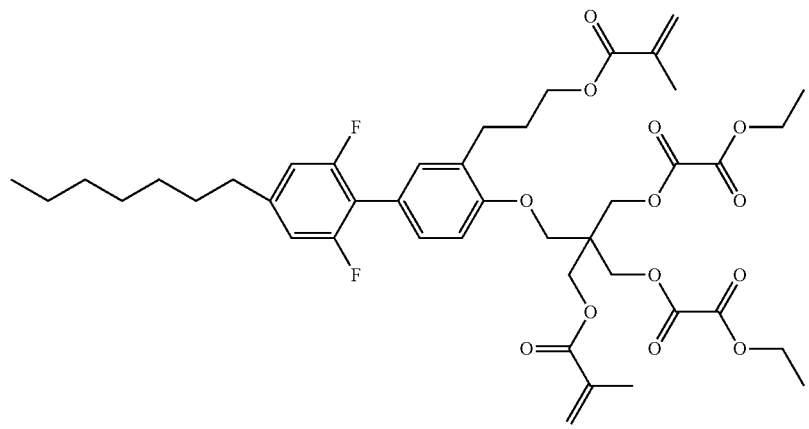
(P-304)
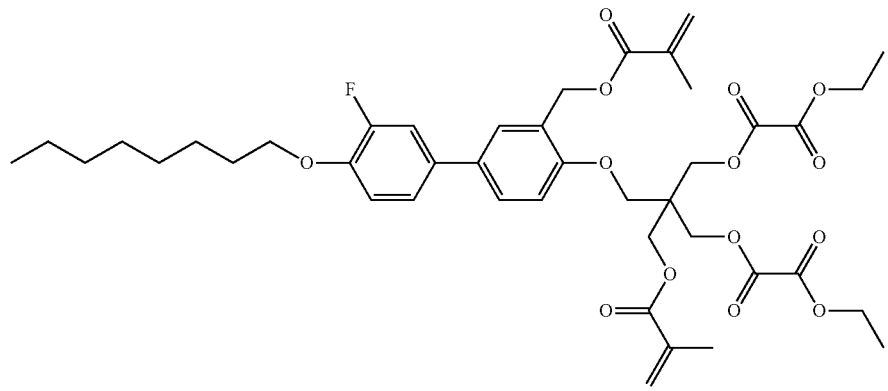
(P-305)

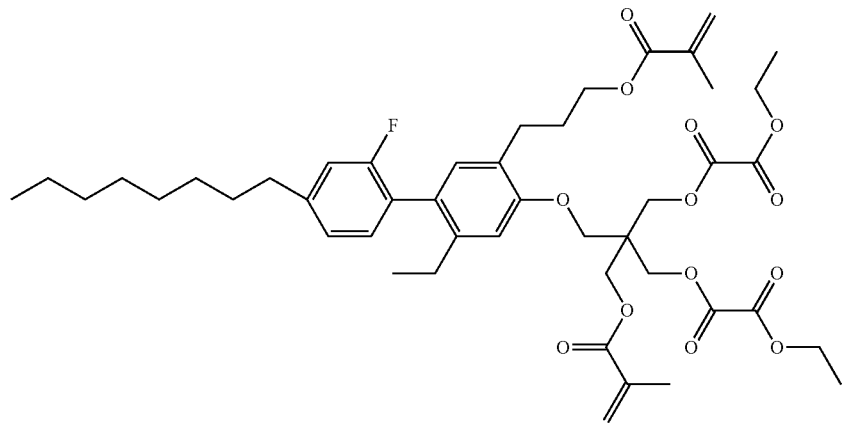
(P-306)
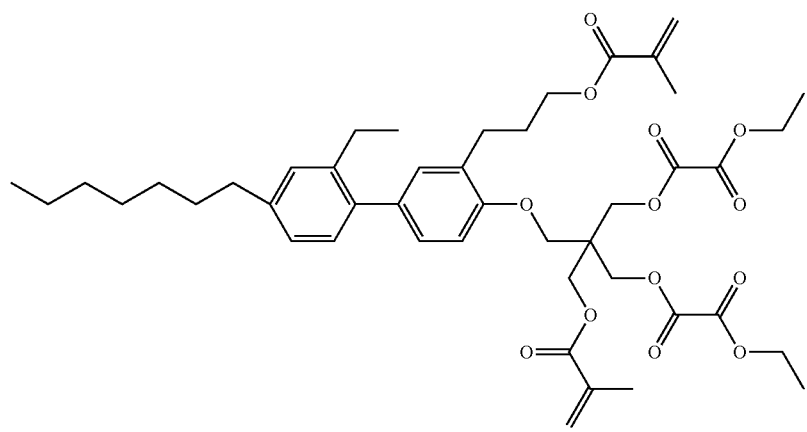
(P-307)
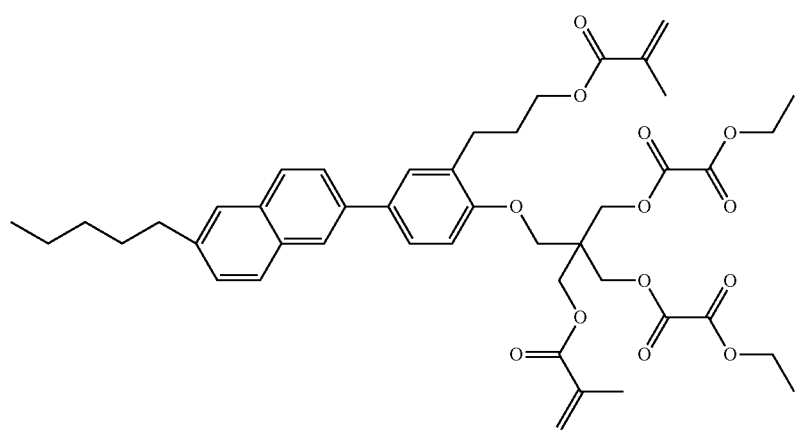
(P-308)

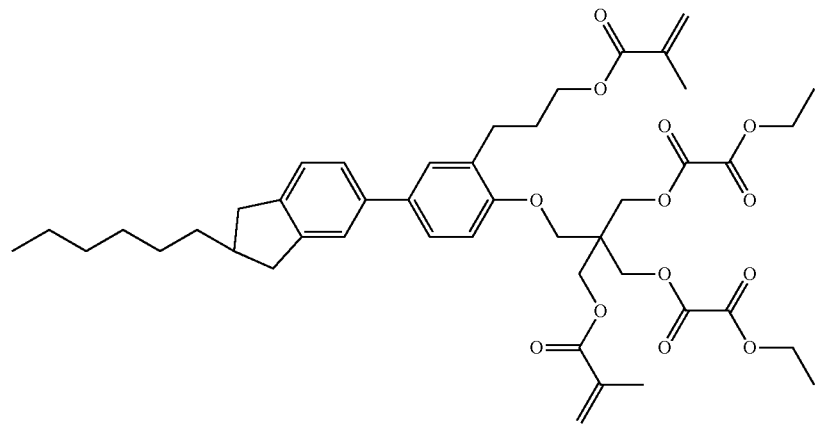
(P-309)
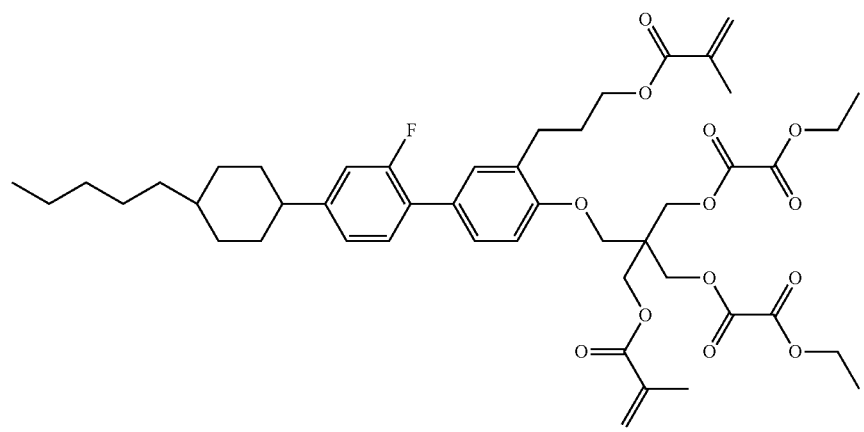
(P-310)
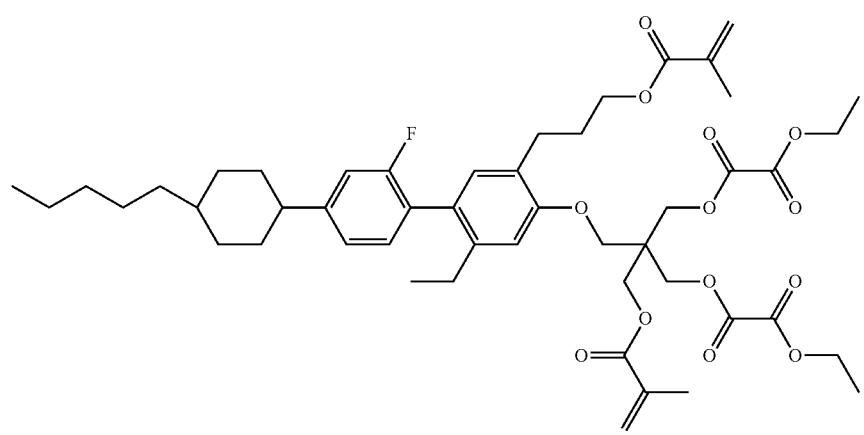
(P-311)

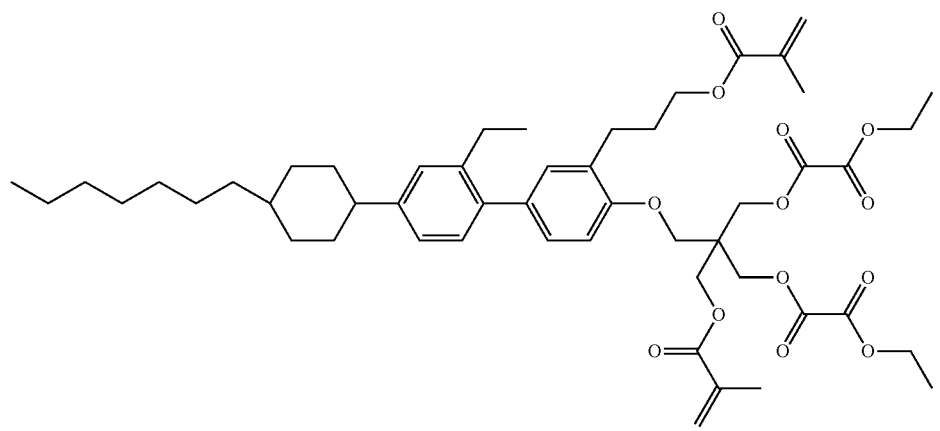
(P-312)
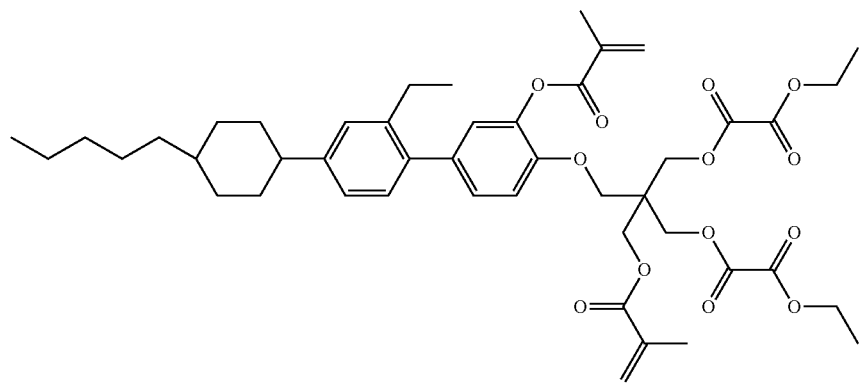
(P-313)
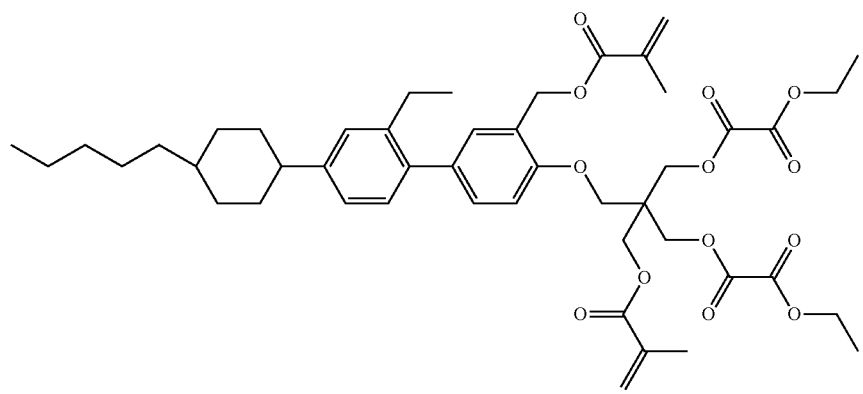
(P-314)
[Chem. 86]
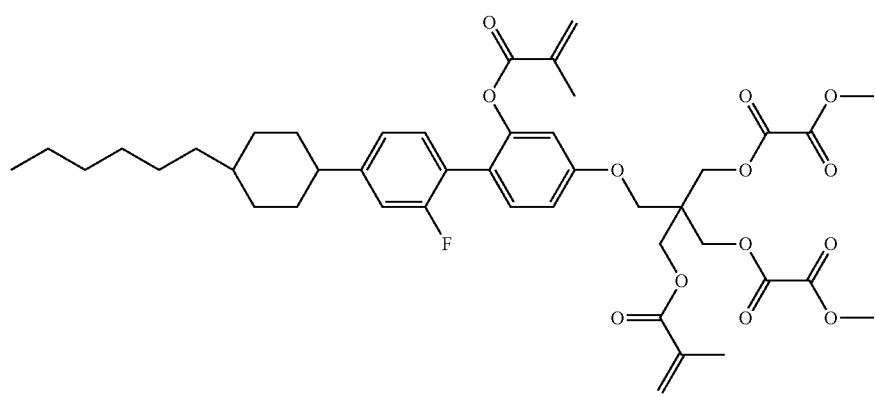
(P-315)

-continued
(P-316)
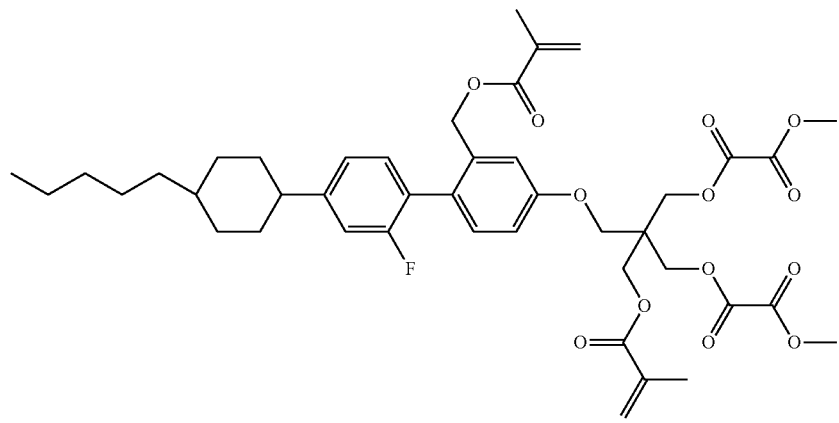
(P-317)
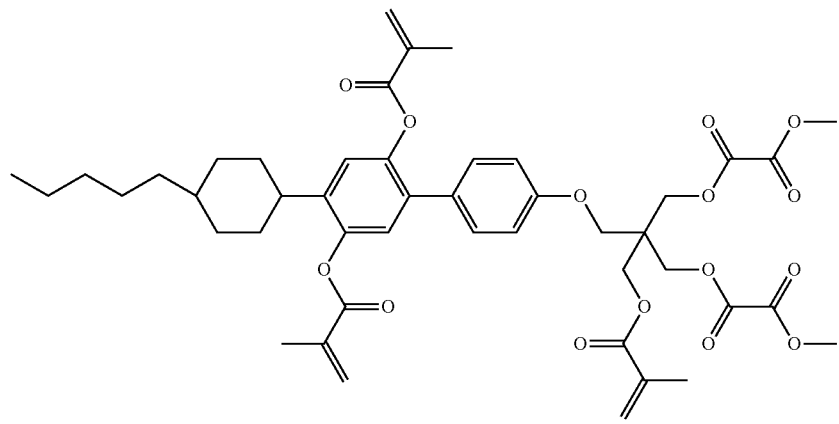
(P-318)
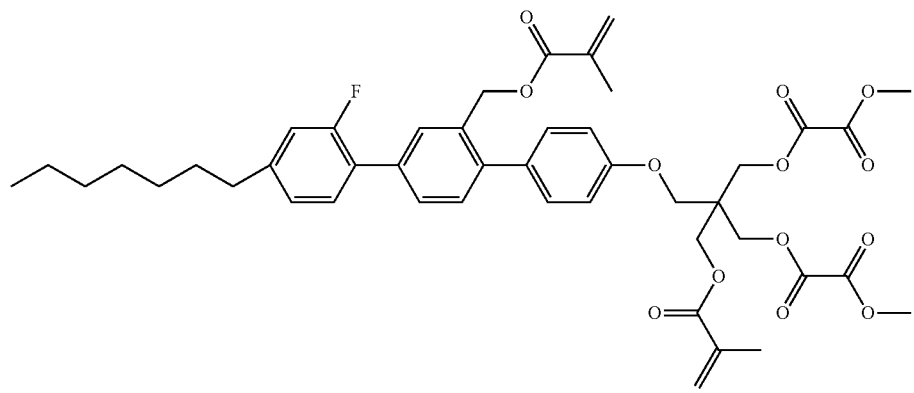
(P-319)
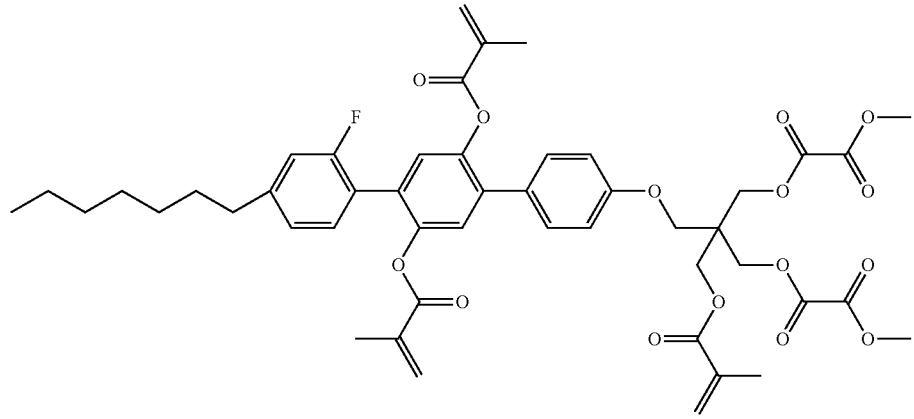

-continued
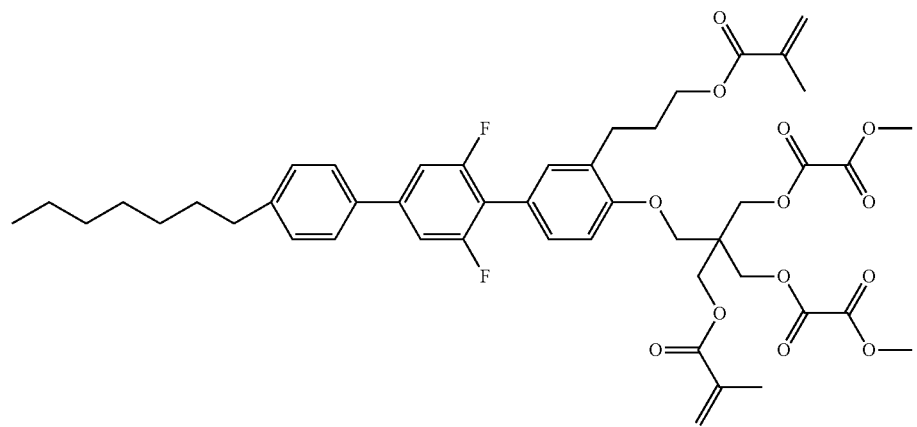
(P-320)
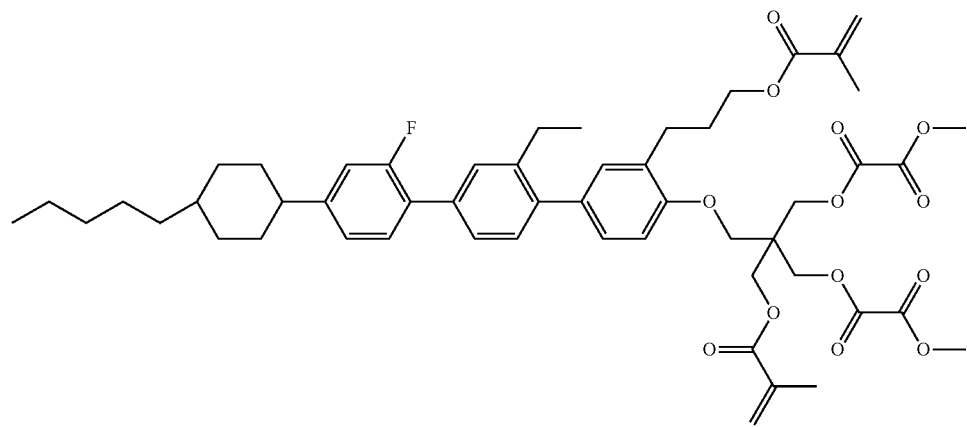
(P-321)
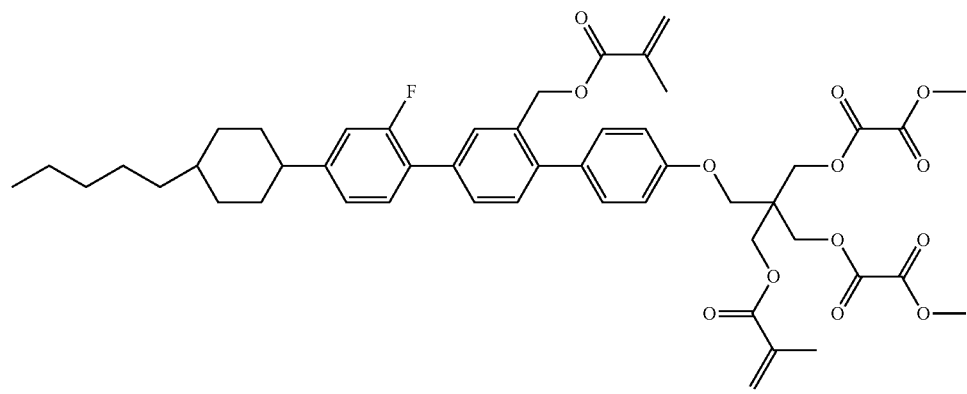
(P-322)

-continued
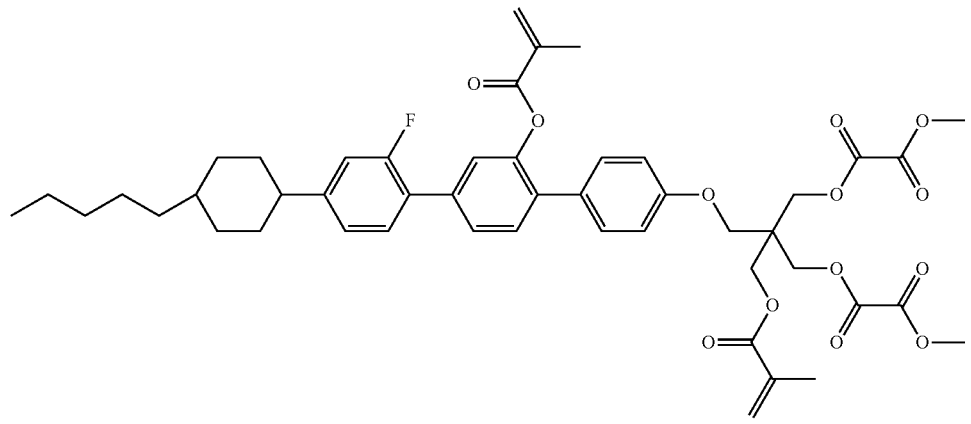
(P-323)
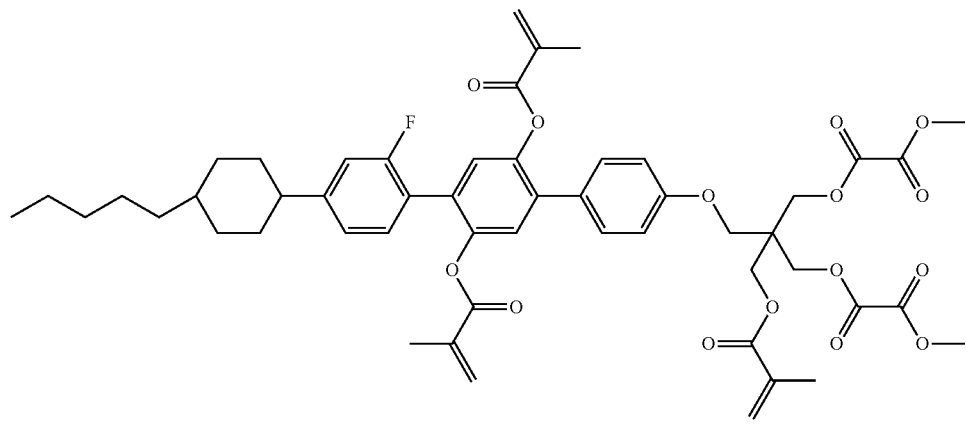
(P-324)
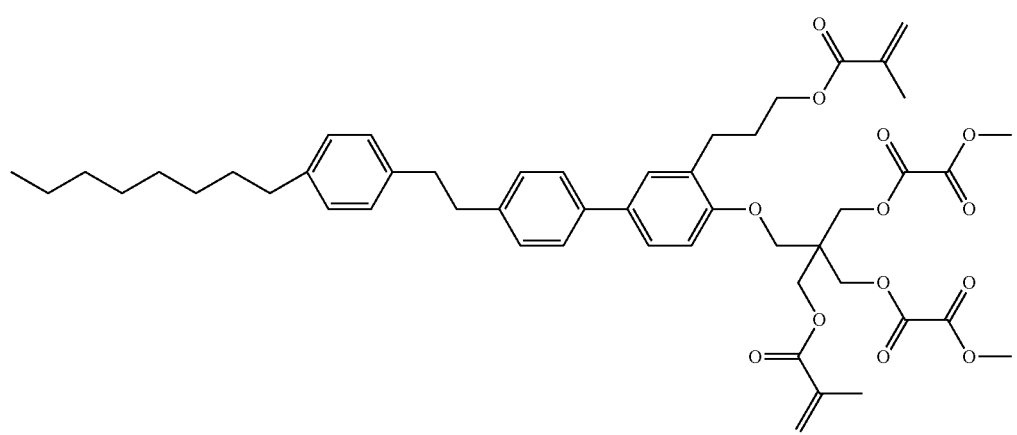
(P-325)

-continued
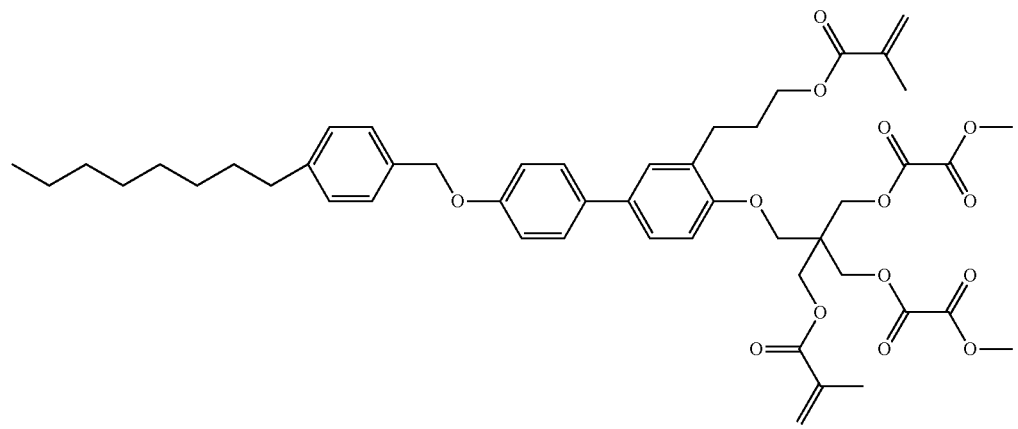
(P-326)
[Chem. 87]
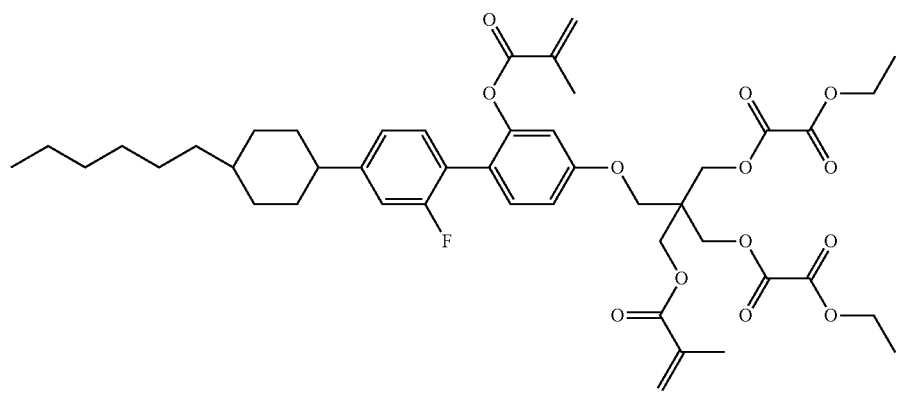
(P-327)
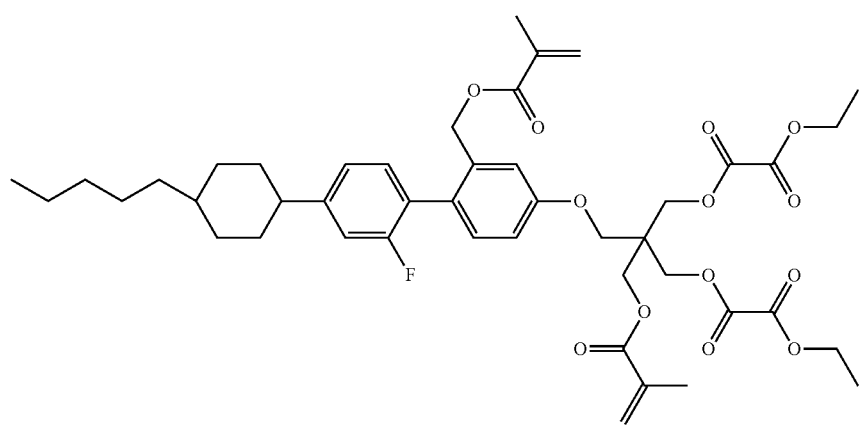
(P-328)

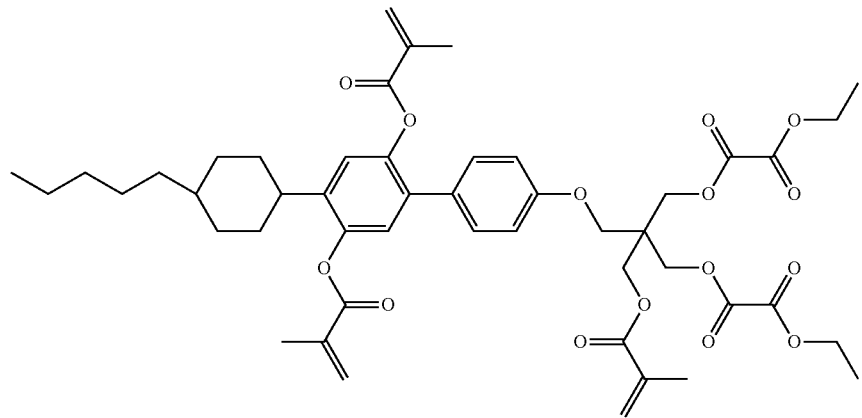
(P-329)
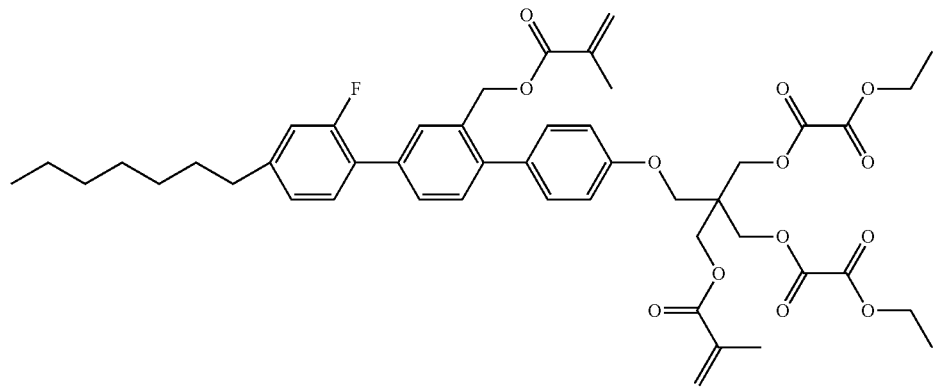
(P-330)
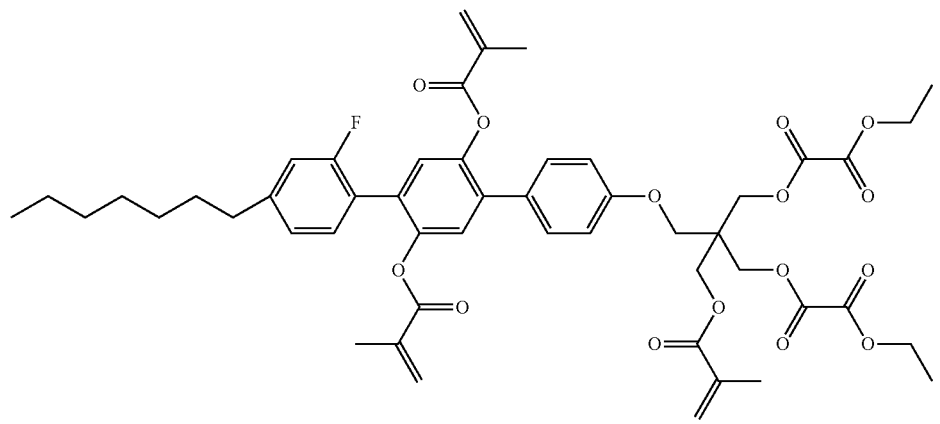
(P-331)

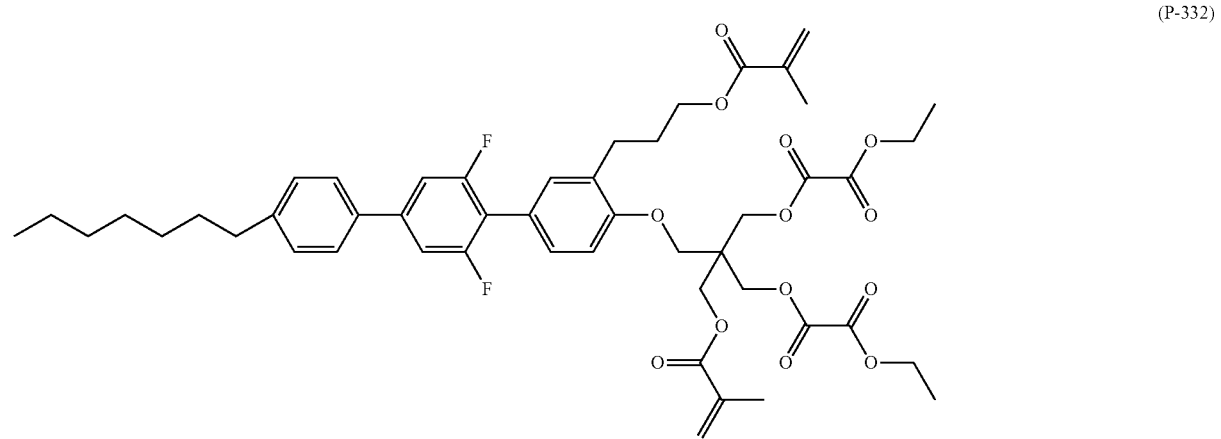
(P-332)
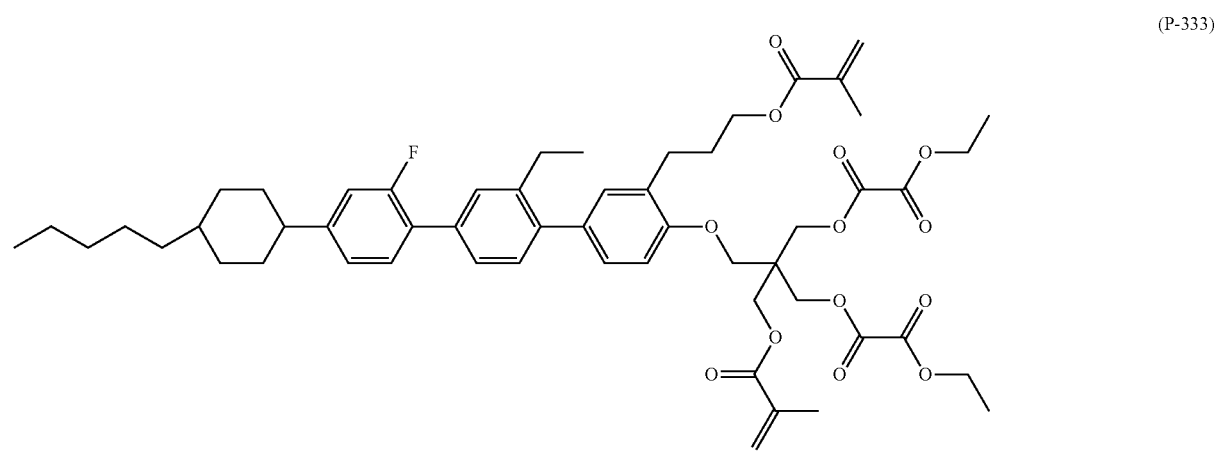
(P-333)
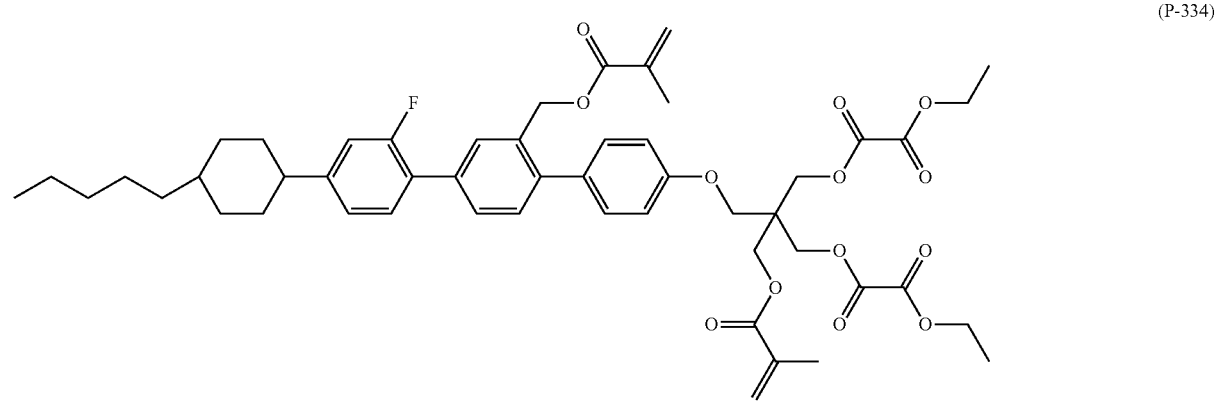
(P-334)

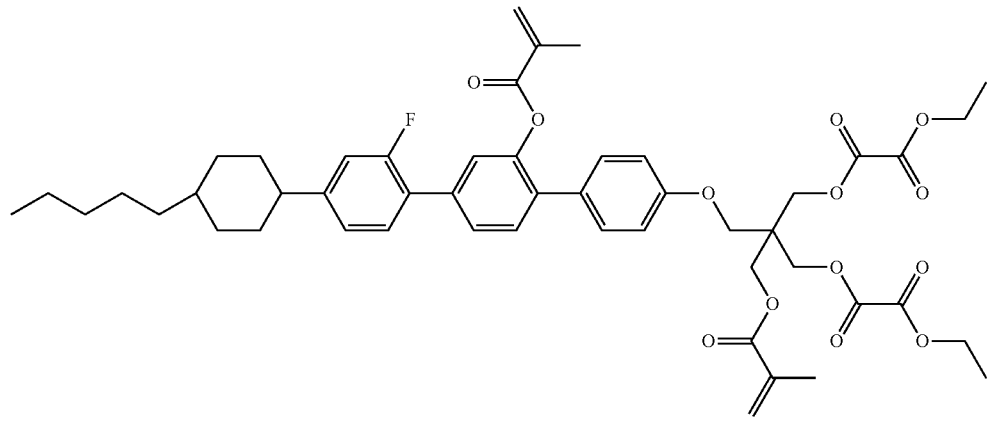
(P-335)
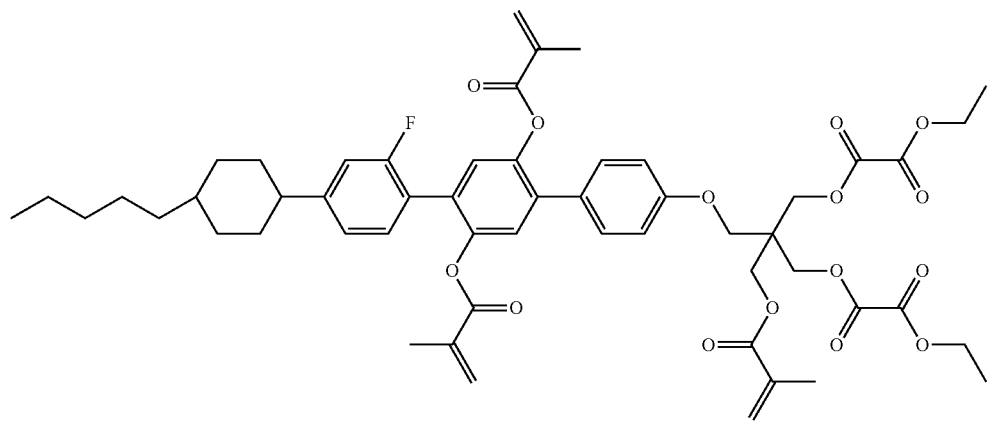
(P-336)
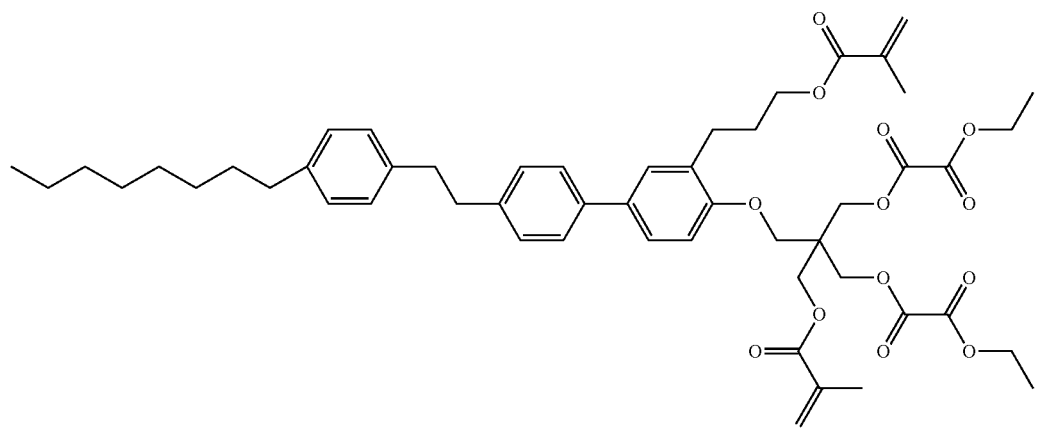
(P-337)

(P-338)
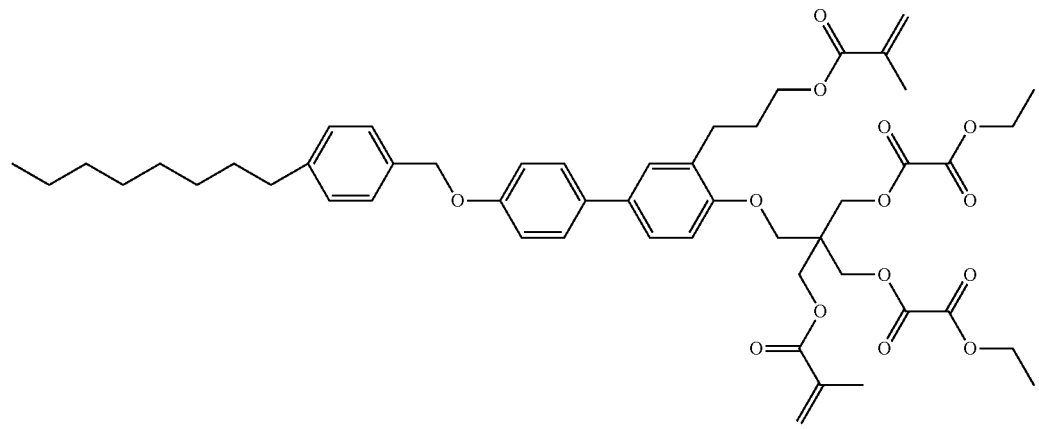
[Chem. 88]
(P-339)
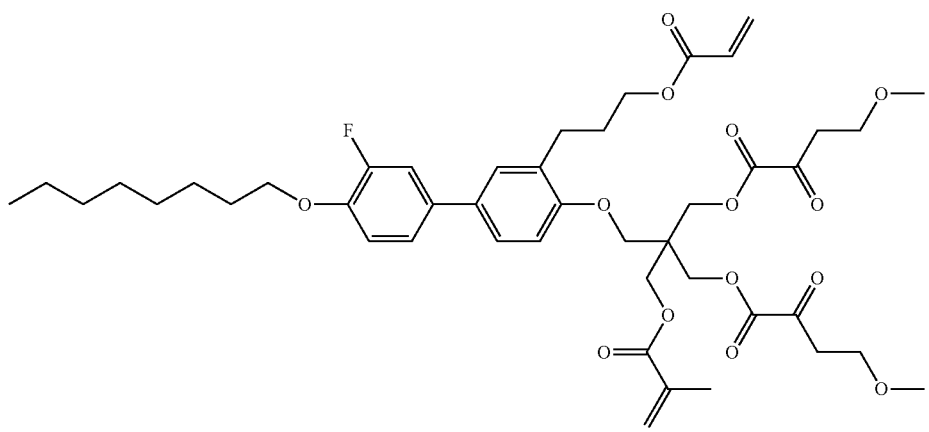
(P-340)
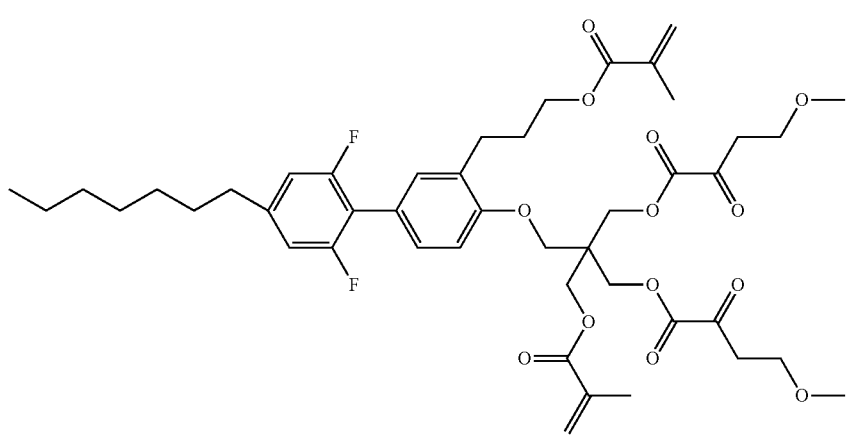

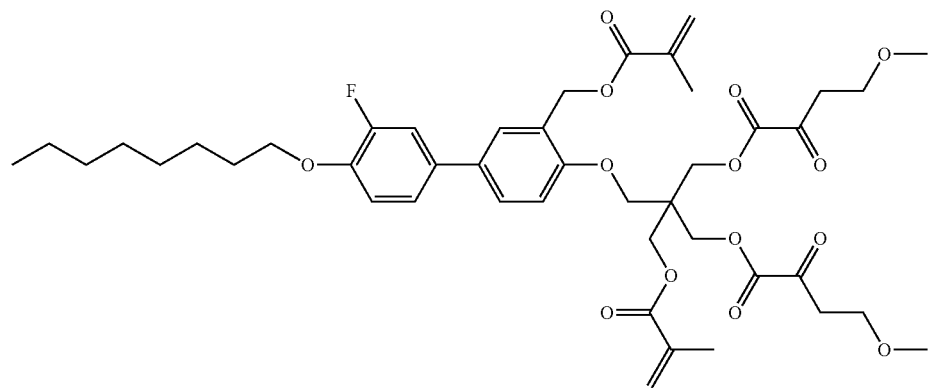
(P-341)
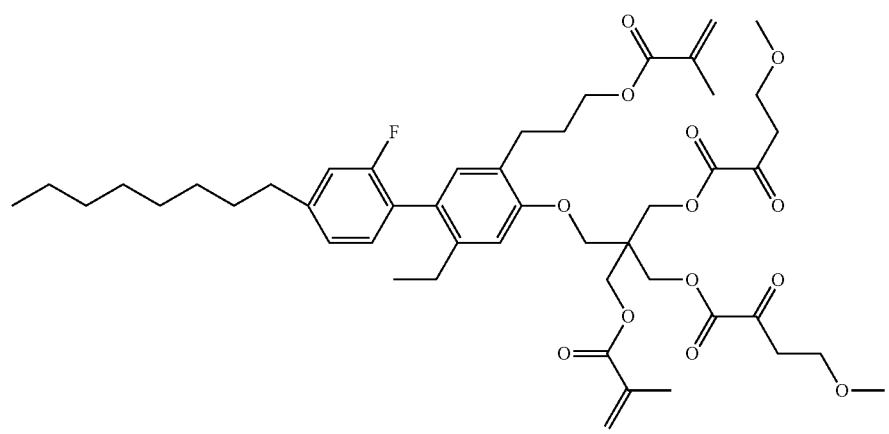
(P-342)
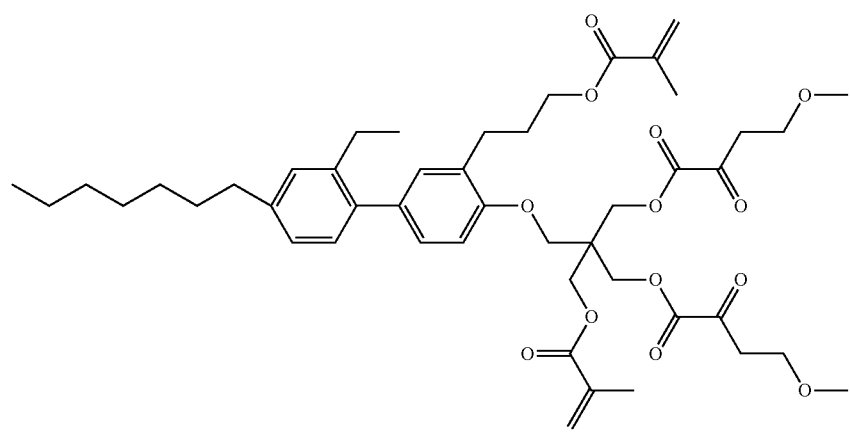
(P-343)

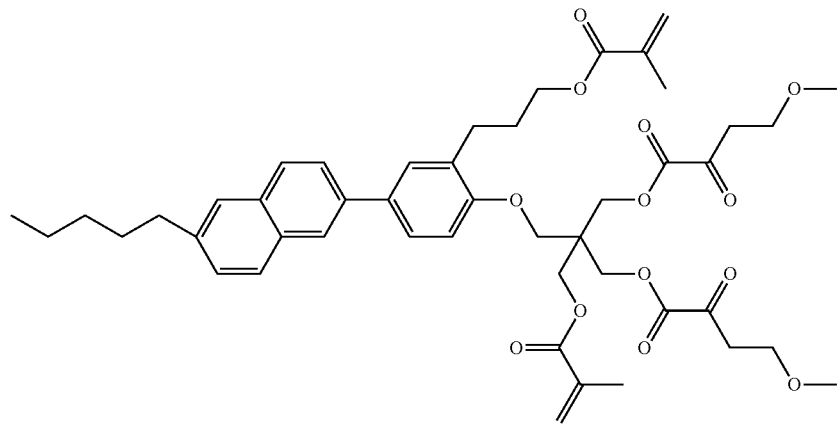
(P-344)
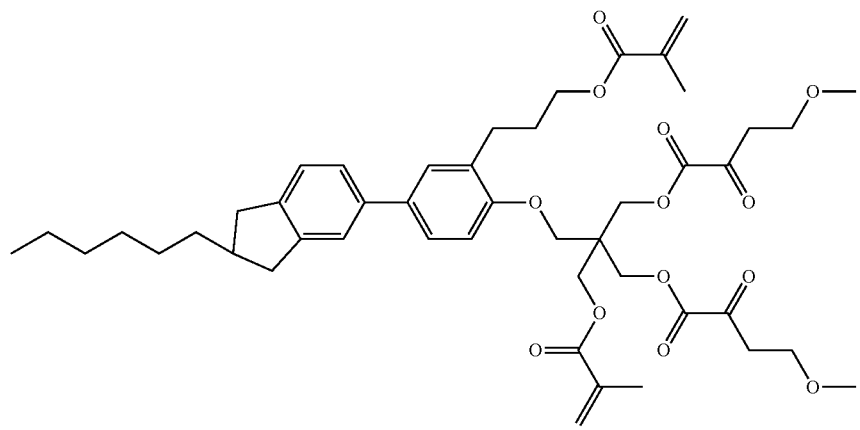
(P-345)
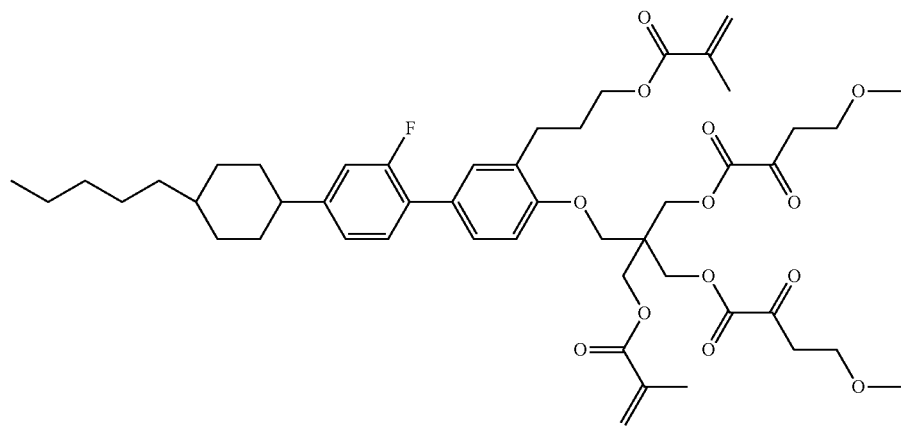
(P-346)

-continued
(P-347)
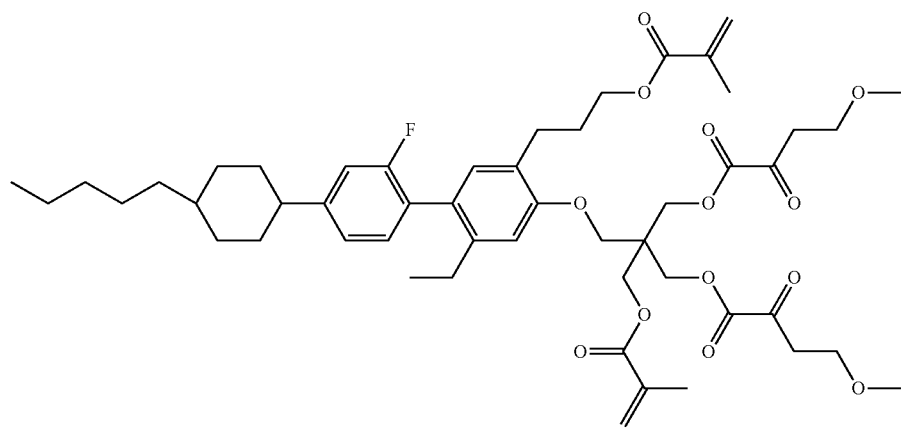
(P-348)
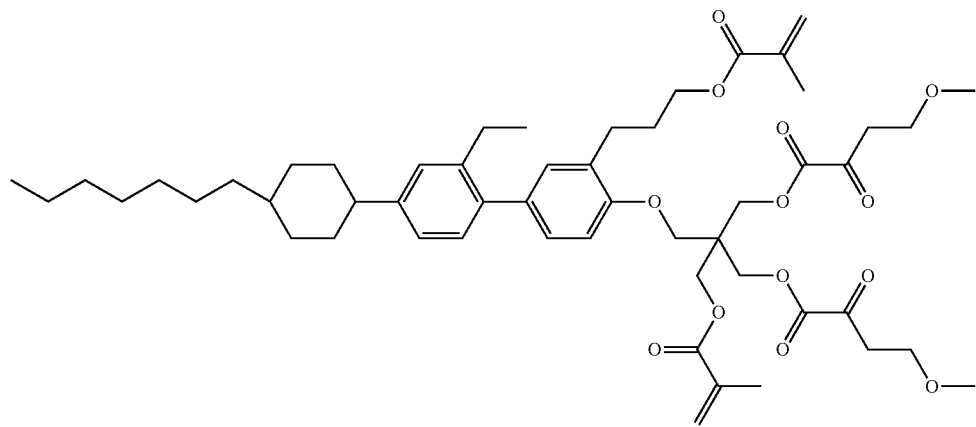
(P-349)
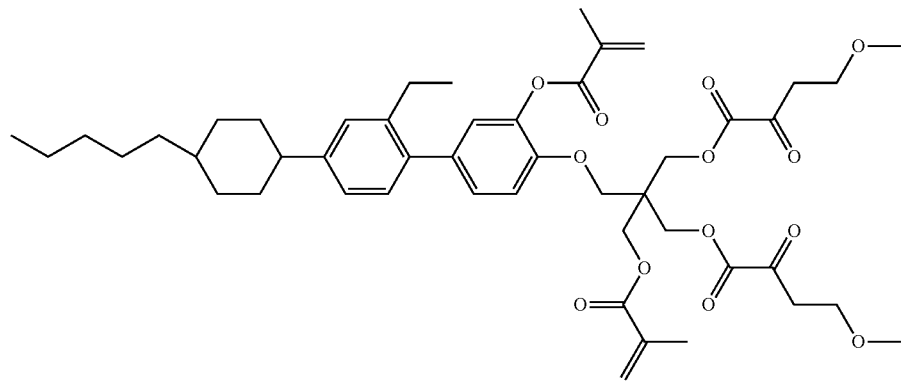
(P-350)
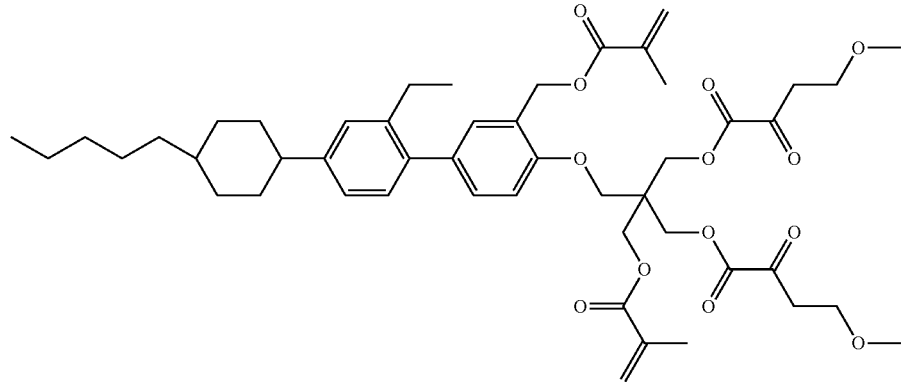

[Chem. 89]
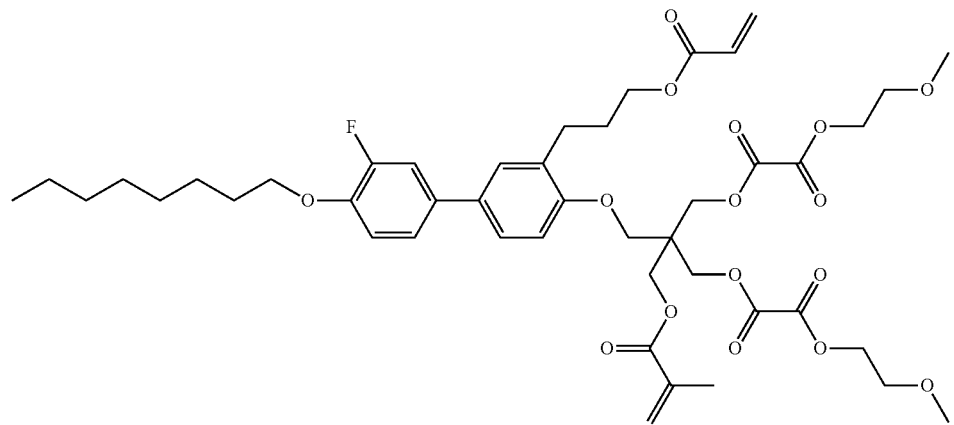
(P-351)
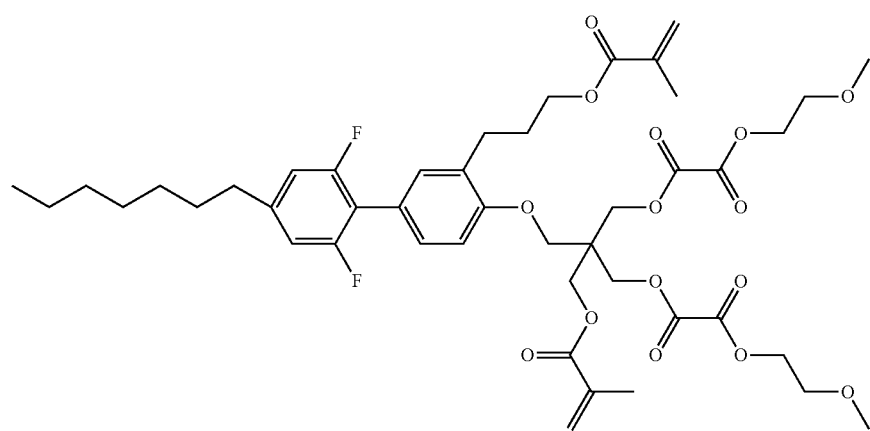
(P-352)
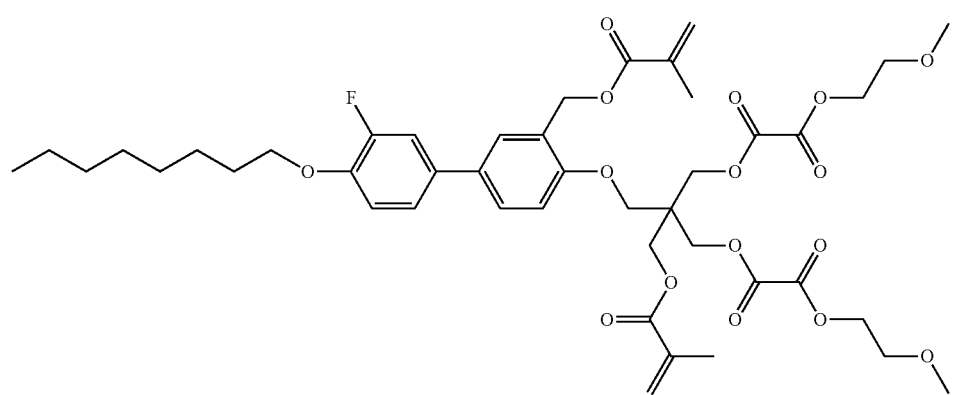
(P-353)

-continued
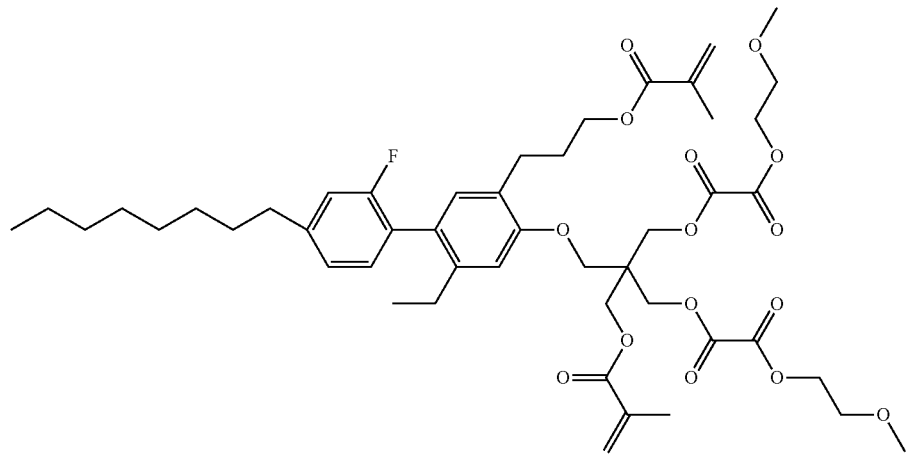
(P-354)
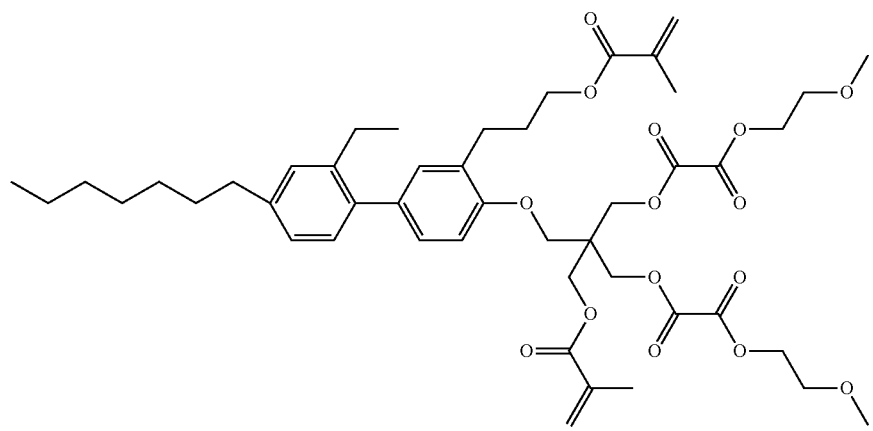
(P-355)
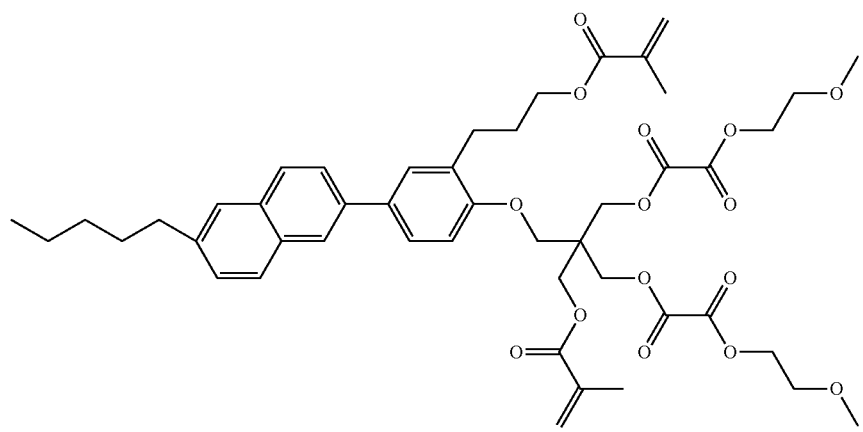
(P-356)

-continued
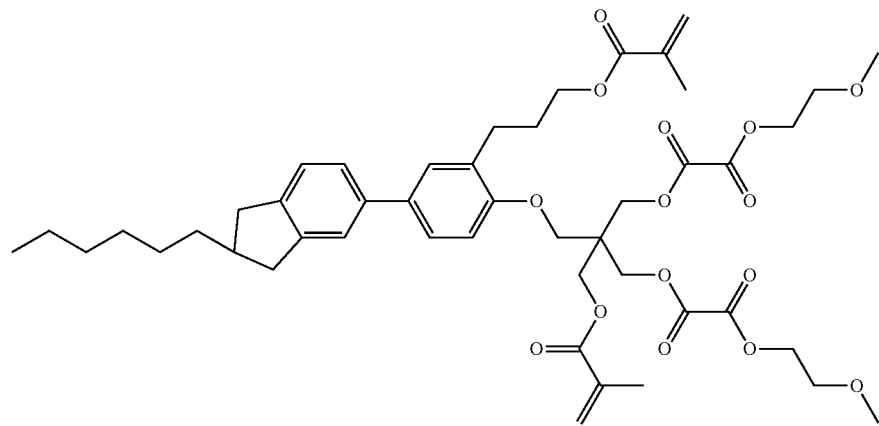
(P-357)
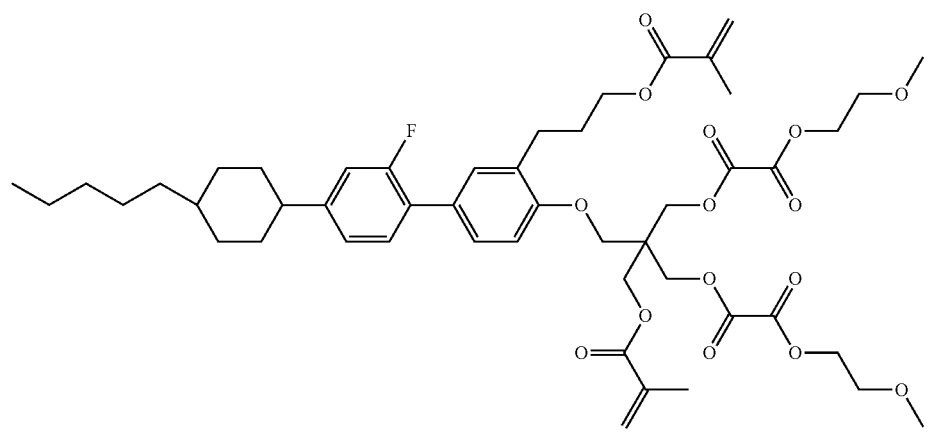
(P-358)
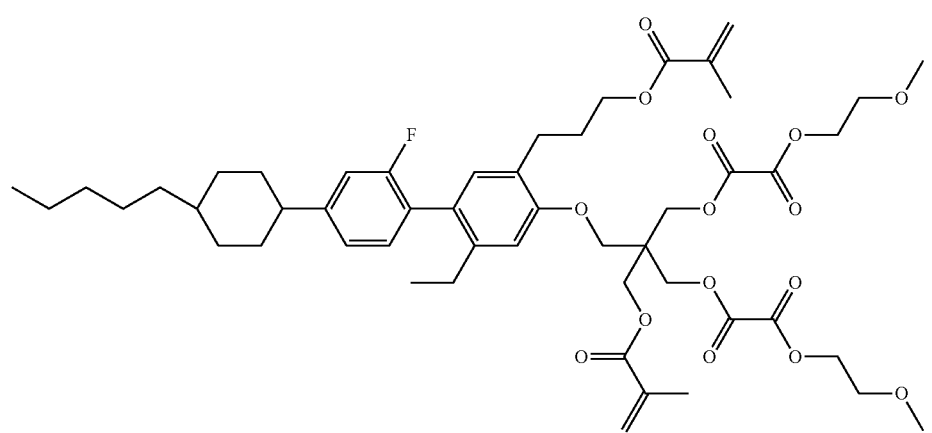
(P-359)

-continued
(P-360)
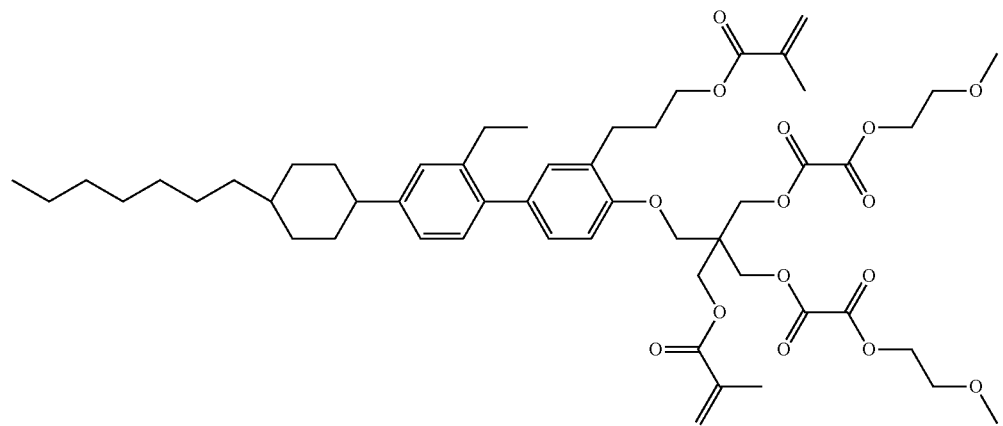
(P-361)
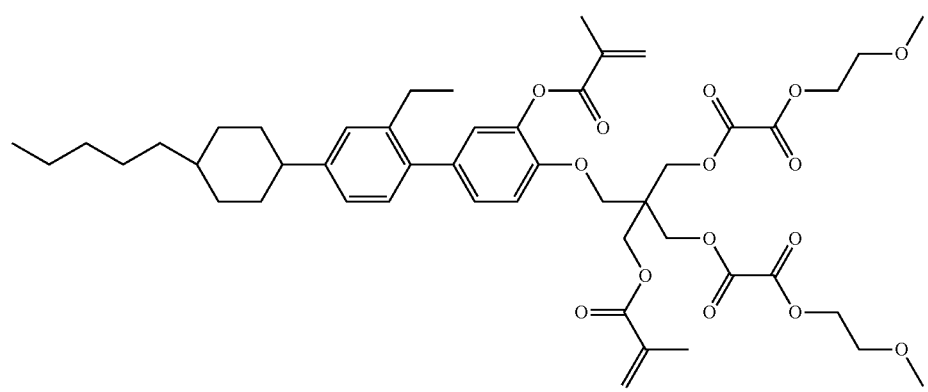
(P-362)
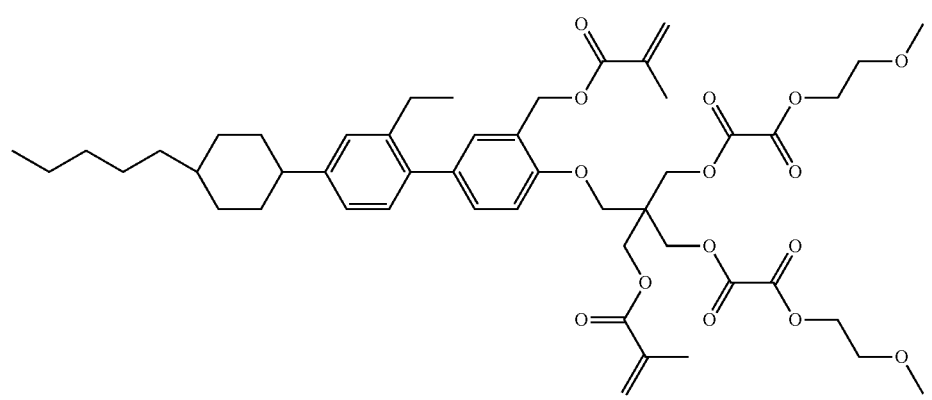

[Chem. 90]
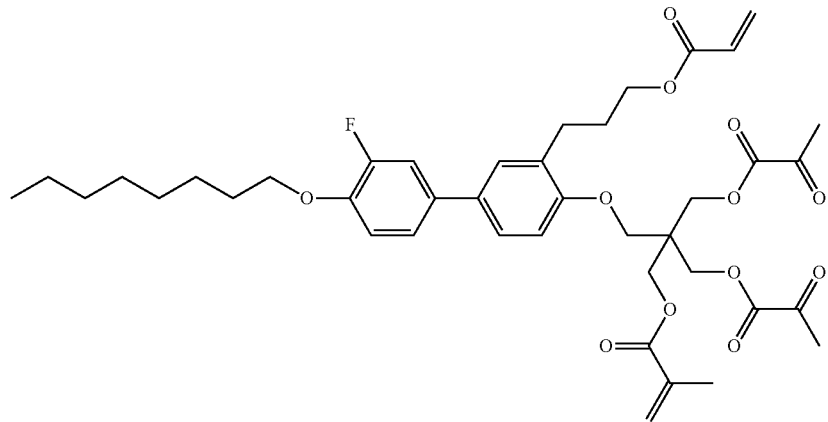
(P-363)
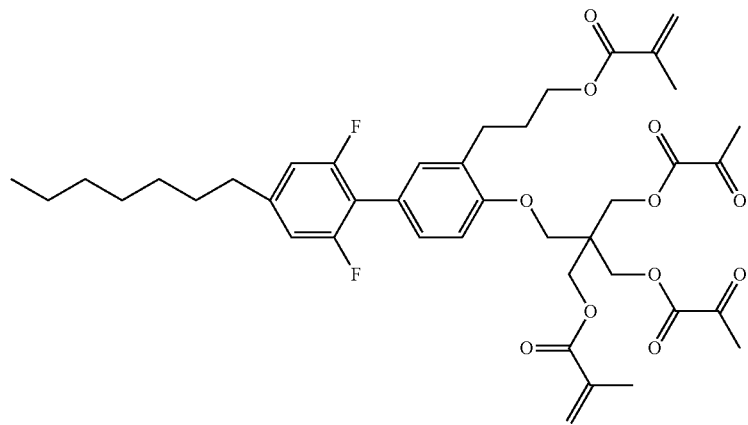
(P-364)
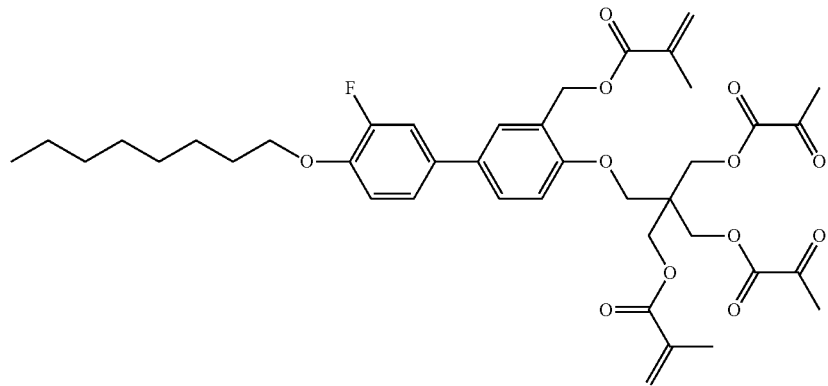
(P-365)

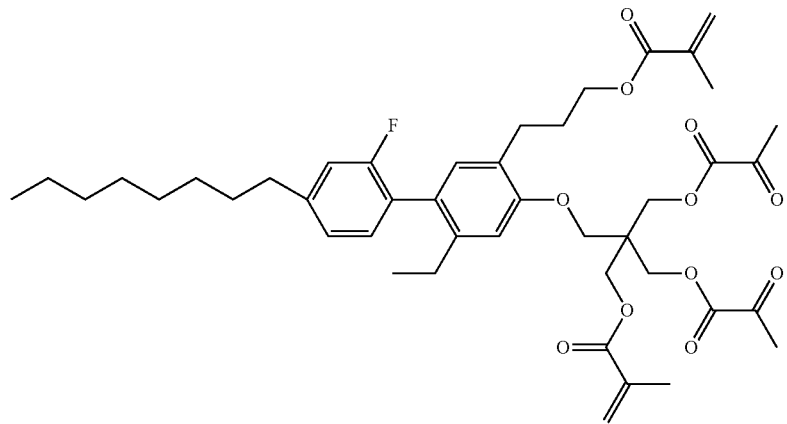
(P-366)
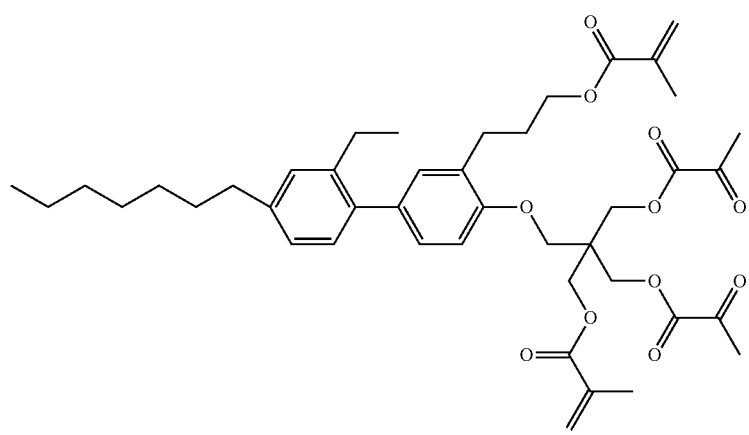
(P-367)
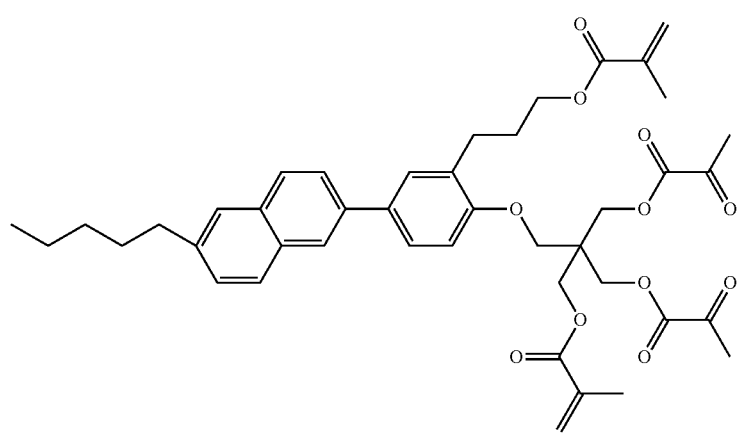
(P-368)

(P-369)
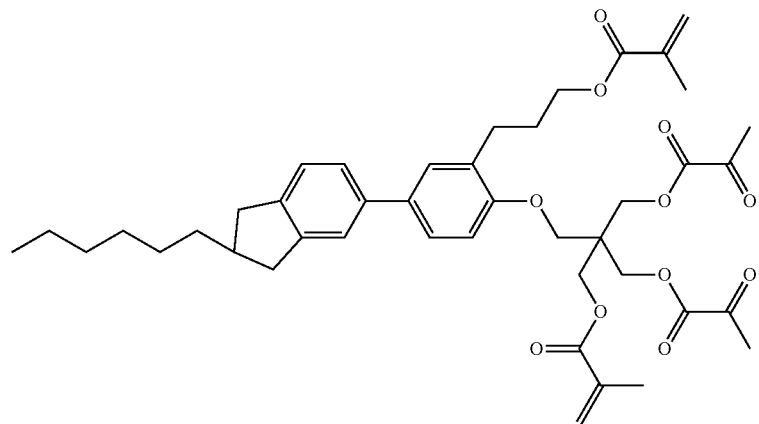
(P-370)
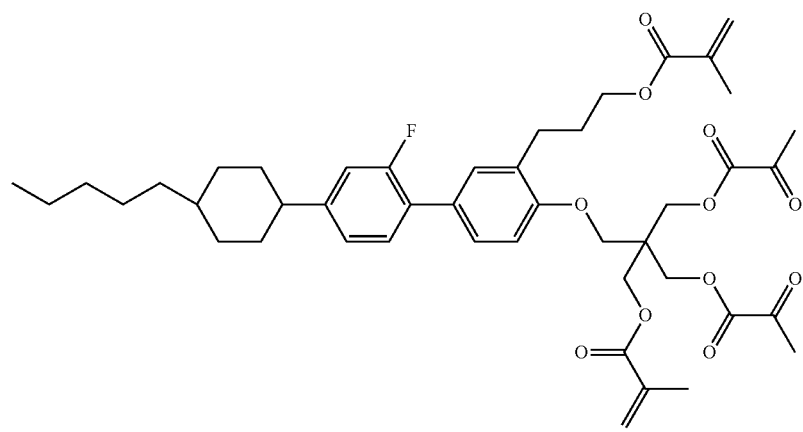
(P-371)
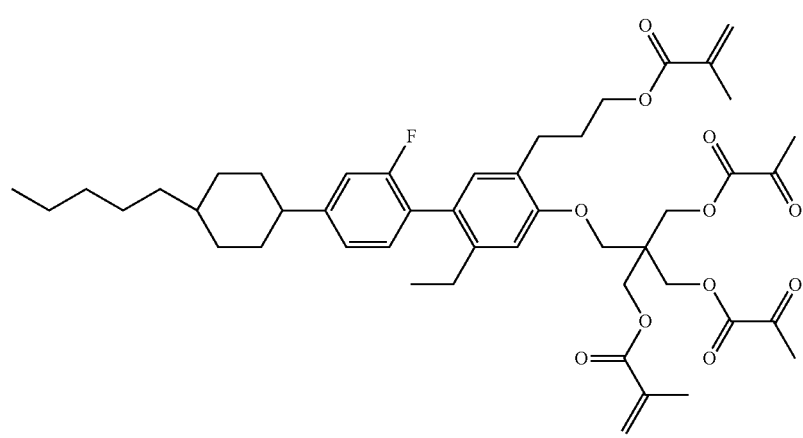

(P-372)
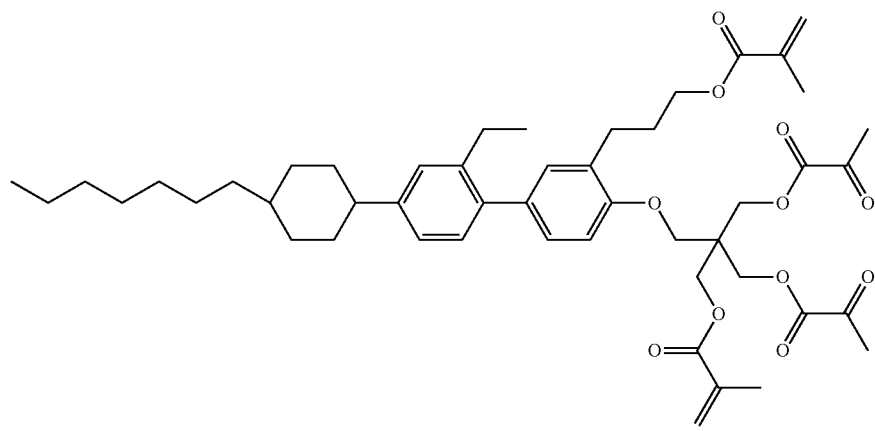
(P-373)
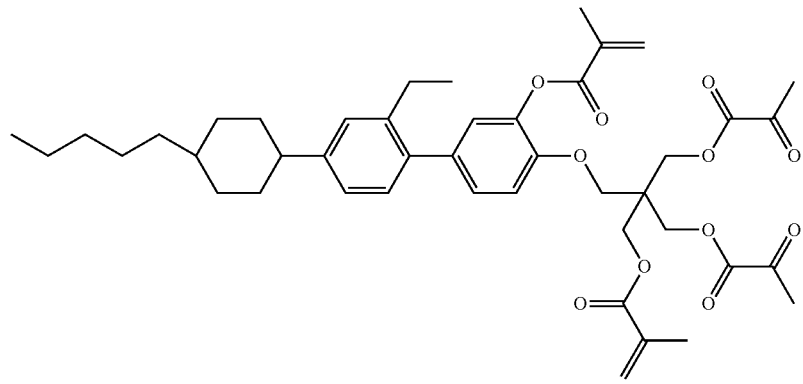
(P-374)
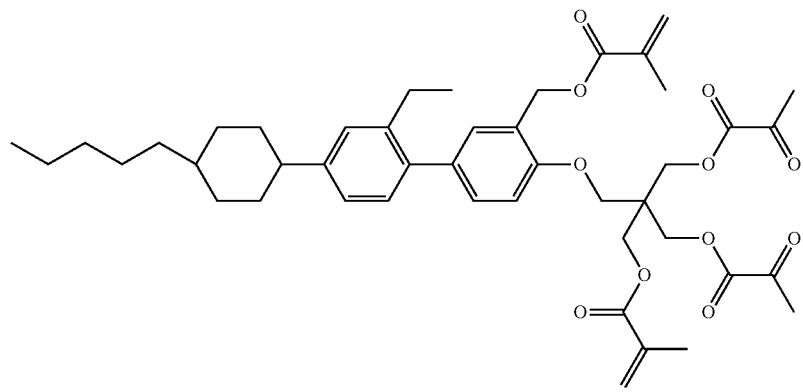
[Chem. 91]
(P-375)
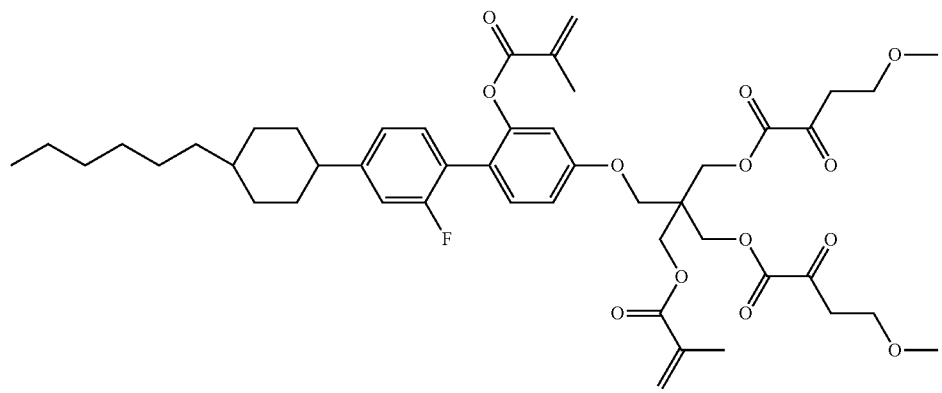

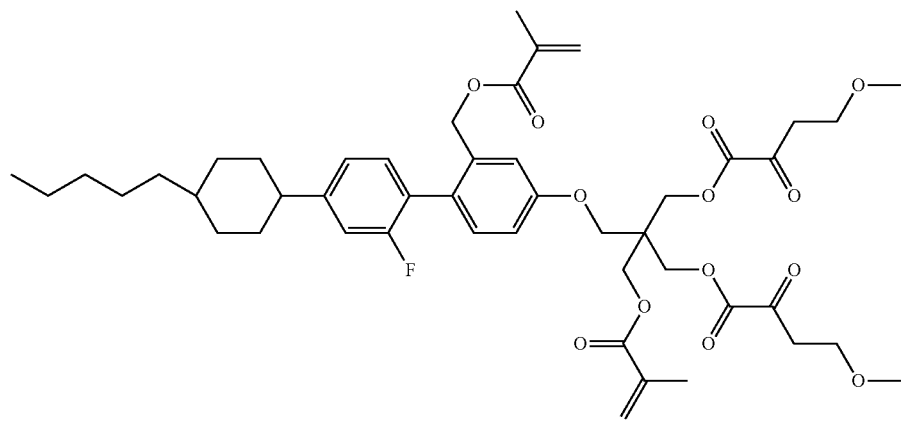
(P-376)

(P-377)
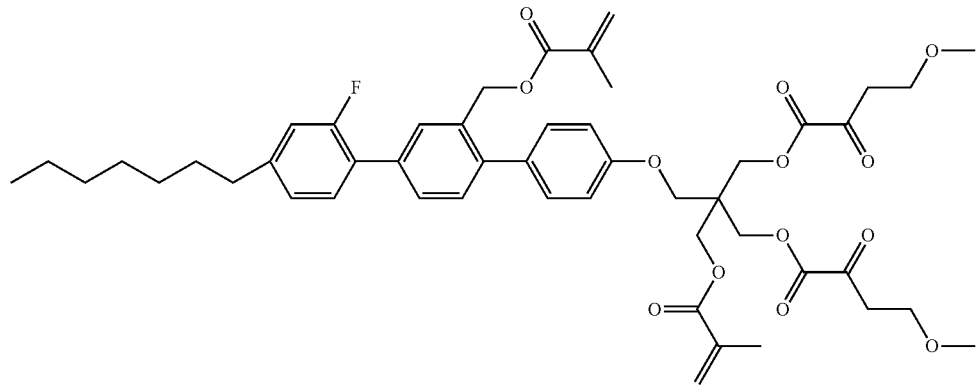
(P-378)
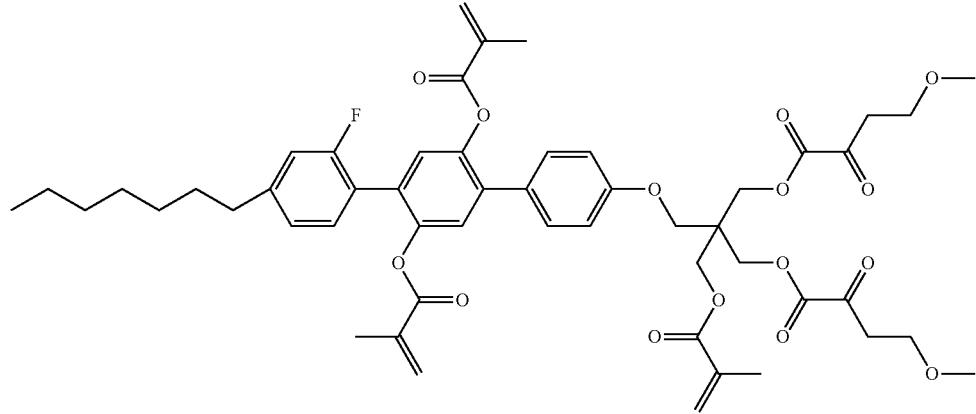
(P-389)

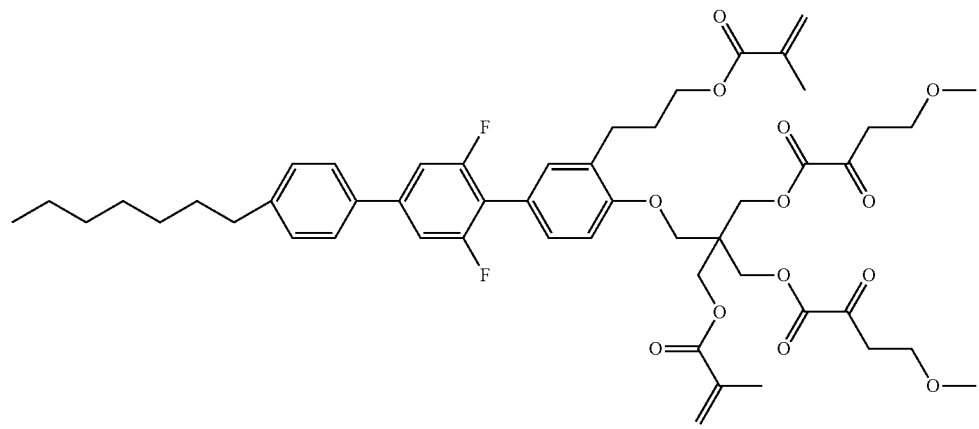
(P-380)
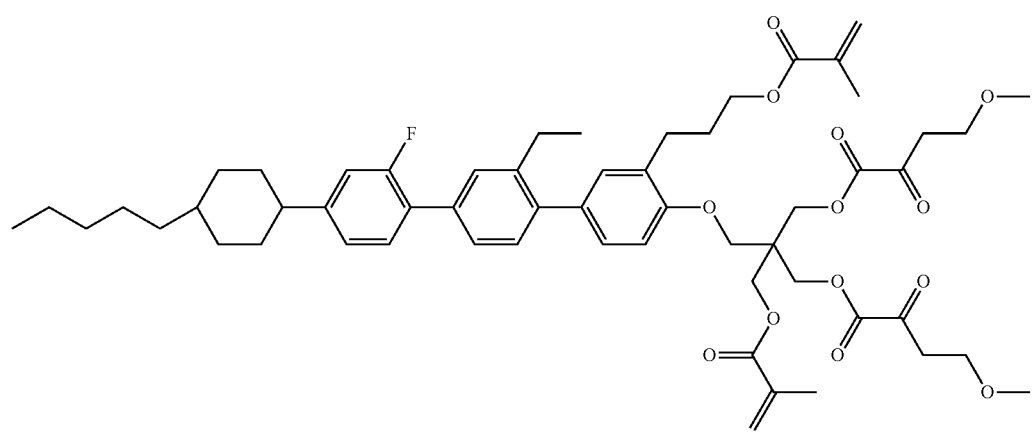
(P-381)
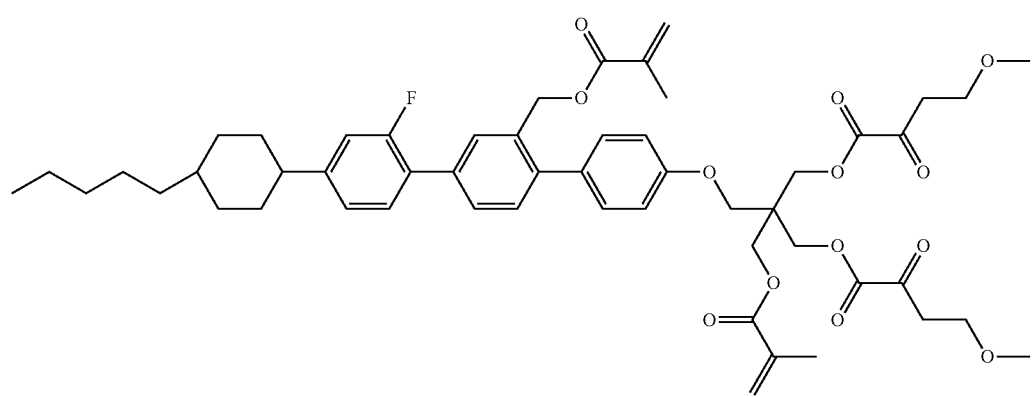
(P-382)

-continued
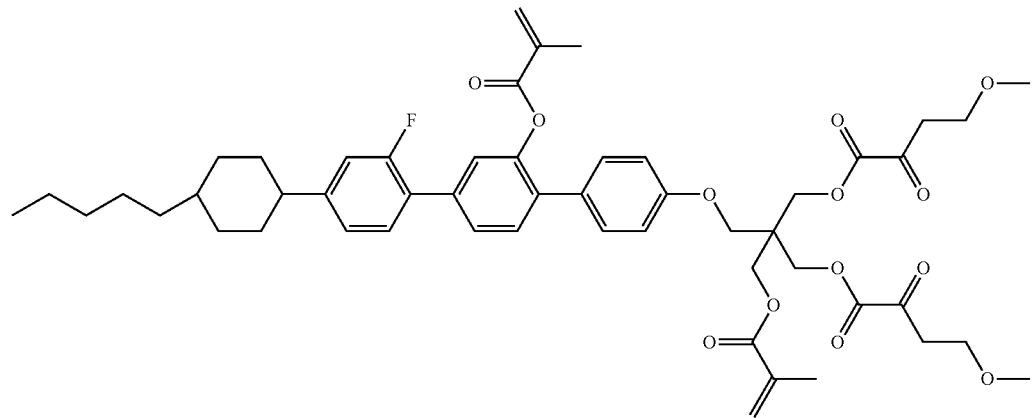
(P-383)
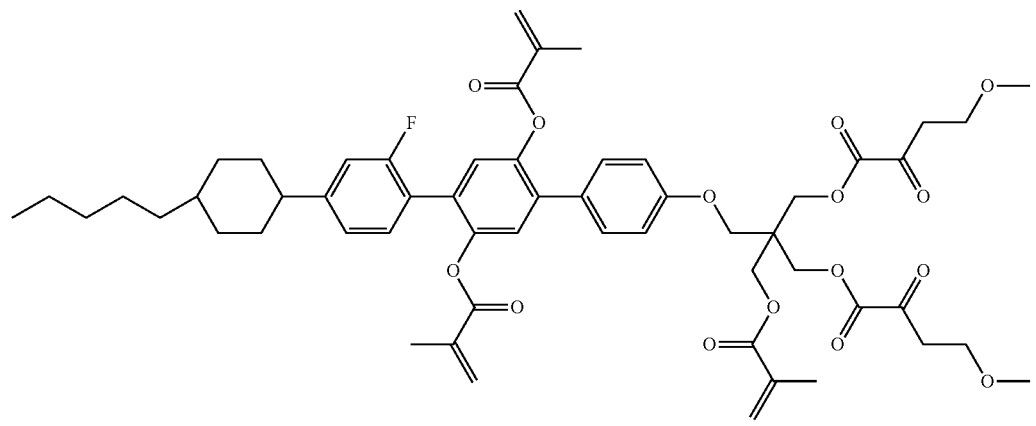
(P-384)
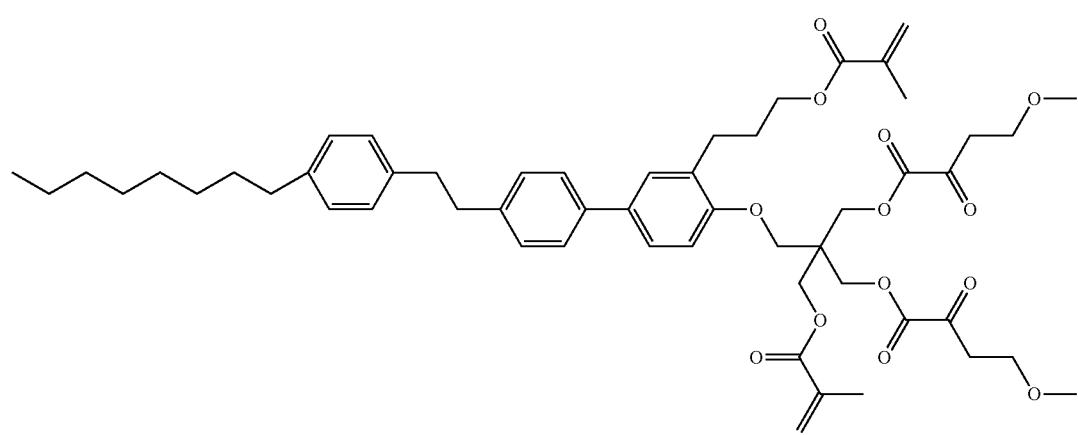
(P-385)

(P-386)
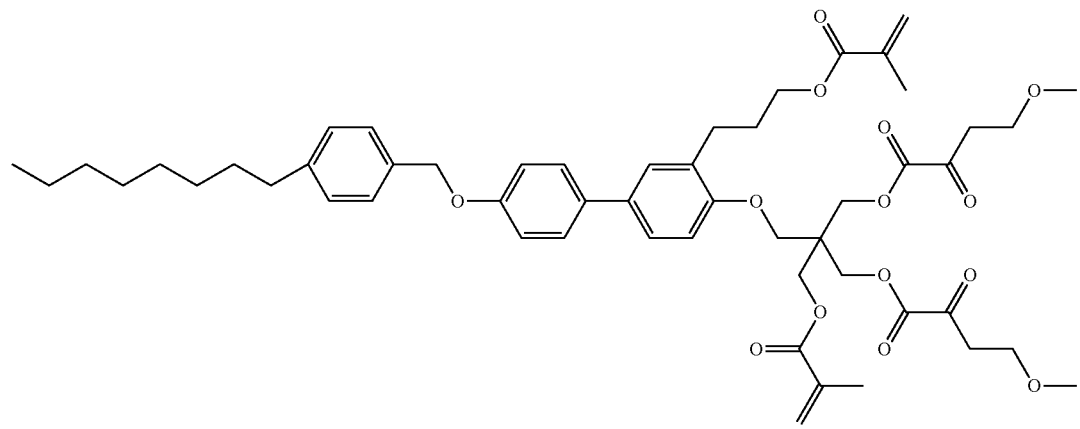
[Chem. 92]
(P-387)
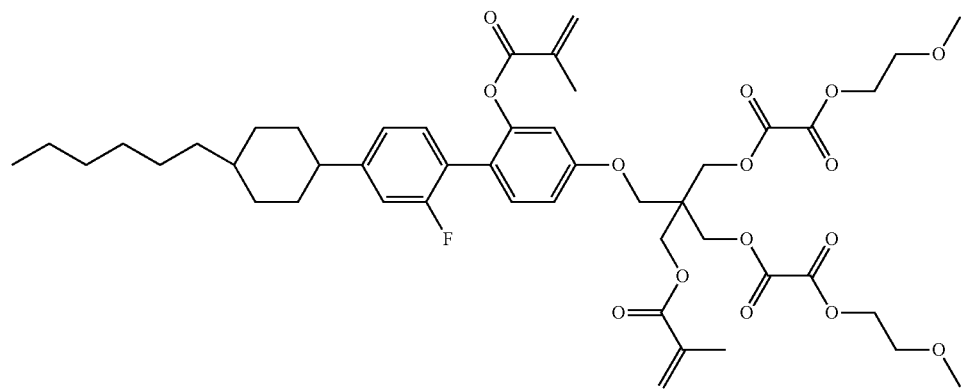
(P-388)
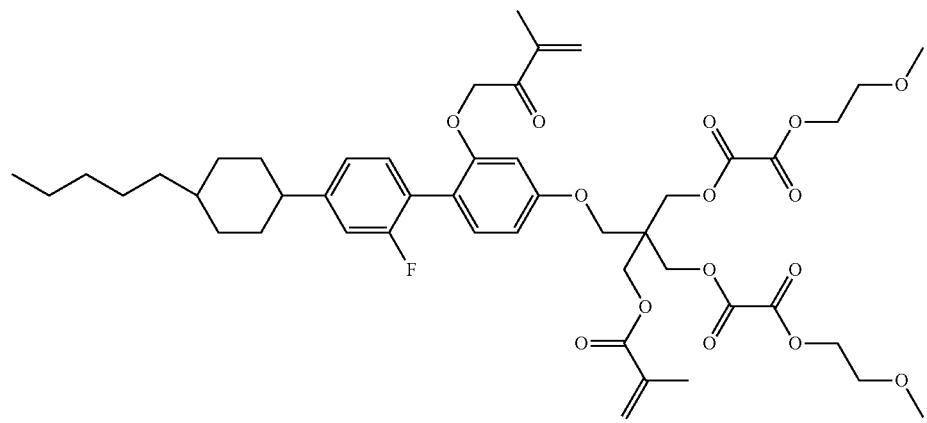

-continued
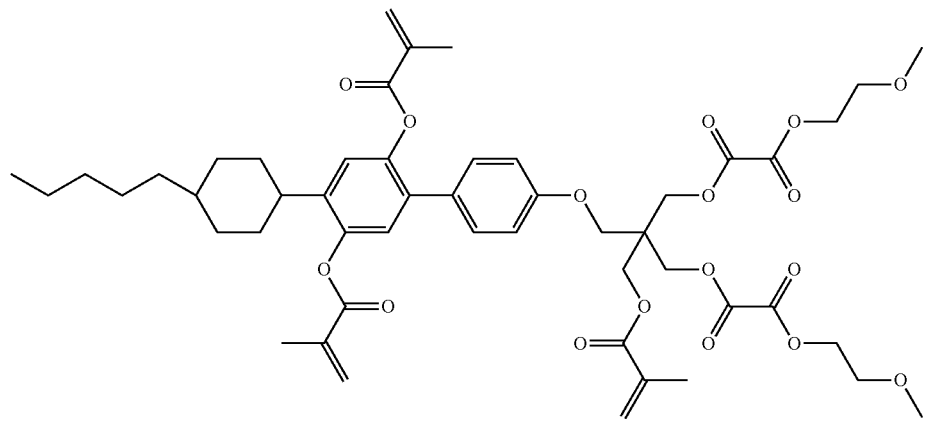
(P-389)
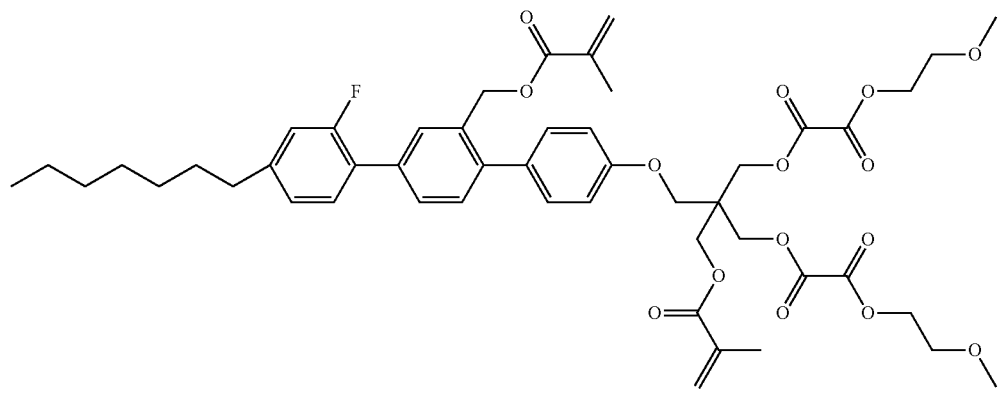
(P-390)
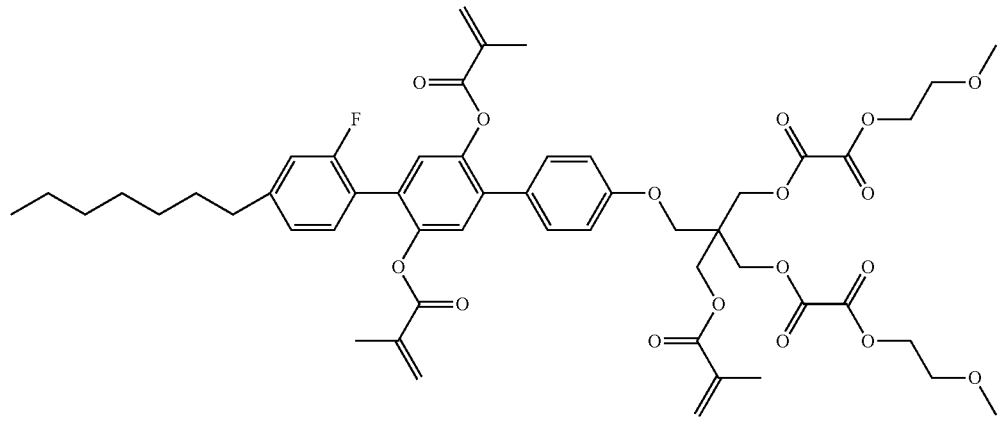
(P-391)
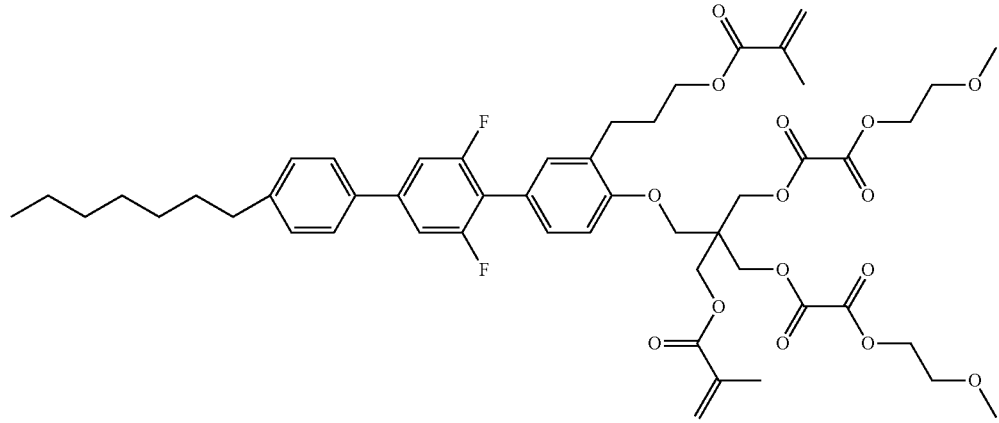
(P-392)

(P-393)
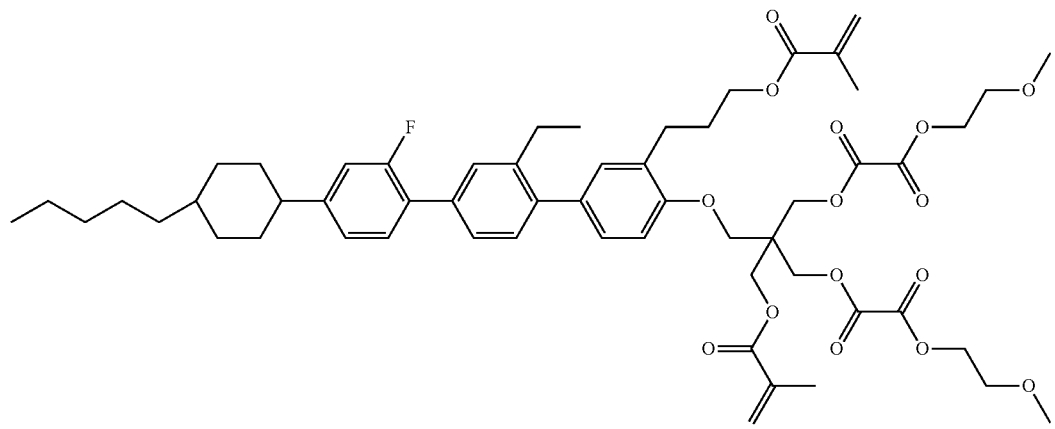
(P-394)
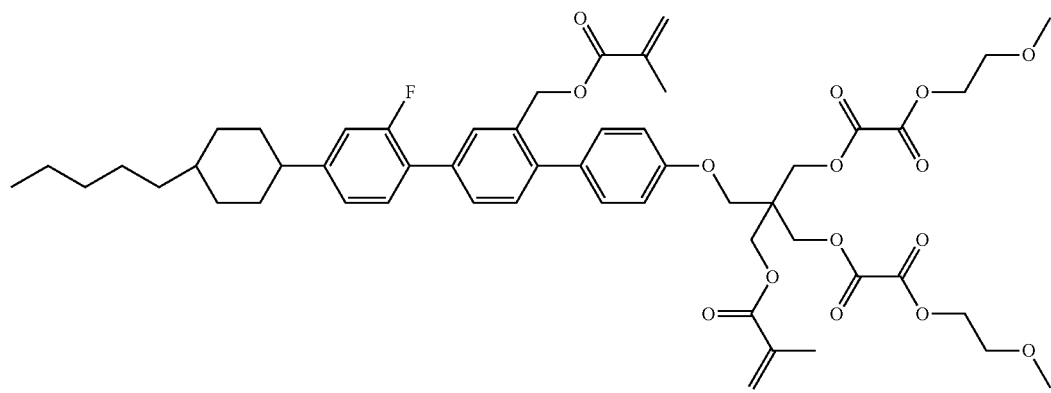
(P-395)
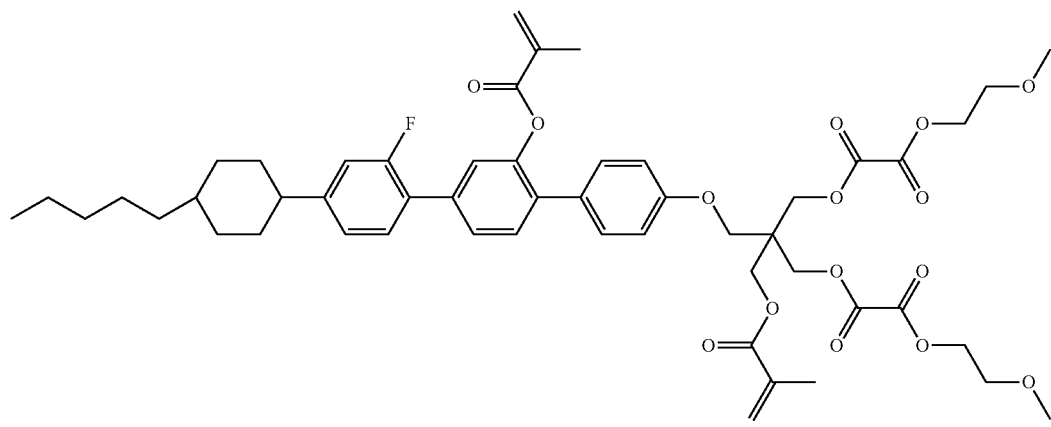
(P-396)
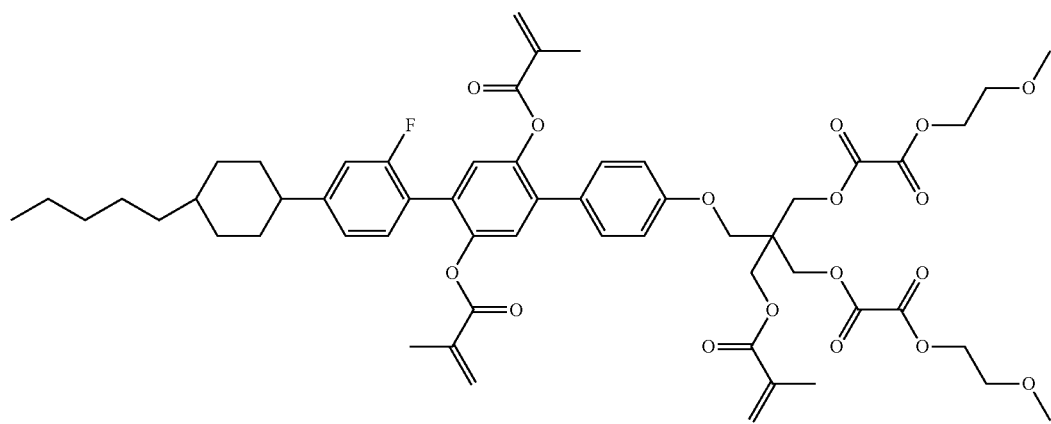

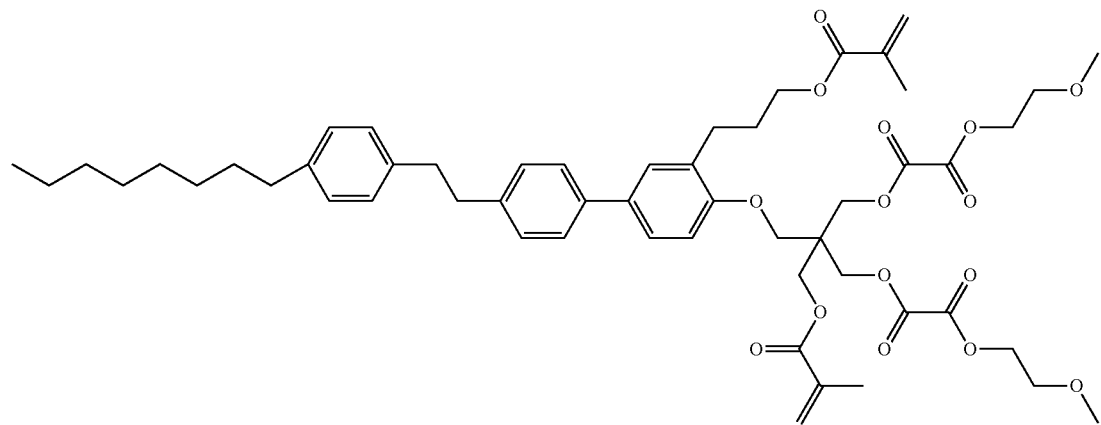
(P-397)
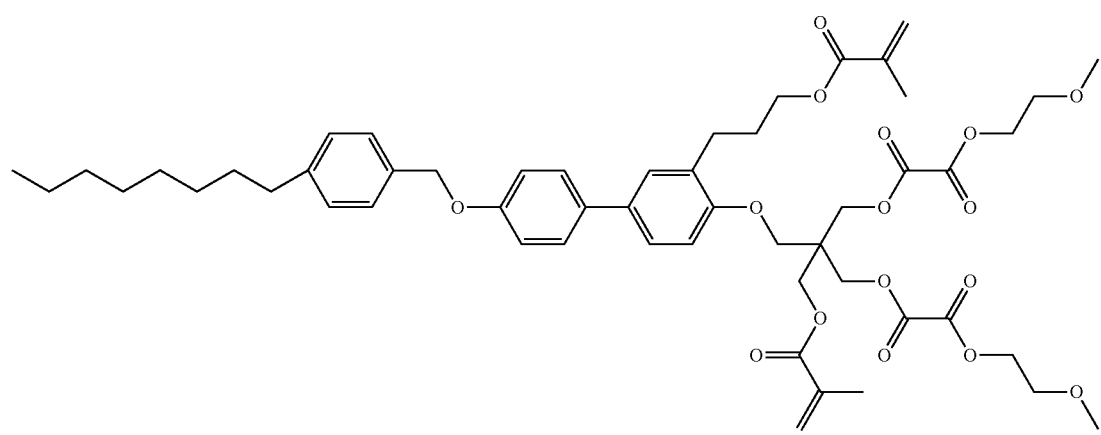
(P-398)
[Chem. 93]
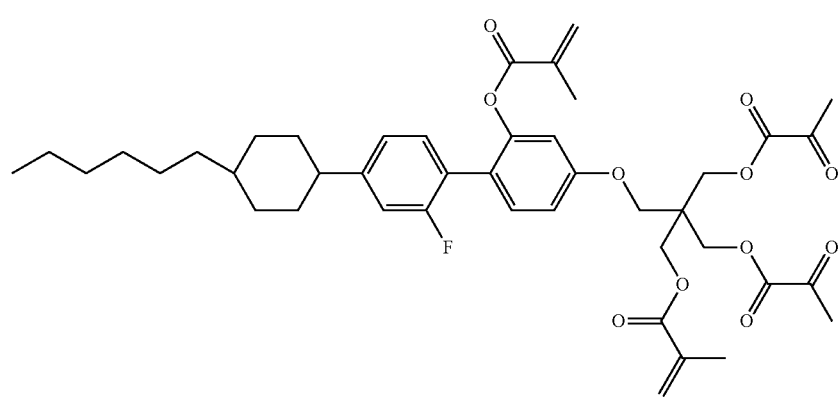
(P-399)

(P-400)
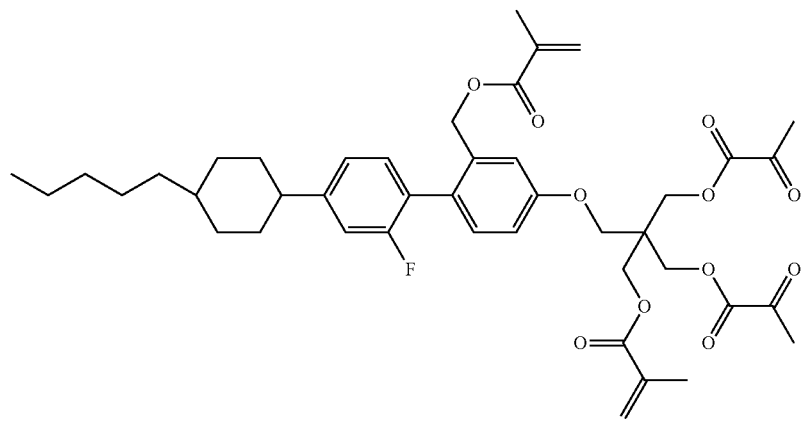
(P-401)
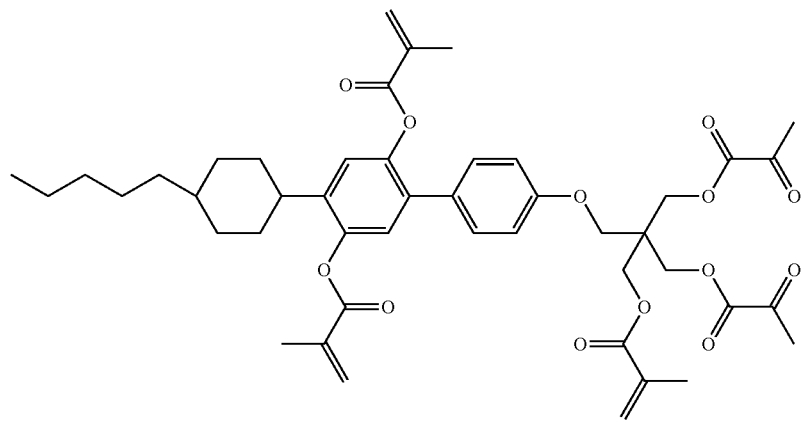
(P-402)
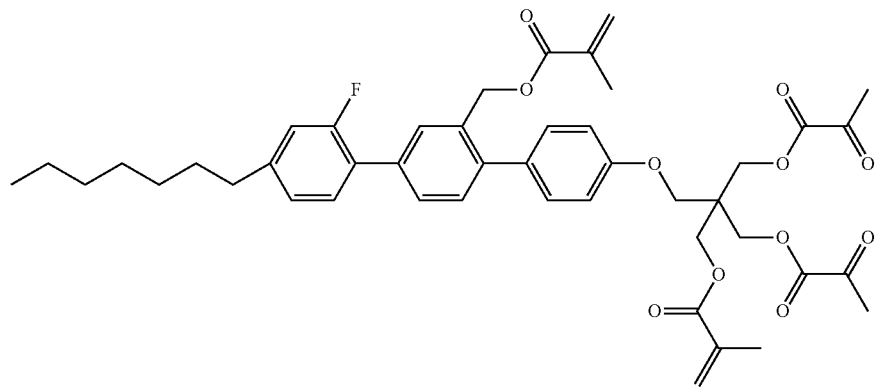
(P-403)
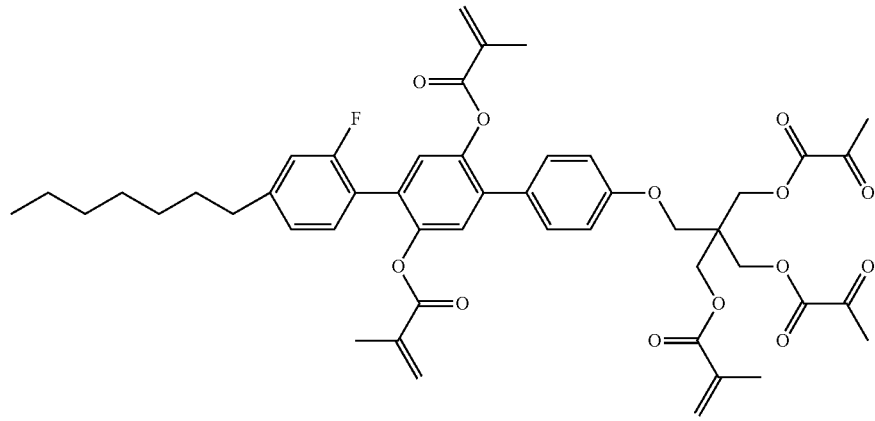

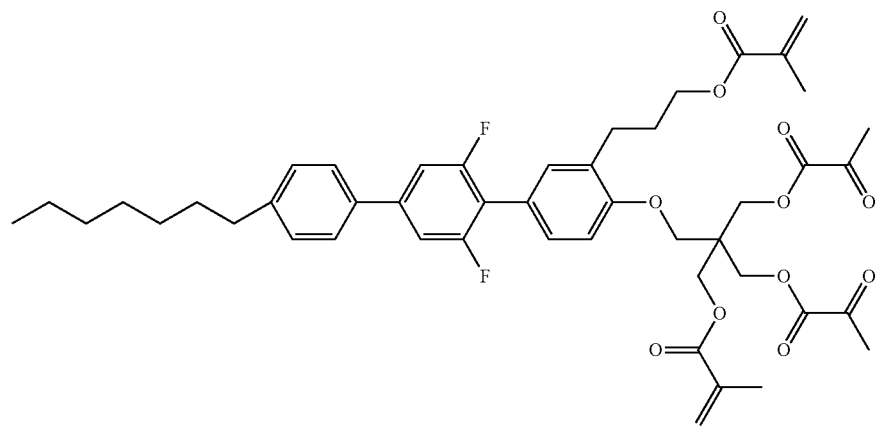
(P-404)
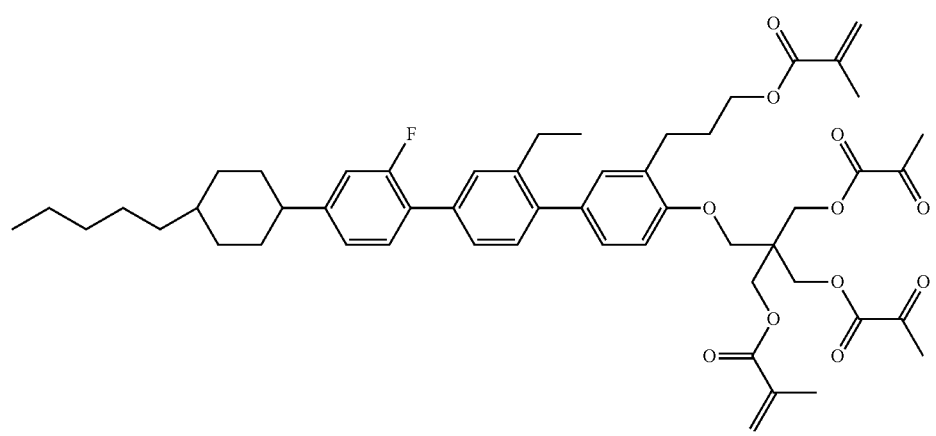
(P-405)
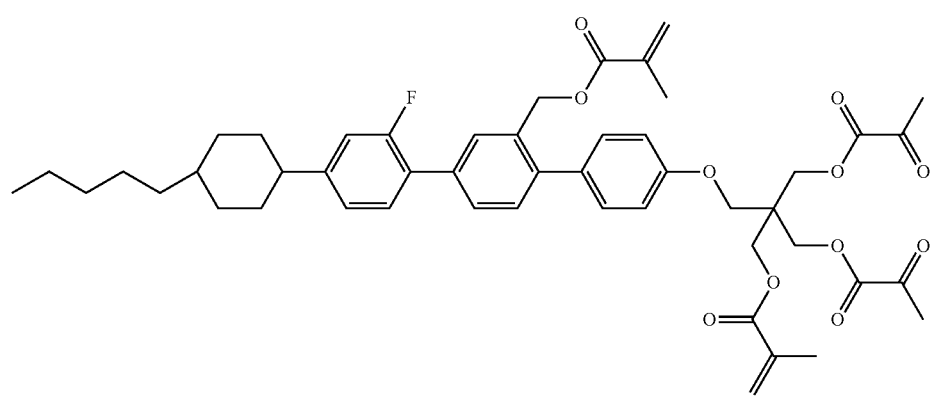
(P-406)

-continued
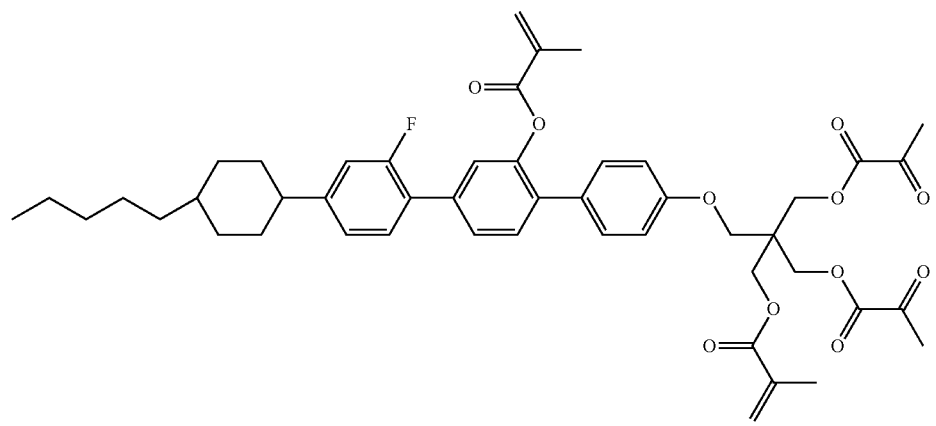
(P-407)
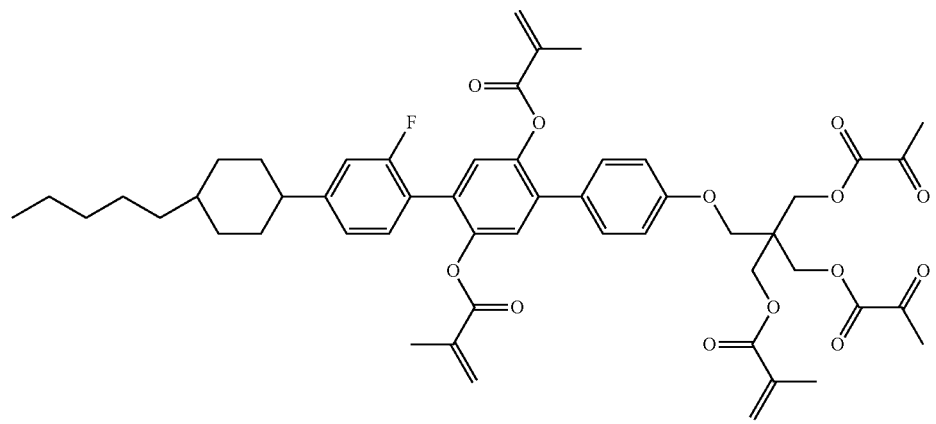
(P-408)
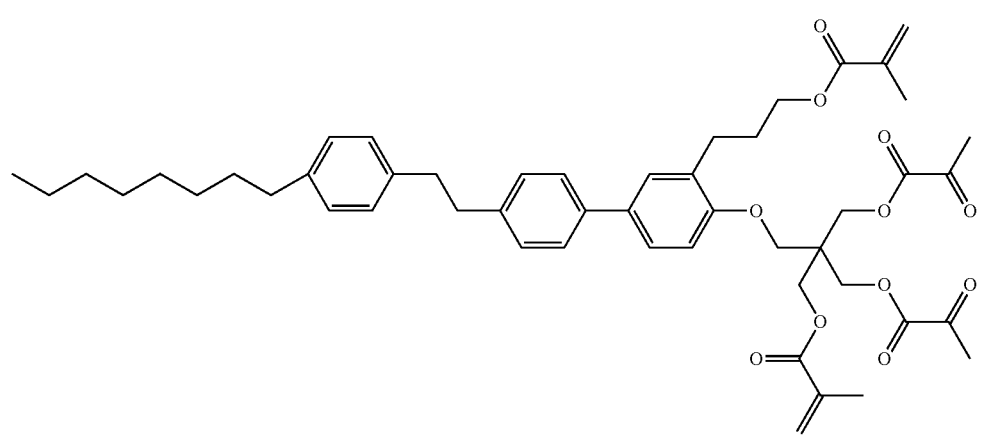
(P-409)

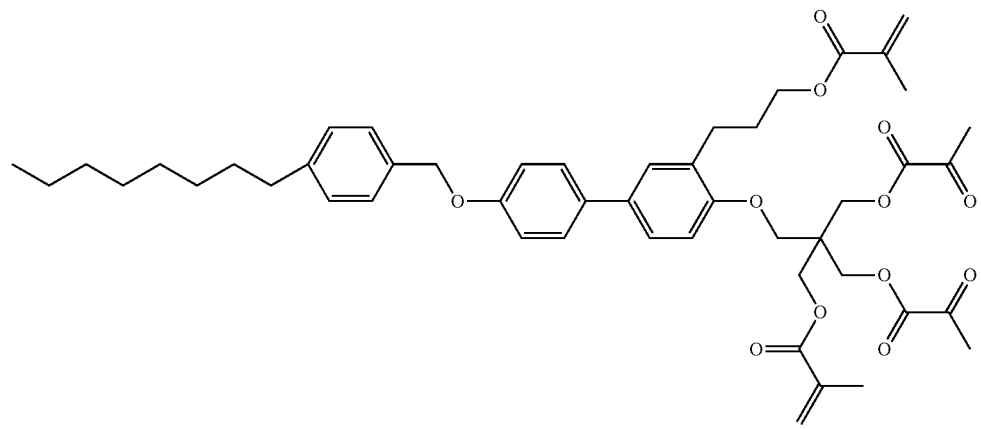
(P-410)
[Chem. 94]
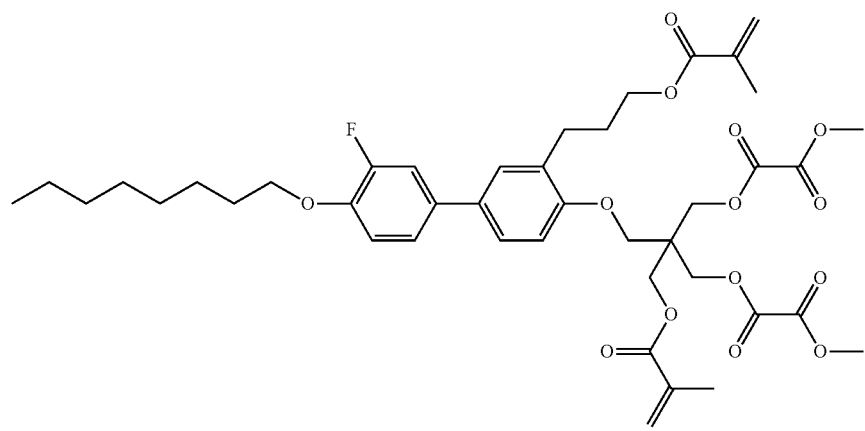
(P-411)
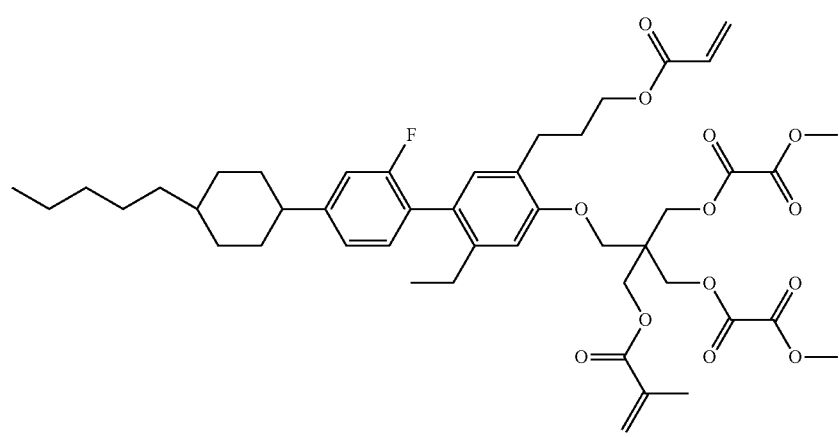
(P-412)

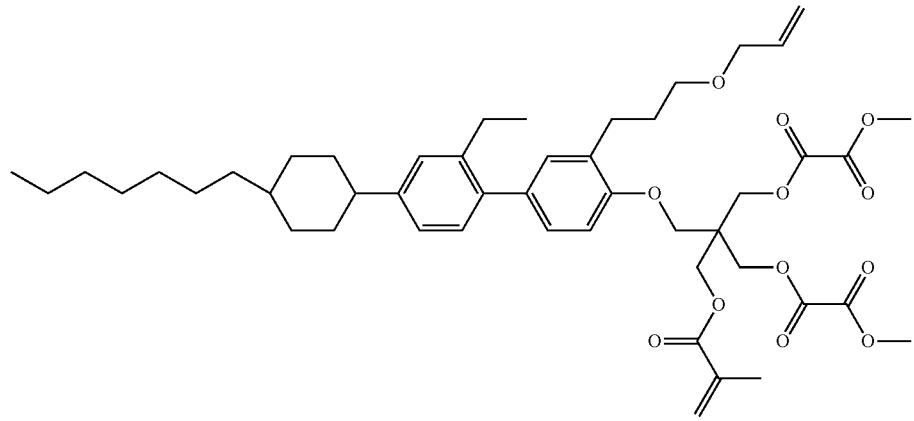
(P-413)
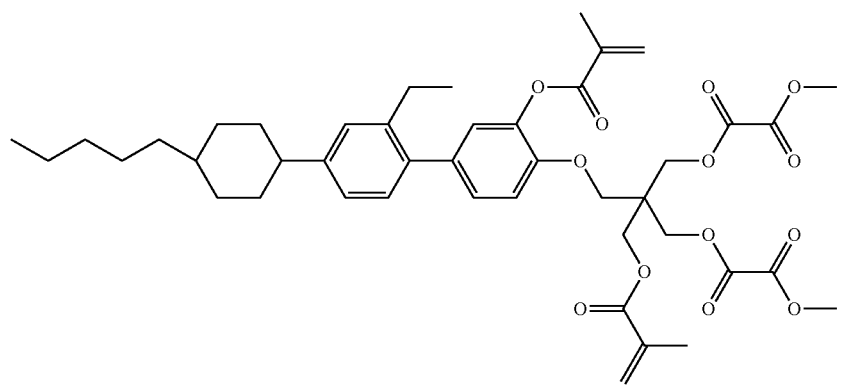
(P-414)
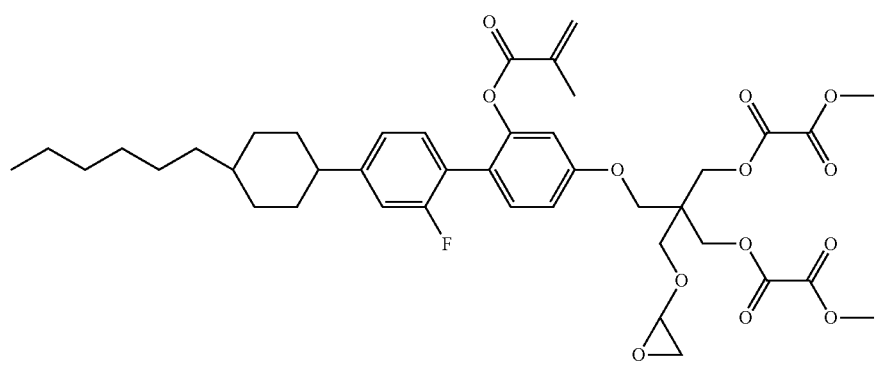
(P-415)
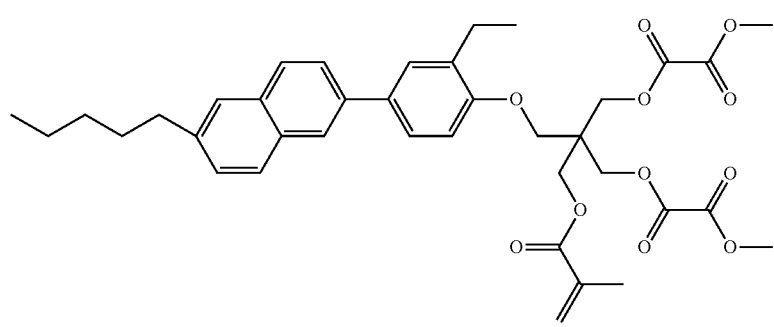
(P-416)

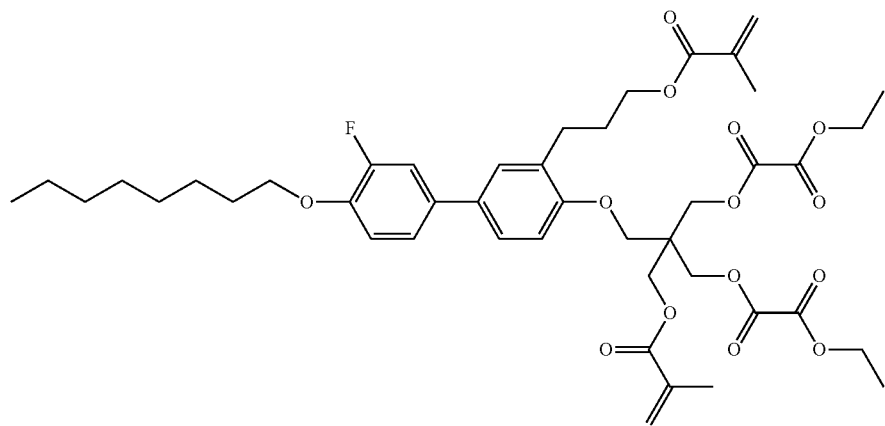
(P-417)
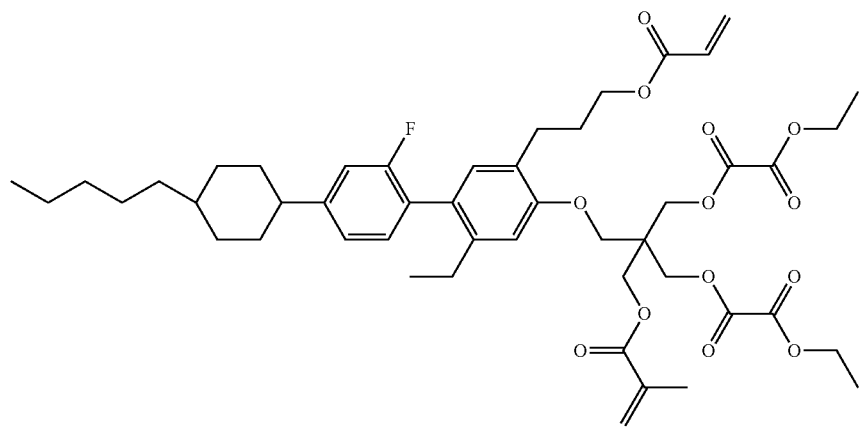
(P-418)
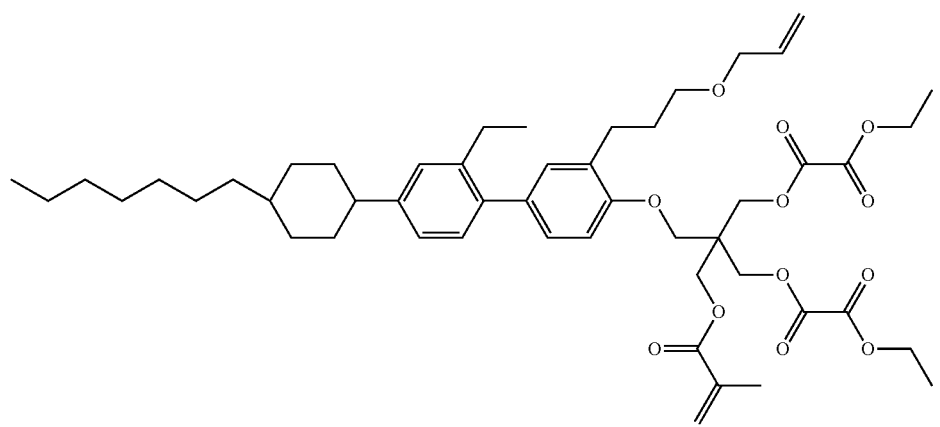
(P-419)

(P-420)
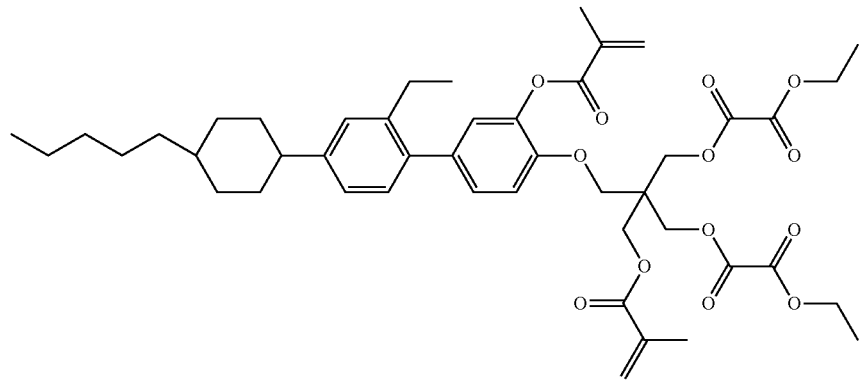
(P-421)
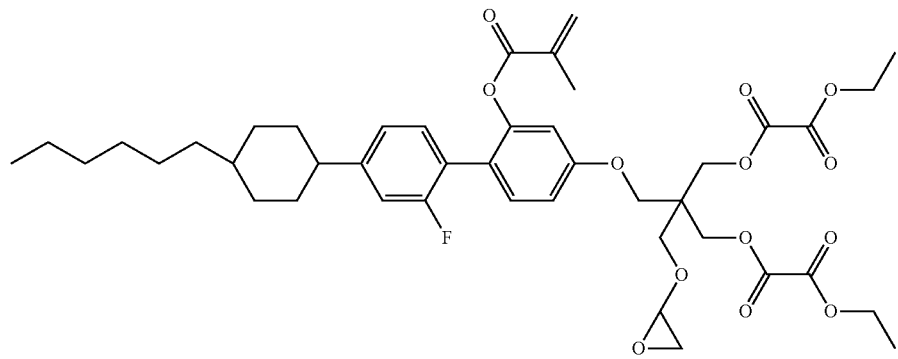
(P-422)
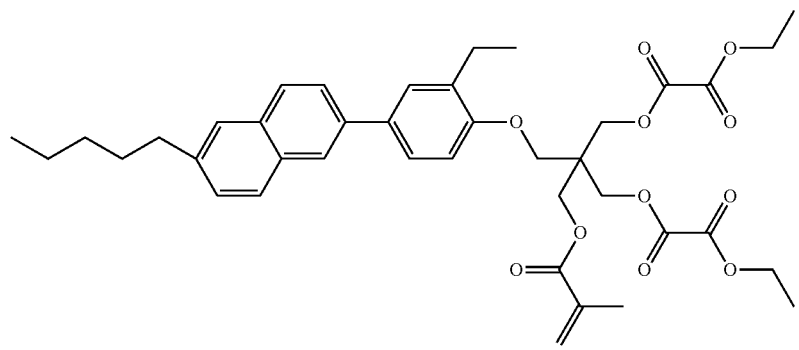
[Chem. 95]
(P-423)
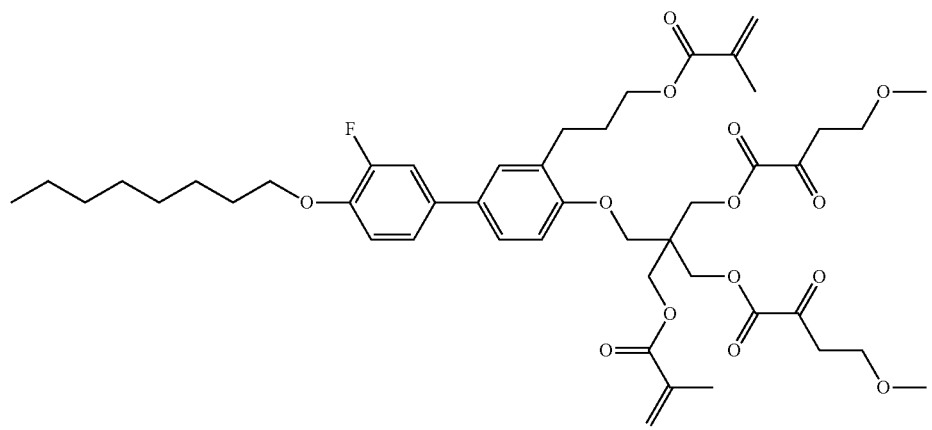

-continued
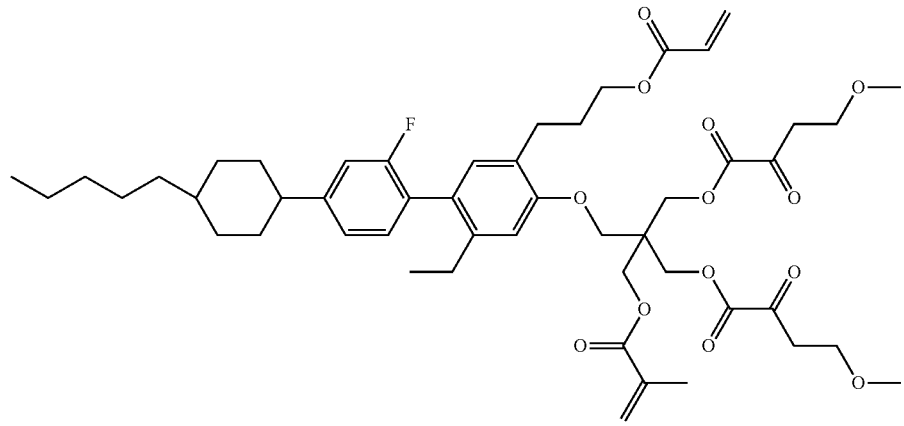
(P-424)
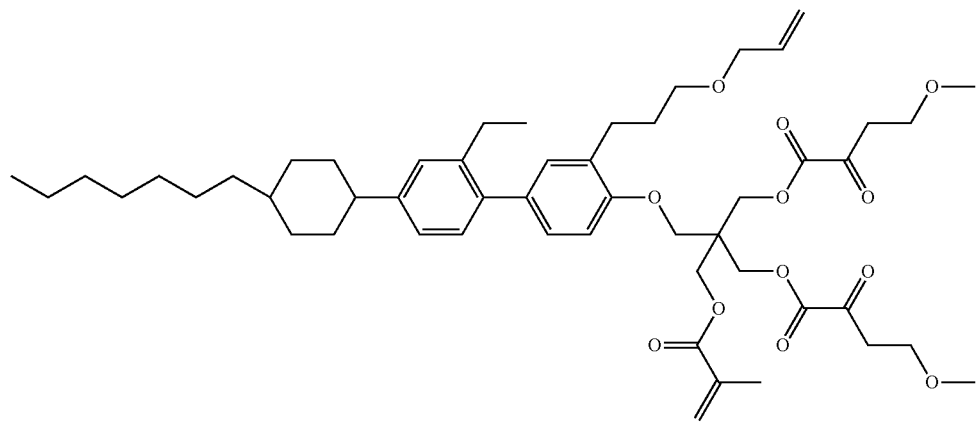
(P-425)
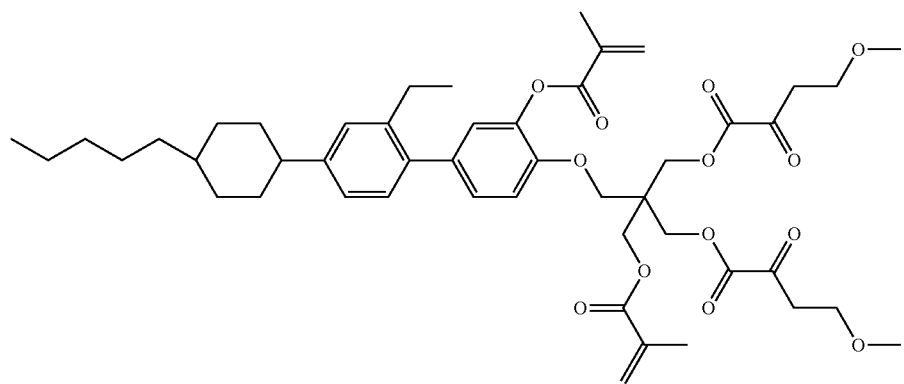
(P-426)
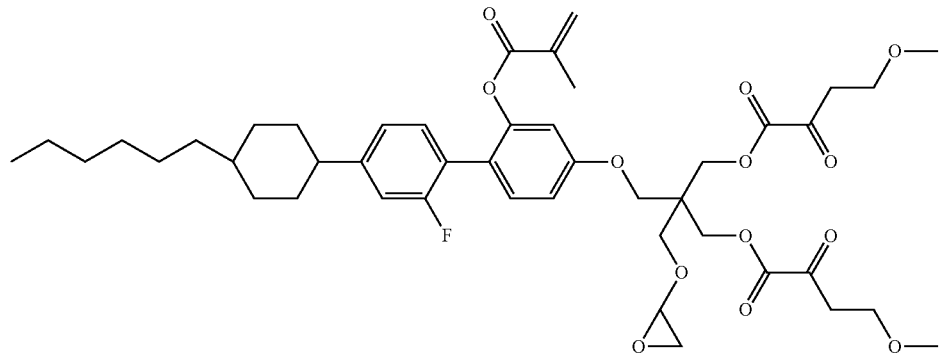
(P-427)

-continued
(P-428)
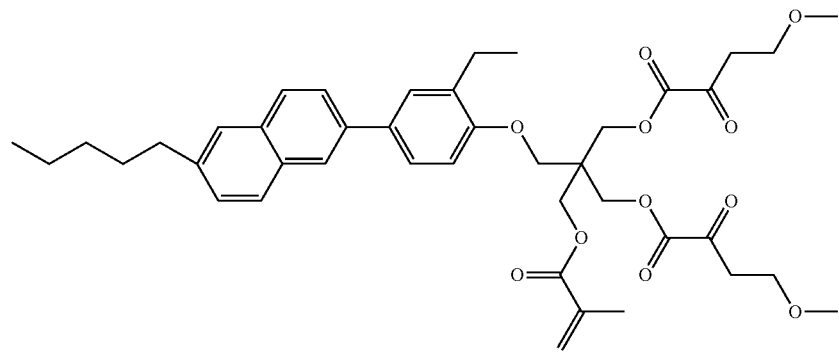
(P-429)
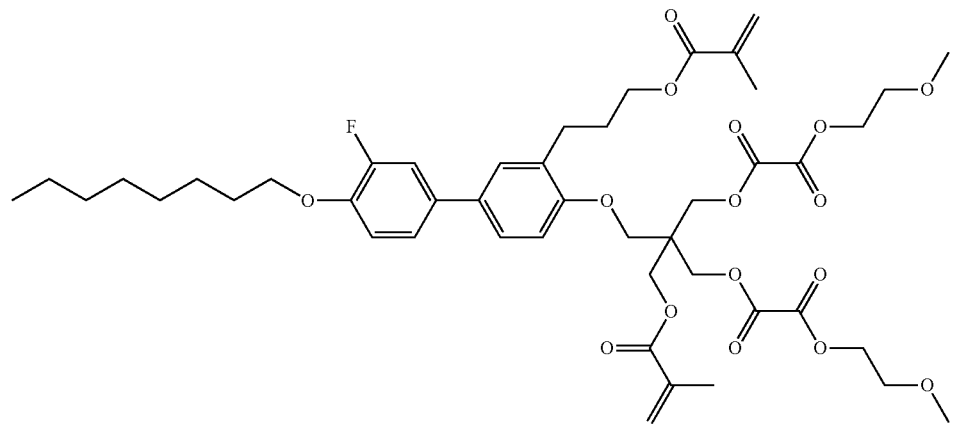
(P-430)
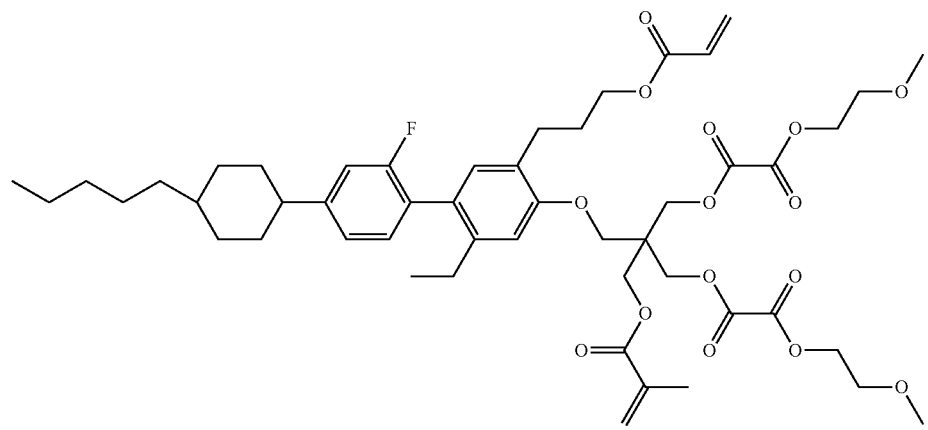
(P-431)
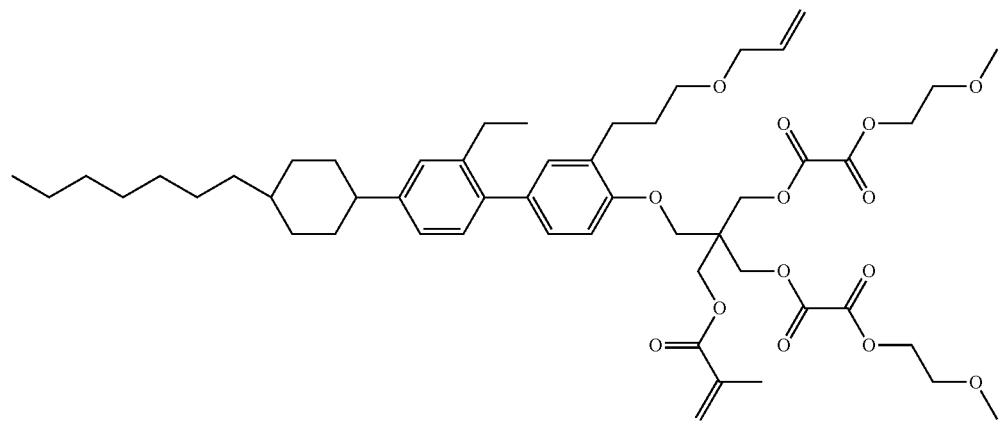

(P-432)
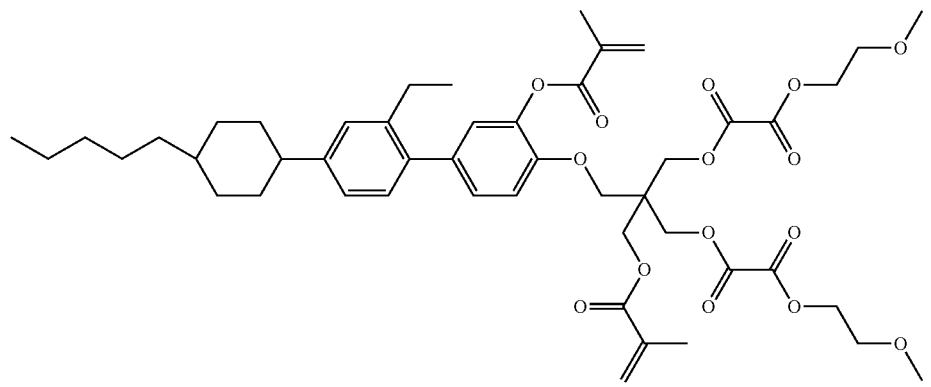
(P-433)
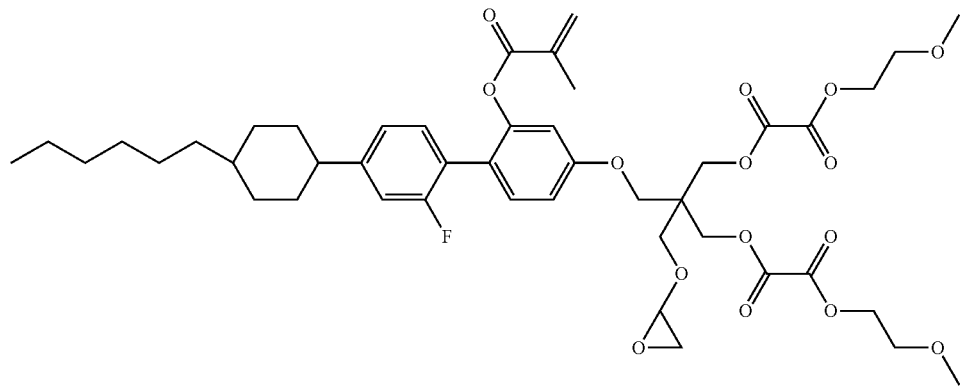
(P-434)
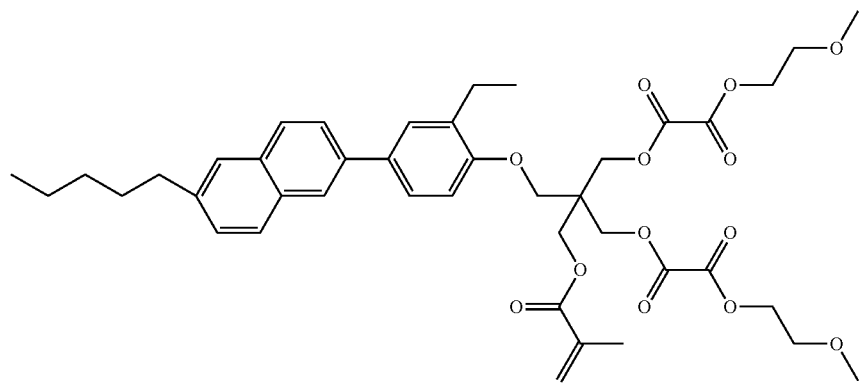
[Chem. 96]
(P-435)
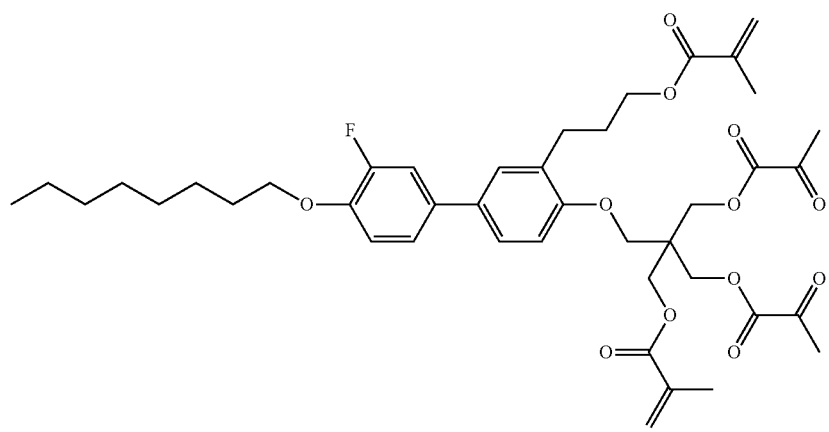

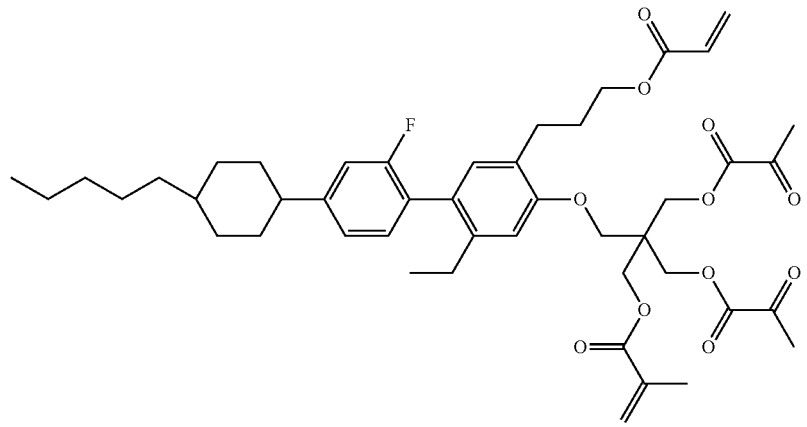
(P-436)
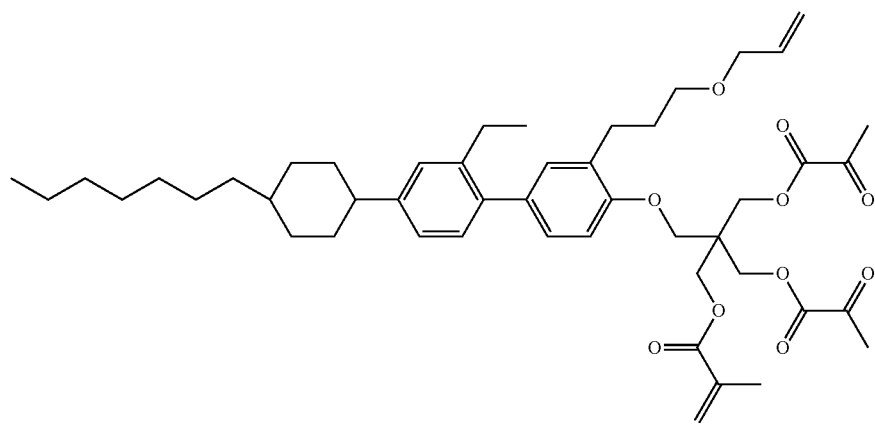
(P-437)
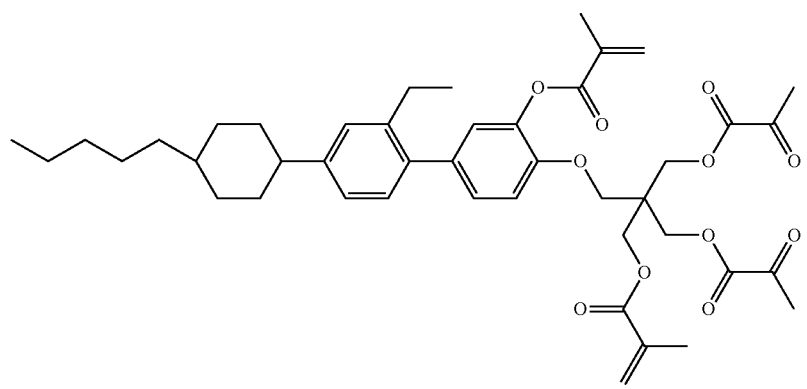
(P-438)
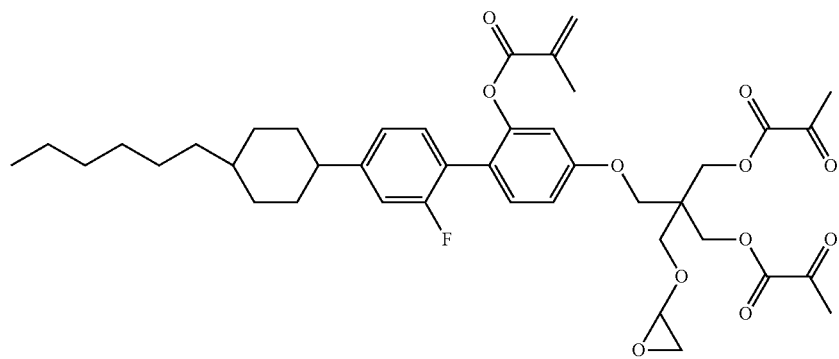
(P-439)

(P-440)
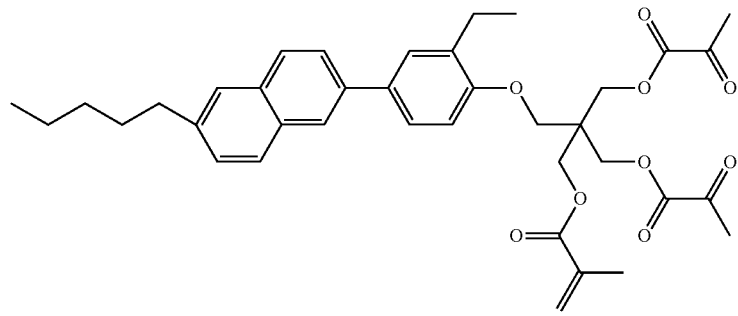
(P-441)
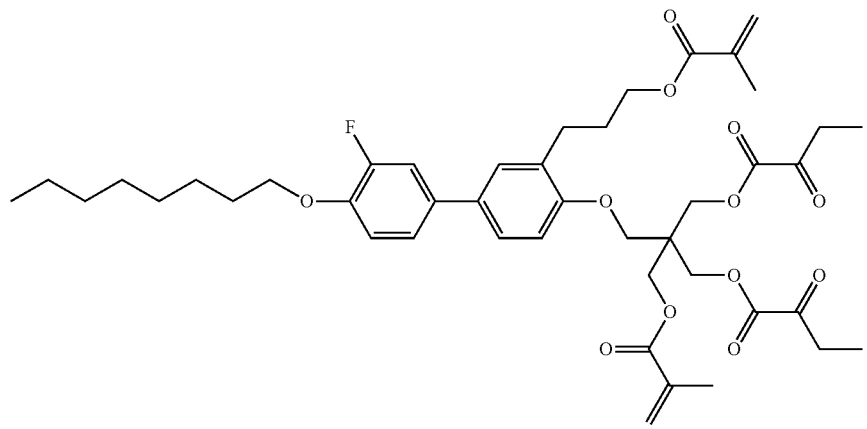
(P-442)
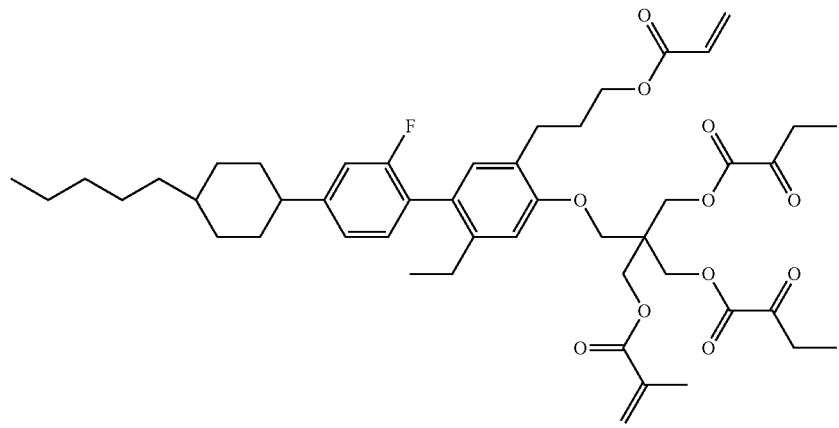
(P-443)
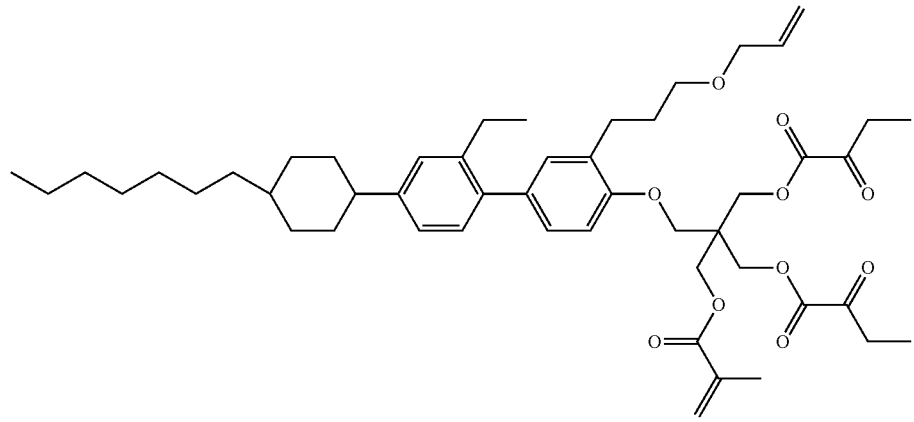

-continued
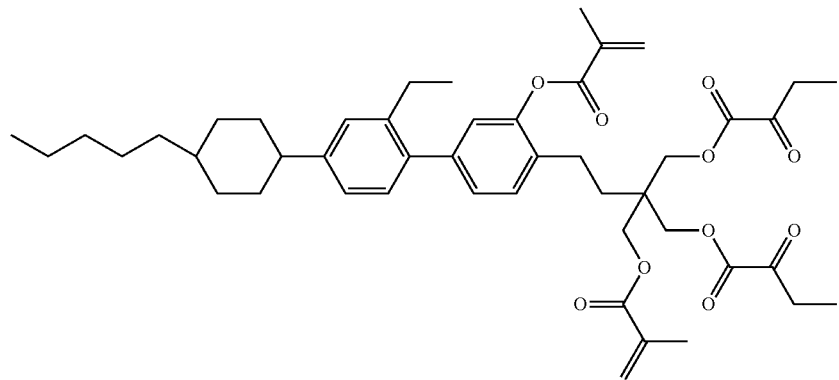
(P-444)
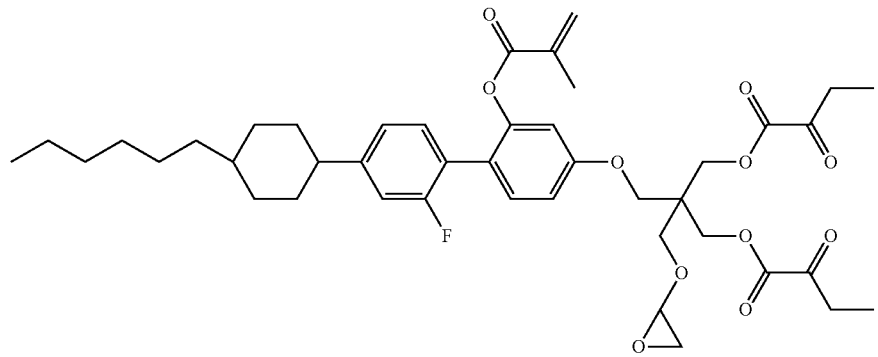
(P-445)
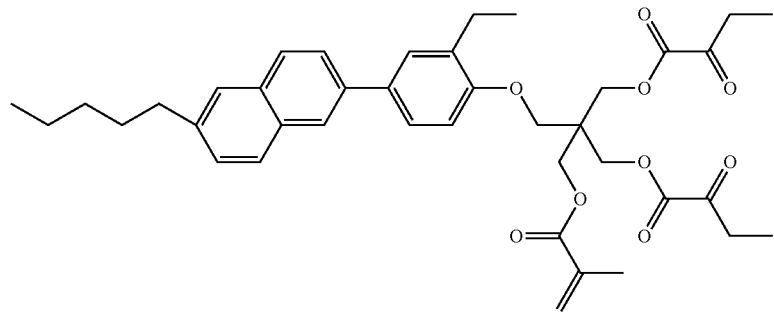
(P-446)
[Chem. 97]
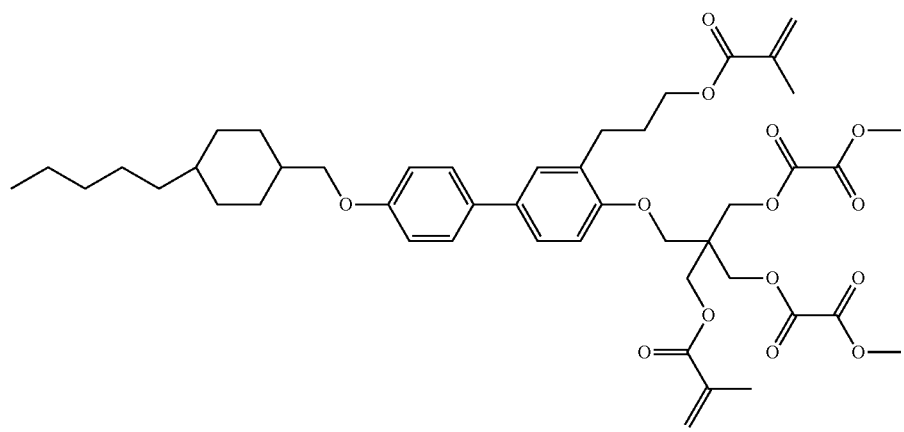
(P-447)

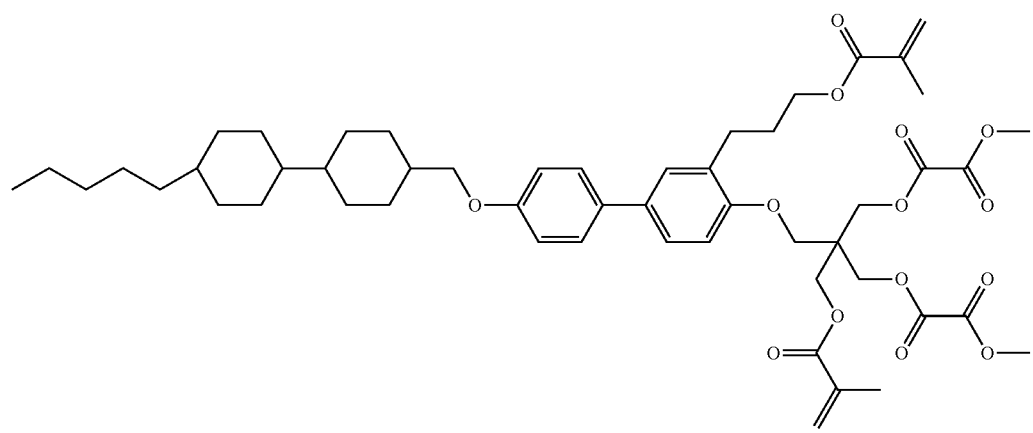
(P-448)
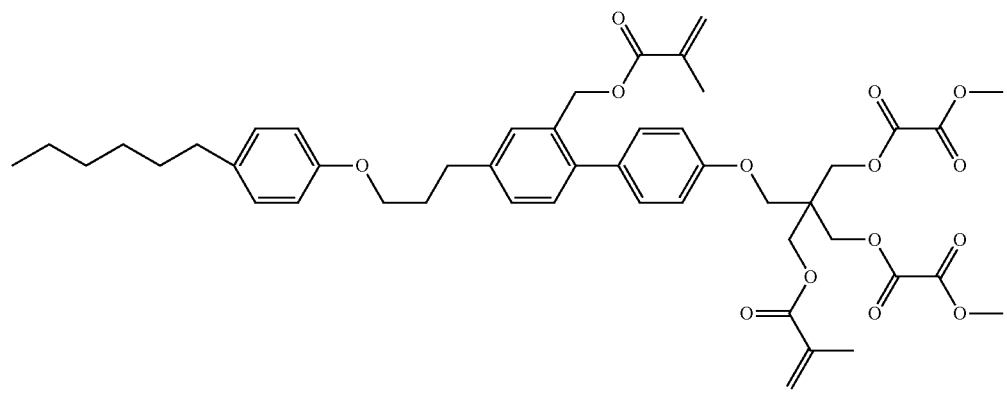
(P-449)
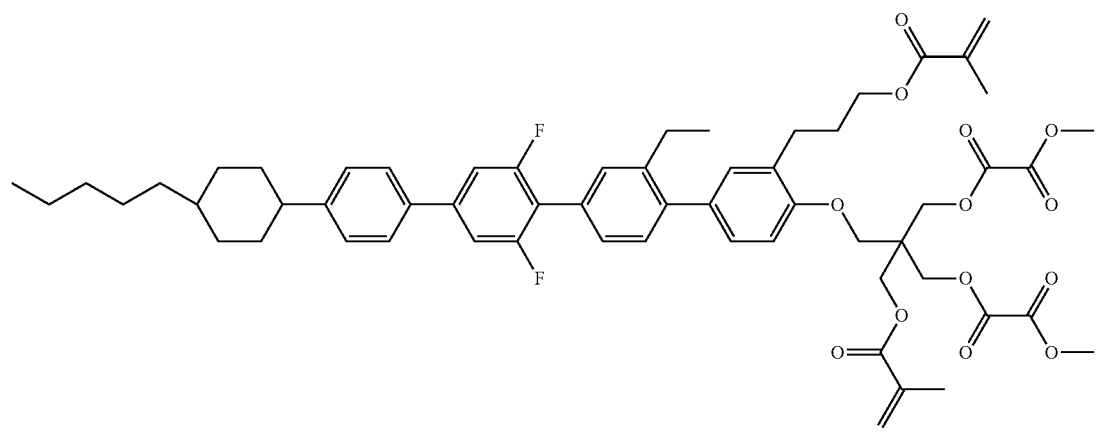
(P-450)

(P-451)
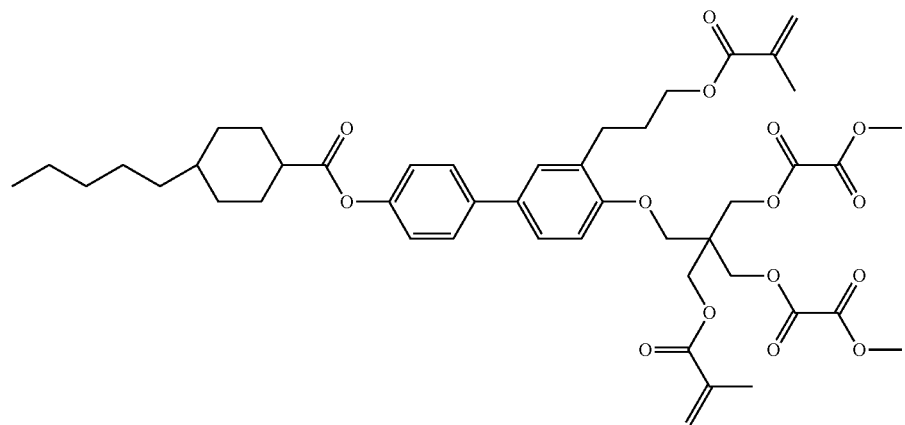
(P-452)
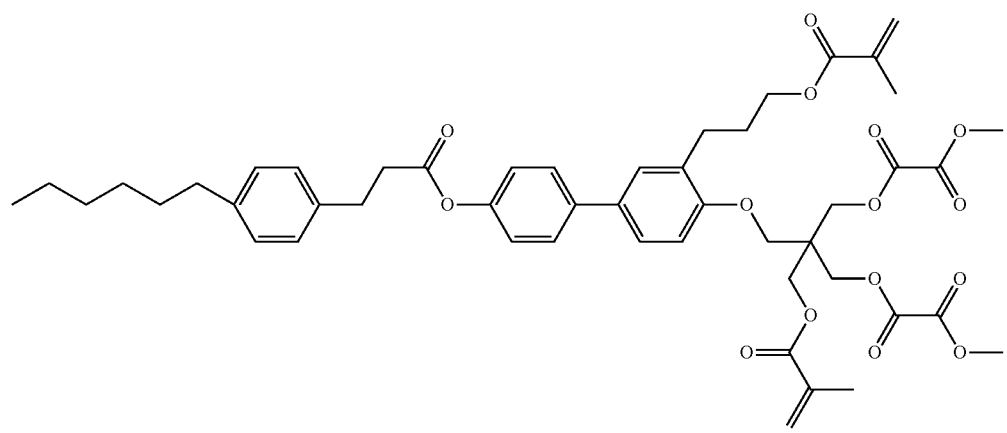
(P-453)
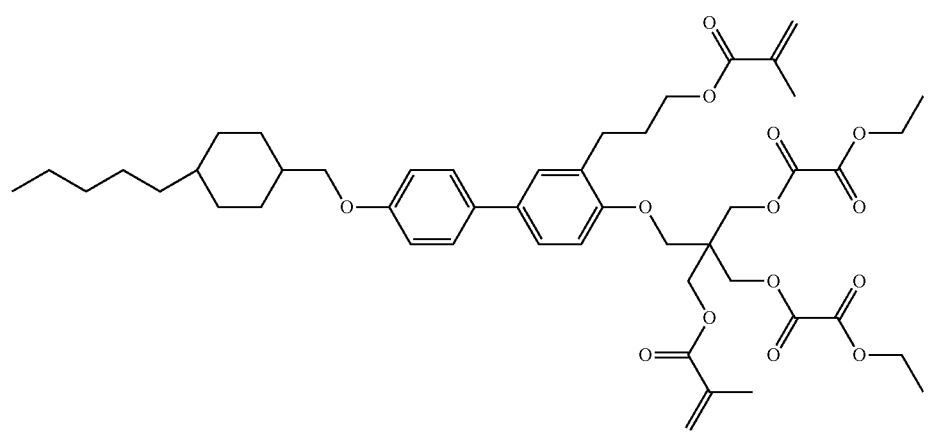

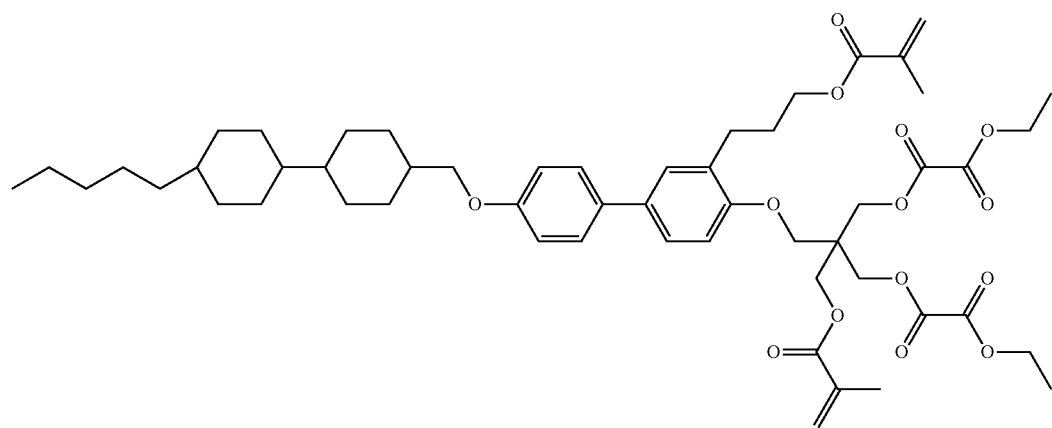
(P-454)
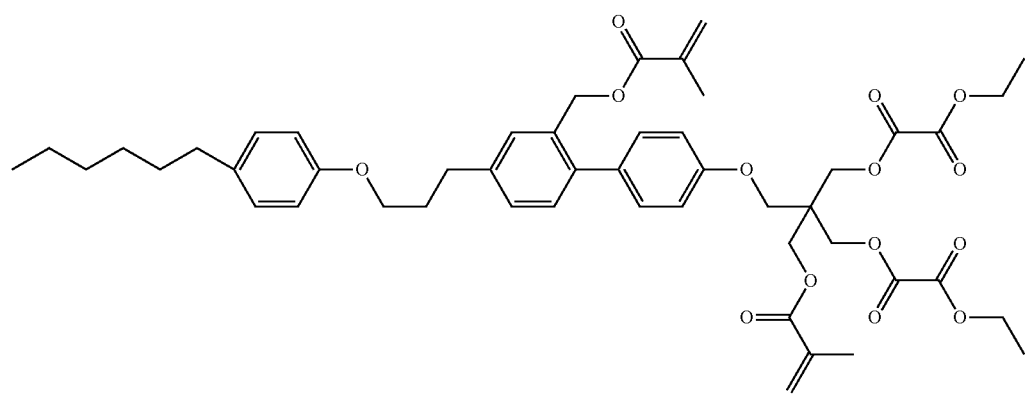
(P-455)
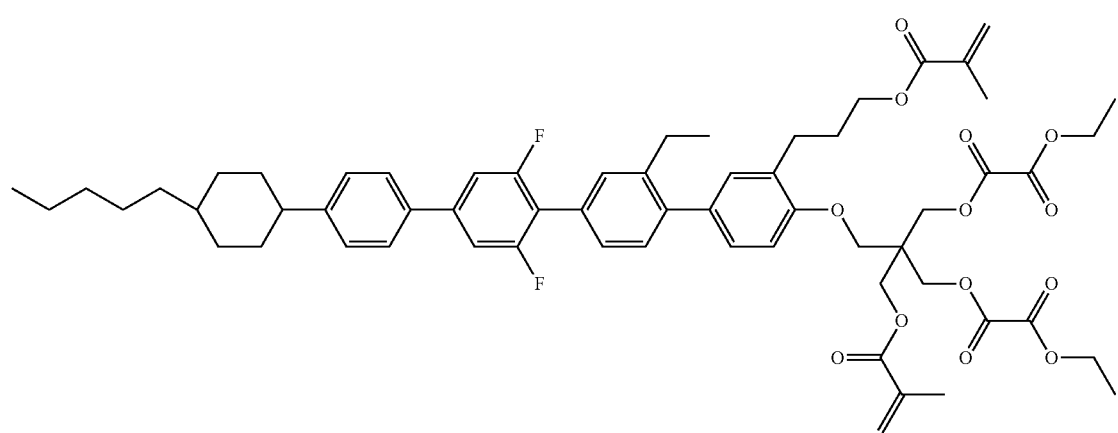
(P-456)

-continued
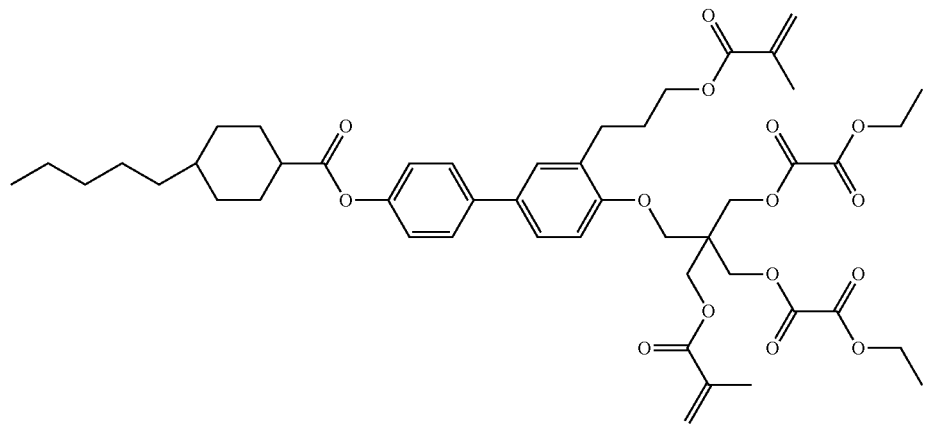
(P-457)
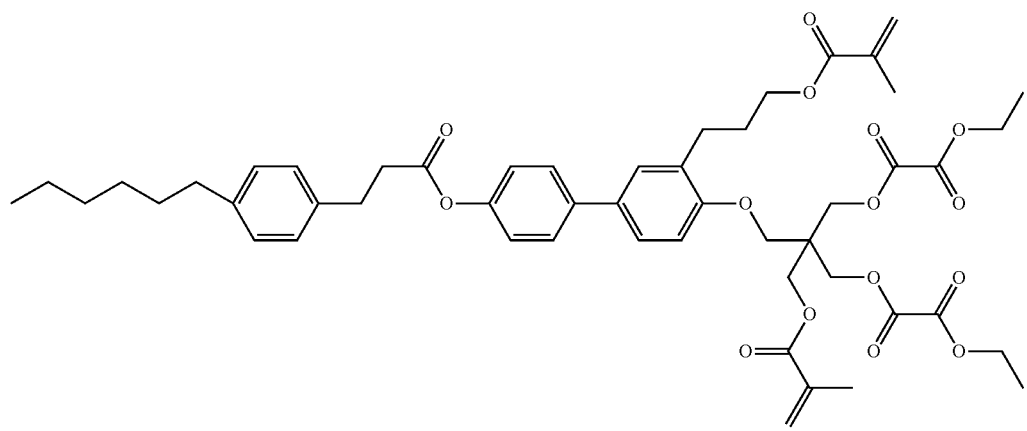
(P-458)
[Chem. 98]
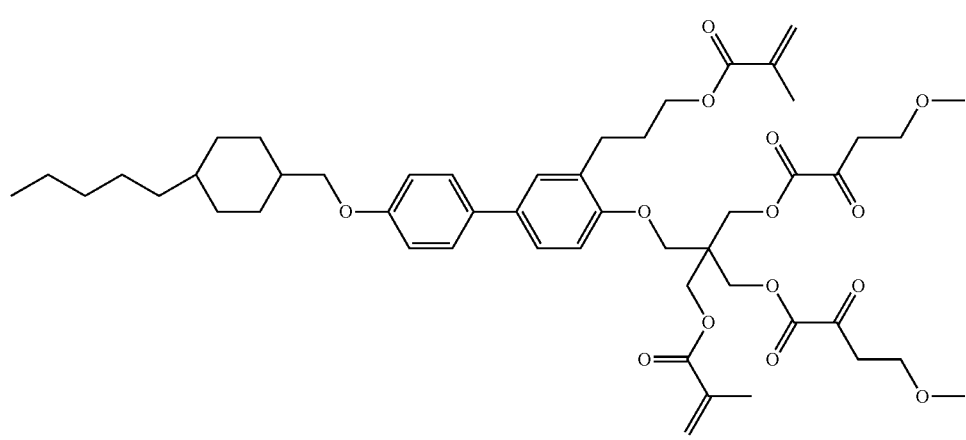
(P-459)

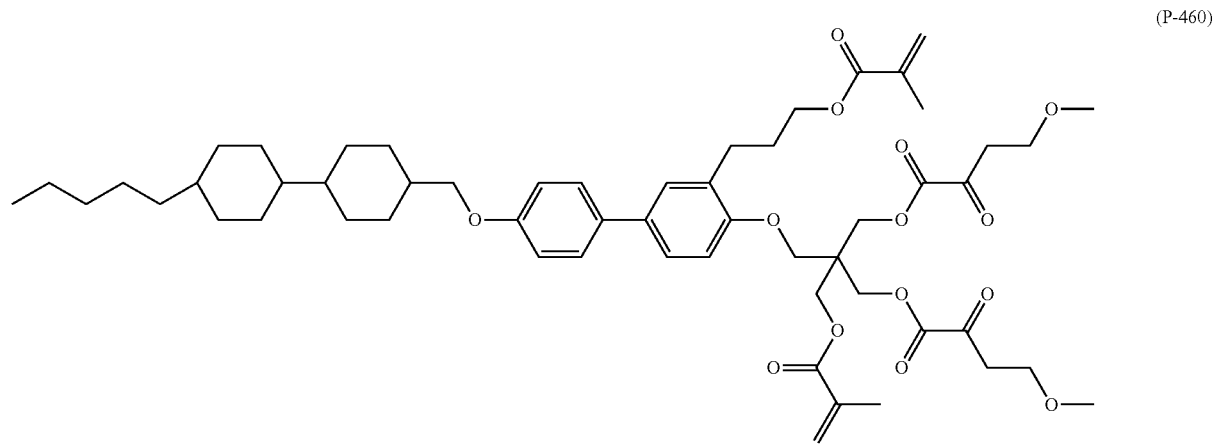
(P-460)
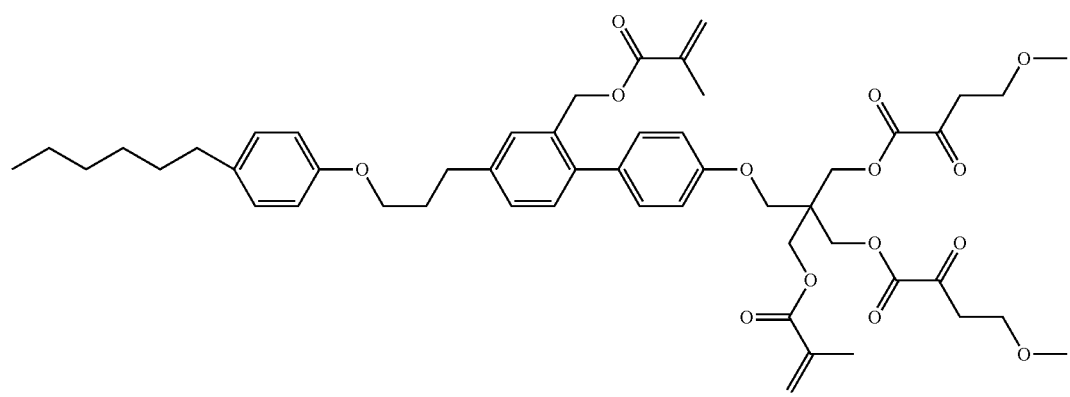
(P-461)
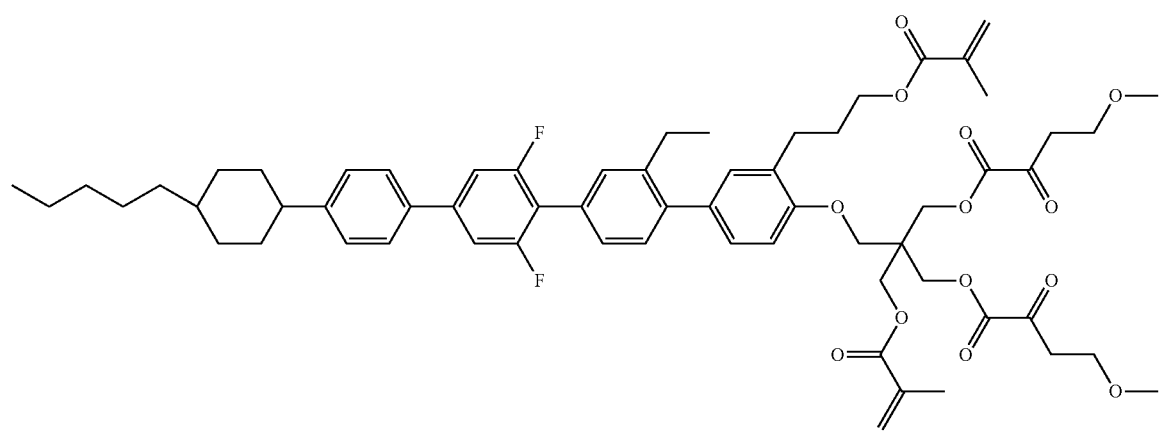
(P-462)

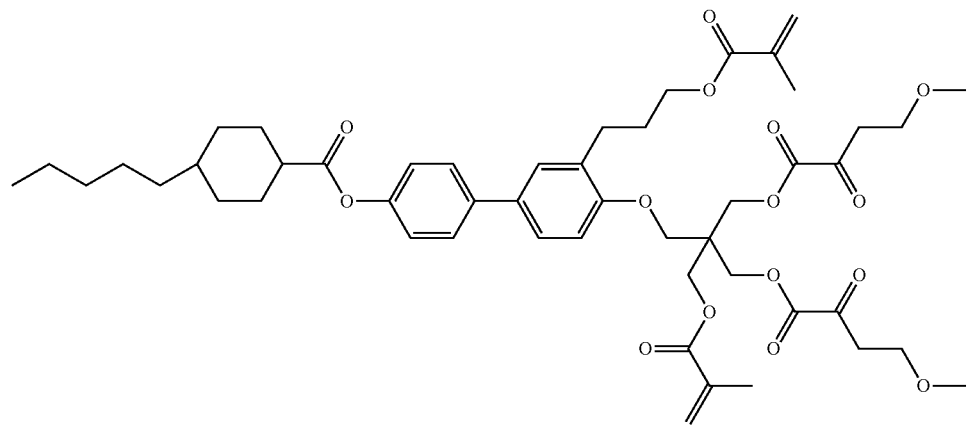
(P-463)
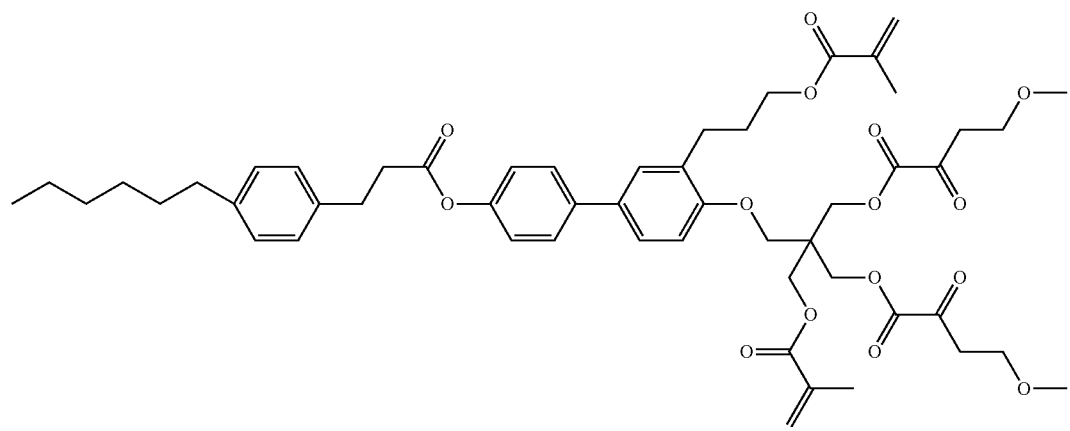
(P-464)
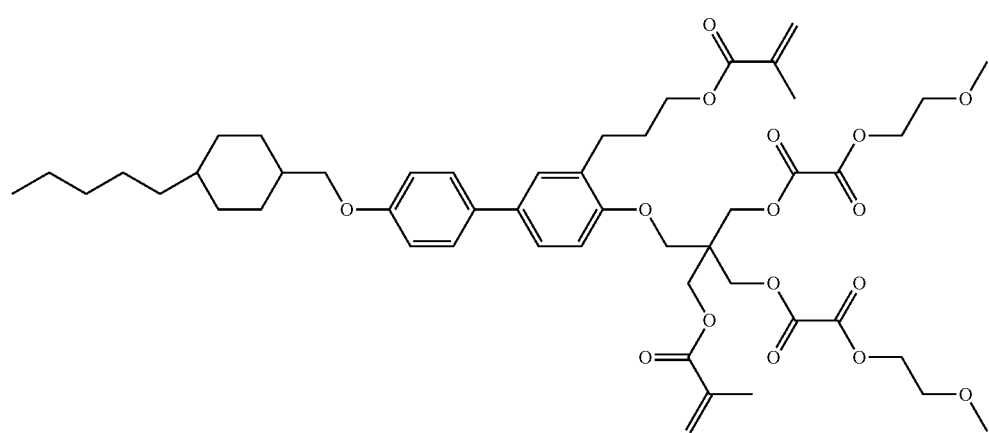
(P-465)

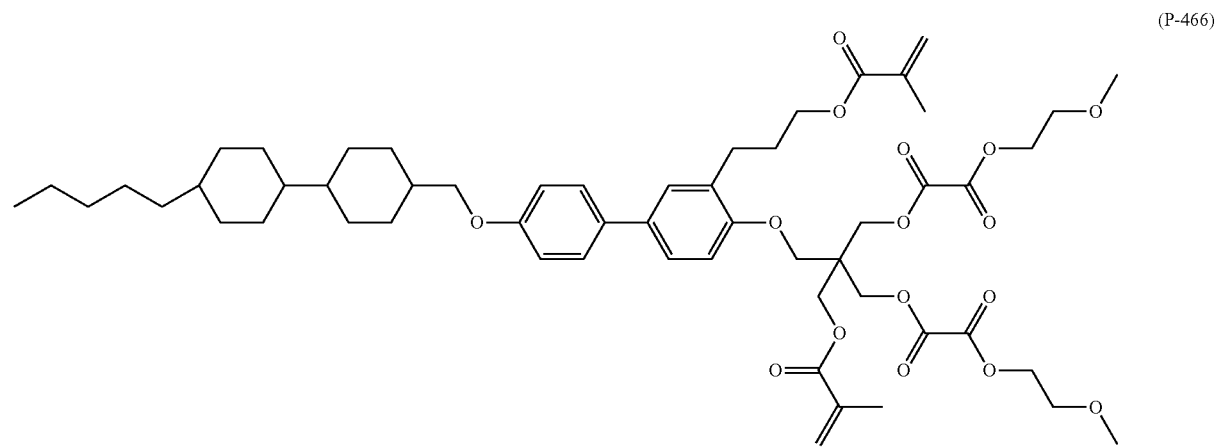
(P-466)
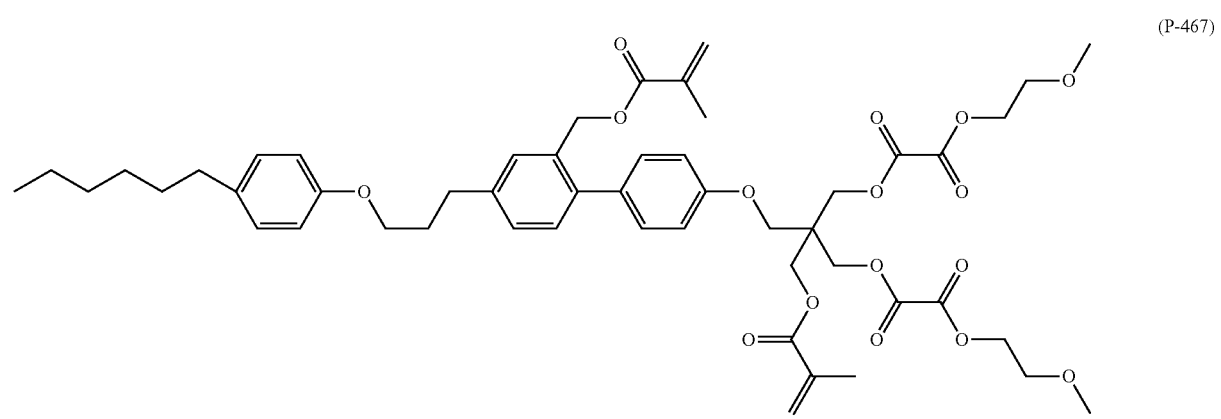
(P-467)
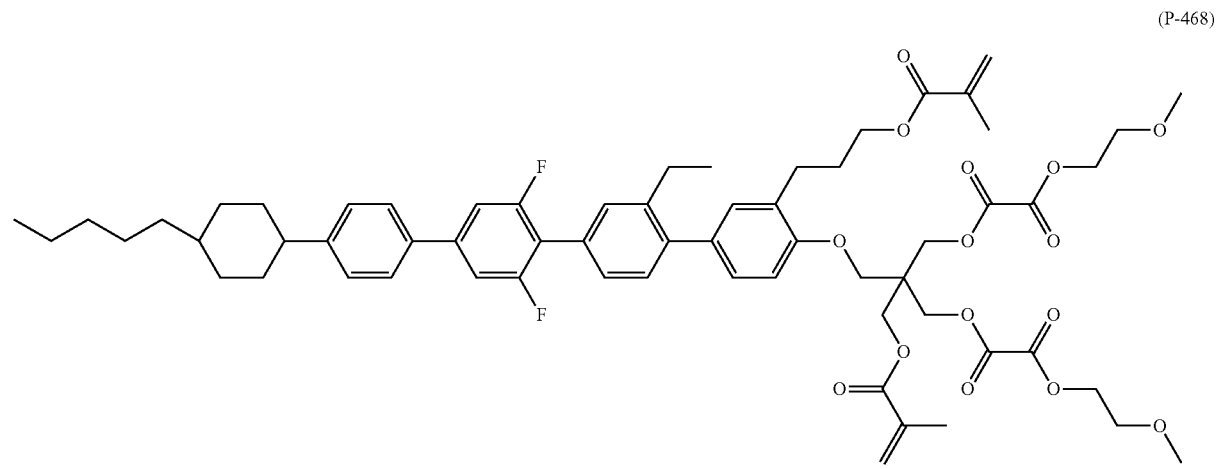
(P-468)

(P-469)
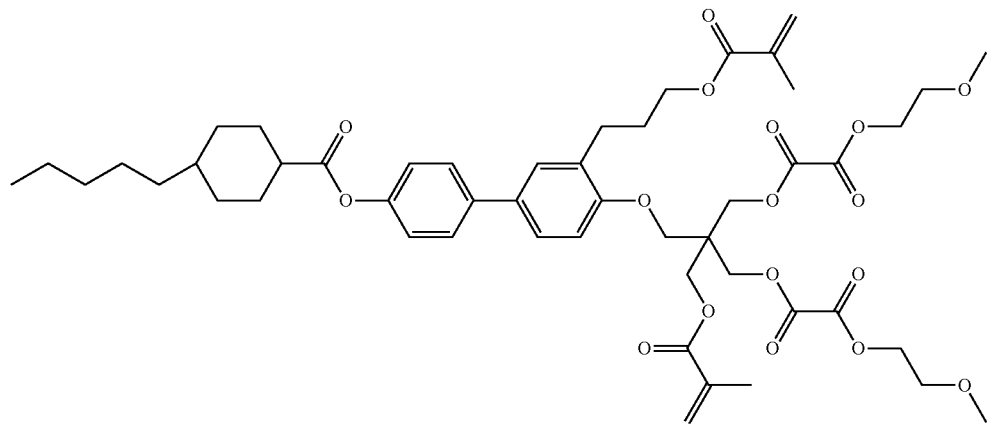
(P-470)
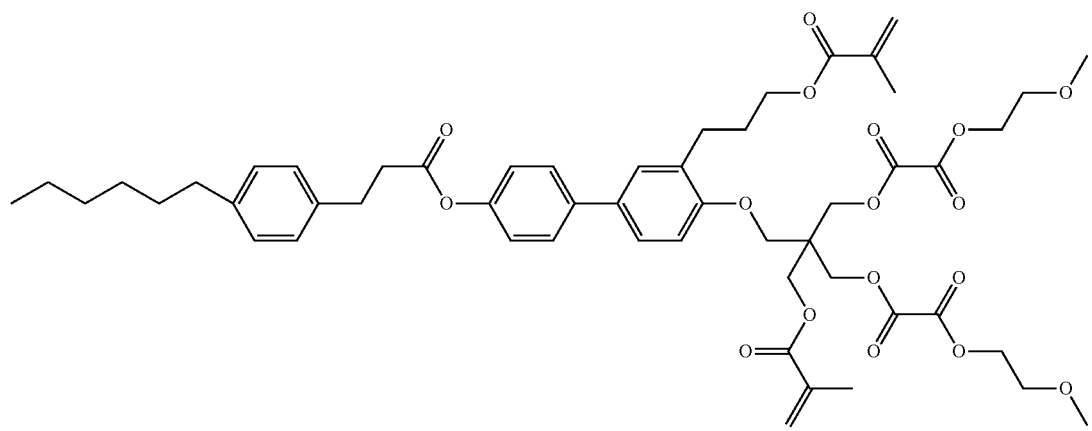
[Chem. 99]
(P-471)
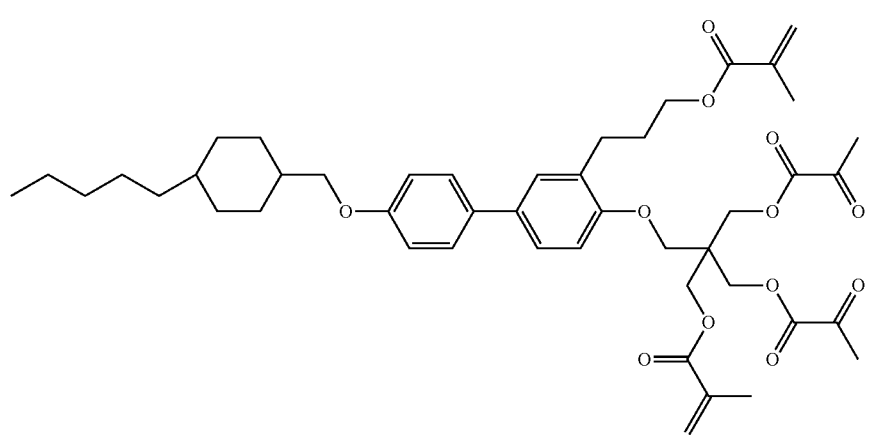

(P-472)
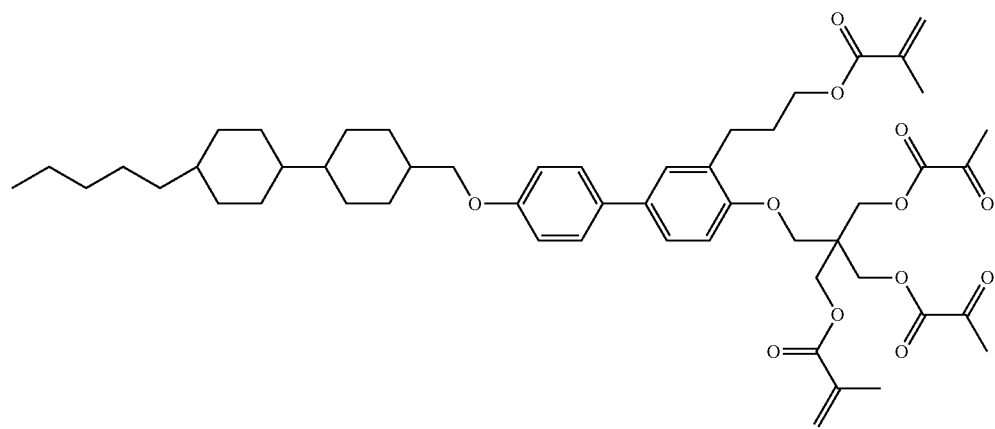
(P-473)
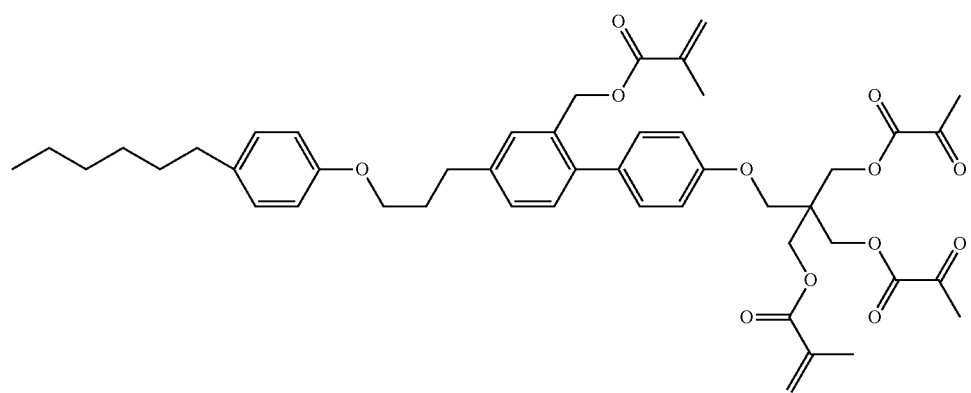
(P-474)
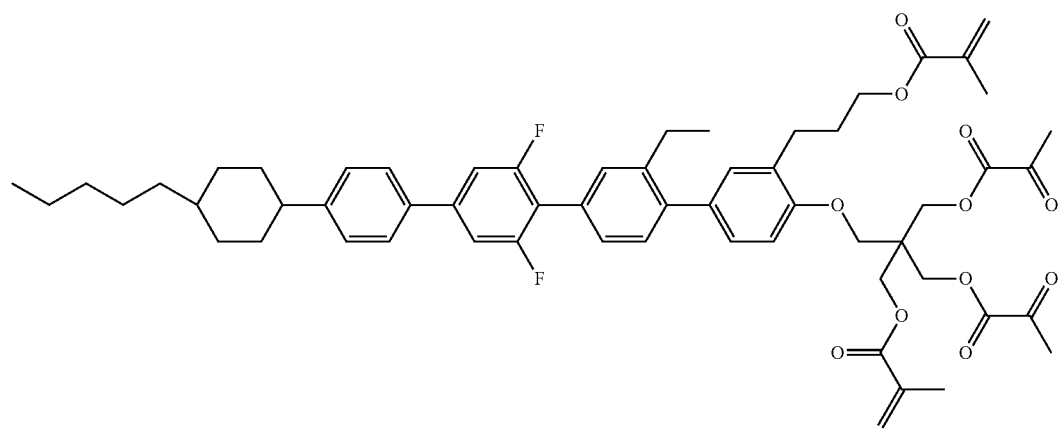

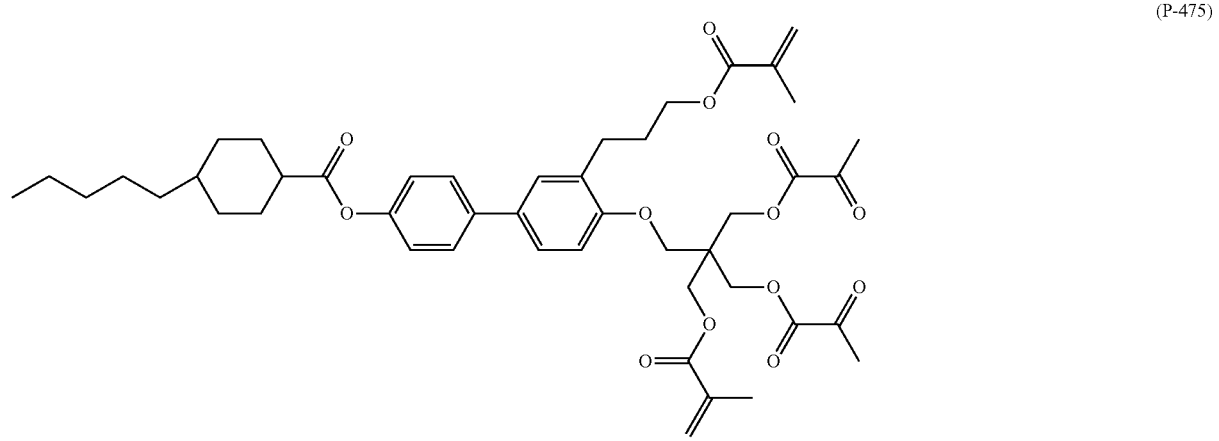
(P-475)
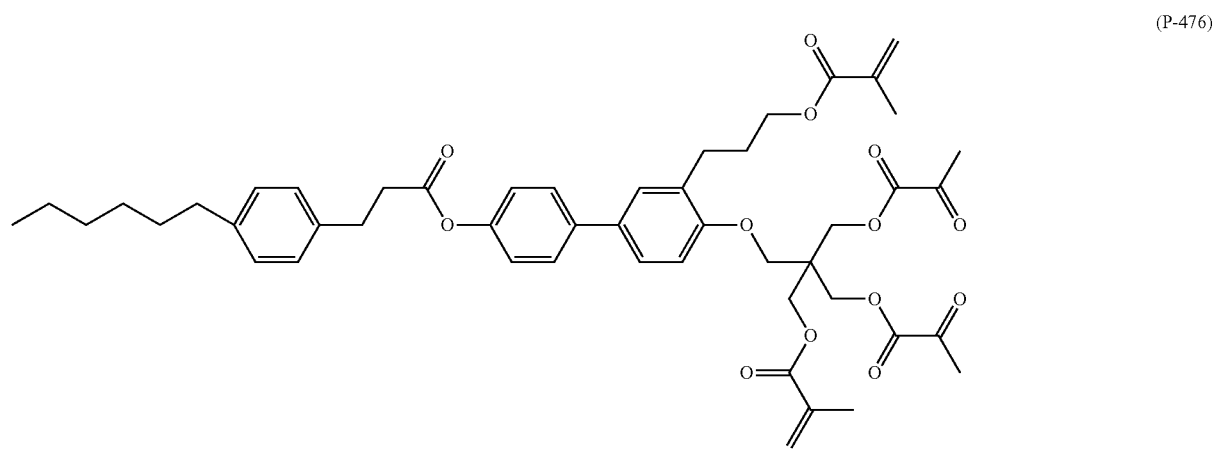
(P-476)
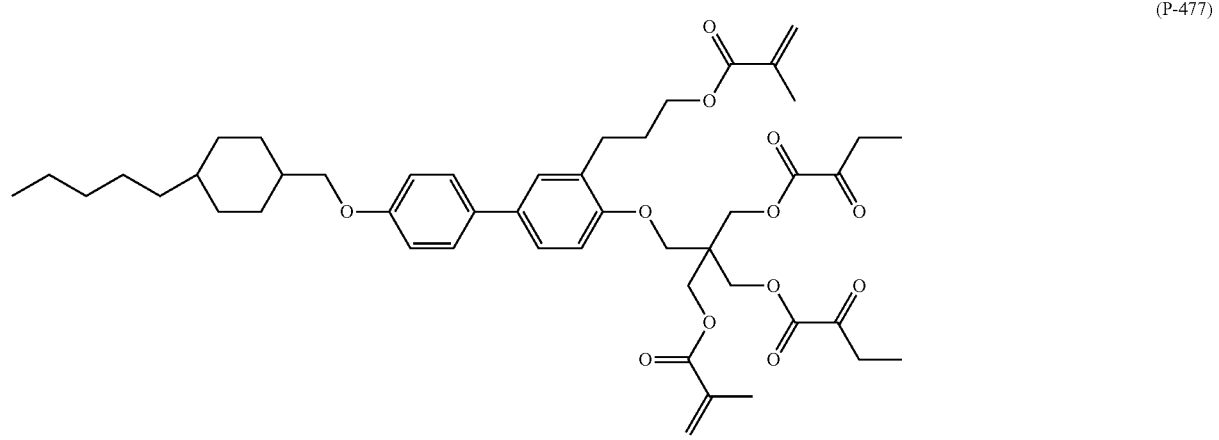
(P-477)

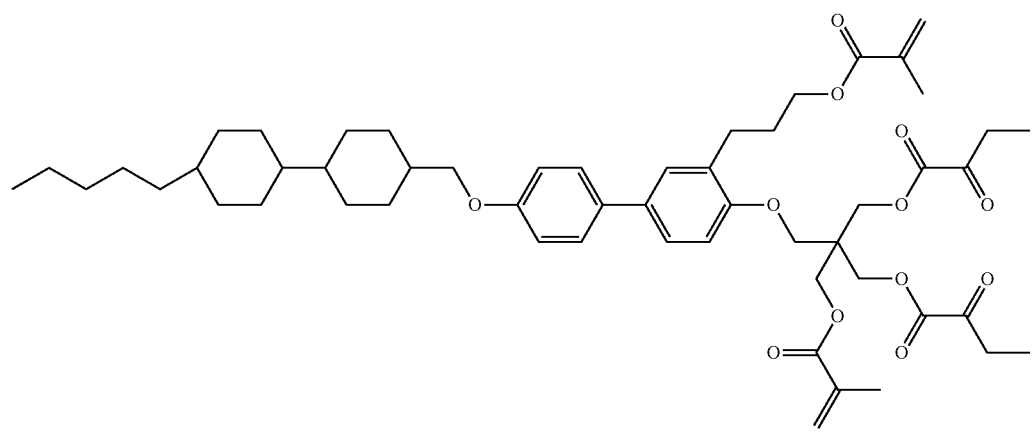
(P-478)
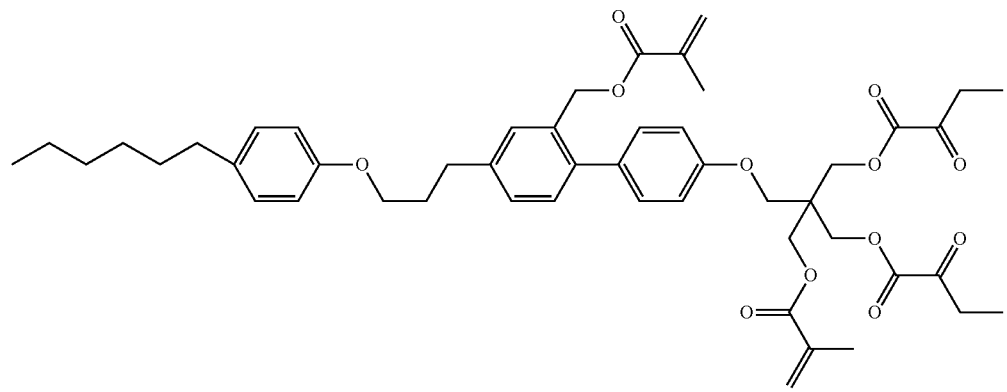
(P-479)
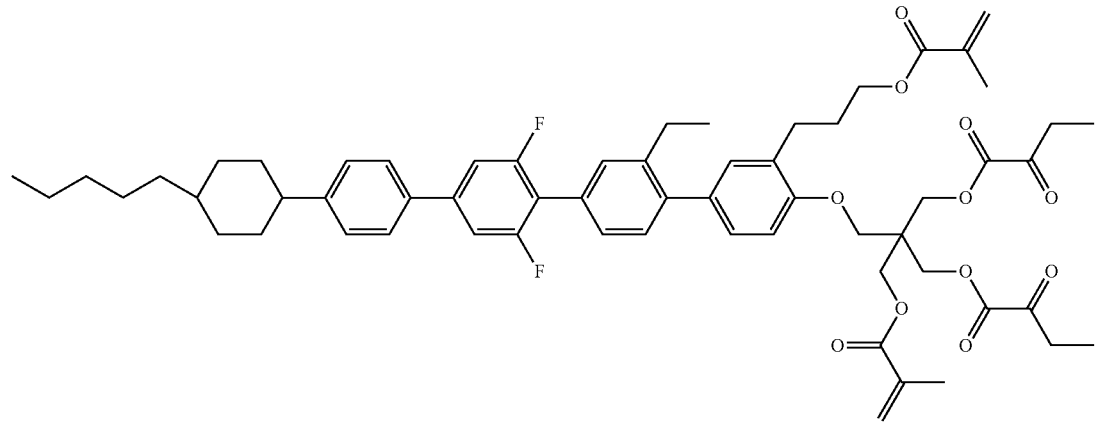
(P-480)

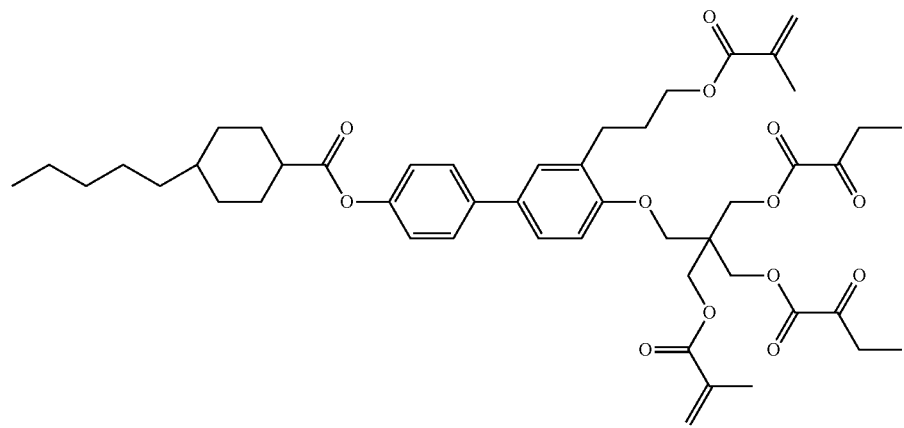
(P-481)
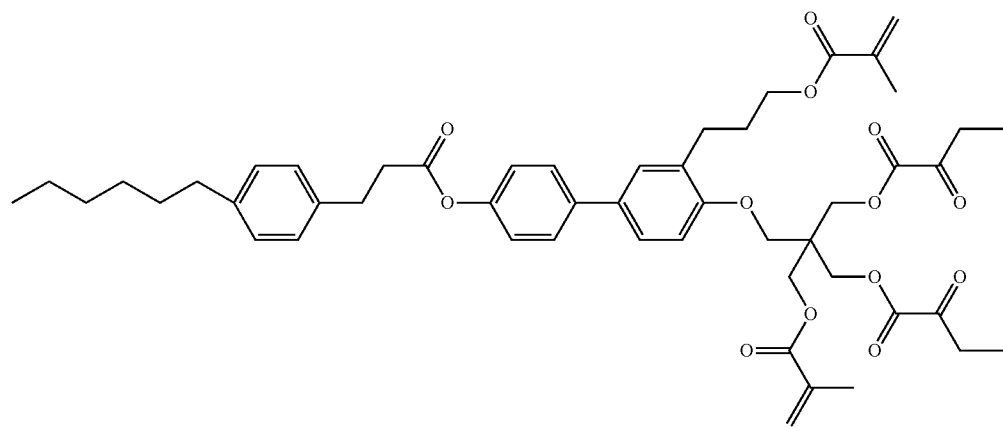
(P-482)
[Chem. 100]
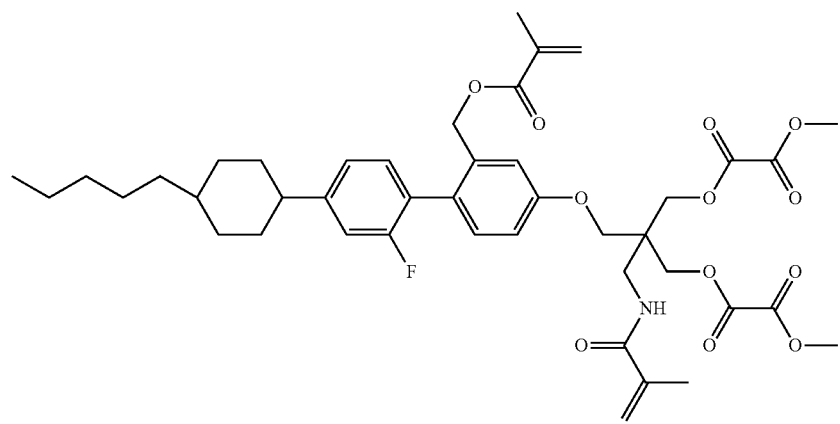
(P-483)

-continued
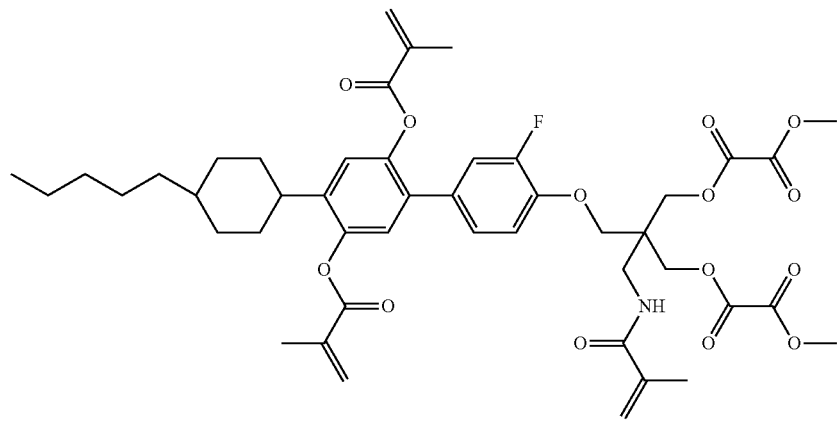
(P-484)
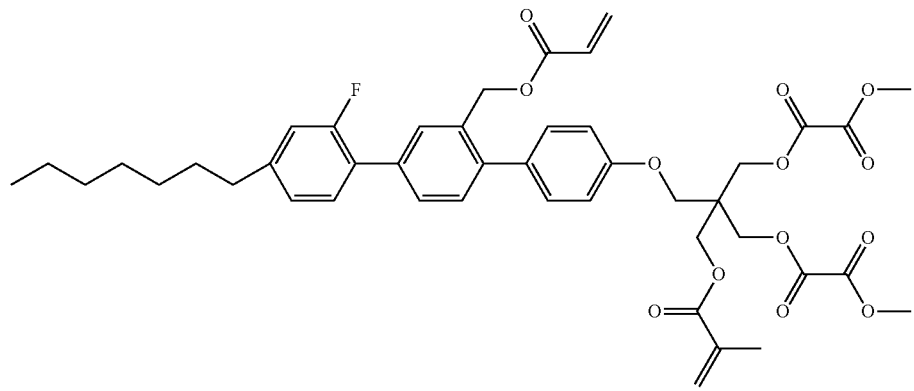
(P-485)
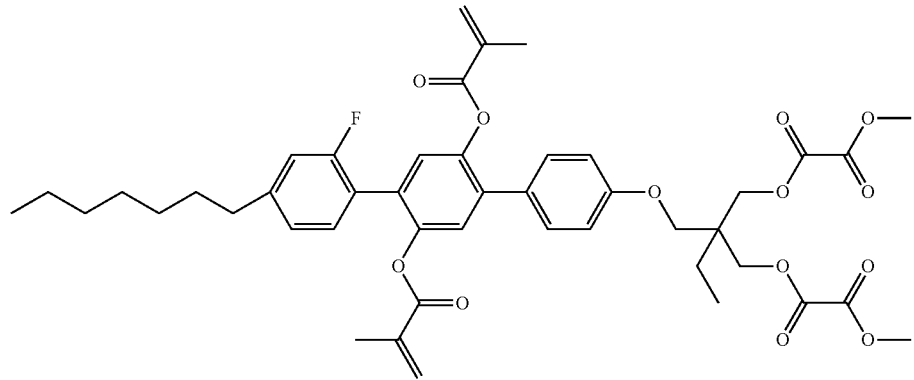
(P-486)
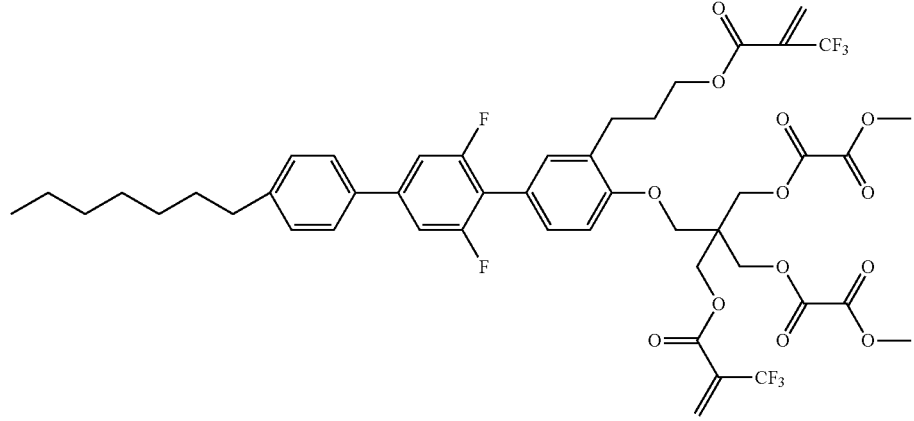
(P-487)

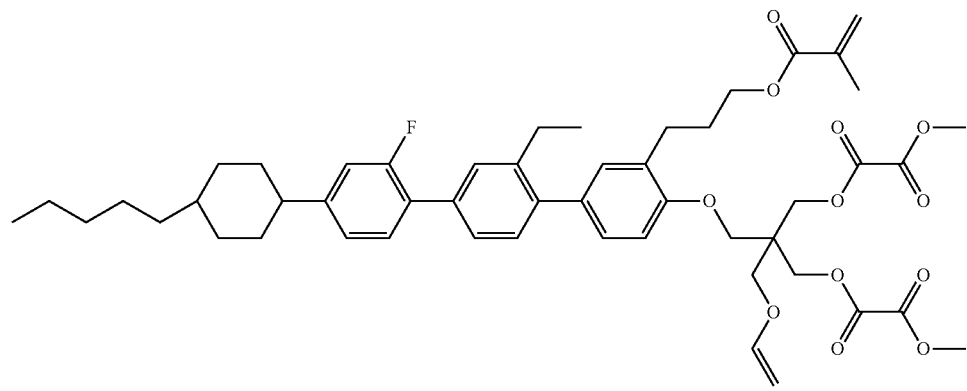
(P-488)
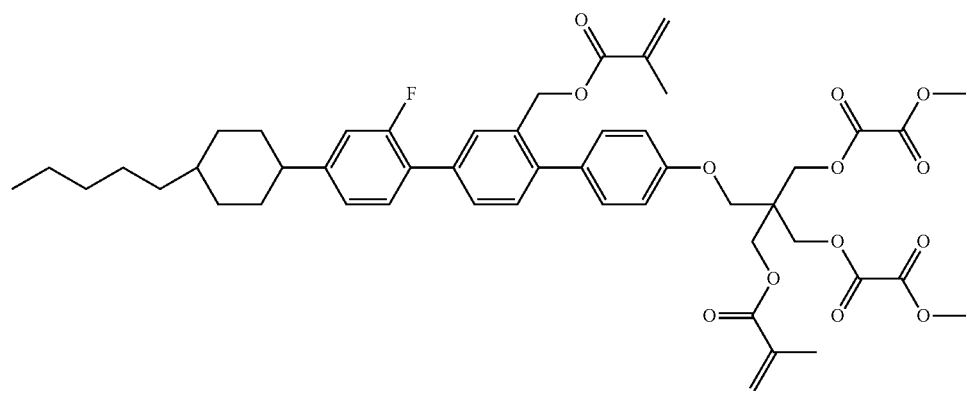
(P-489)
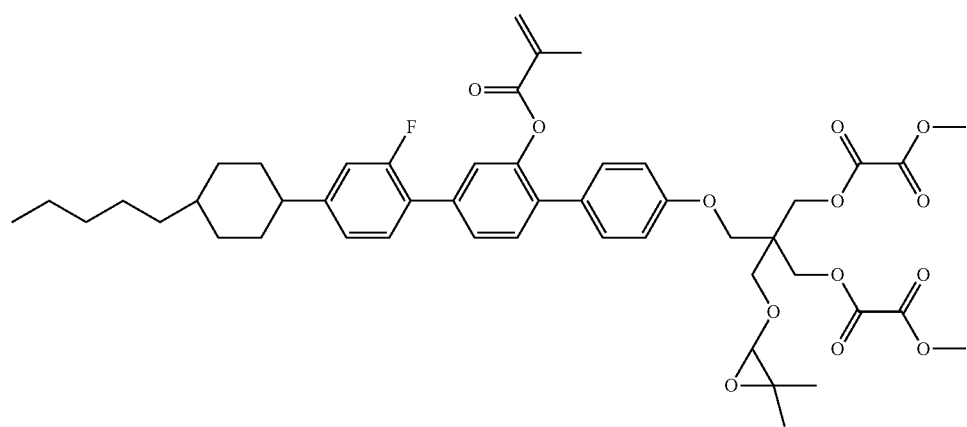
(P-490)

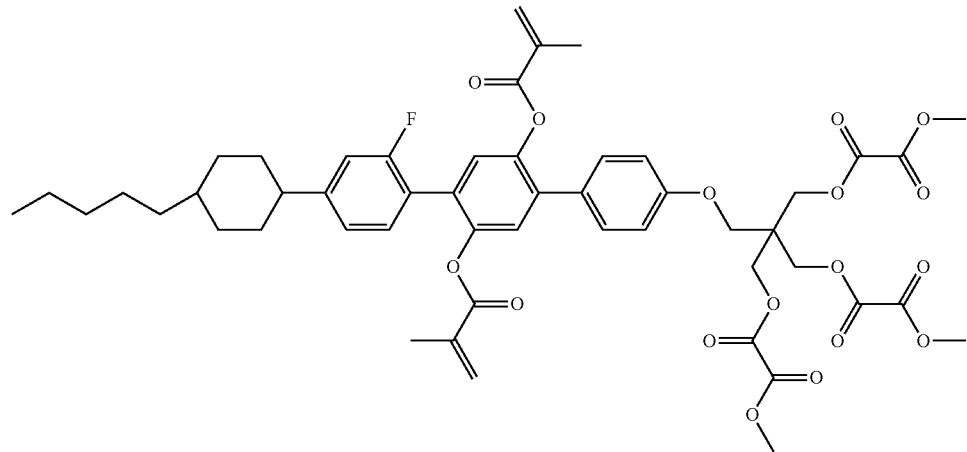
(P-491)
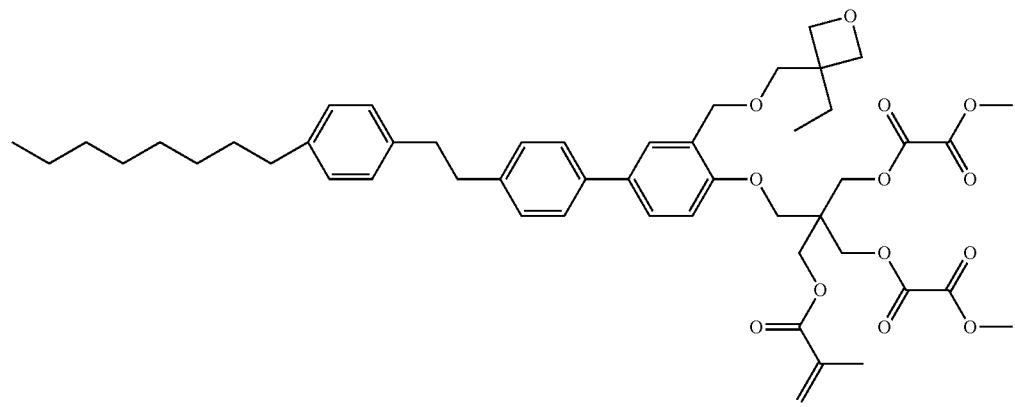
(P-492)
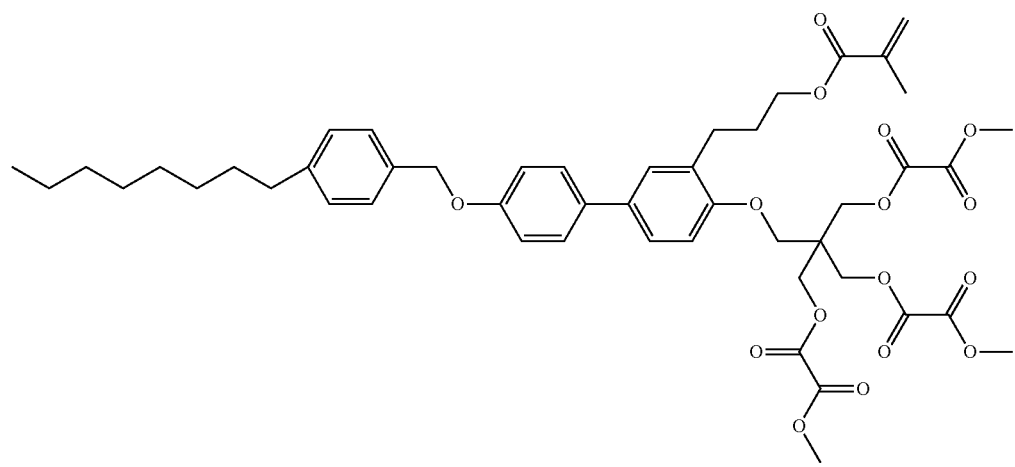
(P-493)

-continued
(P-494)
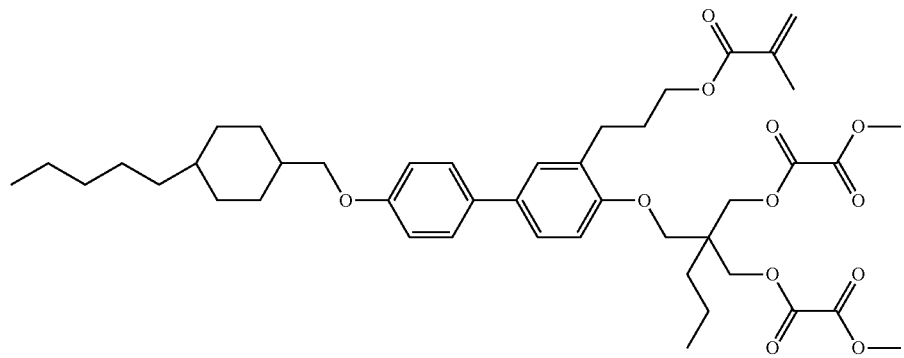
[Chem. 101]
(P-495)
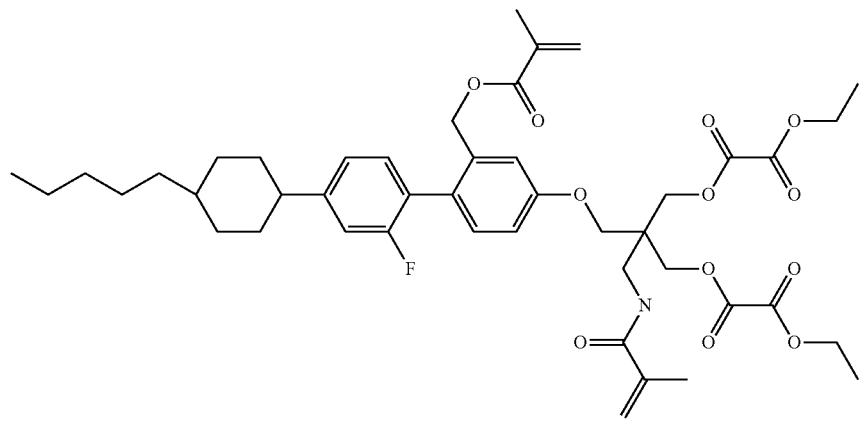
(P-496)
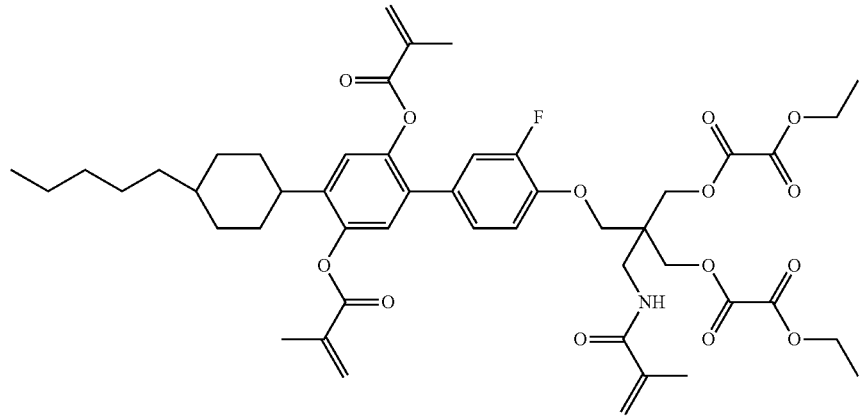
(P-497)
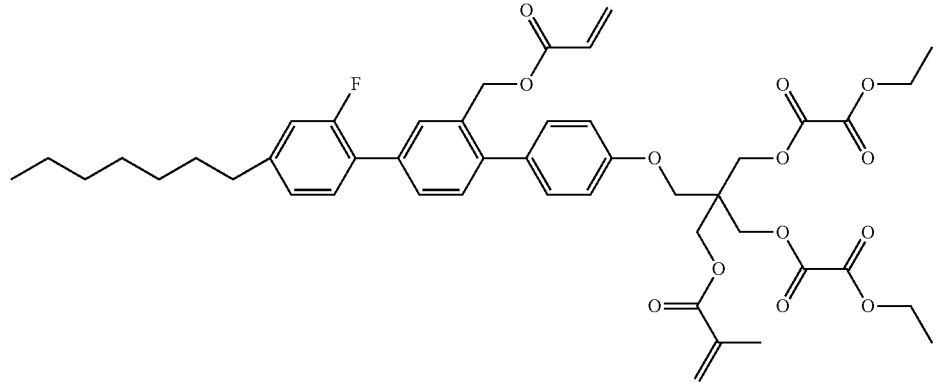

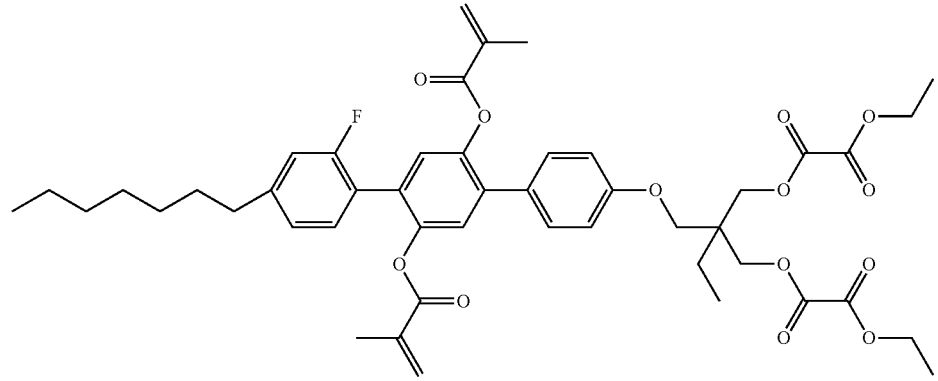
(P-498)
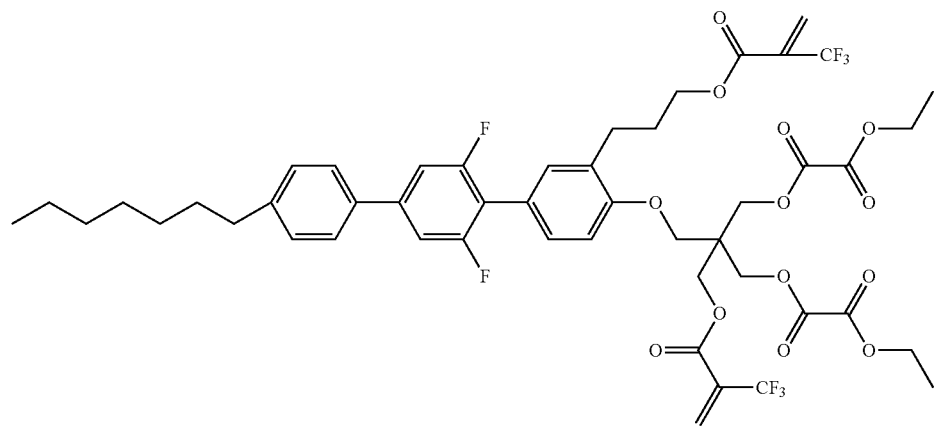
(P-499)
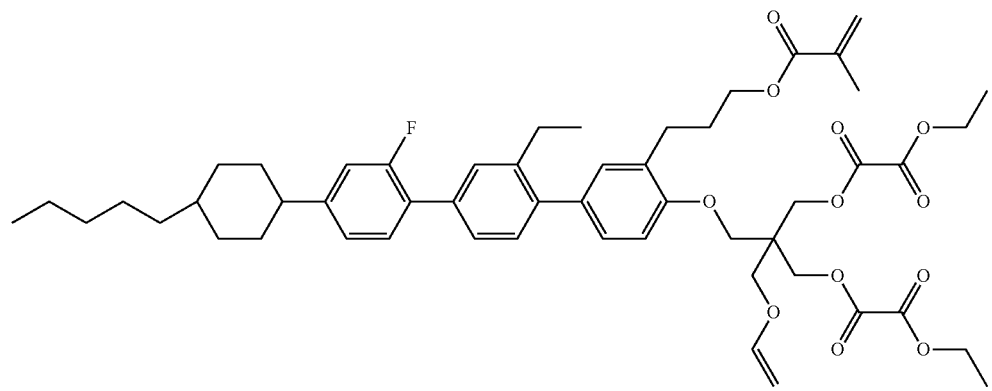
(P-500)
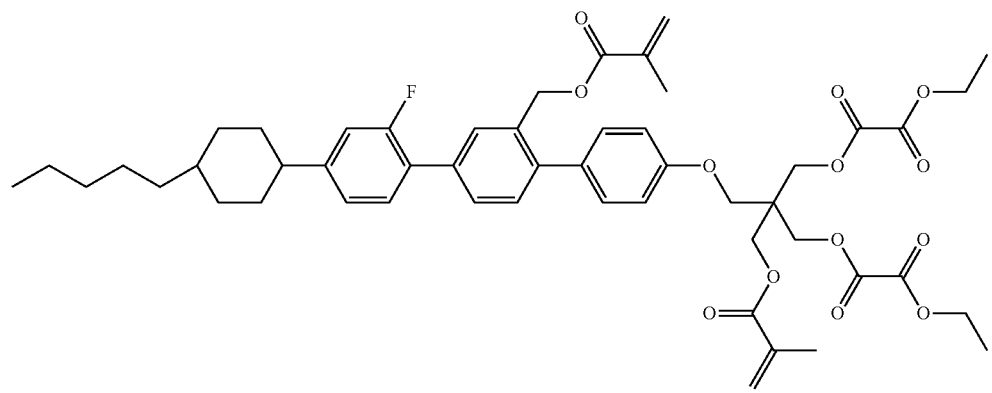
(P-501)

-continued
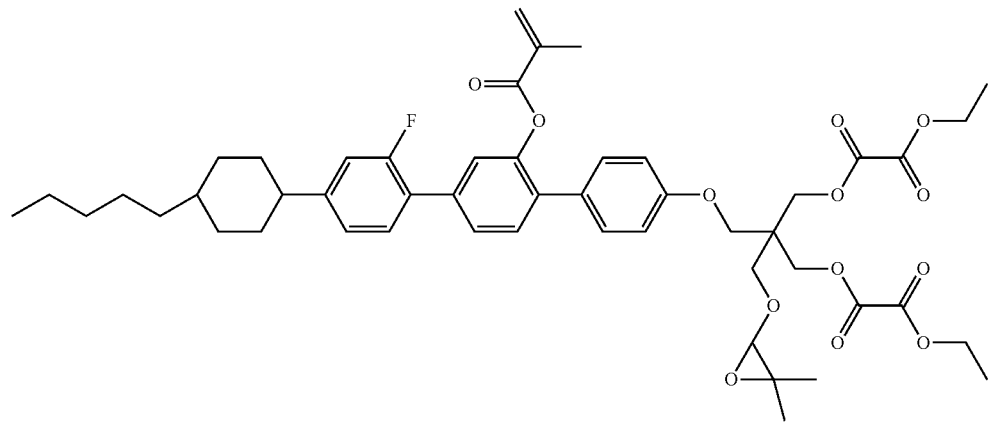
(P-502)
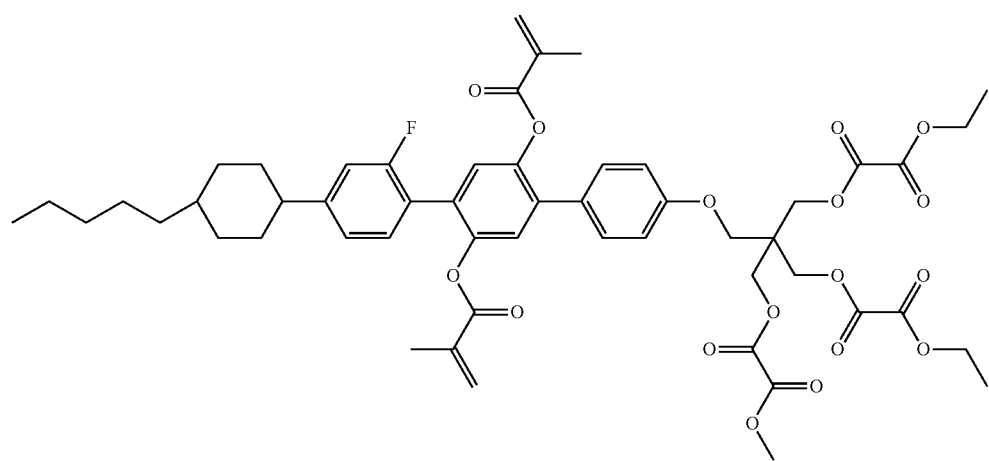
(P-503)
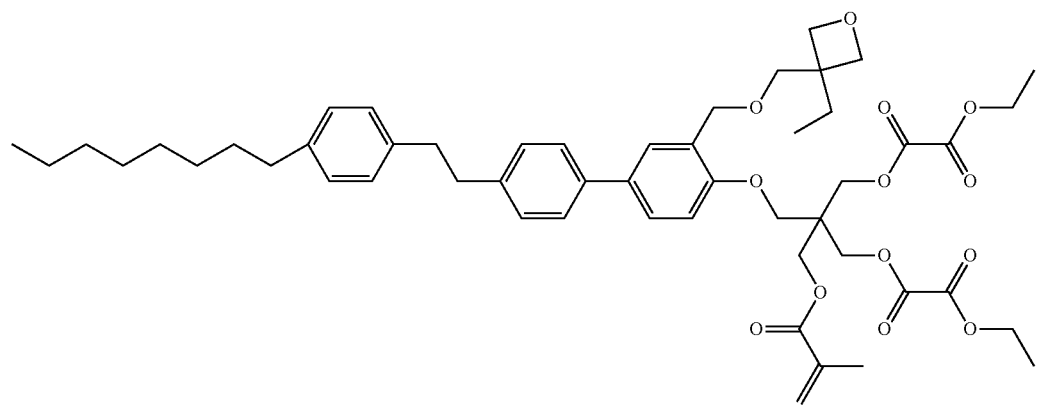
(P-504)

-continued
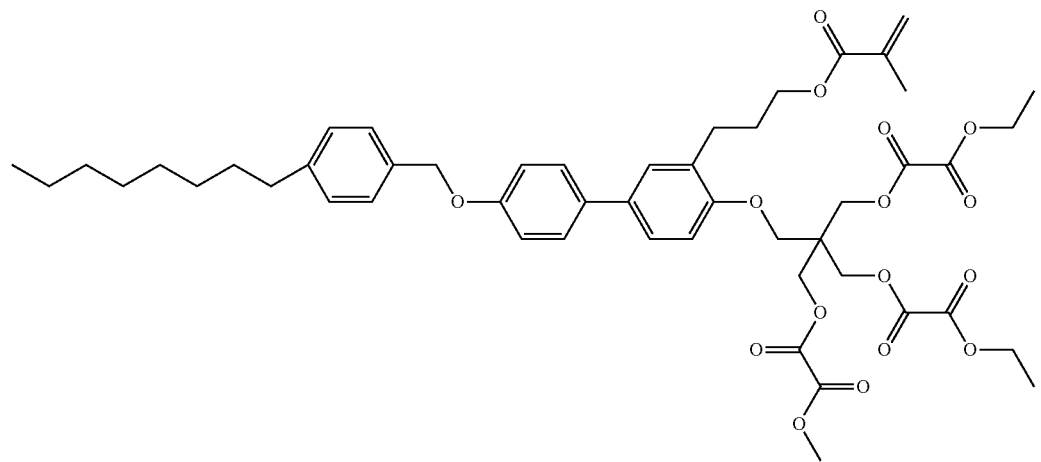
(P-505)
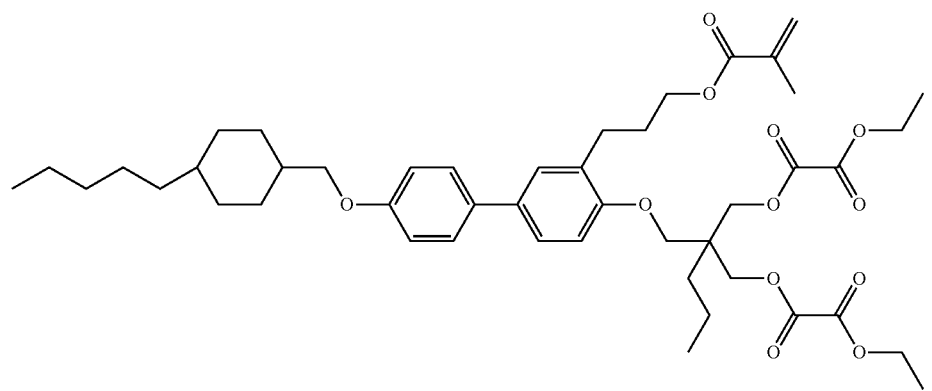
(P-506)
[Chem. 102]
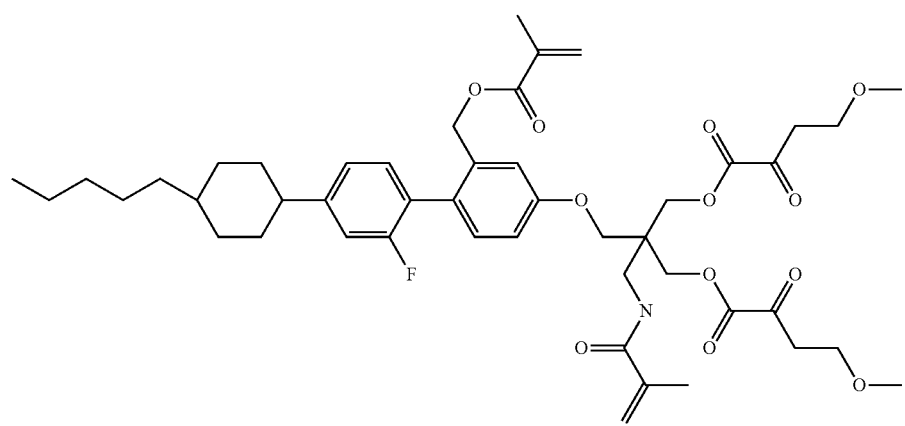
(P-495)

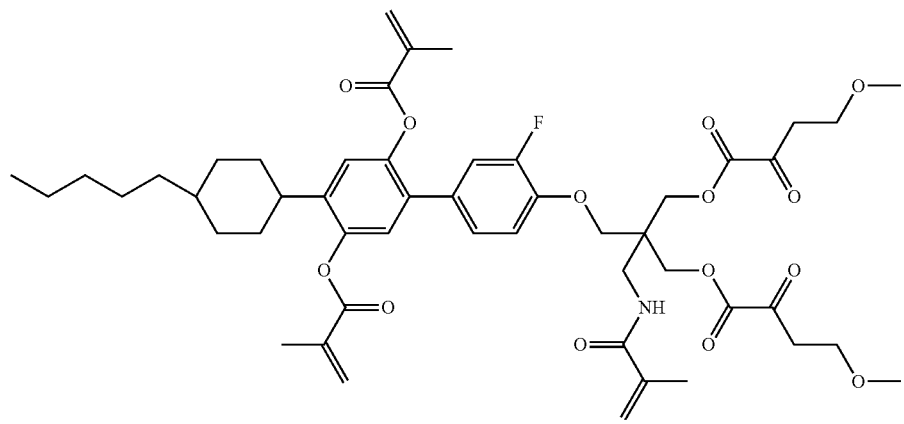
(P-496)
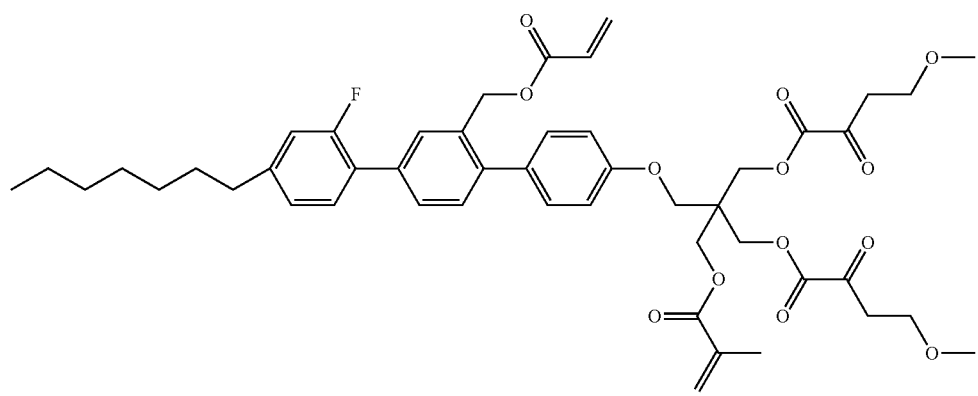
(P-497)
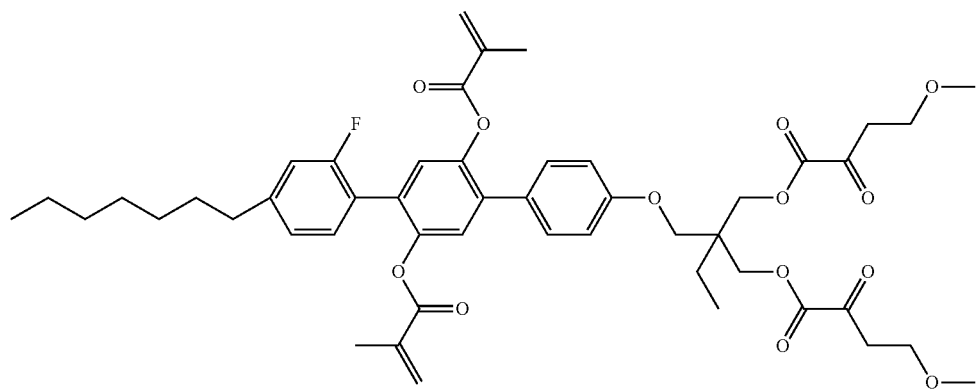
(P-498)
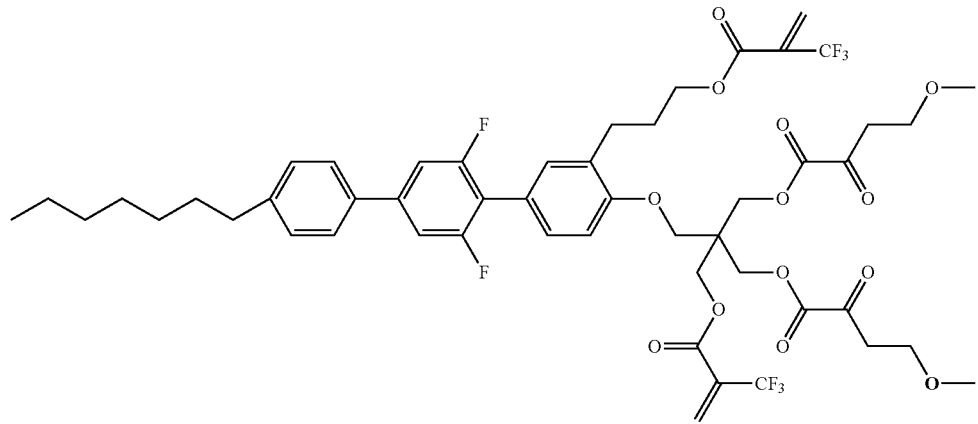
(P-499)

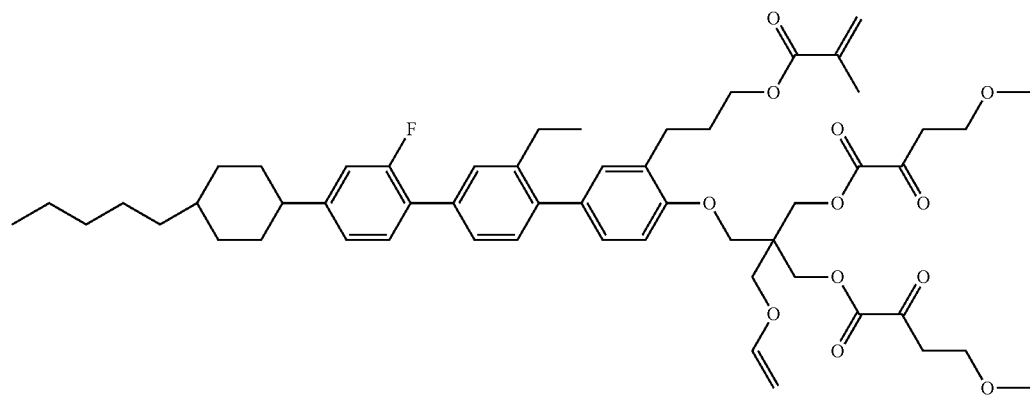
(P-500)
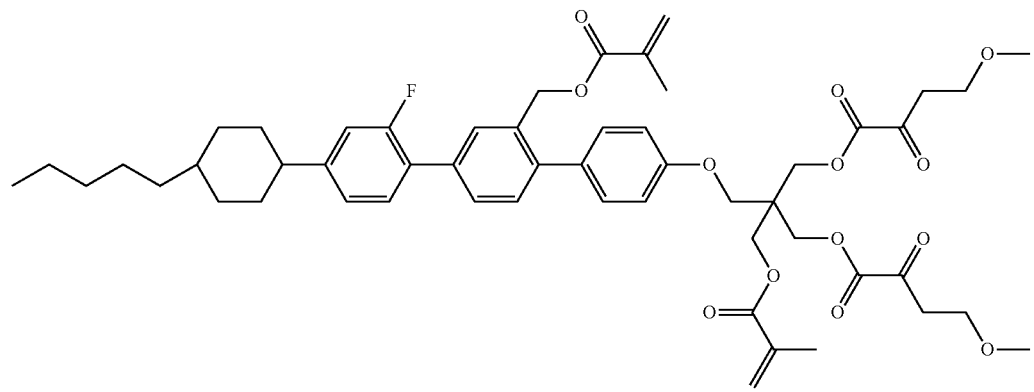
(P-501)
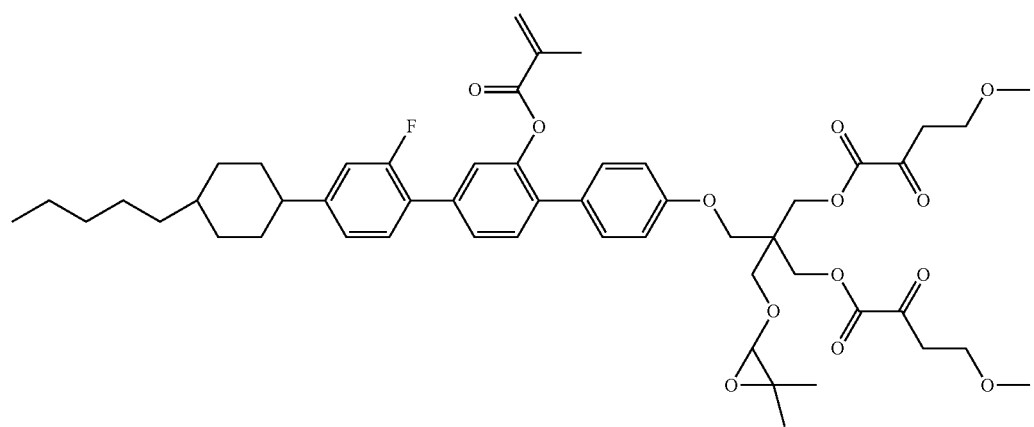
(P-502)

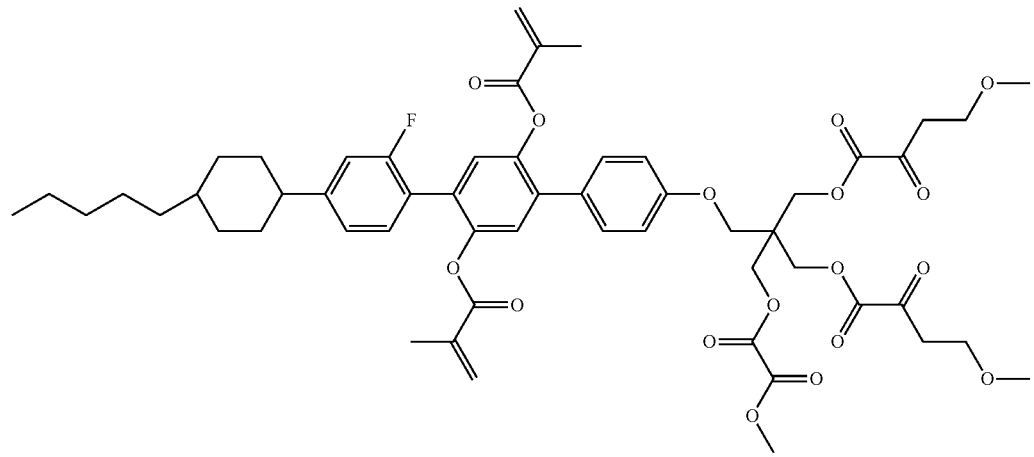
(P-503)
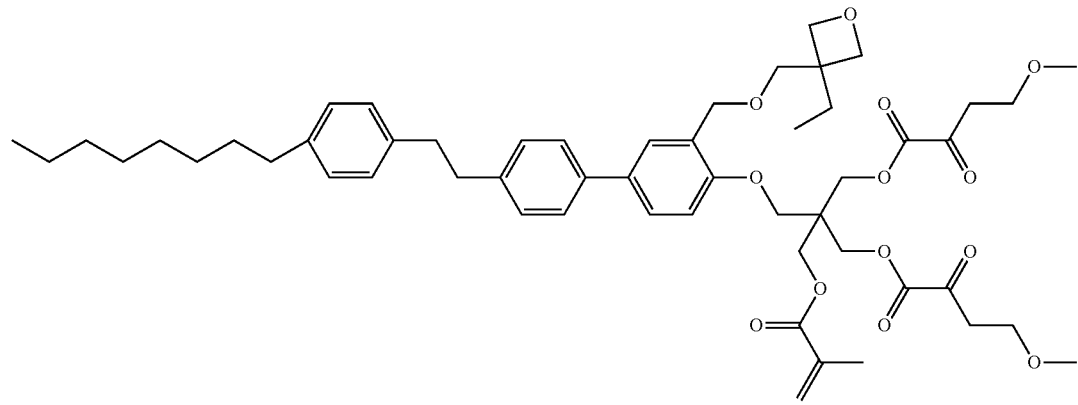
(P-504)
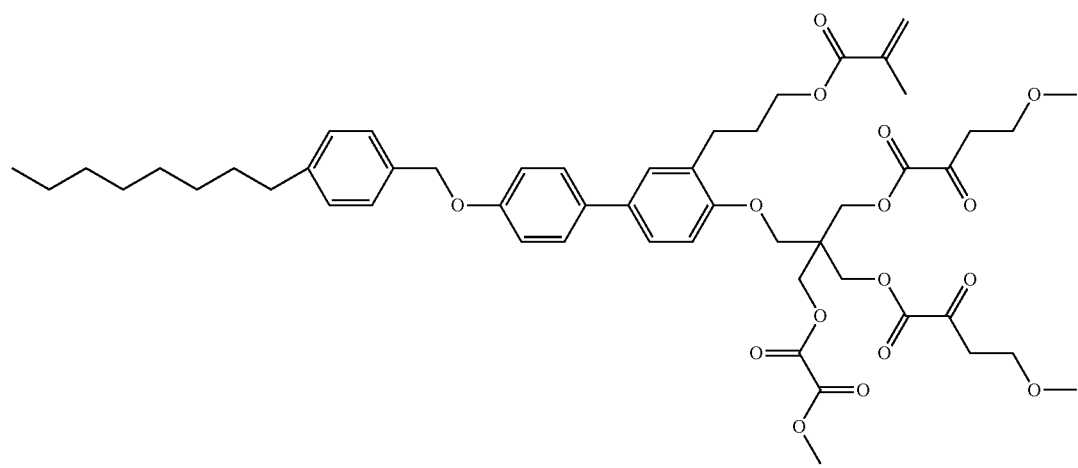
(P-505)

-continued
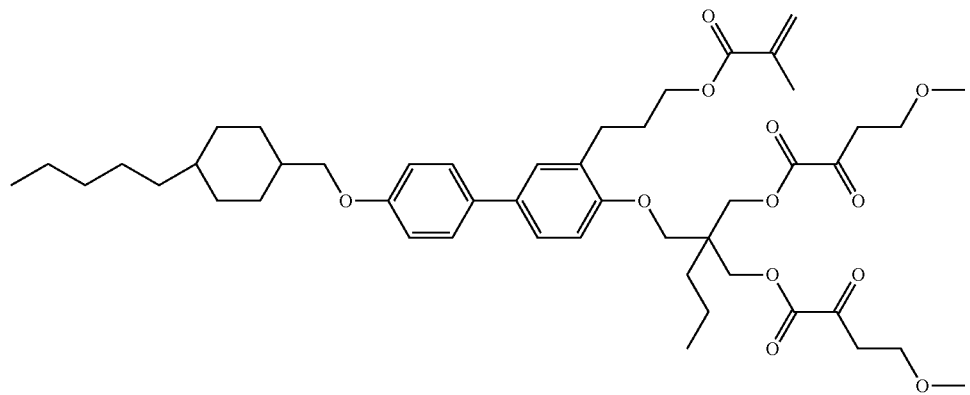
(P-506)
[Chem. 103]
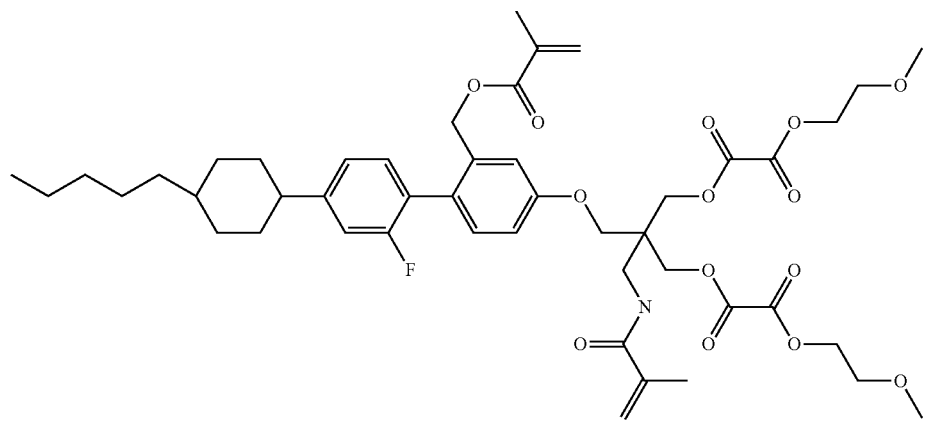
(P-507)
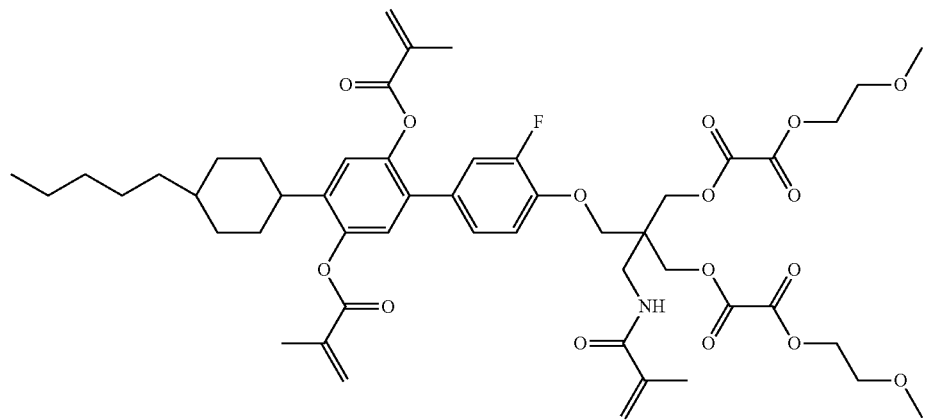
(P-508)

-continued
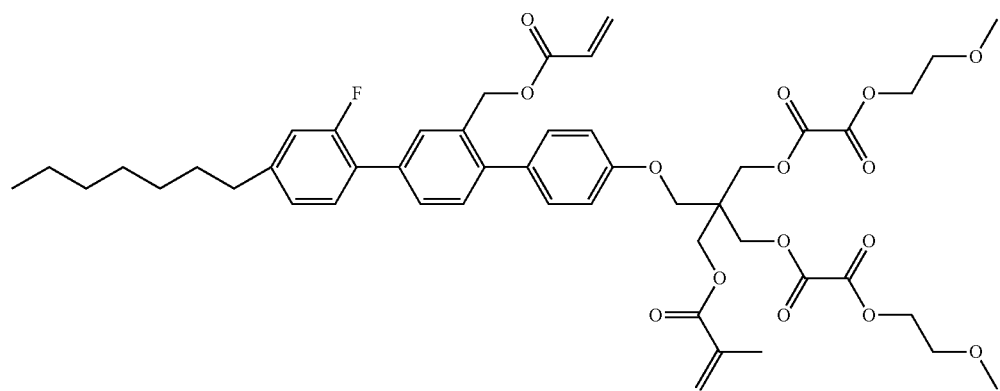
(P-509)
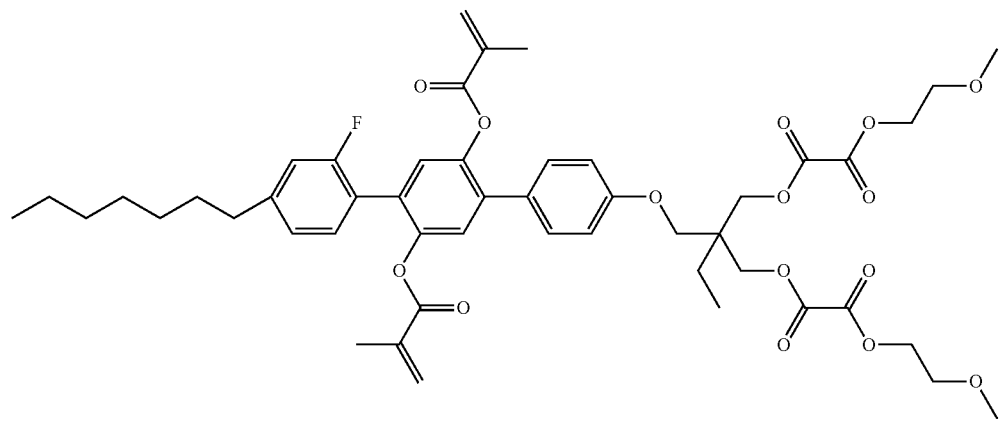
(P-510)
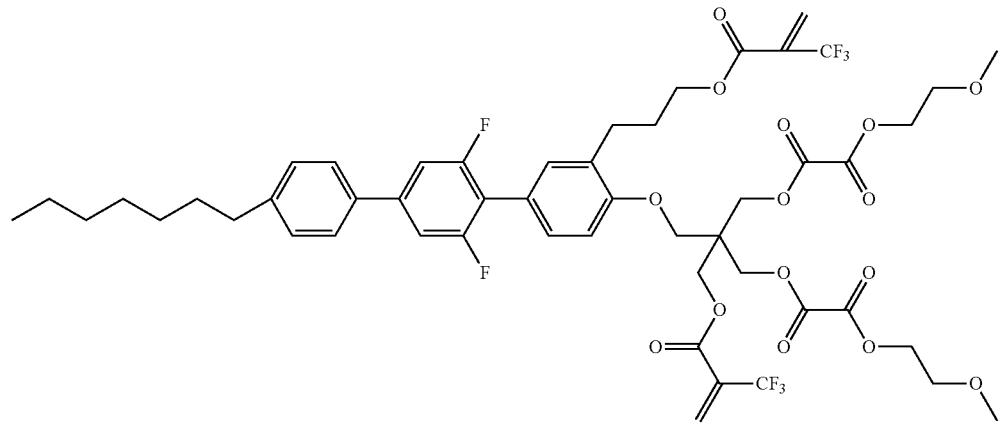
(P-511)
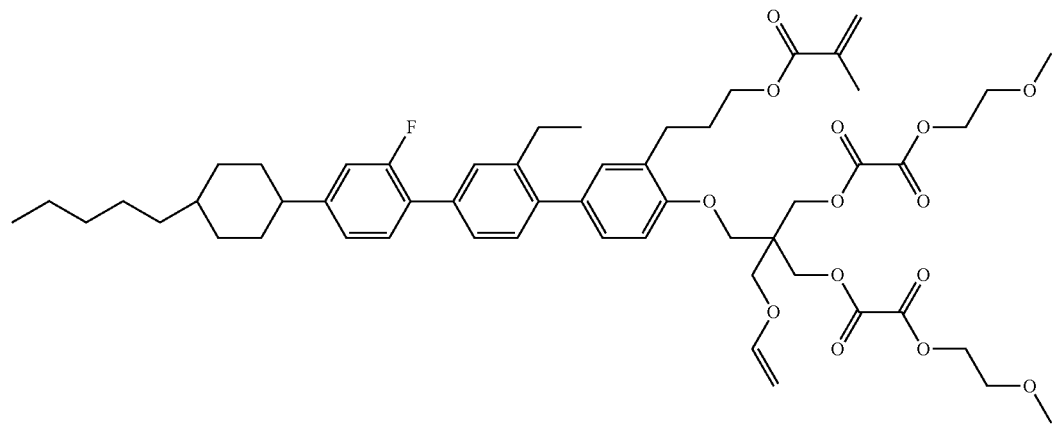
(P-512)

-continued
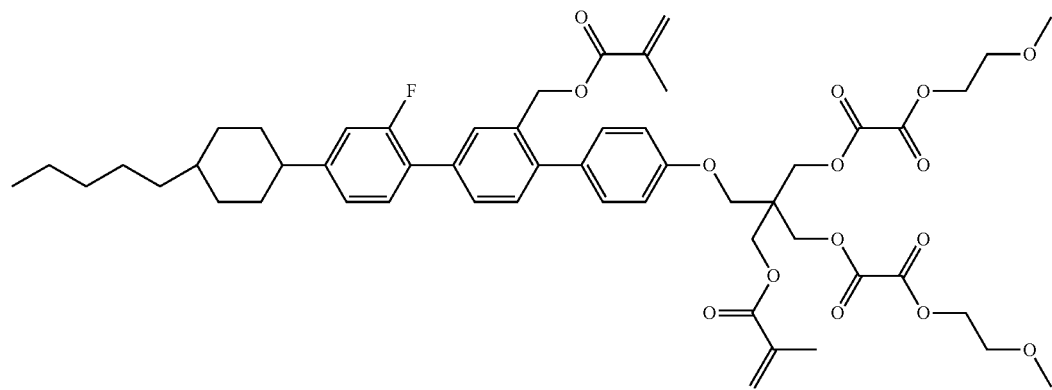
(P-513)
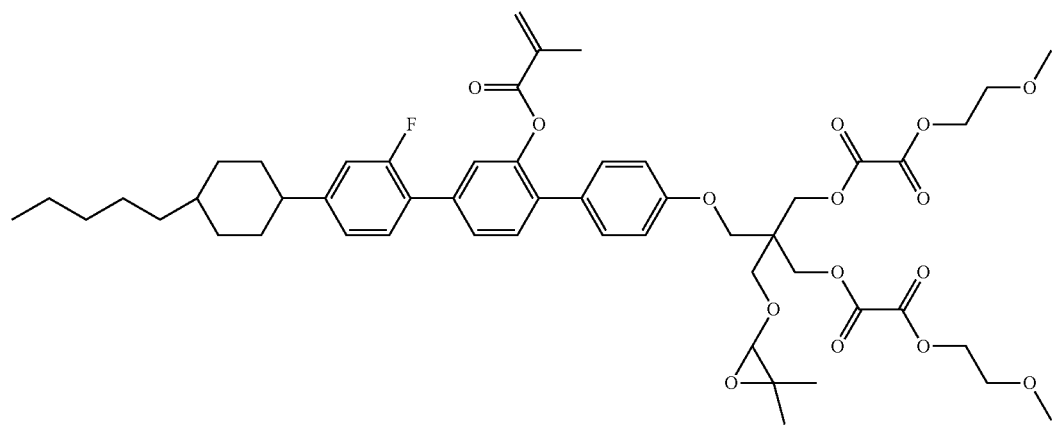
(P-514)
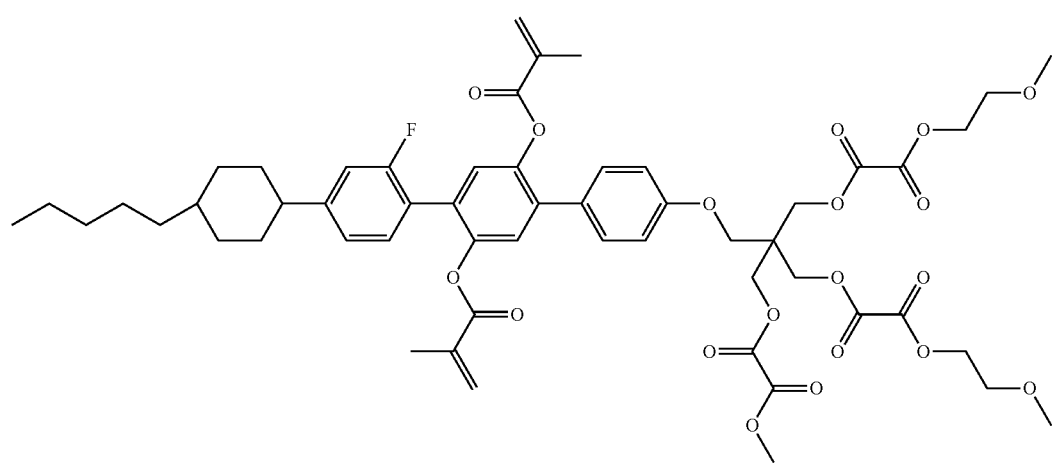
(P-515)

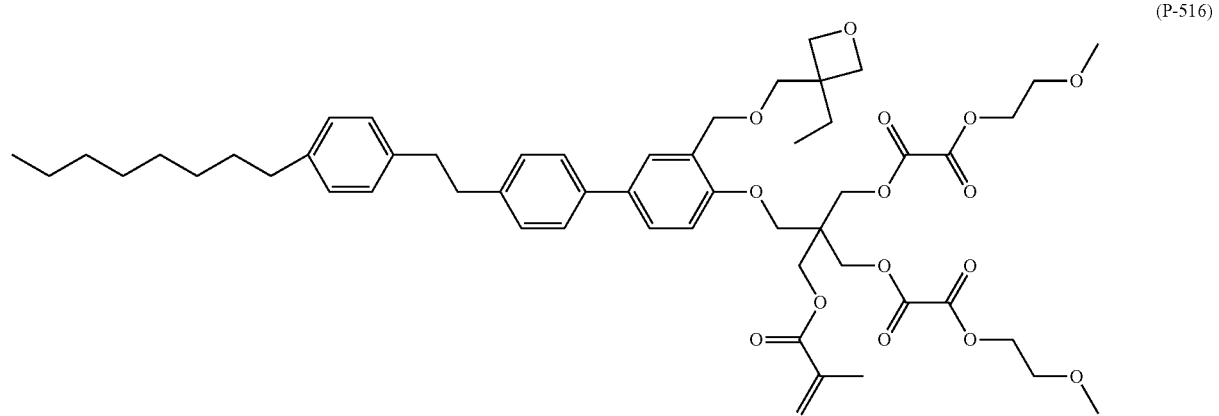
(P-516)
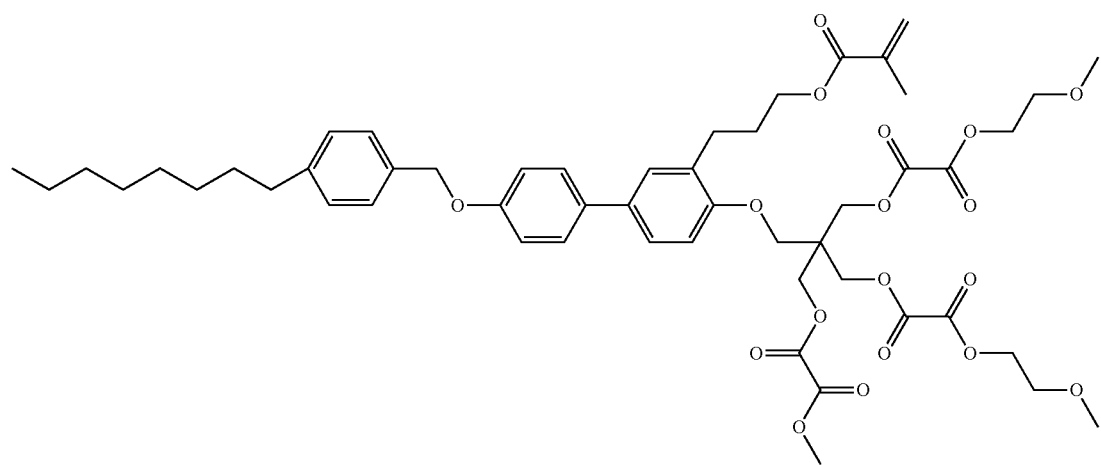
(P-517)
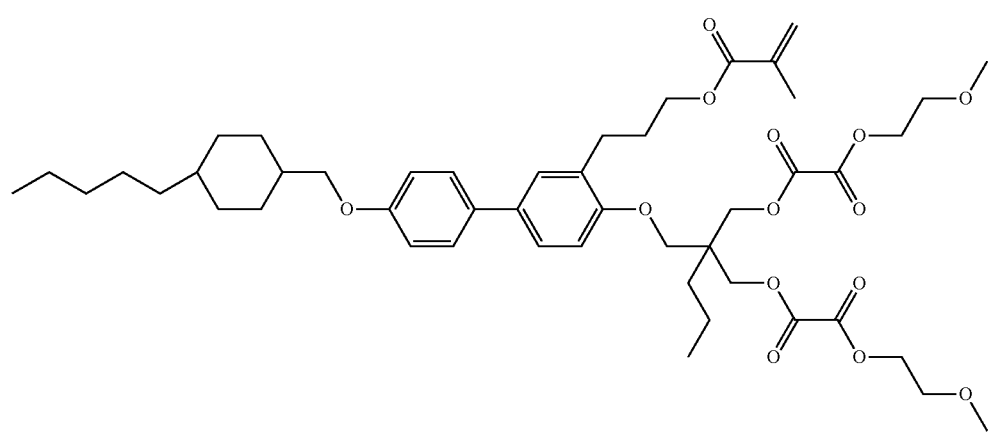
(P-518)

[Chem. 104]
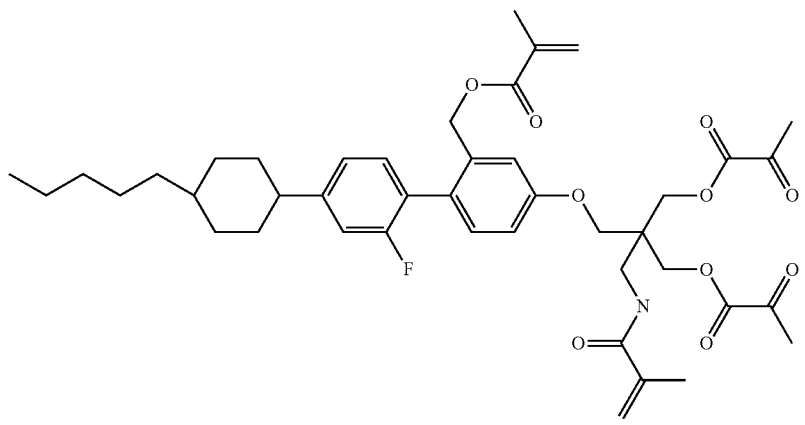
(P-519)
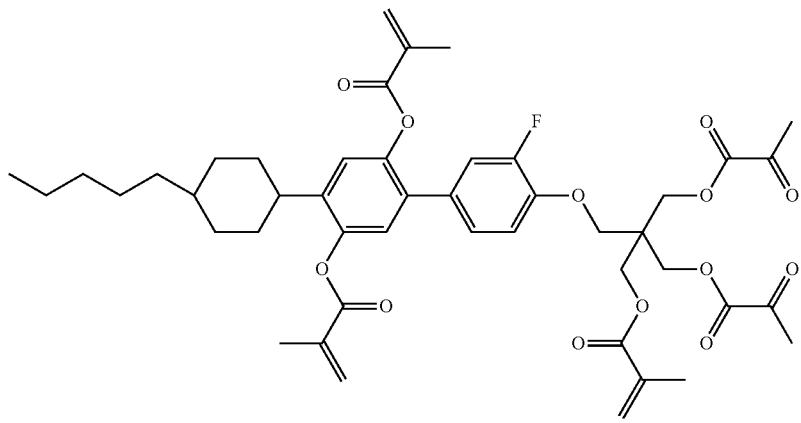
(P-520)
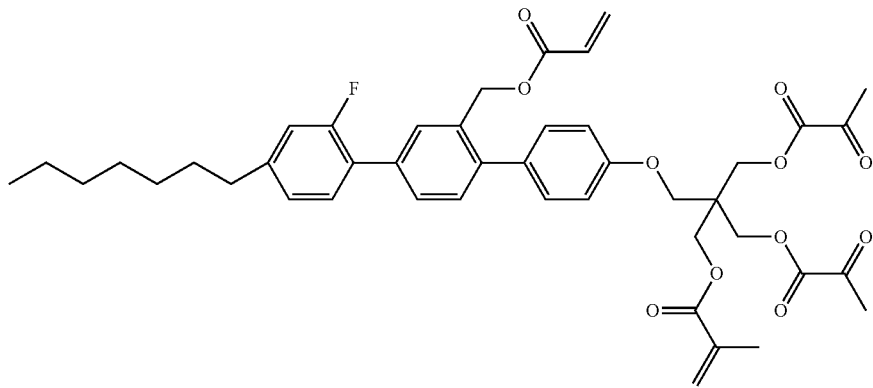
(P-521)

-continued
(P-522)
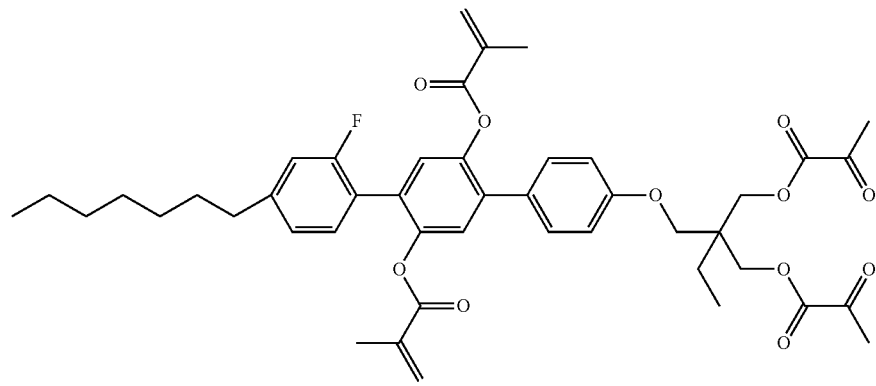
(P-523)
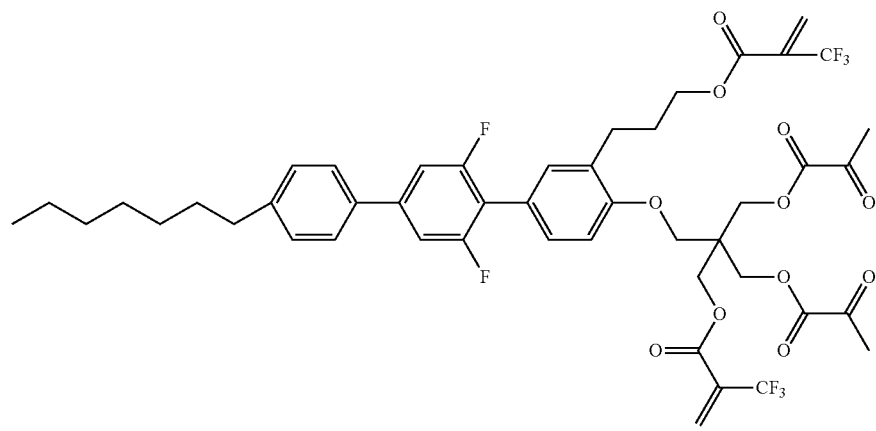
(P-524)
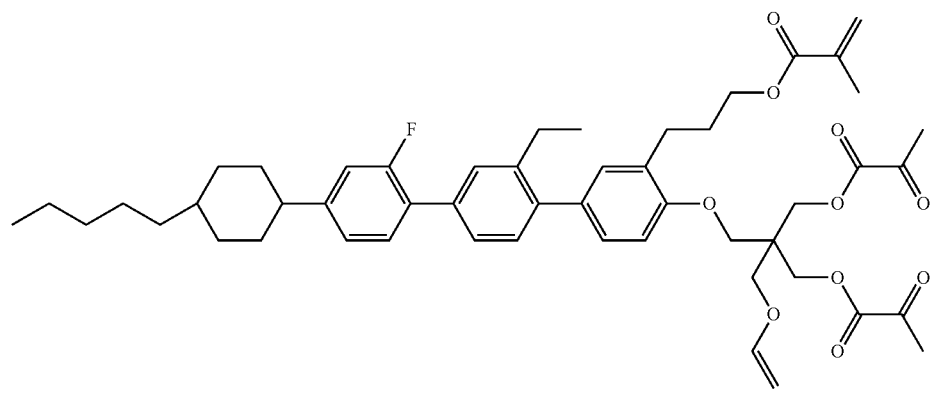
(P-525)
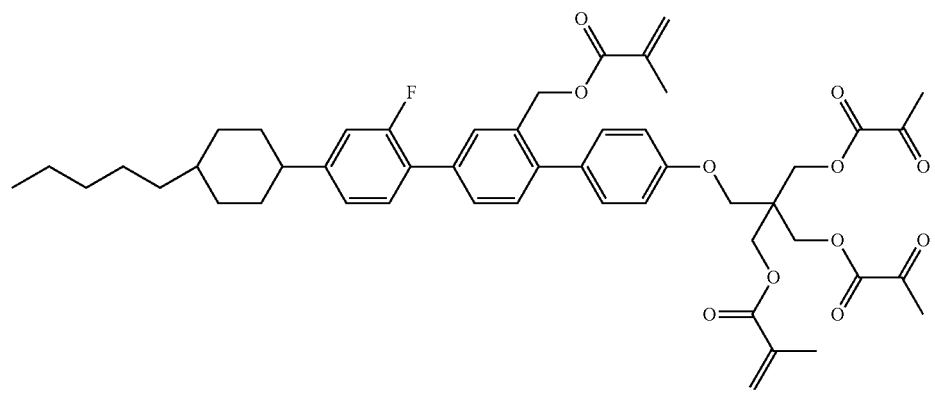

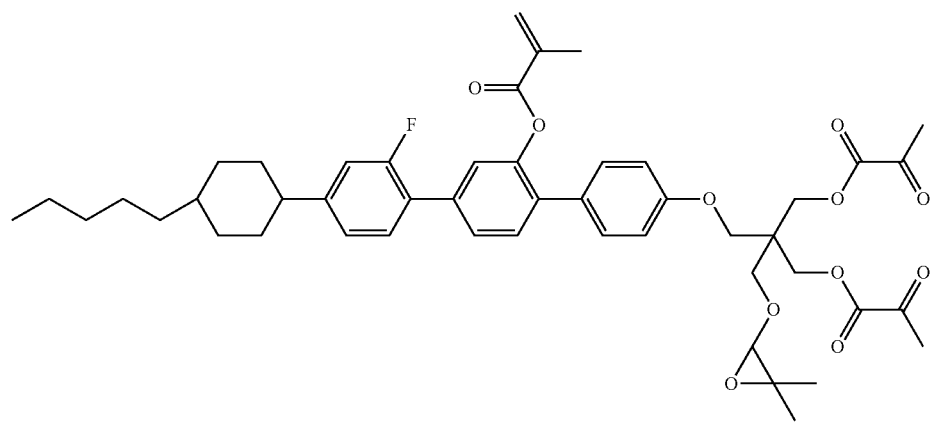
(P-526)
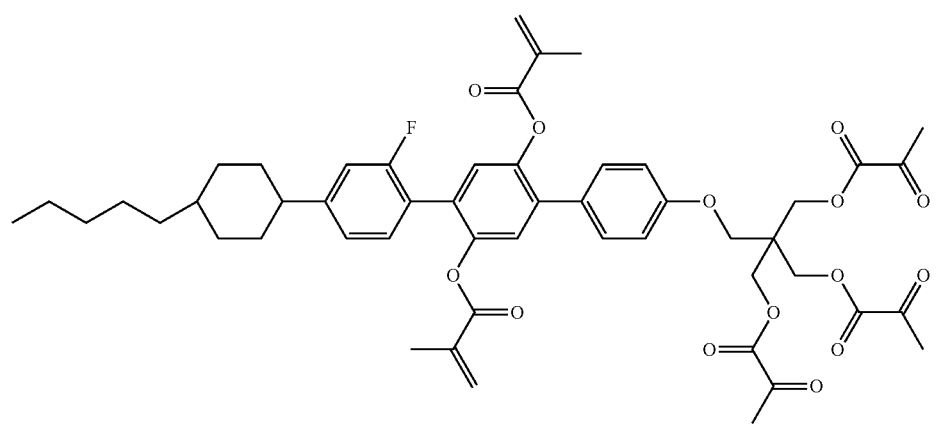
(P-527)
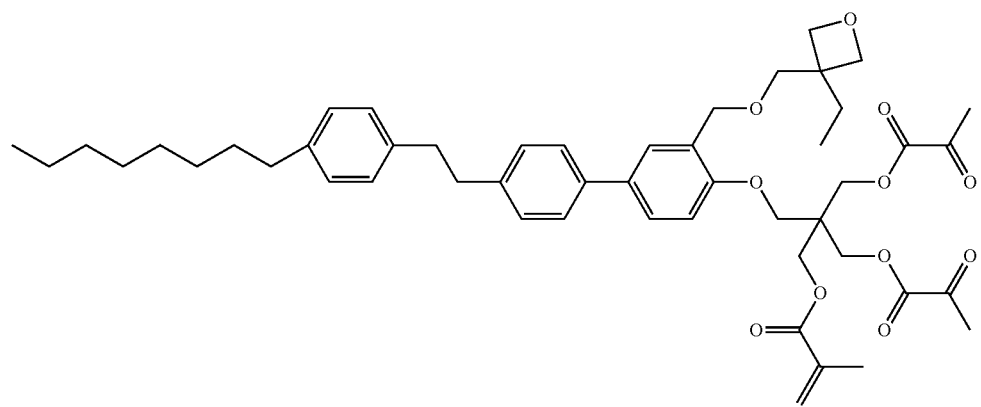
(P-528)

-continued
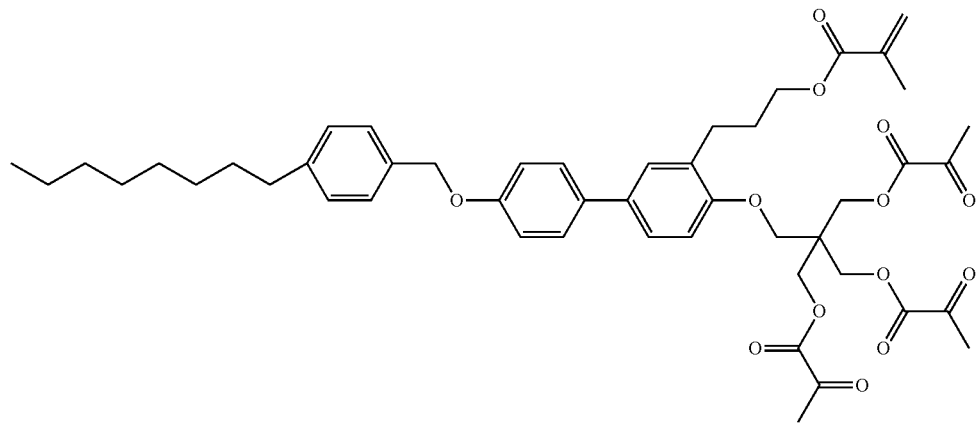
(P-529)
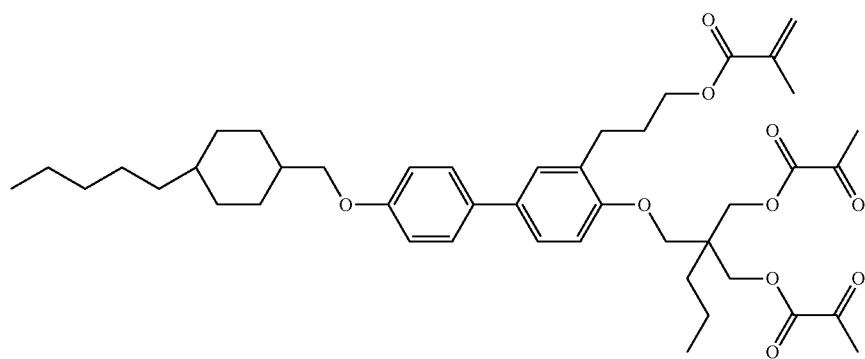
(P-530)
[Chem. 105]
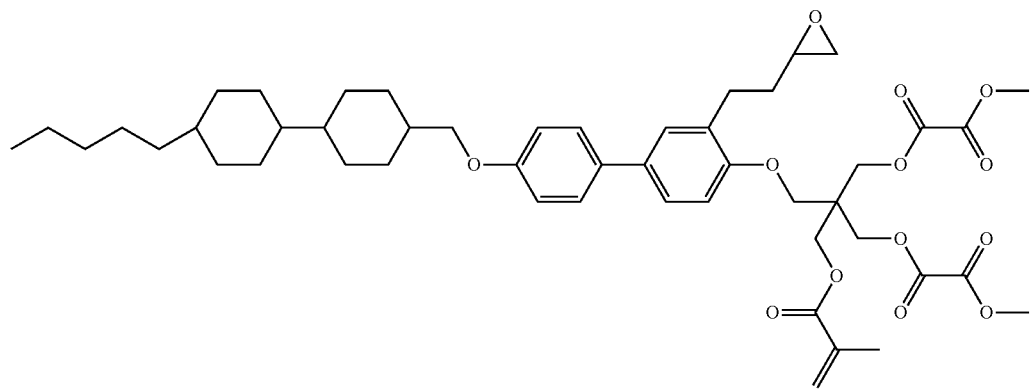
(P-531)
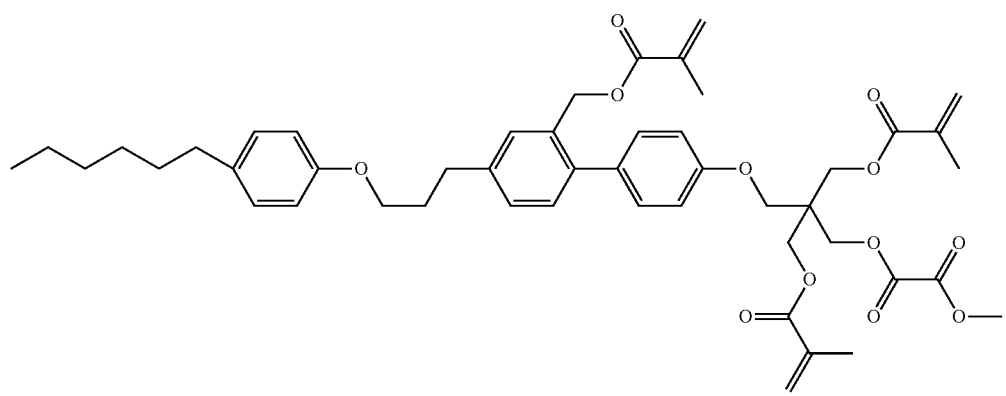
(P-532)

(P-533)
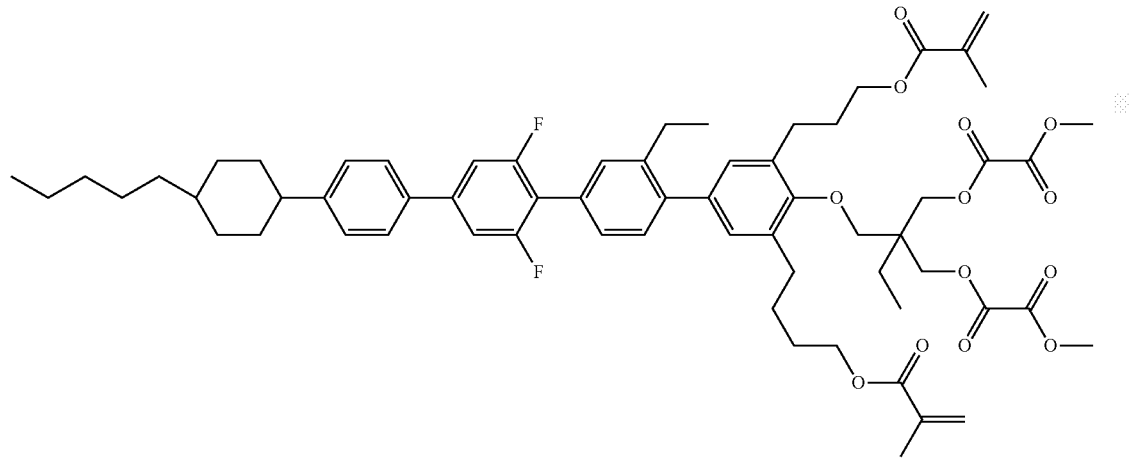
(P-534)
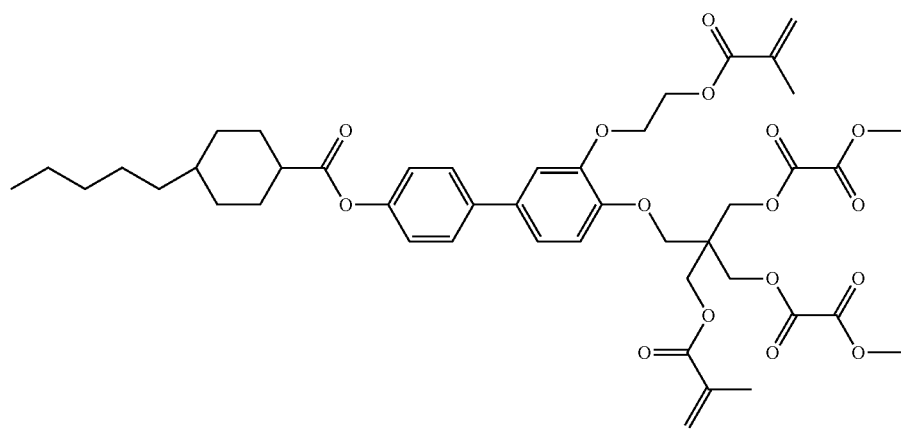
(P-535)
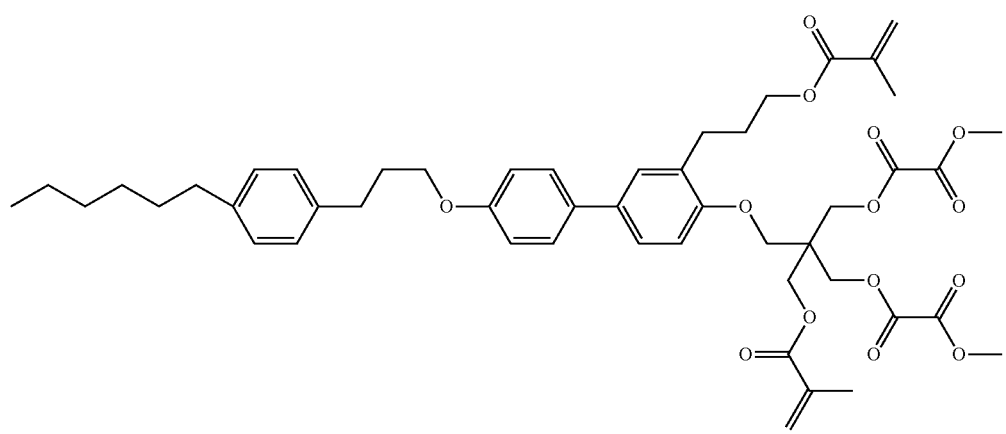

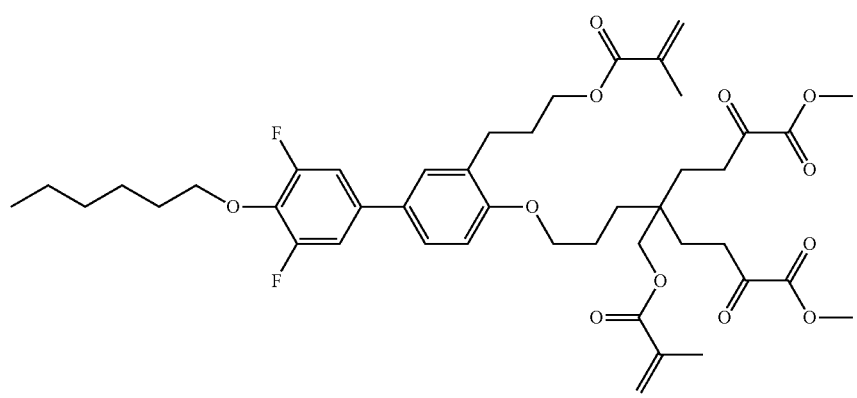
(P-536)
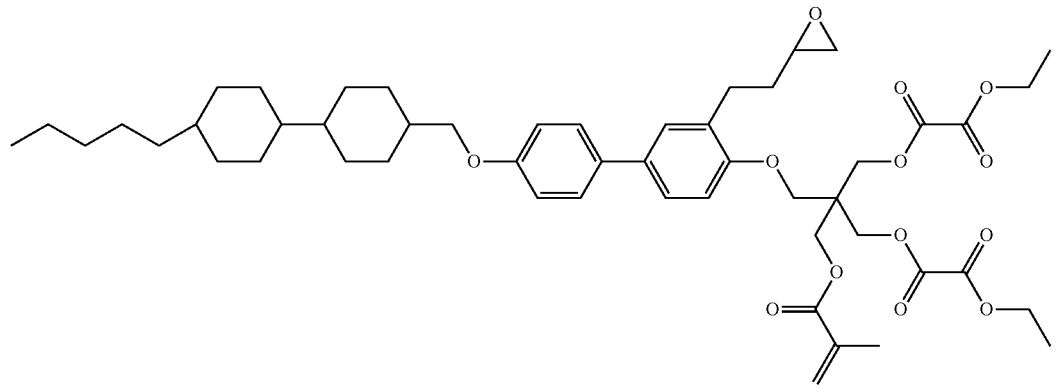
(P-537)
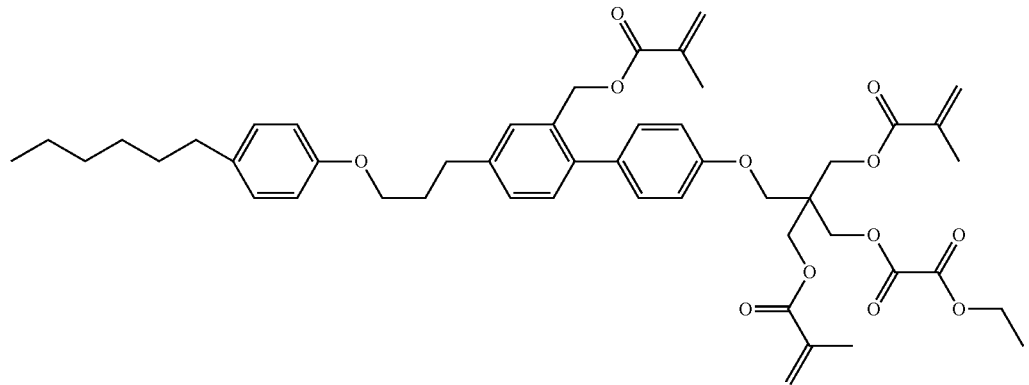
(P-538)
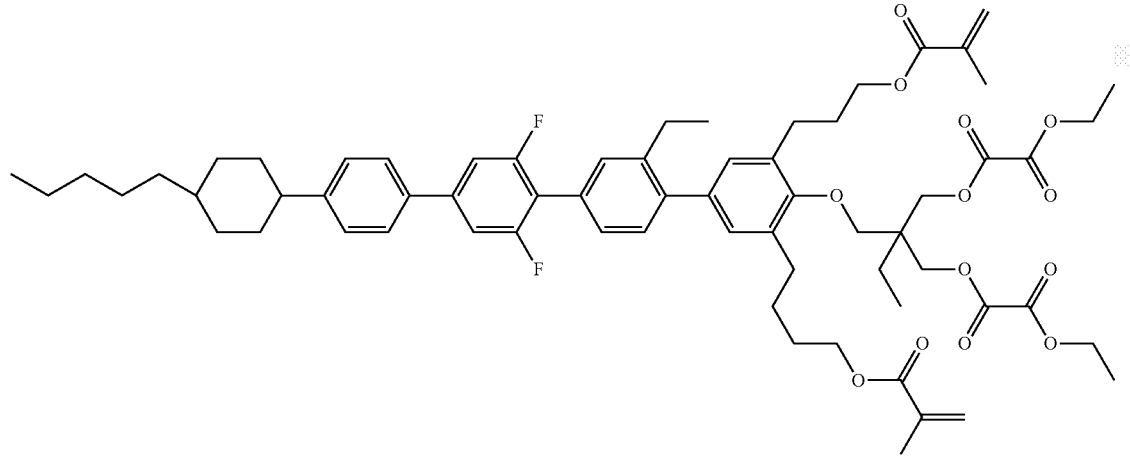
(P-539)

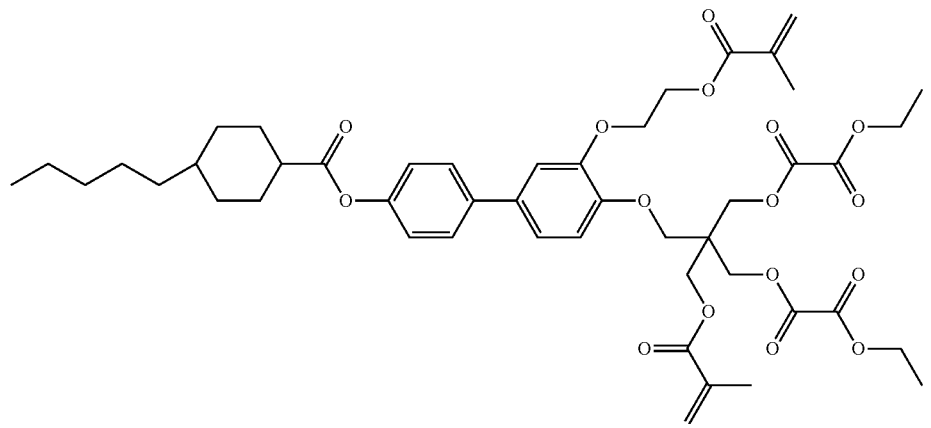
(P-540)
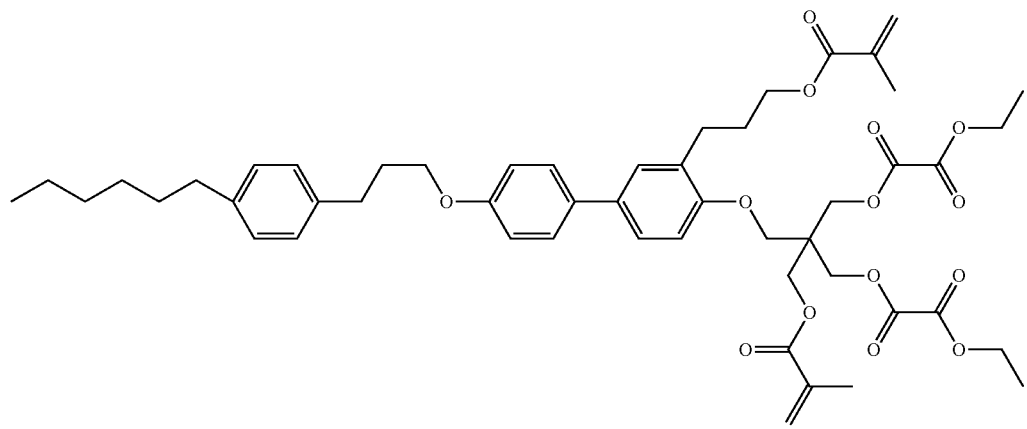
(P-541)
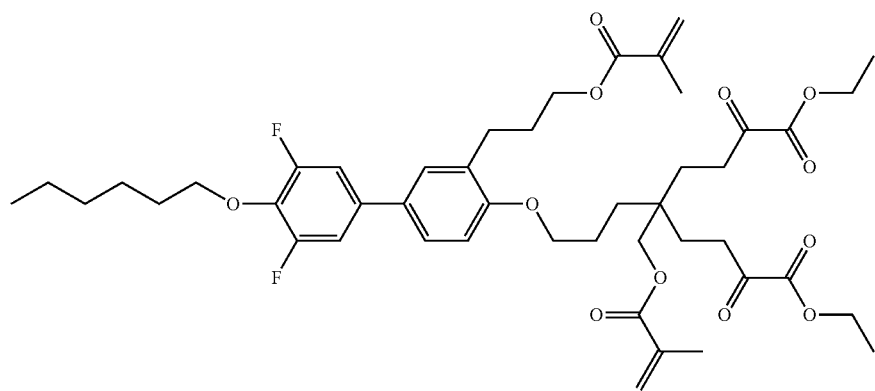
(P-542)

[Chem. 106]
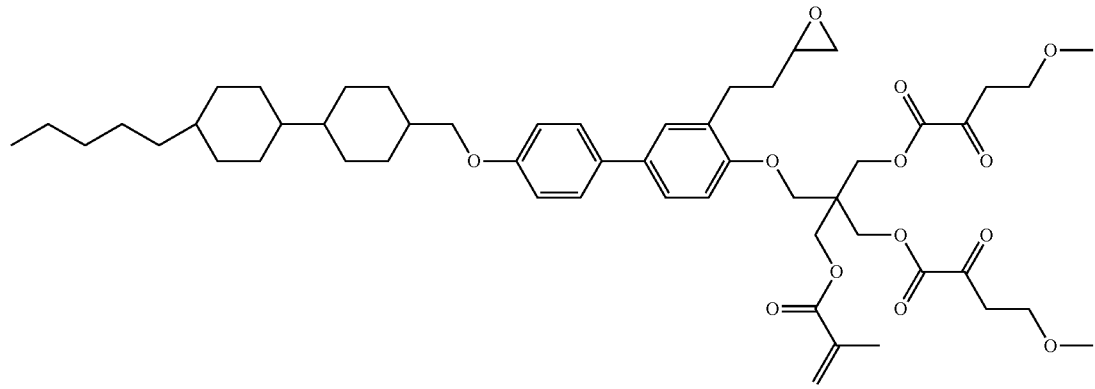
(P-543)
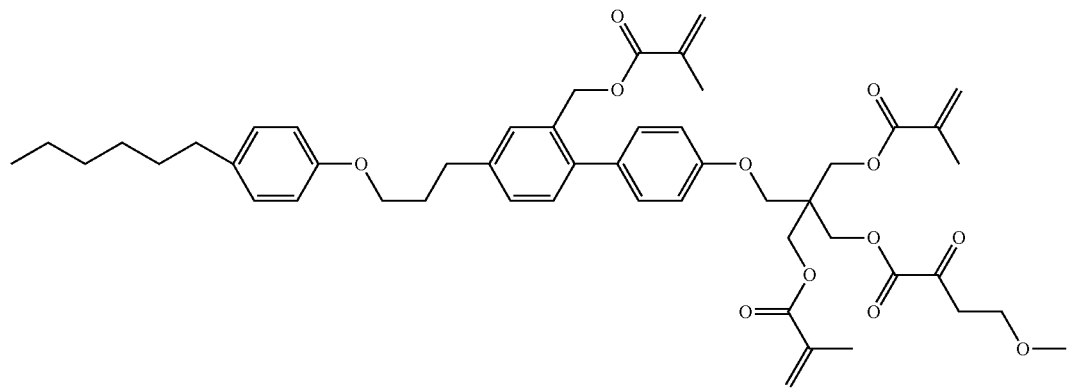
(P-544)
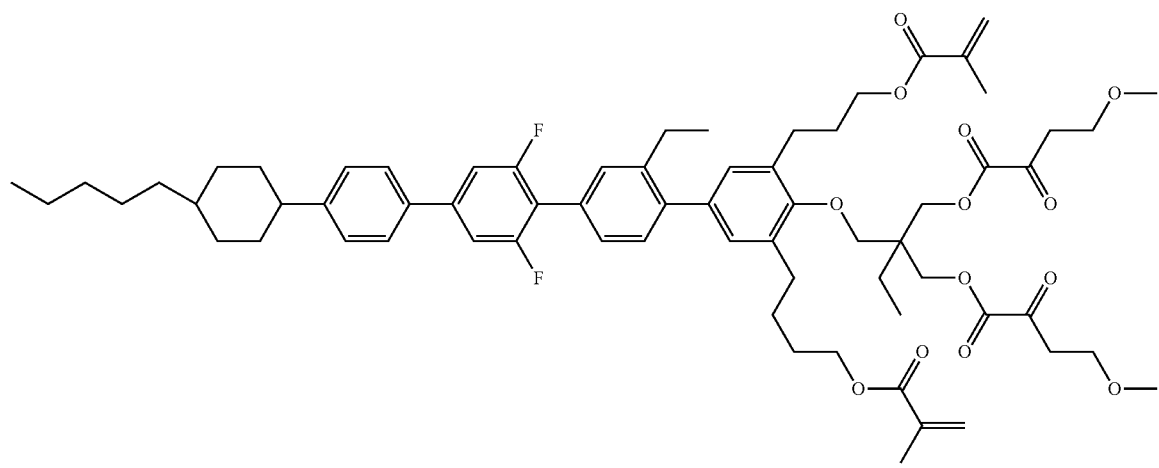
(P-545)

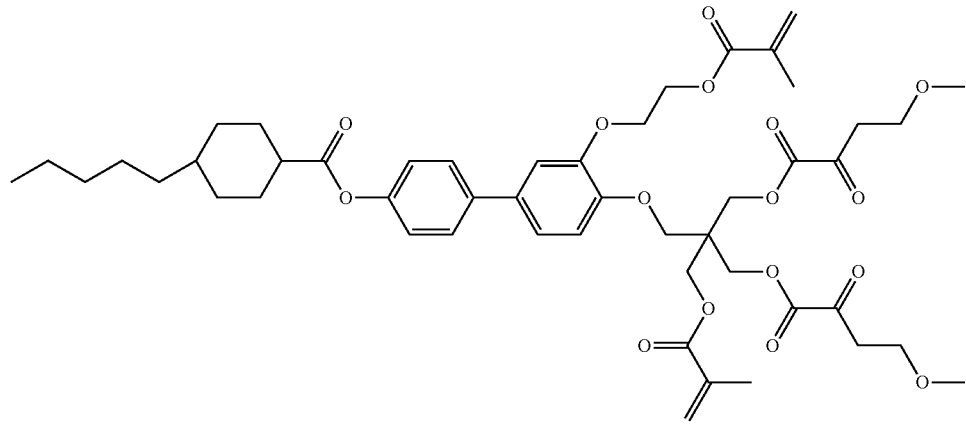
(P-546)
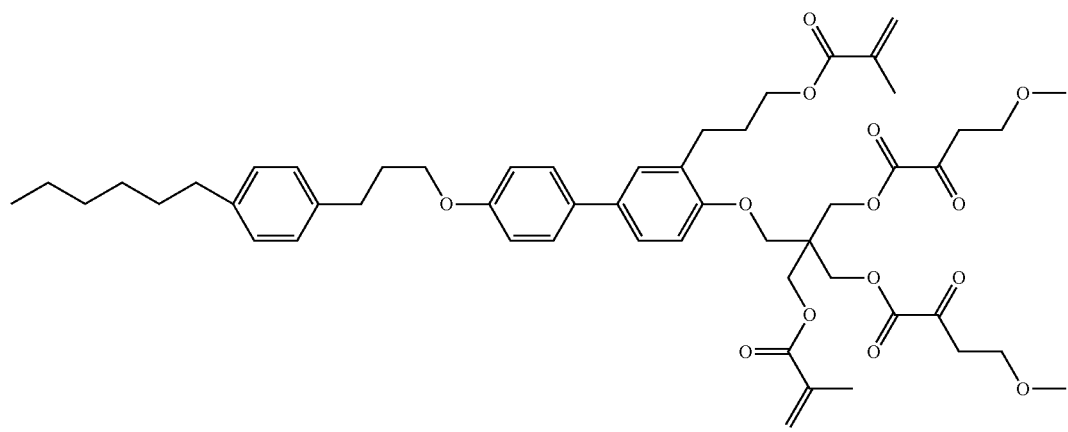
(P-547)
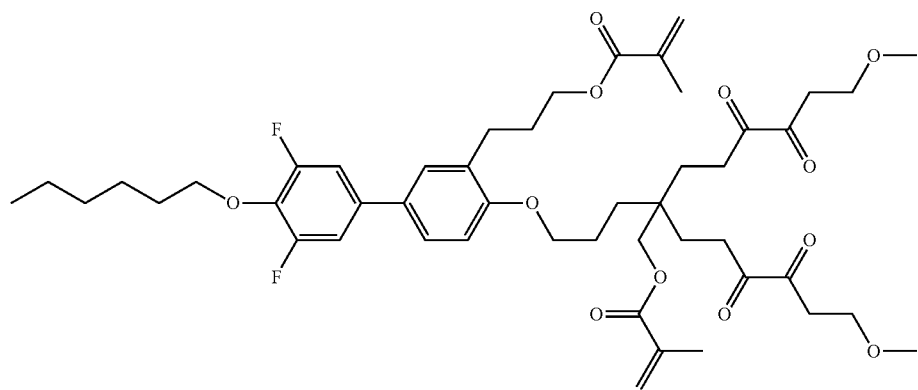
(P-548)

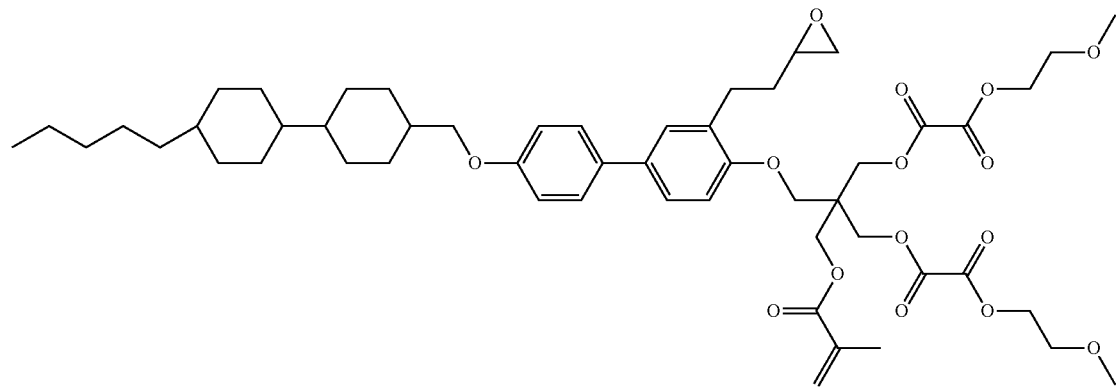
(P-549)
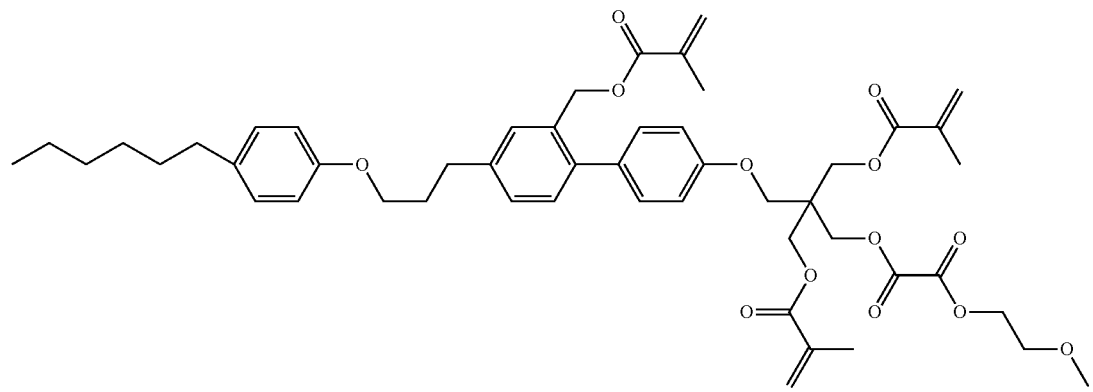
(P-550)
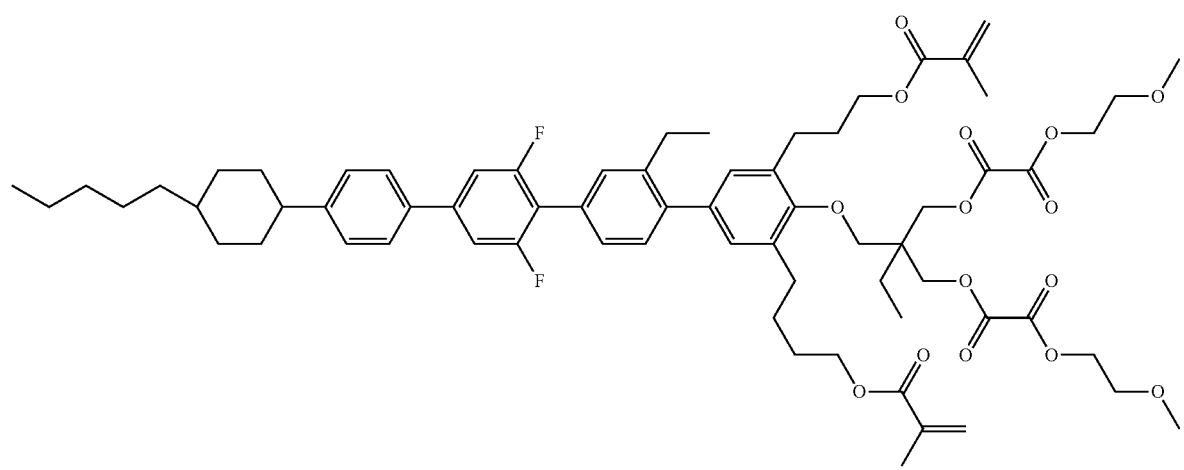
(P-551)

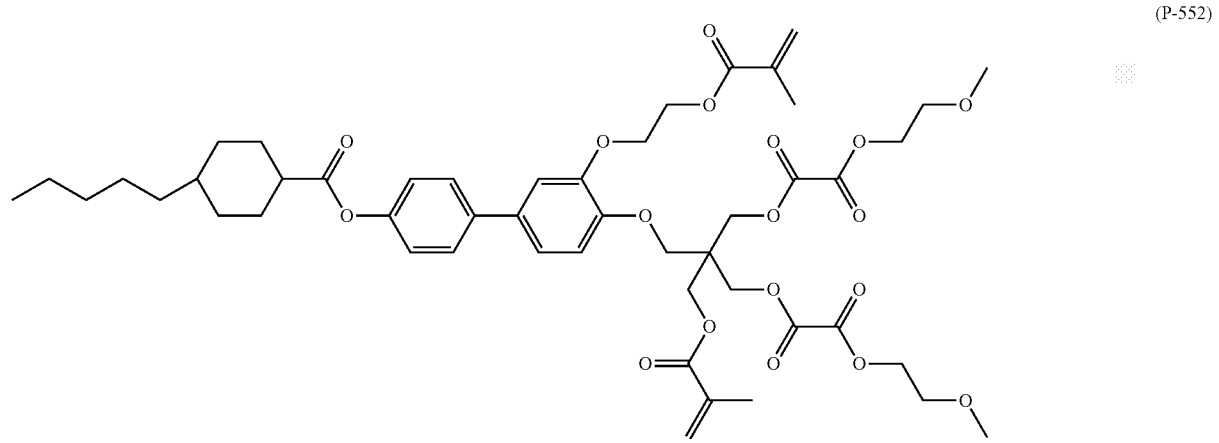
(P-552)
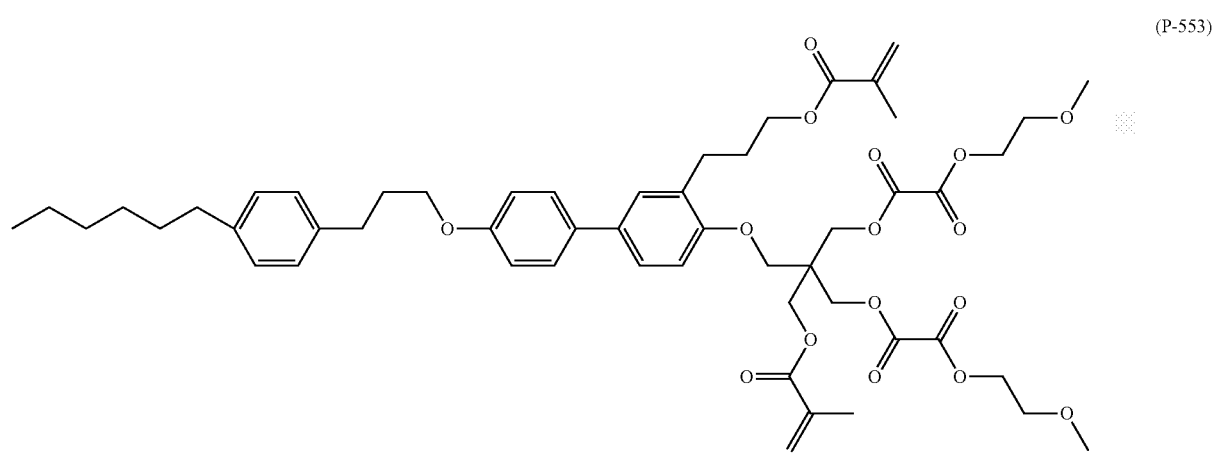
(P-553)
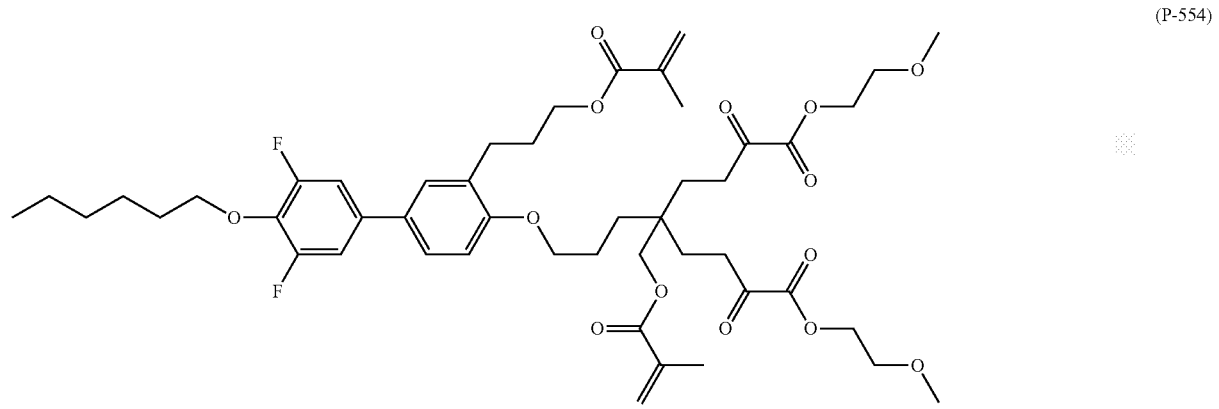
(P-554)

[Chem. 107]
-continued
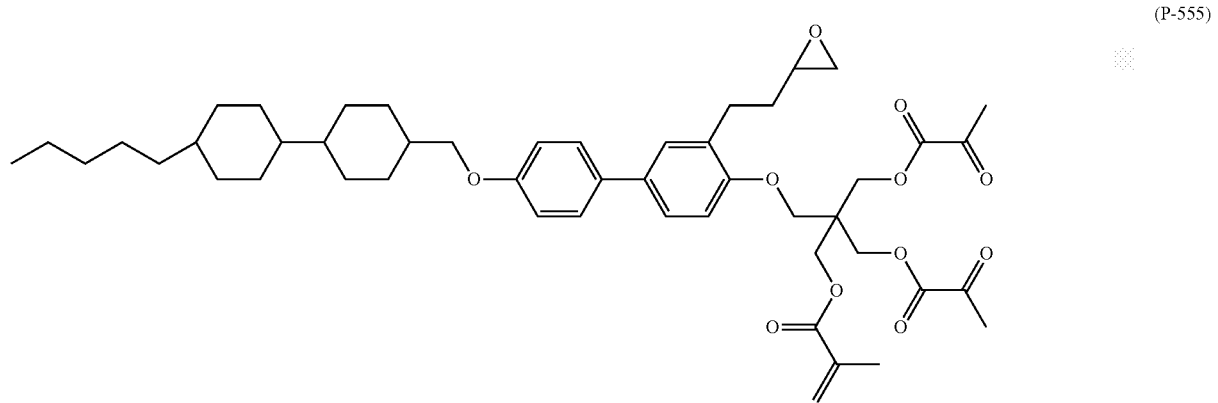
(P-555)
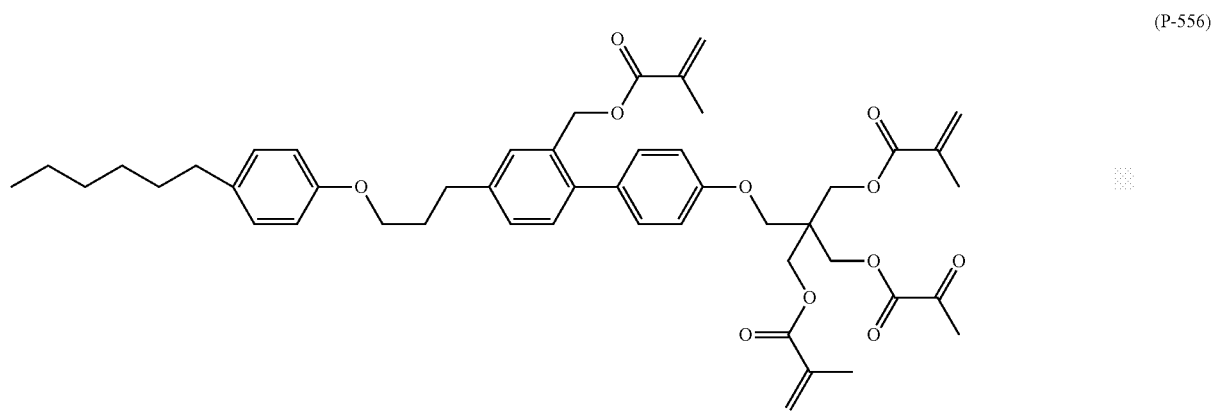
(P-556)
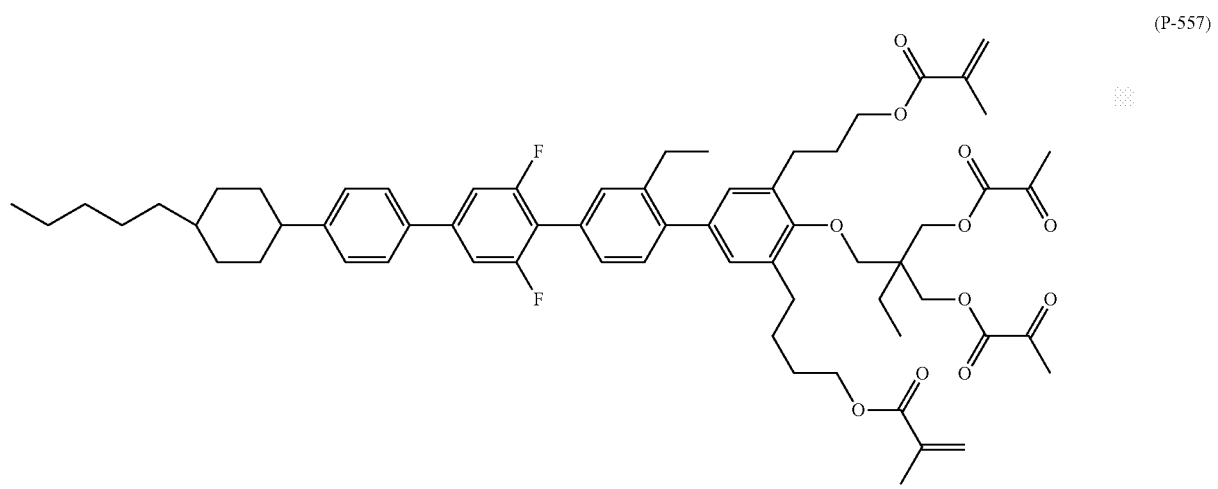
(P-557)

(P-558)
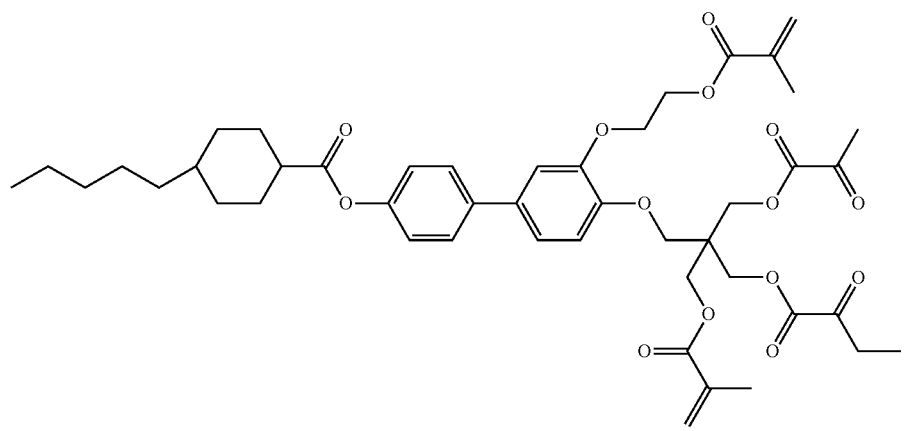
(P-559)
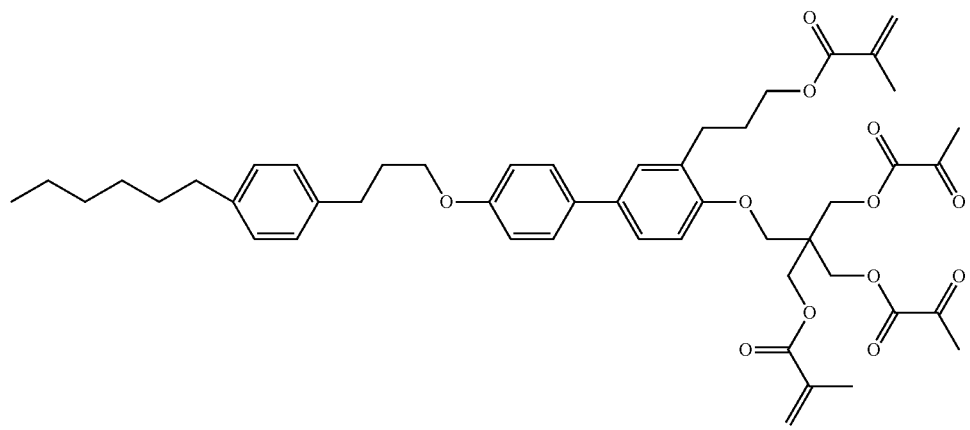
(P-560)
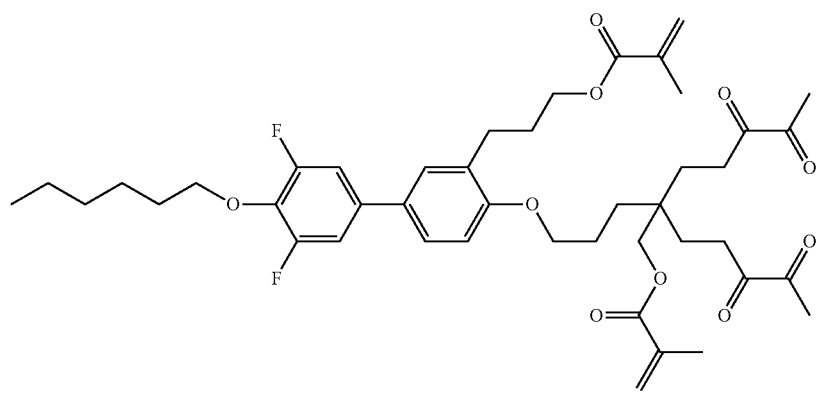
(P-561)
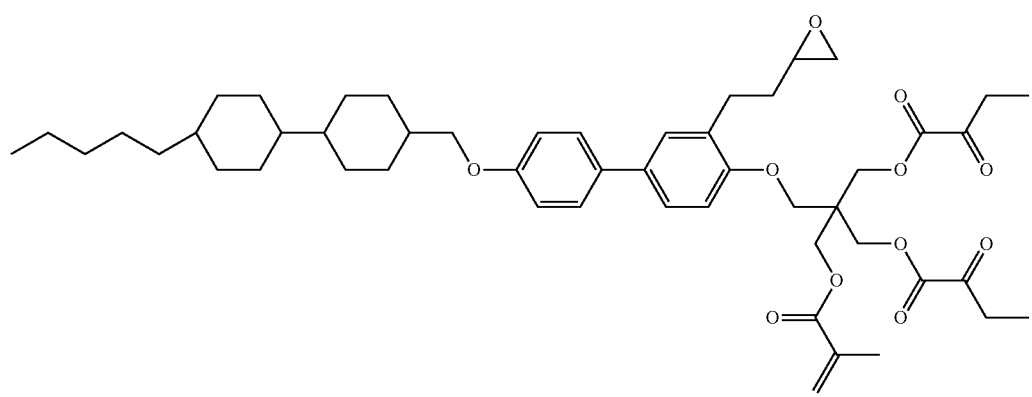

(P-562)
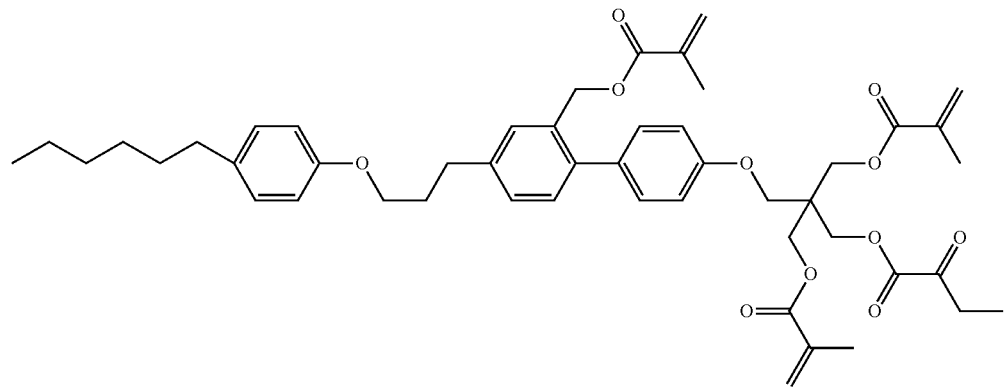
(P-563)
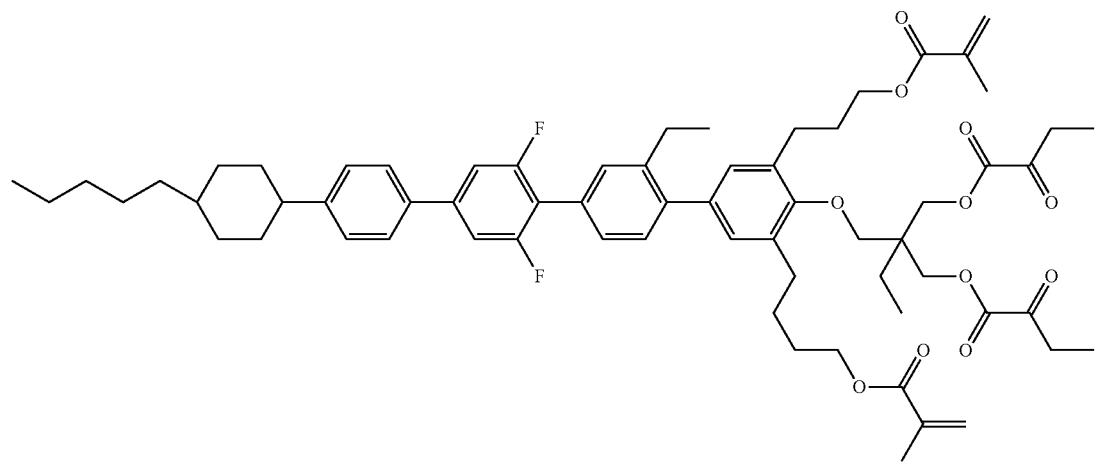
(P-564)
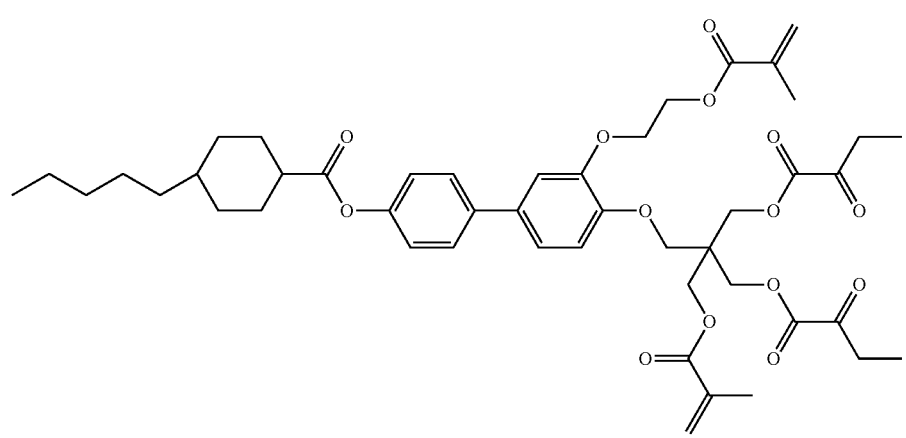

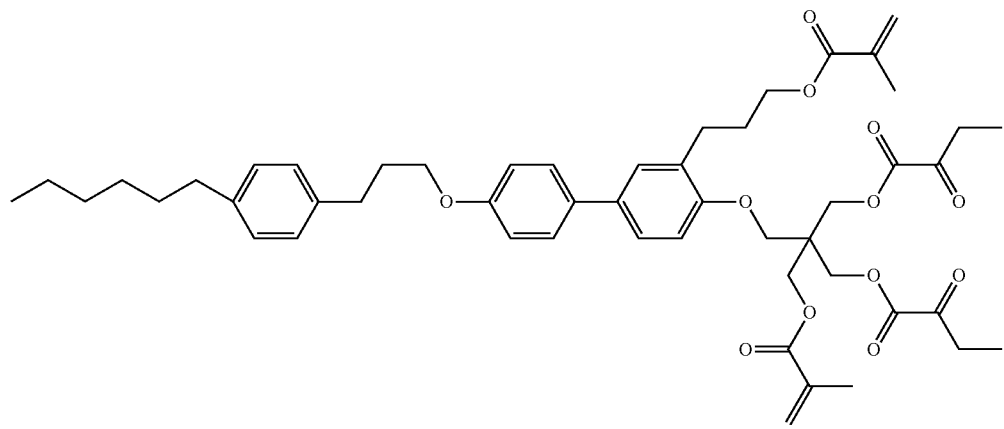
(P-565)
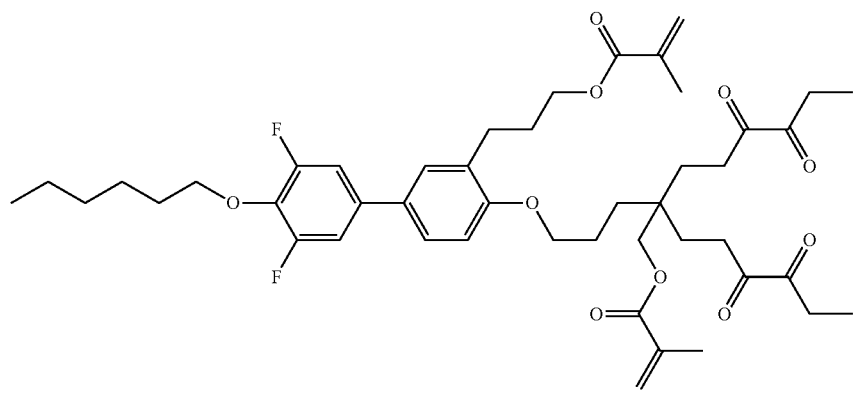
(P-566)
[Chem. 108]
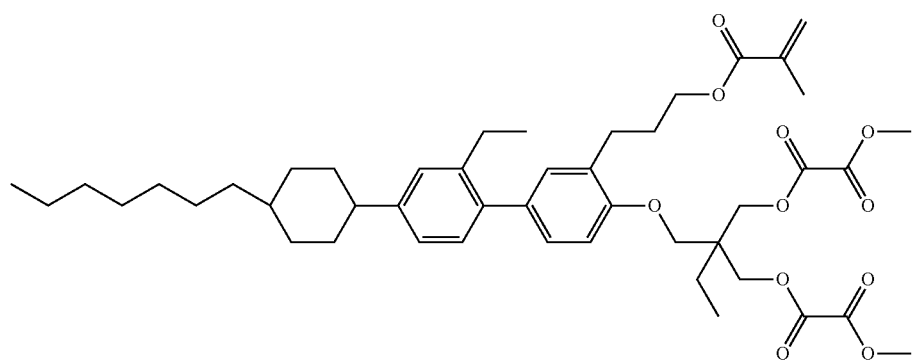
(P-567)
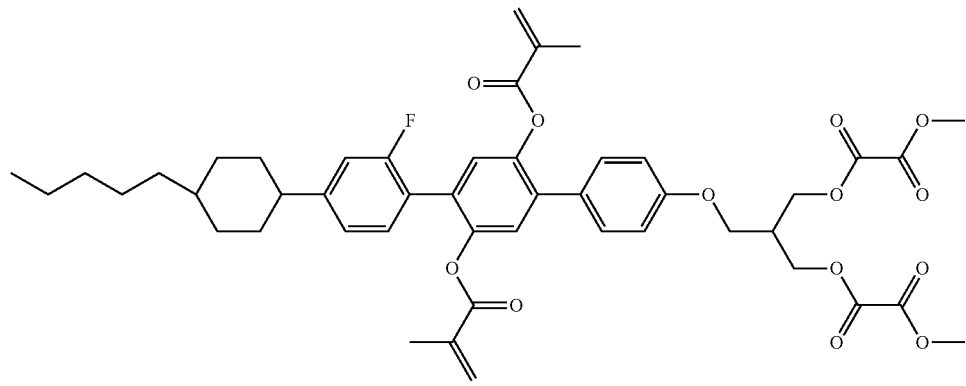
(P-568)

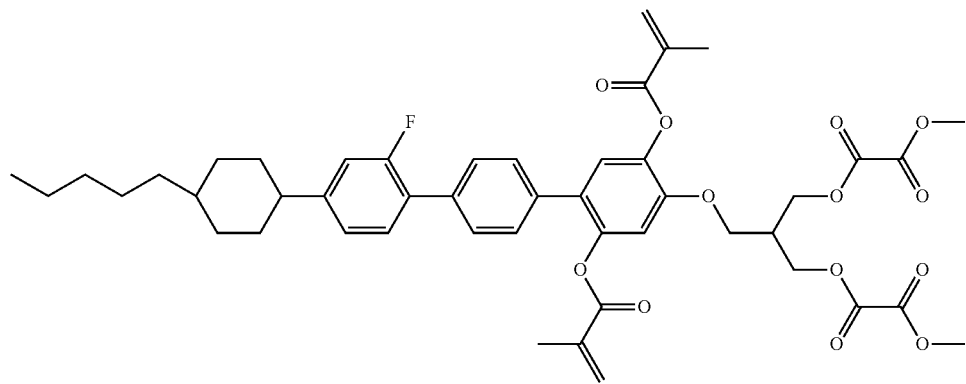
(P-569)
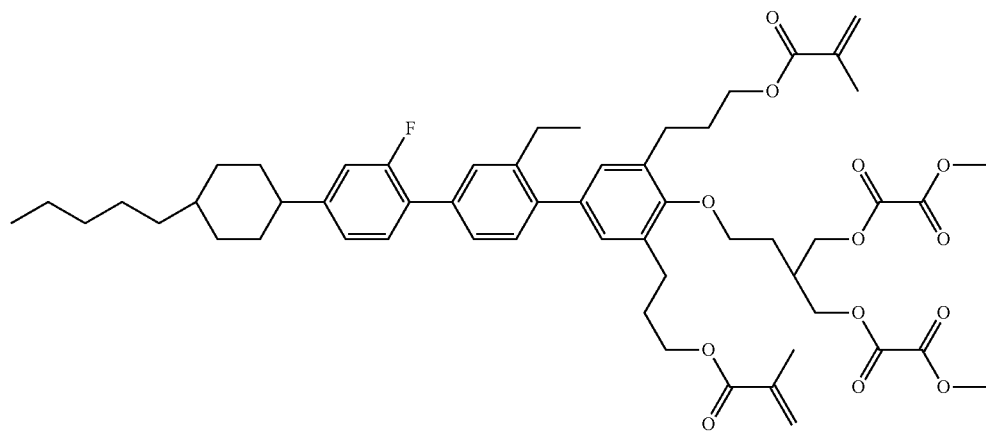
(P-570)
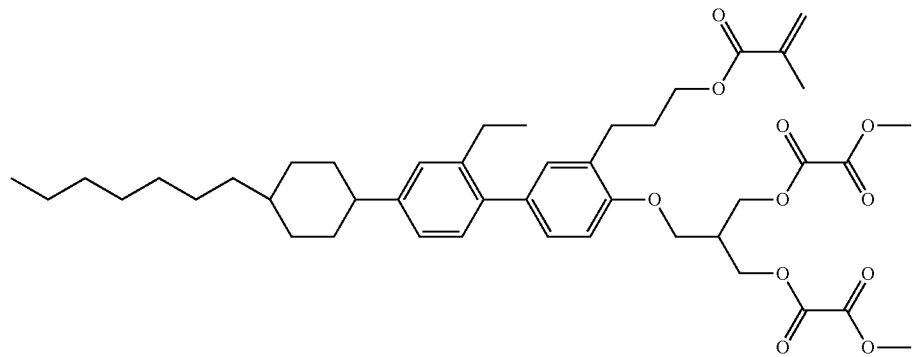
(P-571)
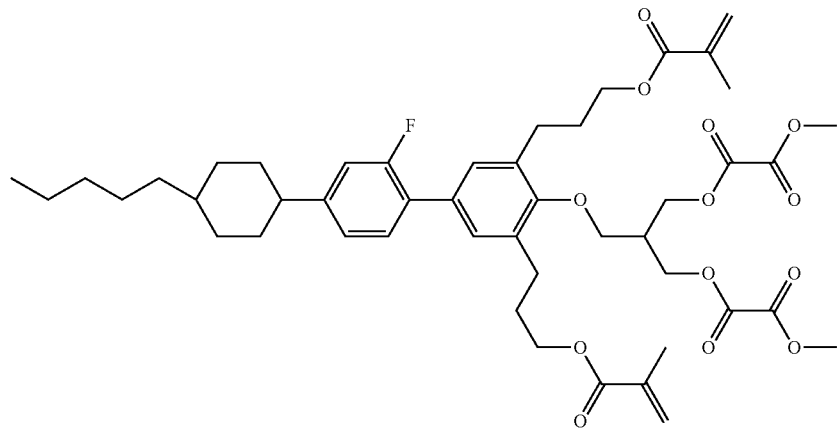
(P-572)

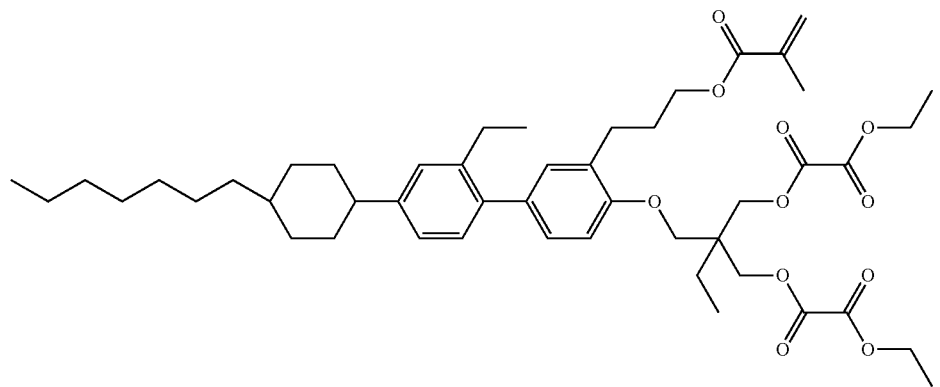
(P-573)
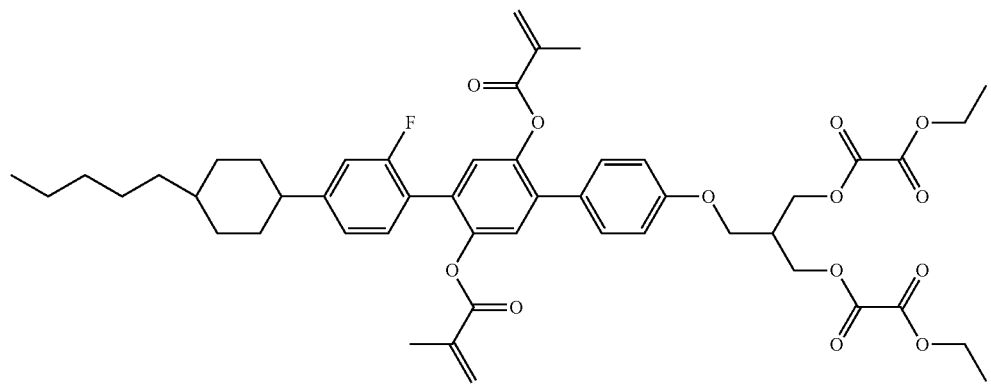
(P-574)
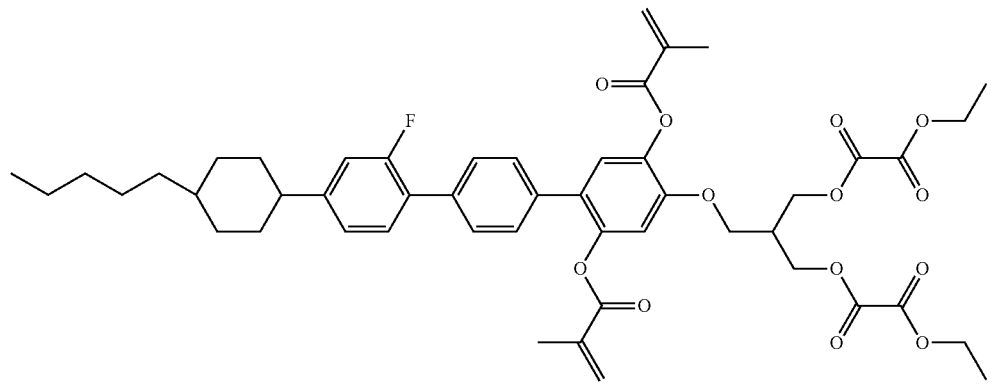
(P-575)
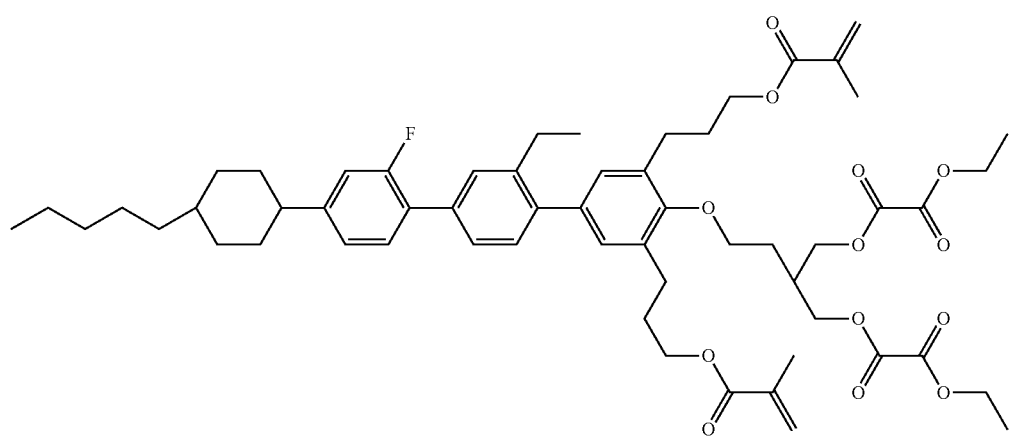
(P-576)

-continued
(P-578)
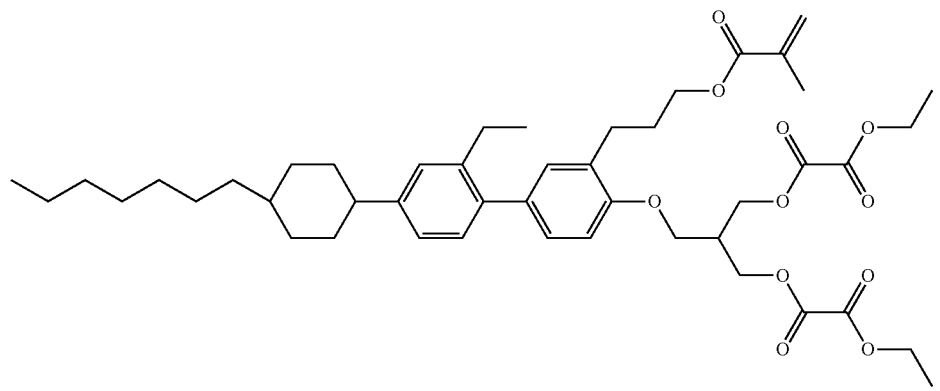
(P-579)
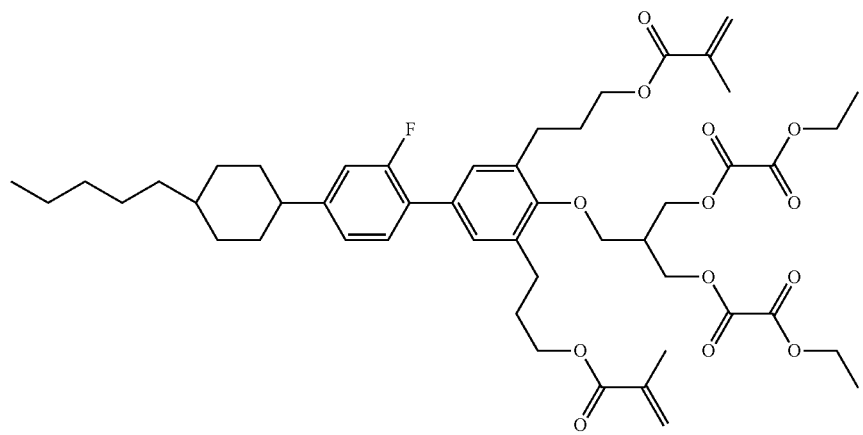
[Chem. 109]
(P-580)
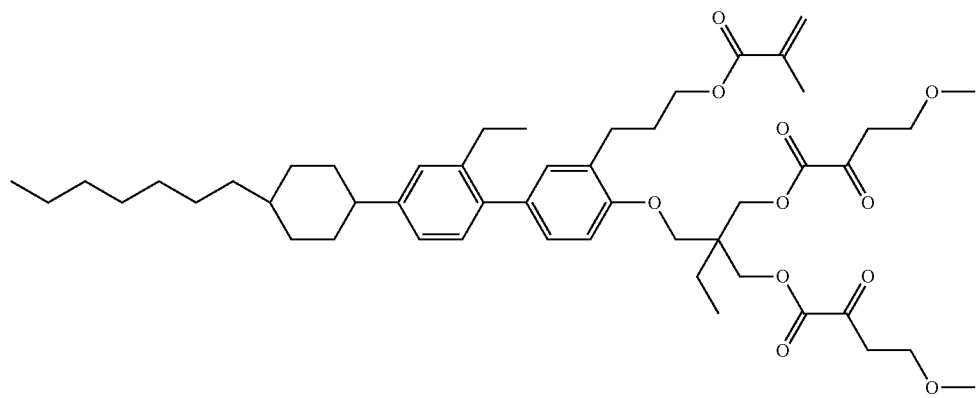
(P-581)
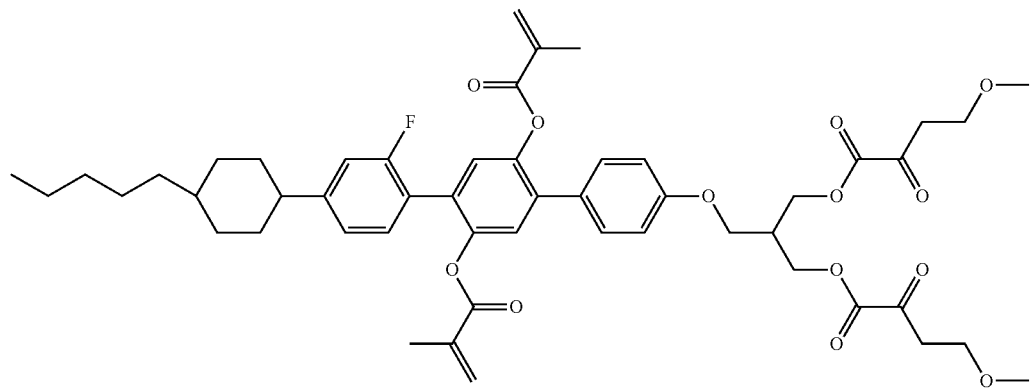

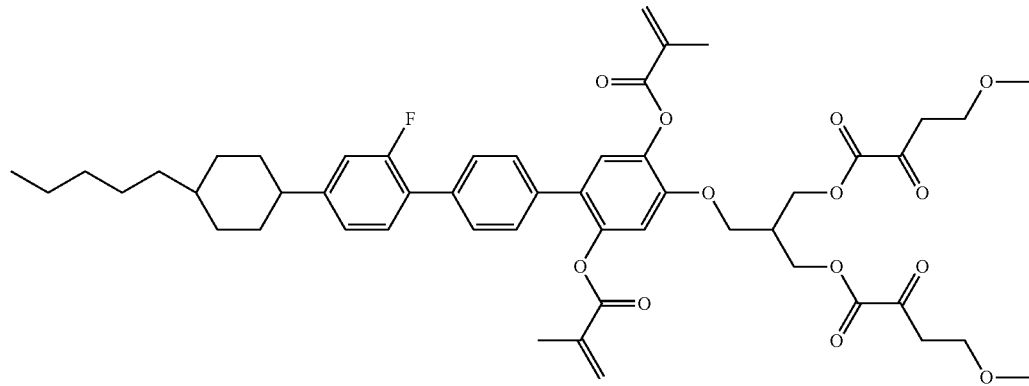
(P-582)
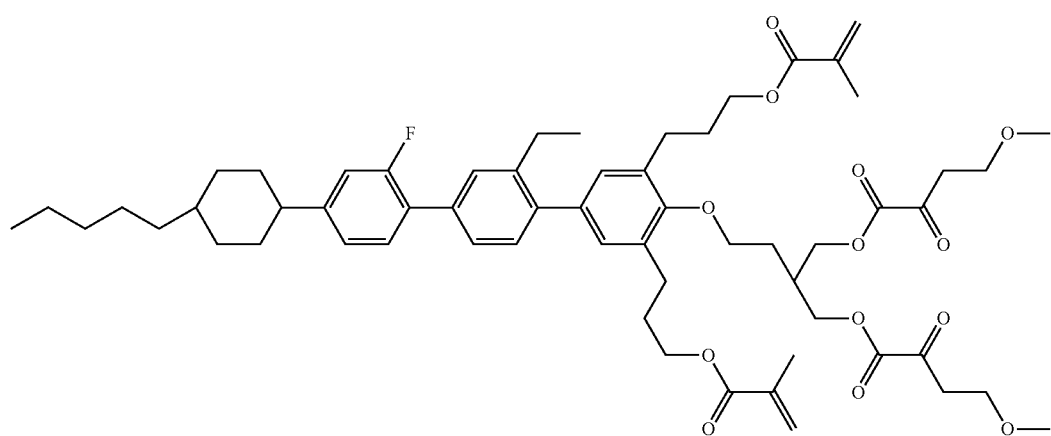
(P-583)
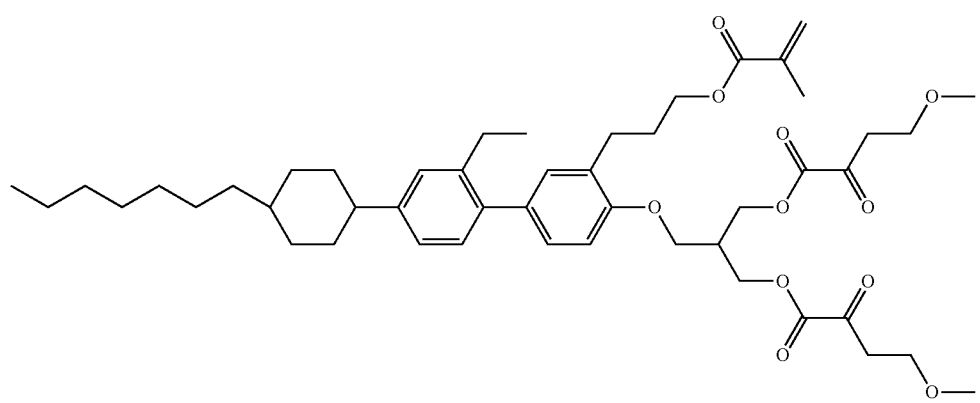
(P-584)

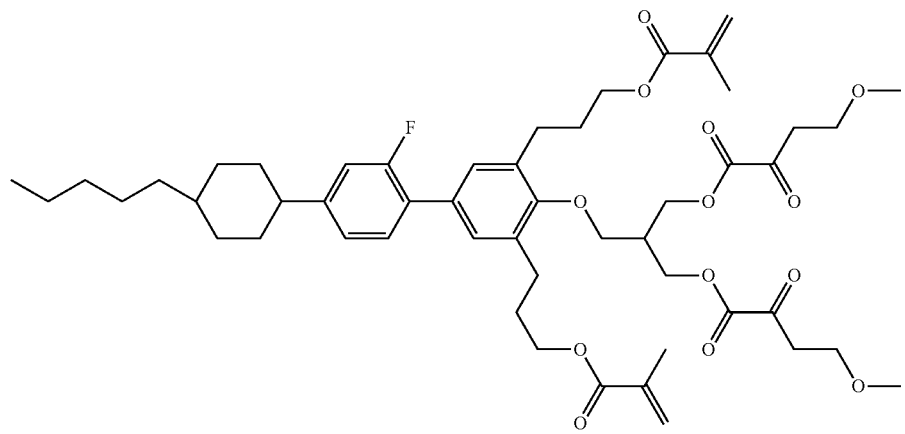
(P-585)
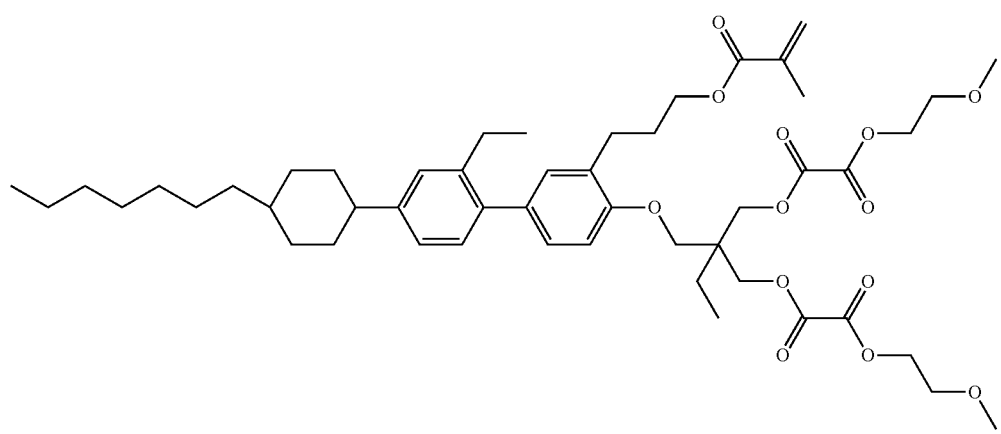
(P-586)
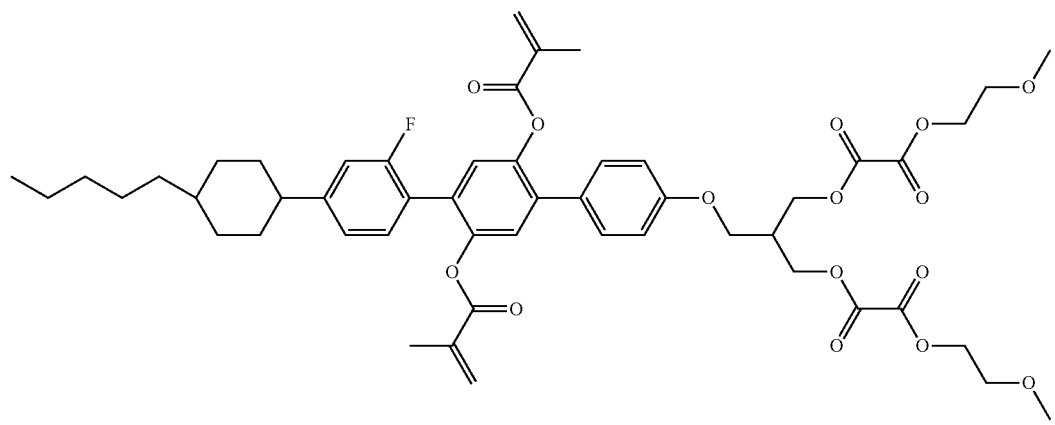
(P-587)

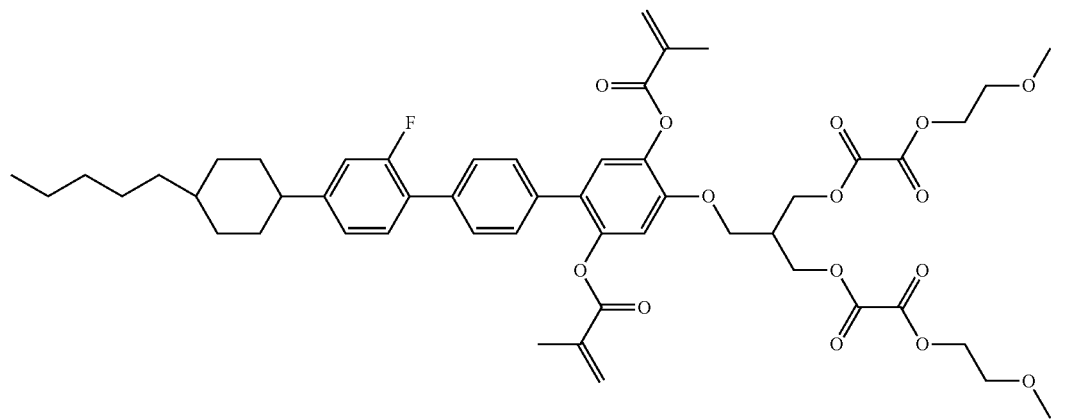
(P-588)
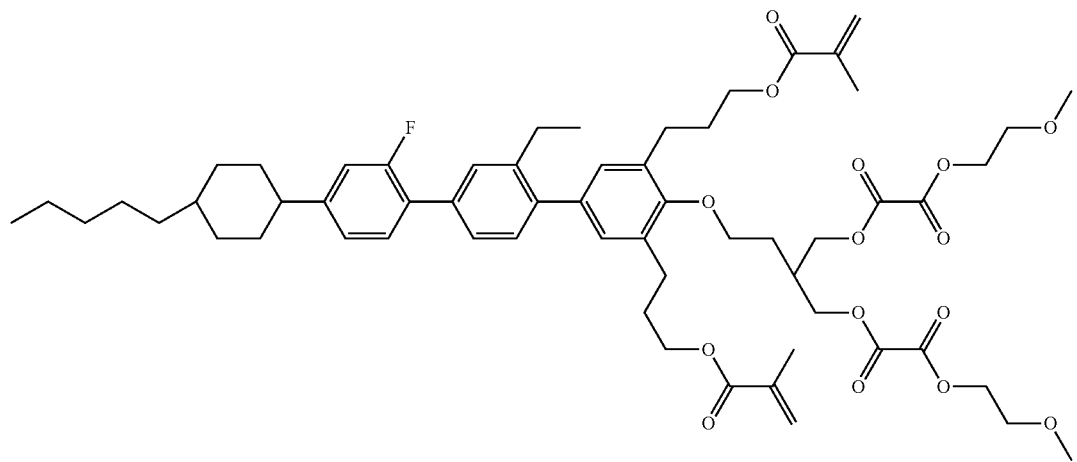
(P-589)
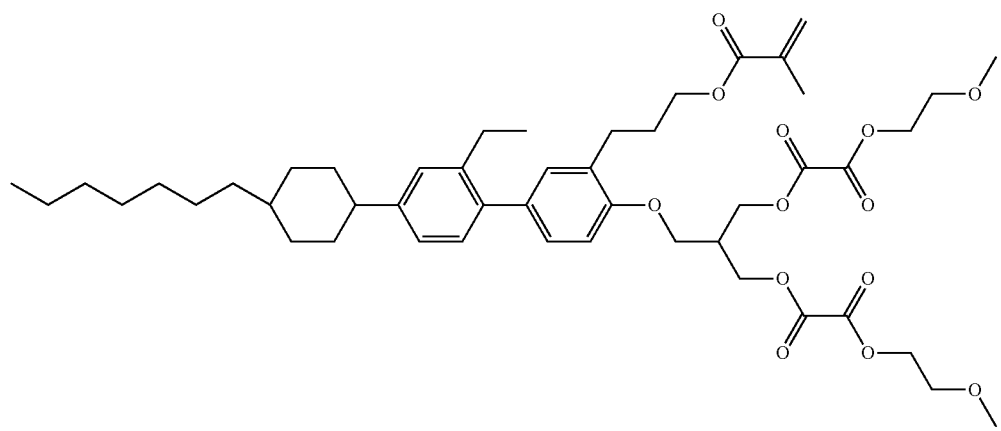
(P-590)

(P-591)
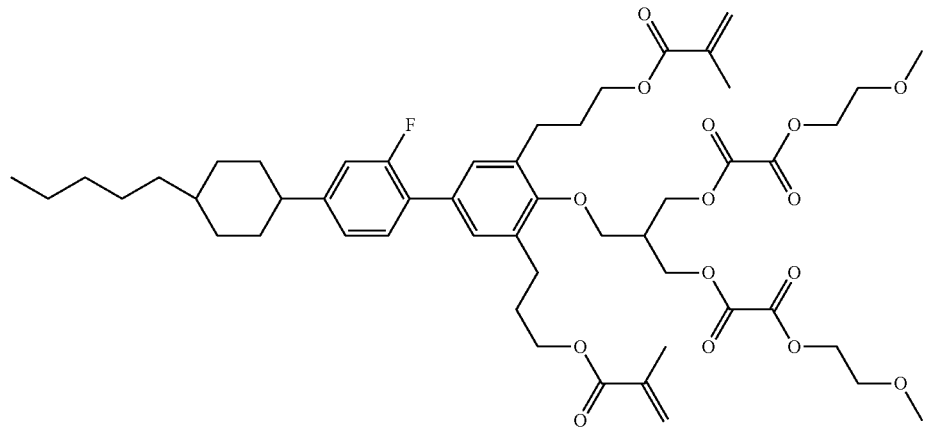
[Chem. 110]
(P-592)
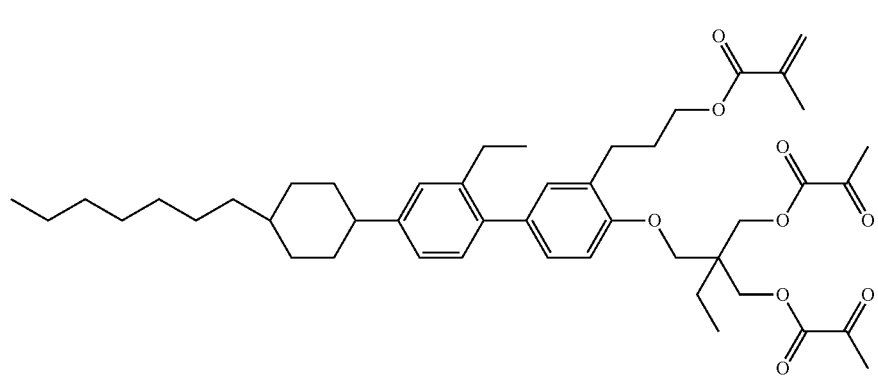
(P-593)
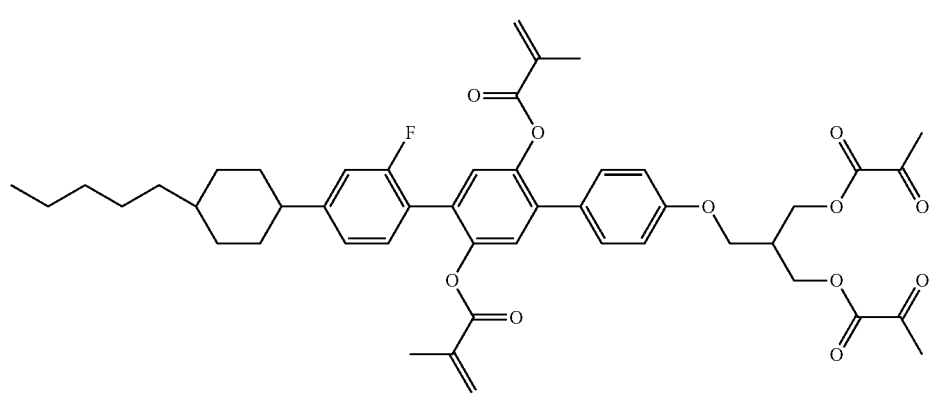
(P-594)
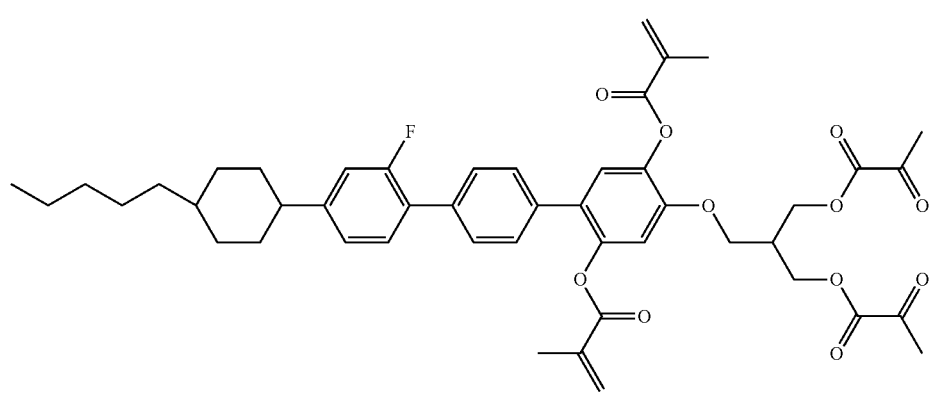

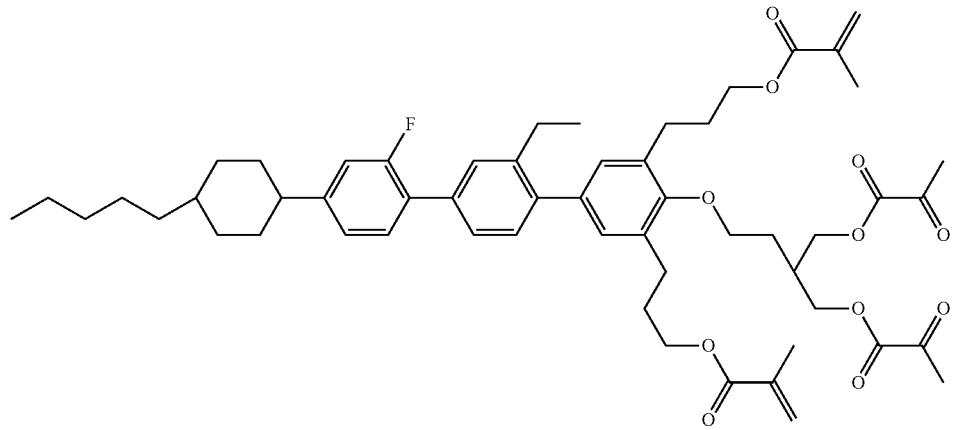
(P-595)
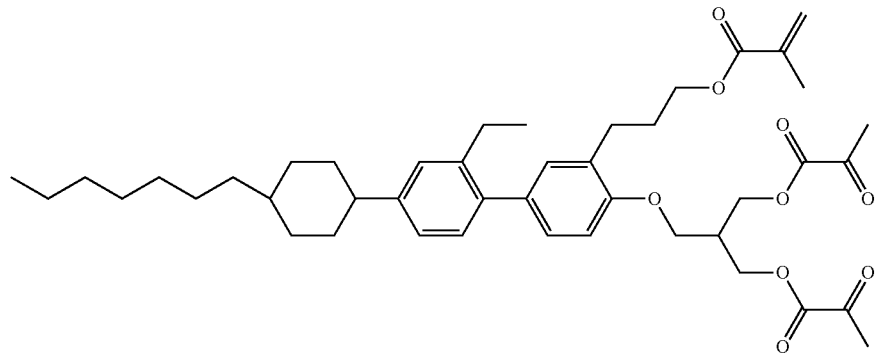
(P-596)
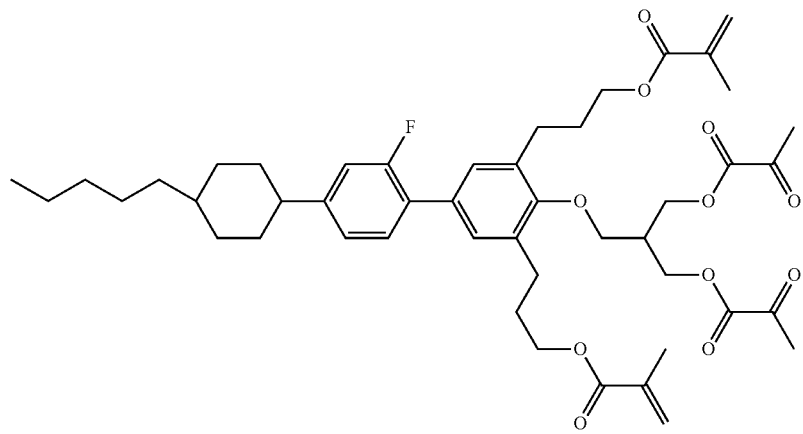
(P-597)
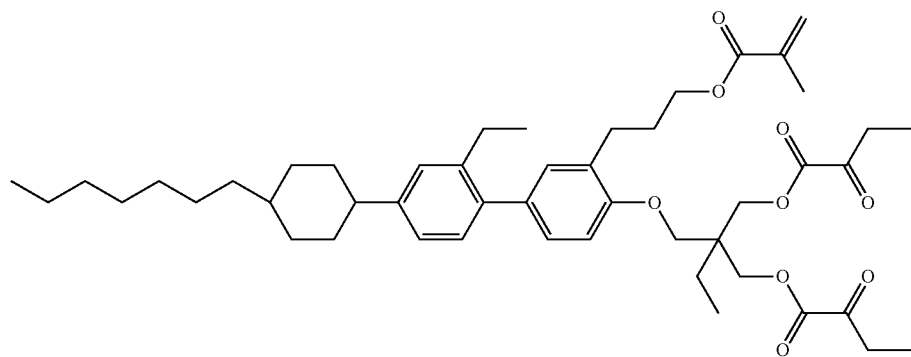
(P-598)

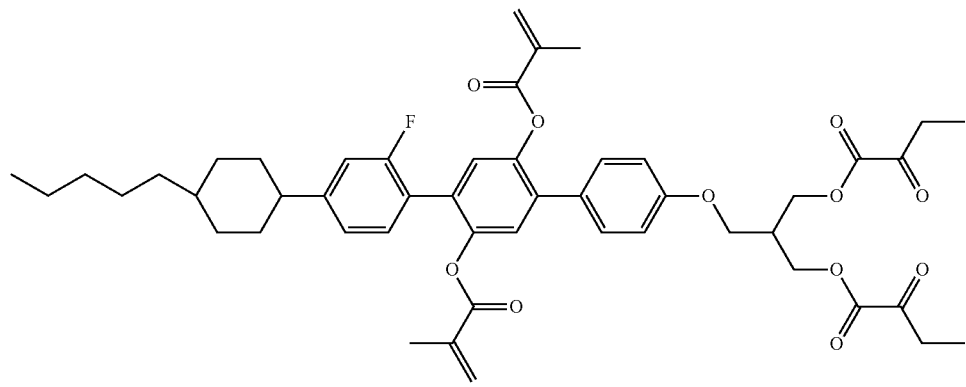
(P-599)
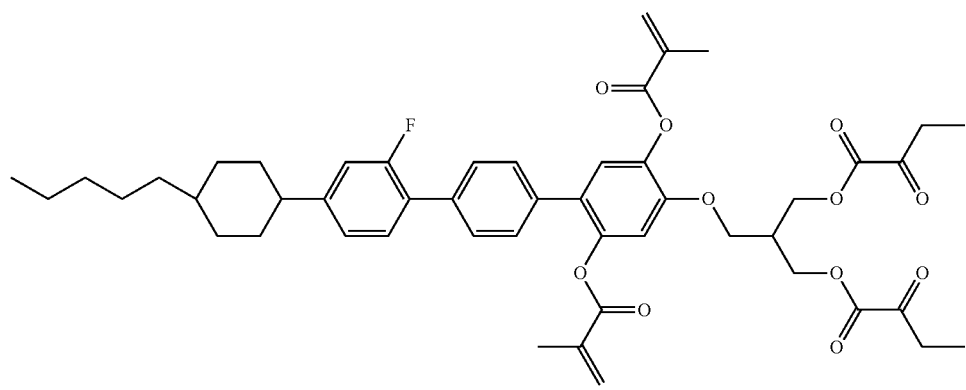
(P-600)
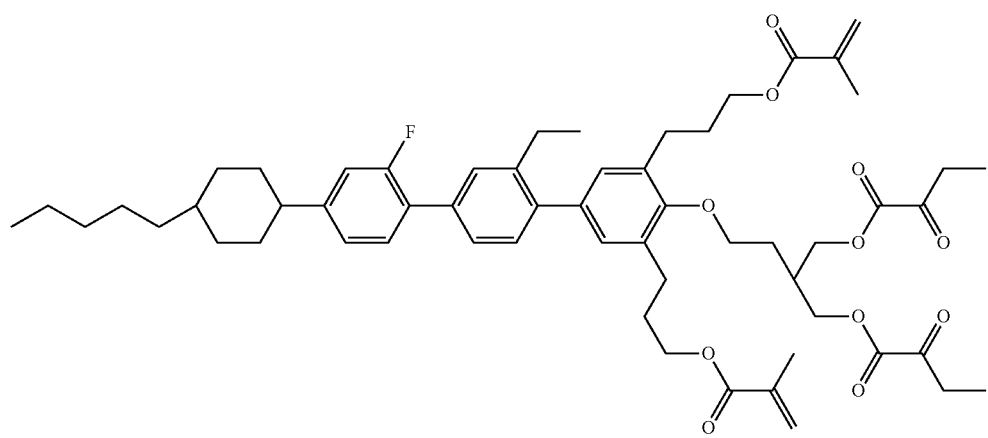
(P-601)
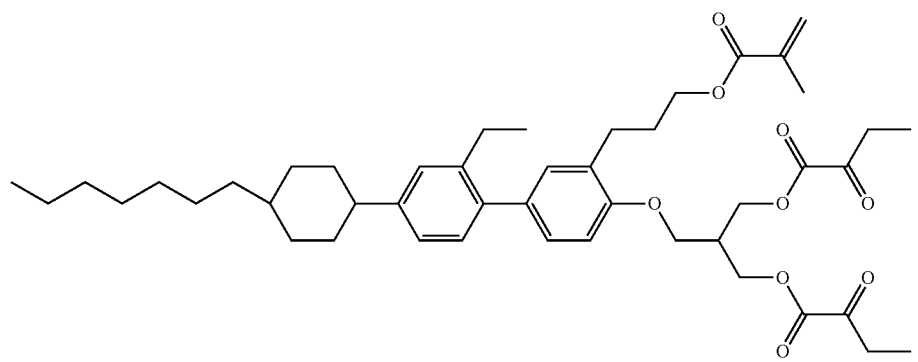
(P-602)

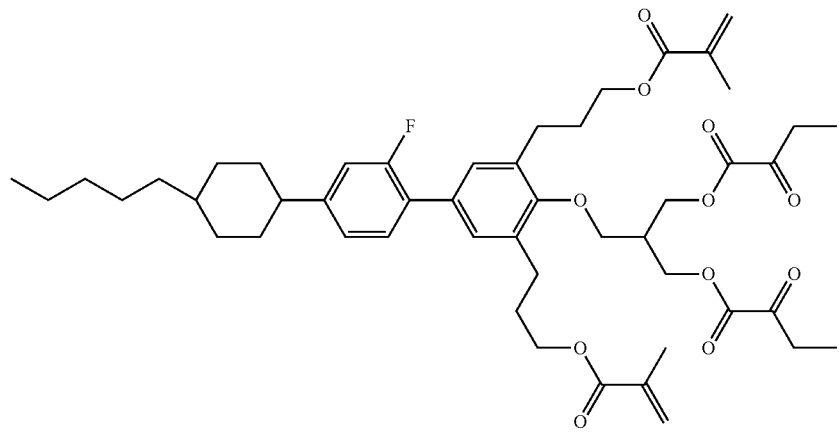
(P-603)
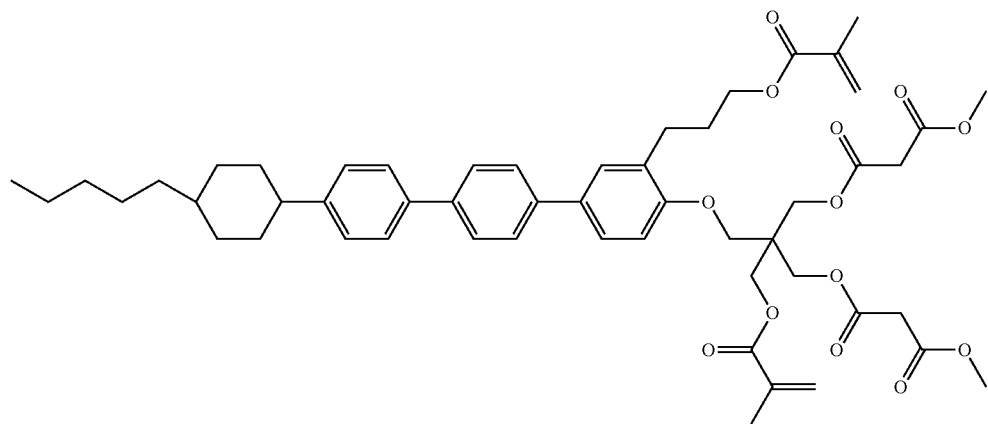
(P-604)
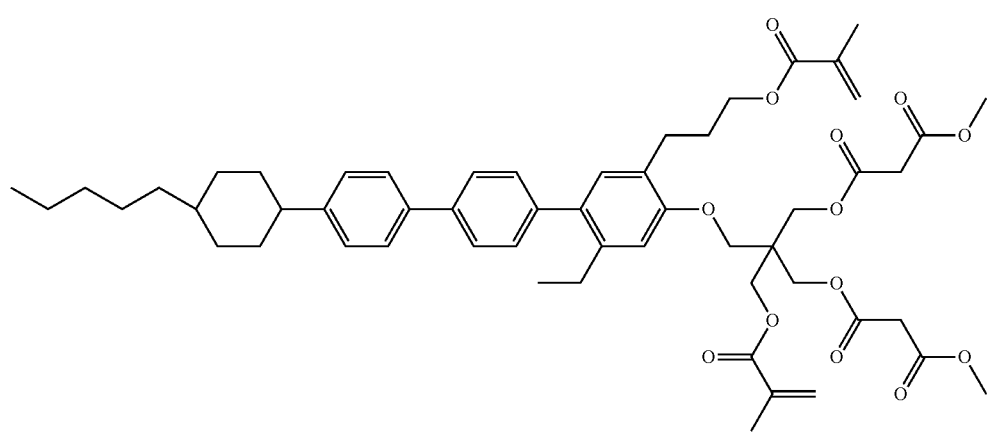
(P-605)
[Chem. 111]

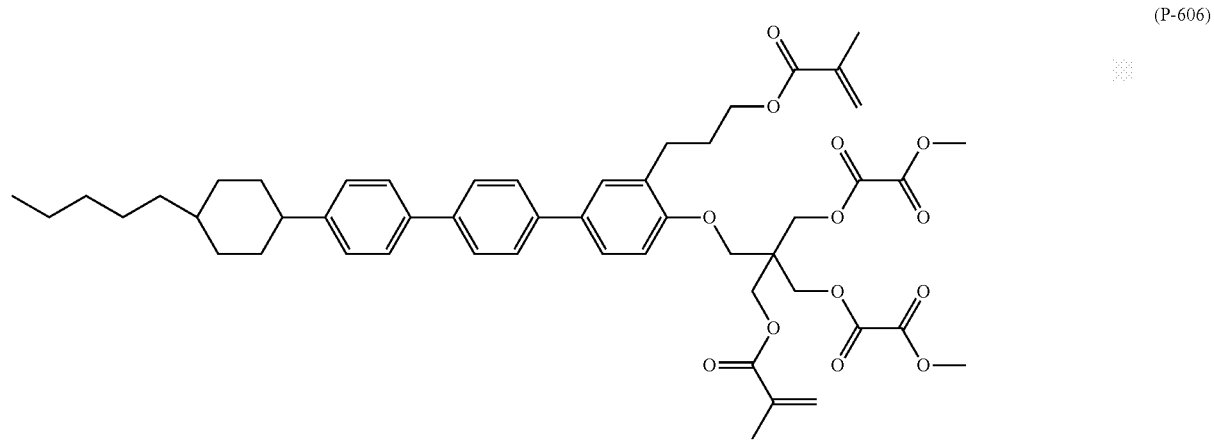
(P-606)
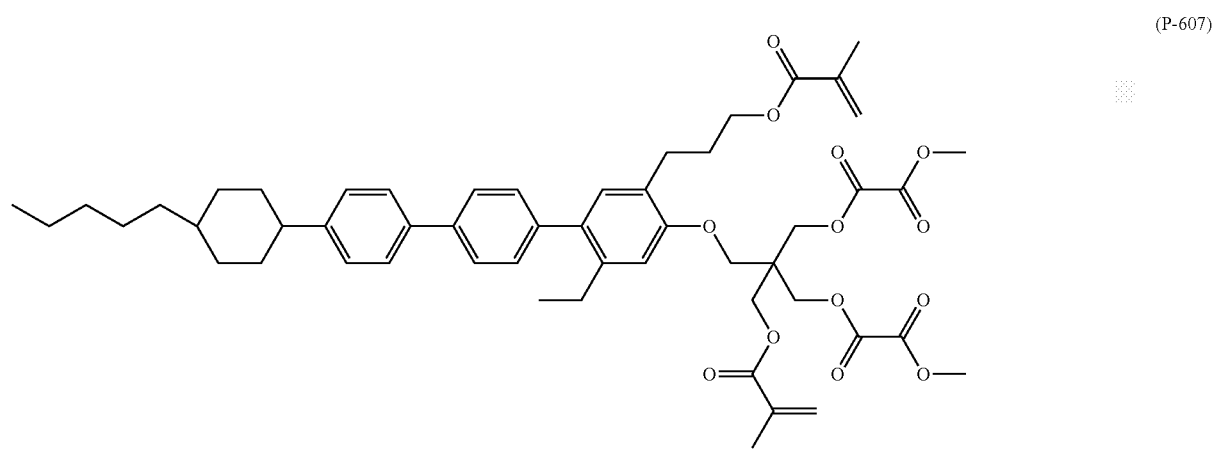
(P-607)
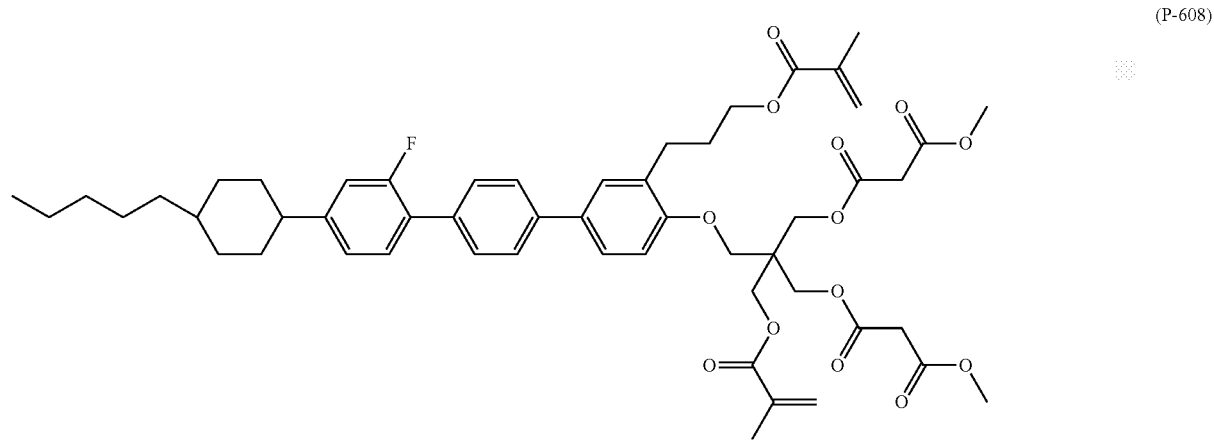
(P-608)

-continued
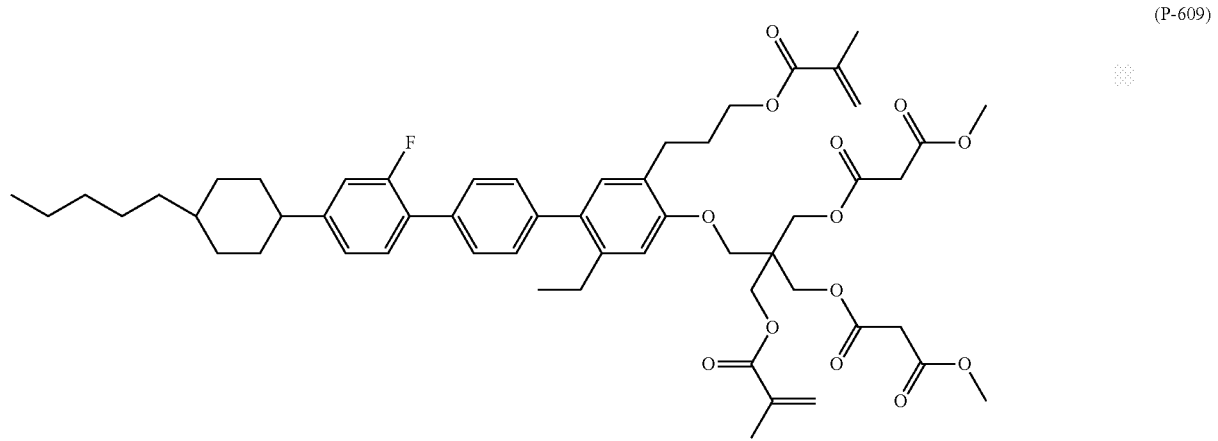
(P-609)
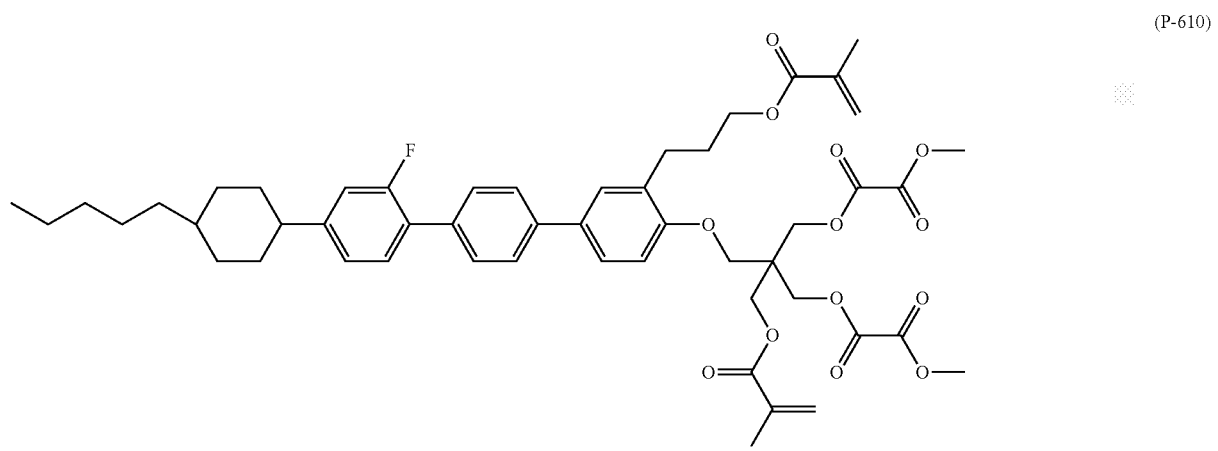
(P-610)
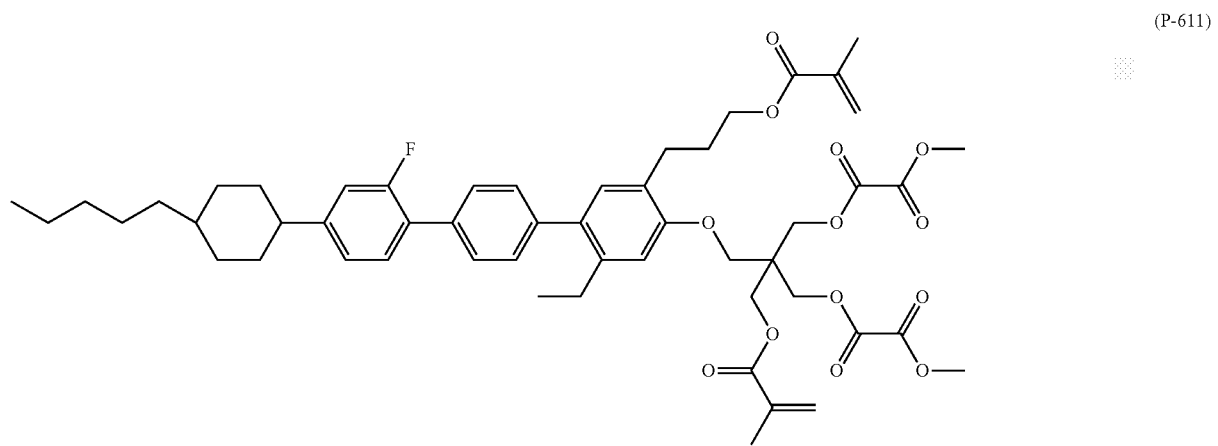
(P-611)

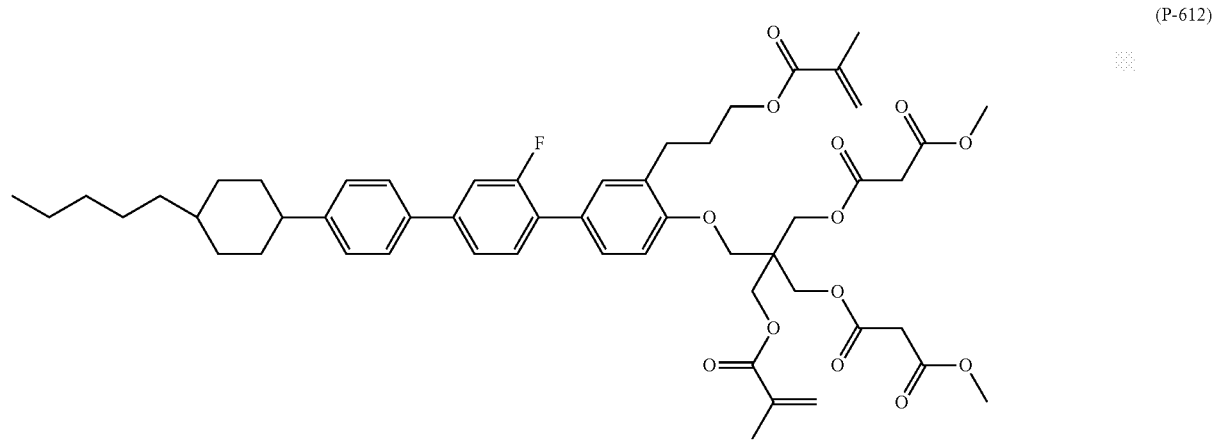
(P-612)
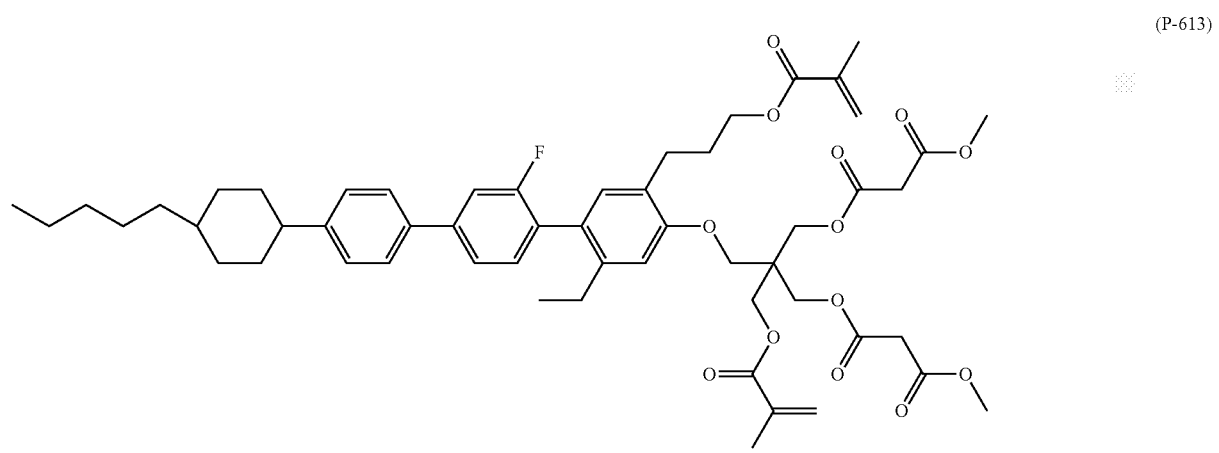
(P-613)
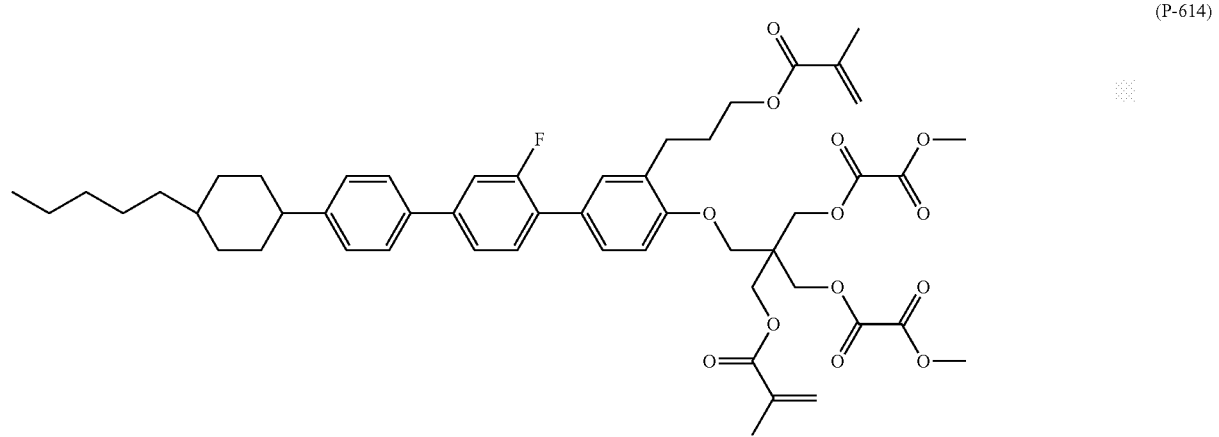
(P-614)

-continued
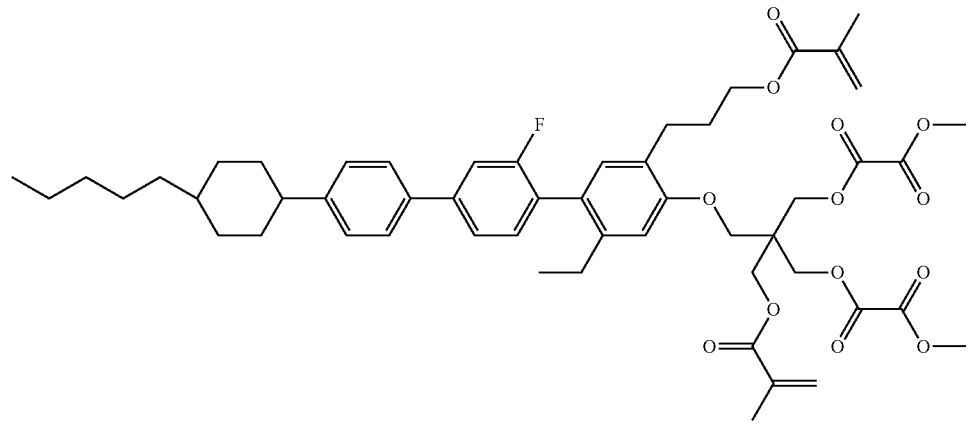
(P-615)
[Chem. 112]
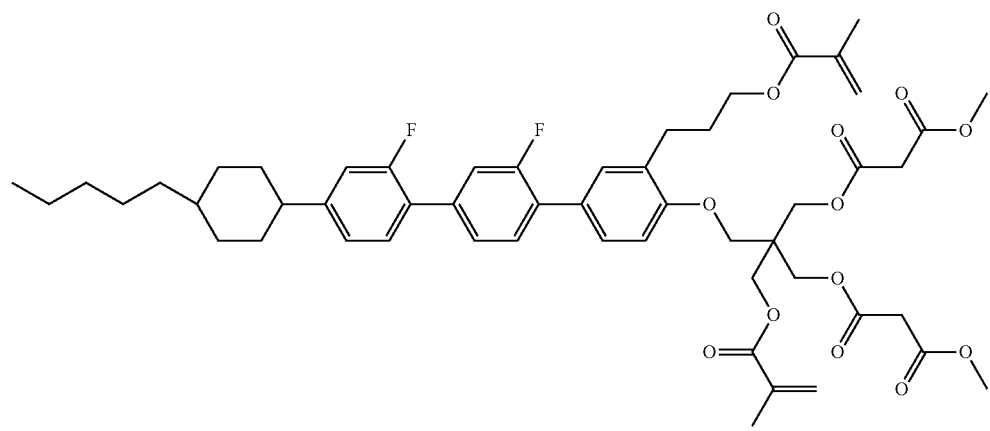
(P-616)
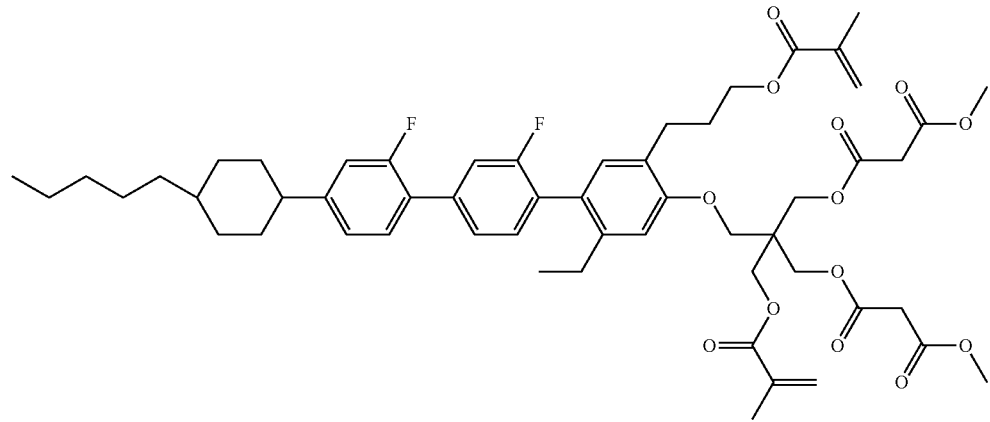
(P-617)

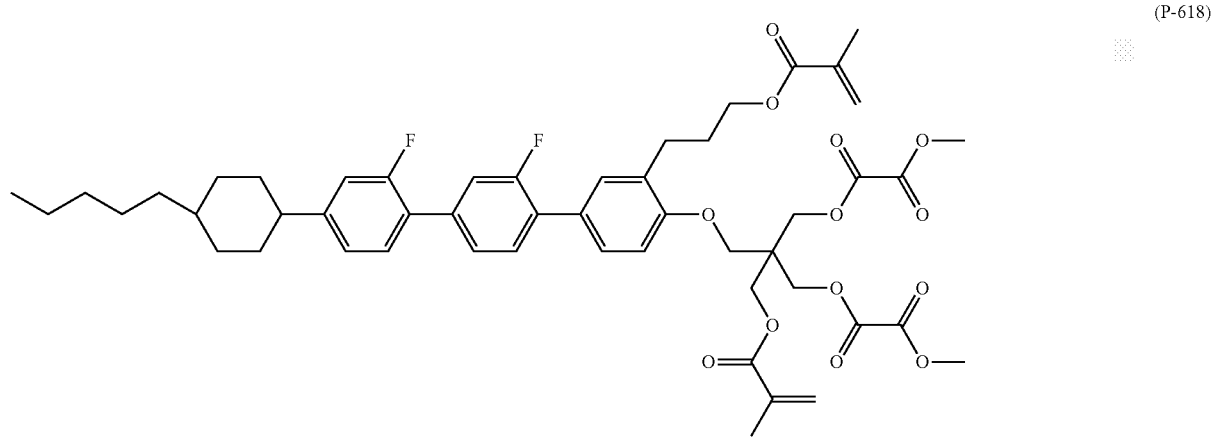
(P-618)
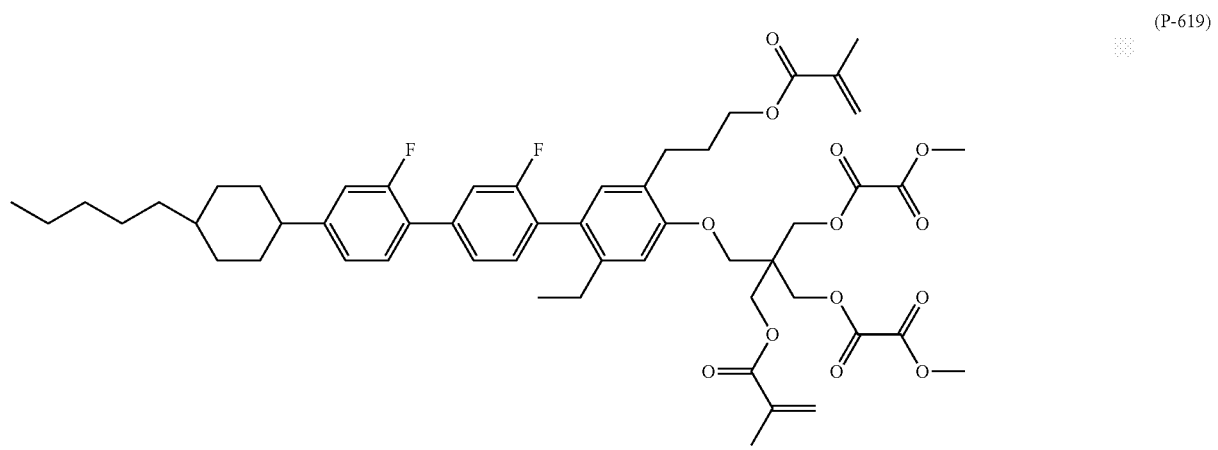
(P-619)
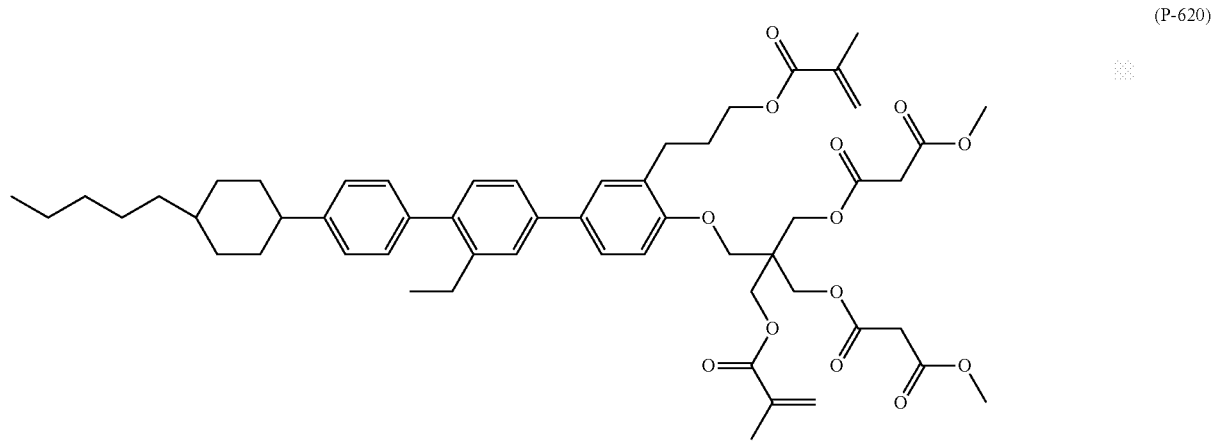
(P-620)

-continued
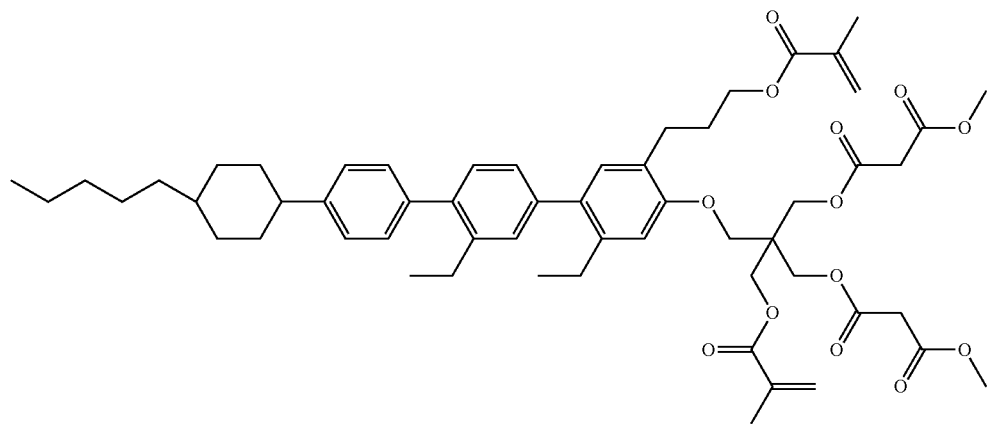
(P-621)
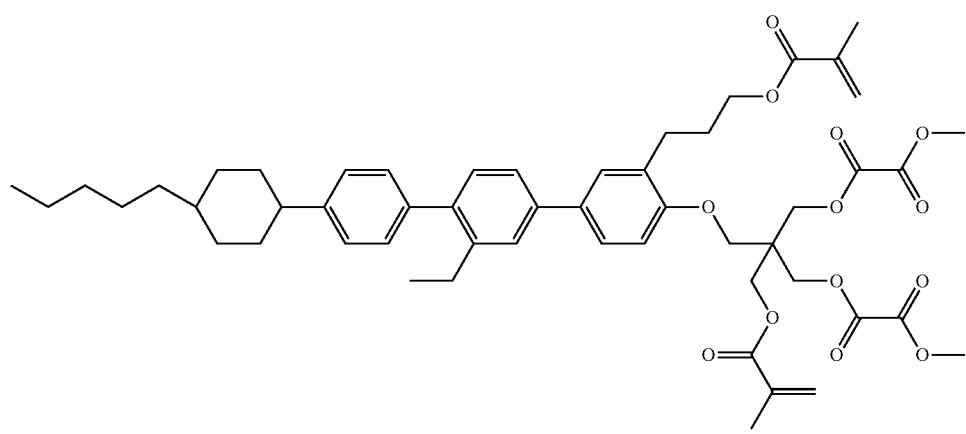
(P-622)
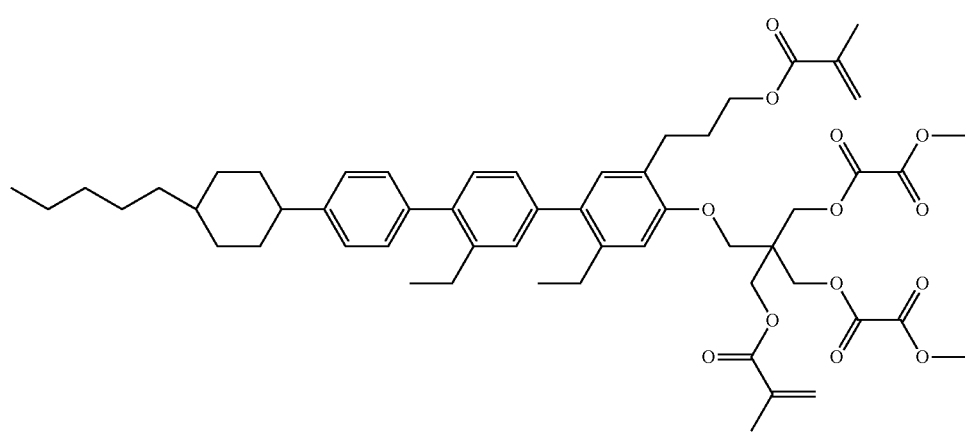
(P-623)

(P-624)
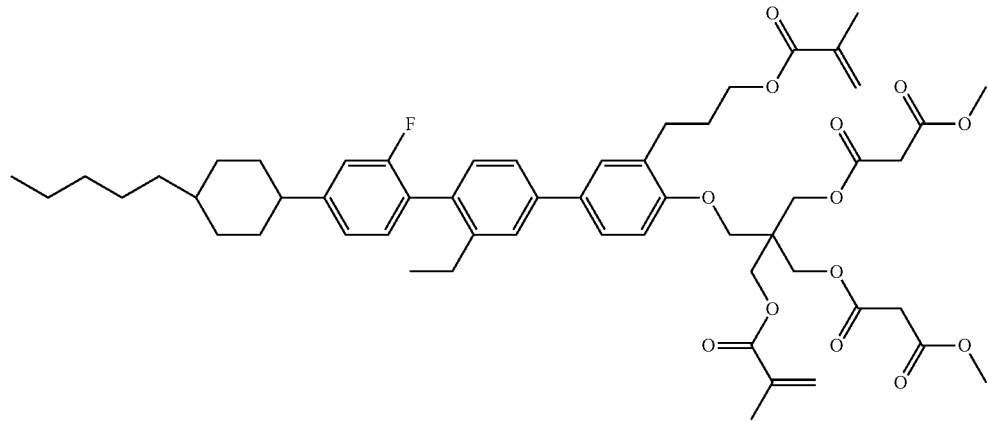
(P-625)
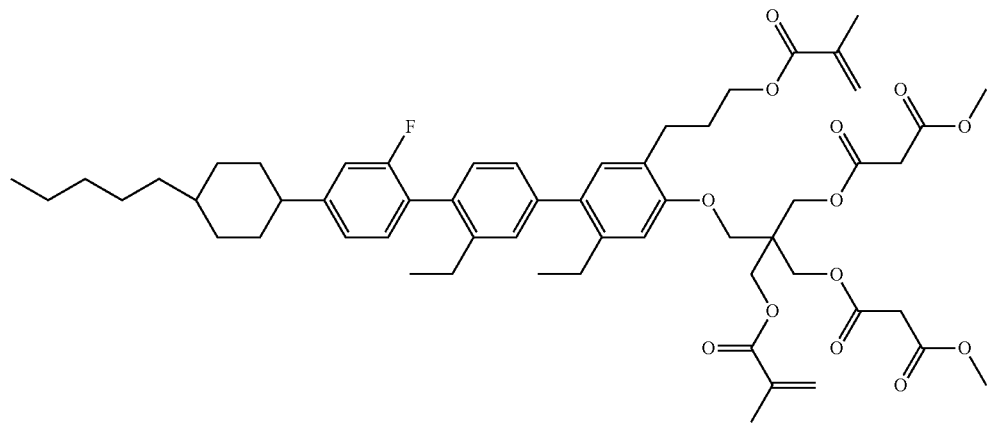
(P-626)
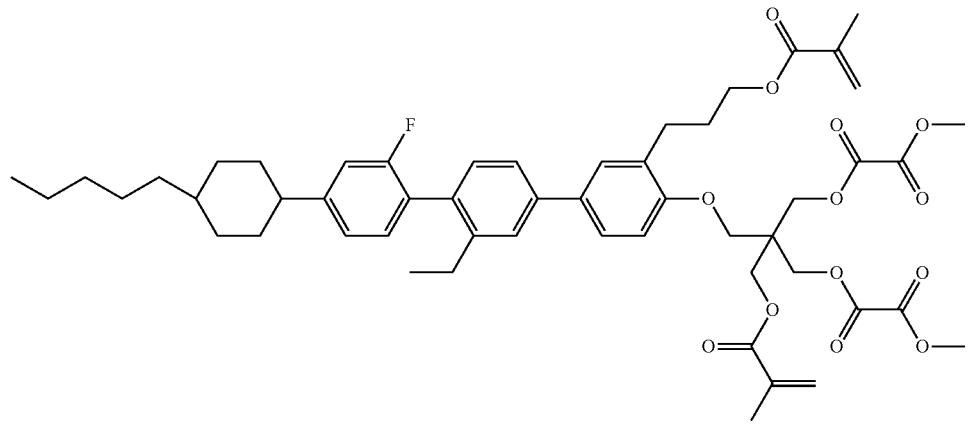

-continued
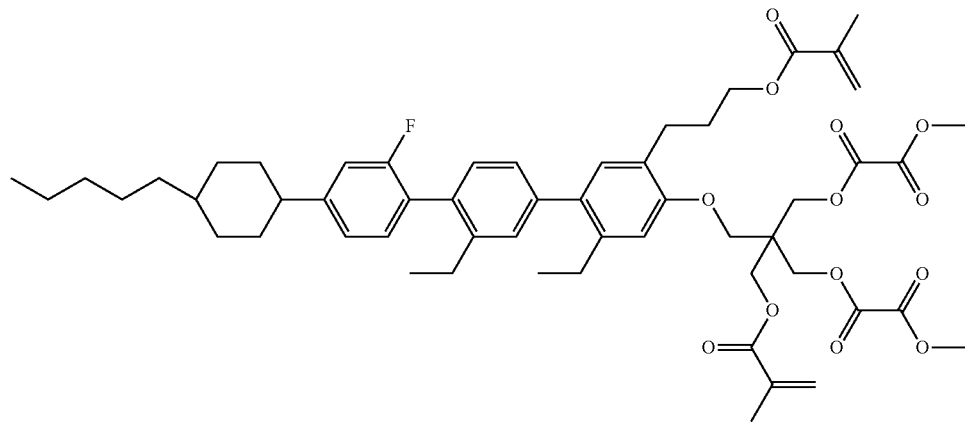
(P-627)
[Chem. 113]
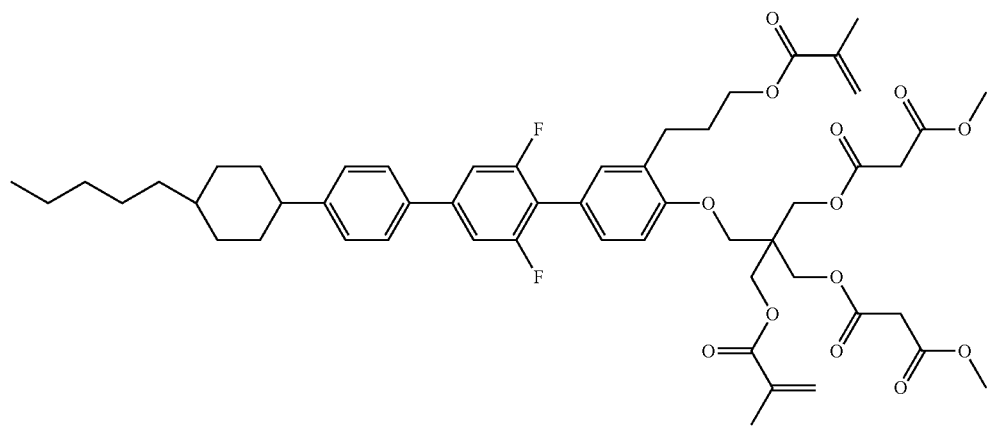
(P-628)
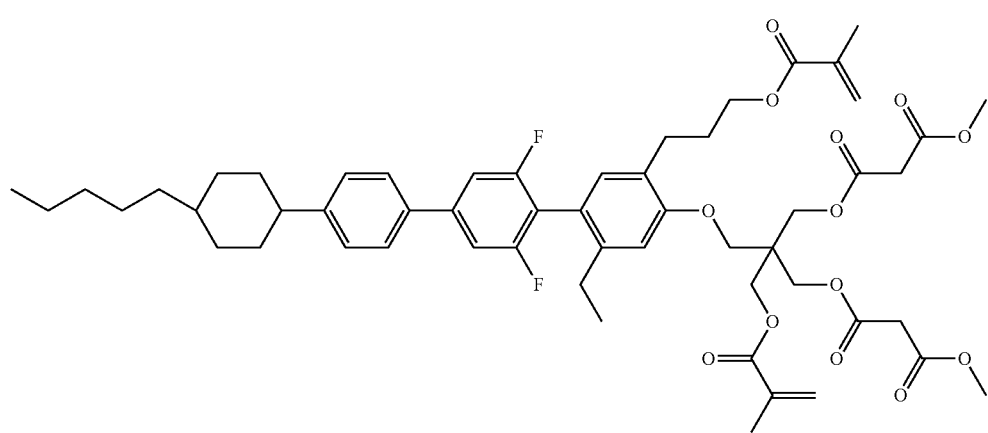
(P-629)

(P-630)
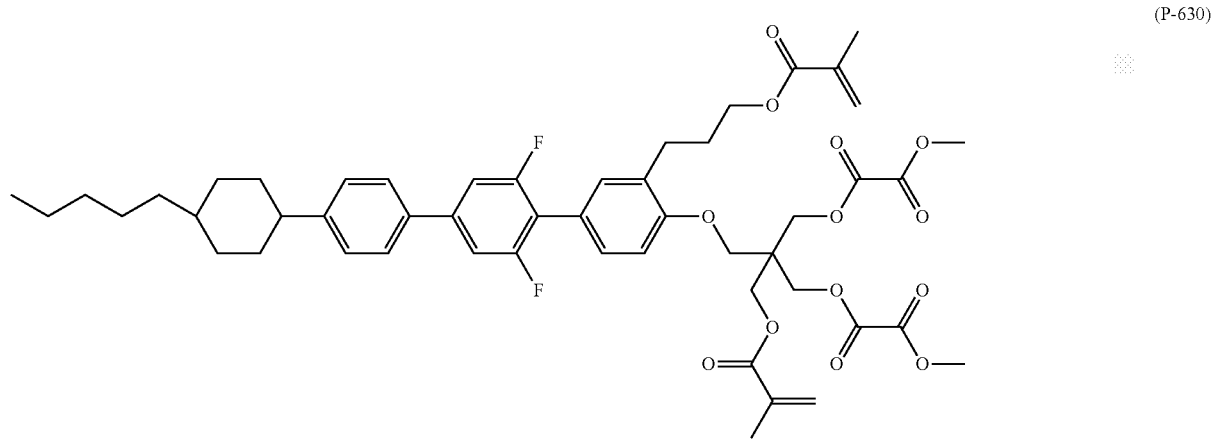
(P-631)
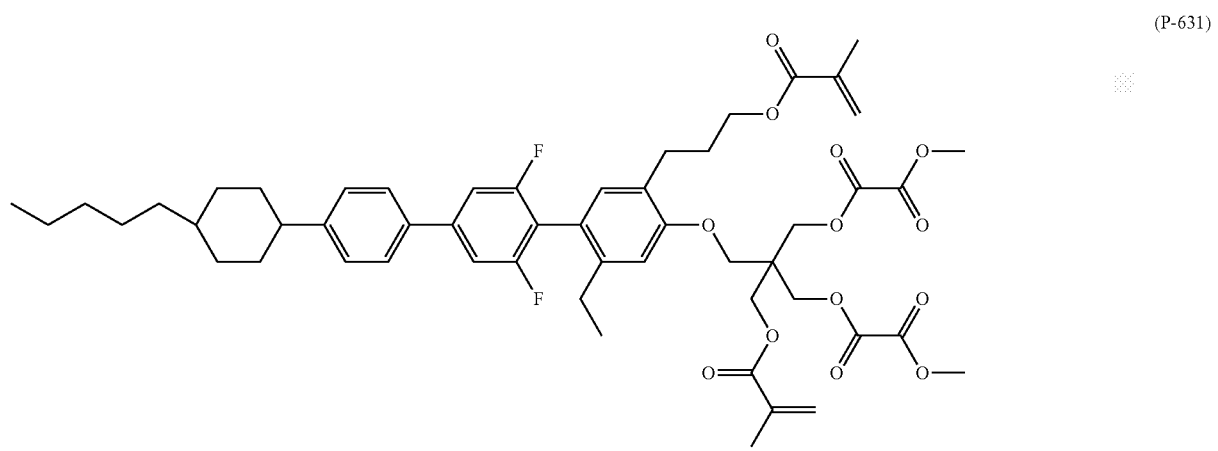
(P-632)
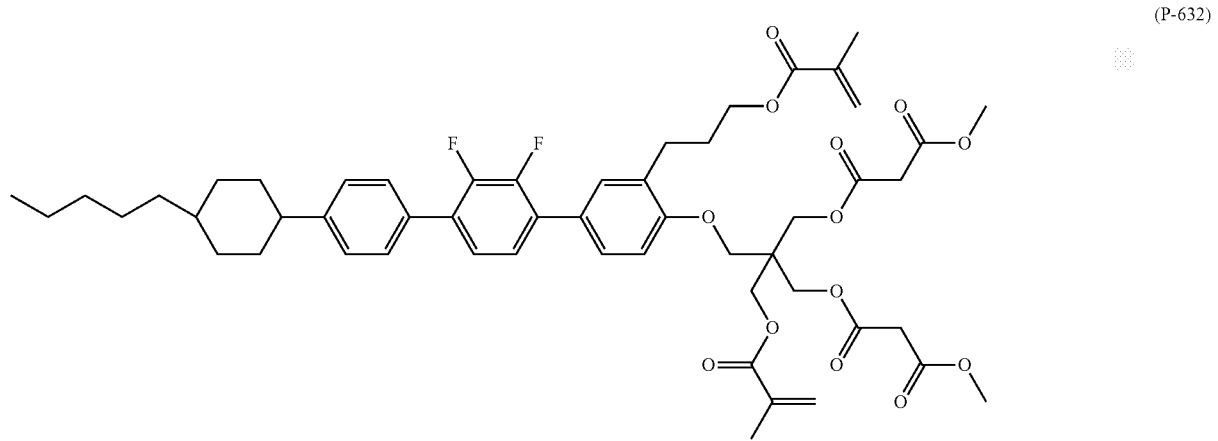

-continued
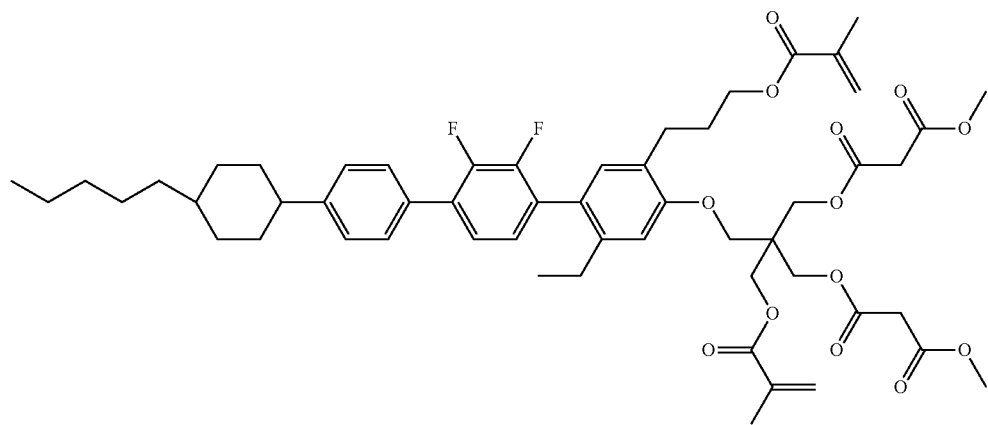
(P-633)
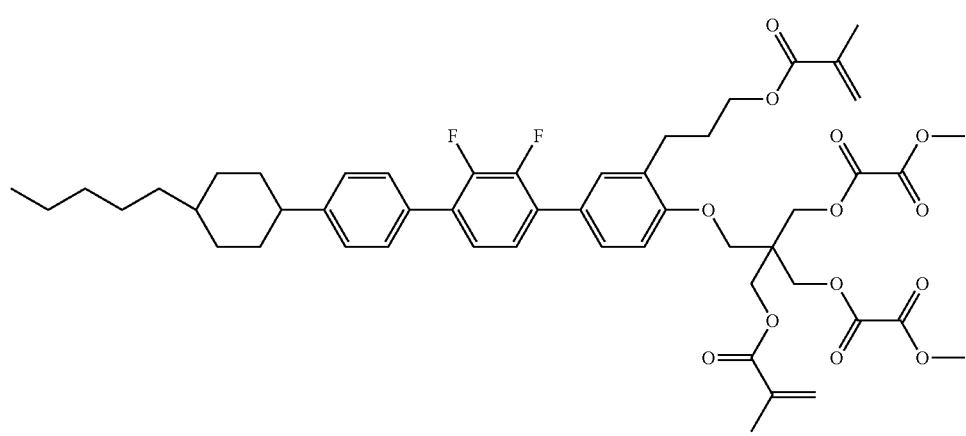
(P-634)
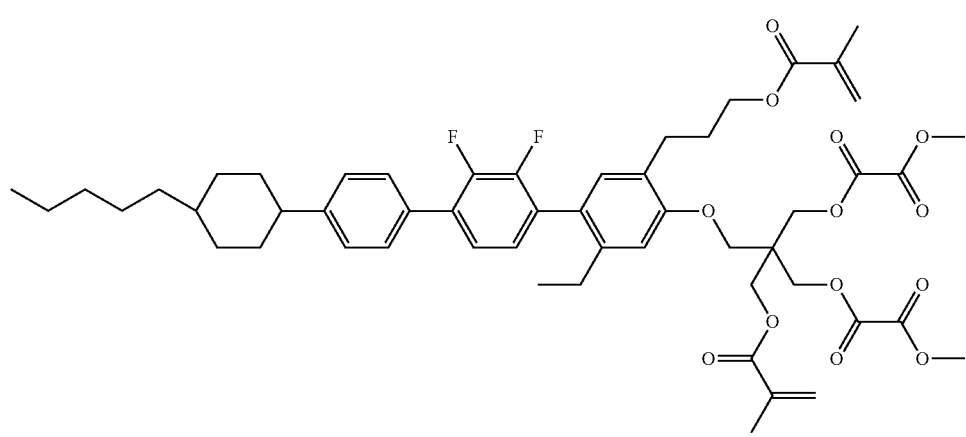
(P-635)

(P-636)
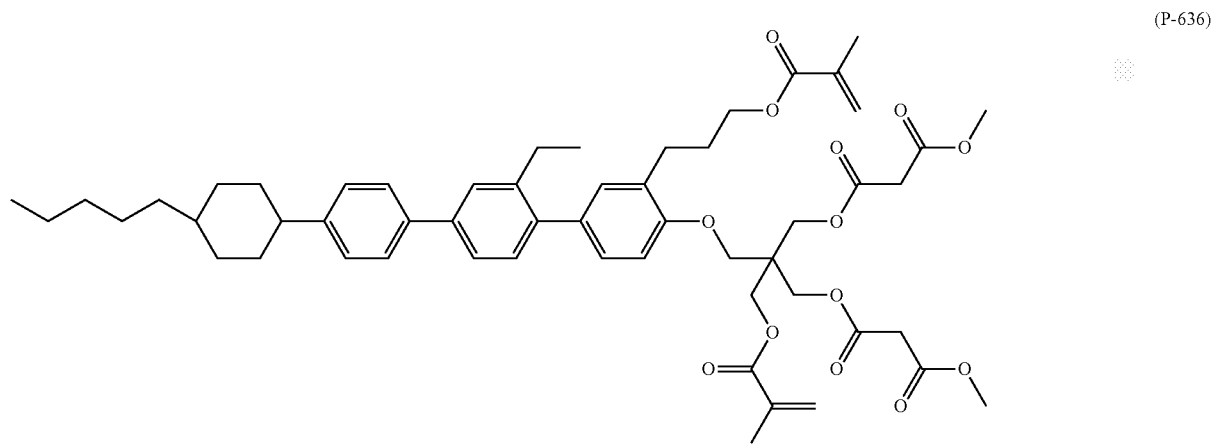
(P-637)
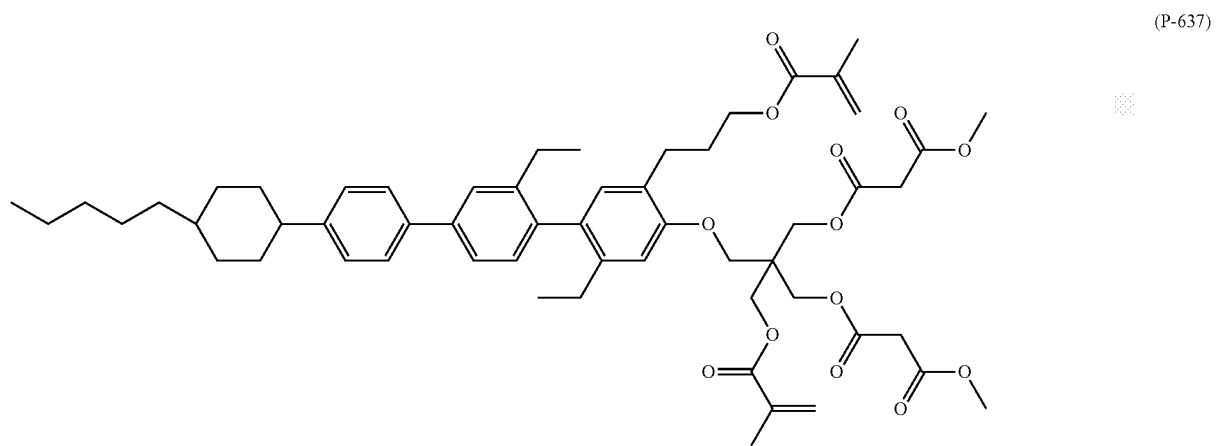
(P-638)
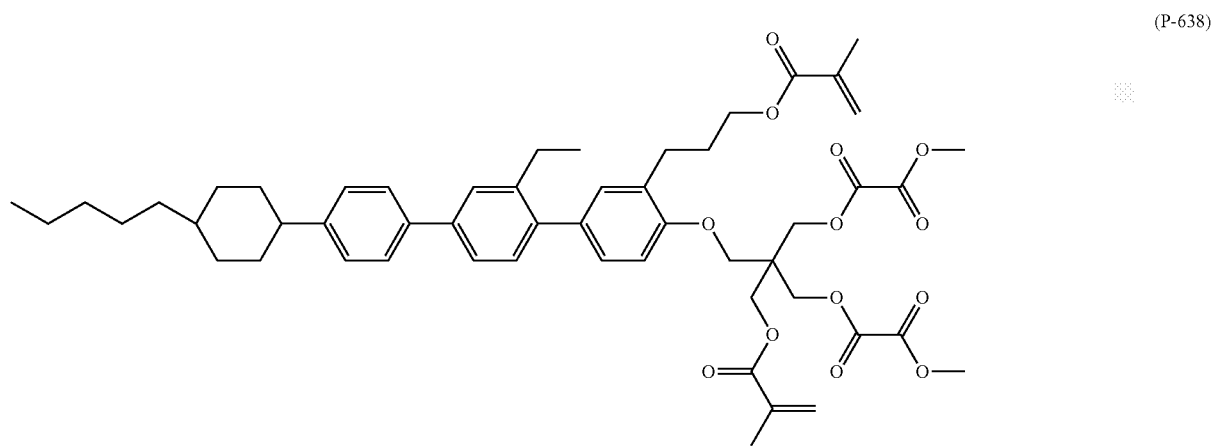

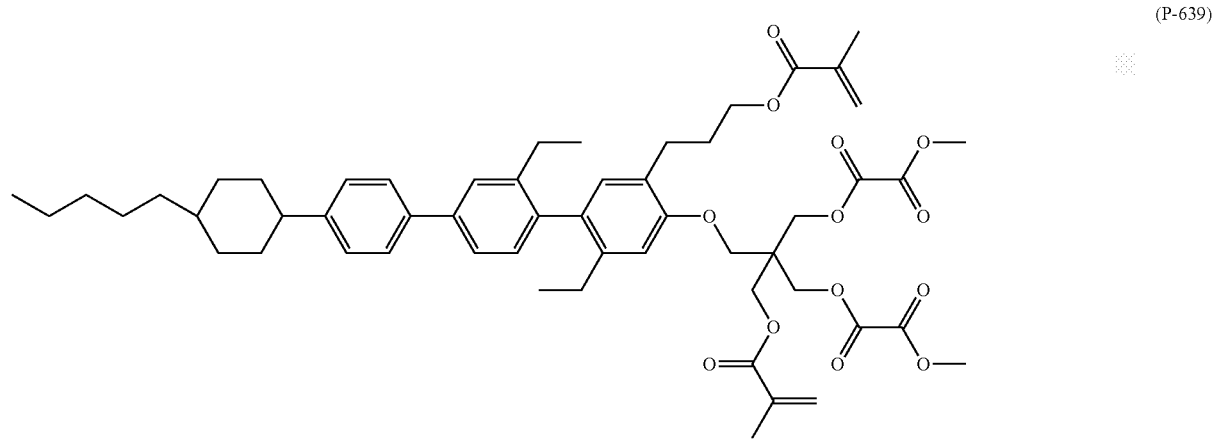
(P-639)
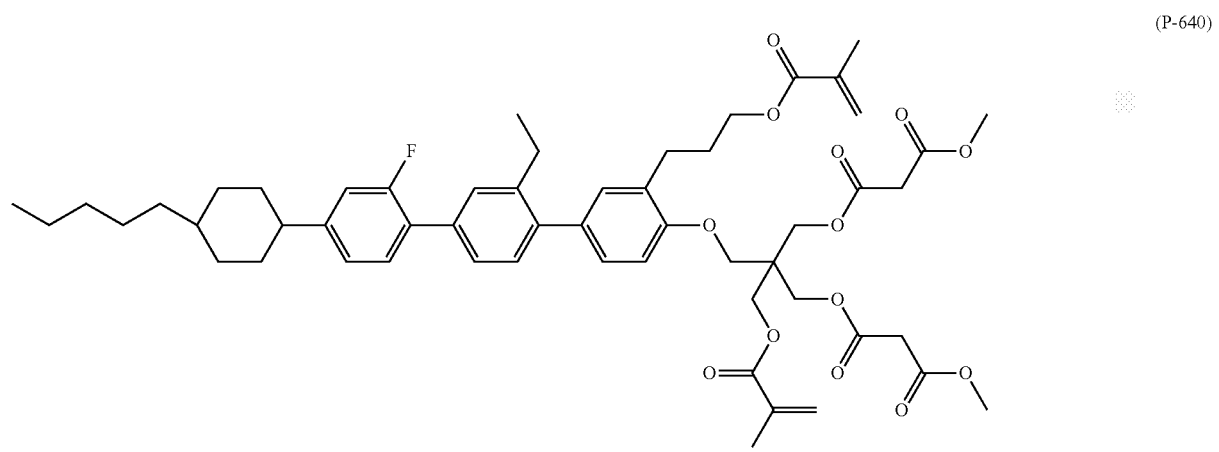
(P-640)
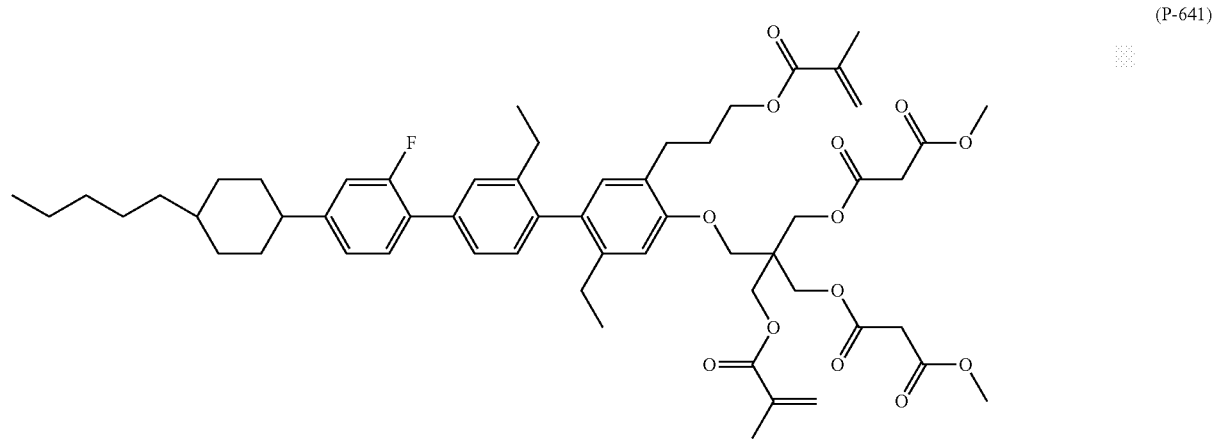
(P-641)

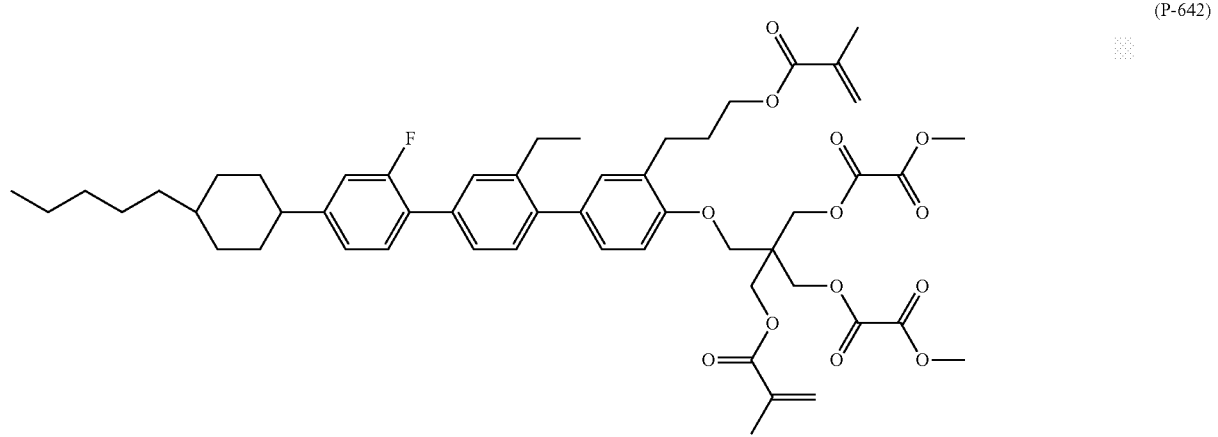
(P-642)
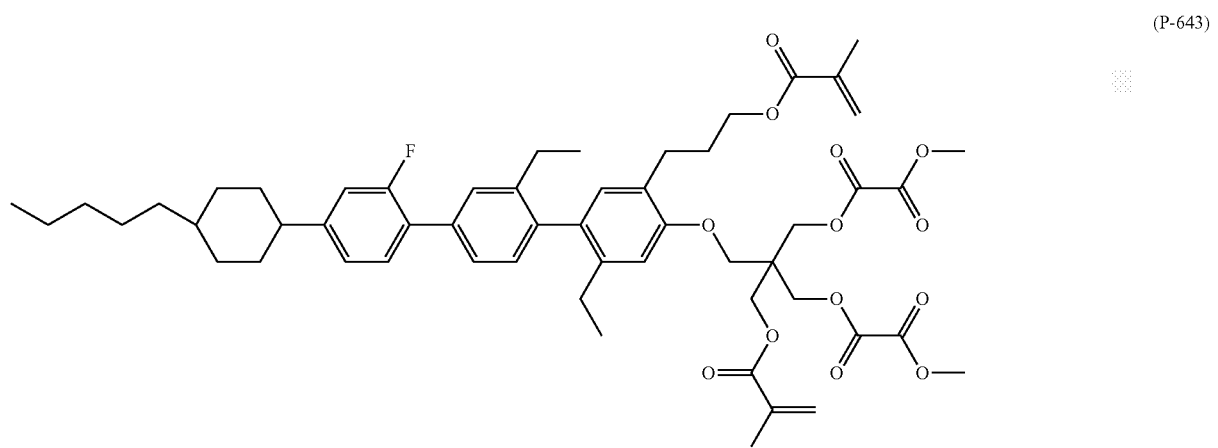
(P-643)
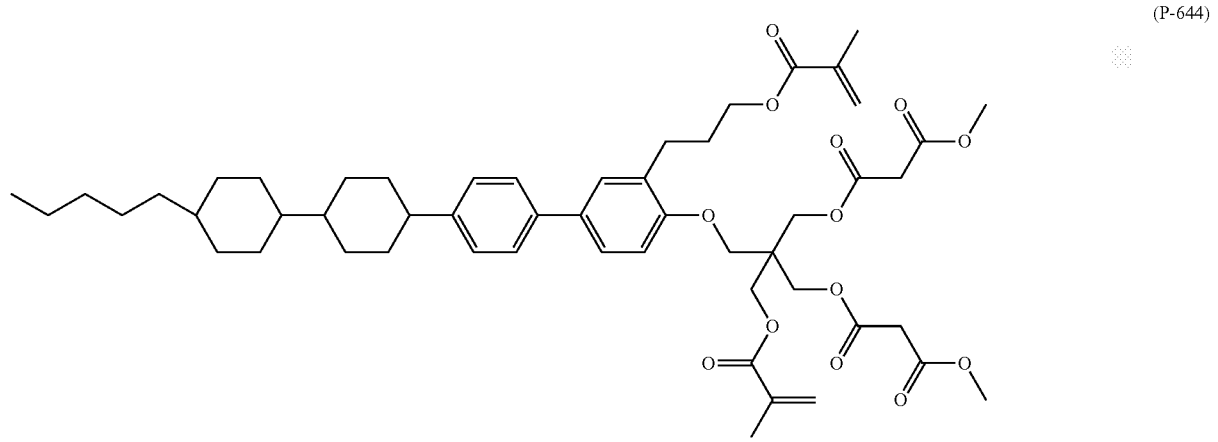
(P-644)

-continued
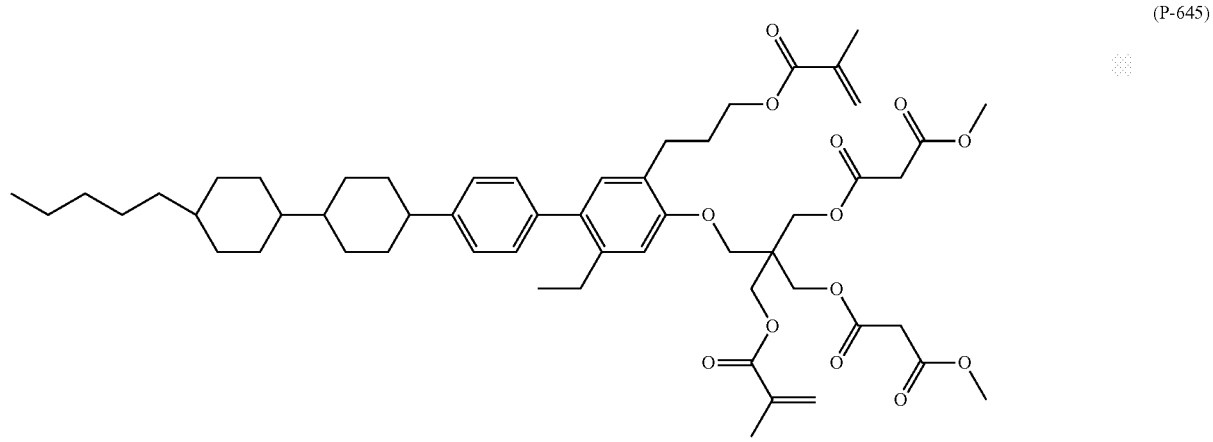
(P-645)
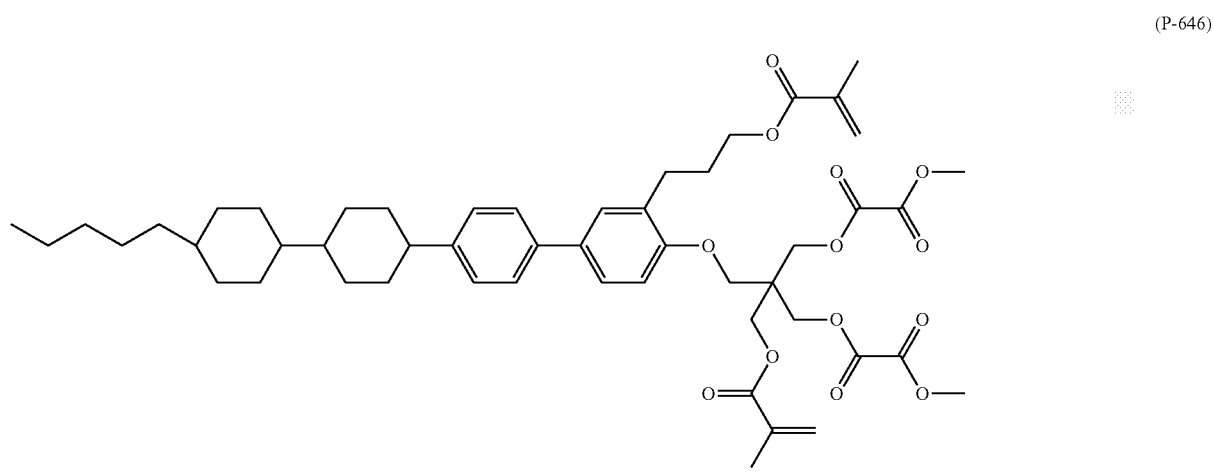
(P-646)
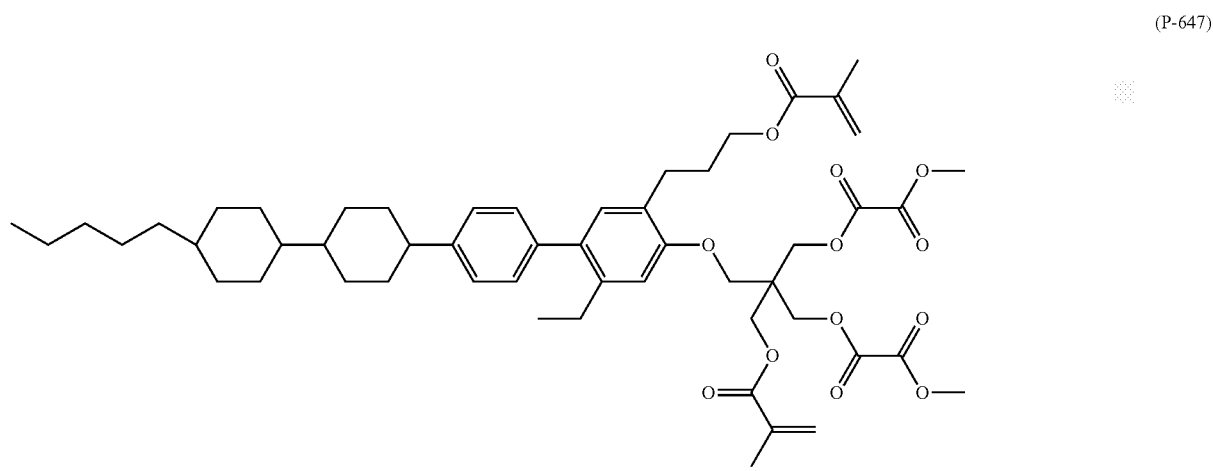
(P-647)

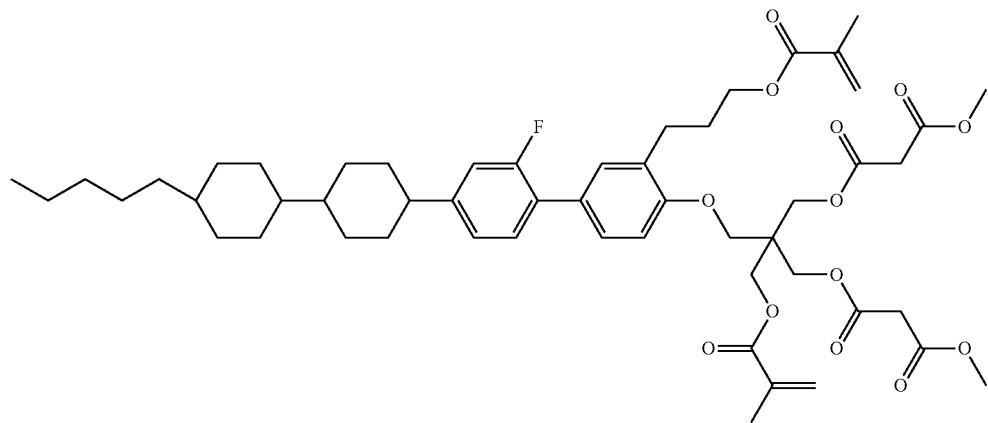
(P-648)
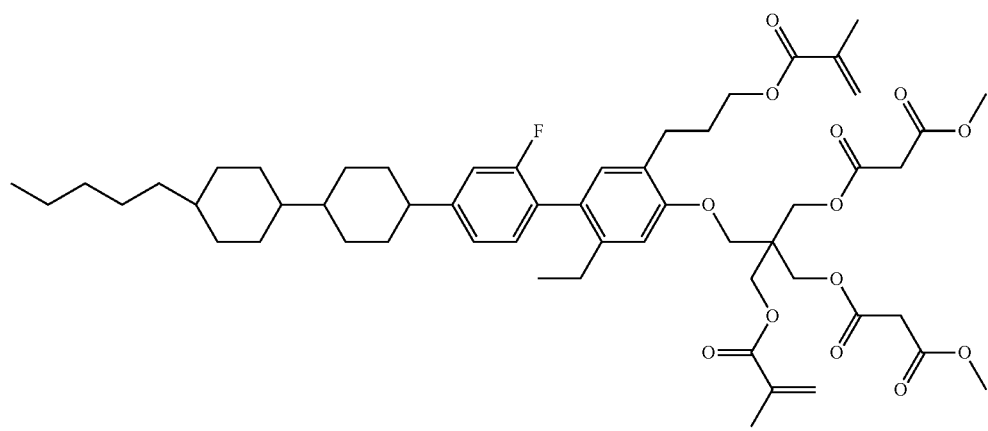
(P-649)
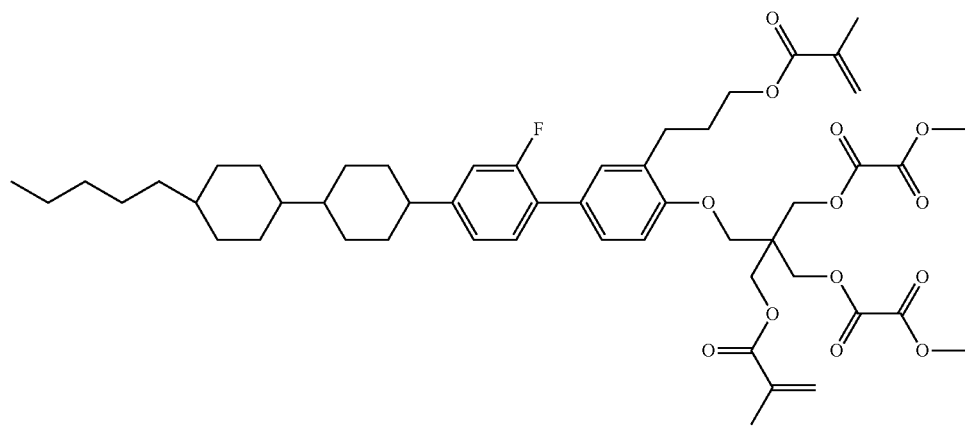
(P-650)

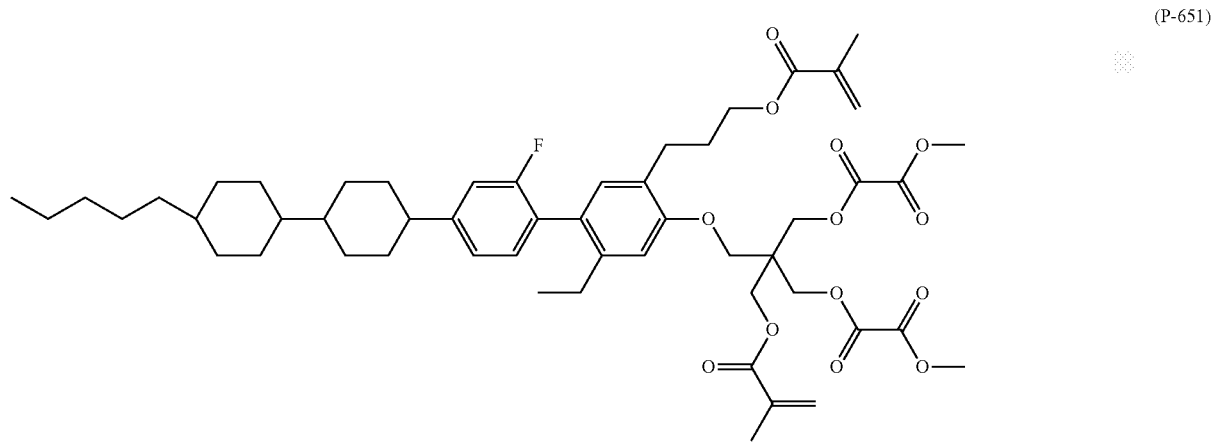
(P-651)
[Chem. 115]
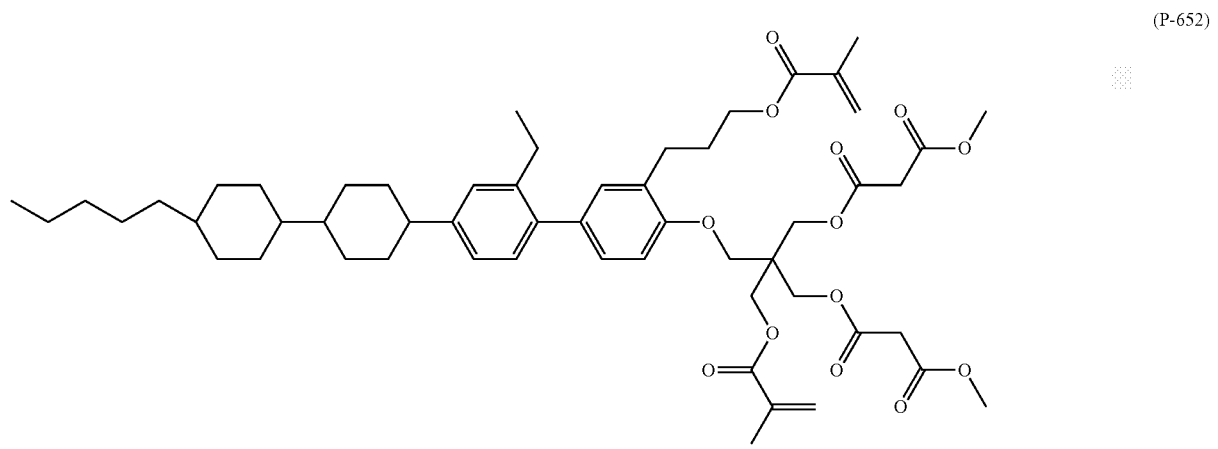
(P-652)
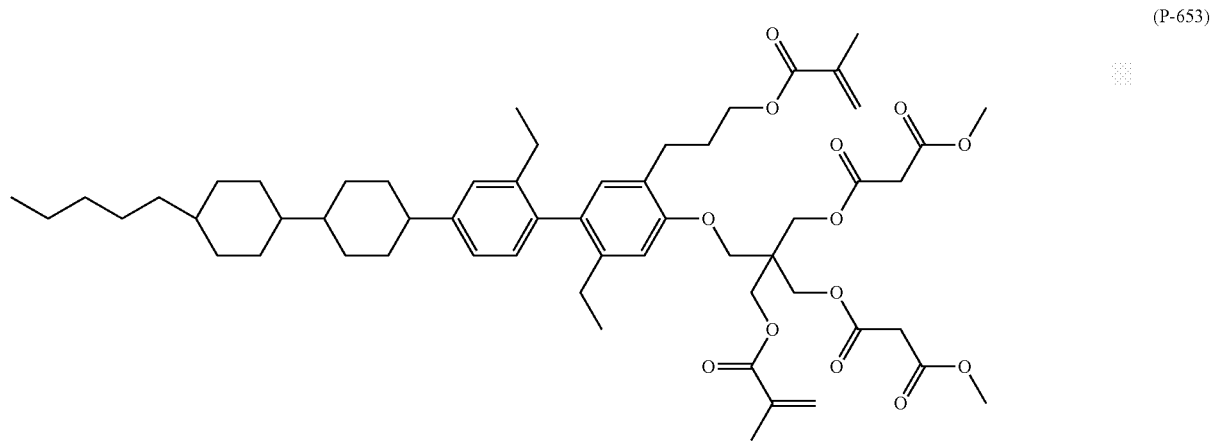
(P-653)

-continued
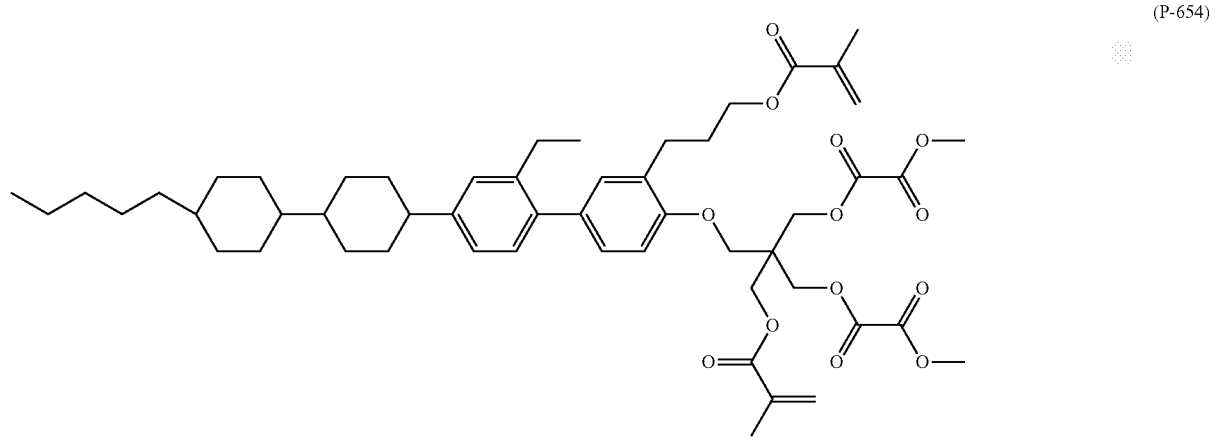
(P-654)
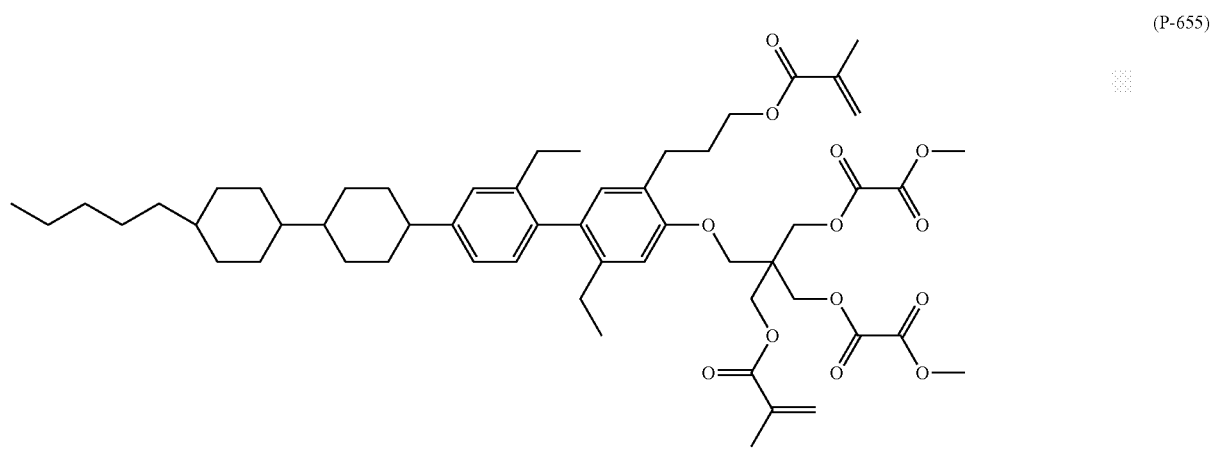
(P-655)
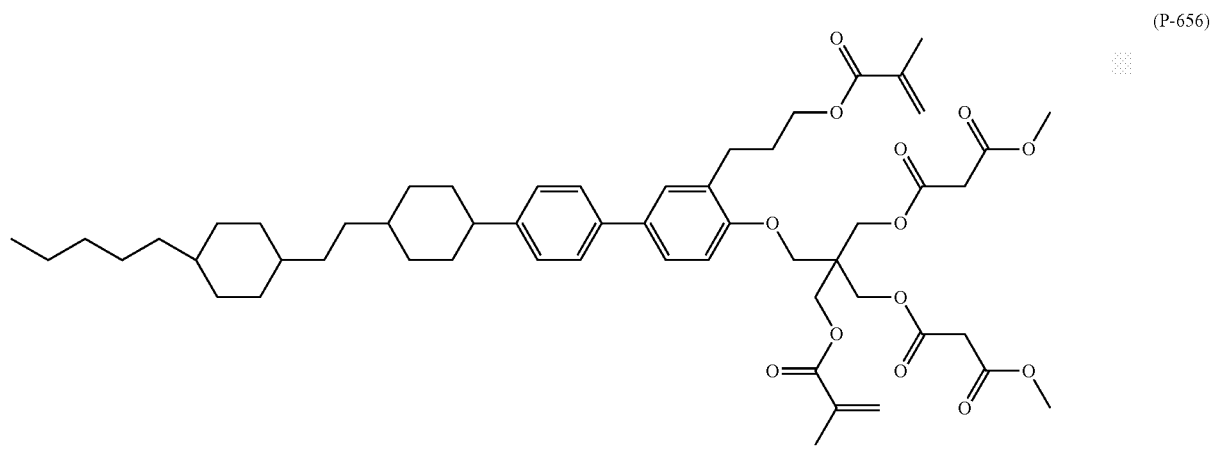
(P-656)

(P-657)
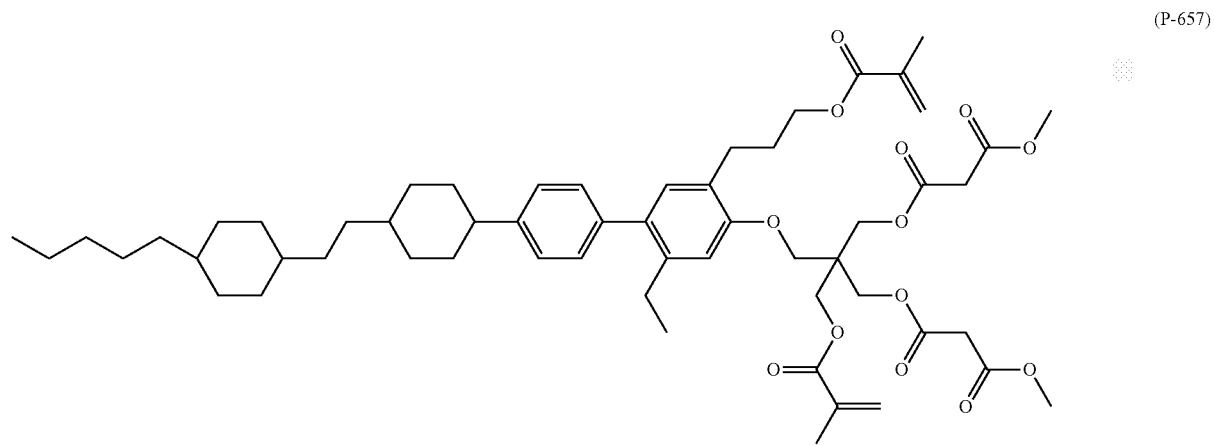
(P-658)
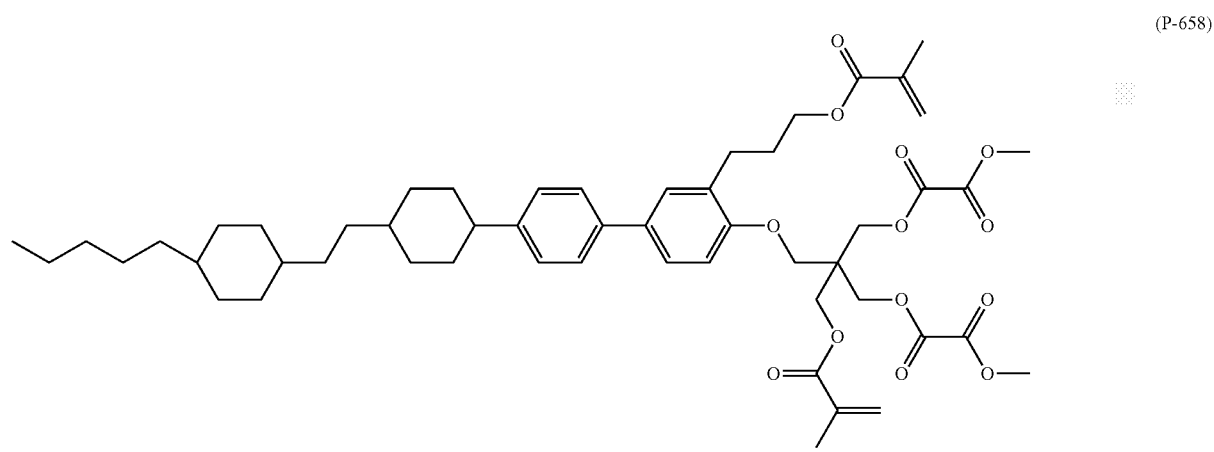
(P-659)
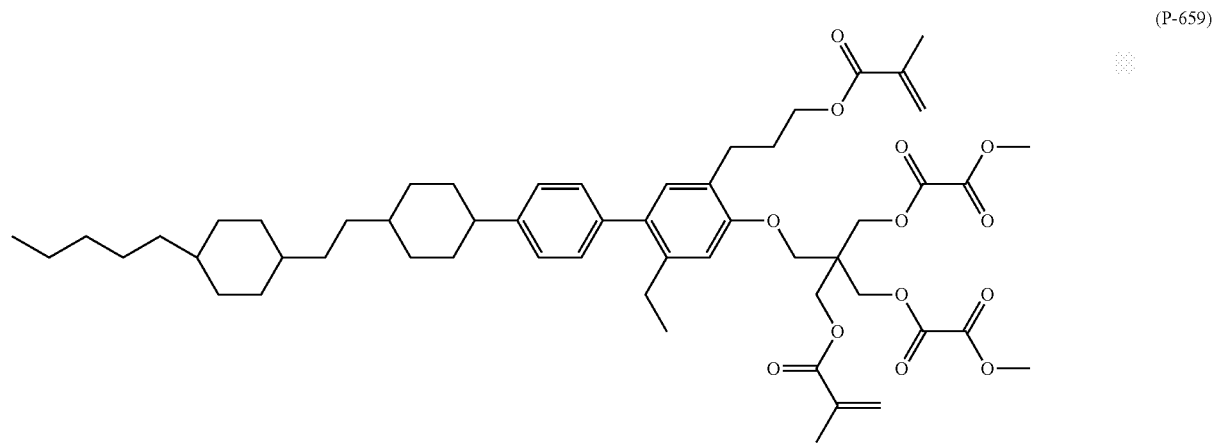

-continued
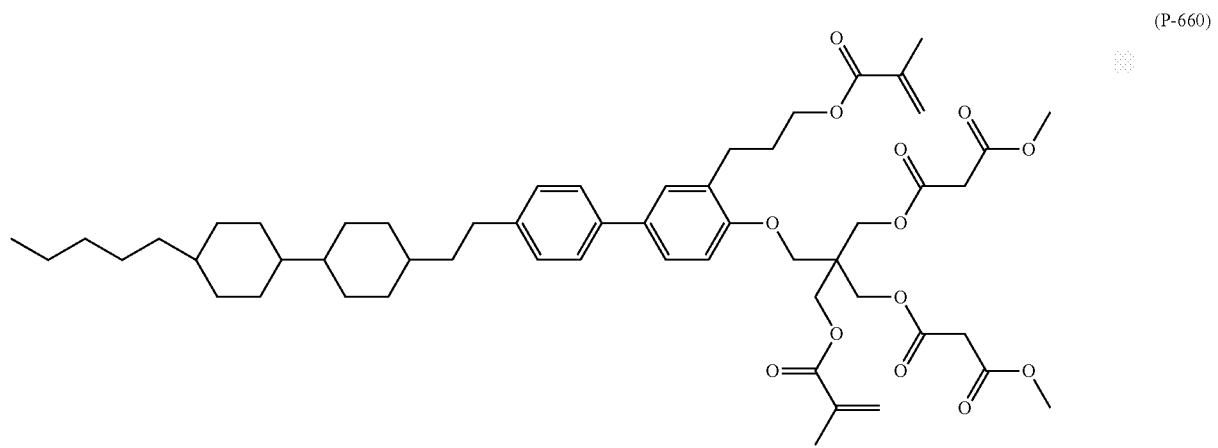
(P-660)
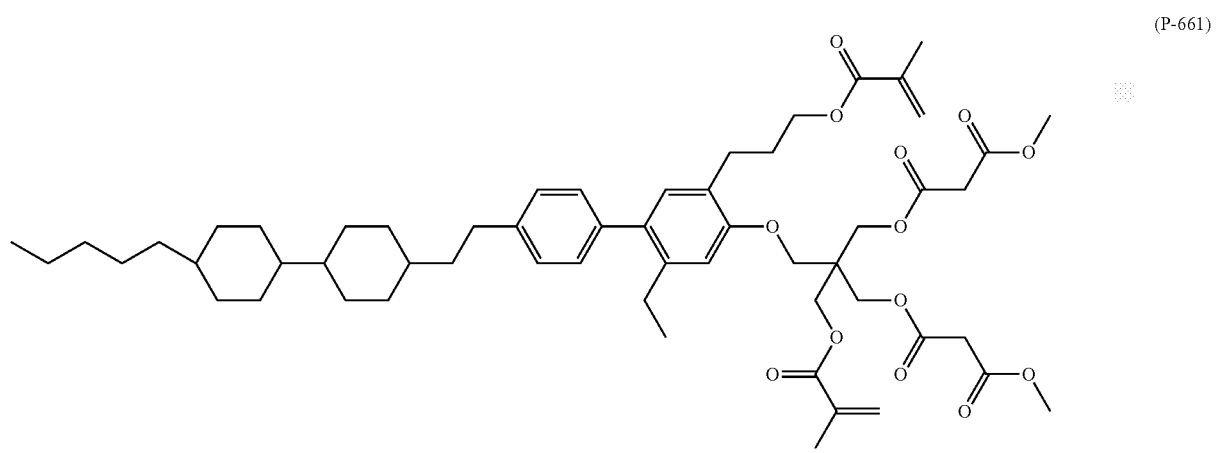
(P-661)
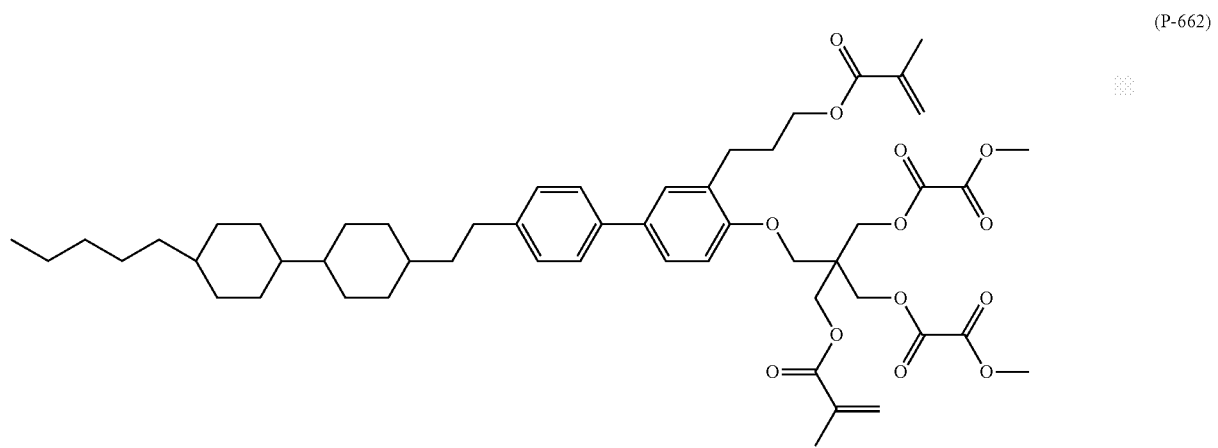
(P-662)

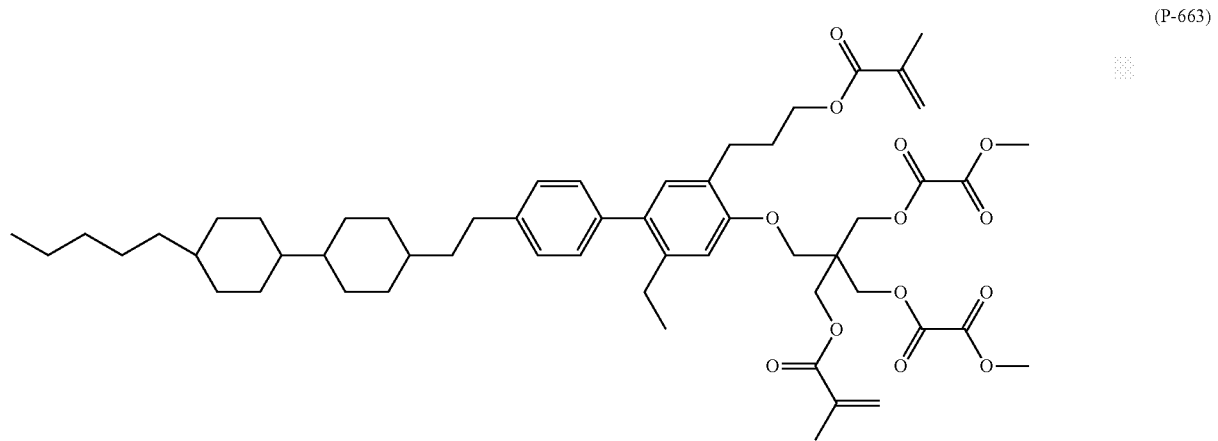
(P-663)
[Chem. 116]
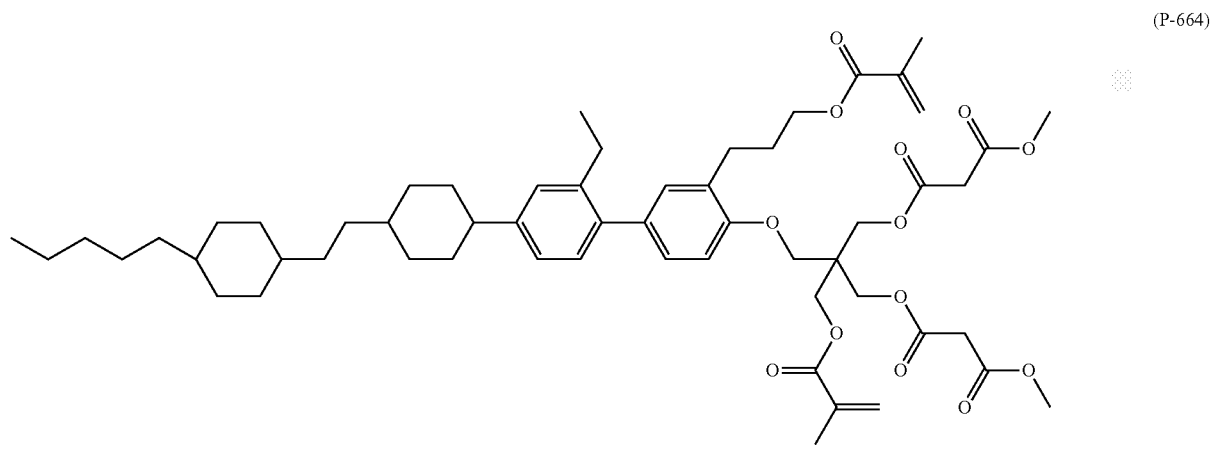
(P-664)
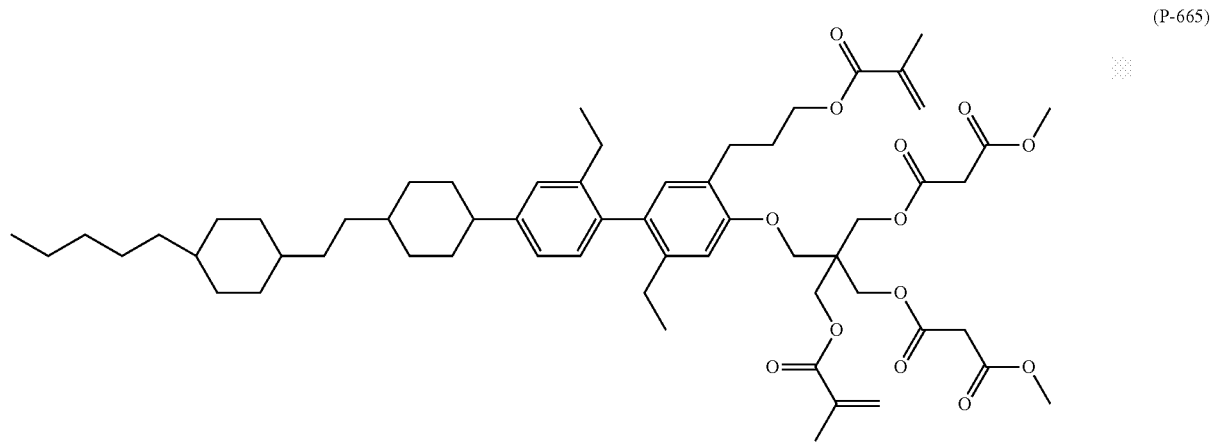
(P-665)

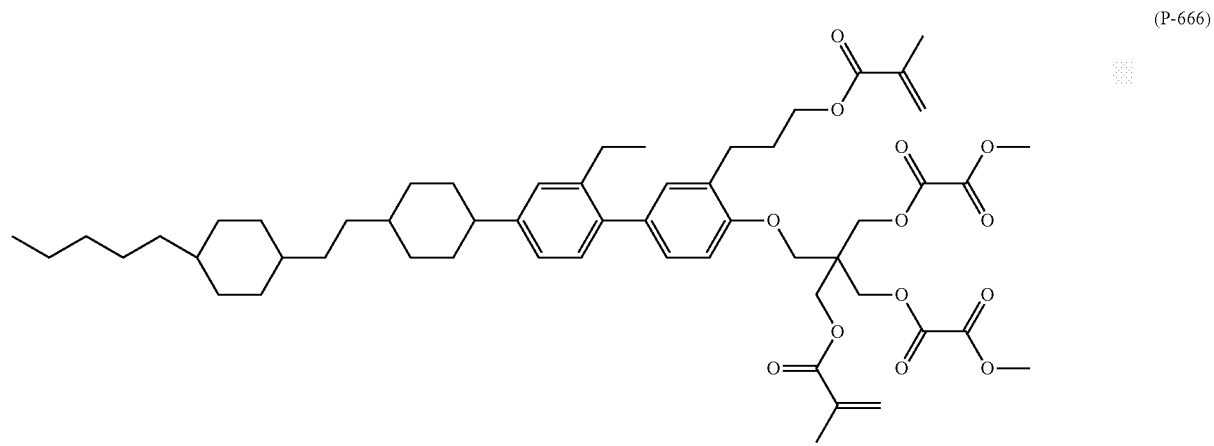
(P-666)
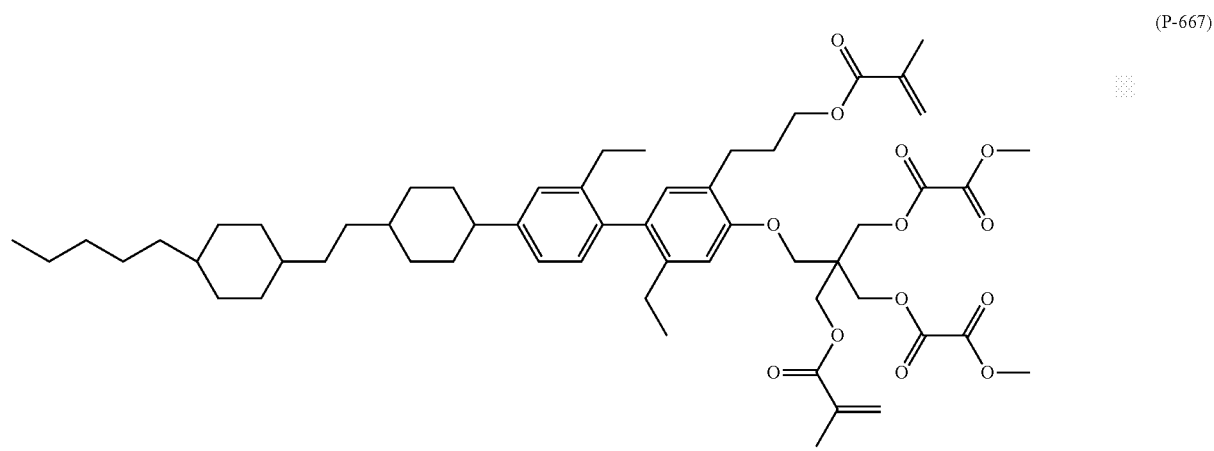
(P-667)
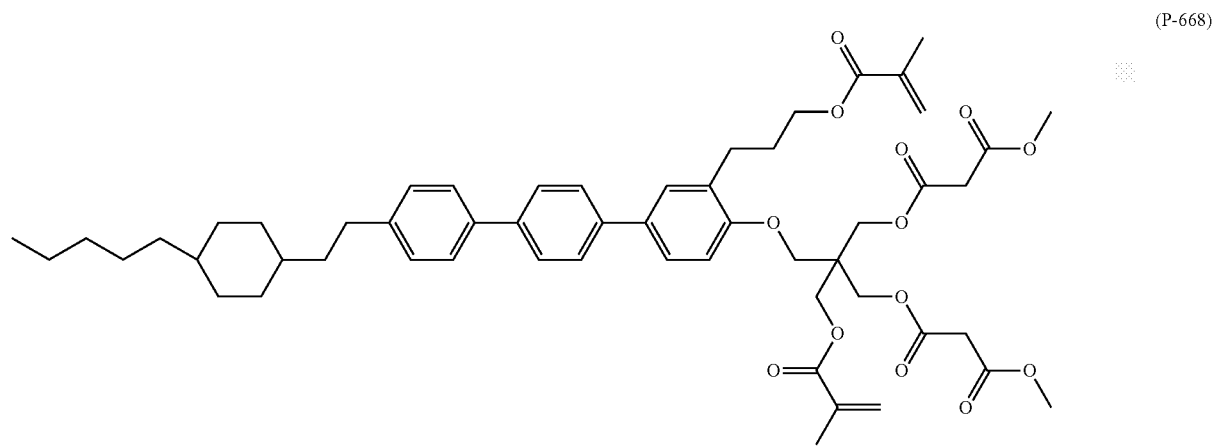
(P-668)

-continued
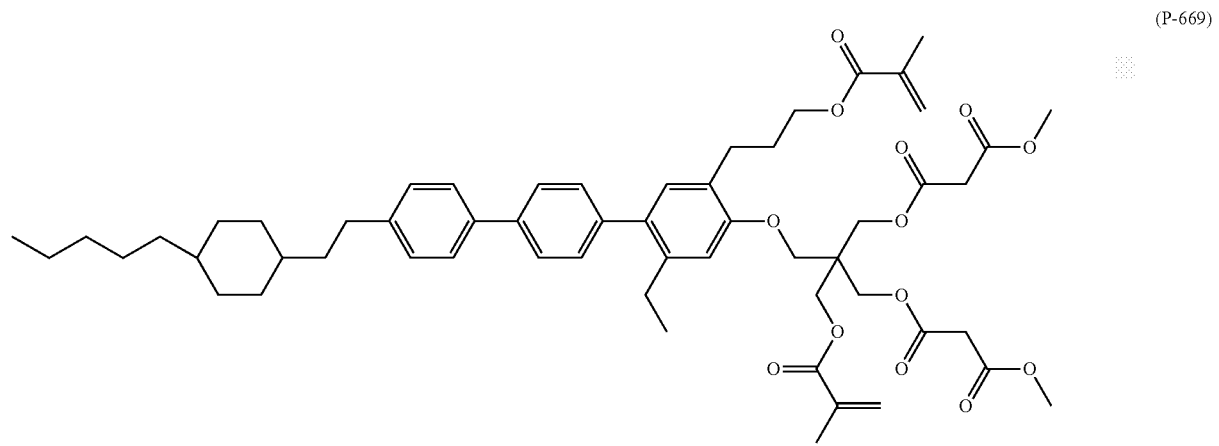
(P-669)
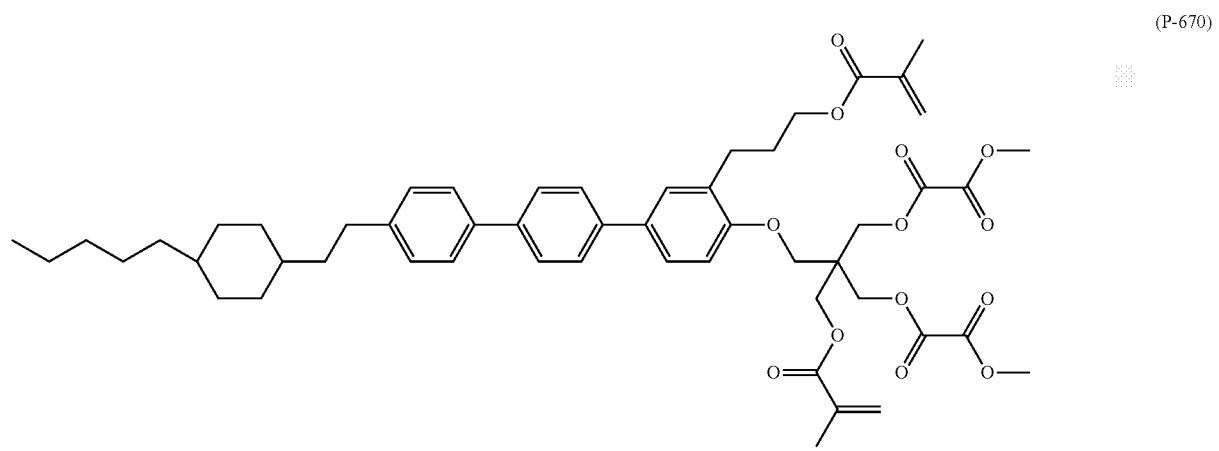
(P-670)
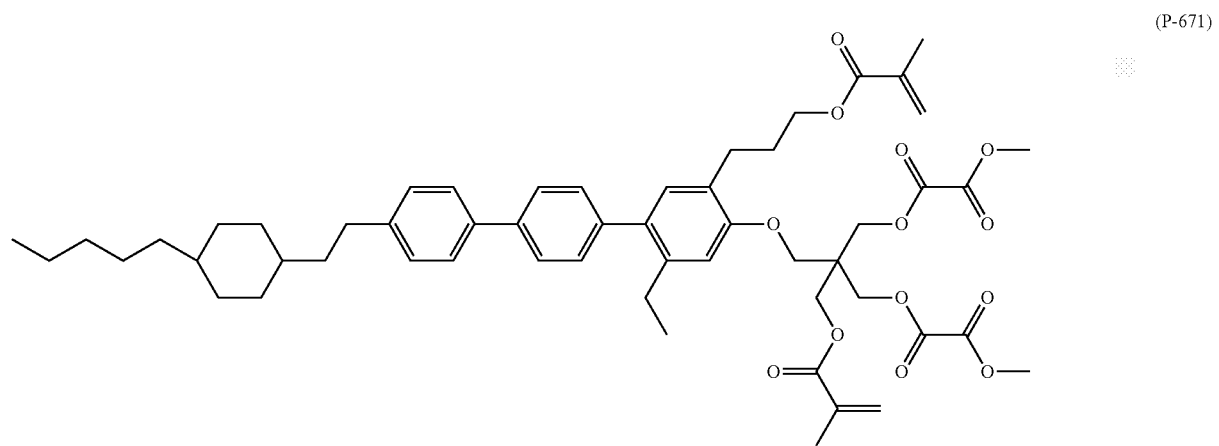
(P-671)

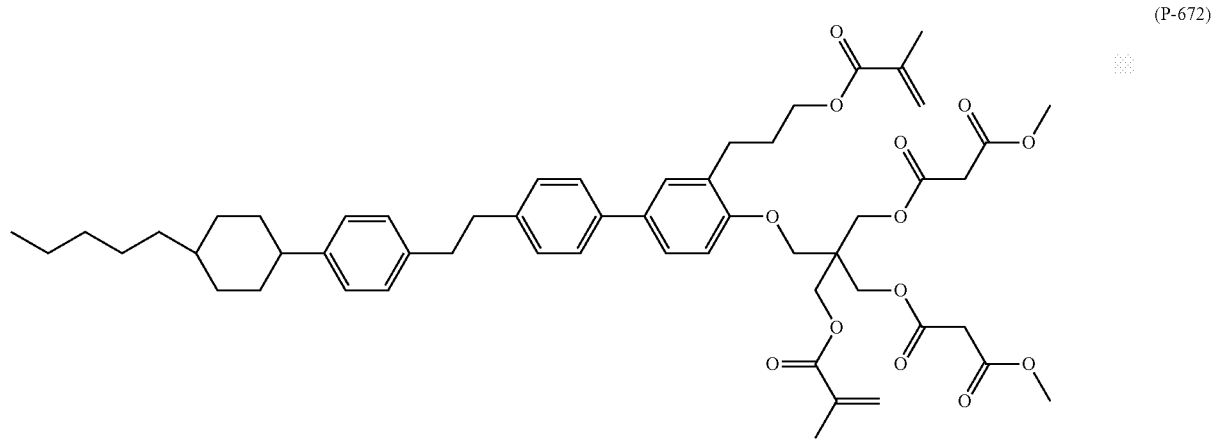
(P-672)
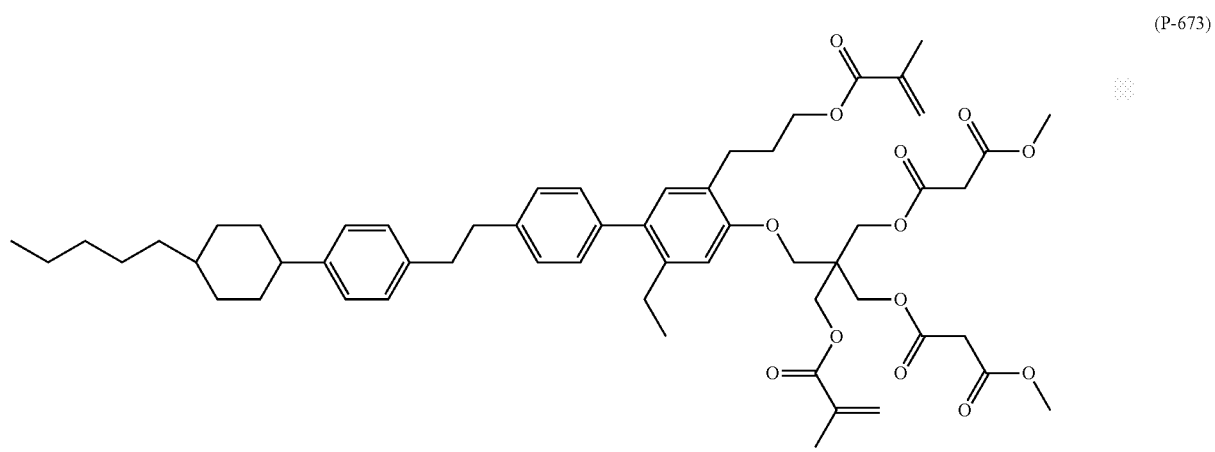
(P-673)
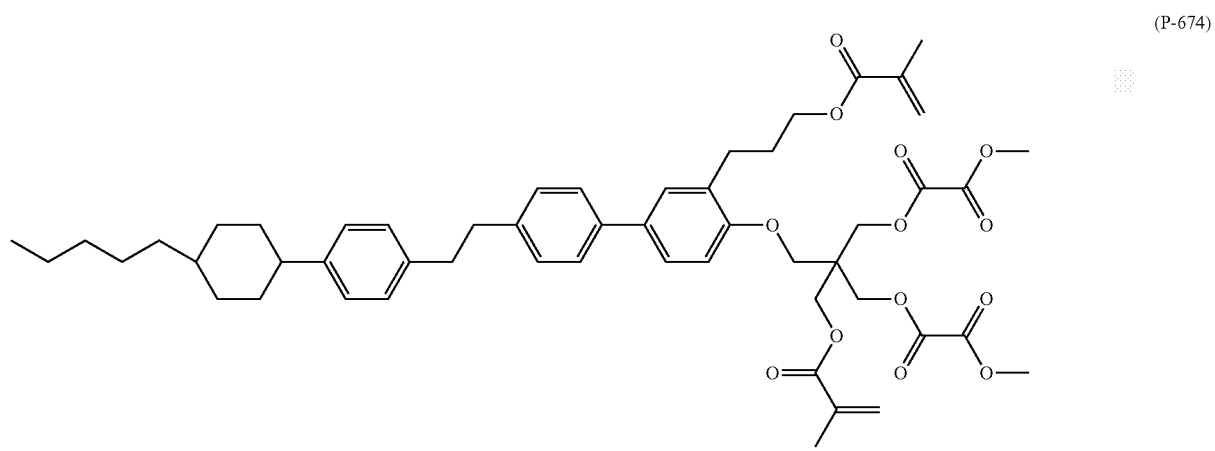
(P-674)

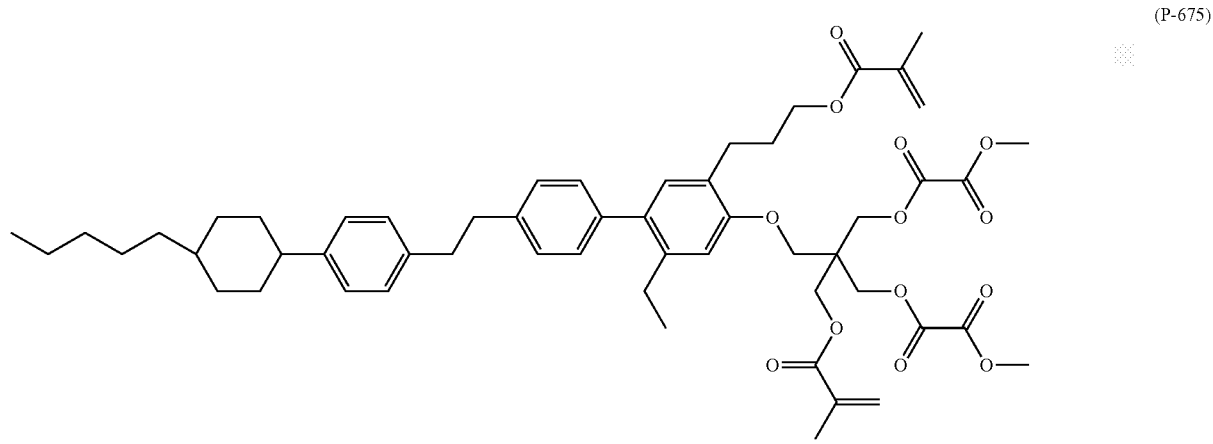
(P-675)
[Chem. 117]
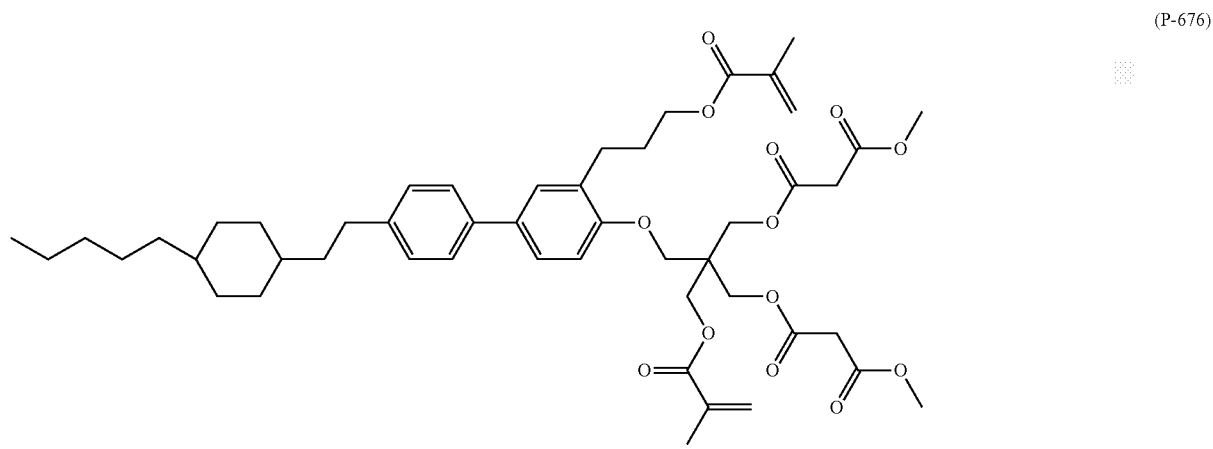
(P-676)
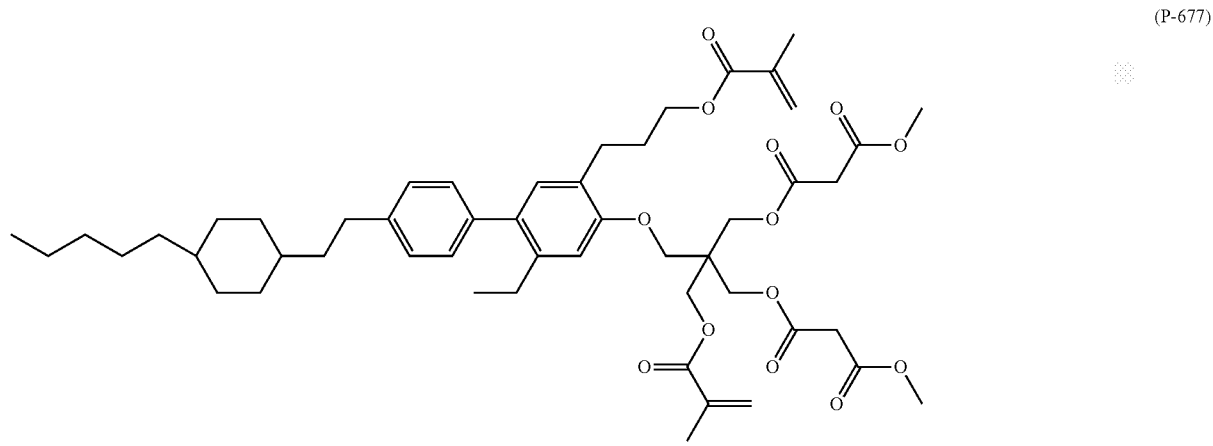
(P-677)

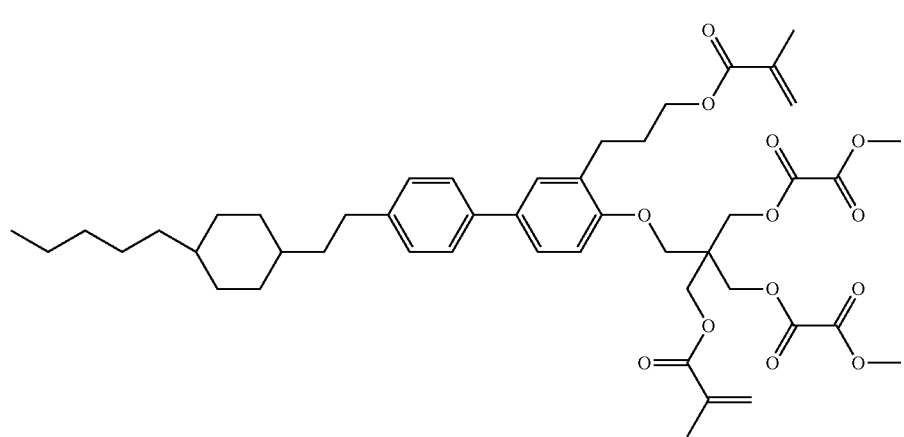
(P-678)
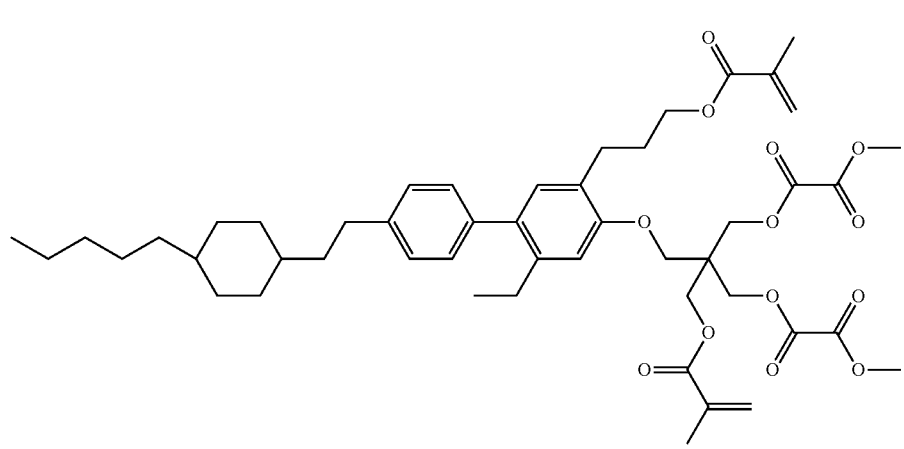
(P-679)
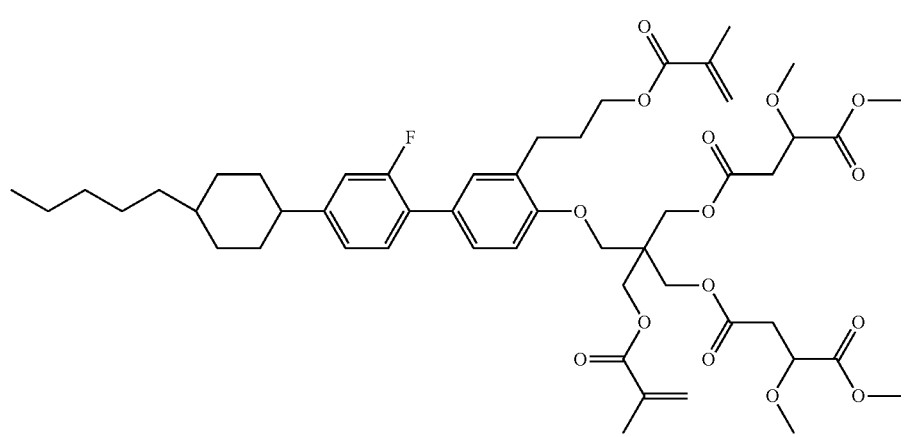
(P-680)

-continued
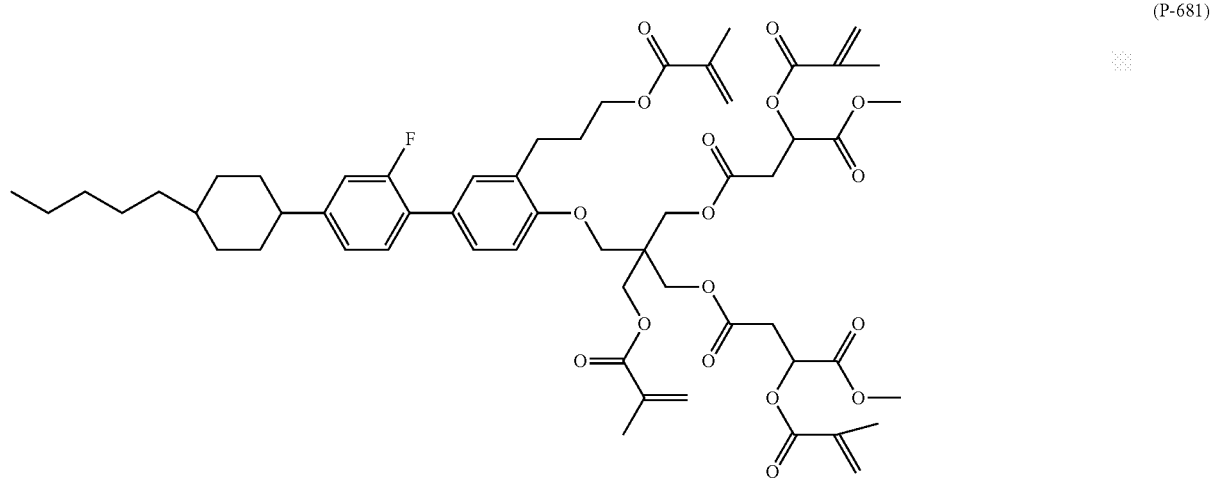
(P-681)
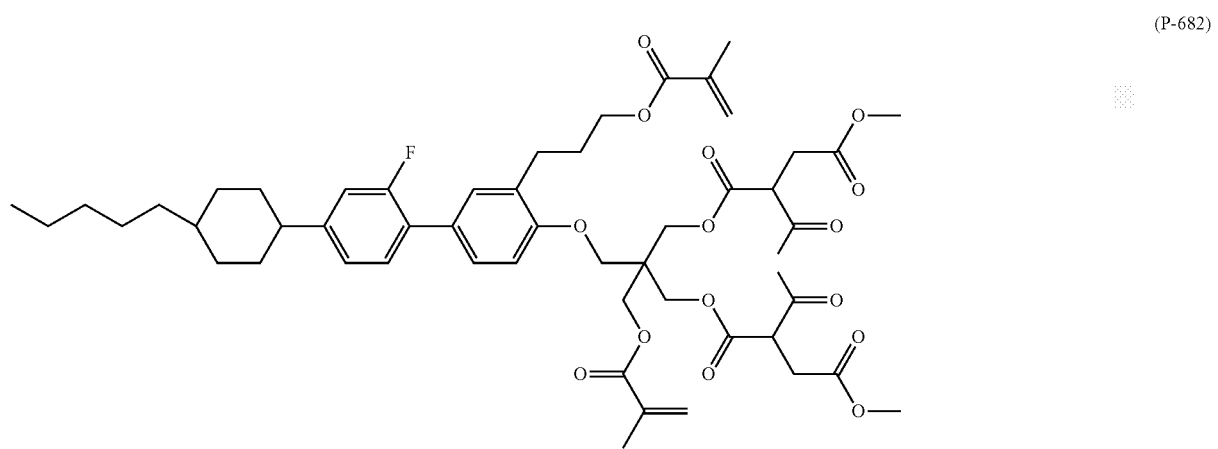
(P-682)
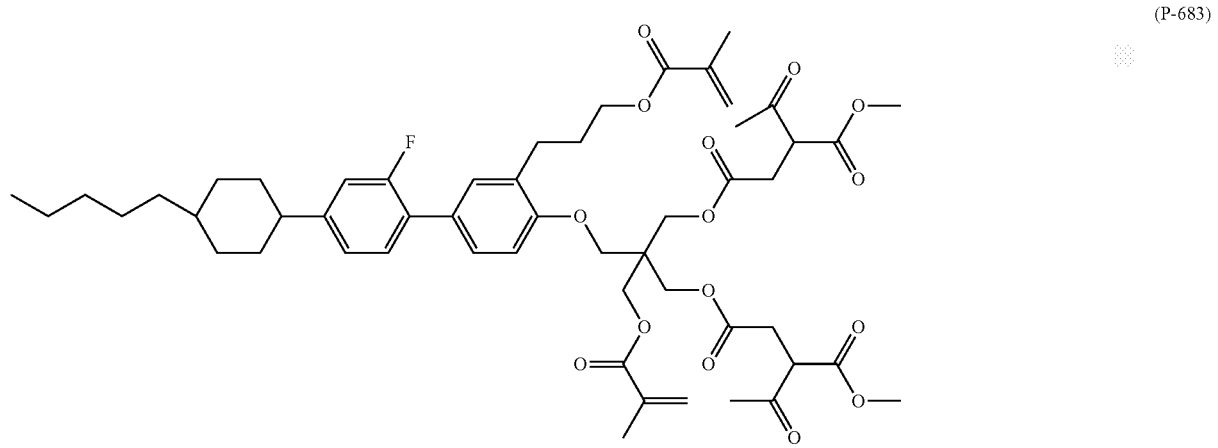
(P-683)

(P-684)
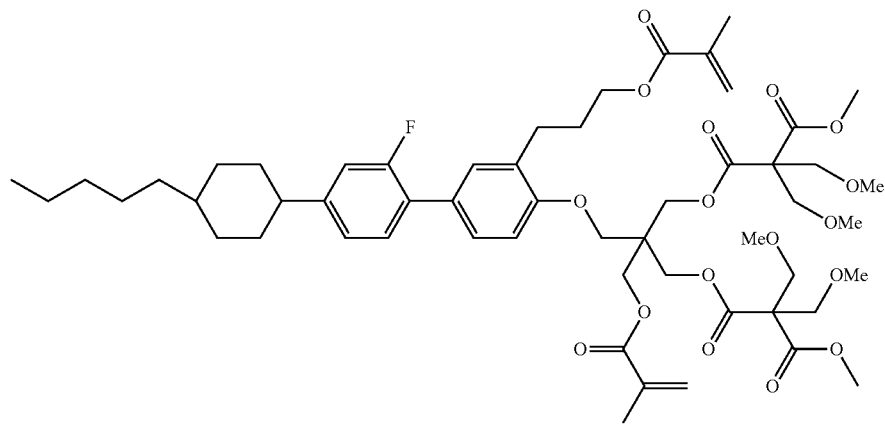
(P-685)
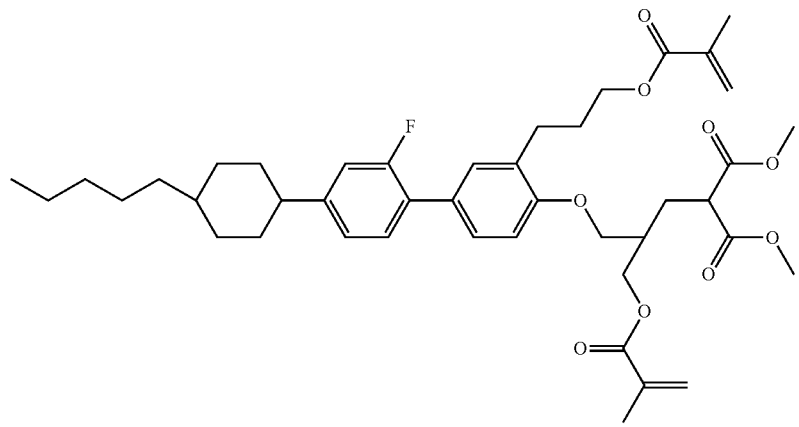
(P-686)
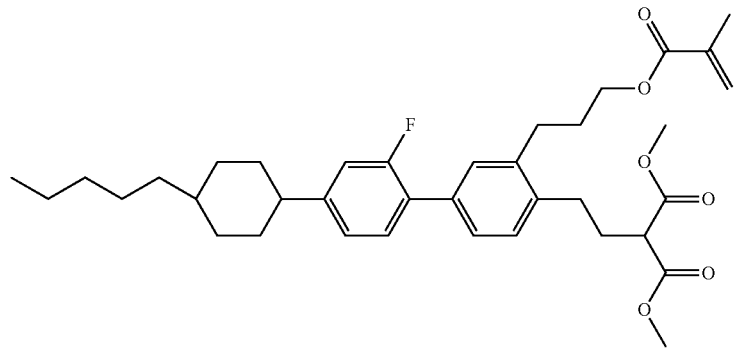
(P-687)
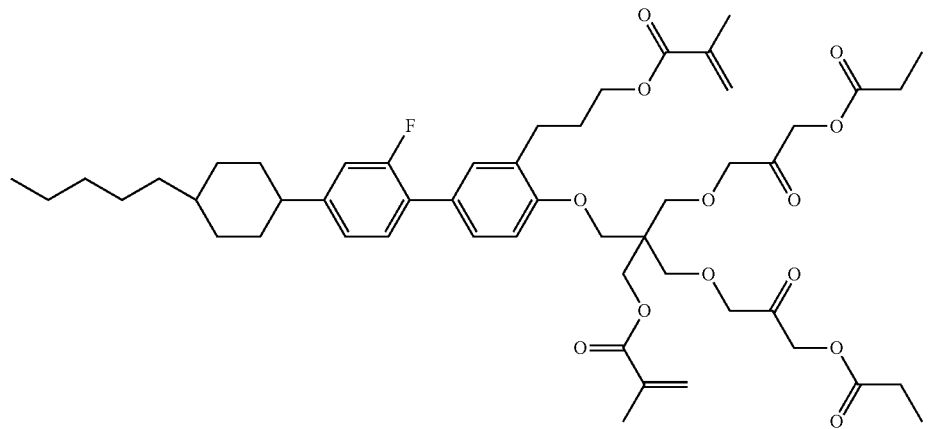

[Chem. 118]
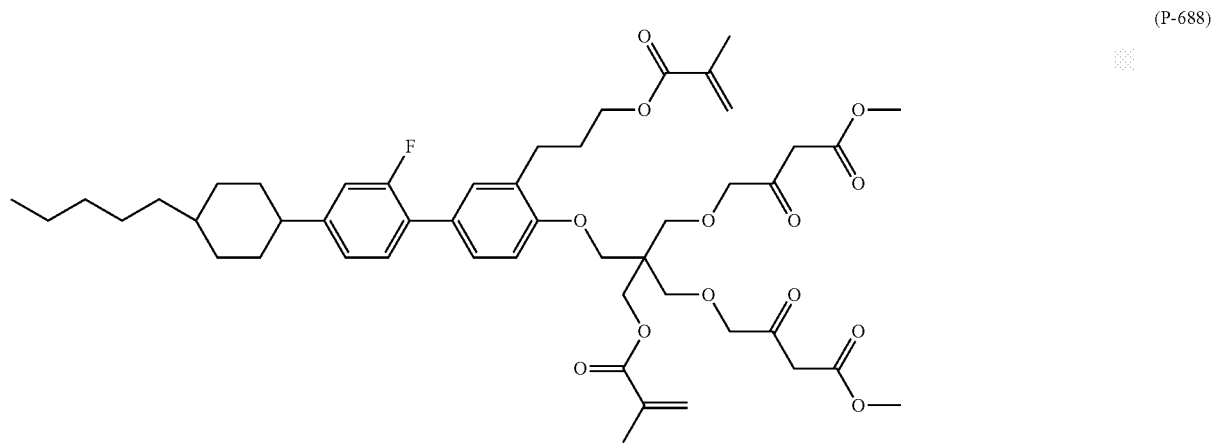
(P-688)
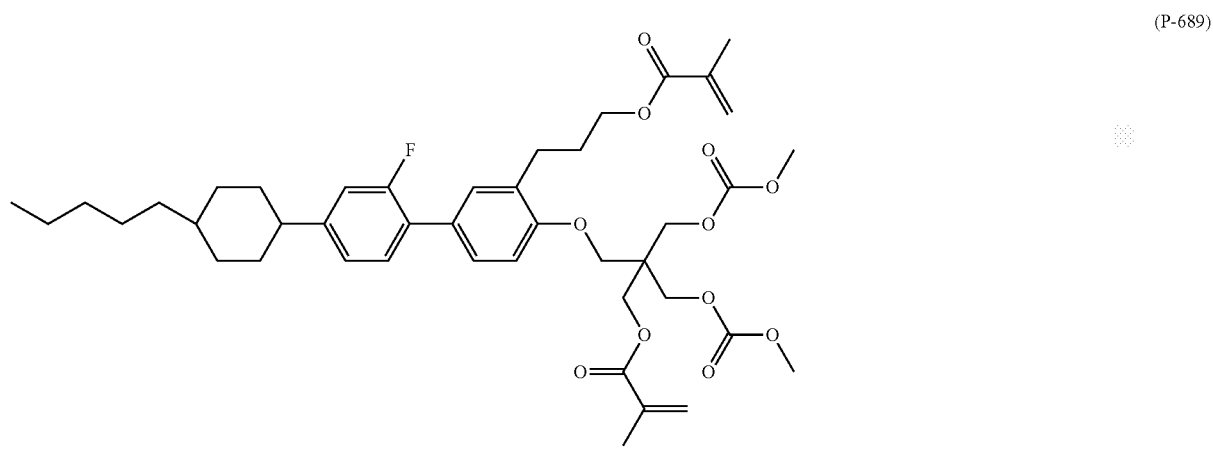
(P-689)
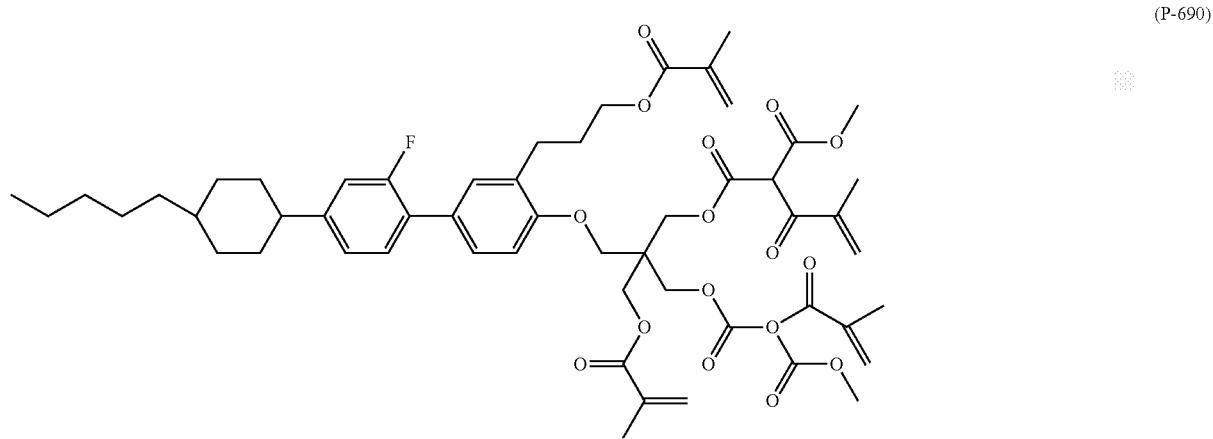
(P-690)

(P-691)
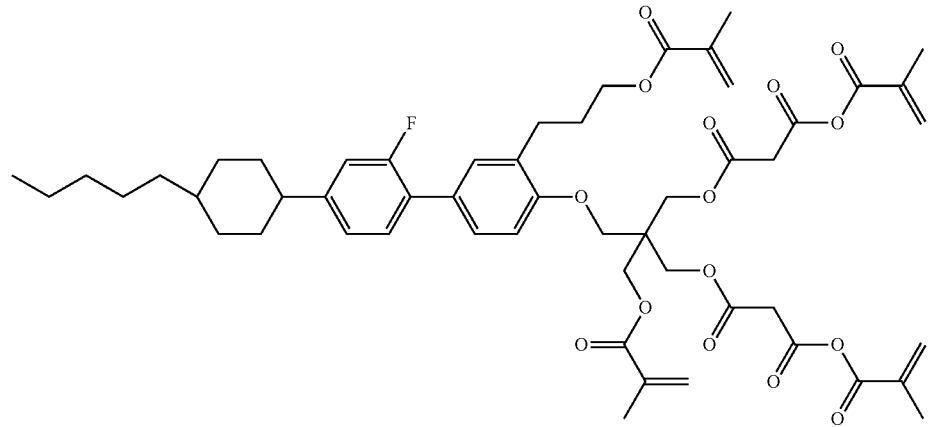
(P-692)
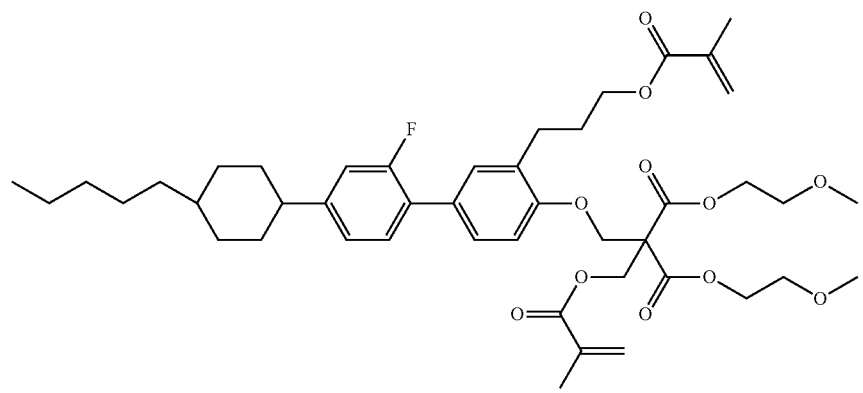
(P-693)
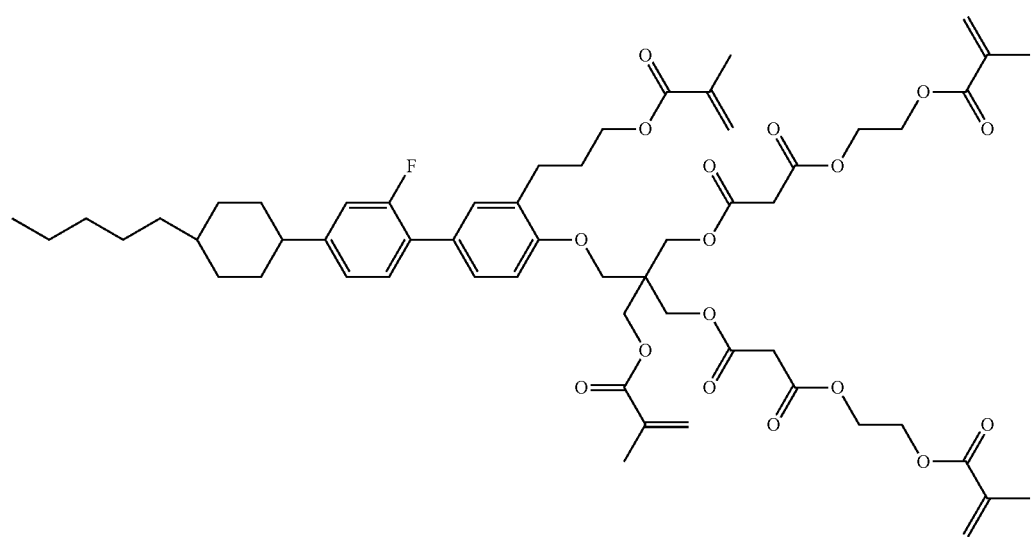

(P-694)

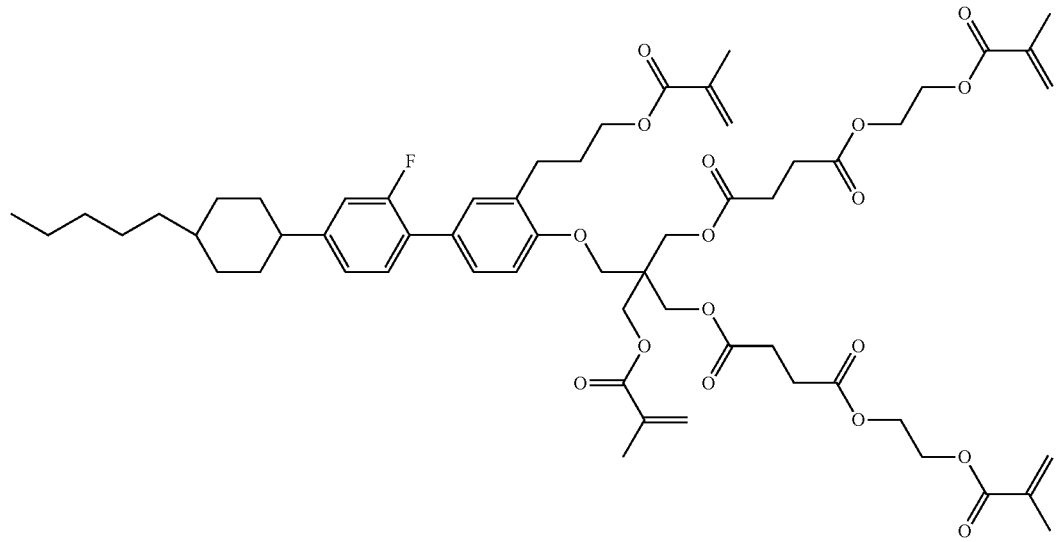

(P-695)

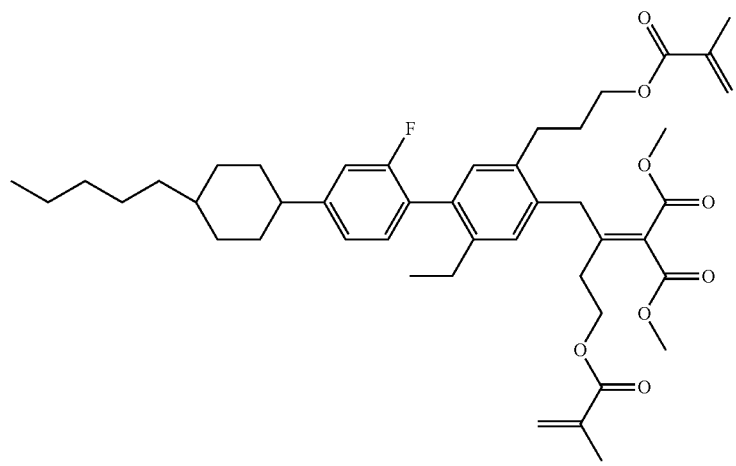

Production Example for Compound Represented by General Formula (i)

(Production Method 1) Production of Compound Represented by General Formula (P-8)

A palladium-catalyzed Suzuki coupling reaction of 3-fluoro-4-(4-pentyl (cyclohexyl))phenylboronic acid with 3-hydroxypropylphenol is performed to obtain (S-1). Next, an etherification reaction with (5-(bromomethyl)-2,2-dimethyl-1,3-dioxan-5-yl)methanol is performed to obtain (S-2). (S-2) is reacted with methacryloyl chloride, and thereafter a deketalization reaction with hydrochloric acid is performed to obtain an alcohol derivative (S-3). Furthermore, an esterification reaction with methyl malonyl chloride is performed. Accordingly, a target compound (P-8) can be obtained.

[Chem. 119]

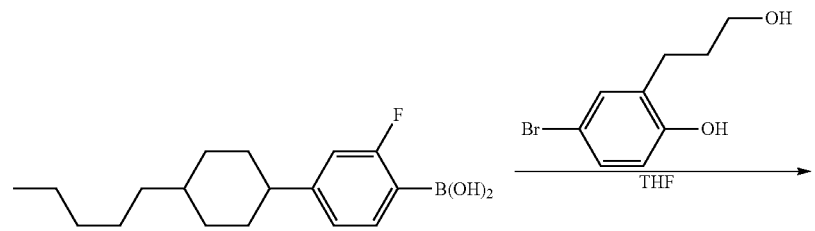

-continued
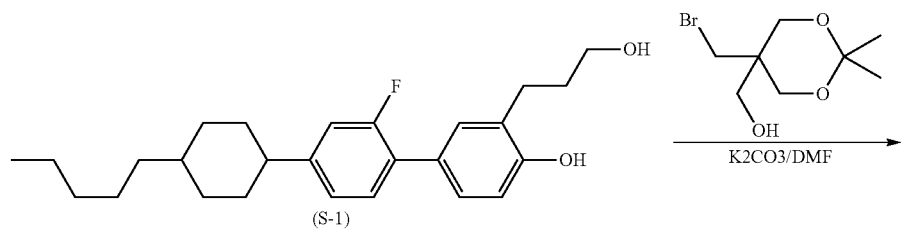
(S-1)
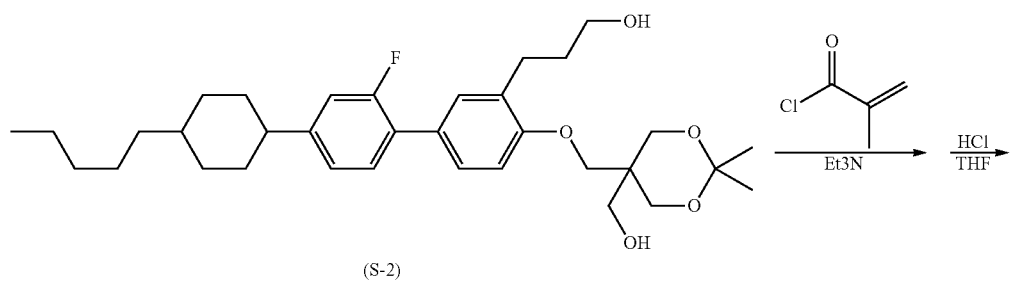
(S-2)
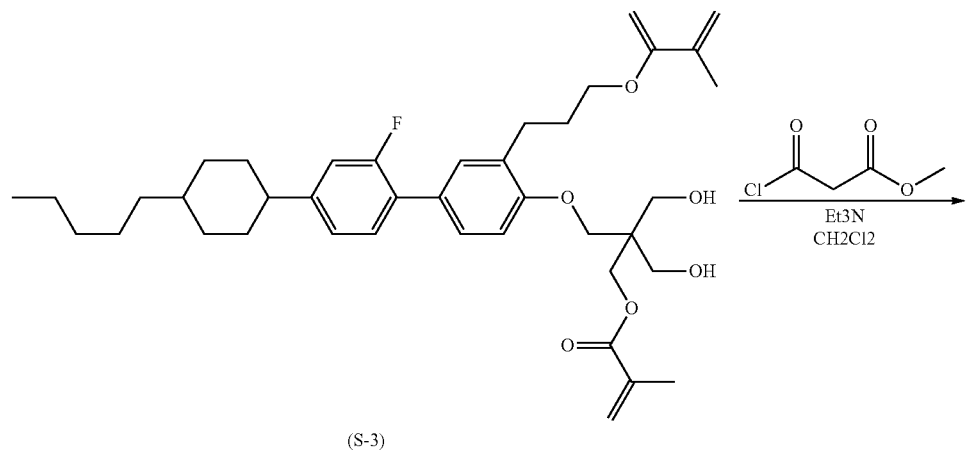
(S-3)
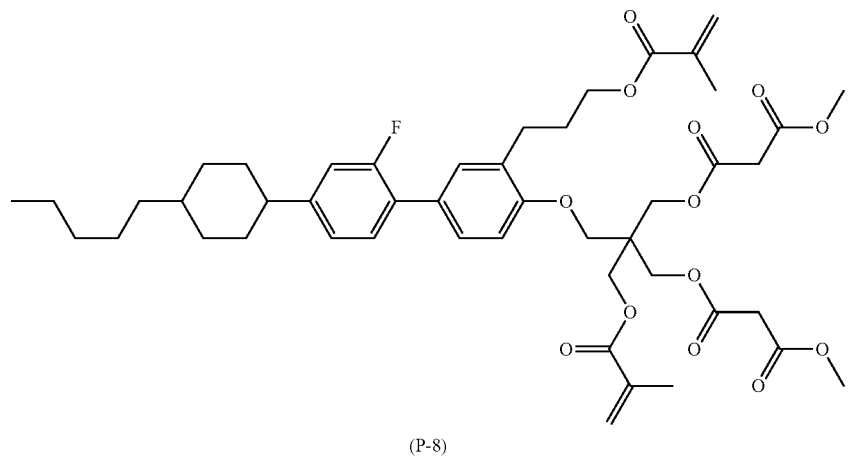
(P-8)

(Production Method 2) Production of Compounds Represented by General Formulae (P-298), (P-310), and (P-370)

Target compounds (P-298), (P-310), and (P-370) can be obtained by performing an esterification reaction of the alcohol derivative (S-3), which is obtained in Production Method 1, with a corresponding acid chloride.

[Chem. 120]

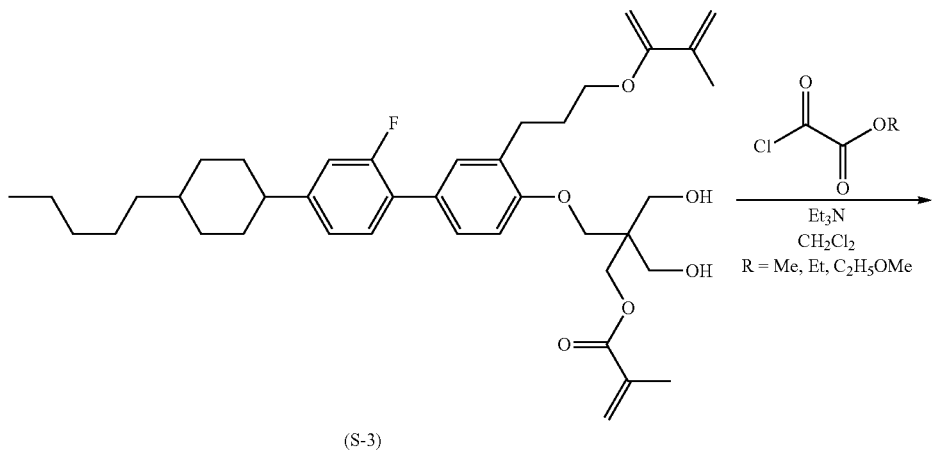

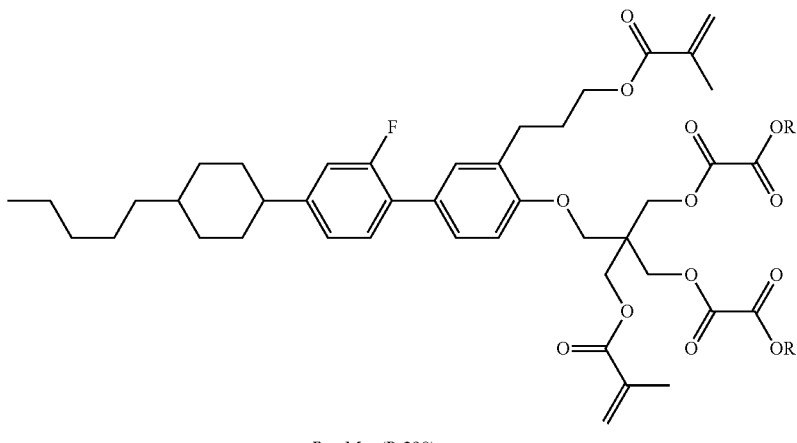

R = Me: (P-298)
= Et: (P-310)
= C$_2$H$_5$OMe: (P-358)

(Production Method 3) Production of Compound Represented by General Formula (P-282)

(S-4) is obtained by iodinating 4-bromophenol. Next, a Sonogashira reaction is performed with propargyl alcohol to obtain (S-5). Next, a hydrogenation reaction is performed to obtain (S-6). Next, an etherification reaction is performed with a corresponding chloride to obtain (S-7), and further, an esterification reaction is performed with methacryl chloride. Accordingly, (S-8) can be obtained. Next, a palladium-catalyzed Suzuki coupling reaction with 2-fluoro-4-(4-pentyl cyclohexyl)phenylboronic acid is performed. Accordingly, a compound (P-282) can be obtained.

[Chem. 121]
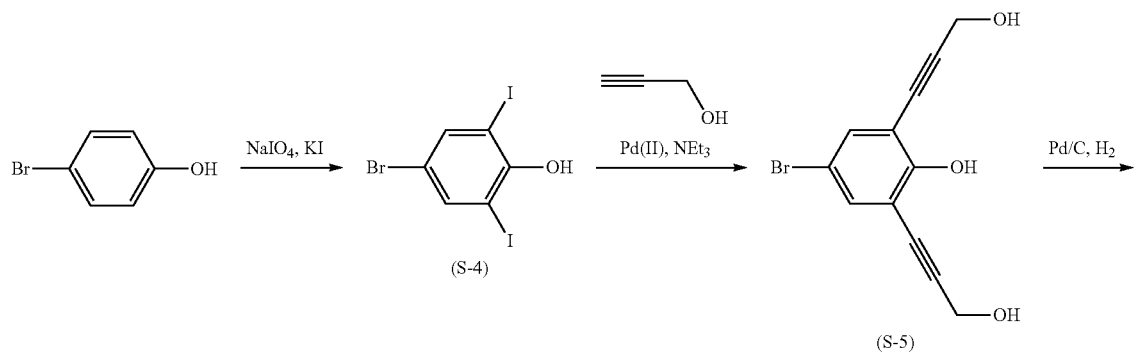
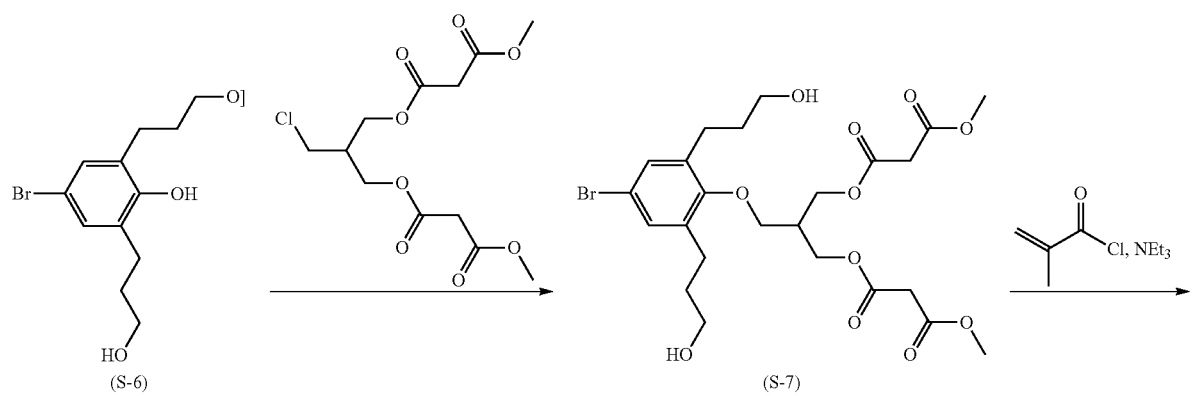
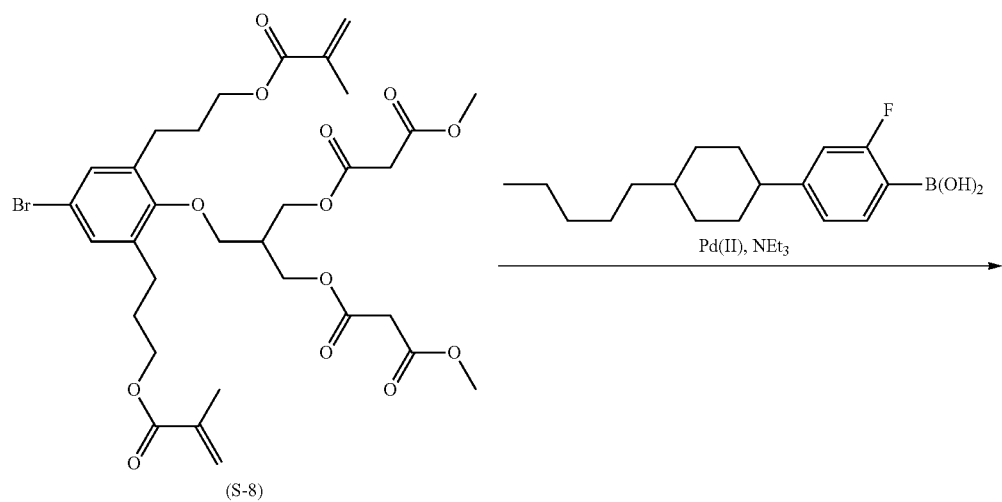

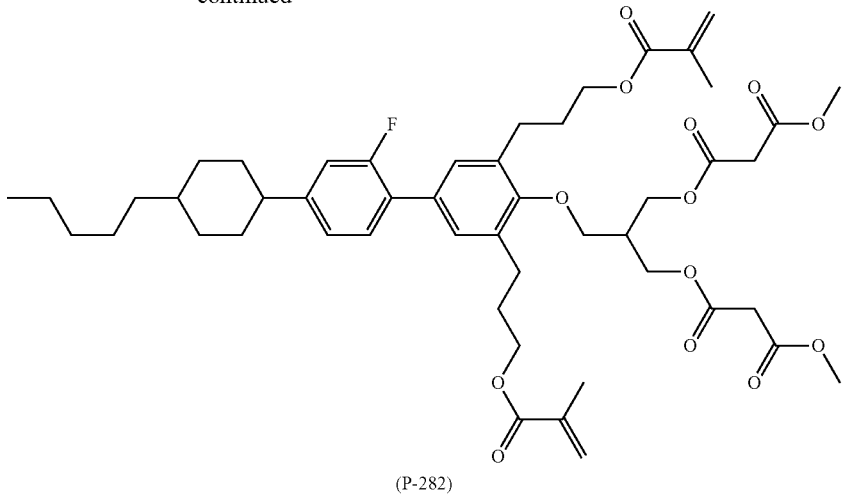
(P-282)
(Production Method 4) Production of Compounds Represented by General Formulae (P-346) and (P-370)
Target compounds (P-346) and (P-370) can be obtained by performing a condensation reaction of the alcohol derivative (S-3), which is obtained in Production Method 1, with a corresponding carboxylic acid.
[Chem. 122]
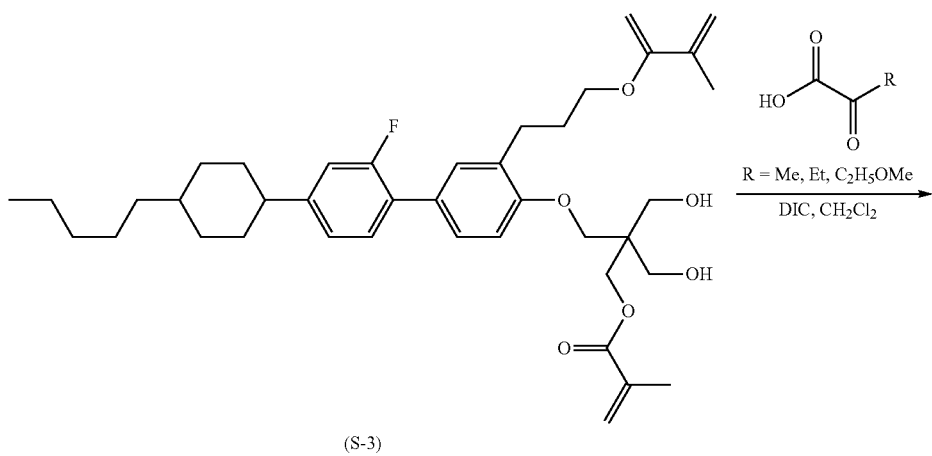
(S-3)
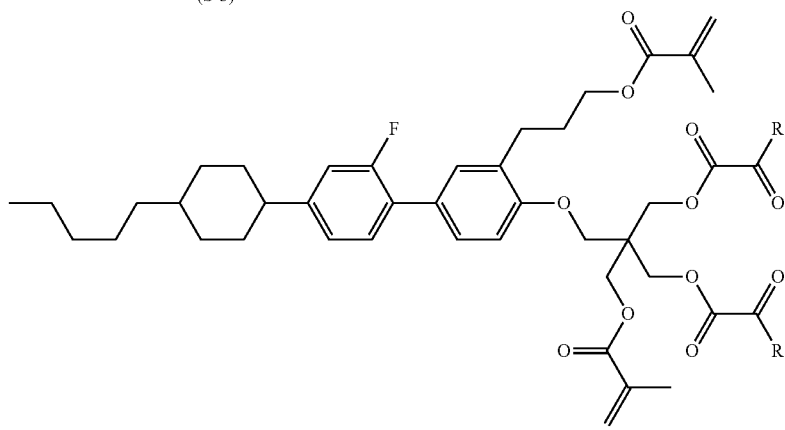
R = Me: (P-346)
= C$_2$H$_5$OMe: (P-370)

(Liquid Crystal Composition)

A liquid crystal composition according to an embodiment includes one or more compounds represented by general formula (i), which is shown above. It is preferable that the liquid crystal composition have a negative dielectric anisotropy (Δε). Note that a description of compounds represented by general formula (i) that may be included in the liquid crystal composition is omitted here because the compounds are the same as compounds (i), which are described above, including the compounds represented by formulae (R-1-1) to (R-1-25).

It is preferable that a content of the compound represented by general formula (i) be 0.01 to 50 mass %. From the standpoint of achieving a more suitable alignment of liquid crystal molecules, it is preferable that the lower limit be greater than or equal to 0.01 mass %, greater than or equal to 0.1 mass %, greater than or equal to 0.5 mass %, greater than or equal to 0.7 mass %, or greater than or equal to 1 mass %, relative to a total amount of the liquid crystal composition. From the standpoint of achieving excellent response characteristics, it is preferable that the upper limit of the content of the compound (i) be less than or equal to 50 mass %, less than or equal to 30 mass %, less than or equal to 10 mass %, less than or equal to 7 mass %, less than or equal to 5 mass %, less than or equal to 4 mass %, or less than or equal to 3 mass %, relative to the total amount of the liquid crystal composition.

General formulae (N-1), (N-2), and (N-3), regarding the liquid crystal composition, are as follows.

[Chem. 123]

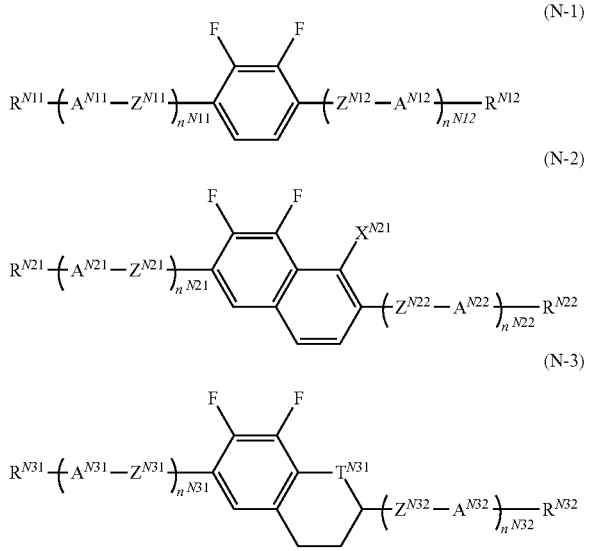

The liquid crystal composition may further include one or more compounds selected from compounds represented by any of the general formulae.

For formulae (N-1), (N-2), and (N-3), the following is noted.

$R^{N11}$, $R^{N12}$, $R^{N21}$, $R^{N22}$, $R^{N31}$, and $R^{N32}$ each independently represent an alkyl group having 1 to 8 carbon atoms, and one —$CH_2$— group or two or more non-adjacent —$CH_2$— groups in the alkyl group are each independently optionally replaced with —CH=CH—, —C≡C—, —O—, —CO—, —COO—, or —OCO—.

$A^{N11}$, $A^{N12}$, $A^{N21}$, $A^{N22}$, $A^{N31}$, and $A^{N32}$ each independently represent a group selected from the following groups:
(a) 1,4-Cyclohexylene group (one —$CH_2$— group or two or more non-adjacent —$CH_2$— groups present in the group are optionally replaced with —O—),
(b) 1,4-Phenylene group (one —CH= group or two or more non-adjacent —CH= groups present in the group are optionally replaced with —N=),
(c) Naphthalene-2,6-diyl group, 1,2,3,4-tetrahydronaphthalene-2,6-diyl group, or decahydronaphthalene-2,6-diyl group (one —CH= group or two or more non-adjacent —CH= groups present in the naphthalene-2,6-diyl group or 1,2,3,4-tetrahydronaphthalene-2,6-diyl group are optionally replaced with —N=), and
(d) 1,4-Cyclohexenylene group, where group (a), group (b), group (c), and group (d), described above, are each independently optionally substituted with a cyano group, a fluorine atom, or a chlorine atom.

$Z^{N11}$, $Z^{N12}$, $Z^{N21}$, $Z^{N22}$, $Z^{N31}$, and $Z^{N32}$ each independently represent a single bond, —$CH_2CH_2$—, —$(CH_2)_4$—, —$OCH_2$—, —$CH_2O$—, —COO—, —OCO—, —$OCF_2$—, —$CF_2O$—, —CH=N—N=CH—, —CH=CH—, —CF=CF—, or —C≡C—.

$X^{N21}$ represents a hydrogen atom or a fluorine atom.

$T^{N31}$ represents —$CH_2$— or an oxygen atom.

$n^{N11}$, $n^{N12}$, $n^{N21}$, $n^{N22}$, $n^{N31}$, and $n^{N32}$ each independently represent an integer of 0 to 3 provided that $n^{N11}+n^{N12}$, $n^{N21}+n^{N22}$, and $n^{N31}+n^{N32}$ are each independently 1, 2, or 3. When any of $A^{N11}$ to $A^{N32}$ and $Z^{N11}$ to $Z^{N32}$ is a plurality of units, the units may be identical to or different from one another.

It is preferable that compounds represented by any of general formulae (N-1), (N-2), and (N-3) be compounds having a negative Δε with the absolute value thereof being greater than 3.

In general formulae (N-1), (N-2), and (N-3), $R^{N11}$, $R^{N12}$, $R^{N21}$, $R^{N22}$, $R^{N31}$, and $R^{N32}$ are each independently preferably an alkyl group having 1 to 8 carbon atoms, an alkoxy group having 1 to 8 carbon atoms, an alkenyl group having 2 to 8 carbon atoms, or an alkenyloxy group having 2 to 8 carbon atoms, preferably an alkyl group having 1 to 5 carbon atoms, an alkoxy group having 1 to 5 carbon atoms, an alkenyl group having 2 to 5 carbon atoms, or an alkenyloxy group having 2 to 5 carbon atoms, more preferably an alkyl group having 1 to 5 carbon atoms or an alkenyl group having 2 to 5 carbon atoms, more preferably an alkyl group having 2 to 5 carbon atoms or an alkenyl group having 2 or 3 carbon atoms, and particularly preferably an alkenyl group having 3 carbon atoms (propenyl group).

Furthermore, when the ring system to which any of the above-mentioned units are to be attached is a phenyl group (aromatic group), the units are preferably a linear alkyl group having 1 to 5 carbon atoms, a linear alkoxy group having 1 to 4 carbon atoms, or an alkenyl group having 4 or 5 carbon atoms, and when the ring system to which any of the above-mentioned units are to be attached is a saturated ring system, such as cyclohexane, pyran, or dioxane, the units are preferably a linear alkyl group having 1 to 5 carbon atoms, a linear alkoxy group having 1 to 4 carbon atoms, or a linear alkenyl group having 2 to 5 carbon atoms. In terms of stabilizing a nematic phase, it is preferable that the total number of carbon atoms and, if present, oxygen atoms is less than or equal to 5, and the chain be linear.

Preferred alkenyl groups are those selected from groups represented by any of formulae (R1) to (R5) (in each of the formulae, the black dot represents a bond).

[Chem. 124]

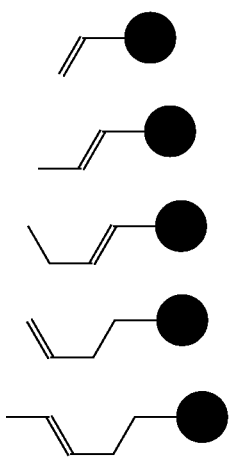

(R1)
(R2)
(R3)
(R4)
(R5)

$A^{N11}$, $A^{N12}$, $A^{N21}$, $A^{N22}$, $A^{N31}$, and $A^{N32}$ are each independently preferably an aromatic group in a case where an increased Δn is required or preferably an aliphatic group in a case where a response speed is to be improved. $A^{N11}$, $A^{N12}$, $A^{N21}$, $A^{N22}$, $A^{N31}$, and $A^{N32}$ each independently preferably represent a trans-1,4-cyclohexylene group, a 1,4-phenylene group, a 2-fluoro-1,4-phenylene group, a 3-fluoro-1,4-phenylene group, a 3,5-difluoro-1,4-phenylene group, a 2,3-difluoro-1,4-phenylene group, a 1,4-cyclohexenylene group, a 1,4-bicyclo[2.2.2]octylene group, a piperidine-1,4-diyl group, a naphthalene-2,6-diyl group, a decahydronaphthalene-2,6-diyl group, or a 1,2,3,4-tetrahydronaphthalene-2,6-diyl group and more preferably represent the following structures.

[Chem. 125]

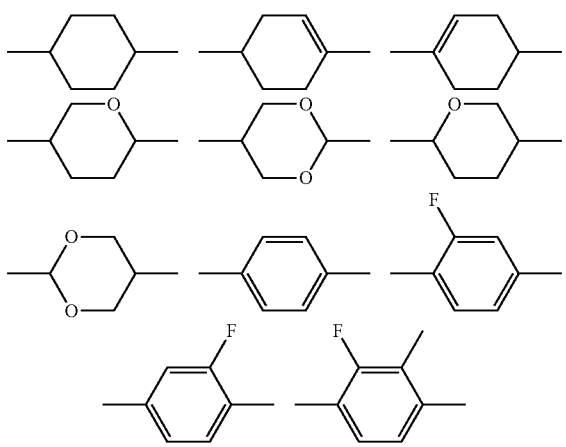

More preferably, a trans-1,4-cyclohexylene group, a 1,4-cyclohexenylene group, or a 1,4-phenylene group is represented.

Preferably, $Z^{N11}$, $Z^{N12}$, $Z^{N21}$, $Z^{N22}$, $Z^{N31}$, and $Z^{N32}$ each independently represent —$CH_2O$—, —$CF_2O$—, —$CH_2CH_2$—, —$CF_2CF_2$—, or a single bond; —$CH_2O$—, —$CH_2CH_2$—, or a single bond is more preferable; and —$CH_2O$— or a single bond is particularly preferable.

Preferably, $X^{N21}$ is a fluorine atom.
Preferably, $T^{N31}$ is an oxygen atom.
Preferably, $n^{N11}+n^{N12}$, $n^{N21}+n^{N22}$, and $n^{N31}+n^{N32}$ are each 1 or 2. The following are preferable: a combination in which $n^{N11}$ is 1, and $n^{N12}$ is 0, a combination in which $n^{N11}$ is 2, and $n^{N12}$ is 0, a combination in which $n^{N11}$ is 1, and $n^{N12}$ is 1, a combination in which $n^{N11}$ is 2, and $n^{N12}$ is 1, a combination in which $n^{N21}$ is 1, and $n^{N22}$ is 0, a combination in which $n^{N21}$ is 2, and $n^{N22}$ is 0, a combination in which $n^{N31}$ is 1, and $n^{N32}$ is 0, and a combination in which $n^{N31}$ is 2, and $n^{N32}$ is 0.

A lower limit of a preferred content of the compound represented by formula (N-1) relative to a total amount of the composition of the embodiment is 1 mass % or greater, 10 mass % or greater, 20 mass % or greater, 30 mass % or greater, 40 mass % or greater, 50 mass % or greater, 55 mass % or greater, 60 mass % or greater, 65 mass % or greater, 70 mass % or greater, 75 mass % or greater, or 80 mass % or greater. An upper limit of the preferred content is 95 mass % or less, 85 mass % or less, 75 mass % or less, 65 mass % or less, 55 mass % or less, 45 mass % or less, 35 mass % or less, 25 mass % or less, or 20 mass % or less.

A lower limit of a preferred content of the compound represented by formula (N-2) relative to the total amount of the composition of the embodiment is 1 mass % or greater, 10 mass % or greater, 20 mass % or greater, 30 mass % or greater, 40 mass % or greater, 50 mass % or greater, 55 mass % or greater, 60 mass % or greater, 65 mass % or greater, 70 mass % or greater, 75 mass % or greater, or 80 mass % or greater. An upper limit of the preferred content is 95 mass % or less, 85 mass % or less, 75 mass % or less, 65 mass % or less, 55 mass % or less, 45 mass % or less, 35 mass % or less, 25 mass % or less, or 20 mass % or less.

A lower limit of a preferred content of the compound represented by formula (N-3) relative to the total amount of the composition of the embodiment is 1 mass % or greater, 10 mass % or greater, 20 mass % or greater, 30 mass % or greater, 40 mass % or greater, 50 mass % or greater, 55 mass % or greater, 60 mass % or greater, 65 mass % or greater, 70 mass % or greater, 75 mass % or greater, or 80 mass % or greater. An upper limit of the preferred content is 95 mass % or less, 85 mass % or less, 75 mass % or less, 65 mass % or less, 55 mass % or less, 45 mass % or less, 35 mass % or less, 25 mass % or less, or 20 mass % or less.

In a case where it is necessary to keep a viscosity of the composition of the embodiment low so as to ensure that the composition has a fast response speed, it is preferable that the lower limit be low, and the upper limit be low. In addition, in a case where it is necessary to keep Tni of the composition of the embodiment high so as to ensure that the composition has good temperature stability, it is preferable that the lower limit be low, and the upper limit be low. Furthermore, in a case where it is desired to increase the dielectric anisotropy to keep the driving voltage low, it is preferable that the lower limit be high, and the upper limit be high.

Compounds represented by general formula (N-1) include compounds represented by general formulae (N-1a) to (N-1g), shown below.

[Chem. 126]

(N-1a)

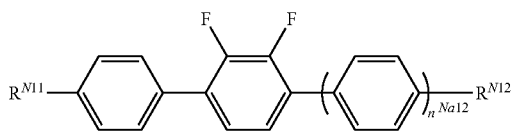

-continued

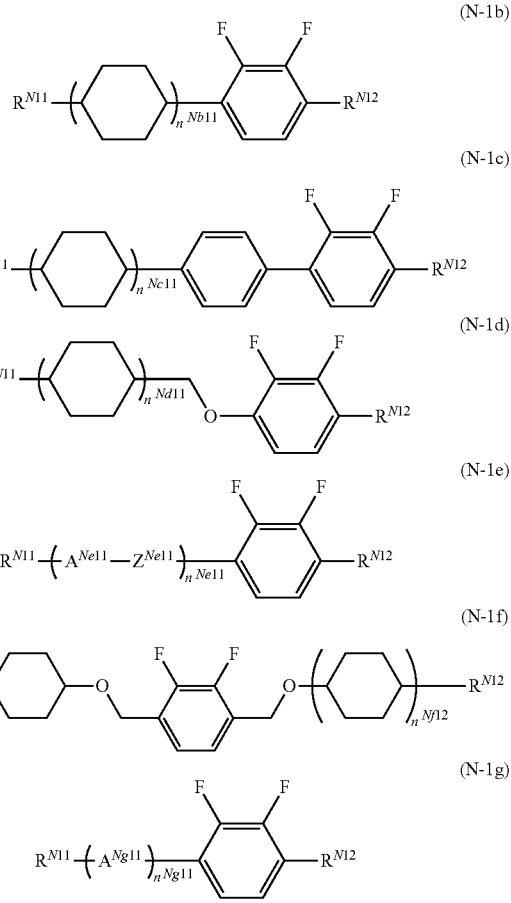

For the formula, the following is noted. $R^{N11}$ and $R^{N12}$ have the same meaning as, respectively, $R^{N11}$ and $R^{N12}$ in general formula (N-1). $n^{Na11}$ represents 0 or 1, $n^{Nb11}$ represents 0 or 1, $n^{Nc11}$ represents 0 or 1, $n^{Nd11}$ represents 0 or 1, $n^{Ne11}$ represents 1 or 2, $n^{Nf11}$ represents 1 or 2, and $n^{Ng11}$ represents 1 or 2. $A^{Ne11}$ represents a trans-1,4-cyclohexylene group or a 1,4-phenylene group, and $A^{Ng11}$ represents a trans-1,4-cyclohexylene group, a 1,4-cyclohexenylene group, or a 1,4-phenylene group provided that at least one unit is a 1,4-cyclohexenylene group. $Z^{Ne11}$ represents a single bond or ethylene provided that at least one unit is ethylene.

More specifically, it is preferable that compounds represented by general formula (N-1) be compounds selected from compounds represented by general formulae (N-1-1) to (N-1-21).

Compounds represented by general formula (N-1-1) are compounds shown below.

[Chem. 127]

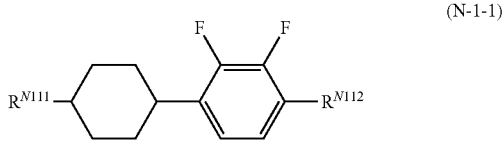

In the formula, $R^{N111}$ and $R^{N112}$ have the same meaning as, respectively, $R^{N11}$ and $R^{N12}$ in general formula (N).

Preferably, $R^{N111}$ is an alkyl group having 1 to 5 carbon atoms or an alkenyl group having 2 to 5 carbon atoms; preferably, $R^{N111}$ is a propyl group, a pentyl group, or a vinyl group. Preferably, $R^{N112}$ is an alkyl group having 1 to 5 carbon atoms, an alkenyl group having 4 or 5 carbon atoms, or an alkoxy group having 1 to 4 carbon atoms; preferably, $R^{N112}$ is an ethoxy group or a butoxy group.

The compounds represented by general formula (N-1-1) may be used alone or in a combination of two or more. Types of compounds that may be combined together are not particularly limited; compounds may be appropriately combined and used in accordance with the properties required, such as solubility at low temperature, a transition temperature, electrical reliability, and birefringence. For example, in one embodiment, one, two, three, four, or five or more types of compounds may be used.

In a case where improvement of $\Delta\varepsilon$ is regarded as important, it is preferable to set the content to be relatively high. In a case where solubility at low temperature is regarded as important, the content may be set to be relatively high to produce a considerable effect. In a case where $T_{NI}$ is regarded as important, the content may be set to be relatively low to produce a considerable effect. In addition, in a case where drop marks and image-sticking characteristics are to be improved, it is preferable to set the range of the content to be in a middle.

A lower limit of a preferred content of the compound represented by formula (N-1-1) relative to the total amount of the composition of the embodiment is 5 mass % or greater, 10 mass % or greater, 13 mass % or greater, 15 mass % or greater, 17 mass % or greater, 20 mass % or greater, 23 mass % or greater, 25 mass % or greater, 27 mass % or greater, 30 mass % or greater, 33 mass % or greater, or 35 mass % or greater. An upper limit of the preferred content relative to the total amount of the composition of the embodiment is 50 mass % or less, 40 mass % or less, 38 mass % or less, 35 mass % or less, 33 mass % or less, 30 mass % or less, 28 mass % or less, 25 mass % or less, 23 mass % or less, 20 mass % or less, 18 mass % or less, 15 mass % or less, 13 mass % or less, 10 mass % or less, 8 mass % or less, 7 mass % or less, 6 mass % or less, 5 mass % or less, or 3 mass % or less.

In addition, it is preferable that compounds represented by general formula (N-1-1) be compounds selected from compounds represented by formulae (N-1-1.1) to (N-1-1.23). Compounds represented by formulae (N-1-1.1) to (N-1-1.4) are preferable, or compounds represented by formula (N-1-1.1) and formula (N-1-1.3) are preferable.

[Chem. 128]

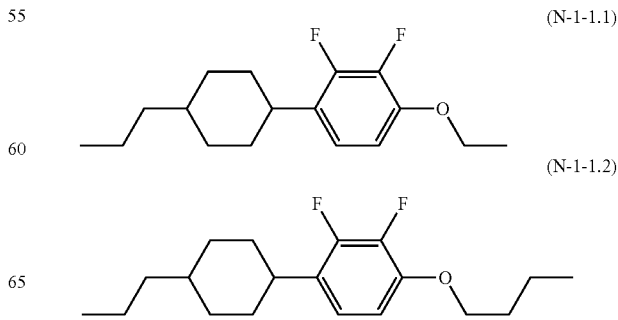

-continued

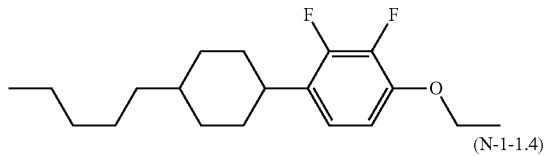
(N-1-1.3)

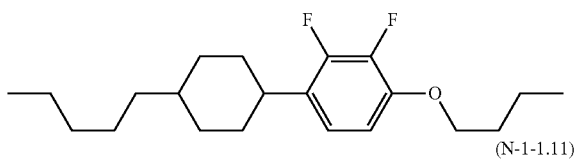
(N-1-1.4)

(N-1-1.11)

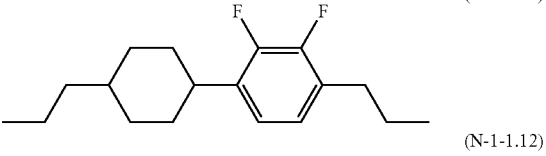
(N-1-1.12)

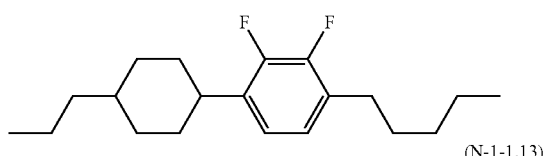
(N-1-1.13)

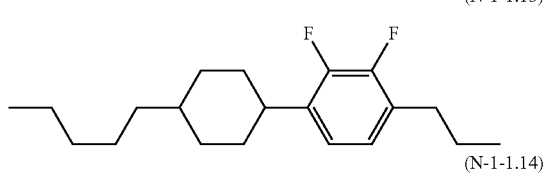
(N-1-1.14)

(N-1-1.20)

(N-1-1.21)

(N-1-1.22)

The compounds represented by formulae (N-1-1.1) to (N-1-1.22) may be used alone or in a combination. A lower limit of a preferred content of one or more of these compounds relative to the total amount of the composition of the embodiment is 5 mass % or greater, and an upper limit thereof relative to the total amount of the composition of the embodiment is 50 mass % or less.

Furthermore, liquid crystal compositions of the present invention may further include another polymerizable compound, which is different from compounds represented by general formula (i). The polymerizable compound may be a known polymerizable compound that can be used in a liquid crystal composition. General formula (P) is shown below.

[Chem. 129]

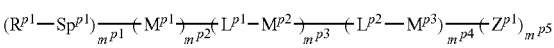
(P)

Examples of the polymerizable compound include compounds represented by general formula (P).

For formula (P), the following is noted.

$Z^{p1}$ represents a fluorine atom, a cyano group, a hydrogen atom, an alkyl group having 1 to 15 carbon atoms in which one or more hydrogen atoms are optionally replaced with a halogen atom, an alkoxy group having 1 to 15 carbon atoms in which one or more hydrogen atoms are optionally replaced with a halogen atom, an alkenyl group having 1 to 15 carbon atoms in which one or more hydrogen atoms are optionally replaced with a halogen atom, an alkenyloxy group having 1 to 15 carbon atoms in which one or more hydrogen atoms are optionally replaced with a halogen atom, or -$Sp^{p2}$-$R^{p2}$.

$R^{p1}$ and $R^{p2}$ represent one of formulae (R-I) to (R-VIII), shown below.

[Chem. 130]

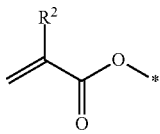
(R-I)

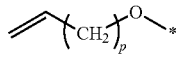
(R-II)

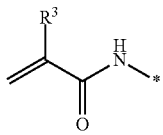
(R-III)

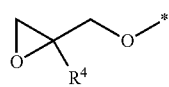
(R-IV)

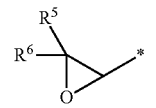
(R-V)

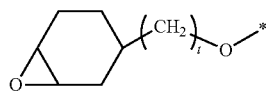
(R-VI)

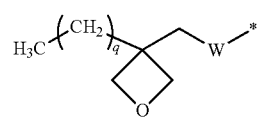
(R-VII)

(R-VIII)

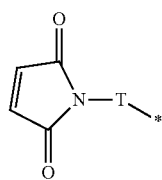

In the formula, * is a point of attachment to $Sp^{p1}$; $R^2$ to $R^6$ each independently represent a hydrogen atom, an alkyl group having 1 to 5 carbon atoms, or a halogenated alkyl group having 1 to 5 carbon atoms; W represents a single bond, —O—, or a methylene group; T represents a single bond or —COO—; and p, t, and q each independently represent 0, 1, or 2.

$Sp^{p1}$ and $Sp^{p2}$ represent a spacer group.

$L^{p1}$ and $L^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_z$—C(=O)—O—, —(CH$_2$)$_z$—O—(C=O)—, —O—(C=O)—(CH$_2$)$_z$—, —(C=O)—O—(CH$_2$)$_z$—, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C—, where $R^a$ independently represents a hydrogen atom or an alkyl group having 1 to 4 carbon atoms, and z represents an integer of 1 to 4.

$M^{p2}$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, a 1,3-dioxane-2,5-diyl group, or a single bond. $M^{p2}$ is unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$.

$M^{p1}$ represents one of formulae (i-11) to (ix-11), shown below.

[Chem. 131]

(i-11)

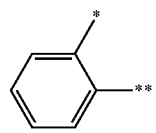

(ii-11)

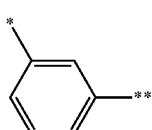

(iii-11)

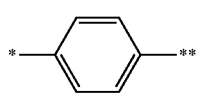

(iv-11)

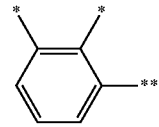

(v-11)

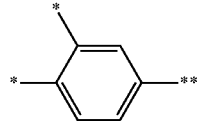

(vi-11)

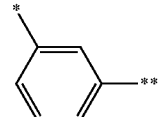

(vii-11)

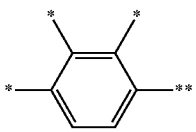

(viii-11)

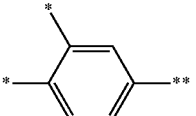

(ix-11)

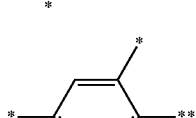

In the formulae, * is a point of attachment to $Sp^{p1}$, and ** is a point of attachment to $L^{p1}$, $L^{p2}$, Or $Z^{p1}$.

Any hydrogen atom of $M^{p1}$ is optionally replaced with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$.

$M^{p3}$ represents one of formulae (i-13) to (ix-13), shown below.

[Chem. 132]

(i-13)

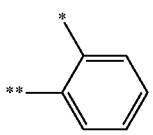

(ii-13)

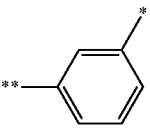

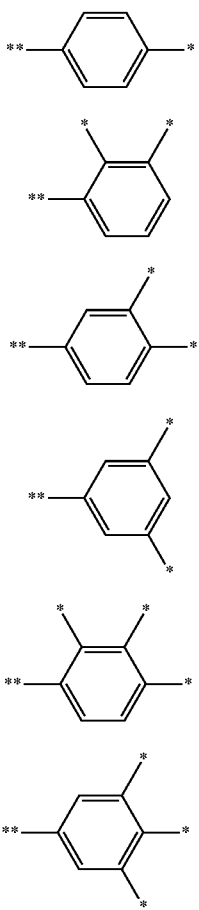

(iii-13)
(iv-13)
(v-13)
(vi-13)
(vii-13)
(viii-13)

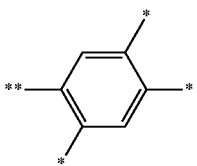

(ix-13)

In the formulae, * is a point of attachment to $Z^{p1}$, and ** is a point of attachment to $L^{p2}$.

Any hydrogen atom of $M^{p3}$ is optionally replaced with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$.

$m^{p2}$ to $m^{p4}$ each independently represent 0, 1, 2, or 3.

$m^{p1}$ and $m^{p5}$ each independently represent 1, 2, or 3.

When $Z^{p1}$ is a plurality of units, the units may be identical to or different from one another. When $R^{p1}$ is a plurality of units, the units may be identical to or different from one another. When $R^{p2}$ is a plurality of units, the units may be identical to or different from one another. When $Sp^{p1}$ is a plurality of units, the units may be identical to or different from one another. When $Sp^{p2}$ is a plurality of units, the units may be identical to or different from one another. When $L^{p1}$ is a plurality of units, the units may be identical to or different from one another. When $M^{p2}$ is a plurality of units, the units may be identical to or different from one another.

In a case where the liquid crystal composition of the embodiment further includes a polymerizable compound represented by general formula (P), in addition to the compound (i), a suitable pretilt angle of liquid crystal molecules can be formed. Specific examples of polymerizable compounds represented by general formula (P) include compounds of (P-2-1) to (P-2-20), shown below.

[Chem. 133]

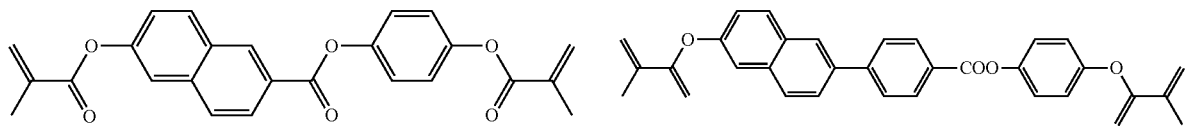

(P-2-1) (P-2-2)

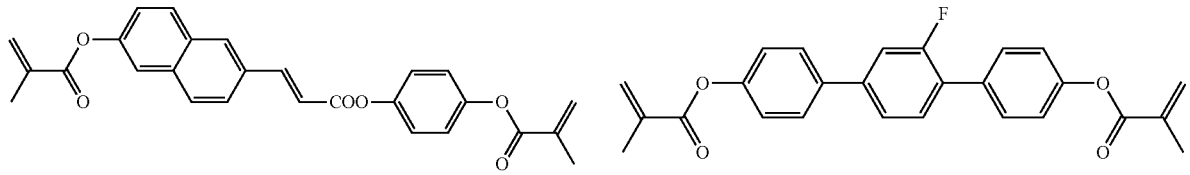

(P-2-3) (P-2-4)

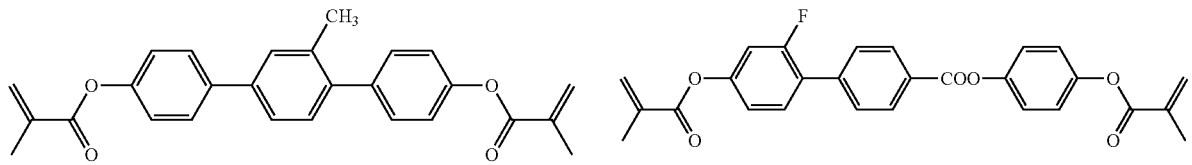

(P-2-5) (P-2-6)

(P-2-7)
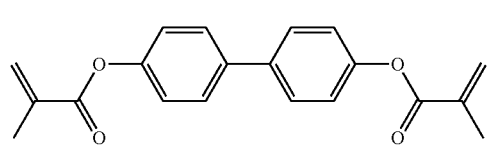
(P-2-8)
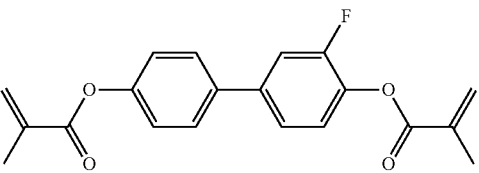
(P-2-9)
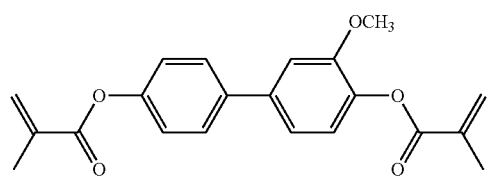
(P-2-10)
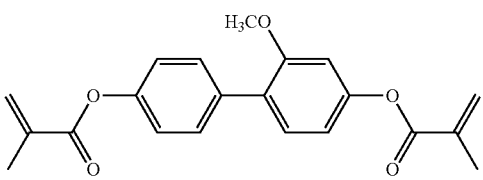
(P-2-11)
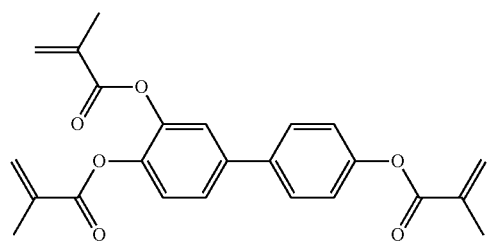
[Chem. 134]
(P-2-12)
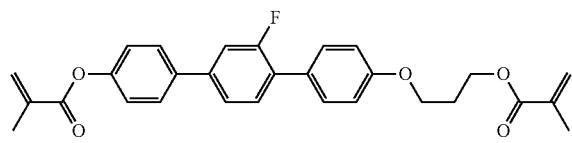
(P-2-13)
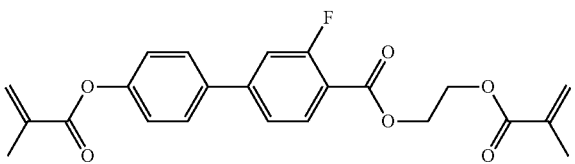
(P-2-14)
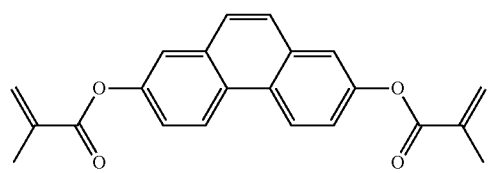
(P-2-15)
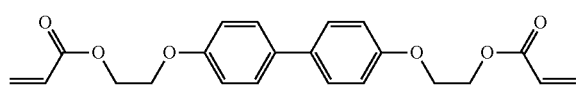
(P-2-16)
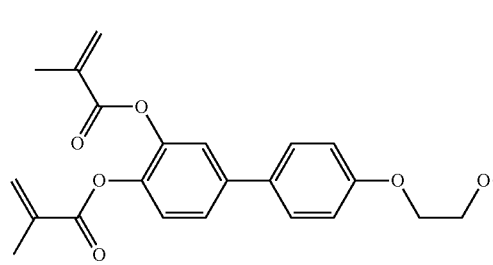
(P-2-17)
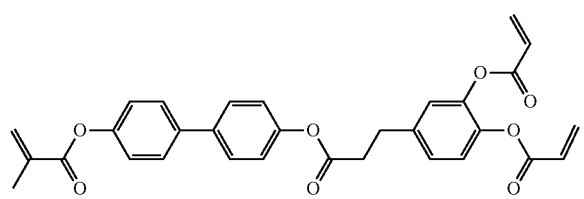
(P-2-18)
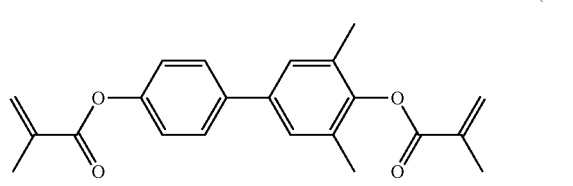

(P-2-19)
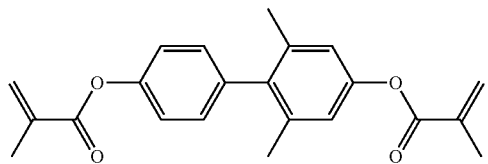

(P-2-20)
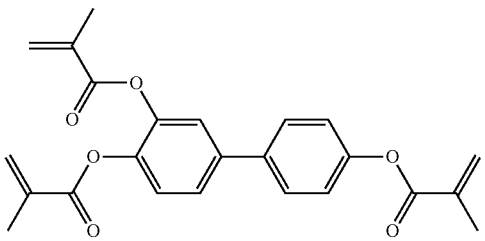

Furthermore, liquid crystal compositions of the present invention may further include a known self-alignment agent for liquid crystal compositions, in addition to a compound represented by general formula (i).

(Liquid Crystal Display Element)

The liquid crystal composition of the embodiment is employed in a liquid crystal display element. The liquid crystal display element may be an active-matrix-driven liquid crystal display element. A liquid crystal display element 1 may be a liquid crystal display element of the PSA type, PSVA type, VA type, IPS type, FFS type, or ECB type and is preferably a liquid crystal display element of the PSA type.

In the liquid crystal display element of the embodiment, a liquid crystal composition including a compound represented by general formula (i) is used, and, therefore, an alignment film, such as a polyimide alignment film, need not be provided on the liquid-crystal-layer sides of a first substrate and a second substrate. That is, the liquid crystal display element of the embodiment may have a configuration in which at least one of the two substrates does not have an alignment film, such as a polyimide alignment film.

EXAMPLES

The present invention will now be described more specifically with reference to examples; however, the present invention is not limited to the examples.

Example 1

42 g of 3-fluoro-4-(4-pentyl (cyclohexyl))phenylboronic acid, 30 g of 4-bromo-2-hydroxypropyl phenol, 27 g of potassium carbonate, 1.5 g of tetrakistriphenylphosphine palladium, and 300 ml of ethanol were added to a reaction vessel equipped with a stirrer, a condenser, and a thermometer, and then a reaction was carried out at 70° C. for 5 hours. After completion of the reaction, the resultant was cooled, and 300 ml of ethyl acid was added. The organic layer was washed with water and saturated brine, the solvent was then evaporated, and then recrystallization was carried out with toluene. Thus, a compound (48 g) represented by (1-1) was obtained.

[Chem. 135]

(1-1)
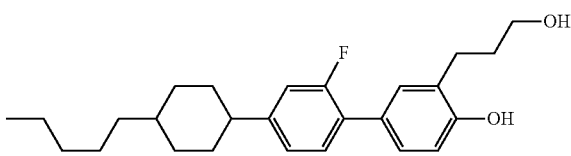

Next, 30 g of the compound (1-1), 18 g of (5-(bromomethyl)-2,2-dimethyl-1,3-dioxan-5-yl)methanol, 21 g of potassium carbonate, and 150 ml of N,N-dimethylformamide were added to a reaction vessel equipped with a stirrer, a condenser, and a thermometer, and then a reaction was carried out at 90° C. for 5 hours. After completion of the reaction, the resultant was cooled, and 200 ml of ethyl acetate was added. The organic layer was washed with water and saturated brine, and then the solvent was evaporated. Subsequently, dispersion washing was carried out with toluene, and purification was carried out in an alumina column. Thus, a compound (40 g) represented by formula (1-2) was obtained.

[Chem. 136]

(1-2)
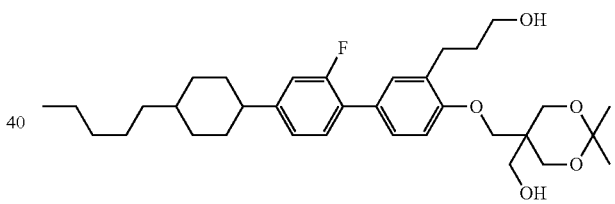

Next, 16 g of the compound (1-2), 7.5 g of triethylamine, and 80 ml of dichloromethane were loaded into a reaction vessel equipped with a stirrer, a condenser, and a thermometer, and the reaction vessel was cooled to 10° C. or lower. Subsequently, 7.6 g of methacryloyl chloride was slowly added dropwise. After completion of the dropwise addition, the reaction vessel was returned to room temperature, and then a reaction was carried out for 3 hours. After completion of the reaction, washing was carried out with water and saturated brine, and then the solvent was evaporated. Subsequently, the extracts and 160 ml of THF were added to a reaction vessel equipped with a stirrer and a thermometer, and then 16 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (16 g) represented by compound (1-3) was obtained.

[Chem. 137]

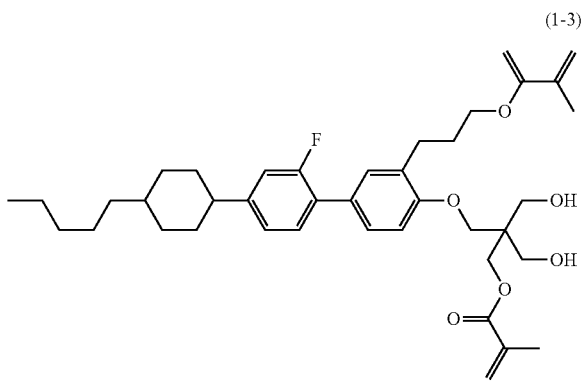

(1-3)

Next, 16 g of the compound (1-3), 160 ml of dichloromethane, and 6.3 g of triethylamine were added to a reaction vessel equipped with a stirrer and a thermometer, and then 8.5 g of methyl malonyl chloride was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a target compound (15 g) represented by formula (1) was obtained.

[Chem. 138]

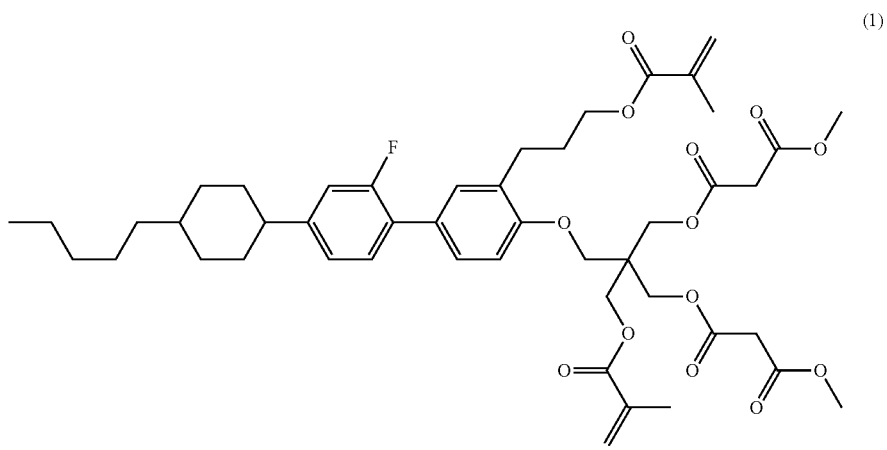

(1)

(Physical Property Values)
Oily
$^1$H-NMR (solvent: deuterated chloroform): δ: 0.88 (t, 3H), 1.20-1.29 (m, 8H), 1.36-1.61 (m, 7H), 1.85-1.92 (m, 4H), 2.00 (s, 6H), 2.62 (t, 2H), 2.75 (quint, 1H), 3.20 (s, 4H), 3.60 (s, 6H), 3.80 (s, 2H), 3.95 (s, 4H), 4.00 (s, 2H), 5.60 (s, 1H), 5.65 (s, 1H), 6.09 (s, 1H), 6.11 (s, 1H), 6.90 (d, 2H), 6.95-7.06 (m, 3H), 7.31-7.42 (m, 3H)

Example 2

30 g of (5-(bromomethyl)-2,2-dimethyl-1,3-dioxan-5-yl) methanol, 24 g of benzyl bromide, 26 g of potassium carbonate, and 150 ml of N,N-dimethylformamide were added to a reaction vessel equipped with a stirrer, a condenser, and a thermometer, and then a reaction was carried out at 50° C. for 6 hours. After completion of the reaction, the resultant was cooled, and 300 ml of ethyl acid was added. The organic layer was washed with water and saturated brine, and then the solvent was evaporated. Subsequently, the extracts and 300 ml of THF were added to a reaction vessel equipped with a stirrer and a thermometer, and then 30 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (32 g) represented by compound (2-1) was obtained.

[Chem. 139]

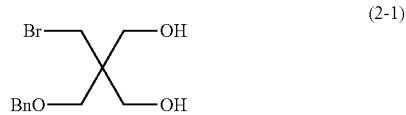

(2-1)

Next, 32 g of the compound (2-1), 32 g of methylsuccinic acid, 1.3 g of 4-dimethylaminopyridine, and 320 ml of dichloromethane were added to a reaction vessel equipped with a stirrer, a condenser, and a thermometer, 50 g of DCC was then slowly added dropwise, and then a reaction was carried out for 8 hours. After completion of the reaction, the resultant was cooled, and 100 ml of dichloromethane was added. The organic layer was washed with water and saturated brine, and then the solvent was evaporated. Subsequently, purification was carried out in a silica gel column. Thus, a compound (49 g) represented by formula (2-2) was obtained.

[Chem. 140]

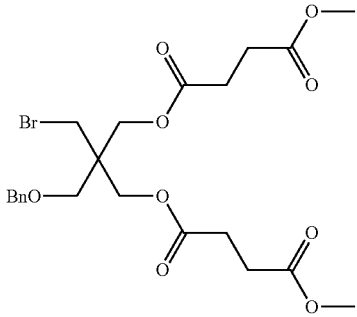

(2-2)

Next, 49 g of the compound (2-2), 22 g of 5-bromo-2-hydroxybenzenepropanol, 26 g of potassium carbonate, and 250 ml of N,N-dimethylformamide were loaded into a reaction vessel equipped with a stirrer, a condenser, and a thermometer, and then a reaction was carried out at 90° C. for 8 hours. After completion of the reaction, the resultant was cooled, and 300 ml of ethyl acetate was added. The organic layer was washed with water and saturated brine, and then the solvent was evaporated. Subsequently, dispersion washing was carried out with toluene, and purification was carried out in a silica gel column. Thus, a compound (43 g) represented by formula (2-3) was obtained.

[Chem. 141]

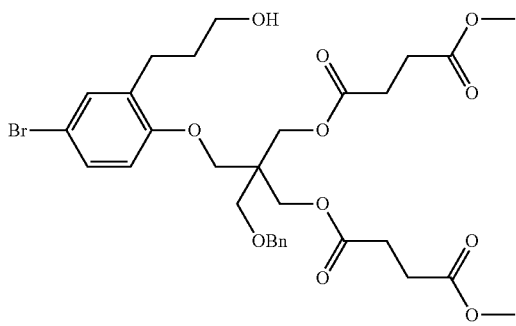

(2-3)

Next, 43 g of the compound (2-4), 200 ml of THF, and 4.3 g of palladium-on-carbon were added to a pressure-resistant reaction vessel, and then a reaction was carried out in a hydrogen atmosphere (0.5 MPa) for 10 hours. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (35 g) represented by formula (2-4) was obtained.

[Chem. 142]

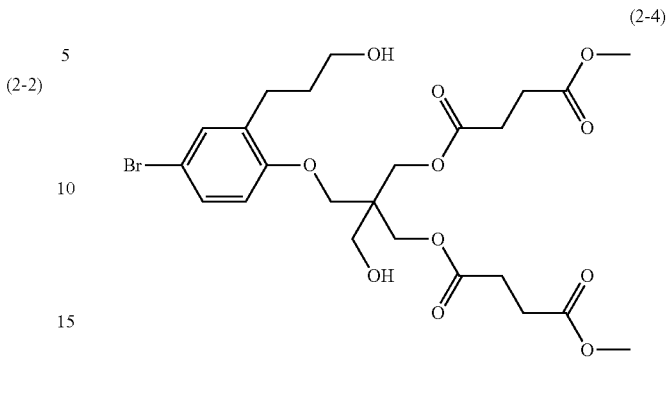

(2-4)

Next, 35 g of the compound (2-4), 14 g of triethylamine, and 350 ml of dichloromethane were added to a reaction vessel equipped with a stirrer, a condenser, and a thermometer, and the reaction vessel was cooled to 10° C. or lower. Subsequently, 14 g of methacryloyl chloride was slowly added dropwise. After completion of the dropwise addition, the reaction vessel was returned to room temperature, and then a reaction was carried out for 6 hours. After completion of the reaction, water was slowly added. Washing was carried out with dichloromethane (100 ml), water, and saturated brine, and then the solvent was evaporated. Subsequently, purification was carried out in a silica column. Thus, a compound (30 g) represented by compound (2-5) was obtained.

[Chem. 143]

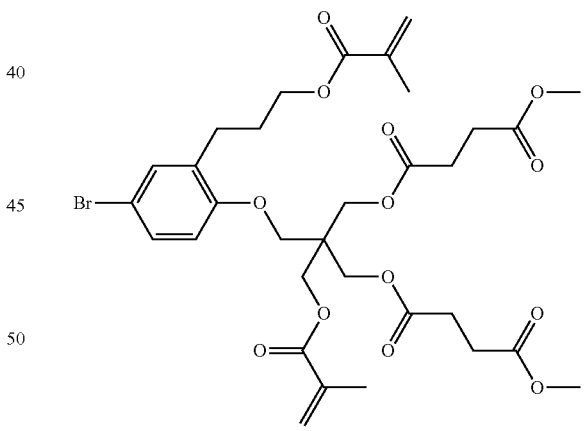

(2-5)

30 g of the compound (2-5), 12.6 g of 4-(4-pentyl (cyclohexyl))phenylboronic acid, 8.7 g of potassium carbonate, 0.5 g of tetrakistriphenylphosphine palladium, 420 ml of THF, and 84 ml of water were added to a reaction vessel equipped with a stirrer, a condenser, and a thermometer, and then a reaction was carried out at 50° C. for 9 hours. After completion of the reaction, the resultant was cooled, and 500 ml of ethyl acid was added. The organic layer was washed with water and saturated brine, the solvent was then evaporated, and a silica gel column and recrystallization with hexane were carried out. Thus, a target compound (19 g) represented by (2) was obtained.

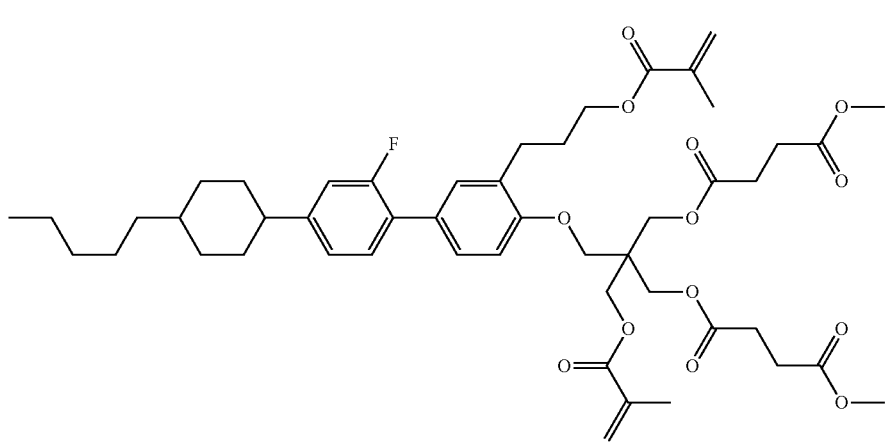
(Physical Property Values)
Oily
$^1$H-NMR (solvent: deuterated chloroform): δ: 0.89 (t, 3H), 1.23-1.61 (m, 11H), 1.80-1.95 (m, 4H), 2.08 (s, 6H), 2.61 (t, 2H), 2.70-2.75 (m, 9H), 3.50 (s, 6H), 3.80 (s, 2H), 3.90 (s, 2H), 3.94 (s, 2H), 4.20 (t, 2H), 5.67 (t, 1H), 5.70 (t, 1H), 5.84 (d, 2H), 5.90 (d, 2H), 6.06 (d, 2H), 6.88 (d, 1H), 7.05-7.24 (m, 3H), 7.34 (d, 2H)
Example 3
A target compound (3) was obtained by using a synthesis method similar to that for Example 2.
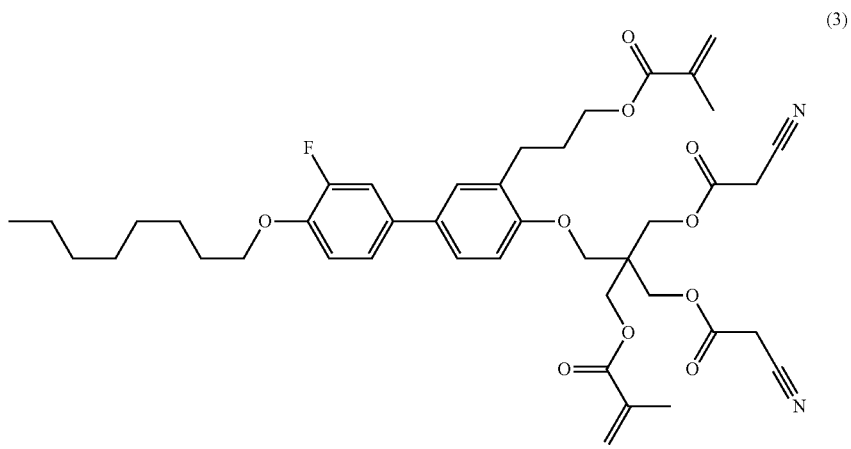
(Physical Property Values)
Oily
$^1$H-NMR (solvent: deuterated chloroform): δ: 0.89 (t, 3H), 1.26-1.48 (m, 10H), 1.75-1.95 (m, 4H), 2.05 (s, 6H), 2.65 (t, 2H), 3.50 (s, 4H), 3.81 (s, 2H), 4.05 (s, 4H), 4.14-4.21 (m, 4H), 5.58 (t, 1H), 5.65 (t, 1H), 6.13 (m, 2H), 6.95 (d, 1H), 7.01 (t, 1H), 7.18-7.26 (m, 2H), 7.31-7.42 (m, 4H)

Example 4

A target compound (4) was obtained by using a synthesis method similar to that for Example 2.

[Chem. 146]

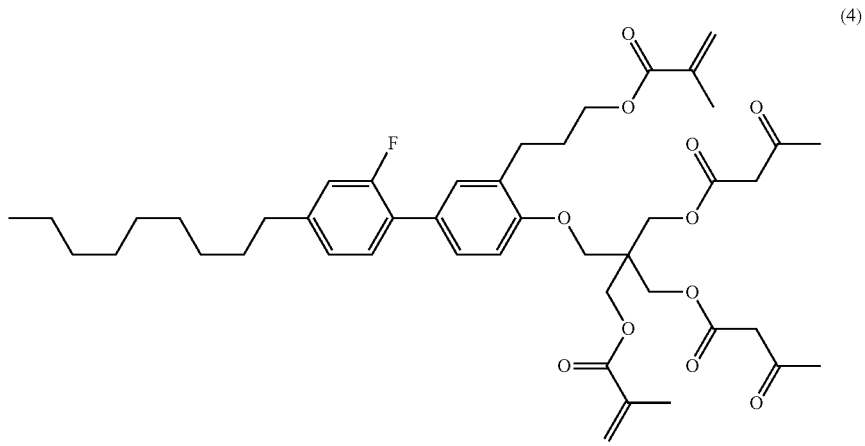

(4)

(Physical Property Values)
Oily
$^1$H-NMR (solvent: deuterated chloroform): δ: 0.87 (t, 3H), 1.26-1.35 (m, 12H), 1.60 (s, 2H), 1.89-2.02 (m, 8H), 2.21 (s, 6H), 2.60-2.65 (m, 4H), 3.38 (s, 4H), 3.88 (s, 2H), 3.95 (s, 4H), 4.05 (s, 2H), 4.25 (t, 2H), 5.60 (t, 1H), 5.65 (t, 1H), 6.21 (m, 2H), 7.05-7.12 (m, 2H), 7.15 (d, 1H), 7.18-7.31 (m, 3H)

Example 5

A target compound (5) was obtained by using a synthesis method similar to that for Example 2.

[Chem. 147]

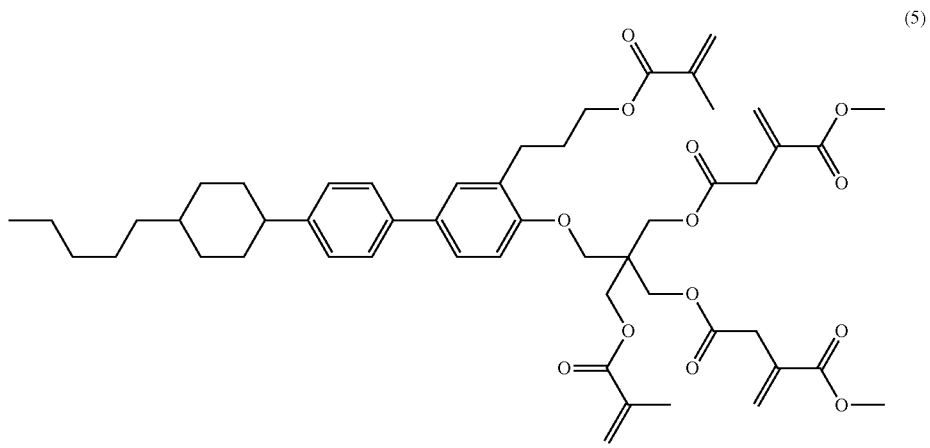

(5)

(Physical Property Values)
Oily
$^1$H-NMR (solvent: deuterated chloroform): δ: 0.90 (t, 3H), 1.20-1.65 (m, 13H), 1.75-1.95 (m, 4H), 2.06 (s, 6H), 2.70-2.73 (m, 1H), 2.64 (t, 2H), 3.56 (s, 4H), 3.63 (s, 6H), 3.80 (s, 2H) 3.88 (s, 4H), 4.05 (s, 2H), 4.18 (t, 2H), 5.60 (t, 1H), 5.65 (t, 1H), 5.81 (d, 2H), 5.98 (d, 2H), 6.06 (d, 2H), 6.13 (m, 2H), 6.89 (d, 1H), 7.11-7.28 (m, 4H), 7.36 (d, 2H)

Example 6

10 g of 3-fluoro-4-(1-octyloxyoxy)phenylboronic acid, 7.5 g of 5-bromosalicylaldehyde, 8.5 g of potassium carbonate, 100 mg of tetrakistriphenylphosphine palladium, and 100 ml of ethanol were loaded into to a reaction vessel equipped with a stirrer, a condenser, and a thermometer, and then a reaction was carried out at 90° C. for 5 hours. After completion of the reaction, the resultant was cooled, and 200 ml of ethyl acid was added. The organic layer was washed with water and saturated brine, the solvent was then evaporated, and then recrystallization was carried out with toluene. Thus, a compound (11 g) represented by (6-1) was obtained.

[Chem. 148]

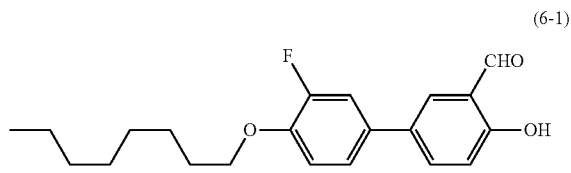
(6-1)

Next, 11 g of the compound (6-1), 8 g of (5-(bromomethyl)-2,2-dimethyl-1,3-dioxan-5-yl)methanol, 9 g of potassium carbonate, and 150 ml of N,N-dimethylformamide were loaded, and then a reaction was carried out at 90° C. for 5 hours. After completion of the reaction, the resultant was cooled, and 250 ml of ethyl acetate was added. The organic layer was washed with water and saturated brine, and then the solvent was evaporated. Subsequently, dispersion washing was carried out with toluene, and purification was carried out in an alumina column. Thus, a compound (15 g) represented by formula (6-2) was obtained.

[Chem. 149]

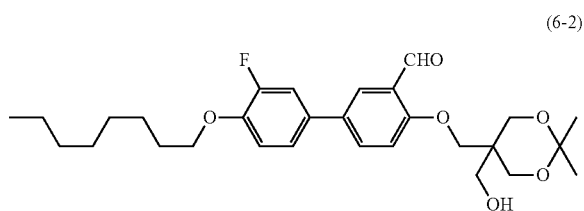
(6-2)

Next, 15 g of the compound (6-2), 1.2 g of sodium borohydride, and 150 ml of methanol were loaded, and then a reaction was carried out at 30° C. for 5 hours. After completion of the reaction, the resultant was cooled, 10% hydrochloric acid was added, and thereafter 150 ml of ethyl acetate was added. The organic layer was washed with water and saturated brine, and then the solvent was evaporated. Thus, a compound (15 g) represented by formula (6-3) was obtained.

[Chem. 150]

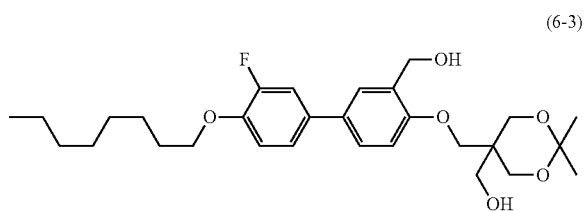
(6-3)

Next, 15 g of the compound (6-3), 9.0 g of triethylamine, and 150 ml of dichloromethane were loaded into a reaction vessel equipped with a stirrer, a condenser, and a thermometer, and the reaction vessel was cooled to 10° C. or lower. Subsequently, 7 g of methacryloyl chloride was slowly added dropwise. After completion of the dropwise addition, the reaction vessel was returned to room temperature, and then a reaction was carried out for 3 hours. After completion of the reaction, water was slowly added. Washing was carried out with dichloromethane (100 ml), water, and saturated brine. The solvent was then evaporated, and thereafter purification was carried out in an alumina column. Thus, a compound (17 g) represented by (6-4) was obtained.

[Chem. 151]

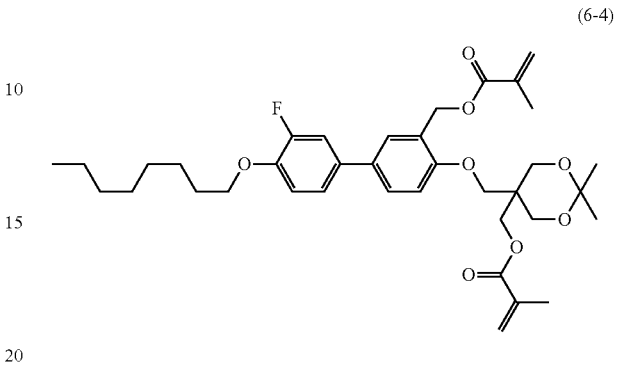
(6-4)

Subsequently, the compound (6-4) and 85 ml of THF were added to a reaction vessel equipped with a stirrer and a thermometer, and then 20 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, dispersion washing was carried out with toluene, and purification was carried out in an alumina column. Thus, a target compound (15 g) represented by formula (6-5) was obtained.

[Chem. 152]

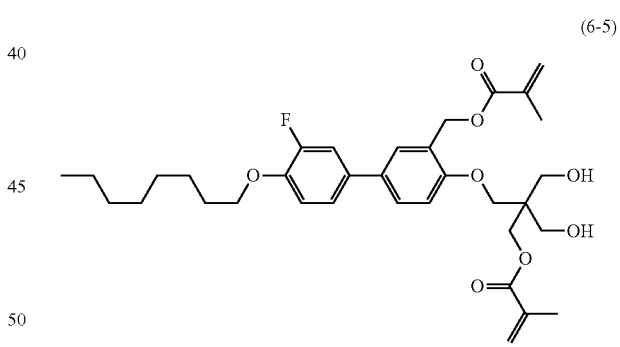
(6-5)

Next, 15 g of the compound (18), 13 g of triethylamine, and 150 ml of dichloromethane were loaded into a reaction vessel equipped with a stirrer, a condenser, and a thermometer, and the reaction vessel was cooled to 10° C. or lower. Subsequently, 10 g of methyl malonyl chloride was slowly added dropwise. After completion of the dropwise addition, the reaction vessel was returned to room temperature, and then a reaction was carried out for 12 hours. After completion of the reaction, water was slowly added. Washing was carried out with dichloromethane (100 ml), water, and saturated brine. The solvent was then evaporated, and thereafter purification was carried out in a silica gel column. Thus, a target compound (16.7 g) represented by (6) was obtained.

[Chem. 153]

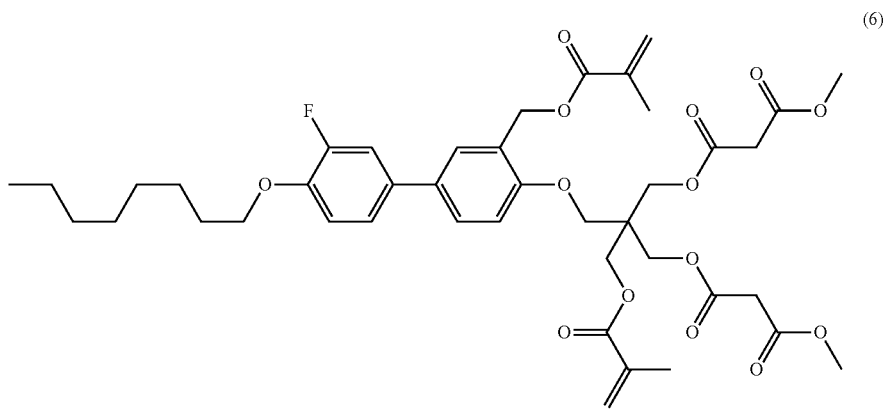

(6)

(Physical Property Values)
Oily
¹H-NMR (solvent: deuterated chloroform): δ: 0.89 (t, 3H), 1.26-1.81 (m, 12H), 1.96-2.38 (m, 6H), 3.22 (s, 4H), 3.68 (s, 6H), 3.81 (s, 2H), 3.93 (s, 4H), 4.16 (t, 2H), 4.00 (s, 2H), 5.13 (s, 2H), 6.14 (d, 2H), 6.95 (m, 2H), 7.20-7.27 (m, 4H), 7.82 (m, 2H)

Comparative Example 1

A target compound (C-1) was obtained by using a synthesis method similar to that for Example 1.

[Chem. 154]

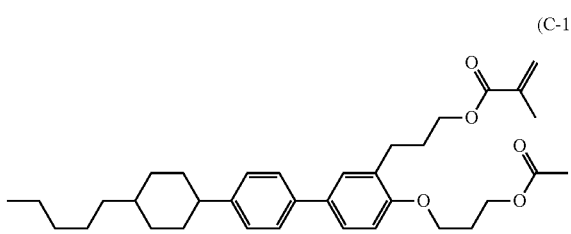

(C-1)

(Physical Property Values)
Solid
¹H-NMR (solvent: deuterated chloroform): δ: 0.90 (t, 3H), 1.21-1.61 (m, 15H), 1.75-1.95 (m, 4H), 2.04 (s, 3H), 2.09 (s, 3H), 2.13 (quint, 2H), 2.64 (t, 2H), 2.70-2.73 (m, 1H), 4.12 (t, 2H), 4.18 (t, 2H), 4.23 (t, 2H), 6.01 (t, 1H), 6.28 (s, 1H), 6.91 (d, 1H), 7.02-7.26 (m, 4H), 7.32 (d, 2H)

Comparative Example 2

A target compound (C-2) was obtained by using a synthesis method similar to that for Example 1.

[Chem. 155]

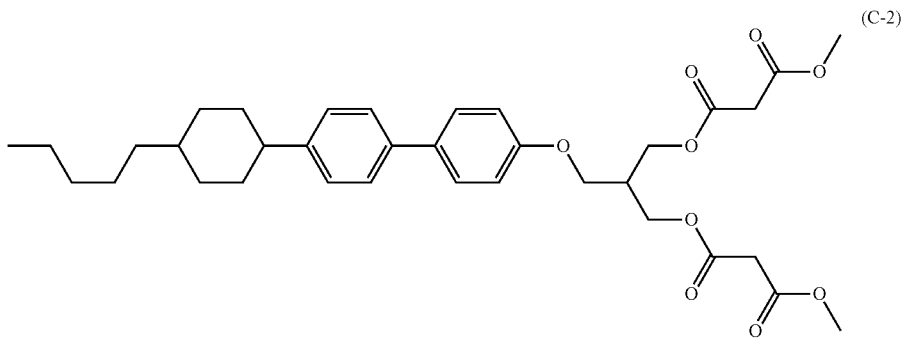

(C-2)

(Physical Property Values)
Solid
¹H-NMR (solvent: deuterated chloroform): δ: 0.90 (t, 3H), 1.19-1.60 (m, 15H), 1.80-1.85 (m, 2H), 2.71-2.73 (m, 1H), 3.20 (s, 4H), 3.23-3.26 (m, 1H), 3.46 (s, 6H), 3.78 (d, 4H), 3.81 (d, 2H), 6.91 (d, 2H), 7.31 (d, 2H), 7.45-7.57 (m, 4H)

For each of the liquid crystal compositions of Examples and Comparative Examples, the following evaluation tests were conducted. The results of the evaluation tests for the liquid crystal compositions of Examples and Comparative Examples are shown in Table 1 and Table 2.

(Evaluation Test for Low-Temperature Stability)

Each of the liquid crystal compositions was filtered with a membrane filter (PTFE, 13 mm-0.2 m, manufactured by Agilent Technologies). The resultant was left to stand for 15 minutes under vacuum or reduced pressure conditions to remove dissolved air. The resultant was washed with acetone, and 0.5 g of the product was weighed into a well-dried vial and then left to stand in a low-temperature environment at −25° C. Subsequently, the presence or absence of precipitation was visually examined, and evaluations were made based on the following four levels of ratings.
  A: No precipitation was observed after 14 days of standing
  B: Precipitation was observed after 7 days of standing
  C: Precipitation was observed after 3 days of standing
  D: Precipitation was observed after 1 day of standing
(Evaluation Test for Vertical Alignment Characteristics)

A first substrate (common electrode substrate) and a second substrate (pixel electrode substrate) were prepared. The first substrate included a transparent electrode layer, which included a transparent common electrode, and a color filter layer. The second substrate included a pixel electrode layer, which included a transparent pixel electrode that was driven by an active element. The first substrate included no alignment film. The second substrate included no alignment film. Each of the liquid crystal compositions was dropped onto the first substrate and was held with the second substrate, and a seal material was cured at normal pressure and 110° C. for 2 hours. Thus, liquid crystal cells having a cell gap of 3.2 m were obtained. Then, an examination regarding vertical alignment characteristics and alignment non-uniformity due to drop marks and the like was conducted using a polarizing microscope. Evaluations were made based on the following four levels of ratings.
  A: Uniform vertical alignment was achieved over the entire surface including end portions
  B: Alignment was at an acceptable level although very slight alignment defects were present
  C: Alignment was at an unacceptable level because numerous alignment defects were present in areas including end portions
  D: Alignment failure was considerably severe
(Evaluation Test for Pretilt Angle Formation)

UV light having an illumination intensity at 365 nm of 100 m/cm² was radiated onto the liquid crystal cell, which was used in the above-described evaluation test for vertical alignment characteristics, for 200 seconds by using a high-pressure mercury lamp, while a square AC wave of 10 V and 100 Hz was applied thereto. Subsequently, regarding the stability of the white display, the following were performed. A physical external force was applied to the cell while a square AC wave of 10 V and 100 Hz was applied thereto. After several minutes of standing, an examination was conducted with crossed nicols. Evaluations were made based on the following four levels of ratings.
  A: Uniform vertical alignment was achieved over the entire surface including end portions
  B: Alignment was at an acceptable level although very slight alignment defects were present
  C: Alignment was at an unacceptable level because numerous alignment defects were present in areas including end portions
  D: Alignment failure was considerably severe
(Evaluation Test for Residual Monomer Amount)

In addition, irradiation (an illumination intensity at 313 nm of 1.7 mW/cm²) was performed on the cell, which was used in the above-described evaluation test for pretilt angle formation, for 60 minutes by using a UV fluorescent lamp manufactured by Toshiba Lighting and Technology Corporation. Thereafter, an amount of the residue of a polymerizable compound (R1-1-1) was quantitatively determined by HPLC. Thus, the residual monomer amount was determined. In accordance with the amount of the residual monomer, evaluations were made based on the following four levels of ratings.
  A: Less than 300 ppm
  B: 300 ppm or greater and less than 500 ppm
  C: 500 ppm or greater and less than 1500 ppm
  D: 1500 ppm or greater
(Evaluation Test for Response Characteristics)

In addition, irradiation (an illumination intensity at 313 nm of 1.7 mW/cm²) was performed on the cell having a cell gap of 3.2 m, which was used in the above-described evaluation test for pretilt angle formation, for 60 minutes by using a UV fluorescent lamp manufactured by Toshiba Lighting and Technology Corporation. A response speed of the resulting cell was measured. The response speed, Voff, at 6 V, was measured at a temperature of 25° C. by using a DMS-703, from Autronic Melchers. Evaluations of response characteristics were made based on the following four levels of ratings.
  A: Less than 5 ms
  B: 5 ms or greater and less than 15 ms
  C: 15 ms or greater and less than 25 ms
  D: 25 ms or greater Example 7

A composition includes compounds at a mixing ratio as shown below.

[Chem. 156]

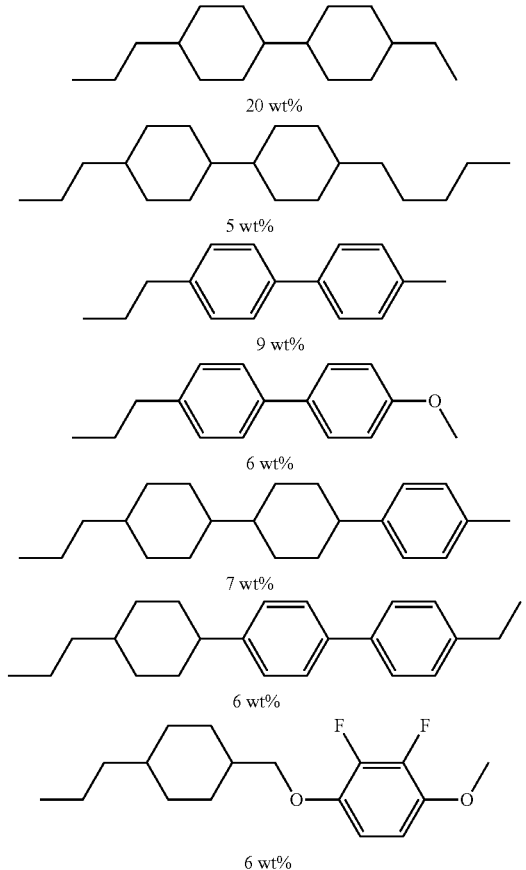

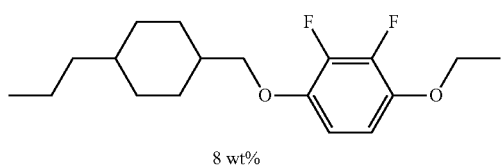

8 wt%

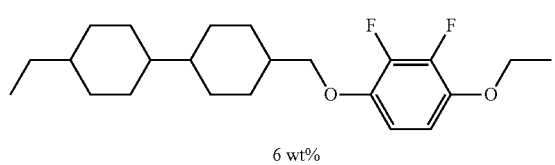

6 wt%

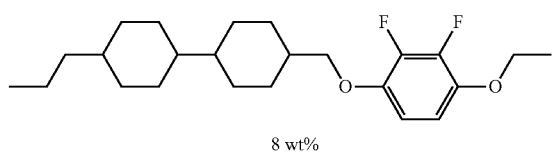

8 wt%

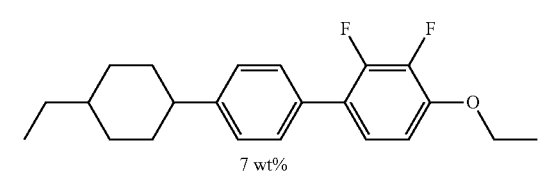

7 wt%

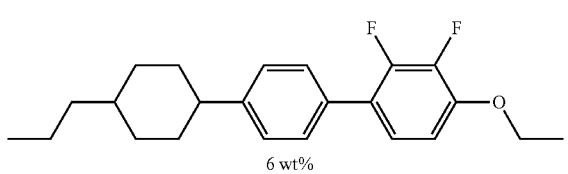

6 wt%

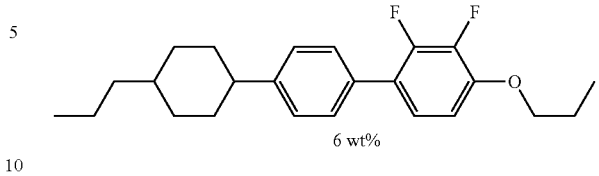

6 wt%

A composition LC-1 was prepared. The composition LC-1 included 100 parts by mass of the composition mentioned above and 0.3 parts by mass of a polymerizable compound (P-2-8), which was a compound added and is shown below.

[Chem. 157]

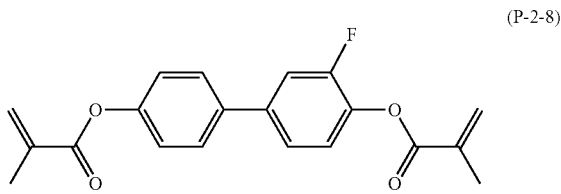

(P-2-8)

Physical property values of LC-1 were as follows.
$T_{n-i}$ (nematic phase-isotropic liquid phase transition temperature): 75° C.
$\Delta\varepsilon$ (dielectric anisotropy at 25° C.): −3
$\Delta n$ (refractive index anisotropy at 25° C.): 0.112
$\gamma_1$ (rotational viscosity coefficient at 25° C.): 122

In addition, a liquid crystal composition was prepared in the following manner: 1.0 parts by mass of the compound (1) prepared in Example 1, which corresponded to the compound (i), was added to 100 parts by mass of LC-1, and the resultant was heated and dissolved.

Examples 8 to 12

Liquid crystal compositions were prepared as in Example 7 except that instead of the compound (1), each of the compounds (2) to (6), which were prepared in Examples 2 to 6, was added in an amount of 1.0 parts by mass to LC-1. The evaluation tests were as shown in Table 1.

TABLE 1

|  | Base composition | Added compound | Low-temperature storage characteristics | Vertical alignment characteristics | Pretilt angle formation | Residual monomer amount | Response characteristics |
|---|---|---|---|---|---|---|---|
| Example 1 | LC-1 | (1) | A | A | A | B | A |
| Example 2 | LC-1 | (2) | A | B | A | B | A |
| Example 3 | LC-1 | (3) | A | B | A | A | A |
| Example 4 | LC-1 | (4) | A | A | A | A | A |
| Example 5 | LC-1 | (5) | A | B | A | B | A |
| Example 6 | LC-1 | (6) | B | A | A | A | A |

Comparative Examples 3 to 5

Liquid crystal compositions were prepared as in Example 7 except that instead of the compound represented by formula (1), each of the following compounds was added in an amount of 1.0% parts by mass to LC-1.

[Chem. 158]

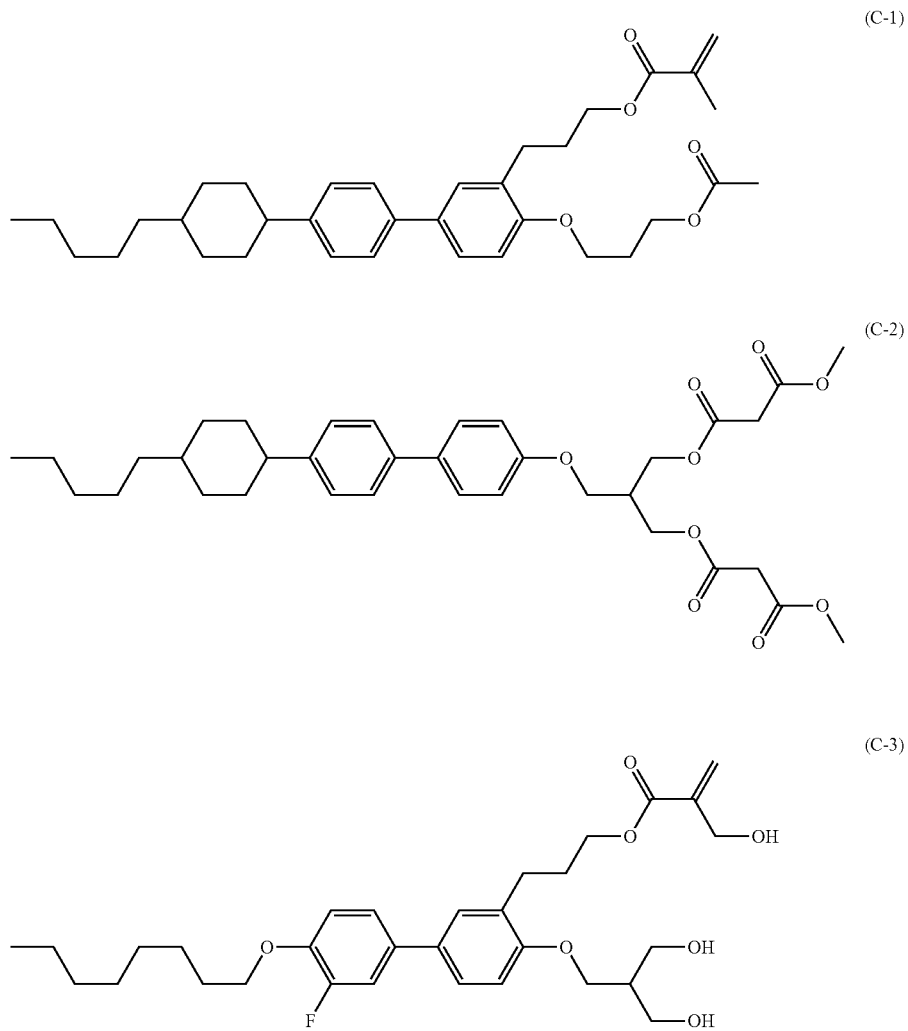

The evaluation tests were as shown in Table 2.

TABLE 2

| | Base composition | Added compound | Low-temperature storage characteristics | Vertical alignment characteristics | Pretilt angle formation | Residual monomer amount | Response characteristics |
|---|---|---|---|---|---|---|---|
| Comparative Example 3 | LC-1 | C-1 | C | C | B | B | B |
| Comparative Example 4 | LC-1 | C-2 | B | A | D | D | B |
| Comparative Example 5 | LC-1 | C-3 | C | C | C | C | D |

As demonstrated above, compounds of the present invention have both alignment characteristics and a storage stability, and, therefore, excellent liquid crystal compositions can be provided.

Example 13

A target compound (7) was obtained by using a synthesis method similar to that for Example 1.

[Chem. 159]

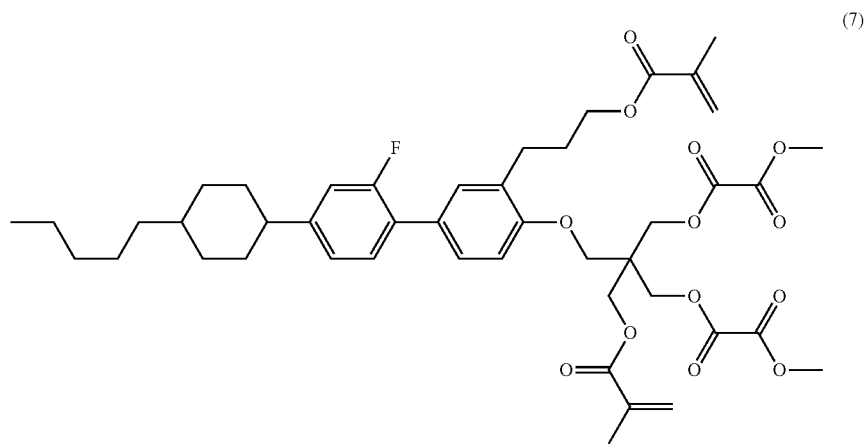

(7)

(Physical Property Values)
Solid
$^1$H-NMR (solvent: deuterated chloroform): δ: 0.90 (t, 3H), 1.03-1.50 (m, 13H), 1.87-2.01 (m, 12H), 2.49 (m, 1H), 2.74 (m, 2H), 3.90 (s, 6H), 4.15 (s, 2H), 4.19 (t, 2H), 4.42 (s, 2H), 4.56 (s, 4H), 5.54 (s, 1H), 5.63 (s, 1H), 6.08 (s, 1H), 6.11 (s, 1H), 6.91 (d, 1H), 6.98 (d, 1H), 7.03 (d, 1H), 7.28 (d, 1H), 7.31 (d, 1H), 7.36 (d, 1H)

Example 14

A target compound (8) was obtained by using a synthesis method similar to that for Example 1.

[Chem. 160]

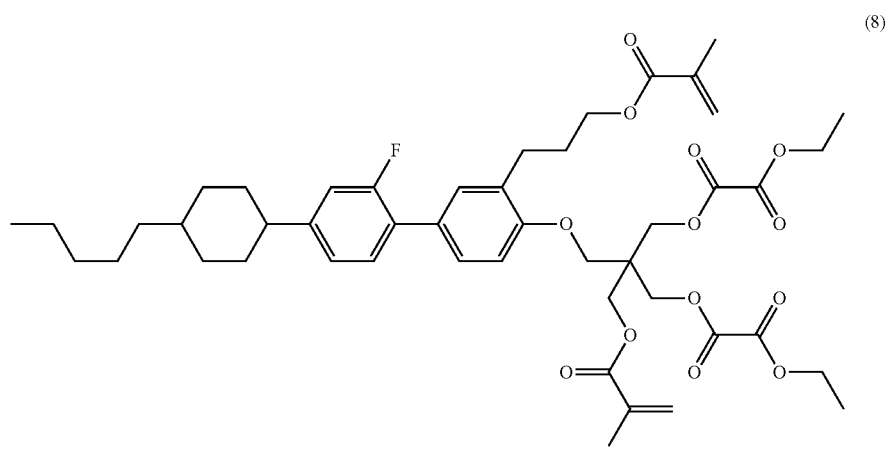

(8)

(Physical Property Values)
Solid
$^1$H-NMR (solvent: deuterated chloroform): δ: 0.90 (t, 3H), 1.03-1.50 (m, 19H), 1.87-2.01 (m, 12H), 2.49 (m, 1H), 2.74 (m, 2H), 3.90 (s, 6H), 4.15 (s, 2H), 4.19 (t, 2H), 4.42 (s, 2H), 4.56 (s, 4H), 5.54 (s, 1H), 5.63 (s, 1H), 6.08 (s, 1H), 6.11 (s, 1H), 6.91 (d, 1H), 6.98 (d, 1H), 7.03 (d, 1H), 7.28 (d, 1H), 7.31 (d, 1H), 7.36 (d, 1H)

Example 15

A target compound (9) was obtained by using a synthesis method similar to that for Example 1.

[Chem. 161]

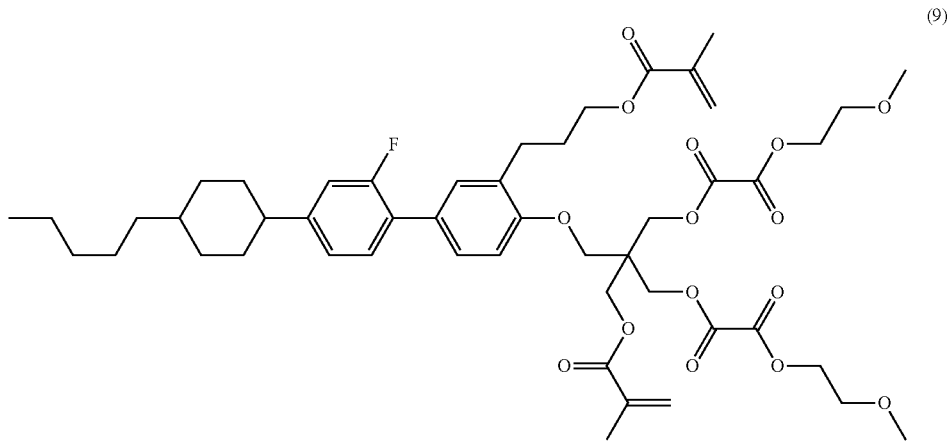

(9)

(Physical Property Values)
Solid
¹H-NMR (solvent: deuterated chloroform): δ: 0.90 (t, 3H), 1.03-1.50 (m, 19H), 1.87-2.01 (m, 12H), 2.49 (m, 1H), 2.74 (m, 2H), 3.34 (s, 6H), 3.63 (t, 4H), 3.90 (m, 4H), 4.15 (s, 2H), 4.19 (t, 2H), 4.42 (s, 2H), 4.56 (s, 4H), 5.54 (s, 1H), 5.63 (s, 1H), 6.08 (s, 1H), 6.11 (s, 1H), 6.91 (d, 1H), 6.98 (d, 1H), 7.03 (d, 1H), 7.28 (d, 1H), 7.31 (d, 1H), 7.36 (d, 1H)

Example 16

5.0 g of the compound (1-3), which was synthesized in Example 1, 37 ml of dichloromethane, 2.0 g of pyruvic acid, and 195 mg of dimethylaminopyridine were added to a reaction vessel equipped with a stirrer and a thermometer, and then 2.9 g of diisopropylcarboximide was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a target compound (4.8 g) represented by formula (10) was obtained.

[Chem. 162]

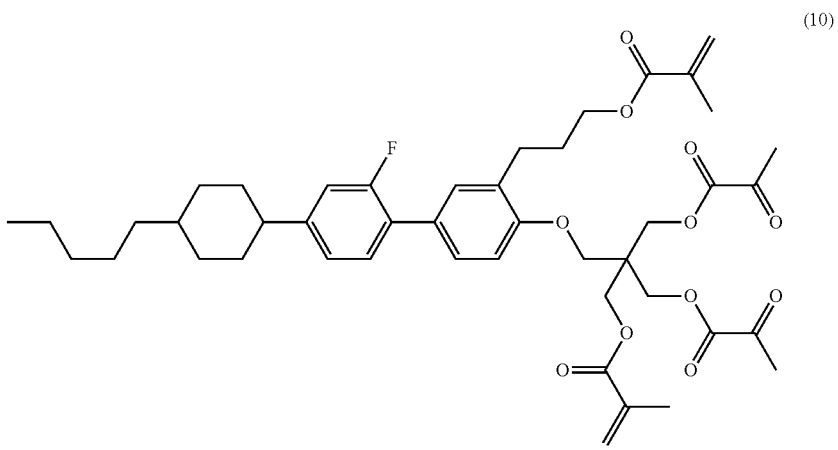

(10)

(Physical Property Values)
Oily
¹H-NMR (solvent: deuterated chloroform): δ: 0.90 (t, 3H), 1.03-1.50 (m, 13H), 1.87-2.01 (m, 12H), 2.17 (s, 6H), 2.49 (m, 1H), 2.74 (m, 2H), 4.15 (s, 2H), 4.19 (t, 2H), 4.42 (s, 2H), 4.56 (s, 4H), 5.54 (s, 1H), 5.63 (s, 1H), 6.08 (s, 1H), 6.11 (s, 1H), 6.91 (d, 1H), 6.98 (d, 1H), 7.03 (d, 1H), 7.28 (d, 1H), 7.31 (d, 1H), 7.36 (d, 1H)

Example 17

A target compound (11) was obtained by using a synthesis method similar to that for Example 16.

[Chem. 163]

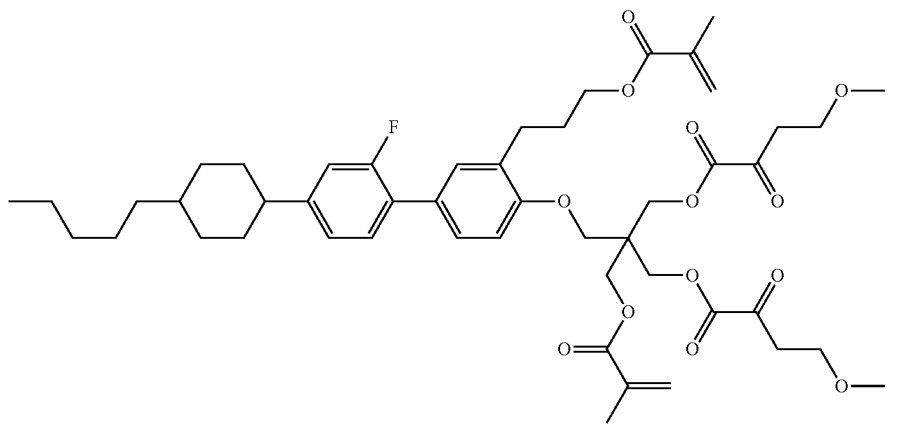

(11)

(Physical Property Values)
Oily
$^1$H-NMR (solvent: deuterated chloroform): δ: 0.90 (t, 3H), 1.03-1.50 (m, 13H), 1.87-2.01 (m, 12H), 2.37 (t, 4H), 2.49 (m, 1H), 2.74 (m, 2H), 3.23 (s, 6H), 3.67 (t, 4H), 4.15 (s, 2H), 4.19 (t, 2H), 4.42 (s, 2H), 4.56 (s, 4H), 5.54 (s, 1H), 5.63 (s, 1H), 6.08 (s, 1H), 6.11 (s, 1H), 6.91 (d, 1H), 6.98 (d, 1H), 7.03 (d, 1H), 7.28 (d, 1H), 7.31 (d, 1H), 7.36 (d, 1H)

Example 18

15 g of 3-ethylphenol, 60 ml of dimethylformamide, 23 g of 1-iodopropane, and 60 g of cesium carbonate were added to a reaction vessel equipped with a stirrer, a Dimroth condenser, and a thermometer and then stirred under heat at 80° C. After completion of the reaction, the resultant was cooled, and a target product was extracted with hexane. The organic layer was washed with water and saturated brine, and then the solvent was evaporated. Subsequently, purification was carried out in a silica column. Thus, a colorless oily compound (19 g) represented by formula (12-1) was obtained.

[Chem. 164]

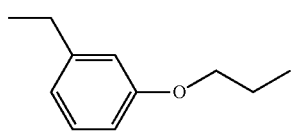

(12-1)

Next, 15 g of the compound represented by formula (12-1), 75 ml of acetonitrile, and 730 mg of ammonium nitrate were added to a reaction vessel equipped with a stirrer and a thermometer, and then 16 g of N-bromosuccinimide, which was dissolved in 160 ml of acetonitrile, was slowly added dropwise. After completion of the reaction, the resultant was cooled, and a target product was extracted with hexane. The organic layer was washed with water and saturated brine, and then the solvent was evaporated. Subsequently, purification was carried out in a silica column. Thus, a colorless oily compound (22 g) represented by formula (12-2) was obtained.

[Chem. 165]

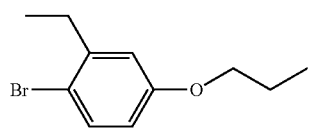

(12-2)

(Physical Property Values)
Oily
$^1$H-NMR (solvent: deuterated chloroform): δ: 1.03 (t, 3H), 1.20 (t, 3H), 1.75-1.84 (m, 2H), 2.71 (q, 2H), 3.88 (t, 2H), 6.60 (dd, 1H), 6.78 (s, 1H), 7.37 (d, 1H)

Next, 26 g of 3-fluoro-4-(4-pentyl (cyclohexyl))phenylboronic acid, 20 g of the compound (12-2), 62 ml of a 2M aqueous potassium carbonate solution, 720 mg of tetrakistriphenylphosphine palladium, and 230 ml of tetrahydrofuran were added to a reaction vessel equipped with a stirrer, a condenser, and a thermometer, and then a reaction was carried out at 70° C. for 5 hours. After completion of the reaction, the resultant was cooled, and hexane was added. The organic layer was washed with water and saturated brine, and then the solvent was evaporated. Thus, a colorless oily compound (35 g) represented by (12-3) was obtained.

[Chem. 166]

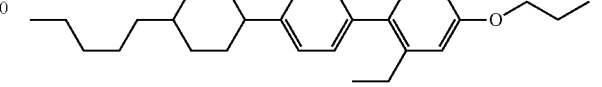

(12-3)

Next, 35 g of the compound represented by formula (12-3) and 250 ml of dichloromethane were added to a reaction vessel equipped with a stirrer and a thermometer, and then 31 g of boron tribromide was slowly added dropwise under ice cooling. After completion of the reaction, the resultant was cooled, 200 ml of water was added, and a target product was extracted with hexane. The organic layer was washed with water and saturated brine, and then the solvent was evaporated. Subsequently, purification was carried out in a silica column. Thus, a colorless crystalline compound (33 g) represented by formula (12-4) was obtained.

[Chem. 167]

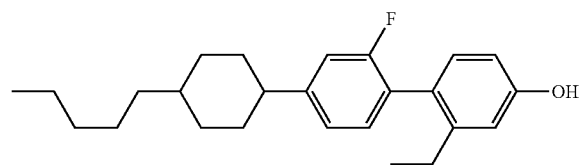

(12-4)

Next, 10 g of the compound represented by formula (12-4), 50 ml of dichloromethane, and 4 g of pyridine were added to a reaction vessel equipped with a stirrer and a thermometer, and then 8 g of trifluoromethanesulfonic anhydride was slowly added dropwise under ice cooling. After completion of the reaction, the resultant was cooled, 100 ml of water was added, and a target product was extracted with hexane. The organic layer was washed with water and saturated brine, and then the solvent was evaporated. Subsequently, purification was carried out in a silica column. Thus, a colorless oily compound (11 g) represented by formula (12-5) was obtained.

[Chem. 168]

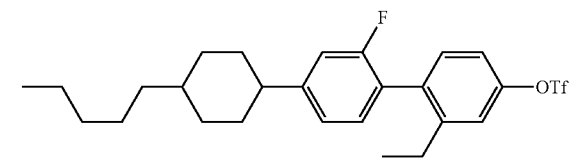

(12-5)

Next, 11 g of the compound represented by formula (12-5), 55 ml of dimethylformamide, 6.4 g of potassium acetate, 5.8 g of bis(pinacolato)diborane, and 530 mg of 1,1'-bis(diphenylphosphino)ferrocene-palladium(II)dichloride were added to a reaction vessel equipped with a stirrer, a condenser tube, and a thermometer and then stirred at 80° C. After completion of the reaction, the resultant was cooled, 100 ml of water was added, and a target product was extracted with ethyl acetate. The organic layer was washed with water and saturated brine, and then the solvent was evaporated. Subsequently, purification was carried out in a silica column. Thus, a colorless crystalline compound (9.1 g) represented by formula (12-6) was obtained.

[Chem. 169]

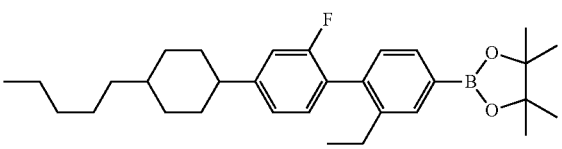

(12-6)

9 g of the compound (12-6), 4.6 g of 4-bromo-2-hydroxypropyl phenol, 14 ml of a 2.0M aqueous potassium carbonate solution, 206 mg of tetrakistriphenylphosphine palladium, and 90 ml of tetrahydrofuran were added to a reaction vessel equipped with a stirrer, a condenser, and a thermometer, and then a reaction was carried out at 70° C. for 5 hours. After completion of the reaction, the resultant was cooled, and 200 ml of ethyl acid was added. The organic layer was washed with water and saturated brine, the solvent was then evaporated, and then recrystallization was carried out with toluene. Thus, a compound (13 g) represented by (12-7) was obtained.

[Chem. 170]

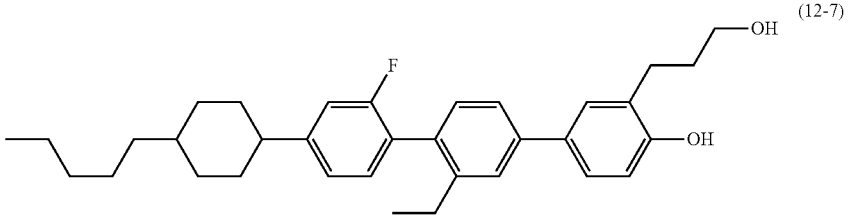

(12-7)

Next, 13 g of the compound (12-7), 16 g of (5-(bromomethyl)-2,2-dimethyl-1,3-dioxan-5-yl)methanol, 21 g of potassium carbonate, and 130 ml of dimethyl sulfide were added to a reaction vessel equipped with a stirrer, a condenser, and a thermometer, and then a reaction was carried out at 90° C. for 5 hours. After completion of the reaction, the resultant was cooled, and 200 ml of ethyl acetate was added. The organic layer was washed with water and saturated brine, and then the solvent was evaporated. Subsequently, dispersion washing was carried out with toluene, and purification was carried out in an alumina column. Thus, a compound (16 g) represented by formula (12-8) was obtained.

[Chem. 171]

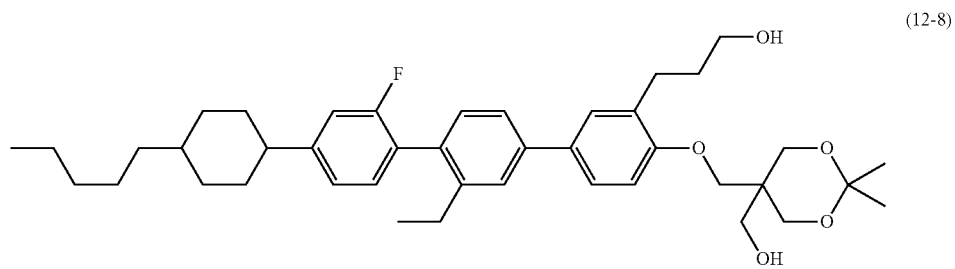

(12-8)

Next, 16 g of the compound (12-8), 7.5 g of triethylamine, and 80 ml of dichloromethane were loaded into a reaction vessel equipped with a stirrer, a condenser, and a thermometer, and the reaction vessel was cooled to 10° C. or lower. Subsequently, 7.6 g of methacryloyl chloride was slowly added dropwise. After completion of the dropwise addition, the reaction vessel was returned to room temperature, and then a reaction was carried out for 3 hours. After completion of the reaction, washing was carried out with water and saturated brine, and then the solvent was evaporated. Subsequently, the extracts and 160 ml of THF were added to a reaction vessel equipped with a stirrer and a thermometer, and then 16 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (16 g) represented by compound (12-9) was obtained.

[Chem. 172]

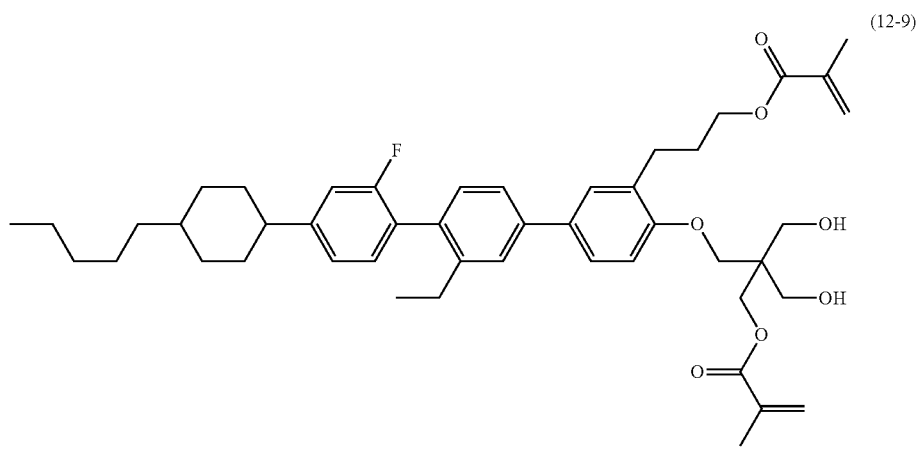

(12-9)

Next, 16 g of the compound (12-9), 160 ml of dichloromethane, and 7.3 g of triethylamine were added to a reaction vessel equipped with a stirrer and a thermometer, and then 7.4 g of methyl malonyl chloride was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a target compound (15 g) represented by formula (12) was obtained.

Next, 28 g of the compound (13-1), 16 ml of pyridine, and 90 ml of tetrahydrofuran were added to a reaction vessel equipped with a stirrer and a thermometer and then stirred. 8.5 g of triphosgene, which was dissolved in 30 ml of tetrahydrofuran, was then added dropwise under ice cooling. After completion of the reaction, the resultant was cooled, and a target product was extracted with hexane. The organic layer was washed with water and saturated brine, and then the solvent was evaporated. A colorless crystalline compound (20 g) represented by formula (13-2) was obtained.

[Chem. 173]

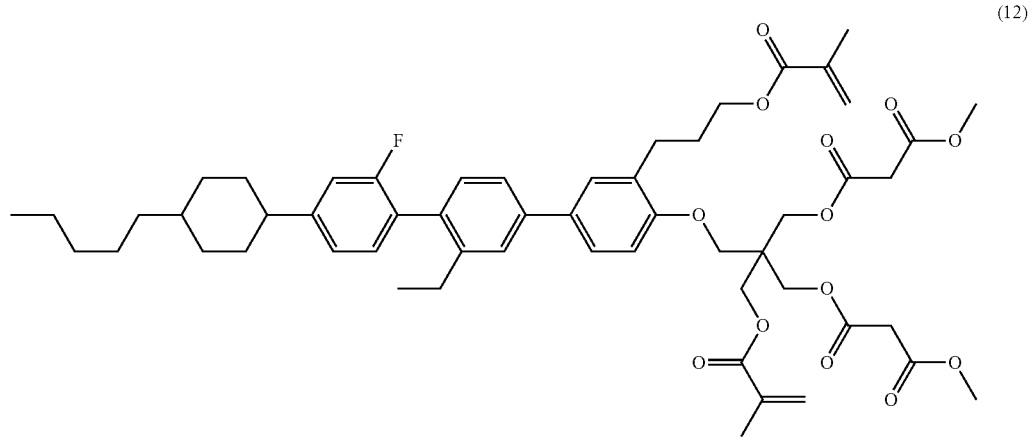

(12)

(Physical Property Values)

Oily $^1$H-NMR (solvent: deuterated chloroform): δ: 0.90 (t, 3H), 1.06-1.49 (m, 16H), 1.89-2.02 (m, 12H), 2.52-2.60 (m, 3H), 2.78 (t, 2H), 3.43 (s, 4H), 3.71 (s, 6H), 4.07 (s, 2H), 4.21 (t, 2H), 4.35 (s, 2H), 4.41 (s, 4H), 5.55 (s, 1H), 5.61 (s, 1H), 6.10 (s, 2H), 6.92 (d, 1H), 6.98 (d, 1H), 7.04 (d, 1H), 7.17 (t, 1H), 7.23 (d, 1H), 7.38-7.47 (m, 4H)

Example 19

20 g of 4-bromoanisole, 80 ml of tetrahydrofuran, and 2.9 g of magnesium were added to a reaction vessel equipped with a stirrer, a Dimroth condenser, and a thermometer and then stirred. 22 g of 4'-pentyl-[1,1'-bi(cyclohexane)]-4-one, which was dissolved in 50 ml of tetrahydrofuran, was then added dropwise. After completion of the reaction, the resultant was cooled, and a target product was extracted with hexane. The organic layer was washed with water and saturated brine, and then the solvent was evaporated. A colorless crystalline compound (32 g) represented by formula (13-1) was obtained.

[Chem. 174]

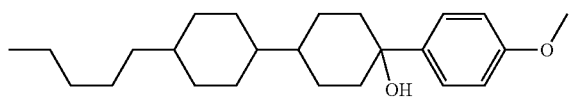

(13-1)

[Chem. 175]

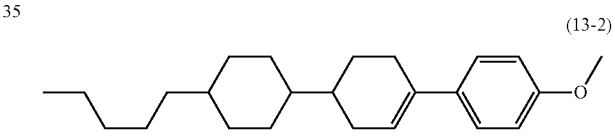

(13-2)

Next, 20 g of the compound (13-2), 1 g of 5% palladium on carbon, and 120 ml of tetrahydrofuran were added to an autoclave equipped with a stirrer and then stirred under a hydrogen pressure of 0.5 MPa. After completion of the reaction, the resultant was cooled, and a target product was extracted with ethyl acetate. Subsequently, purification was carried out in a silica column. Thus, a colorless crystalline compound (20 g) represented by formula (13-3) was obtained.

[Chem. 176]

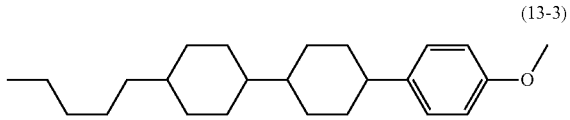

(13-3)

Next, 20 g of the compound (13-3) and 140 ml of dichloromethane were added to a reaction vessel equipped with a stirrer and a thermometer, and then 22 g of boron tribromide was added dropwise under ice cooling. After completion of the reaction, the resultant was cooled, and a target product was extracted with ethyl acetate. Subsequently, purification was carried out by recrystallization.

Thus, a colorless crystalline compound (9.1 g) represented by formula (13-4) was obtained.

[Chem. 177]

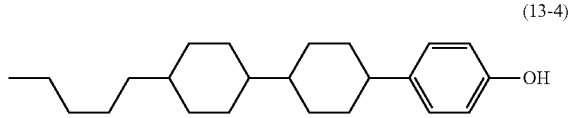

(13-4)

Next, 9.1 g of the compound (13-4), 4.5 ml of pyridine, and 100 ml of dichloromethane were added to a reaction vessel equipped with a stirrer and a thermometer, and then 9.4 g of trifluoromethanesulfonic anhydride was added dropwise under ice cooling. After completion of the reaction, the resultant was cooled, and a target product was extracted with dichloromethane. Subsequently, purification was carried out by using alumina. Thus, a colorless crystalline compound (13 g) represented by formula (13-5) was obtained.

[Chem. 178]

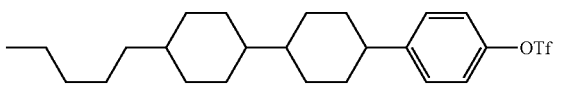

(13-5)

Next, 13 g of the compound represented by formula (13-5), 64 ml of dimethylformamide, 8.2 g of potassium acetate, 7.4 g of bis(pinacolato)diborane, and 680 mg of 1,1'-bis(diphenylphosphino)ferrocene-palladium(II)dichloride were added to a reaction vessel equipped with a stirrer, a condenser tube, and a thermometer and then stirred at 80° C. After completion of the reaction, the resultant was cooled, 200 ml of water was added, and a target product was extracted with ethyl acetate. The organic layer was washed with water and saturated brine, and then the solvent was evaporated. Thus, a colorless crystalline compound (9.3 g) represented by formula (13-6) was obtained.

[Chem. 179]

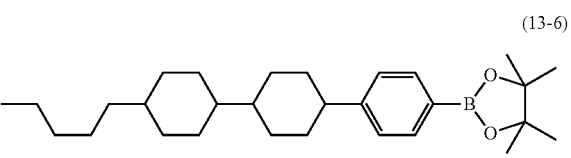

(13-6)

5.7 g of the compound (13-6), 3.9 g of 4-bromo-5 ethyl-2-hydroxypropyl phenol, 13 ml of a 2.0M aqueous potassium carbonate solution, 206 mg of tetrakistriphenylphosphine palladium, and 60 ml of tetrahydrofuran were added to a reaction vessel equipped with a stirrer, a condenser, and a thermometer, and then a reaction was carried out at 60° C. for 5 hours. After completion of the reaction, the resultant was cooled, and 60 ml of ethyl acid was added. The organic layer was washed with water and saturated brine, the solvent was then evaporated, and then recrystallization was carried out with toluene. Thus, a compound (7.7 g) represented by (13-7) was obtained.

[Chem. 180]

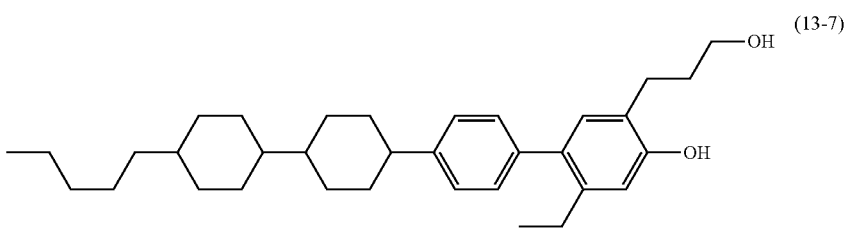

(13-7)

Next, 7.7 g of the compound (13-7), 11 g of (5-(bromomethyl)-2,2-dimethyl-1,3-dioxan-5-yl)methanol, 10 g of tripotassium phosphate, and 80 ml of dimethyl sulfide were added to a reaction vessel equipped with a stirrer, a condenser, and a thermometer, and then a reaction was carried out at 100° C. for 5 hours. After completion of the reaction, the resultant was cooled, and 200 ml of ethyl acetate was added. The organic layer was washed with water and saturated brine, and then the solvent was evaporated. Subsequently, dispersion washing was carried out with toluene, and purification was carried out in an alumina column. Thus, a compound (5.9 g) represented by formula (13-8) was obtained.

[Chem. 181]

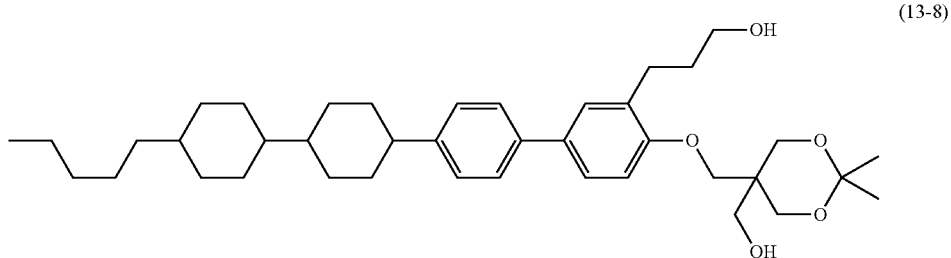

(13-8)

Next, 5.9 g of the compound (13-8), 4.5 g of triethylamine, and 45 ml of dichloromethane were loaded into a reaction vessel equipped with a stirrer, a condenser, and a thermometer, and the reaction vessel was cooled to 10° C. or lower. Subsequently, 3.6 g of methacryloyl chloride was slowly added dropwise. After completion of the dropwise addition, the reaction vessel was returned to room temperature, and then a reaction was carried out for 3 hours. After completion of the reaction, washing was carried out with water and saturated brine, and then the solvent was evaporated. Subsequently, the extracts and 43 ml of THF were added to a reaction vessel equipped with a stirrer and a thermometer, and then 8.6 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (4.2 g) represented by compound (13-9) was obtained.

[Chem. 182]

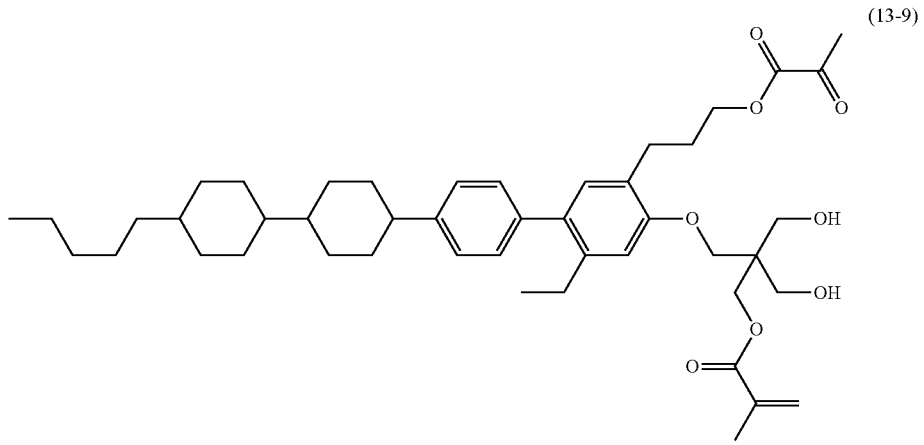

(13-9)

Next, 4.2 g of the compound (13-9), 36 ml of dichloromethane, and 1.6 ml of triethylamine were added to a reaction vessel equipped with a stirrer and a thermometer, and then 1.7 g of methyl malonyl chloride was slowly added dropwise. After completion of the reaction, the resultant was cooled, and a target product was extracted with dichloromethane. The organic layer was washed with water and saturated brine, and then the solvent was evaporated. Subsequently, purification was carried out in a silica column. Thus, a target compound (3.5 g) represented by formula (13) was obtained.

[Chem. 183]

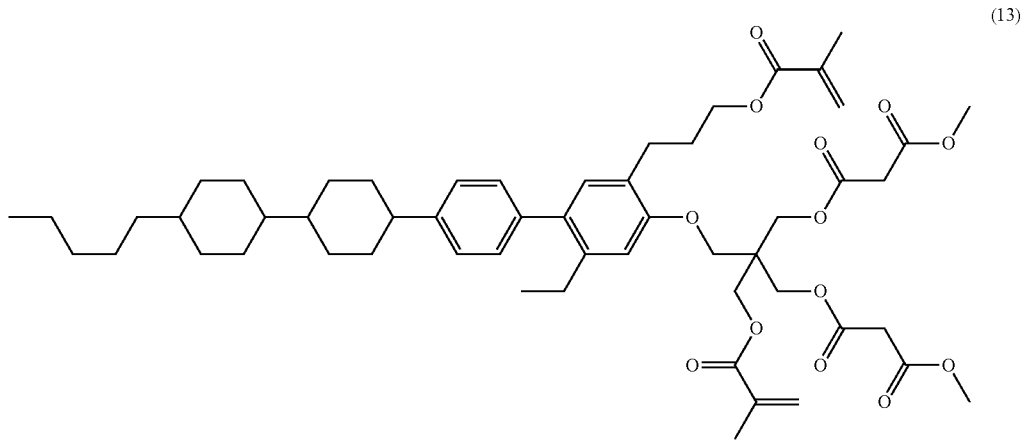

(Physical Property Values)
Oily $^1$H-NMR (solvent: deuterated chloroform): δ: 0.88 (t, 3H), 1.11-1.98 (m, 38H), 2.50-2.53 (m, 1H), 2.58 (q, 2H), 2.68 (t, 2H), 3.43 (s, 4H), 3.71 (s, 6H), 4.07 (s, 2H), 4.17 (t, 2H), 4.34 (s, 2H), 4.40 (s, 4H), 5.53 (s, 1H), 5.62 (s, 1H), 6.07 (s, 1H), 6.11 (s, 1H), 6.76 (s, 1H), 6.98 (s, 1H), 7.16 (d, 2H), 7.21 (d, 2H)

Example 20

A target compound (14) was obtained by using a synthesis method similar to that for Example 18.

[Chem. 184]

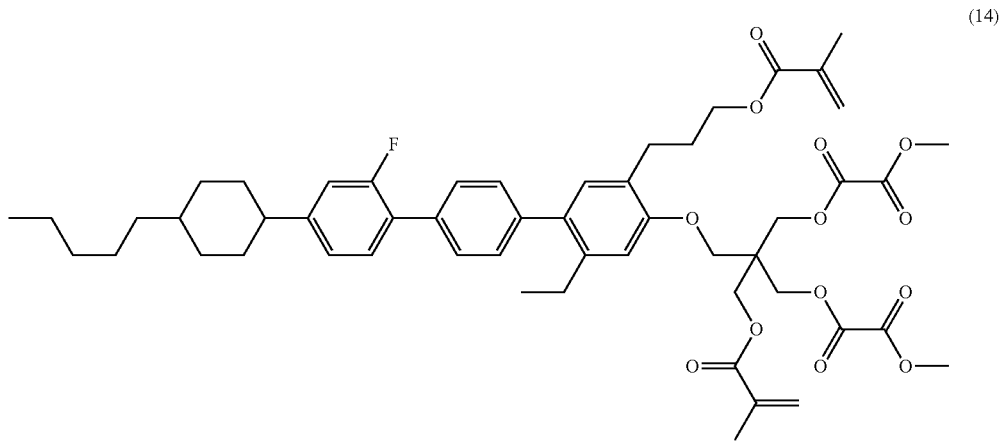

(Physical Property Values)
Solid $^1$H-NMR (solvent: deuterated chloroform): δ: 0.90 (t, 3H), 1.06-1.49 (m, 16H), 1.89-2.02 (m, 12H), 2.52-2.60 (m, 3H), 2.78 (t, 2H), 3.71 (s, 6H), 4.07 (s, 2H), 4.21 (t, 2H), 4.35 (s, 2H), 4.41 (s, 4H), 5.55 (s, 1H), 5.61 (s, 1H), 6.10 (s, 2H), 6.92 (d, 1H), 6.98 (d, 1H), 7.04 (d, 1H), 7.17 (t, 1H), 7.23 (d, 1H), 7.38-7.47 (m, 4H)

Example 21

26 g of 4-(4-pentyl (cyclohexyl))phenylboronic acid, 17 g of 4-bromo-2-fluorophenol, 65 ml of a 2M aqueous potassium carbonate solution, 763 mg of tetrakistriphenylphosphine palladium, and 230 ml of tetrahydrofuran were added to a reaction vessel equipped with a stirrer, a condenser, and a thermometer, and then a reaction was carried out at 70° C. for 5 hours. After completion of the reaction, the resultant was cooled, and hexane was added. The organic layer was washed with water and saturated brine, and then the solvent was evaporated. Thus, a colorless solid compound (27 g) represented by (15-1) was obtained.

[Chem. 185]

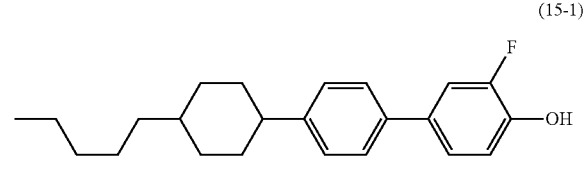

Next, 27 g of the compound represented by formula (15-1), 135 ml of dichloromethane, and 11 g of pyridine were added to a reaction vessel equipped with a stirrer and a thermometer, and then 20 g of trifluoromethanesulfonic anhydride was slowly added dropwise under ice cooling. After completion of the reaction, the resultant was cooled, 300 ml of water was added, and a target product was extracted with ethyl acetate. The organic layer was washed with water and saturated brine, and then the solvent was evaporated. Subsequently, purification was carried out in a silica column. Thus, a brown solid compound (38 g) represented by formula (15-2) was obtained.

[Chem. 186]

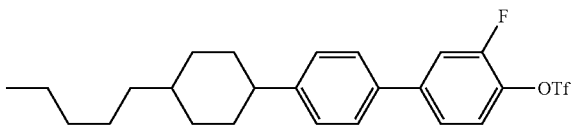

(15-2)

Next, 32 g of the compound represented by formula (15-2), 160 ml of dimethylformamide, 18 g of potassium acetate, 17 g of bis(pinacolato)diborane, and 1.5 g of 1,1'-bis(diphenylphosphino)ferrocene-palladium(II)dichloride were added to a reaction vessel equipped with a stirrer, a condenser tube, and a thermometer and then stirred at 80° C. After completion of the reaction, the resultant was cooled, 300 ml of water was added, and a target product was extracted with ethyl acetate. The organic layer was washed with water and saturated brine, and then the solvent was evaporated. Subsequently, purification was carried out in a silica column. Thus, a colorless crystalline compound (32 g) represented by formula (15-3) was obtained.

[Chem. 187]

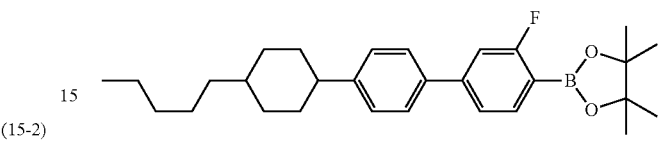

(15-3)

32 g of the compound (15-3), 17.4 g of 4-bromo-5 ethyl-2-hydroxypropyl phenol, 56 ml of a 2.0M aqueous potassium carbonate solution, 803 mg of tetrakistriphenylphosphine palladium, and 360 ml of tetrahydrofuran were added to a reaction vessel equipped with a stirrer, a condenser, and a thermometer, and then a reaction was carried out at 70° C. for 5 hours. After completion of the reaction, the resultant was cooled, and 600 ml of ethyl acid was added. The organic layer was washed with water and saturated brine, the solvent was then evaporated, and then recrystallization was carried out with toluene. Thus, a compound (31.8 g) represented by (15-4) was obtained.

[Chem. 188]

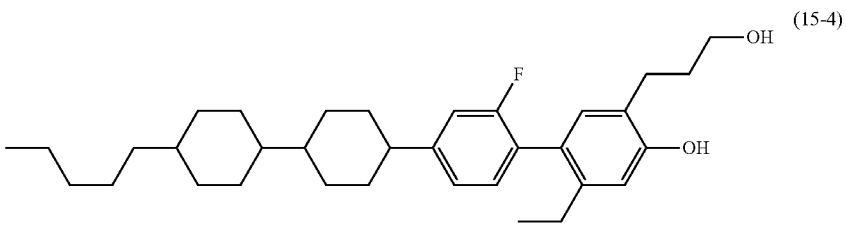

(15-4)

10 g of the compound (15-4), 402 mg of diisopropylamine, and 100 ml of dichloromethane were added to a reaction vessel equipped with a stirrer and a thermometer and stirred under ice cooling, and then 4.7 g of N-iodosuccinimide, which was dissolved in 50 ml of acetonitrile, was slowly added dropwise. After 1 hour, 200 ml of a 10% aqueous sodium thiosulfate solution was added to perform separation of liquids. The organic layer was washed with water and saturated brine, and then the solvent was evaporated. Thus, a compound (11.6 g) represented by (15-5) was obtained.

[Chem. 189]

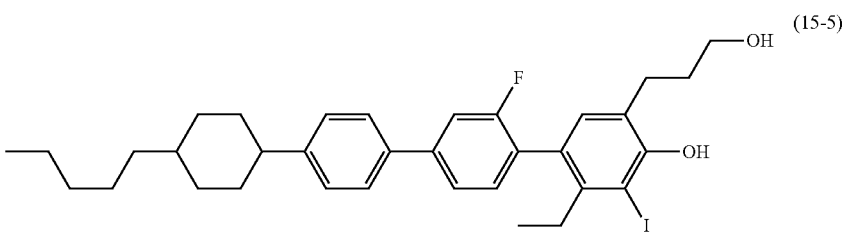

(15-5)

Next, 11.6 g of the compound (15-5), 16.5 g of (2,2,5-trimethyl-1,3-dioxan-5-yl)methylmethane sulfonate, 15 g of tripotassium phosphate, and 120 ml of dimethyl sulfide were added to a reaction vessel equipped with a stirrer, a condenser, and a thermometer, and then a reaction was carried out at 100° C. for 5 hours. After completion of the reaction, the resultant was cooled, and 300 ml of ethyl acetate was added. The organic layer was washed with water and saturated brine, and then the solvent was evaporated. Subsequently, dispersion washing was carried out with toluene, and purification was carried out in an alumina column. Thus, a compound (12.0 g) represented by formula (15-6) was obtained.

[Chem. 190]

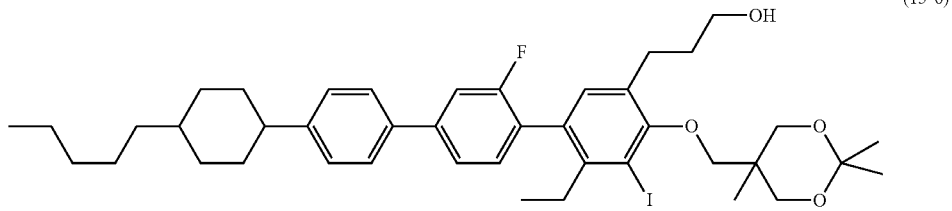

(15-6)

Next, 12.0 g of the compound (15-6), 1.7 g of propargyl alcohol, 12 ml of ethanolamine, 878 mg of tetrakistriphenylphosphine palladium, 289 mg of copper (I) iodide, and 60 ml of tetrahydrofuran were added to a reaction vessel equipped with a stirrer, a condenser, and a thermometer, and then a reaction was carried out at 65° C. for 5 hours. After completion of the reaction, the resultant was cooled, and 200 ml of ethyl acid was added. The organic layer was washed with water and saturated brine, and then the solvent was evaporated. Thus, a compound (9.4 g) represented by (15-7) was obtained.

[Chem. 191]

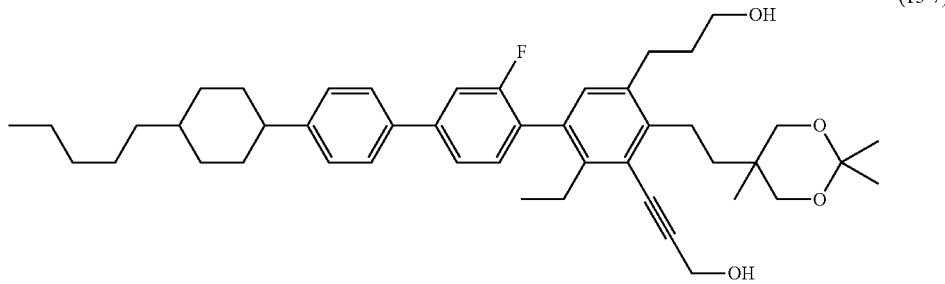

(15-7)

Next, 9.4 g of the compound (15-7), 1.7 g of propargyl alcohol, 470 mg of 5% palladium on carbon, and 60 ml of tetrahydrofuran were added to an autoclave equipped with a stirrer, and then a reaction was carried out at 45° C. for 5 hours under a hydrogen pressure of 0.5 MPa. After completion of the reaction, the resultant was cooled, and 100 ml of ethyl acid was added. Purification was carried out in an alumina column, and then the solvent was evaporated. Thus, a compound (9.5 g) represented by (15-8) was obtained.

[Chem. 192]

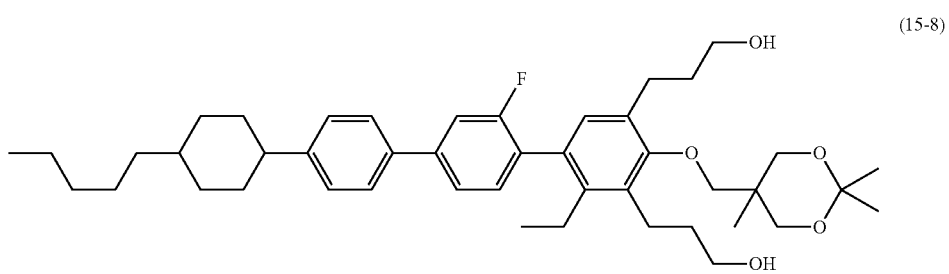

(15-8)

Next, 9.5 g of the compound (15-8), 9.0 g of triethylamine, and 90 ml of dichloromethane were loaded into a reaction vessel equipped with a stirrer, a condenser, and a thermometer, and the reaction vessel was cooled to 10° C. or lower. Subsequently, 7.2 g of methacryloyl chloride was slowly added dropwise. After completion of the dropwise addition, the reaction vessel was returned to room temperature, and then a reaction was carried out for 3 hours. After completion of the reaction, washing was carried out with water and saturated brine, and then the solvent was evaporated. Subsequently, the extracts and 90 ml of THF were added to a reaction vessel equipped with a stirrer and a thermometer, and then 14 ml of 10% hydrochloric acid was slowly added dropwise. After completion of the reaction, the resultant was cooled, and a target product was extracted with ethyl acetate. The organic layer was washed with water and saturated brine, and then the solvent was evaporated. Subsequently, purification was carried out in a silica column. Thus, a compound (8.6 g) represented by compound (15-8) was obtained.

[Chem. 193]

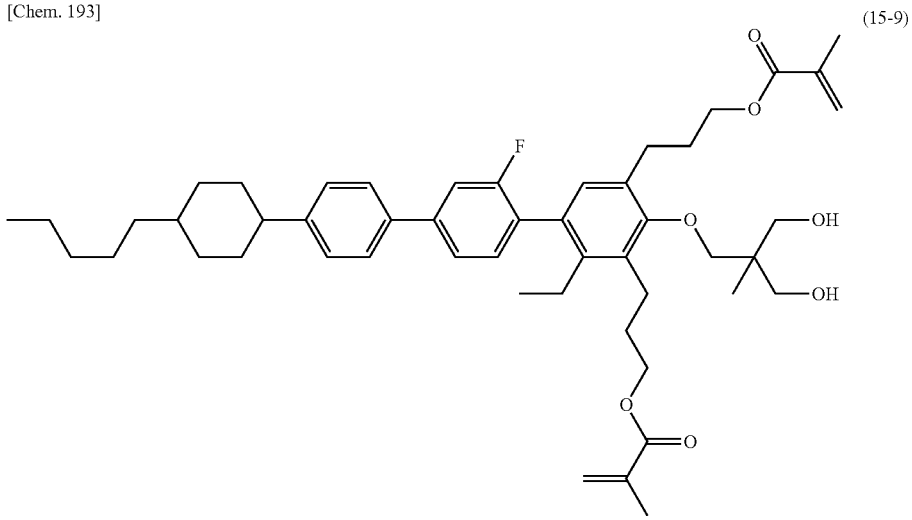

(15-9)

Next, 8.6 g of the compound (15-9), 80 ml of dichloromethane, and 3.5 ml of triethylamine were added to a reaction vessel equipped with a stirrer and a thermometer, and then 3.0 g of methyl oxalyl chloride was slowly added dropwise. After completion of the reaction, the resultant was cooled, and a target product was extracted with dichloromethane. The organic layer was washed with water and saturated brine, and then the solvent was evaporated. Subsequently, purification was carried out in a silica column. Thus, a target compound (3.1 g) represented by formula (15) was obtained.

[Chem. 194]

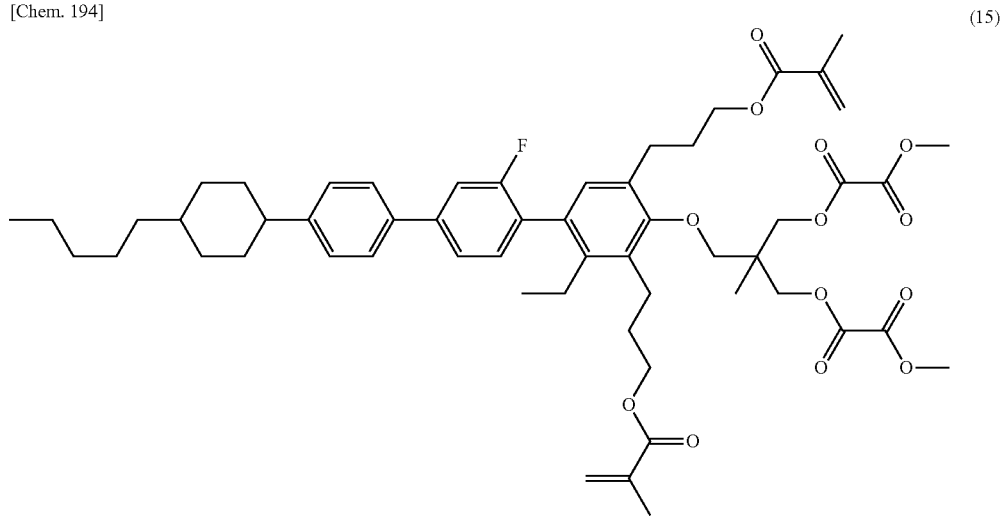

(15)

(Physical Property Values)
Solid
$^1$H-NMR (solvent: deuterated chloroform): δ: 0.90 (t, 6H), 1.06-2.02 (m, 28H), 2.52-2.78 (m, 7H), 3.61 (s, 6H), 3.71 (s, 2H), 4.07 (s, 4H), 4.21 (t, 6H), 6.40 (s, 2H), 6.48 (s, 2H), 7.01 (d, 1H), 7.38 (d, 2H), 7.50 (d, 2H), 7.51-7.60 (m, 3H)

Example 22

10.6 g of the compound (15-4), 15.5 g of 2-(5-(bromomethyl)-2,2-dimethyl-1,3-dioxan-5-yl)ethan-1-ol, 14 g of tripotassium phosphate, and 100 ml of dimethyl sulfide were added to a reaction vessel equipped with a stirrer, a condenser, and a thermometer, and then a reaction was carried out at 100° C. for 5 hours. After completion of the reaction, the resultant was cooled, and 300 ml of ethyl acetate was added. The organic layer was washed with water and saturated brine, and then the solvent was evaporated. Subsequently, dispersion washing was carried out with toluene, and purification was carried out in an alumina column. Thus, a compound (11.0 g) represented by formula (16-1) was obtained.

[Chem. 195]

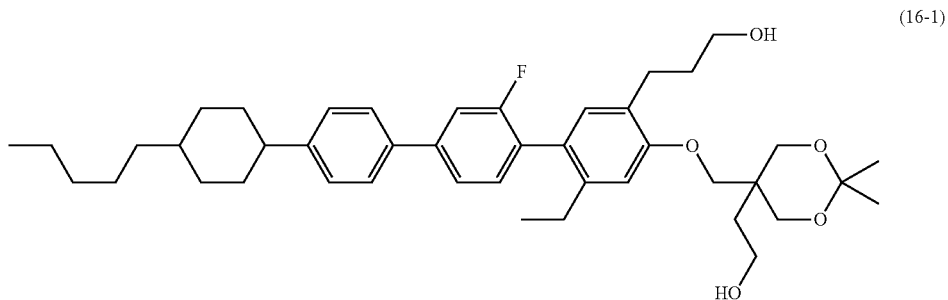

(16-1)

Subsequently, the following formula (16) was produced by using the method for producing the compound (15) from the compound (15-8).

[Chem. 196]

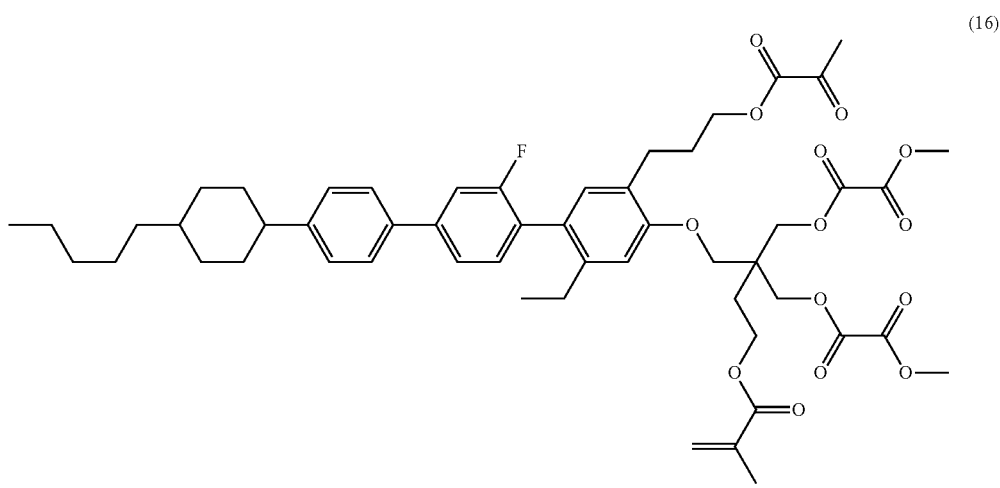

(16)

(Physical Property Values)
Solid
$^1$H-NMR (solvent: deuterated chloroform): δ: 0.90 (t, 3H), 1.06-1.49 (m, 16H), 1.89-2.02 (m, 12H), 2.52-2.78 (m, 5H), 3.71 (s, 6H), 4.07 (s, 2H), 4.21 (t, 2H), 4.35 (s, 2H), 4.41 (s, 4H), 5.52 (s, 1H), 5.62 (s, 1H), 6.08 (s, 1H), 6.12 (s, 1H), 6.81 (s, 1H), 7.00 (s, 1H), 7.22-7.41 (m, 5H), 7.56 (d, 2H)

Example 23

Next, 10 g of the compound (15-5), 16.5 g of (5-(bromomethyl)-2,2-dimethyl-1,3-dioxan-5-yl)methanol, 16 g of tripotassium phosphate, and 100 ml of dimethyl sulfide were added to a reaction vessel equipped with a stirrer, a condenser, and a thermometer, and then a reaction was carried out at 100° C. for 5 hours. After completion of the reaction, the resultant was cooled, and 300 ml of ethyl acetate was added. The organic layer was washed with water and saturated brine, and then the solvent was evaporated. Subsequently, dispersion washing was carried out with toluene, and purification was carried out in an alumina column. Thus, a compound (10.5 g) represented by formula (17-1) was obtained.

[Chem. 197]

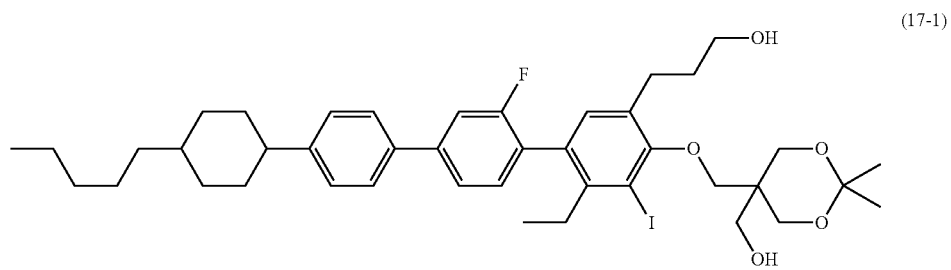

(17-1)

Next, 10.5 g of the compound (17-1), 2.3 g of 1-heptyne, 11 ml of ethanolamine, 829 mg of tetrakistriphenylphosphine palladium, 205 mg of copper (I) iodide, and 50 ml of tetrahydrofuran were added to a reaction vessel equipped with a stirrer, a condenser, and a thermometer, and then a reaction was carried out at 65° C. for 5 hours. After completion of the reaction, the resultant was cooled, and 200 ml of ethyl acid was added. The organic layer was washed with water and saturated brine, and then the solvent was evaporated. Thus, a compound (8.7 g) represented by (17-2) was obtained.

[Chem. 198]

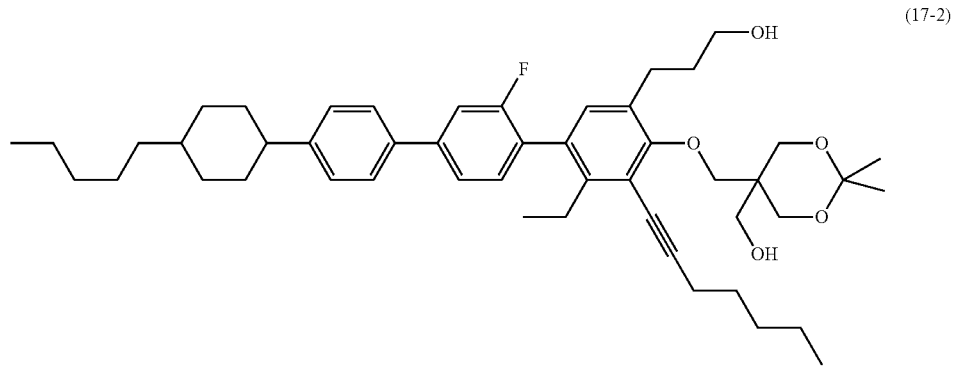

(17-2)

Subsequently, the following formula (17) was produced by using the method for producing the compound (15) from the compound (15-7).
[Chem. 199]
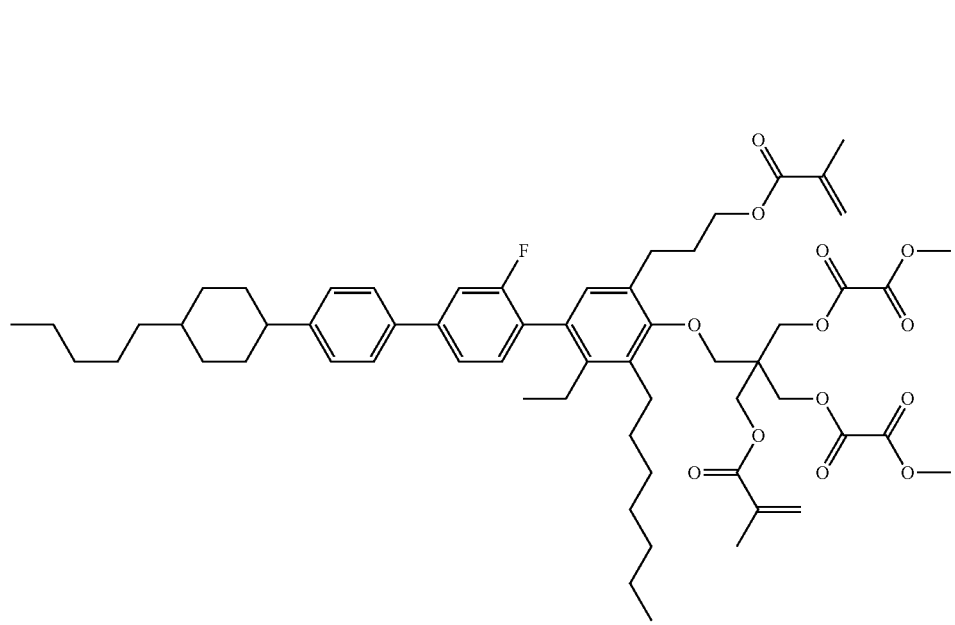
(Physical Property Values)
Solid
$^1$H-NMR (solvent: deuterated chloroform): δ: 0.89 (t, 6H), 1.06-1.49 (m, 26H), 1.89-2.02 (m, 12H), 2.52-2.78 (m, 7H), 3.71 (s, 6H), 4.07 (s, 2H), 4.21 (t, 2H), 4.35 (s, 2H), 4.41 (s, 4H), 5.52 (s, 1H), 5.62 (s, 1H), 6.08 (s, 1H), 6.12 (s, 1H), 7.00 (s, 1H), 7.22-7.41 (m, 5H), 7.56 (d, 2H)
By using a similar method and a known method, compounds represented by formulae (18) to (47) below were produced.
[Chem. 200]
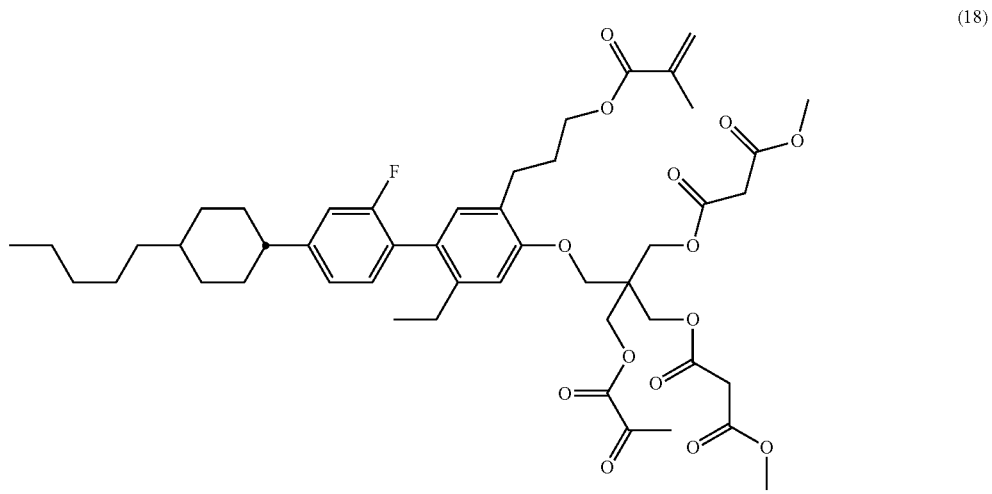

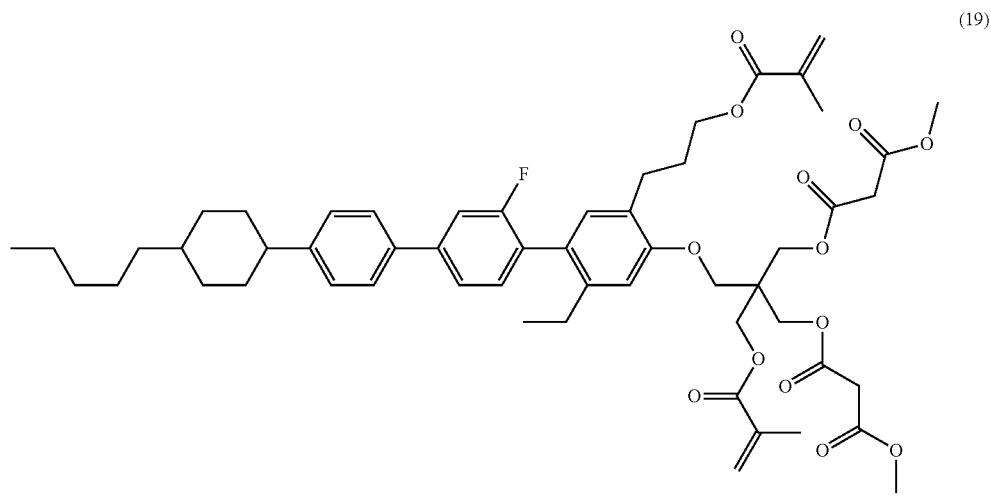
(19)
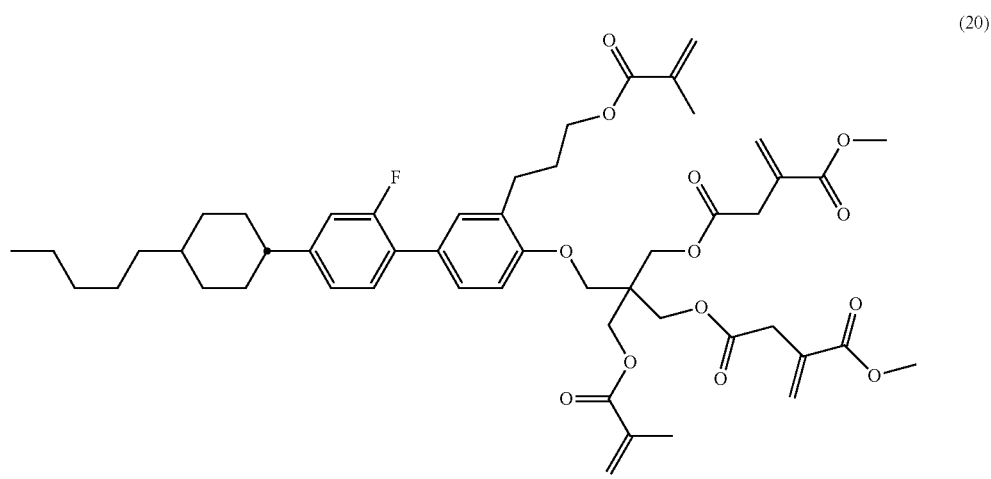
(20)
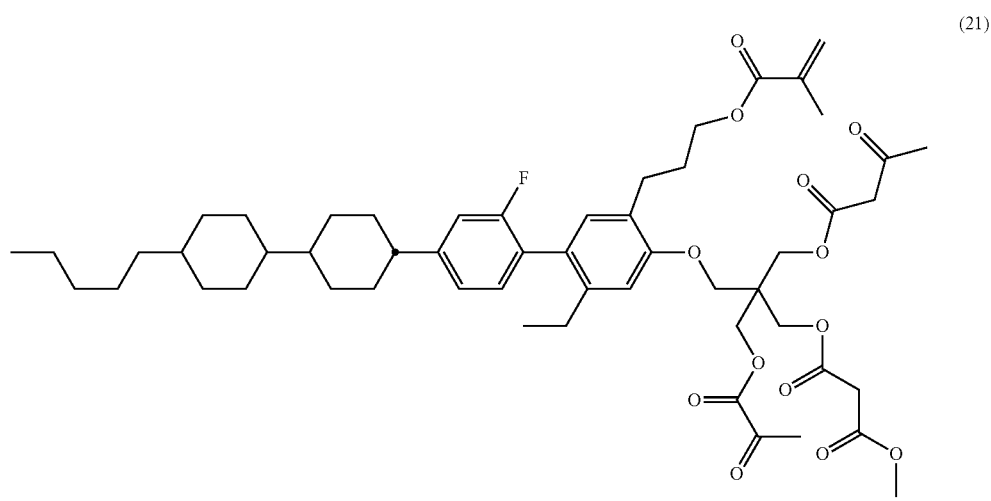
(21)

(22)
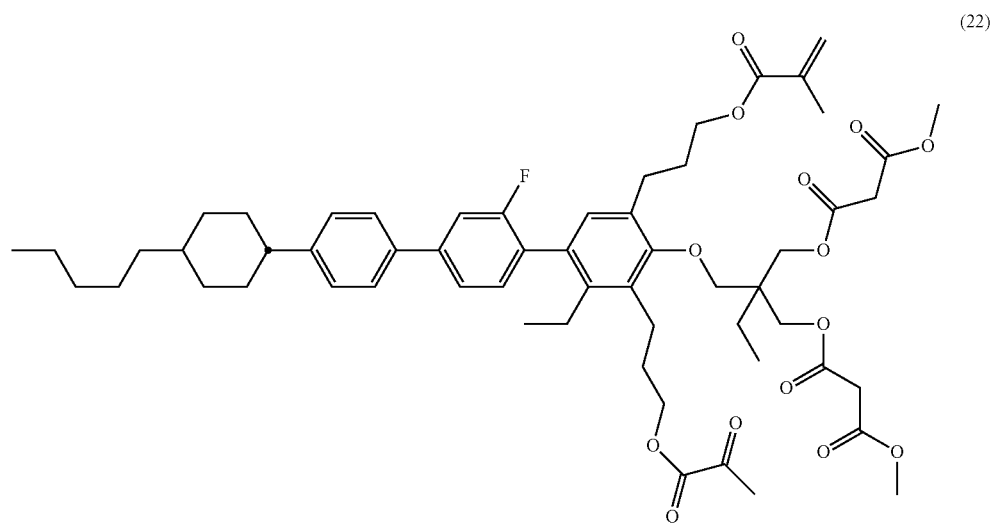
(23)
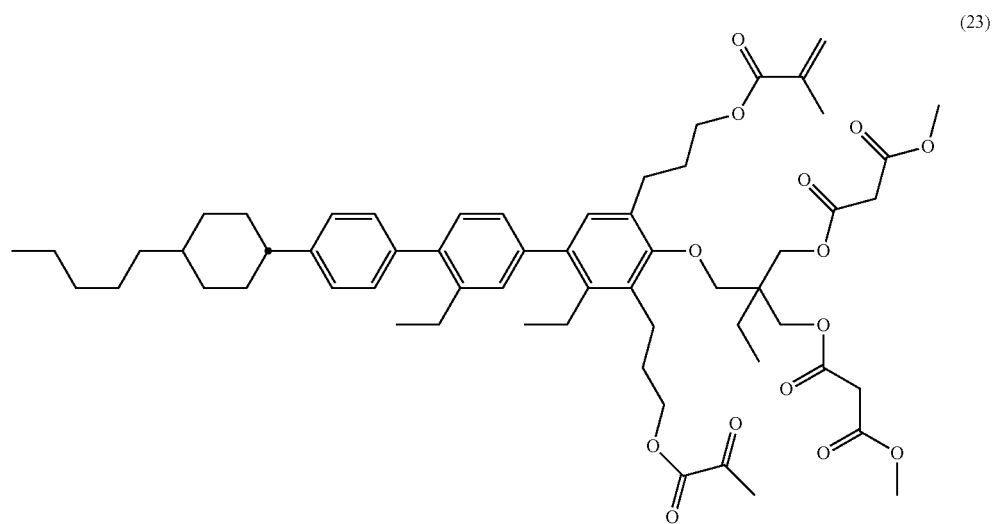
[Chem. 201]
(24)
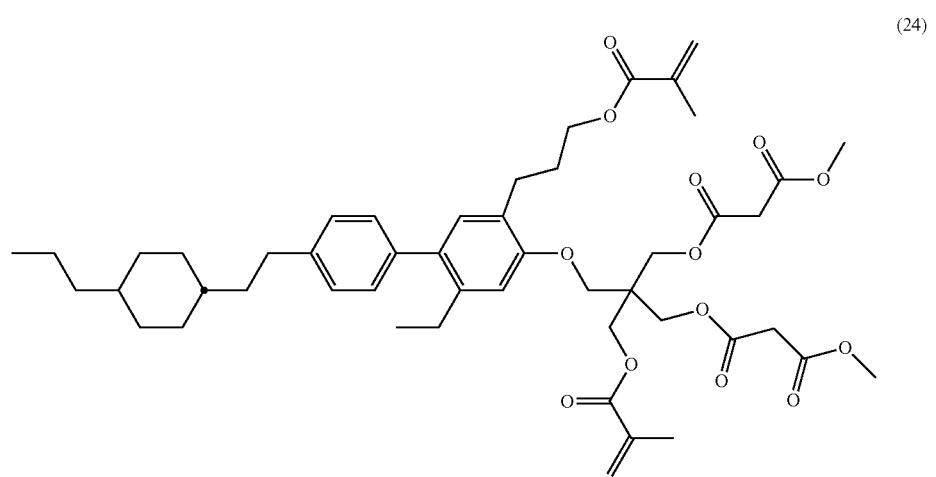

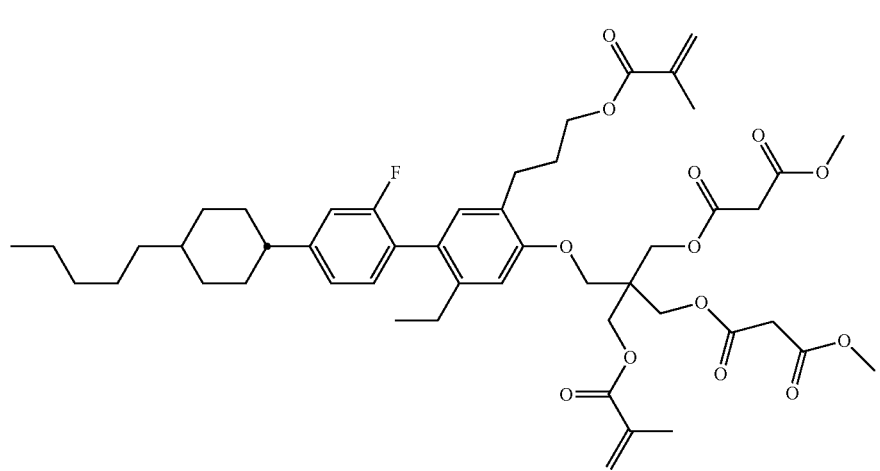
(25)
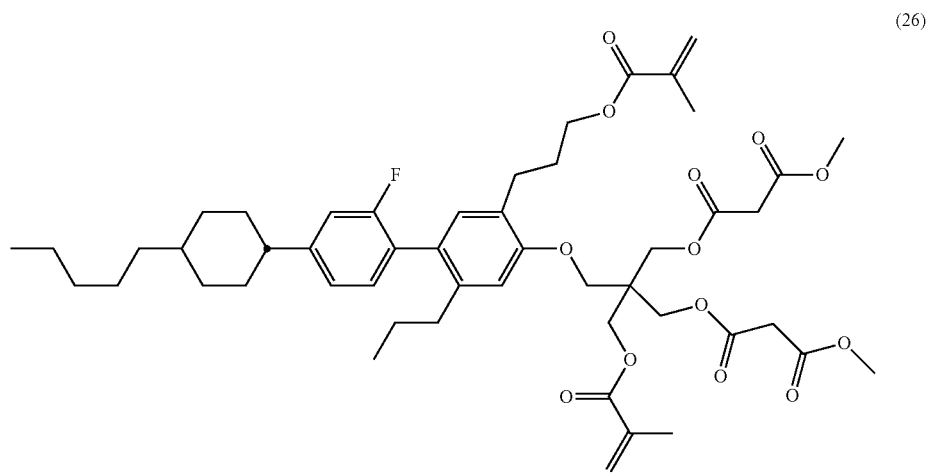
(26)
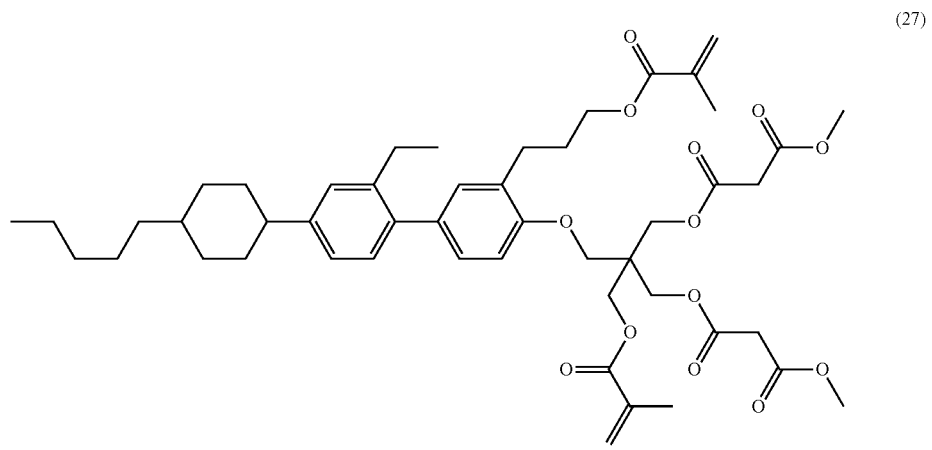
(27)

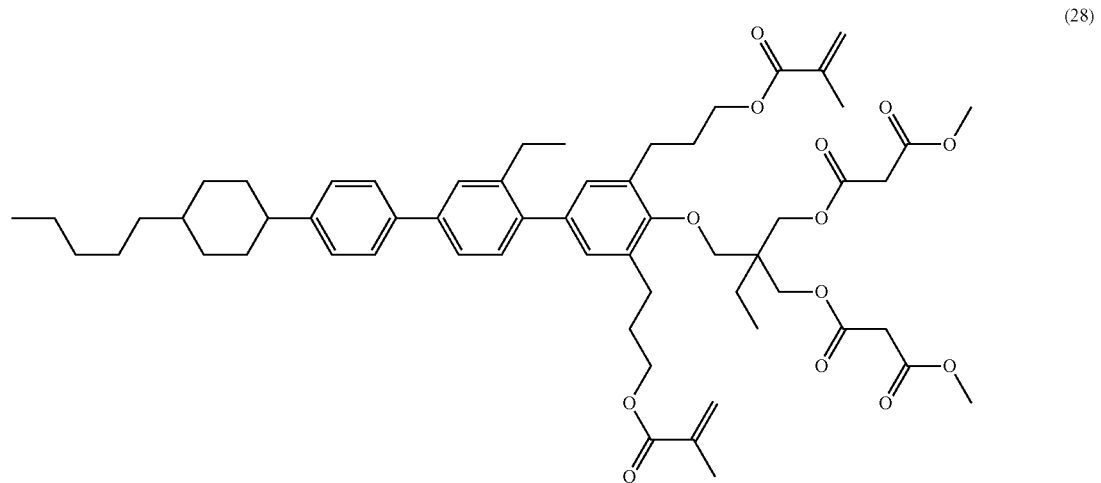
(28)
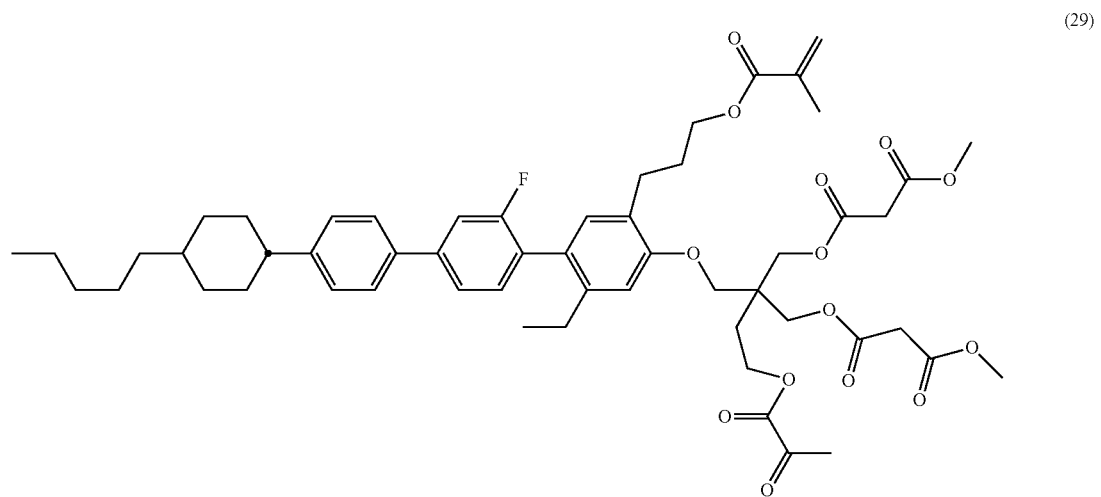
(29)
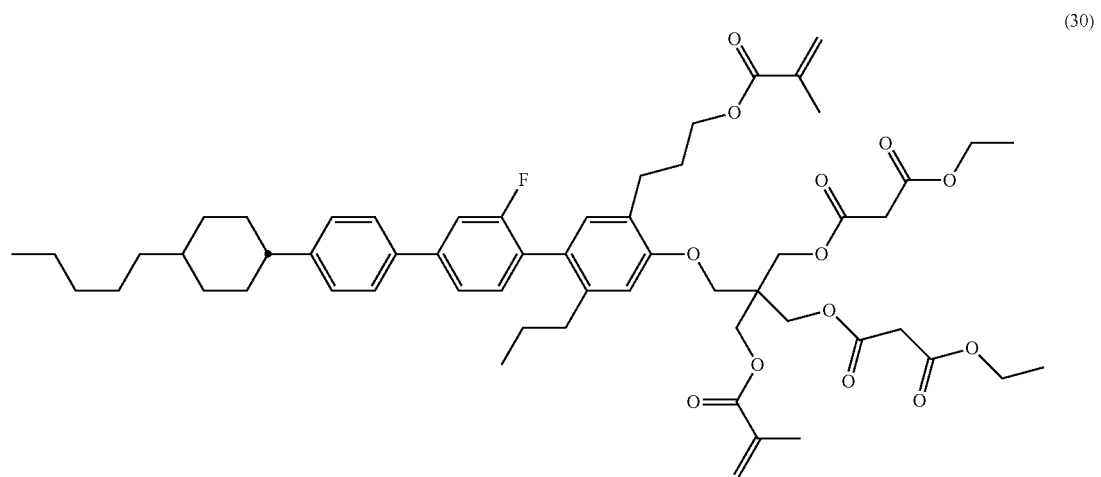
(30)

[Chem. 202]
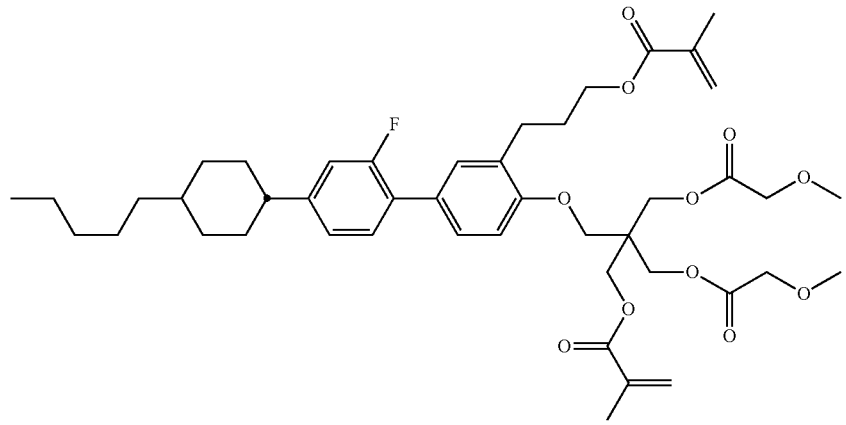
(31)
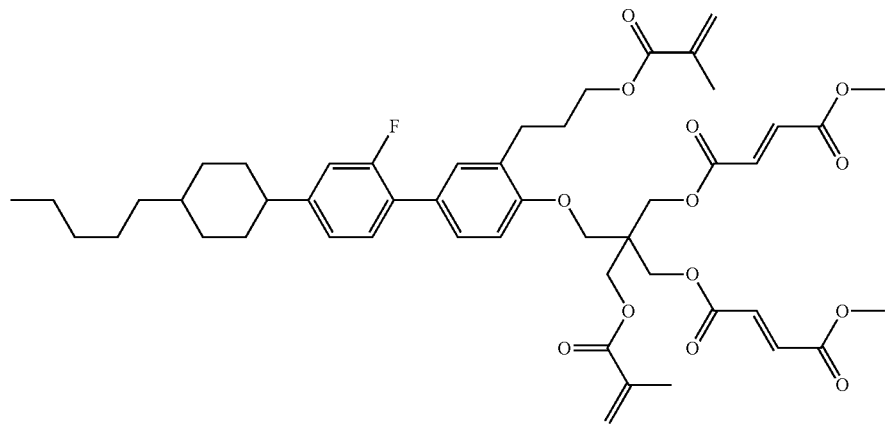
(32)
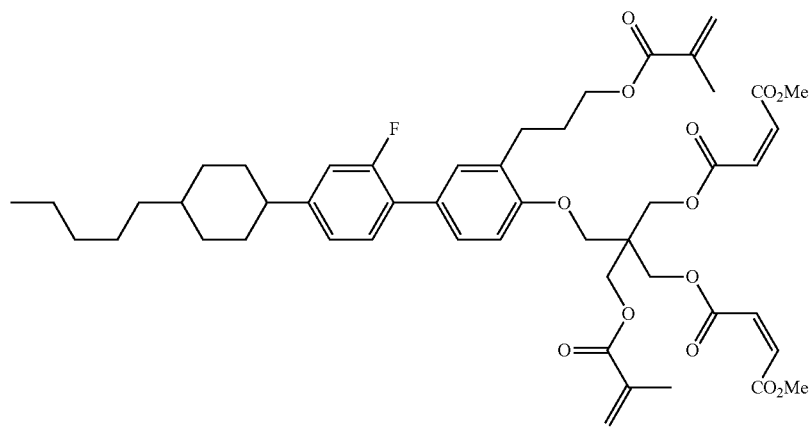
(33)

(34)
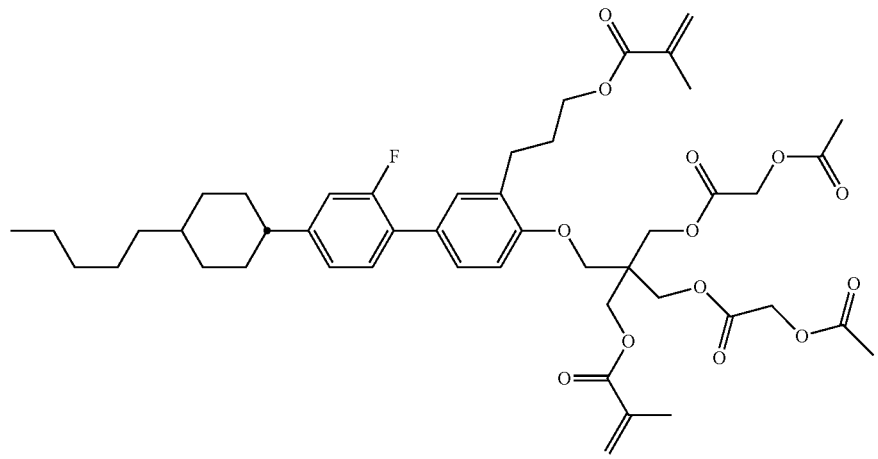
[Chem. 203]
(35)
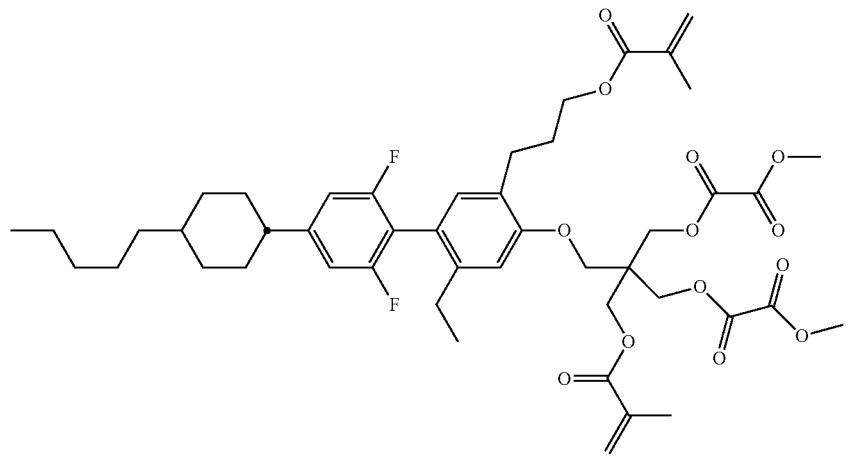
(36)
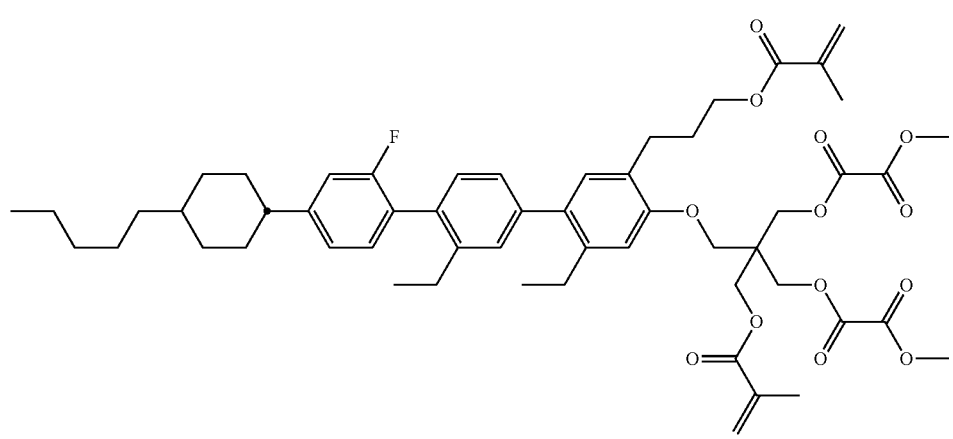

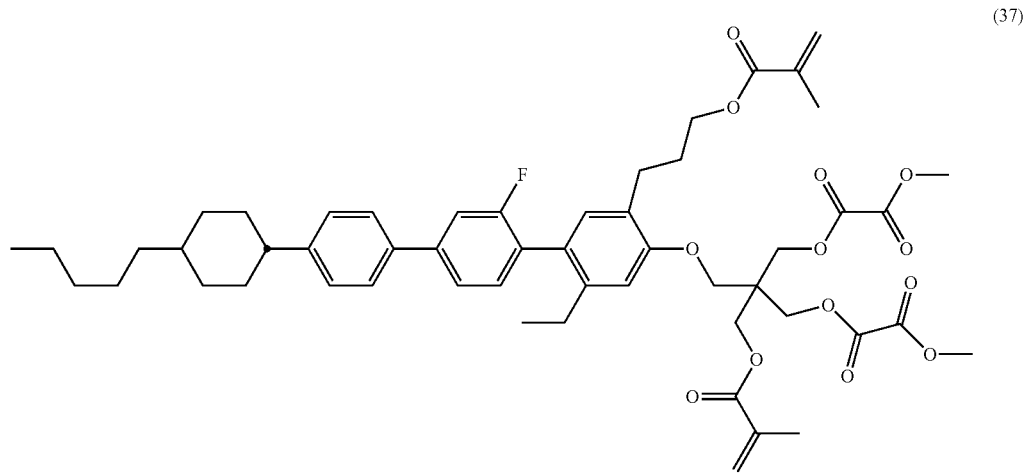
(37)
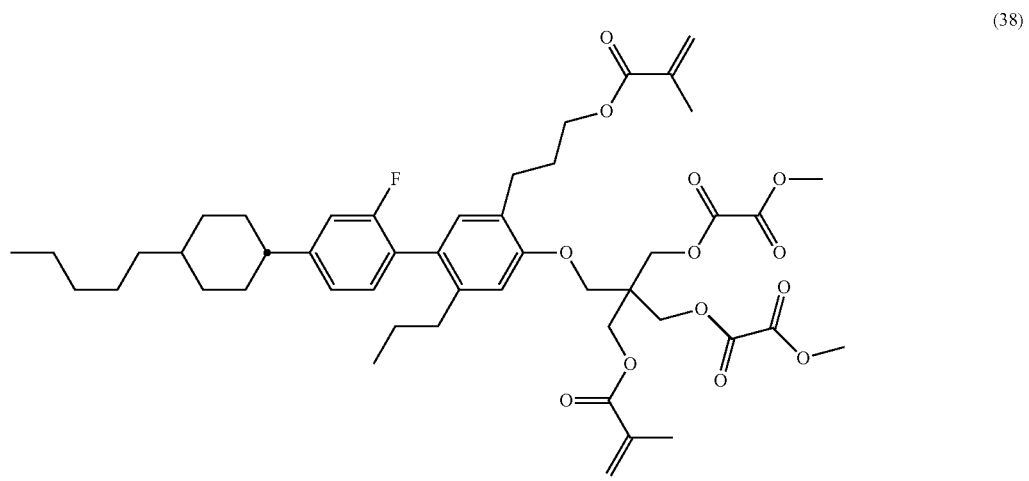
(38)
[Chem. 204]
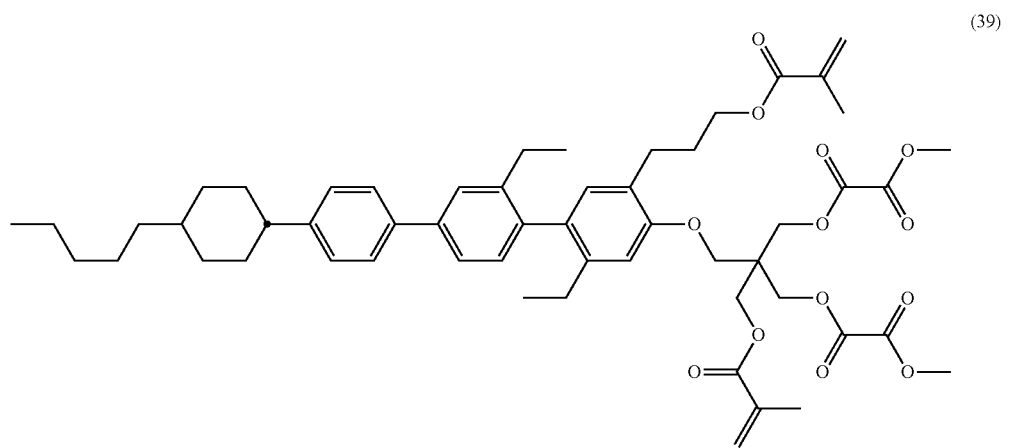
(39)

-continued
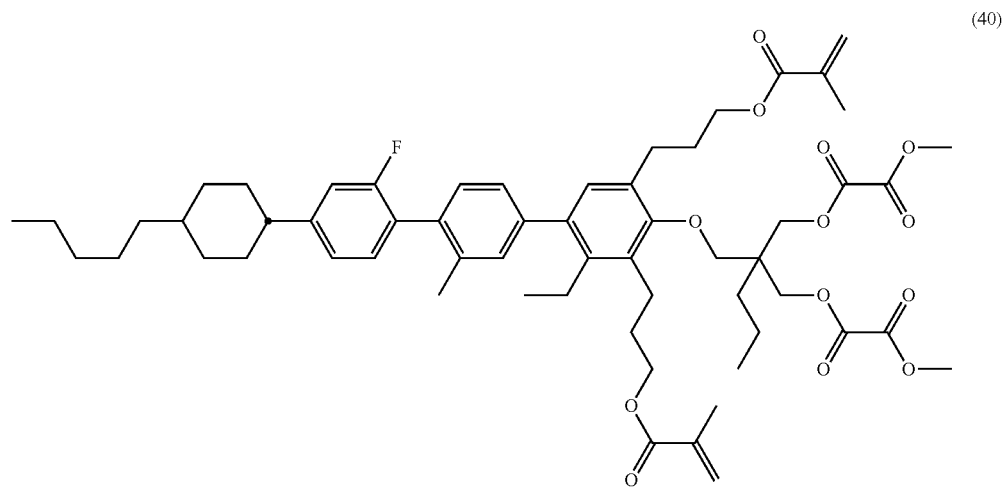
(40)
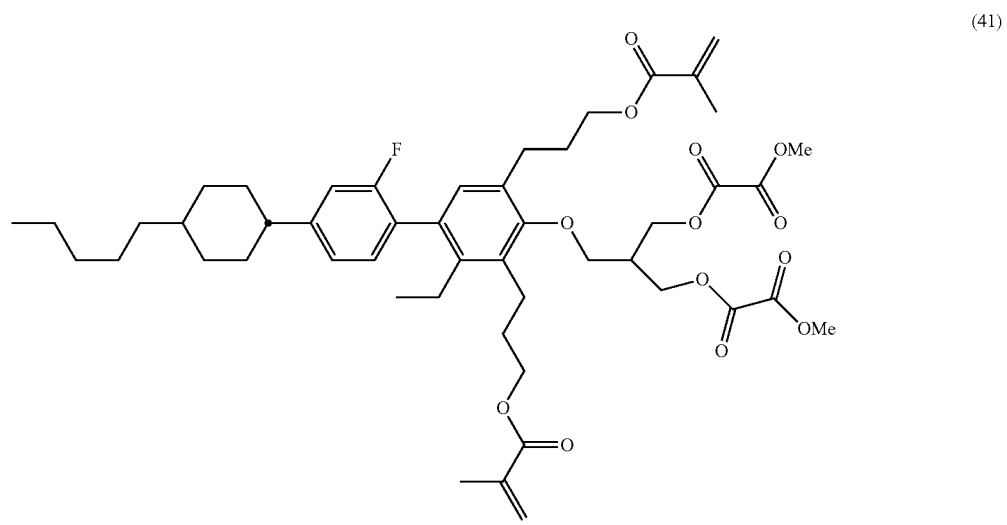
(41)
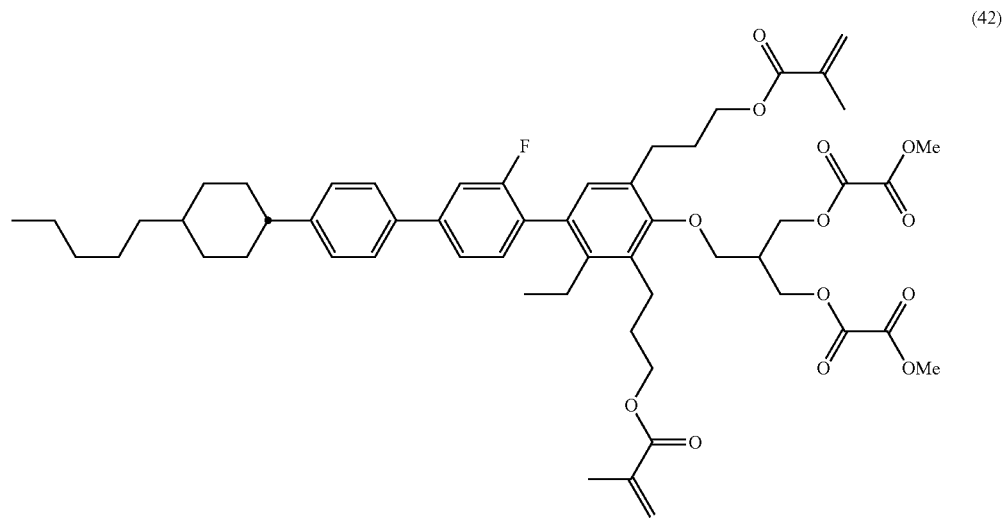
(42)

[Chem. 204]
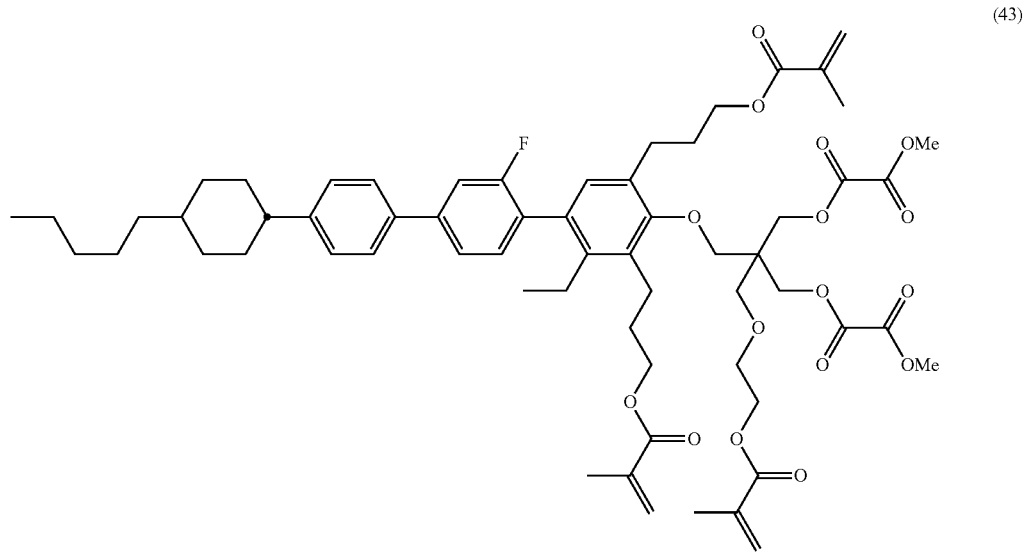
(43)
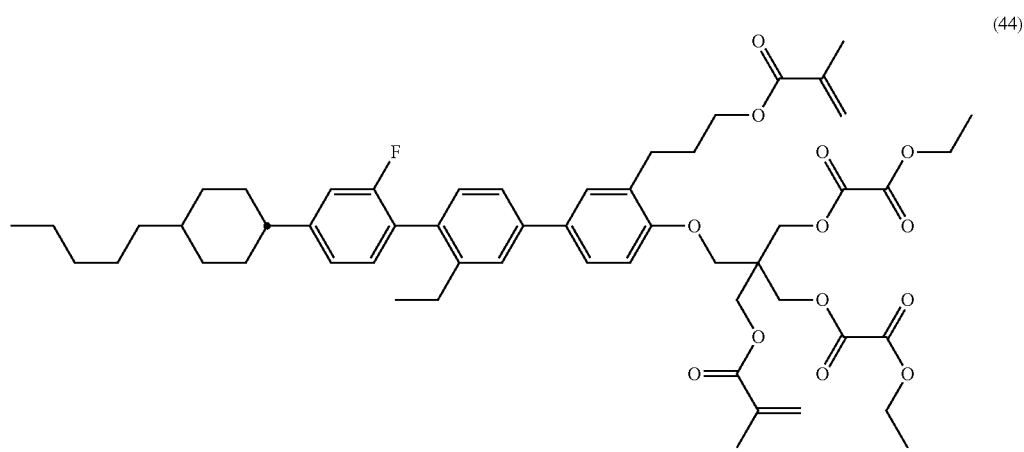
(44)
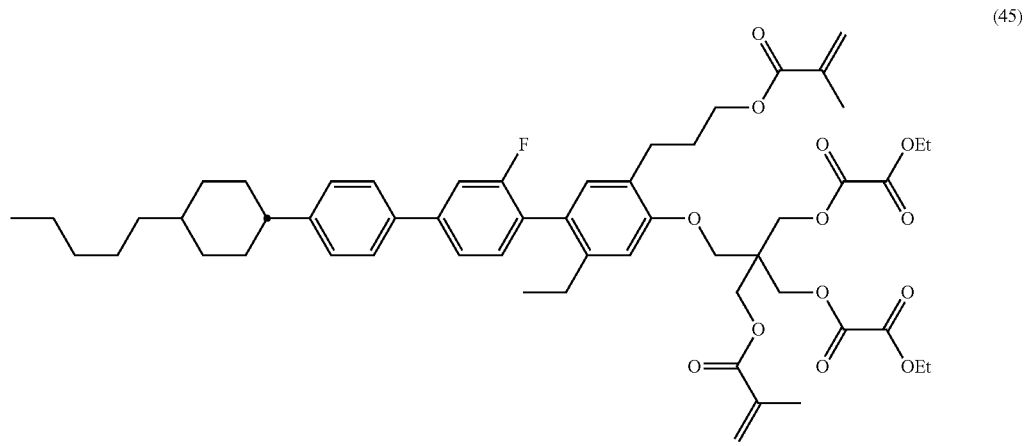
(45)

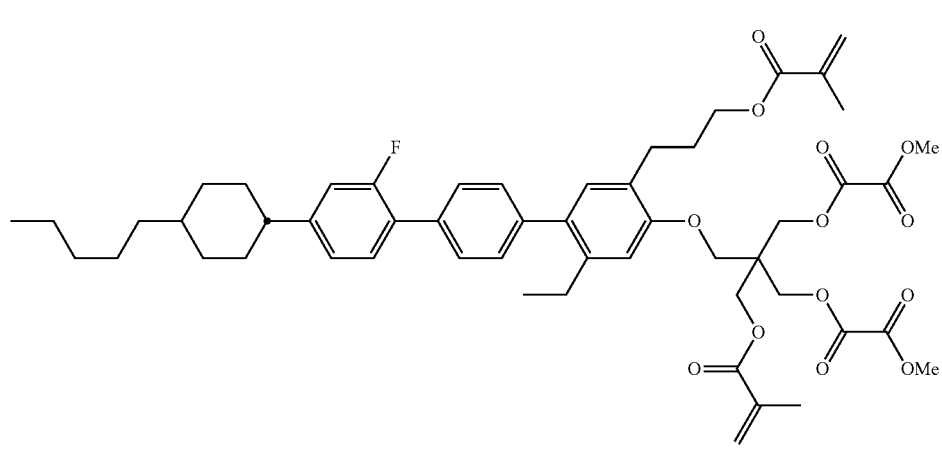

(46)

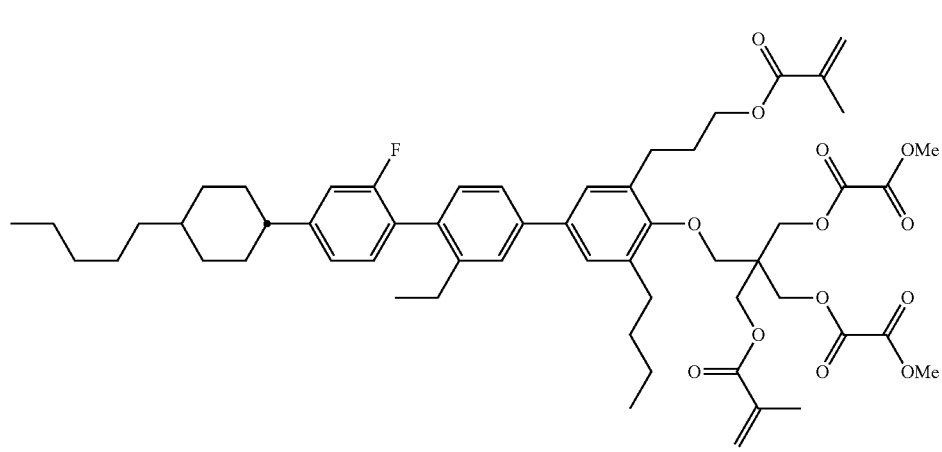

(47)

Example 24

A liquid crystal composition was prepared in the following manner: 0.5 parts by mass of the compound (1) prepared in Example 1, which corresponded to the compound (i), was added to 100 parts by mass of LC-1, and the resultant was heated and dissolved.

Examples 25 to 32

Liquid crystal compositions were prepared as in Example 24 except that instead of the compound (1), each of the compounds (7) to (14), which were prepared in Examples 13 to 20, was added in an amount of 0.5 parts by mass to LC-1.

Comparative Examples 6 to 8

Liquid crystal compositions were prepared as in Example 24 except that instead of the compound (1), each of the compounds (C-1) to (C-3), which were used in Comparative Examples 3 to 5, was added in an amount of 0.5 parts by mass to LC-1. With regard to the liquid crystal compositions obtained in Examples 24 to 32, properties that were additionally measured, other than the properties measured in Examples 7 to 12, are as follows.

VHR: a voltage holding ratio (%) at 333 K, at a frequency of 60 Hz and an applied voltage of 1 V, was evaluated based on three levels of ratings.
A: 98 to 100%
B: 95 to 98%
C: 95% or less Heating VHR: after each of the measurement cells was heated at 120° C. for 1 hour, the voltage holding ratio (%) at 333 K, at a frequency of 0.6 Hz and an applied voltage of 1 V, was evaluated based on three levels of ratings.
A: 80 to 100%
B: 70 to 80%
C: 70% or less Light-fastness VHR: ultraviolet light was radiated at 180 J/m² to the liquid crystal composition through glass having a thickness of 0.5 mm, by using a super high-pressure mercury lamp. The voltage holding ratio of the liquid crystal after ultraviolet light irradiation was measured in a manner similar to that for the VHR measurement described above. In this case, the irradiation intensity was 0.1 W/m² at 366 nm. Evaluations were made based on the following three levels of ratings.
A: 90 to 100%
B: 75 to 90%
C: 75% or less The evaluation tests were as shown in Table 3.

TABLE 3

| | Added compound | Low-temperature storage characteristics | Vertical alignment characteristics | Pretilt angle formation | Residual monomer amount | Response characteristics | VHR | Heating VHR | Light-fastness VHR |
|---|---|---|---|---|---|---|---|---|---|
| Example 24 | (1) | A | B | A | B | A | B | C | B |
| Example 25 | (7) | A | A | A | A | A | B | A | A |
| Example 26 | (8) | A | A | A | A | A | B | A | A |
| Example 27 | (9) | A | A | A | A | A | B | A | A |
| Example 28 | (10) | A | B | A | A | A | B | C | B |
| Example 29 | (11) | A | B | A | A | A | B | C | B |
| Example 30 | (12) | A | A | A | A | A | B | C | B |
| Example 31 | (13) | A | A | A | A | A | B | C | B |
| Example 32 | (14) | A | A | A | A | A | B | A | A |
| Example 33 | (15) | A | A | A | A | A | B | A | A |
| Example 34 | (16) | A | A | A | A | A | B | A | A |
| Example 35 | (17) | A | A | A | A | A | B | A | A |
| Comparative Example 6 | C-1 | B | C | C | B | B | C | C | B |
| Comparative Example 7 | C-2 | A | B | D | C | B | C | C | C |
| Comparative Example 8 | C-3 | B | C | D | B | C | B | A | A |

As demonstrated above, compounds of the present invention have both alignment characteristics and a storage stability, and, therefore, excellent liquid crystal compositions having a high voltage holding ratio can be provided depending on a polar group of a compound added.

The invention claimed is:
1. A compound represented by general formula (i),

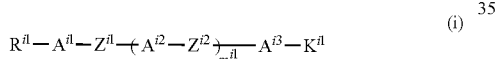
(i)

wherein
$R^{i1}$ independently represents a linear alkyl or halogenated alkyl group having 1 to 40 carbon atoms, or a branched alkyl having 3 to 40 carbon atoms, and a secondary carbon atom in the group is optionally replaced with —O—, —CH=CH—, or —C≡C— provided that oxygen atoms are not directly adjacent to each other,
$A^{i1}$, $A^{i2}$, and $A^{i3}$ each independently represent a divalent aromatic group, a divalent cycloaliphatic group, or a divalent heterocyclic compound group; a hydrogen atom in $A^{i1}$ is optionally replaced with $L^{i1}$, and hydrogen atoms in $A^{i2}$ and $A^{i3}$ are optionally replaced with $L^{i1}$, $P^{i1}$-$Sp^{i1}$-, or $K^{i1}$; and $L^{i1}$ represents a halogen atom, a cyano group, a nitro group, a linear alkyl or halogenated alkyl group having 1 to 40 carbon atoms, or a branched alkyl having 3 to 40 carbon atoms, and a secondary carbon atom in the alkyl group is optionally replaced with —CH=CH—, —C≡C—, —O—, —NH—, —COO—, or —OCO— provided that oxygen atoms are not directly adjacent to each other,
$Z^{i1}$ and $Z^{i2}$ each independently represent a single bond, —CH=CH—, —CF=CF—, —C≡C—, —COO—, —OCO—, —OCOO—, —CF$_2$O—, —OCF$_2$—, —CH=CHCOO—, —OCOCH=CH—, —CH=C(CH$_3$)COO—, —OCOC(CH$_3$)=CH—, —CH$_2$—CH(CH$_3$)COO—, —OCOCH(CH$_3$)—CH$_2$—, —OCH$_2$CH$_2$O—, or an alkylene group having 2 to 20 carbon atoms, and one —CH$_2$— group or two or more non-adjacent —CH$_2$— groups in the alkylene group are optionally replaced with —O—, —COO—, or —OCO—,
$K^{i1}$ is a group represented by one of general formulae (K-1) to (K-5),

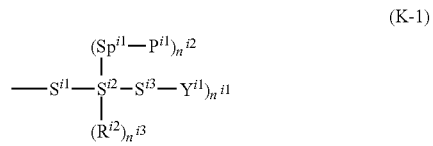
(K-1)

wherein
$Y^{i1}$ represents a linear or branched alkyl, halogenated alkyl, or cyanogenated alkyl group having 3 to 20 carbon atoms; at least two secondary carbon atoms in the alkyl group are replaced with —C(=$X^{i1}$)— and/or —CH(—CN)—; a secondary carbon atom in the alkyl group is optionally replaced with —CH=CH—, —C≡C—, —O—, —NH—, —COO—, or —OCO— provided that oxygen atoms are not directly adjacent to each other; a hydrogen atom in the alkyl group is optionally replaced with $P^{i1}$-$Sp^{i1}$-; and $X^{i1}$ represents an oxygen atom, a sulfur atom, NH, or $NR^{i1}$,
$S^{i1}$ and $S^{i3}$ each independently represent an alkylene group having 1 to 6 carbon atoms or a single bond, and —CH$_2$— in the alkylene group is optionally replaced with —CH=CH—, —C≡C—, —C(=CH$_2$)—, —C(=CHR$^{i3}$)—, —C(=CR$^{i32}$)—, —O—, —NH—, —C(=O)—, —COO—, or —OCO— provided that oxygen atoms are not directly adjacent to each other, $R^{i3}$ represents a linear alkyl group having 1 to 20 carbon atoms, or a branched alkyl group having 3 to 20 carbon atoms, and a secondary carbon atom in the alkyl group is optionally replaced with —O—, —CH=CH—, or —C≡C— provided that oxygen atoms are not directly adjacent to each other,
$S^{i2}$ represents a carbon atom,
$R^{i2}$ represents a hydrogen atom or a linear alkyl having 1 to 20 carbon atoms or branched alkyl having 3 to 20 carbon atoms, and a secondary carbon atom in the group is optionally replaced with —O—, —CH=CH— or —C≡C— provided that oxygen atoms are not directly adjacent to each other, $P^{i1}$ represents a polymerizable group selected from the group consisting of the groups represented by general formulae (P-1) to (P-16),

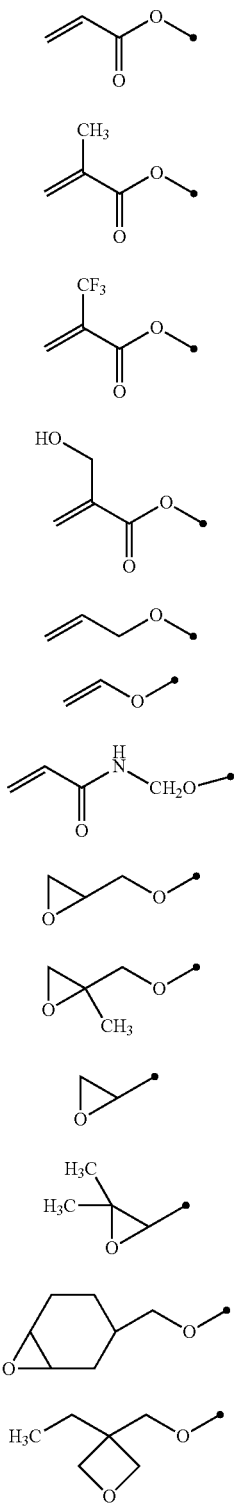

(P-1)
(P-2)
(P-3)
(P-4)
(P-5)
(P-6)
(P-7)
(P-8)
(P-9)
(P-10)
(P-11)
(P-12)
(P-13)

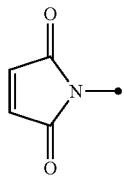

(P-14)

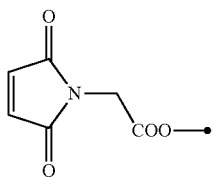

(P-15)

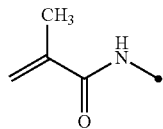

(P-16)

wherein a black dot at a right end represents a bond, $SP^{i1}$ represents a spacer group or a single bond, $n^{i1}$ represents an integer of 1 to 3, and $n^{i2}$ represents 1 or 2, and $n^{i3}$ represents an integer of 0 to 2; and $n^{i1}+n^{i2}+n^{i3}$ is 3, $R^{i3}$ has a same meaning as $R^{i3}$ in general formula (i), in general formula (K-1), when any of $R^{i2}$, $X^{i1}$, $Y^{i1}$, $S^{i1}$, $S^{i3}$, $P^{i1}$, and $SP^{i1}$ is a plurality of units, the units are identical to or different from one another,

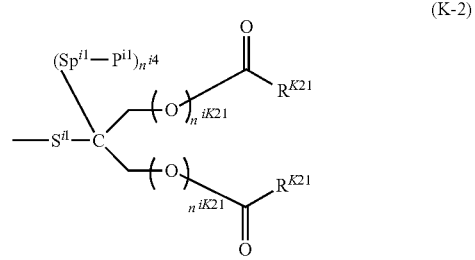

(K-2)

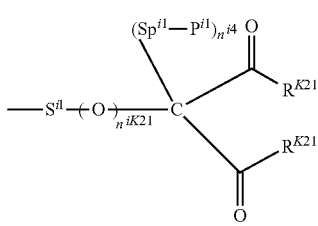

(K-3)

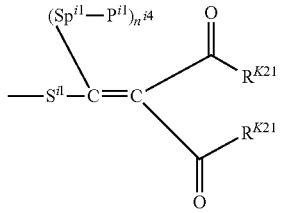

(K-4)

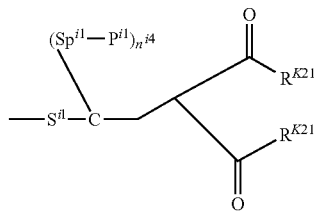

(K-5)

wherein $S^{i1}$, $P^{i1}$, and $SP^{i1}$ have a same meaning as, respectively, $S^{i1}$, $P^{i1}$, and $SP^{i1}$ in general formula (K-1); $R^{K21}$ represents a linear alkyl group having 1 to 10 carbon atoms, branched alkyl group having 3 to 10 carbon atoms, or halogenated alkyl or cyanogenated alkyl group having 1 to 10 carbon atoms, and at least one secondary carbon atom in the alkyl group is optionally replaced with —CH=CH—, —C≡C—, —O—, or —NH— provided that oxygen atoms are not directly adjacent to each other; and $n^{i4}$ represents 1, and $n^{iK21}$ represents 0 or 1

$P^{i1}$ is the same meaning as in general formula (K-1), $SP^{i1}$ represents a spacer group or a single bond, $m^{i1}$ represents an integer of 0 to 3, and in general formula (i), when any of $R^{i1}$, $A^{i2}$, $Z^{i2}$, $L^{i1}$, $K^{i1}$, $X^{i1}$, $P^{i1}$, and $SP^{i1}$ is a plurality of units, the units are identical to or different from one another.

2. The compound according to claim 1, wherein $A^{i1}$, $A^{i2}$, and $A^{i3}$ in general formula (i) represent a ring system selected from a 1,4-phenylene group, a 1,4-cyclohexylene group, a 1,4-cyclohexenylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, and a 1,3-dioxane-2,5-diyl group, and a hydrogen atom in $A^{i1}$ is optionally replaced with $L^{i1}$, and hydrogen atoms in $A^{i2}$ and $A^{i3}$ are optionally replaced with $L^{i1}$, $P^{i1}$-$Sp^{i1}$-, or $K^{i1}$.

3. The compound according to claim 1, wherein $P^{i1}$ in general formula (i) represents the general formula (P-1) or (P-2).

4. The compound according to claim 1, wherein $R^{i1}$ in general formula (i) represents an alkyl group having 3 or more carbon atoms, and —CH$_2$— in the alkyl group is optionally replaced with —O— provided that oxygen atoms are not directly adjacent to each other.

5. The compound according to claim 1, wherein $Y^{i1}$ in general formula (K-1) represents a group selected from general formula (Y-1),

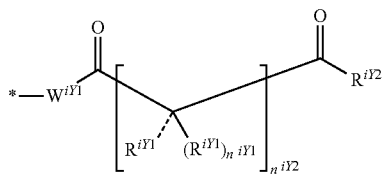

(Y-1)

wherein $W^{iY1}$ represents a single bond or an oxygen atom; a dashed line represents a single bond or a double bond; when the dashed line represents a single bond, $R^{iY1}$ represents a hydrogen atom or a linear alkyl group having 1 to 20 carbon atoms or a branched alkyl group having 3 to 20 carbon atoms, and a secondary carbon atom in the alkyl group is optionally replaced with —O—, —CH=CH— or —C≡C— provided that oxygen atoms are not directly adjacent to each other; when the dashed line represents a double bond, $R^{iY1}$ represents =CH$_2$, =CHR$^{iY4}$, or =CR$^{iY4}_2$, where $R^{iY4}$ represents a hydrogen atom or a linear alkyl group having 1 to 20 carbon atoms or a branched alkyl group having 3 to 20 carbon atoms, and a secondary carbon atom in the alkyl group is optionally replaced with —O—, —CH=CH—, or —C≡C— provided that oxygen atoms are not directly adjacent to each other; $R^{iY3}$ has a same meaning as $R^{iY1}$ associated with a case where the dashed line represents a single bond; $R^{iY2}$ represents a hydrogen atom or a linear alkyl group having 1 to 20 carbon atoms or a branched alkyl group having 3 to 20 carbon atoms, and a secondary carbon atom in the alkyl group is optionally replaced with —O—, —CH=CH—, or —C≡C— provided that oxygen atoms are not directly adjacent to each other; $n^{iY1}$ is 0 when the dashed line represents a double bond and is 1 when the dashed line represents a single bond; $n^{iY2}$ represents an integer of 0 to 5; when any of $R^{iY1}$, $R^{iY3}$, and $R^{iY4}$ is a plurality of units, the units are identical to or different from one another; and * is a point of attachment to $S^{i3}$.

6. A liquid crystal composition comprising the compound represented by general formula (i) according to claim 1, another polymerizable compound, which is different from a compound represented by general formula (i), and a non-polymerizable liquid crystal compound.

7. The liquid crystal composition according to claim 6, wherein the polymerizable compound comprises one or more compounds represented by general formula (P),

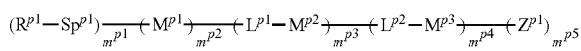

(P)

wherein $Z^{p1}$ represents a fluorine atom, a cyano group, a hydrogen atom, an alkyl group having 1 to 15 carbon atoms in which a hydrogen atom is optionally replaced with a halogen atom, an alkoxy group having 1 to 15 carbon atoms in which a hydrogen atom is optionally replaced with a halogen atom, an alkenyl group having 2 to 15 carbon atoms in which a hydrogen atom is optionally replaced with a halogen atom, an alkenyloxy group having 2 to 15 carbon atoms in which a hydrogen atom is optionally replaced with a halogen atom, or -Sp$^{p2}$-R$^{p2}$, $R^{p1}$ and $R^{p2}$ represent one of formulae (R-I) to (R-VIII), shown below,

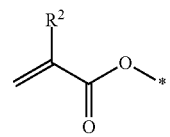

(R-I)

(R-II)

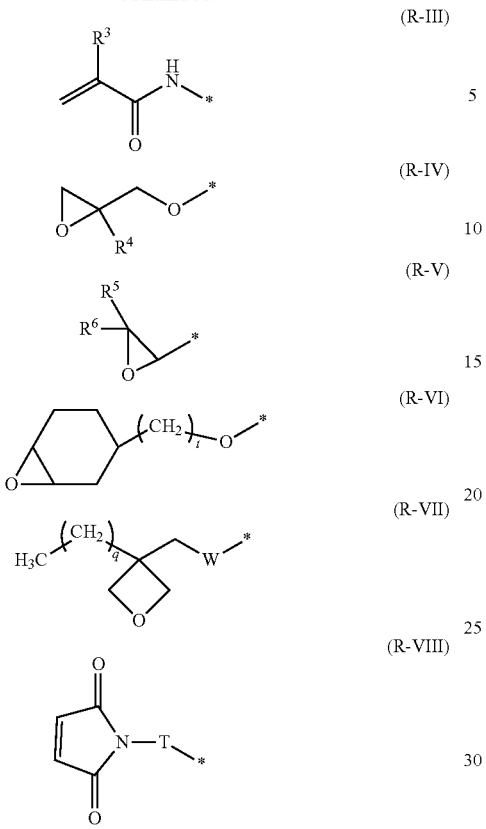

(R-III)

(R-IV)

(R-V)

(R-VI)

(R-VII)

(R-VIII)

wherein is a point of attachment to $Sp^{p1}$, $R^2$ to $R^6$ each independently represent a hydrogen atom, an alkyl group having 1 to 5 carbon atoms, or a halogenated alkyl group having 1 to 5 carbon atoms, W represents a single bond, —O—, or a methylene group, T represents a single bond or —COO—, and p, t, and q each independently represent 0, 1, or 2, $Sp^{p1}$ and $Sp^{p2}$ represent a spacer group, $L^{p1}$ and $L^{p2}$ each independently represent a single bond, —O—, —S—, —CH$_2$—, —OCH$_2$—, —CH$_2$O—, —CO—, —C$_2$H$_4$—, —COO—, —OCO—, —OCOOCH$_2$—, —CH$_2$OCOO—, —OCH$_2$CH$_2$O—, —CO—NR$^a$—, —NR$^a$—CO—, —SCH$_2$—, —CH$_2$S—, —CH=CR$^a$—COO—, —CH=CR$^a$—OCO—, —COO—CR$^a$=CH—, —OCO—CR$^a$=CH—, —COO—CR$^a$=CH—COO—, —COO—CR$^a$=CH—OCO—, —OCO—CR$^a$=CH—COO—, —OCO—CR$^a$=CH—OCO—, —(CH$_2$)$_z$—C(=O)—O—, —(CH$_2$)$_z$—O—(C=O)—, —O—(C=O)—(CH$_2$)$_z$—, —(C=O)—O—(CH$_2$)$_z$—, —CH$_2$(CH$_3$)C—C(=O)—O—, —CH$_2$(CH$_3$)C—O—(C=O)—, —O—(C=O)—C(CH$_3$)CH$_2$, —(C=O)—O—C(CH$_3$)—CH$_2$, —CH=CH—, —CF=CF—, —CF=CH—, —CH=CF—, —CF$_2$—, —CF$_2$O—, —OCF$_2$—, —CF$_2$CH$_2$—, —CH$_2$CF$_2$—, —CF$_2$CF$_2$—, or —C≡C—, where $R^a$ independently represents a hydrogen atom or an alkyl group having 1 to 4 carbon atoms, and z represents an integer of 1 to 4, $M^{p2}$ represents a 1,4-phenylene group, a 1,4-cyclohexylene group, an anthracene-2,6-diyl group, a phenanthrene-2,7-diyl group, a pyridine-2,5-diyl group, a pyrimidine-2,5-diyl group, a naphthalene-2,6-diyl group, an indan-2,5-diyl group, a 1,2,3,4-tetrahydronaphthalene-2,6-diyl group, a 1,3-dioxane-2,5-diyl group, or a single bond, and $M^{p2}$ is unsubstituted or optionally substituted with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$, $M^{p1}$ represents one of formulae (i-11) to (ix-11), shown below,

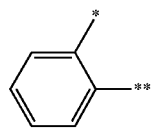

(i-11)

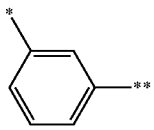

(ii-11)

(iii-11)

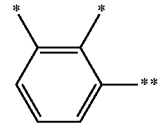

(iv-11)

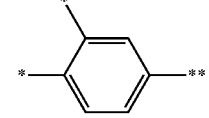

(v-11)

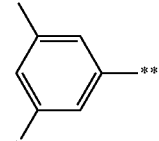

(vi-11)

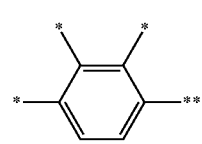

(vii-11)

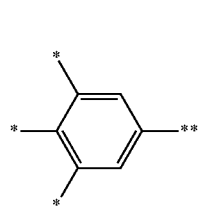

(viii-11)

-continued (ix-11)

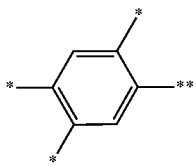

wherein * is a point of attachment to $Sp^{p1}$, and ** is a point of attachment to $L^{p1}$, $LP^{p2}$, or $Z^{p1}$,
any hydrogen atom of $M^{p1}$ is optionally replaced with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$
$M^{p3}$ represents one of formulae (i-13) to (ix-13), shown below, (i-13)

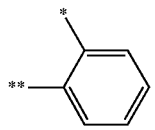

(ii-13)

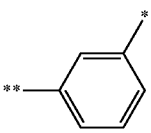

(iii-13)

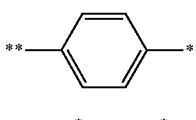

(iv-13)

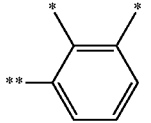

(v-13)

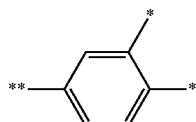

(vi-13)

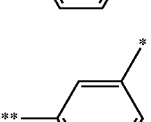

-continued (vii-13)

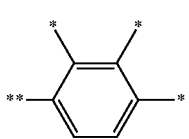

(viii-13)

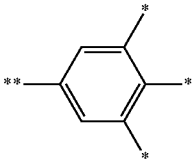

(ix-13)

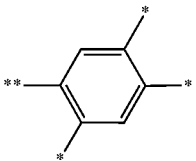

wherein * is a point of attachment to $Z^{p1}$, and ** is a point of attachment to $L^{p2}$,
any hydrogen atom of $M^{p3}$ is optionally replaced with an alkyl group having 1 to 12 carbon atoms, a halogenated alkyl group having 1 to 12 carbon atoms, an alkoxy group having 1 to 12 carbon atoms, a halogenated alkoxy group having 1 to 12 carbon atoms, a halogen atom, a cyano group, a nitro group, or —$R^{p1}$,
$m^{p2}$ to $m^{p4}$ each independently represent 0, 1, 2, or 3,
$m^{p1}$ and $m^{p5}$ each independently represent 1, 2, or 3, and
when $Z^{p1}$ is a plurality of units, the units are identical to or different from one another; when $R^{p1}$ is a plurality of units, the units are identical to or different from one another; when $R^{p2}$ is a plurality of units, the units are identical to or different from one another; when $Sp^{p1}$ is a plurality of units, the units are identical to or different from one another; when $Sp^{p2}$ is a plurality of units, the units are identical to or different from one another; when $L^{p1}$ is a plurality of units, the units are identical to or different from one another; and when $M^{p2}$ is a plurality of units, the units are identical to or different from one another.

8. A liquid crystal display element in which the liquid crystal composition according to claim 6 is used, the liquid crystal display element including two substrates, at least one of the two substrates having no alignment film.

* * * * *